US012662489B2

(12) United States Patent
Mazzacani et al.

(10) Patent No.: US 12,662,489 B2
(45) Date of Patent: Jun. 23, 2026

(54) COMPOUNDS

(71) Applicant: Sitryx Therapeutics Limited, Oxford (GB)

(72) Inventors: Alessandro Mazzacani, Oxford (GB); Paulette Greenidge, Oxford (GB); Barry Teobald, Oxford (GB); Matthew Fyfe, Oxford (GB); Oscar Barba, Oxford (GB); Paolo Ricci, Saffron Walden (GB); Carlos Turrado Garcia, Saffron Walden (GB); Nelly Piton, Saffron Walden (GB); Christopher Matheson, Saffron Walden (GB)

(73) Assignee: Sitryx Therapeutics Limited, Oxford (GB)

(*) Notice: Subject to any disclaimer, the term of this patent is extended or adjusted under 35 U.S.C. 154(b) by 0 days.

(21) Appl. No.: 18/910,967

(22) Filed: Oct. 9, 2024

(65) Prior Publication Data

US 2025/0122212 A1 Apr. 17, 2025

(30) Foreign Application Priority Data

Oct. 9, 2023 (EP) .................................... 23202514
Mar. 18, 2024 (EP) .................................... 24164069

(51) Int. Cl.

*C07D 491/052* (2006.01)
*A61K 31/496* (2006.01)
*A61K 31/5383* (2006.01)
*C07D 519/00* (2006.01)

(52) U.S. Cl.

CPC ........ *C07D 491/052* (2013.01); *A61K 31/496* (2013.01); *A61K 31/5383* (2013.01); *C07D 519/00* (2013.01)

(58) Field of Classification Search

CPC .............. C07D 491/052; C07D 519/00; A61K 31/496; A61K 31/5383

See application file for complete search history.

(56) References Cited

U.S. PATENT DOCUMENTS

2019/0284198 A1* 9/2019 Ota .................... C07D 491/052

FOREIGN PATENT DOCUMENTS

EP 0 623 592 A1 11/1994
WO 2022/104010 A1 5/2022

OTHER PUBLICATIONS

International Search Report and Written Opinion mailed Dec. 19, 2024 in International Application No. PCT/GB2024/052586.

Chemcats et al: "sulfanamido-benzoic acid derivative", registry, Nov. 18, 2018 (Nov. 18, 2018), pp. 1-1, XP093135270.

Ota, M., et al; J. Med. Chem.; 2019; 62(22), pp. 10204-10220.

Ota, M et al; ACS Medicinal Chemistry Letters; 2019; 10(6), pp. 893-898.

Registry 2249380-bVI; Nov. 18, 2018, 2018; Benzoic acld 1 3-[[[(l-ethylcyclopropyl)sulfonyl]amino]carbonyl]-5-methyl·(CA Index Name).

* cited by examiner

*Primary Examiner* — Erich A Leeser

(74) *Attorney, Agent, or Firm* — Faegre Drinker Biddle & Reath LLP

(57) ABSTRACT

The invention relates to compounds of formula (I)

(I)

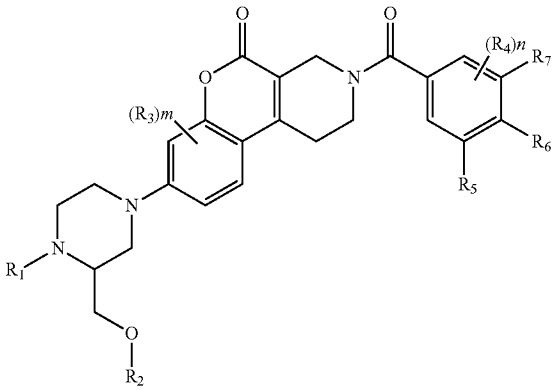

and related aspects.

18 Claims, No Drawings

COMPOUNDS

The application claims priority of European patent application nos. 23202514.8, filed on Oct. 9, 2023, and 24164069.7, filed on Mar. 18, 2024, which are incorporated by reference herein in their entirety.

FIELD OF THE INVENTION

The present invention relates to compounds and their use in treating or preventing various proliferative diseases, and to related compositions, methods and intermediate compounds.

BACKGROUND OF THE INVENTION

Inflammation, autoimmunity, fibrosis and in addition cancer share numerous underlying disease mechanisms, in particular aberrant cell proliferation and in some situations shared pathology.

Autoimmunity is best described as adherent recognition of self-antigens that lead to tissue destruction by lymphocytes of the T-cell and B-cell lineage, rheumatoid arthritis (RA) being a typical example. Inflammation, while encompassing these mechanisms can also be primarily driven by innate immunity through metabolic imbalances or repeated injury and irritation, an example being non-alcoholic steatohepatitis (NASH): initiated and sustained by accumulating lipids in the liver and potentially microfauna from the gastro-intestinal system. All these mechanisms can also lead to organ sclerosis, scarring and fibrosis through the activation and proliferation of fibroblasts, although in some instances fibrosis can occur without obvious evidence of inflammation or autoimmunity: an example being idiopathic pulmonary fibrosis (IPF).

These exemplified diseases highlight that our current knowledge of mechanistic progression in pathologies of the immune system is poor and as a result clinical unmet need for patients remains high. In the case of cancer our understanding of disease progression is significantly more advanced with many genetic mutations identified that lead to loss of cell cycle regulation and uncontrolled proliferation the primary hallmarks of oncological diseases. Unmet clinical need in cancer also remains high however due to the number and diversity of mutations present that make targeted therapy challenging.

In many of these diseases, compounds that primarily target excessive cell proliferation via metabolic processes are a mainstay of therapeutic intervention. Example drugs include methotrexate (MTX) and fluorouracil (5-FU) that are used to treat both cancer and autoimmune diseases such as RA via suppressing proliferation of the cancer cells and T and B cells in the case of autoimmunity. MTX and 5-FU target enzymes on the one-carbon (1C) metabolism pathway which involves the transfer of single carbon units between molecules used for redox balance and the biosynthesis of methyl donors, purines and thymidylates. The 1C metabolism is significantly upregulated in rapidly dividing cells including lymphocytes and numerous cancer cells. (Ducker and Rabinowitz, 2017; Yang and Vousden, 2016). Despite being in clinical use for decades for the treatment of cancer and auto-immune diseases (Grem J L. 2000; Chan E S L. & Cronstein B N. 2010) and demonstrating significant disease modifying efficacy, side effects such as anemia, vomiting, diarrhoea, parathesis, lethargy and joint pain limit effectiveness of these drugs. MTX is a strong suppressor of the 1C cycle acting as an inhibitor of dihydrofolate reductase (DHRF), blocking the conversion of folate to tetrahydrofolate. This drives efficacy but at the cost of numerous side effects as previously described.

Targeting 1C metabolism in a more specific and disease relevant context is likely to maintain therapeutic benefit but reduce the side effect burden associated with current 1C targeted medication (Cuthbertson C R. et al., 2021). Since the inception of MTX and 5-FU, the understanding of the enzymes involved in 1C metabolism has greatly improved and it is recognised that more selective and focused modulation of 1C metabolism could lead to more effective therapies, with an improved risk to benefit profile. Enzymes of interest for selective targeting of 1C targeting include cytoplasmic methylene tetrahydrofolate dehydrogenase 1 (MTHFD1) and mitochondrial methylene tetrahydrofolate dehydrogenase 2 (MTHFD2).

In the cytoplasm the trifunctional enzyme MTHFD1 converts 5,10-methylenetetrahydrofolate (5,10 me-tetrahydrofolate) into formate. MTHFD1 dehydrogenase/cyclohydrolase domain (D/C-d) first converts 5,10 me-tetrahydrofolate to 10-formyl tetrahydrofolate via oxidation mediated by NADP. In a second ATP driven reaction, MTHFD1 synthetase domain (S-d) converts 10-formyl tetrahydrofolate to formate (Kurniawan H. et al., 2021).

In the mitochondria the dehydrogenase and cyclohydrolase functionality are carried out by MTHFD2 with preference for oxidization mediated by nicotinamide adenine dinucleotide (NAD).

It is recognised that MTHFD1 cytoplasmic 1C metabolism is required largely for homeostatic function whereas mitochondrial MTHFD2 flux supports highly proliferating cells and disease progression in several inflammation states, autoimmune diseases, and cancers. MTHFD2 expression is increased in diseases where rapid cell division is also present, most notably in inflammation and cancer; in addition, other key enzymes in the mitochondrial 1C pathway are also increased (Eich M L. et al., 2019; Adewale F. et al., 2017; Lee D. et al., 2017; Nilsson R. et al., 2014). Thus, the use of inhibitors of MTHFD2 that selective target the 1C pathway in cells driving disease could lead to new therapies with an enhanced safety prolife in comparison to MTX and 5-FU.

RNA-seq analysis from immune cells in peripheral blood showed that MTHFD2 was consistently overexpressed across multiple inflammatory conditions including ulcerative colitis, Crohn's disease, Celiac disease, systemic lupus erythematosus (SLE), psoriatic arthritis, multiple sclerosis (MS), Sjogren's syndrome and RA (Aune T M. et al., 2017). Furthermore, activated $CD4^+$ T-cells showed a significant increase in MTHFD2 mRNA after activation, with protein expression peaking at 48 hours. In particular the $CD4^+$ T-cell subsets Th17 and Th1 that are strongly associated with inflammatory diseases had the highest expression of MTHFD2.

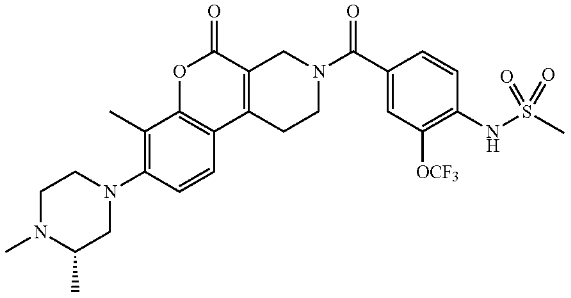

Reference Example 1
DS18561882

Moreover, treatment with an MTHFD2 inhibitor DS18561882 (disclosed by Daiichi Sankyo in US2019/0284198 as Example 5, herein referred to as "Reference Example 1") greatly decreased the number of Th1 and Th17 cells differentiated in vitro from $CD4^+$ T-cells and expression of the respective Th1 and Th17 cytokines. IFNγ and IL-17 were also significantly reduced (Kawai J., 2019). DS18561882 treatment also increased immune-suppressive Treg cells, suggesting that inhibition of MTHFD2 can also deviate the immune response from pro-inflammatory to anti-inflammatory affects. Further assessment in vivo demonstrated that DS18561882 could reduce ear-swelling in a murine keyhole limpet hemocyanin (KLH) contact sensitization model ((Sugiura A. et al., 2022) However, as shown hereinbelow, Reference Example 1, has activity on certain receptors not involved in the 1C pathway. This may ultimately lead to off-target effects, which may limit the development of such molecules into medications.

Further validation for therapeutic targeting the MTHFD2 in the context of autoimmune disease was demonstrated in a murine experimental autoimmune encephalomyelitis (EAE) model of multiple sclerosis (MS). The disease was induced and from day 4 to day 26 the mice were treated with the oral dual MTHFD1 D/C-d and MTHDF2 inhibitor LY345899 (Gustafsson R. et al., 2017); treatment led to significantly reduced disease severity and cumulative clinical score compared to vehicle with reduced immune cell infiltrate into the spinal cord also noted. Given these observations, it is possible that dual MTHFD1 D/C-d and MTHFD2 inhibitors may be more effective in certain indications than inhibitors targeting MTHFD2 alone. Dual MTHFD1 D/C-d and MTHFD2 inhibitors may present a different risk benefit profile and lead to new therapies with an enhanced safety prolife in comparison to MTX and 5-FU.

Both DS18561882 and LY345899 were well tolerated at the therapeutic doses used [Sugiura A. et al., 2022]. Further validation for MTHFD2 as suitable target in inflammation was demonstrated in a murine model of heart transplantation. T-cell specific ablation of MTHFD2 in the host protected the allografted heart from vascular occlusion and fibrosis and significantly increased survival of the grafted mice [Li Y. et al., 2023].

There remains a need to identify and develop new compounds possessing enhanced properties compared to existing MTHFD2 inhibitors, for example that the compounds are more suitable drug candidates. The inventors have now developed compounds which, as well as being potent MTHFD2 and MTHFD1 D/C-d inhibitors, or selective MTHFD2 inhibitors over MTHFD1 D/C-d, also avoid the problem of off-target effects compared with other compounds of the prior art.

SUMMARY OF THE INVENTION

The present invention provides a compound of formula (I):

(I)

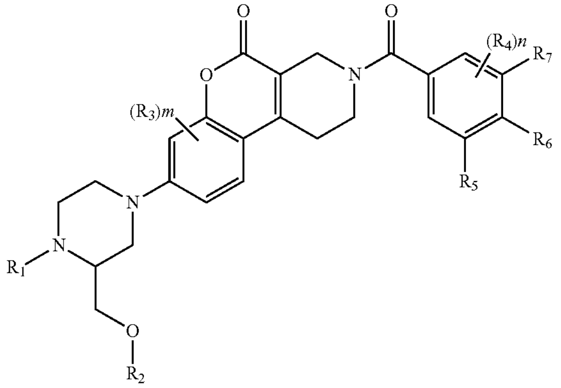

wherein:

$R_1$ is $C_{1-4}$ alkyl or $C_{3-5}$ cycloalkyl;

$R_2$ is $C_{1-4}$ alkyl; or $R_1$ and $R_2$ join to form a 5-7 membered heterocycloalkyl;

$R_3$ is selected from the group consisting of $C_{1-3}$ alkyl and halo;

$R_4$ is selected from the group consisting of $C_{1-3}$ alkyl, halo, $C_{1-3}$ haloalkyl, $C_{1-3}$ alkoxy, $C_{1-3}$ haloalkoxy, $NR_{4a}R_{4b}$ and 4-7 membered heterocycloalkyl;

wherein:

$R_{4a}$ is selected from the group consisting of H and $C_{1-3}$ alkyl;

$R_{4b}$ is selected from the group consisting of H and $C_{1-3}$ alkyl;

m is 0, 1 or 2;

n is 0, 1 or 2;

and $R_5$, $R_6$ and $R_7$ are defined as follows:

(a) $R_6$ is

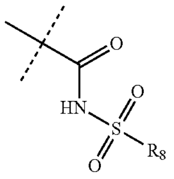

and $R_7$ is absent;

$R_5$ is selected from the group consisting of H, halo, $C_{1-3}$ alkyl, $C_{1-3}$ haloalkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{5b}$ is selected from the group consisting of H and $C_{1-3}$ alkyl; and $R_{5c}$ is selected from the group consisting of $C_{1-3}$ alkyl and $C_{3-6}$ cycloalkyl; and $R_8$ is selected from the group consisting of $C_{3-6}$ cycloalkyl, $NR_{8b}R_{8c}$ and 4-10 membered heterocycloalkyl, wherein the $C_{3-6}$ cycloalkyl and 4-10 membered heterocycloalkyl are optionally substituted by one or more $R_{8a}$, wherein:

$R_{8a}$ is selected from the group consisting of $C_{1-3}$ alkyl, $C_{1-3}$ alkyl substituted by OH, $C_{1-2}$ alkyl substituted by $OC_{1-2}$ alkyl, $C_{1-3}$ alkoxy, halo and $C_{1-3}$ haloalkyl;

$R_{8b}$ is selected from the group consisting of H, $C_{1-3}$ alkyl and $C_{3-6}$ cycloalkyl;

$R_{8c}$ is selected from the group consisting of H, $C_{1-3}$ alkyl and $C_{3-6}$ cycloalkyl; or:

(b) $R_7$ is

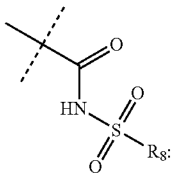

and (i) $R_6$ is H and $R_5$ is selected from the group consisting of H, halo, $C_{1-3}$ alkyl, $C_{1-3}$ haloalkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring, $R_{5b}$ is selected from the group consisting of H and $C_{1-3}$ alkyl; and $R_{5c}$ is selected from the group consisting of $C_{1-3}$ alkyl and $C_{3-6}$ cycloalkyl;

or (ii) $R_5$ is H and $R_6$ is selected from the group consisting of H, halo, $C_{1-3}$ alkyl, $C_{1-3}$ haloalkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{6b}R_{6c}$ and 4-7 membered heterocycloalkyl, wherein the $OC_{3-10}$ cycloalkyl and 4-7 membered heterocycloalkyl are optionally substituted by one or more $R_{6a}$;

wherein:

$R_{6a}$ is selected from the group consisting of halo and $C_{1-3}$ alkyl, or two $R_{6a}$ groups which are attached to the same carbon atom join to form a $C_{3-6}$ cycloalkyl or 4-7 membered heterocycloalkyl ring, $R_{6b}$ is selected from the group consisting of H and $C_{1-3}$ alkyl; and $R_{6c}$ is selected from the group consisting of $C_{1-3}$ alkyl and $C_{3-6}$ cycloalkyl;

or (iii) $R_5$ and $R_6$ join to form a 4-8 membered heterocyclic ring;

and $R_8$ is selected from the group consisting of $C_{3-6}$ cycloalkyl, $NR_{8b}R_{8c}$ and 4-10 membered heterocycloalkyl, wherein the $C_{3-6}$ cycloalkyl and 4-10 membered heterocycloalkyl are optionally substituted by one or more $R_{8a}$ wherein:

$R_{8a}$ is selected from the group consisting of $C_{1-3}$ alkyl, $C_{1-3}$ alkyl substituted by OH, $C_{1-2}$ alkyl substituted by $OC_{1-2}$ alkyl, $C_{1-3}$ alkoxy, halo and $C_{1-3}$ haloalkyl;

$R_{8b}$ is selected from the group consisting of H, $C_{1-3}$ alkyl and $C_{3-6}$ cycloalkyl; and $R_{8c}$ is selected from the group consisting of H, $C_{1-3}$ alkyl and $C_{3-6}$ cycloalkyl; or a pharmaceutically acceptable salt and/or solvate thereof.

In one embodiment, the present invention also provides a compound of formula (I):

(I)

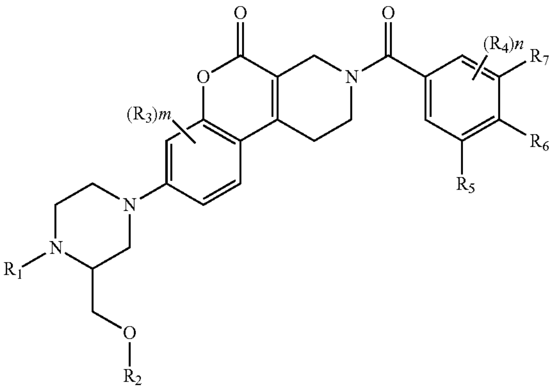

wherein:

$R_1$ is $C_{1-4}$ alkyl or $C_{3-5}$ cycloalkyl;

$R_2$ is $C_{1-4}$ alkyl; or $R_1$ and $R_2$ join to form a 5-7 membered heterocycloalkyl;

$R_3$ is selected from the group consisting of $C_{1-3}$ alkyl and halo;

$R_4$ is selected from the group consisting of $C_{1-3}$ alkyl, halo, $C_{1-3}$ haloalkyl, $C_{1-3}$ alkoxy, $C_{1-3}$ haloalkoxy, $NR_{4a}R_{4b}$ and 4-7 membered heterocycloalkyl;

wherein:

$R_{4a}$ is selected from the group consisting of H and $C_{1-3}$ alkyl;

$R_{4b}$ is selected from the group consisting of H and $C_{1-3}$ alkyl;

m is 0, 1 or 2;

n is 0, 1 or 2;

and $R_5$, $R_6$ and $R_7$ are defined as follows:

(a) $R_6$ is

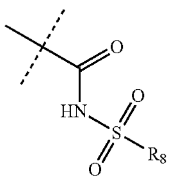

and $R_7$ is absent;

$R_5$ is selected from the group consisting of H, halo, $C_{1-3}$ alkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{5b}$ is selected from the group consisting of H and $C_{1-3}$ alkyl; and $R_{5c}$ is selected from the group consisting of $C_{1-3}$ alkyl and $C_{3-6}$ cycloalkyl; and $R_8$ is selected from the group consisting of $C_{3-6}$ cycloalkyl, $NR_{8b}R_{8c}$ and 4-8 membered heterocycloalkyl, wherein the $C_{3-6}$ cycloalkyl and 4-8 membered heterocycloalkyl are optionally substituted by one or more $R_{8a}$, wherein:

$R_{8a}$ is selected from the group consisting of $C_{1-3}$ alkyl, halo and $C_{1-3}$ haloalkyl;

$R_{8b}$ is selected from the group consisting of H, $C_{1-3}$ alkyl and $C_{3-6}$ cycloalkyl;

$R_{8c}$ is selected from the group consisting of H, $C_{1-3}$ alkyl and $C_{3-6}$ cycloalkyl; or:

(b) $R_7$ is

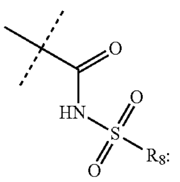

and (i) $R_6$ is H and $R_5$ is selected from the group consisting of H, halo, $C_{1-3}$ alkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring, $R_{5b}$ is selected from the group consisting of H and $C_{1-3}$ alkyl; and $R_{5c}$ is selected from the group consisting of $C_{1-3}$ alkyl and $C_{3-6}$ cycloalkyl;

or (ii) $R_5$ is H and $R_6$ is selected from the group consisting of H, halo, $C_{1-3}$ alkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{6b}R_{6c}$ and 4-7 membered heterocycloalkyl, wherein the $OC_{3-10}$ cycloalkyl and 4-7 membered heterocycloalkyl are optionally substituted by one or more $R_{6a}$;

wherein:

$R_{6a}$ is selected from the group consisting of halo and $C_{1-3}$ alkyl, or two $R_{6a}$ groups which are attached to the same carbon atom join to form a $C_{3-6}$ cycloalkyl or 4-7 membered heterocycloalkyl ring, $R_{6b}$ is selected from the group consisting of H and $C_{1-3}$ alkyl; and $R_{6c}$ is selected from the group consisting of $C_{1-3}$ alkyl and $C_{3-6}$ cycloalkyl;

or (iii) $R_5$ and $R_6$ join to form a 4-8 membered heterocyclic ring;

and $R_8$ is selected from the group consisting of $C_{3-6}$ cycloalkyl, $NR_{8b}R_{8c}$ and 4-8 membered heterocycloalkyl, wherein the $C_{3-6}$ cycloalkyl and 4-8 membered heterocycloalkyl are optionally substituted by one or more $R_{8a}$ wherein:

$R_{8a}$ is selected from the group consisting of $C_{1-3}$ alkyl, halo and $C_{1-3}$ haloalkyl;

$R_{8b}$ is selected from the group consisting of H, $C_{1-3}$ alkyl and $C_{3-6}$ cycloalkyl; and $R_{8c}$ is selected from the group consisting of H, $C_{1-3}$ alkyl and $C_{3-6}$ cycloalkyl; or a pharmaceutically acceptable salt and/or solvate thereof.

In one embodiment, the present invention also provides a compound of formula (I):

(I)

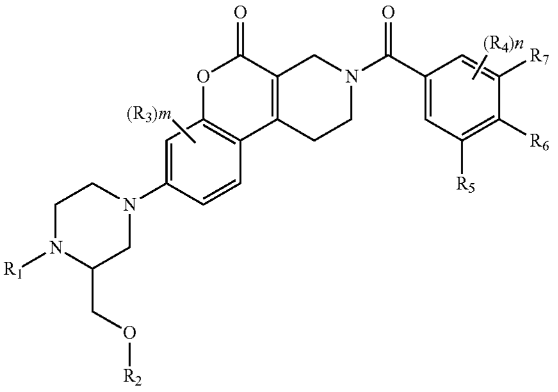

wherein:

$R_1$ is $C_{1-4}$ alkyl or $C_{3-5}$ cycloalkyl;

$R_2$ is $C_{1-4}$ alkyl; or $R_1$ and $R_2$ join to form a 5-7 membered heterocycloalkyl;

$R_3$ is selected from the group consisting of $C_{1-3}$ alkyl and halo;

$R_4$ is selected from the group consisting of $C_{1-3}$ alkyl, halo, $C_{1-3}$ haloalkyl, $C_{1-3}$ alkoxy, $C_{1-3}$ haloalkoxy and 4-7 membered heterocycloalkyl;

$R_6$ is

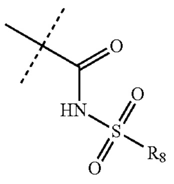

and $R_7$ is absent; or $R_7$ is

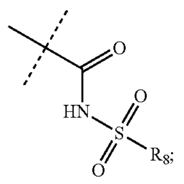

wherein:

when $R_6$ is

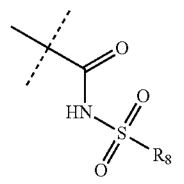

and $R_7$ is absent:

$R_5$ is selected from the group consisting of H, halo, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring; $R_{5b}$ is selected from the group consisting of H and $C_{1-3}$ alkyl; and $R_{5c}$ is selected from the group consisting of $C_{1-3}$ alkyl and $C_{3-6}$ cycloalkyl; and $R_8$ is selected from the group consisting of $C_{3-6}$ cycloalkyl, $N(C_{1-3}\ alkyl)_2$ and 4-8 membered heterocycloalkyl, wherein the $C_{3-6}$ cycloalkyl and 4-8 membered heterocycloalkyl are optionally substituted by one or more $R_{8a}$, wherein $R_{8a}$ is selected from the group consisting of $C_{1-3}$ alkyl, halo and $C_{1-3}$ haloalkyl;

or:

when $R_7$ is

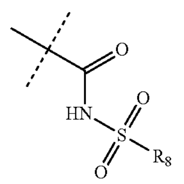

$R_6$ is H and $R_5$ is selected from the group consisting of H, halo, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring, $R_{5b}$ is selected from the group consisting of H and $C_{1-3}$ alkyl; and $R_{5c}$ is selected from the group consisting of $C_{1-3}$ alkyl and $C_{3-6}$ cycloalkyl;

or $R_5$ is H and $R_6$ is selected from the group consisting of H, halo, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{6b}R_{6c}$ and 4-7 membered heterocycloalkyl, wherein the $OC_{3-10}$ cycloalkyl and 4-7 membered heterocycloalkyl are optionally substituted by one or more $R_{6a}$;

wherein:

$R_{6a}$ is selected from the group consisting of halo and $C_{1-3}$ alkyl, or two $R_{6a}$ groups which are attached to the same carbon atom join to form a $C_{3-6}$ cycloalkyl or 4-7 membered heterocycloalkyl ring, $R_{6b}$ is selected from the group consisting of H and $C_{1-3}$ alkyl; and $R_{6c}$ is selected from the group consisting of $C_{1-3}$ alkyl and $C_{3-6}$ cycloalkyl;

or $R_5$ and $R_6$ join to form a 4-8 membered heterocyclic ring; and $R_8$ is selected from the group consisting of $C_{3-6}$ cycloalkyl, $N(C_{1-3}\ alkyl)_2$ and 4-8 membered heterocycloalkyl, wherein the $C_{3-6}$ cycloalkyl and 4-8 membered heterocycloalkyl are optionally substituted by one or more $R_{8a}$ wherein $R_{8a}$ is selected from the group consisting of $C_{1-3}$ alkyl, halo and $C_{1-3}$ haloalkyl;

m is 0, 1 or 2; and n is 0, 1 or 2;

or a pharmaceutically acceptable salt and/or solvate thereof.

DETAILED DESCRIPTION OF THE INVENTION

Compounds of Formula (I)

Embodiments and preferences set out herein with respect to the compound of formula (I) apply equally to the pharmaceutical composition, compound or pharmaceutically acceptable salt and/or solvate thereof for use, pharmaceutical composition for use, use and method aspects of the invention, as well as intermediates used in the synthesis of the compounds of formula (I). These also apply equally well, where appropriate, to compounds of formula (IA), (IB), (IC), (IC-1) and (ID).

The term "alkyl" (e.g. $C_{1-4}$ alkyl or $C_{1-3}$ alkyl) as used herein refers to a straight or branched fully saturated hydrocarbon group having the specified number of carbon atoms. The term encompasses methyl, ethyl, n-propyl, isopropyl, n-butyl, isobutyl, sec-butyl and tert-butyl. The term "alkyl" also encompasses "alkylene" which is a bifunctional straight or branched fully saturated hydrocarbon group having a specified number of carbon atoms. Example "alkylene" groups include methylene, ethylene, n-propylene and n-butylene.

The term “halo” as used herein refers to fluoro, chloro, bromo and iodo. Particular examples of halo are fluorine and chlorine, especially fluorine.

The term “alkoxy” (e.g. $C_{1-3}$ alkoxy) as used herein refers to an alkyl group (e.g. $C_{1-3}$ alkyl) as defined above, singularly bonded via an oxygen atom. The term encompasses methoxy, ethoxy, 1-propoxy and 2-propoxy.

The term “haloalkyl” (e.g. $C_{1-3}$ haloalkyl) as used herein refers to a straight or a branched fully saturated hydrocarbon chain containing the specified number of carbon atoms and at least one halogen atom, such as fluoro or chloro, especially fluoro. An example of haloalkyl is $CF_3$.

The term “haloalkoxy” (e.g. $C_{1-3}$ haloalkoxy) as used herein refers to a haloalkyl group (e.g. $C_{1-3}$ haloalkyl), as defined above, singularly bonded via an oxygen atom. Examples of haloalkoxy groups include $OCF_3$, $OCHF_2$ and $OCH_2CF_3$.

The term “cycloalkyl” (e.g. $C_{3-6}$ cycloalkyl, $C_{3-5}$ cycloalkyl or $OC_{3-10}$ cycloalkyl) as used herein refers to a fully saturated cyclic hydrocarbon group having the specified number of carbon atoms.

The term encompasses cyclopropyl, cyclobutyl, cyclopentyl, cyclohexyl, cycloheptyl, cyclooctyl, cyclononyl and cyclodecyl, as well as bridged and fused systems such as bicyclo[1.1.1]pentyl, bicyclo[3.1.0]hexyl and 2-adamantanyl:

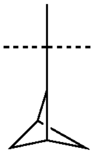

bicyclo [1.1.1] pentyl

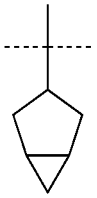

bicyclo [3.1.0] hexyl

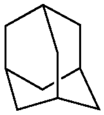

2-adamantanyl

The term “heterocycloalkyl” (e.g. 4-10 membered heterocycloalkyl, 4-8 membered heterocycloalkyl, 4-7 membered heterocycloalkyl or 5-7 membered heterocycloalkyl) as used herein refers to a non-aromatic cyclic group having the specified number of ring atoms, at least one of which is a heteroatom selected from N, O, S and B such as N or O, e.g. N. The term “heterocycloalkyl” is interchangeable with “heterocyclic ring”. Heterocyclic groups can typically be substituted by one or more (e.g. one or two) oxo groups. Suitably, thietanyl is substituted by one or two oxo groups. The term encompasses oxetanyl, thietanyl, azetidinyl, pyrrolidinyl, tetrahydrofuranyl, tetrahydrothienyl, piperidinyl, tetrahydropyranyl, piperazinyl, morpholinyl, thiomorpholinyl, azepanyl and oxepanyl, as well as bridged, fused and spirocyclic ring systems such as 5,8-dioxaspiro[3.4]octanyl, 3-azabicyclo[3.1.0]hexyl, 2-azabicyclo(2.2.1)heptyl, 7-azanorbornanyl and 5-azaspiro[2.5]octyl:

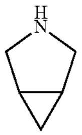

3-azabicyclo [3.1.0]hexyl

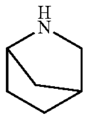

2-azabicyclo [2.2.1]heptyl

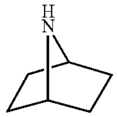

7-azanorbonanyl

-continued

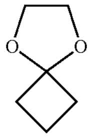

5, 8-dioxaspiro [3.4] octanyl

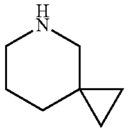

5-azaspiro [2.5] octyl

Further examples of fused ring systems include the following:

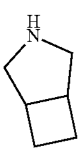

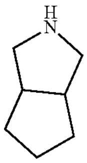

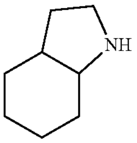

Further examples of bridged ring systems include the following:

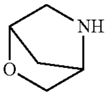

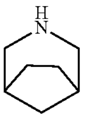

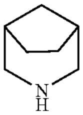

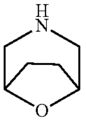

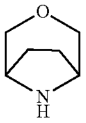

Further examples of spiro ring systems include the following:

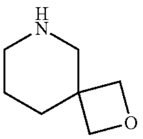

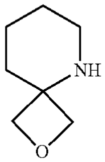

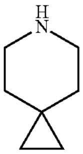

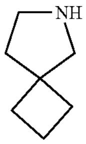

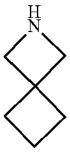

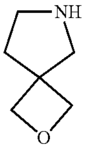

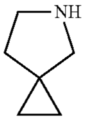

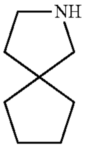

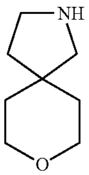

Most suitable heterocycloalkyl groups contain one N atom and no other heteroatoms or contain one N atom and one O atom.

Such groups may be joined to the compound of formula (I) via the NH atom (in which case the H atom is replaced by a group joined to the heterocycloalkyl group) or via an available carbon atom, meaning that the carbon atom must have at least one C—H bond, and the H is replaced by a group joined to the heterocycloalkyl group.

In some suitable compounds of formula (I), $R_1$ is $C_{1-4}$ alkyl, such as methyl. In other suitable compounds of formula (I), $R_1$ is $C_{3-5}$ cycloalkyl, such as cyclopropyl.

Most suitably, $R_1$ is methyl or cyclopropyl.

In some suitable compounds of formula (I), $R_2$ is $C_{1-4}$ alkyl, such as methyl.

Alternatively, in some suitable compounds of formula (I), $R_1$ and $R_2$ join to form a 5-7 membered heterocycloalkyl, such as a 6 membered heterocycloalkyl.

In such compounds of formula (I), the following structure may form:

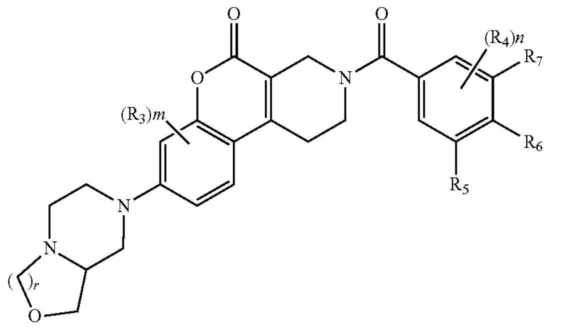

wherein r is 1, 2 or 3, most suitably 2.

In some suitable compounds of formula (I), $R_3$ is $C_{1-3}$ alkyl, such as methyl. In other suitable compounds of formula (I), $R_3$ is halo, such as chloro.

Most suitably, $R_3$ is methyl or chloro.

In some suitable compounds of formula (I), when m is 1 or 2, $R_3$ is attached in the following positions:

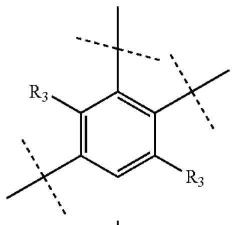

or

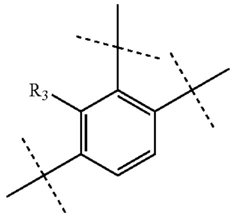

or

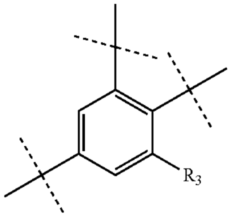

wherein

represents the point of connection to the remainder of the compound of formula (I).

In some suitable compounds of formula (I), m is 0. In other suitable compounds of formula (I), m is 1. In other suitable compounds of formula (I), m is 2.

Most suitably, m is 1 or 2.

In some suitable compounds of formula (I), $R_3$ is methyl and m is 2. In some suitable compounds of formula (I), $R_3$ is selected from methyl and halo (e.g. chloro) and m is 2 e.g. one occurrence is methyl and the other occurrence is methyl or halo (e.g. chloro).

In some suitable compounds of formula (I), $R_1$ is $C_{1-4}$ alkyl, such as methyl, $R_2$ is $C_{1-4}$ alkyl, such as methyl and $R_3$ is $C_{1-4}$ alkyl, such as methyl.

In some suitable compounds of formula (I), $R_4$ is $C_{1-3}$ alkyl, such as methyl. In other suitable compounds of formula (I), $R_4$ is halo, such as fluoro or chloro e.g. fluoro. In other suitable compounds of formula (I), $R_4$ is $C_{1-3}$ haloalkyl, such as trifluoromethyl. In other suitable compounds of formula (I), $R_4$ is $C_{1-3}$ alkoxy, such as methoxy. In other suitable compounds of formula (I), $R_4$ is $C_{1-3}$ haloalkoxy. In other suitable compounds of formula (I), $R_4$ is 4-7 membered heterocycloalkyl, such as pyrrolidinyl. In other suitable compounds of formula (I), $R_4$ is $NR_{4a}R_{4b}$.

In some suitable compounds of formula (I), $R_{4a}$ is H. In other suitable compounds of formula (I), $R_{4a}$ is $C_{1-3}$ alkyl, such as methyl.

In some suitable compounds of formula (I), $R_{4b}$ is H. In other more suitable compounds of formula (I), $R_{4b}$ is $C_{1-3}$ alkyl, such as is methyl.

Most suitably, $R_4$ is fluoro.

In some suitable compounds of formula (I), $R_1$ is $C_{1-4}$ alkyl, such as methyl, $R_2$ is $C_{1-4}$ alkyl, such as methyl, $R_3$ is $C_{1-4}$ alkyl, such as methyl and $R_4$ is halo, such as fluoro.

In some compounds of formula (I), $R_4$ is a 4-7 membered heterocycloalkyl group wherein the group is attached via a nitrogen atom, i.e.

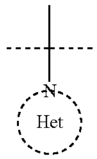

wherein

is the 4-7 membered heterocycloalkyl group and ------ indicates the join to the remainder of the compound of formula (I).

For example, and when the 4-7 membered heterocycloalkyl group is pyrrolidinyl, the pyrrolidinyl group is attached via the nitrogen atom, and is referred to as 1-pyrrolidinyl:

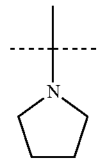

1-pyrrolidinyl wherein ------ indicates the join to the remainder of the compound of formula (I).

In some suitable compounds of formula (I), n is 0. In other suitable compounds of formula (I), n is 1. In other suitable compounds of formula (I), n is 2.

Most suitably, n is 0 or 1.

In some suitable compounds of formula (I), and when n is 1, $R_4$ is attached to the phenyl ring in the following position:

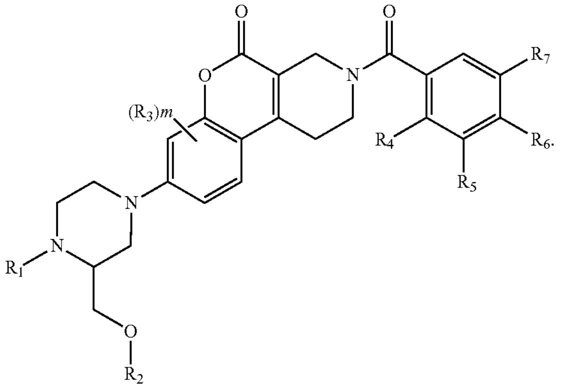

In other suitable compounds of formula (I), and when n is 1, $R_4$ is attached to the phenyl ring in the following position:

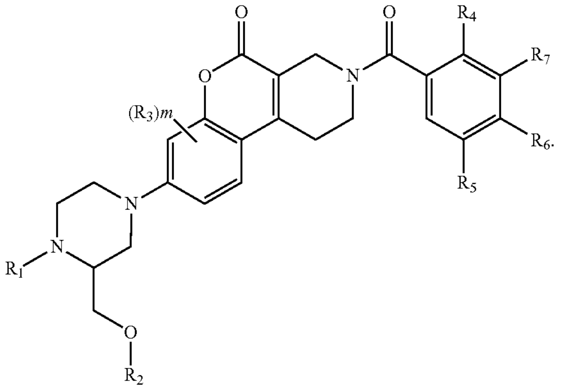

As stated above, in some suitable compounds of formula (I), $R_7$ is absent such that the following structure forms:

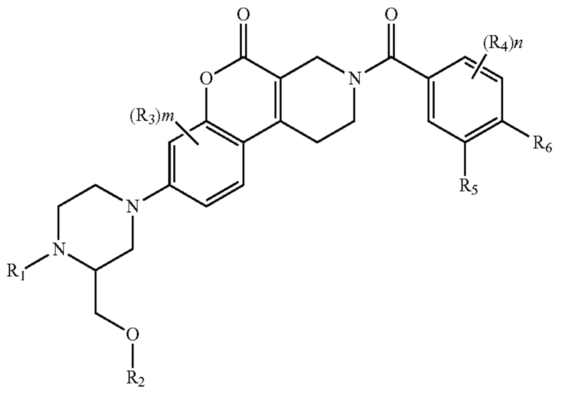

wherein all other variables are defined above.

In such suitable compounds, $R_4$ may be present in any unsubstituted position on the phenyl ring. By "unsubstituted position" it is meant any position where there is a C—H bond. The substituent $R_4$ replaces the H atom, thus forming a C—$R_4$ bond as shown below.

As such, in some suitable compounds of formula (I), $R_7$ being absent means a hydrogen atom is present in position $R_7$. In other suitable compounds of formula (I), and when $R_7$ is absent, $R_4$ may be in the position of $R_7$, as shown below.

Thus, in some suitable compounds of formula (I) wherein $R_7$ is absent and when n is 1, $R_4$ is attached to the phenyl ring in the following position:

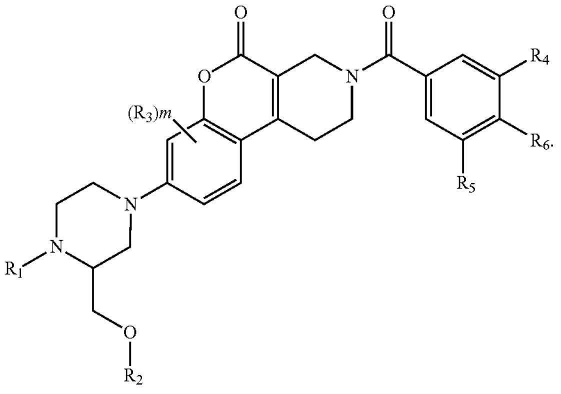

In some suitable compounds of formula (I) wherein $R_7$ is absent and when n is 1, $R_4$ is attached to the phenyl ring in the following position:

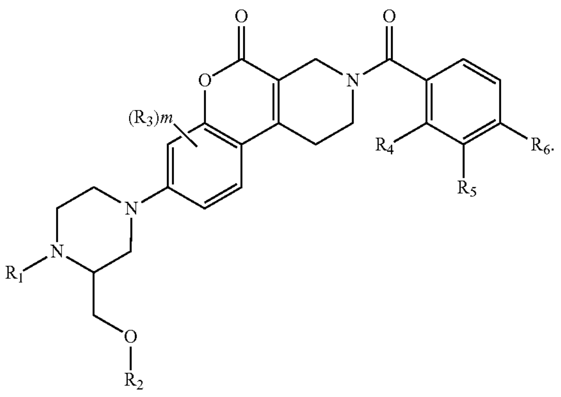

In some suitable compounds of formula (I) wherein $R_7$ is absent and when n is 1, $R_4$ is attached to the phenyl ring in the following position:

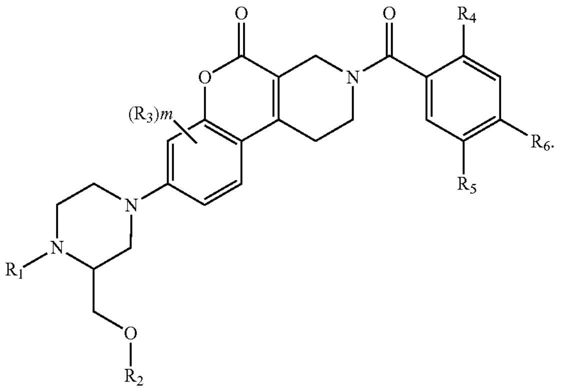

In some suitable compounds of formula (I), and when n is 2, $R_4$ is attached to the phenyl ring in the following position, wherein both $R_4$ are identical:

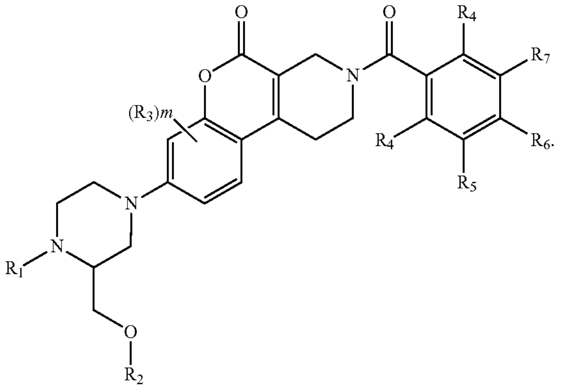

In some suitable compounds of formula (I), and when n is 2, $R_4$ is attached to the phenyl ring in the following position, wherein both $R_4$ are non-identical:

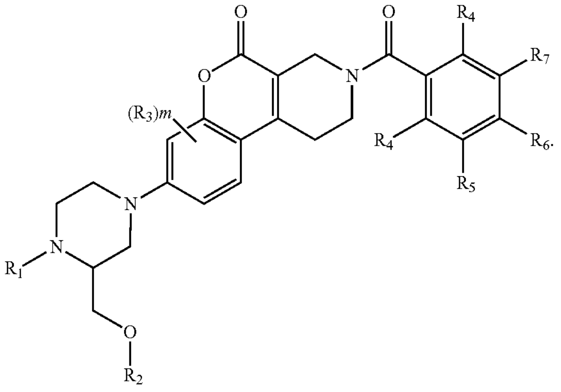

Option (a)

In some compounds of formula (I), $R_6$ is

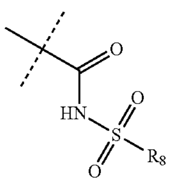

and $R_7$ is absent.

In such compounds, $R_5$ is selected from the group consisting of H, halo, $C_{1-3}$ alkyl, $C_{1-3}$ haloalkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{5b}$ is selected from the group consisting of H and $C_{1-3}$ alkyl; and $R_{5c}$ is selected from the group consisting of $C_{1-3}$ alkyl and $C_{3-6}$ cycloalkyl.

In some such compounds, $R_5$ is selected from the group consisting of H, halo, $C_{1-3}$ alkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{5b}$ is selected from the group consisting of H and $C_{1-3}$ alkyl; and $R_{5c}$ is selected from the group consisting of $C_{1-3}$ alkyl and $C_{3-6}$ cycloalkyl.

In some such compounds, $R_5$ is selected from the group consisting of H, halo, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{5b}$ is selected from the group consisting of H and $C_{1-3}$ alkyl; and $R_{5c}$ is selected from the group consisting of $C_{1-3}$ alkyl and $C_{3-6}$ cycloalkyl.

In some suitable compounds of formula (I), $R_5$ is H. In other suitable compounds of formula (I), $R_5$ is halo, such as chloro. In other suitable compounds of formula (I), $R_5$ is $C_{1-3}$alkyl, such as methyl or ethyl. In other suitable compounds of formula (I), $R_5$ is $C_{1-3}$ alkoxy, such as methoxy or ethoxy, e.g. methoxy. In other suitable compounds of formula (I), $R_5$ is $C_{1-3}$ haloalkoxy. In other suitable compounds of formula (I), $R_5$ is $SC_{1-3}$ alkyl. In other suitable compounds of formula (I), $R_5$ is $SC_{1-3}$ haloalkyl. In other suitable compounds of formula (I), $R_5$ is $OC_{3-10}$ cycloalkyl, such as cyclobutyloxy, cyclopentyloxy, cyclohexyloxy, bicyclo [3.1.0]hexyloxy and 2-adamantanyloxy. In other suitable compounds of formula (I), $R_5$ is 4-7 membered heterocycloalkyl, such as pyrrolidinyl, piperidinyl, 3-azabicyclo [3.1.0]hexyl, 2-azabicyclo(2.2.1)heptyl and 7-azanorbornanyl. In other suitable compounds of formula (I), $R_5$ is $NR_{5b}R_{5c}$.

Most suitably, $R_5$ is $C_{1-3}$ alkoxy, such as methoxy or ethoxy, e.g. methoxy, or $OC_{3-10}$ cycloalkyl, such as cyclobutyloxy or cyclopentyloxy.

In some compounds of formula (I), $R_5$ is a 4-7 membered heterocycloalkyl group wherein the group is attached via a nitrogen atom, i.e.

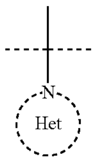

wherein

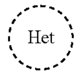

is the 4-7 membered heterocycloalkyl group and ------ indicates the join to the remainder of the compound of formula (I).

For example, and when the 4-7 membered heterocycloalkyl group is pyrrolidinyl, the pyrrolidinyl group is attached via the nitrogen atom, and is referred to as 1-pyrrolidinyl:

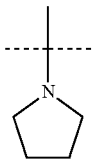

1-pyrrolidinyl wherein ------ indicates the join to the remainder of the compound of formula (I).

In some such suitable compounds of formula (I), and when $R_5$ is $OC_{3-10}$ cycloalkyl, the $OC_{3-10}$ cycloalkyl is unsubstituted. In other suitable compounds of formula (I), and when $R_5$ is 4-7 membered heterocycloalkyl, the 4-7 membered heterocycloalkyl is unsubstituted. In other suitable compounds of formula (I), and when $R_5$ is $OC_{3-10}$ cycloalkyl, the $OC_{3-10}$ cycloalkyl is substituted by one or more (such as one, two or three, e.g. one) $R_{5a}$. In other suitable compounds of formula (I), and when $R_5$ is 4-7 membered heterocycloalkyl, the 4-7 membered heterocycloalkyl is substituted by one or more (such as one, two or three, e.g. one) $R_{5a}$.

In some such suitable compounds of formula (I), $R_{5a}$ is halo, such as fluoro. In other suitable compounds of formula (I), $R_{5a}$ is $C_{1-3}$ alkyl, such as methyl.

In some such suitable compounds of formula (I), $R_5$ is substituted by one $R_{5a}$ group, such as methyl. In other suitable compounds of formula (I), $R_5$ is substituted by two $R_{5a}$ groups, such as methyl and fluoro. In other suitable compounds of formula (I), $R_5$ is substituted by three $R_{5a}$ groups. In other suitable compounds of formula (I), $R_5$ is substituted by two $R_{5a}$ groups which are attached to the same carbon atom and join to form a $C_{3-6}$ cycloalkyl ring, such as a $C_3$ cycloalkyl ring.

In some such suitable compounds of formula (I), $R_{5b}$ is H. In other suitable compounds of formula (I), $R_{5b}$ is $C_{1-3}$ alkyl, such as methyl.

In some such suitable compounds of formula (I), $R_{5c}$ is $C_{1-3}$ alkyl, such as methyl or isopropyl. In other suitable compounds of formula (I), $R_{5c}$ is $C_{3-6}$ cycloalkyl, such as cyclopropyl.

Most suitably, $R_{5b}$ and $R_{5c}$ are both methyl. Most suitably, $R_5$ is $NR_{5b}R_{5c}$ and $R_{5b}$ and $R_{5c}$ are both methyl.

Option (b)

In some alternative compounds of formula (I), $R_7$ is

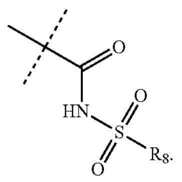

Option (b)(i)

In some such compounds, $R_6$ is H and $R_5$ is selected from the group consisting of H, halo, $C_{1-3}$ alkyl, $C_{1-3}$ haloalkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{5b}$ is selected from the group consisting of H and $C_{1-3}$ alkyl; and $R_{5c}$ is selected from the group consisting of $C_{1-3}$ alkyl and $C_{3-6}$ cycloalkyl.

In some such compounds, $R_6$ is H and $R_5$ is selected from the group consisting of H, halo, $C_{1-3}$ alkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{5b}$ is selected from the group consisting of H and $C_{1-3}$ alkyl; and $R_{5c}$ is selected from the group consisting of $C_{1-3}$ alkyl and $C_{3-6}$ cycloalkyl.

For example, $R_6$ is H and $R_5$ is selected from the group consisting of H, halo, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring, $R_{5b}$ is selected from the group consisting of H and $C_{1-3}$ alkyl; and $R_{5c}$ is selected from the group consisting of $C_{1-3}$ alkyl and $C_{3-6}$ cycloalkyl.

In some such suitable compounds of formula (I), $R_5$ is H. In other suitable compounds of formula (I), $R_5$ is halo. In other suitable compounds of formula (I), $R_5$ is $C_{1-3}$alkyl, such as methyl or ethyl. In some other suitable compounds of formula (I), $R_5$ is $C_{1-3}$ alkoxy. In other suitable compounds of formula (I), $R_5$ is $C_{1-3}$ haloalkoxy. In some other suitable compounds of formula (I), $R_5$ is $SC_{1-3}$ alkyl. In other suitable compounds of formula (I), $R_5$ is $SC_{1-3}$ haloalkyl. In other suitable compounds of formula (I), $R_5$ is $OC_{3-10}$ cycloalkyl, such as cyclobutyloxy. In other suitable compounds of formula (I), $R_5$ is 4-7 membered heterocycloalkyl. In some other suitable compounds of formula (I), $R_5$ is $NR_{5b}R_{5c}$.

In some such compounds of formula (I), $R_5$ is a 4-7 membered heterocycloalkyl group wherein the group is attached via a nitrogen atom, i.e.

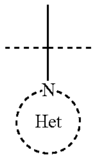

wherein

is the 4-7 membered heterocycloalkyl group and ------ indicates the join to the remainder of the compound of formula (I).

For example, and when the 4-7 membered heterocycloalkyl group is pyrrolidinyl, the pyrrolidinyl group is attached via the nitrogen atom, and is referred to as 1-pyrrolidinyl:

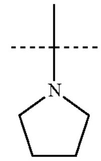

1-pyrrolidinyl wherein ------ indicates the join to the remainder of the compound of formula (I).

In some such suitable compounds of formula (I), and when $R_5$ is $OC_{3-10}$ cycloalkyl, the $OC_{3-10}$ cycloalkyl is unsubstituted. In other suitable compounds of formula (I), and when $R_5$ is 4-7 membered heterocycloalkyl, the 4-7 membered heterocycloalkyl is unsubstituted. In other suitable compounds of formula (I), and when $R_5$ is $OC_{3-10}$ cycloalkyl, the $OC_{3-10}$ cycloalkyl is substituted by one or more (such as one, two or three, e.g. one) $R_{5a}$. In other suitable compounds of formula (I), and when $R_5$ is 4-7 membered heterocycloalkyl, the 4-7 membered heterocycloalkyl is substituted by one or more (such as one, two or three, e.g. one) $R_{5a}$.

In some such suitable compounds of formula (I), $R_{5a}$ is halo. In other suitable compounds of formula (I), $R_{5a}$ is $C_{1-3}$ alkyl.

In some suitable compounds of formula (I), $R_5$ is substituted by two $R_{5a}$ groups which are attached to the same carbon atom and join to form a $C_{3-6}$ cycloalkyl or 4-7 membered heterocycloalkyl ring.

In some such suitable compounds of formula (I), $R_{5b}$ is H. In other suitable compounds of formula (I), $R_{5b}$ is $C_{1-3}$ alkyl.

In some such suitable compounds of formula (I), $R_{5c}$ is $C_{1-3}$ alkyl. In other suitable compounds of formula (I), $R_{5c}$ is $C_{3-6}$ cycloalkyl.

Option (b)(ii)

Alternatively, in some such compounds, $R_5$ is H and $R_6$ is selected from the group consisting of H, halo, $C_{1-3}$ alkyl, $C_{1-3}$ haloalkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{6b}R_{6c}$ and 4-7 membered heterocycloalkyl, wherein the $OC_{3-10}$ cycloalkyl and 4-7 membered heterocycloalkyl are optionally substituted by one or more $R_{6a}$;

wherein:

$R_{6a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{6b}$ is selected from the group consisting of H and $C_{1-3}$ alkyl; and $R_{6c}$ is selected from the group consisting of $C_{1-3}$ alkyl and $C_{3-6}$ cycloalkyl.

In some such compounds, $R_5$ is H and $R_6$ is selected from the group consisting of H, halo, $C_{1-3}$ alkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{6b}R_{6c}$ and 4-7 membered heterocycloalkyl, wherein the $OC_{3-10}$ cycloalkyl and 4-7 membered heterocycloalkyl are optionally substituted by one or more $R_{6a}$;

wherein:

$R_{6a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{6b}$ is selected from the group consisting of H and $C_{1-3}$ alkyl; and $R_{6c}$ is selected from the group consisting of $C_{1-3}$ alkyl and $C_{3-6}$ cycloalkyl.

For example, $R_5$ is H and $R_6$ is selected from the group consisting of H, halo, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{6b}R_{6c}$ and 4-7 membered heterocycloalkyl, wherein the $C_{3-10}$ cycloalkyl and 4-7 membered heterocycloalkyl are optionally substituted by one or more $R_{6a}$;

wherein:

$R_{6a}$ is selected from the group consisting of halo and $C_{1-3}$ alkyl, or two $R_{6a}$ groups which are attached to the same carbon atom join to form a $C_{3-6}$ cycloalkyl or 4-7 membered heterocycloalkyl ring, $R_{6b}$ is selected from the group consisting of H and $C_{1-3}$ alkyl; and $R_{6c}$ is selected from the group consisting of $C_{1-3}$ alkyl and $C_{3-6}$ cycloalkyl.

In some suitable compounds of formula (I), $R_6$ is H. In other suitable compounds of formula (I), $R_6$ is halo. In other suitable compounds of formula (I), $R_6$ is $C_{1-3}$alkyl, such as methyl or ethyl. In other suitable compounds of formula (I), $R_6$ is $C_{1-3}$ alkoxy. In other suitable compounds of formula (I), $R_6$ is $C_{1-3}$ haloalkoxy. In other suitable compounds of formula (I), $R_6$ is $SC_{1-3}$ alkyl. In other suitable compounds of formula (I), $R_6$ is $SC_{1-3}$ haloalkyl. In other suitable compounds of formula (I), $R_6$ is $OC_{3-10}$ cycloalkyl, such as cyclobutyloxy. In other suitable compounds of formula (I), $R_6$ is 4-7 membered heterocycloalkyl. In other suitable compounds of formula (I), $R_6$ is $NR_{6b}R_{6c}$.

In some compounds of formula (I), $R_6$ is a 4-7 membered heterocycloalkyl group wherein the group is attached via a nitrogen atom, i.e.

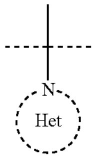

wherein

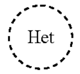

is the 4-7 membered heterocycloalkyl group and ------ indicates the join to the remainder of the compound of formula (I).

For example, and when the 4-7 membered heterocycloalkyl group is pyrrolidinyl, the pyrrolidinyl group is attached via the nitrogen atom, and is referred to as 1-pyrrolidinyl:

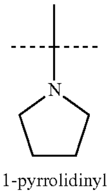

1-pyrrolidinyl wherein ------ indicates the join to the remainder of the compound of formula (I).

In some suitable compounds of formula (I), and when $R_6$ is $OC_{3-10}$ cycloalkyl, the $OC_{3-10}$ cycloalkyl is unsubstituted. In other suitable compounds of formula (I), and when $R_6$ is 4-7 membered heterocycloalkyl, the 4-7 membered heterocycloalkyl is unsubstituted. In other suitable compounds of formula (I), and when $R_6$ is $OC_{3-10}$ cycloalkyl, the $OC_{3-10}$ cycloalkyl is substituted by one or more (such as one, two or three, e.g. one) $R_{6a}$. In other suitable compounds of formula (I), and when $R_6$ is 4-7 membered heterocycloalkyl, the 4-7 membered heterocycloalkyl is substituted by one or more (such as one, two or three, e.g. one) $R_{6a}$.

In some suitable compounds of formula (I), $R_{6a}$ is halo. In other suitable compounds of formula (I), $R_{6a}$ is $C_{1-3}$ alkyl.

In some suitable compounds of formula (I), $R_6$ is substituted by two $R_{6a}$ groups which are attached to the same carbon atom and join to form a $C_{3-6}$ cycloalkyl or 4-7 membered heterocycloalkyl ring.

In some suitable compounds of formula (I), $R_{6b}$ is H. In other suitable compounds of formula (I), $R_{6b}$ is $C_{1-3}$ alkyl.

In some suitable compounds of formula (I), $R_{6c}$ is $C_{1-3}$ alkyl. In other suitable compounds of formula (I), $R_{6c}$ is $C_{3-6}$ cycloalkyl.

Option (b)(iii)

Alternatively, in some such compounds $R_5$ and $R_6$ join to form a 4-8 membered heterocyclic ring, such as a 5,8-dioxaspiro[3.4]octanyl ring.

$R_8$ Group

In some suitable compounds of formula (I), $R_8$ is $C_{3-6}$ cycloalkyl, such as cyclopropyl. In other suitable compounds of formula (I), $R_8$ is 4-10 (e.g. 4-8) membered heterocycloalkyl, such as pyrrolidinyl (e.g. pyrrolidin-1-yl), piperidinyl (e.g. piperidin-1-yl), 7-azanorbornanyl, 3-azabicyclo[3.1.0]hexyl (e.g. 3-azabicyclo[3.1.0]hexan-3-yl), 6-azaspiro[2.5]octyl (e.g. 6-azaspiro[2.5]octan-6-yl) and 3-oxa-6-azabicyclo[3.2.1]octyl (e.g. 3-oxa-8-azabicyclo[3.2.1]octan-8-yl), suitably pyrrolidinyl (e.g. pyrrolidin-1-yl). Further examples include 7-azabicyclo[2.2.1]heptan-7-yl, (3aR,6aS)-hexahydrocyclopenta[c]pyrrol-2(1H)-yl, octahydro-2H-isoindol-2-yl, 2-azaspiro[3.3]heptan-2-yl, (1 S,4S)-2-oxa-5-azabicyclo[2.2.1]heptan-5-yl), 2-azabicyclo[2.2.1]heptan-2-yl) and 8-azabicyclo[3.2.1]octan-8-yl.

In other suitable compounds of formula (I), $R_8$ is $NR_{8b}R_{8c}$.

In some suitable compounds of formula (I), $R_{8b}$ is H. In other suitable compounds of formula (I), $R_{8b}$ is $C_{1-3}$ alkyl, such as methyl. In other suitable compounds of formula (I) $R_{8b}$ is $C_{3-6}$ cycloalkyl, such as cyclopropyl or cyclopentyl.

In some suitable compounds of formula (I), $R_{8c}$ is H. In other suitable compounds of formula (I), $R_{8c}$ is $C_{1-3}$ alkyl, such as methyl. In other suitable compounds of formula (I) $R_{8c}$ is $C_{3-6}$ cycloalkyl such as cyclopropyl or cyclopentyl.

For example, $R_8$ is $N(C_{1-3}\ alkyl)_2$, such as $N(CH_3)_2$ or $N(CH_3)(CH(CH_3)_2)$. Alternatively, $R_8$ is $N(cyclopropyl)_2$, NMe(cyclopropyl) or NMe(cyclopentyl).

In some compounds of formula (I), $R_8$ is a 4-8 membered heterocycloalkyl group wherein the group is attached via a nitrogen atom, i.e.

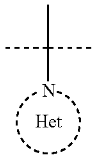

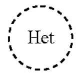

wherein is the 4-10 (e.g. 4-8) membered heterocycloalkyl group and ------ indicates the join to the remainder of the compound of formula (I).

For example, and when the 4-10 (e.g. 4-8) membered heterocycloalkyl group is pyrrolidinyl, the pyrrolidinyl group is attached via the nitrogen atom, and is referred to as 1-pyrrolidinyl:

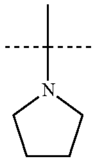

1-pyrrolidinyl wherein ------ indicates the join to the remainder of the compound of formula (I).

Examples of substituted heterocycloalkyl groups that $R_8$ may represent include ($3-CF_3$)-pyrrolidin-1-yl, ($2-CH_2OMe$)-pyrrolidin-1-yl, ($2-CH_2OCH_2Me$)-pyrrolidin-1-yl, ($4-CF_3$)-piperidin-1-yl, (3-OMe)-piperidin-1-yl, (3-OMe)-pyrrolidin-1-yl, ($2-CF_3$)-pyrrolidin-1-yl, (4-OMe)-piperidin-1-yl, (3-diF)-piperidin-1-yl, (3-diF)-pyrrolidin-1-yl, (3-diMe)-pyrrolidin-1-yl, (2,5-diMe)-pyrrolidin-1-yl, (4-F)-piperidin-1-yl, and (3-F)-pyrrolidin-1-yl.

In some suitable compounds of formula (I), and when $R_8$ is $C_{3-6}$ cycloalkyl, the $C_{3-6}$ cycloalkyl is unsubstituted. In other suitable compounds of formula (I), and when $R_8$ is 4-10 (e.g. 4-8) membered heterocycloalkyl, the 4-10 (e.g. 4-8) membered heterocycloalkyl is unsubstituted. In other suitable compounds of formula (I), and when $R_8$ is $C_{3-6}$ cycloalkyl, the $C_{3-6}$ cycloalkyl is substituted by one or more (such as one, two or three, e.g. one) $R_{8a}$. For example, $R_8$ represents 1-methyl-cyclopropyl. In other suitable compounds of formula (I), and when $R_8$ is 4-10 (e.g. 4-8) membered heterocycloalkyl, the 4-10 (e.g. 4-8)_membered heterocycloalkyl is substituted by one or more (such as one, two or three, e.g. one or two e.g. one) $R_{8a}$.

In some suitable compounds of formula (I), $R_{8a}$ is $C_{1-3}$ alkyl, such as methyl. In other suitable compounds of formula (I), $R_{8a}$ is $C_{1-3}$ alkyl substituted by OH such as $—CH_2OH$. In other suitable compounds of formula (I), $R_{8a}$ is $C_{1-2}$ alkyl substituted by $OC_{1-2}$ alkyl such as $—CH_2OMe$ or $CH_2OCH_2Me$. In other suitable compounds of formula (I), $R_{8a}$ is $C_{1-3}$ alkoxy such as OMe. In other suitable compounds of formula (I), $R_{8a}$ is halo such as F. In other suitable compounds of formula (I), $R_{8a}$ is $C_{1-3}$ haloalkyl such as $CF_3$.

In some suitable compounds of formula (I), $R_8$ is substituted by two $R_{8a}$ groups, such as two methyl groups.

In some suitable compounds of formula (I), $R_1$ and $R_2$ are methyl, m is 1 or 2, $R_3$ is selected from methyl and halo (e.g. chloro) such as is methyl, n is 1 and $R_4$ is fluoro, $R_5$ is $OC_{3-10}$ cycloalkyl, such as cyclobutyloxy, $R_6$ is

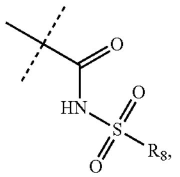

$R_7$ is absent and $R_8$ is 4-8 membered heterocycloalkyl such as 1-pyrrolidinyl. In such compounds of formula (I), suitably $R_4$ is attached ortho to $R_5$ i.e. compounds of formula (IA) defined below:

(IA)

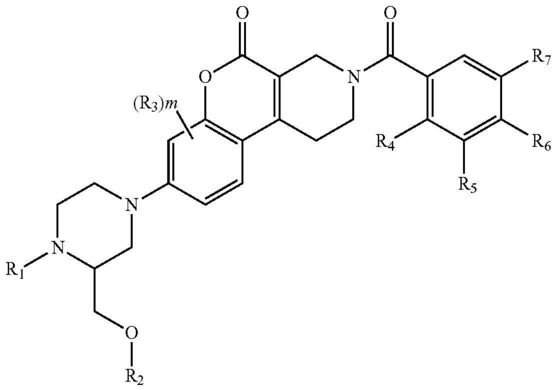

wherein $R_1$ and $R_2$ are methyl, m is 1 or 2, $R_3$ is selected from methyl and halo (e.g. chloro) (for example m is 1 or 2 and $R_3$ is methyl), $R_4$ is fluoro, $R_5$ is $OC_{3-10}$ cycloalkyl, such as cyclobutyloxy, $R_6$ is

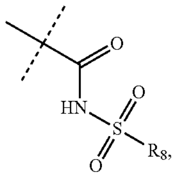

$R_7$ is absent i.e. hydrogen and $R_8$ is 4-10 (e.g. 4-8) membered heterocycloalkyl such as 1-pyrrolidinyl. When m is 2 for example one occurrence of $R_3$ is methyl and the other occurrence is methyl or halo (e.g. chloro).

In other suitable compounds of formula (I), $R_1$ and $R_2$ are methyl, m is 1 or 2, $R_3$ is methyl, n is 1 and $R_4$ is fluoro, $R_5$ is $C_{1-3}$ alkoxy, such as methoxy and ethoxy, or $NR_{5b}R_{5c}$, wherein $R_{5b}$ and $R_{5c}$ are each independently $C_{1-3}$ alkyl, such as methyl, $R_6$ is

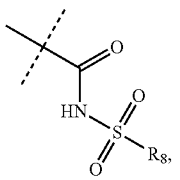

$R_7$ is absent and $R_8$ is 4-8 membered heterocycloalkyl or $C_{3-6}$ cycloalkyl which is substituted by one $R_{5a}$ wherein $R_{5a}$ is $C_{1-3}$ alkyl. In such suitable compounds of formula (I), and when $R_5$ is $C_{1-3}$ alkoxy, such as methoxy or ethoxy, suitably, $R_4$ is attached ortho to $R_5$ i.e. compounds of formula (IB) defined below:

(IB)

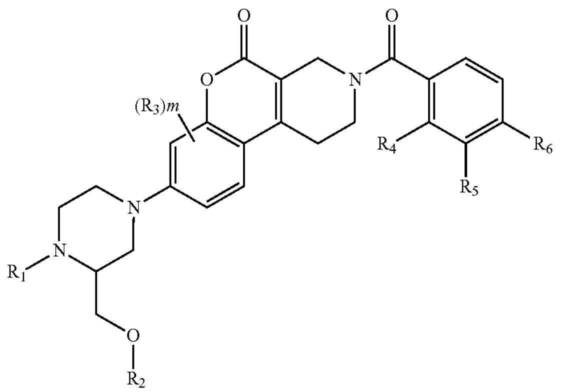

wherein $R_1$ and $R_2$ are methyl, m is 1 or 2, $R_3$ is selected from methyl and halo (e.g. chloro) (for example m is 1 or 2 and $R_3$ is methyl), n is 1, $R_4$ is fluoro, $R_5$ is $C_{1-3}$ alkoxy, such as methoxy and ethoxy, or $NR_{5b}R_{5c}$, wherein $R_{5b}$ and $R_{5c}$ are each independently $C_{1-3}$ alkyl, such as methyl, $R_6$ is —C(═O)NHSO$_2$R$_8$ and $R_8$ is 4-10 (e.g. 4-8) membered heterocycloalkyl or $C_{3-6}$ cycloalkyl which is substituted by one $R_{8a}$ wherein $R_{8a}$ is $C_{1-3}$ alkyl and $R_5$ is $C_{1-3}$ alkoxy, such as methoxy or ethoxy.

When m is 2 for example one occurrence of $R_3$ is methyl and the other occurrence is methyl or halo (e.g. chloro).

In other such suitable compounds of formula (I), and when $R_5$ is methoxy, ethoxy, cyclopropyloxy or $NR_{5b}R_{5c}$ (for example, $R_5$ is $NR_{5b}R_{5c}$ (such as $NMe_2$)), suitably, $R_4$ is attached para to $R_5$ i.e. compounds of formula (IC) defined below:

(IC)

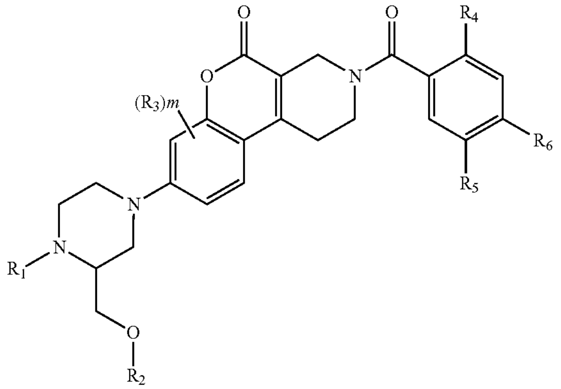

wherein $R_1$, $R_2$, $R_3$, m, $R_4$ and $R_6$ are as defined elsewhere herein and $R_5$ is methoxy, ethoxy, cyclopropyloxy or $NR_{5b}R_{5c}$ (such as $NMe_2$).

In compounds of formula (IC) suitably:

$R_1$ is methyl, $R_2$ is methyl, m is 1 or 2 and more suitably 2, $R_3$ is selected from methyl and halo (e.g. chloro), $R_4$ is fluoro, $R_5$ is methoxy, ethoxy, cyclopropyloxy or $NR_{5b}R_{5c}$ in which $R_{5b}$ and $R_{5c}$ are each methyl, $R_6$ is —C(═O)NHSO$_2$R$_8$ and $R_8$ is $R_8$ is 4-10 (e.g. 4-8) membered heterocycloalkyl containing one nitrogen atom and wherein the $R_8$ groups is connected to the remainder of the molecule via said nitrogen atom. When m is 2 for example one occurrence of $R_3$ is methyl and the other occurrence is methyl or halo (e.g. chloro).

Some suitable compounds of formula (IC) are compounds of formula (IC-1)

(IC-1)

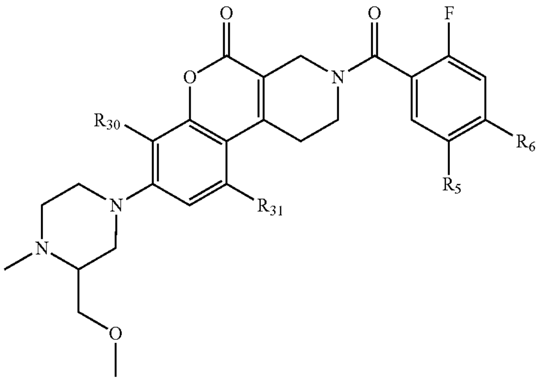

wherein $R_{50}$ is methoxy, ethoxy, cyclopropyloxy or $NMe_2$, $R_6$ is —C(═O)NHSO$_2$R$_8$ and $R_8$ is 4-10 (e.g. 4-8) membered heterocycloalkyl containing one nitrogen atom and optionally one oxygen atom and wherein the $R_8$ groups is connected to the remainder of the molecule via said nitrogen atom and wherein said 4-10 (e.g. 4-8) membered heterocycloalkyl may optionally be substituted by one or two $R_{8a}$ groups and wherein $R_{30}$ and $R_{31}$ are independently selected from methyl and halo (e.g. chloro) and for example $R_{30}$ is methyl and $R_{31}$ is methyl or halo (e.g. chloro). Suitably in compounds of formula (IC-1), $R_8$ is 4-10 (e.g. 4-8) membered heterocycloalkyl containing one nitrogen atom and no other heteroatoms. For example, in compounds of formula (IC-1), the 4-10 (e.g. 4-8) membered heterocycloalkyl group is not substituted by an $R_{5a}$ group. In one embodiment $R_{50}$ is methoxy. In one embodiment $R_{50}$ is ethoxy. In one embodiment $R_{50}$ is cyclopropyloxy. In one embodiment $R_{50}$ is $NMe_2$.

The invention also provides compounds of formula (ID):

(ID)

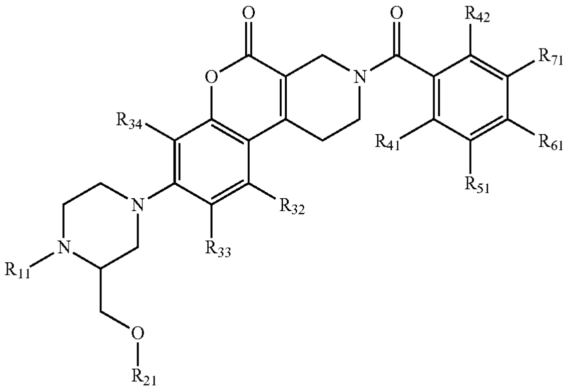

wherein:

$R_{11}$ is $C_{1-4}$ alkyl or $C_{3-5}$ cycloalkyl;

$R_{21}$ is $C_{1-4}$ alkyl; or $R_{11}$ and $R_{21}$ join to form a 5-7 membered heterocycloalkyl;

$R_{32}$, $R_{33}$ and $R_{34}$ are independently selected from the group consisting of H, $C_{1-3}$ alkyl and halo provided that at least one of $R_{32}$, $R_{33}$ and $R_{34}$ is H; $R_{41}$ and $R_{42}$ are independently selected from H, $C_{1-3}$ alkyl, halo, $C_{1-3}$ haloalkyl, $C_{1-3}$ alkoxy, $C_{1-3}$ haloalkoxy, $NR_{4a}R_{4b}$ and 4-7 membered heterocycloalkyl;

wherein:

$R_{4a}$ is selected from the group consisting of H and $C_{1-3}$ alkyl;

$R_{4b}$ is selected from the group consisting of H and $C_{1-3}$ alkyl;

provided that at least one of $R_{41}$, $R_{42}$ and $R_{71}$ is H;

$R_{51}$, $R_{61}$ and $R_{71}$ are independently selected from the group consisting of —C(=O)NHSO$_2$R$_8$, H, halo, $C_{1-3}$ alkyl, $C_{1-3}$ haloalkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{5b}$ is selected from the group consisting of H and $C_{1-3}$ alkyl; and $R_{5c}$ is selected from the group consisting of $C_{1-3}$ alkyl and $C_{3-6}$ cycloalkyl;

or $R_{51}$ and $R_{61}$ join to form a 4-8 membered heterocyclic ring;

provided that one and only one of $R_{51}$, $R_{61}$ and $R_{71}$ is —C(=O)NHSO$_2$R$_8$, and $R_8$ is selected from the group consisting of $C_{3-6}$ cycloalkyl, $NR_{8b}R_{8c}$ and 4-8 membered heterocycloalkyl, wherein the $C_{3-6}$ cycloalkyl and 4-8 membered heterocycloalkyl are optionally substituted by one or more $R_{8a}$, wherein:

$R_{8a}$ is selected from the group consisting of $C_{1-3}$ alkyl, halo and $C_{1-3}$ haloalkyl;

$R_{8b}$ is selected from the group consisting of H, $C_{1-3}$ alkyl and $C_{3-6}$ cycloalkyl;

$R_{8c}$ is selected from the group consisting of H, $C_{1-3}$ alkyl and $C_{3-6}$ cycloalkyl;

or a pharmaceutically acceptable salt and/or solvate thereof.

Compounds of formula (ID) are of use according to the invention as provided for compounds of formula (I).

In compounds of formula (ID), for example, $R_{61}$ is —C(=O)NHSO$_2$R$_8$.

In compounds of formula (ID), for example, $R_{71}$ is selected from the group consisting of H, halo, $C_{1-3}$ alkyl, $C_{1-3}$ haloalkyl, $C_{1-3}$ alkoxy, $C_{1-3}$ haloalkoxy, $NR_{5b}R_{5c}$ and 4-7 membered heterocycloalkyl.

In compounds of formula (ID), for example, $R_{41}$, $R_{42}$ and $R_{71}$ are independently selected from H, and halo (such as F or Cl). In an embodiment $R_{41}$ is H, $R_{42}$ is H and $R_{71}$ is H. In an embodiment $R_{41}$ is halo e.g. Cl or F, $R_{42}$ is H and $R_{71}$ is H. In an embodiment $R_{41}$ is H, $R_{42}$ is halo e.g. Cl or F (especially F) and $R_{71}$ is H. In an embodiment $R_{41}$ is H, $R_{42}$ is H and $R_{71}$ is halo e.g. Cl or F. In compounds of formula (ID), suitably $R_{33}$ is H In compounds of formula (ID), for example, $R_{32}$ and $R_{34}$ are independently selected from methyl and halo (e.g. chloro) and, for example, $R_{34}$ is methyl and $R_{32}$ is methyl or halo (e.g. chloro).

In compounds of formula (I), (IA), (IB), (IC) and (IC-1), and correspondingly for compounds of formula (ID), suitably the stereochemistry around the piperazine ring is as follows:

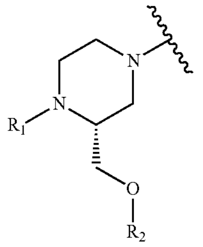

Suitably, the compound of formula (I) is selected from the group consisting of any one of Examples 1 to 180, or a pharmaceutically acceptable salt and/or solvate thereof.

Suitably, the compound of formula (I) is selected from the group consisting of any one of Examples 1 to 270 e.g. 181-270, or a pharmaceutically acceptable salt and/or solvate thereof.

Suitably, the compound of formula (I) is selected from the group consisting of any one of Examples 1 to 331 e.g. 271-331, or a pharmaceutically acceptable salt and/or solvate thereof.

Suitably, the compound of formula (I) is selected from the group consisting of:

(R)-2-(cyclopentyloxy)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-3-fluoro-2-isopropoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-(cyclopentyloxy)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

(R)-2-cyclobutoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(cyclopentyloxy)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

N-((3-azabicyclo[3.1.0]hexan-3-yl)sulfonyl)-3-fluoro-2-methoxy-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide; and 2-(((1R,3s,5S)-bicyclo[3.1.0]hexan-3-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

or a pharmaceutically acceptable salt and/or solvate thereof.

Suitably, the compound of formula (I) is selected from the group consisting of:

(R)-2-(cyclopentyloxy)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-3-fluoro-2-isopropoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-(cyclopentyloxy)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

(R)-2-cyclobutoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(cyclopentyloxy)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

N-((3-azabicyclo[3.1.0]hexan-3-yl)sulfonyl)-3-fluoro-2-methoxy-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

2-(((1R,3s,5S)-bicyclo[3.1.0]hexan-3-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide; and (R)-2-cyclopropoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

or a pharmaceutically acceptable salt and/or solvate thereof.

Suitably, the compound of formula (I) is selected from the group consisting of:

(R)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)-N-(pyrrolidin-1-ylsulfonyl)benzamide;

(R)-2-(dimethylamino)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)-2-(dimethylamino)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-5-chloro-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-5-chloro-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)-N-(pyrrolidin-1-ylsulfonyl)benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-(pyrrolidin-1-yl)benzamide;

2-(3-azabicyclo[3.1.0]hexan-3-yl)-6-chloro-N—(N,N-dimethylsulfamoyl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide; and 2-(3-azabicyclo[3.1.0]hexan-3-yl)-6-chloro-N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

or a pharmaceutically acceptable salt and/or solvate thereof.

Suitably, the compound of formula (I) is selected from the group consisting of:

(R)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)-N-(pyrrolidin-1-ylsulfonyl)benzamide;

(R)-2-(dimethylamino)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)-2-(dimethylamino)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-5-chloro-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-5-chloro-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)-N-(pyrrolidin-1-ylsulfonyl)benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-(pyrrolidin-1-yl)benzamide;

2-(3-azabicyclo[3.1.0]hexan-3-yl)-6-chloro-N—(N,N-dimethylsulfamoyl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

2-(3-azabicyclo[3.1.0]hexan-3-yl)-6-chloro-N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-fluoro-2-(methoxy-$d_3$)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-ethoxy-4-(10-ethyl-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-N-(pyrrolidin-1-ylsulfonyl)benzamide;

(R)-2-(dimethylamino)-4-(10-ethyl-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-N-(pyrrolidin-1-ylsulfonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(pyrrolidin-1-ylsulfonyl)benzamide;

(R)—N—(N-cyclopropyl-N-methylsulfamoyl)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluoro-N-(pyrrolidin-1-ylsulfonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-N—(N,N-dimethylsulfamoyl)-5-fluorobenzamide; and (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-methoxy-N-(pyrrolidin-1-ylsulfonyl)benzamide;

or a pharmaceutically acceptable salt and/or solvate of any one thereof.

Suitably, the compound of formula (I) is selected from the group consisting of:

(R)—N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

N-((3-oxa-8-azabicyclo[3.2.1]octan-8-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

(R)—N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-methoxybenzamide;

(R)—N-((7-azabicyclo[2.2.1]heptan-7-yl)sulfonyl)-2-cyclopropoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((2-azaspiro[3.3]heptan-2-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide or a pharmaceutically acceptable salt and/or solvate of any one thereof.

The invention provides each of the aforesaid example compounds (i.e. Examples 1-331) and pharmaceutically acceptable salts and/or solvates thereof in all stereoisomeric forms (such as, for example, in the (S) form instead of the (R) form as indicated above, referring to the stereocentre involving the attachment of the —$CH_2OR_2$ moiety to the piperazine ring) including all mixtures of stereoisomeric forms, such as racemic mixtures.

Compounds of formula (I) may be synthesised as shown in the scheme below and as shown in the Examples section. For each scheme, variables are as defined above unless otherwise stated.

Scheme 1: Synthesis of Compounds of Formula (I)

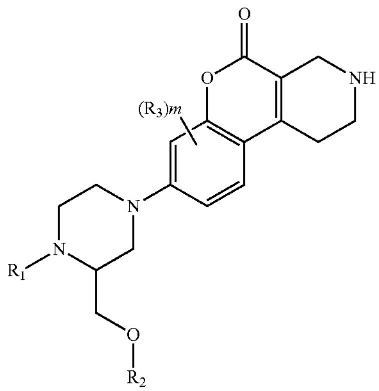

(II)

+

-continued

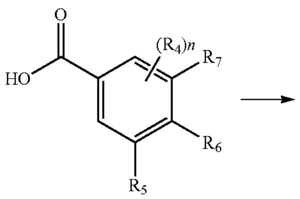

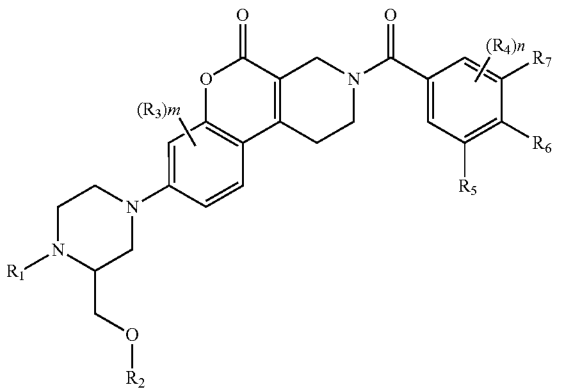

(I)

-continued

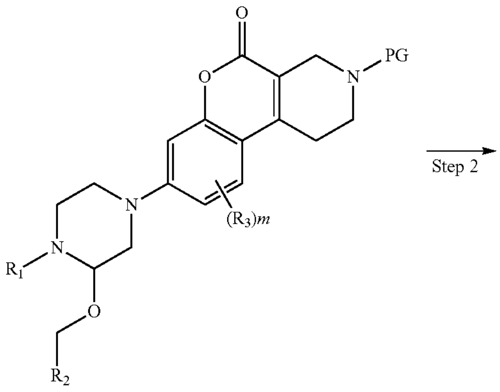

(IV)

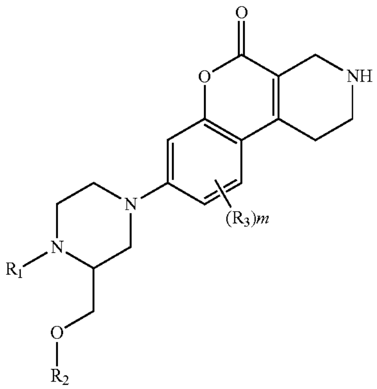

(II)

Compounds of formula (I) may be prepared by coupling amine intermediate (II) with carboxylic acid (III) using coupling agents (such as EDCI and HOBt) in the presence of an organic base (such as TEA) in a solvent (such as DCM).

Compounds of formula (II) and formula (III) may be synthesised for example as set out in the Example section below, or according to the following Schemes.

Scheme 2: Synthesis of Compounds of Formula (II)

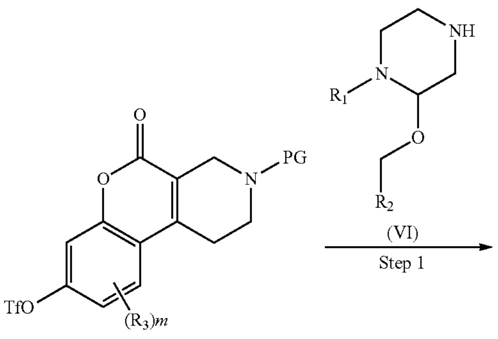

(V)

wherein $R_1$, $R_2$, $R_3$ and m are defined elsewhere herein and PG is a nitrogen protecting group. Compounds of formula (V) may be prepared according to literature (such as the Daiichi Sankyo patent application disclosed above).

Step 1: Compounds of formula (V) are reacted with compounds of formula (VI) under palladium-catalysed reaction conditions to form compounds of formula (IV).

Step 2: The nitrogen protecting group is removed under standard deprotection conditions which are known to the person skilled in the art, to give compounds of formula (II). For example, if PG is Boc, this group may be removed under acidic conditions such as HCl in 1,4-dioxane, amongst other known methods such as those described herein.

Scheme 3: Synthesis of Compounds of Formula (VI)

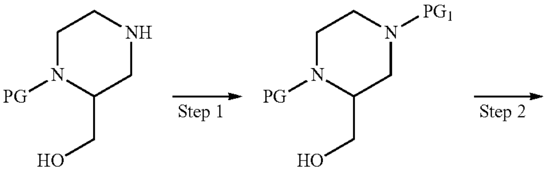

(XII)

(XI)

-continued

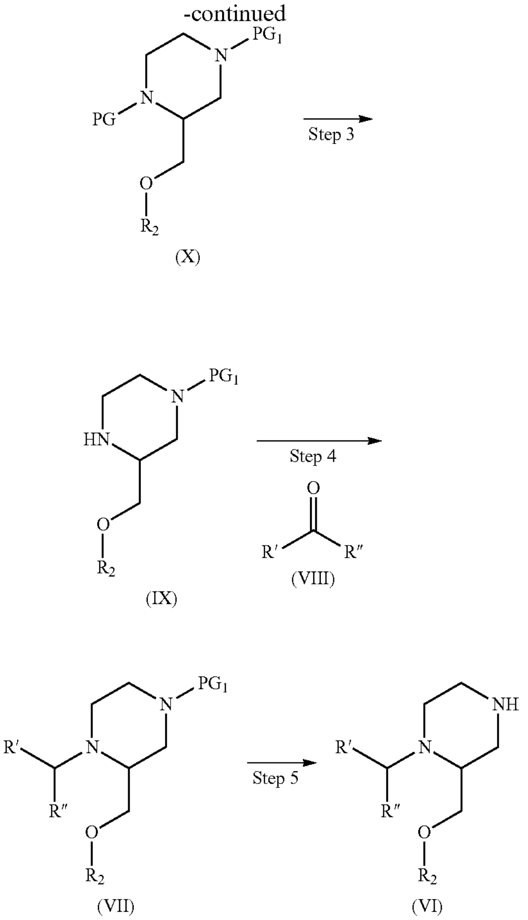

(X) (IX) (VIII) (VII) (VI)

wherein $R_2$ is defined elsewhere herein, —CH(R')(R") corresponds to $R^1$, and PG and $PG_1$ are orthogonal nitrogen protecting groups.

Step 1: Compounds of formula (XII) are reacted with $PG_1$-X (wherein X is a leaving group such as halo e.g. chloro) to give compounds of formula (XI).

Step 2: Compounds of formula (XI) are reacted with alkyl halide $R_2$—$X_1$ wherein $X_1$ is a leaving group such as bromo, iodo or tosyl, to give compounds of formula (X).

Step 3: PG is removed from compounds of formula (X) under standard deprotection conditions which are known to the person skilled in the art, to give compounds of formula (IX). For example, if PG is Boc, this group may be removed under acidic conditions such as TFA in DCM, amongst other known methods such as those described herein.

Step 4: Compounds of formula (IX) undergo a reductive amination with compounds of formula (VIII) under standard reductive amination conditions (such as $NaBH(OAc)_3$ in acetonitrile and water) to give compounds of formula (VII). Since —CH(R')(R") corresponds to $R^1$, R' and R" may independently be H or $C_{1-3}$ alkyl, or join to form a $C_{3-5}$ cycloalkyl ring.

Step 5: $PG_1$ is removed from compounds of formula (VII) under standard deprotection conditions which are known to the person skilled in the art, to give compounds of formula (VI). For example, if $PG_1$ is Cbz, this group may be removed under hydrogenation conditions such as Pd/C, $H_2$ in MeOH, amongst other known methods.

Scheme 4: Alternative Synthesis of Compounds of Formula (VI)

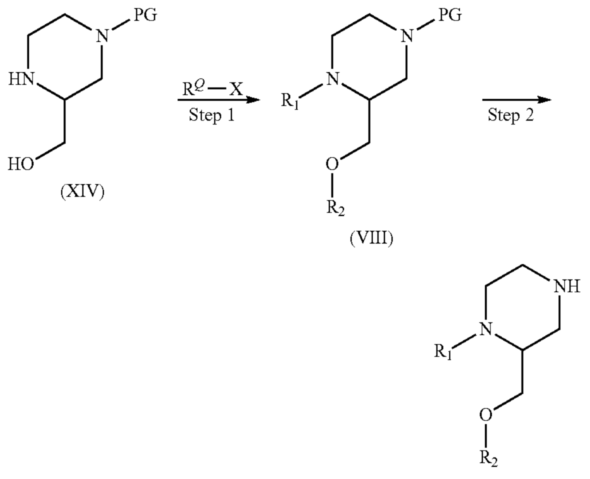

(XIV) (VIII) (VI)

wherein $R^Q$ is $R_1$ and $R_2$, PG is a nitrogen protecting group and X is a leaving group such as bromo, iodo or tosyl. This route may be used when $R_1$ is the same as $R_2$.

Step 1: Compounds of formula (XIV) are reacted with $R^Q$—X wherein $R^Q$=$R_1$=$R_2$ under basic conditions such as NaH/THF or N-methyl-2-pyrrolidone, to give compounds of formula (VIII).

Step 2: The nitrogen protecting group is removed under standard deprotection conditions which are known to the person skilled in the art, to give compounds of formula (VI). For example, if PG is Boc, this group may be removed under acidic conditions such as HCl in 1,4-dioxane or EtOAc, amongst other known methods such as those described herein.

Scheme 5: Method A for Preparing Compounds of Formula (III) when $R_5$ is OR''' and $R_7$ is Absent

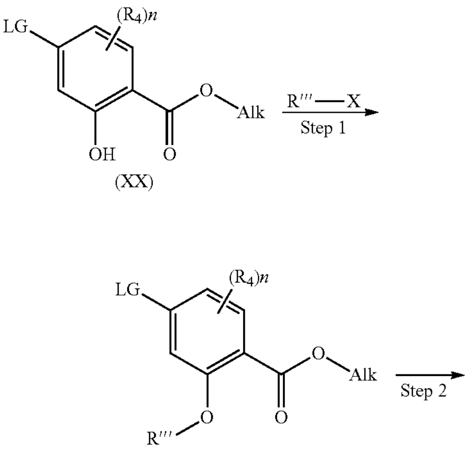

(XX) (XIX)

-continued

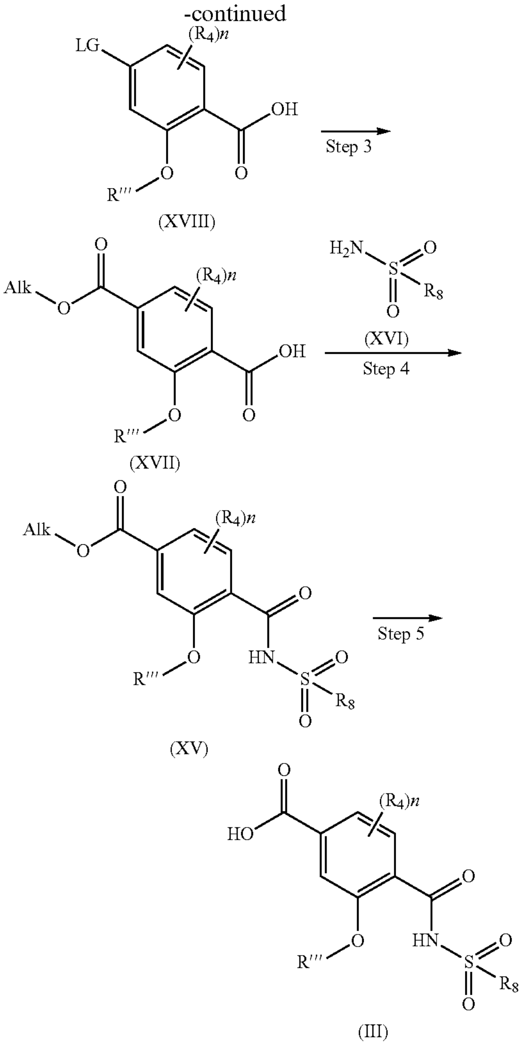

(XVIII)
(XVII)
(XV)
(III)

wherein $R_4$, n and $R_8$ are defined elsewhere herein, R''' is $C_{1-3}$ alkyl, $C_{1-3}$ haloalkyl or $C_{3-10}$ cycloalkyl, Alk is $C_{1-4}$alkyl, LG is a leaving group such as halo e.g. bromo and X is halo or OH.

Step 1: Compounds of formula (XX) are reacted with R'''—X under $S_N2$ reaction conditions (X is halo such as chloro or bromo) in the presence of a base such as $Cs_2CO_3$ in DMA or Mitsunobu reaction conditions (X is OH) in the presence of DIAD, $PPh_3$, in a solvent such as THE to give compounds of formula (XIX).

Step 2: The alkyl ester in compounds of formula (XIX) is hydrolysed under basic conditions (such as LiOH in MeOH/$H_2O$) to give carboxylic acids of formula (XVIII).

Step 3: Compounds of formula (XVIII) are carbonylated under palladium catalysed conditions to give compounds of formula (XVII) e.g. Pd catalyst, a base such as TEA, CO, an alcohol e.g. EtOH and DMA.

Step 4: Compounds of formula (XVII) are coupled with compounds of formula (XVI) under standard coupling conditions (such as EDCI, DMAP and DCM, or other conditions disclosed herein) to give compounds of formula (XV).

Step 5: Hydrolysis of the alkyl ester in compounds of formula (XV), for example under basic conditions e.g. LiOH in MeOH/$H_2O$, provides compounds of formula (III).

For Method A, it is also possible to swap Steps 3 and 4.

Scheme 6: Alternative Synthesis of Compounds of Formula (XVIII) when $R_5$ is OR'''

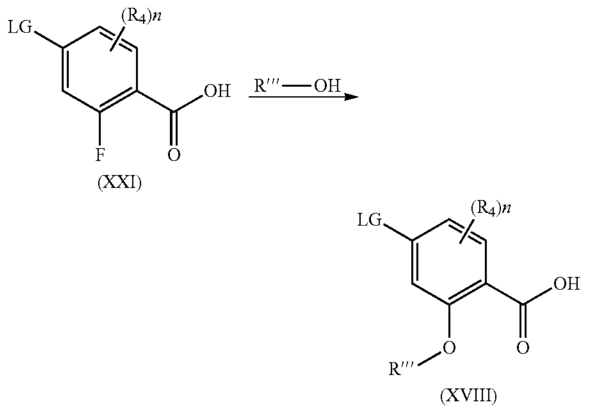

(XXI)
(XVIII)

wherein $R_4$ and n are defined elsewhere herein, R''' is $C_{1-3}$ alkyl, $C_{1-3}$ haloalkyl or $C_{3-10}$ cycloalkyl and LG is a leaving group such as halo e.g. bromo.

Compounds of formula (XXI) are reacted with R'''—OH under basic conditions (e.g. NaH in DMF) to give compounds of formula (XVIII).

Scheme 7: Method B for Preparing Compounds of Formula (III) when $R_5$ is OR''' and $R_8$ is a N-Linked Group Such as $N(C_{1-3}\ Alkyl)_2$ or a N-Linked 4-8 Membered Heterocycloalkyl and $R_7$ is Absent

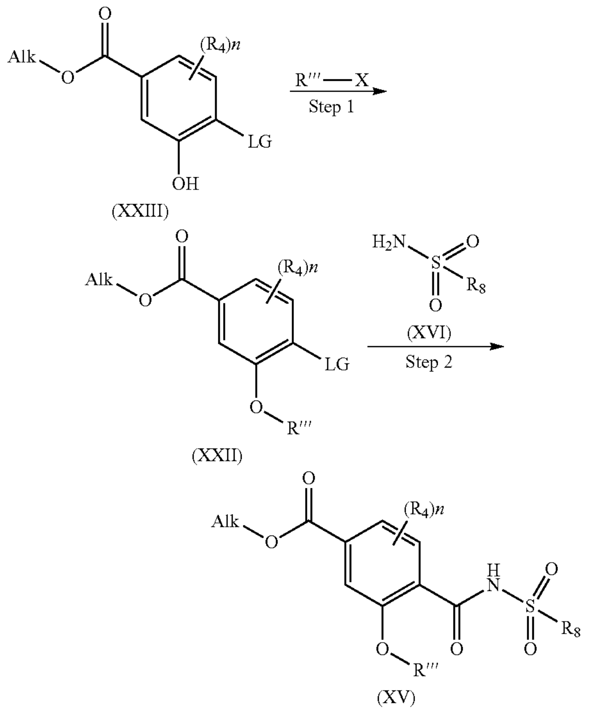

(XXIII)
(XXII)
(XV)

wherein $R_4$ and n are defined elsewhere herein, R''' is $C_{1-3}$ alkyl, $C_{1-3}$ haloalkyl or $C_{3-10}$ cycloalkyl, Alk is $C_{1-4}$alkyl, LG is a leaving group such as halo e.g. bromo and X is halo or OH.

Step 1: Compounds of formula (XXIII) are reacted with R'''—X under $S_N2$ reaction conditions (X is halo such as chloro or bromo) in the presence of a base such as $Cs_2CO_3$ in DMA or Mitsunobu reaction conditions (X is OH) in the presence of DIAD, $PPh_3$, in a solvent such as THE to give compounds of formula (XXII).

Step 2: Compounds of formula (XXII) are reacted with compounds of formula (XVI) under palladium catalysed reaction conditions (such as Herrmann's palladacycle, $[(tBu)_3PH]BF_4$, $Mo(CO)_6$, DBU and 1,4-dioxane) to give compounds of formula (XV).

Compounds of formula (XV) can be converted to compounds of formula (III) using methods disclosed herein.

It is possible to hydrolyse the alkyl ester in compounds of formula (XXII) before performing Step 2. This route can also be used to synthesis compounds of formula (III) which are precursors to compounds of formula (I) wherein $R_5$ is H, $R_6$ is —OR''' and $R_7$ is

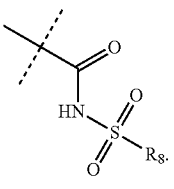

Scheme 8: Method C for Preparing Compounds of Formula (III) Wherein at Least One $R_4$ is Fluoro, $R_5$ is OR''', $R_7$ is Absent and $R_8$ is a N-Linked Group Such as $N(C_{1-3}\ Alkyl)_2$ or a N-Linked 4-8 Membered Heterocycloalkyl

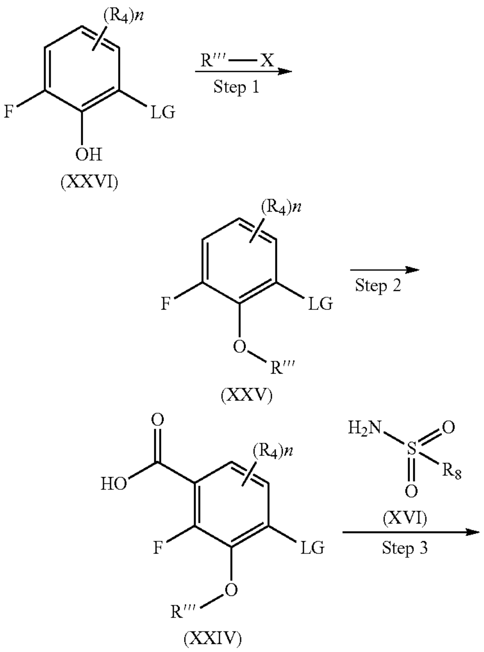

(XXVI)

(XXV)

(XXIV)

-continued

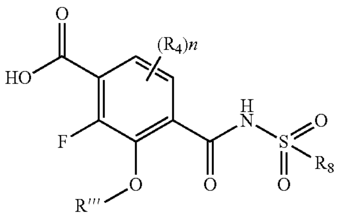

(III)

wherein $R_4$ and n are defined elsewhere herein, R''' is $C_{1-3}$ alkyl, $C_{1-3}$ haloalkyl or $C_{3-10}$ cycloalkyl, Alk is $C_{1-4}$alkyl, LG is a leaving group such as halo e.g. bromo and X is halo or OH.

Step 1: Compounds of formula (XXVI) are reacted with R'''—X under $S_N2$ reaction conditions (X is halo such as chloro or bromo) in the presence of a base such as $Cs_2CO_3$ in DMA or Mitsunobu reaction conditions (X is OH) in the presence of DIAD, $PPh_3$, in a solvent such as THE to give compounds of formula (XXV).

Step 2: Compounds of formula (XXV) can be carbonylated using a strong base such as LDA, $CO_2$ in THE to give compounds of formula (XXIV).

Step 3: Compounds of formula (XXIV) are reacted with compounds of formula (XVI) under palladium catalysed reaction conditions (such as Herrmann's palladacycle, $[(tBu)_3PH]BF_4$, $Mo(CO)_6$, DBU and 1,4-dioxane) to give compounds of formula (III).

Scheme 9: Method D for Preparing Compounds of Formula (III) when $R_5$ is an N-Linked Group Such as $NR_{5b}R_{5c}$ or an N-Linked 4-7 Membered Heterocycloalkyl and $R_7$ is Absent

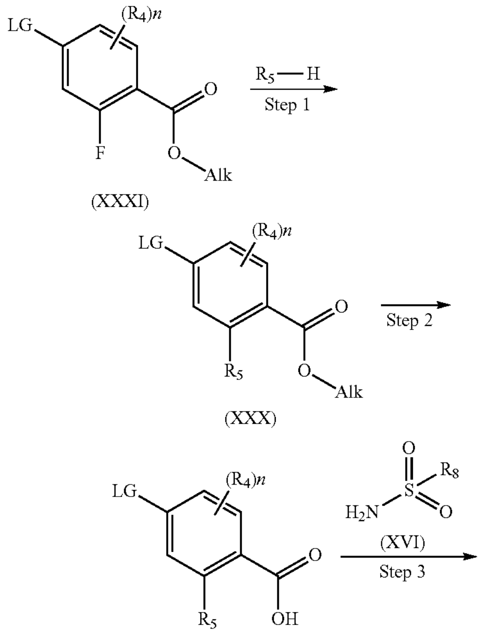

(XXXI)

(XXX)

(XXIX)

-continued

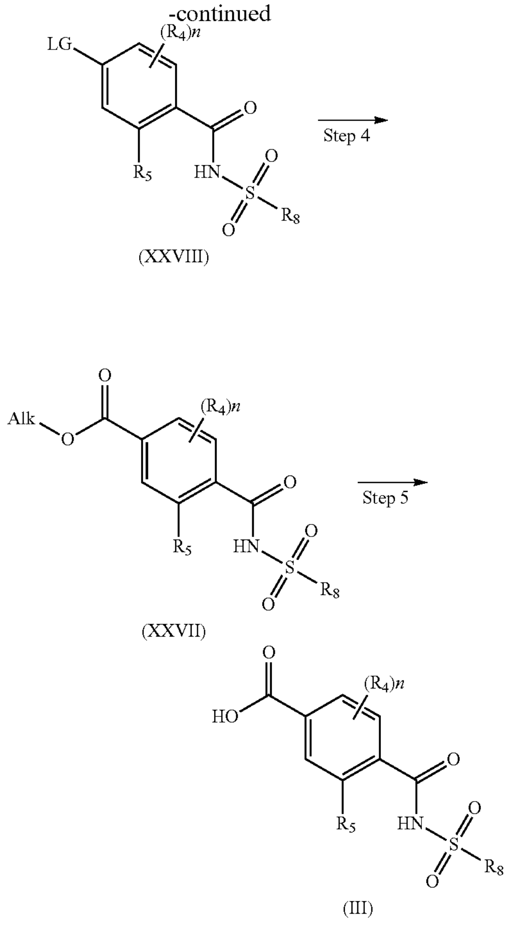

(XXVIII)

(XXVII)

(III)

wherein $R_4$, $R_8$, n are defined elsewhere herein, $R_5$ is an N-linked group such as $NR_{5b}R_{5c}$ or an N-linked 4-7 membered heterocycloalkyl, Alk is $C_{1-4}$alkyl, LG is a leaving group such as halo e.g. bromo and X is halo or OH.

Step 1: Compounds of formula (XXXI) are reacted with $R_5$—H under basic conditions such as $K_2CO_3$ and KI in DMSO, to give compounds of formula (XXX).

Step 2: The alkyl ester in compounds of formula (XXX) is hydrolysed, for example under basic conditions e.g. LiOH, MeOH/THF/$H_2O$, to give compounds of formula (XXIX).

Step 3: Compounds of formula (XXIX) are coupled with compounds of formula (XVI) under conditions such as HATU, DIPEA, NaH in DMF, or other conditions disclosed herein to give compounds of formula (XXVIII).

Step 4: Compounds of formula (XXVIII) can be carbonylated under palladium catalysed reaction conditions (such as Pd catalyst, KOAc, CO and an alcohol such as EtOH) to give compounds of formula (XXVII).

Step 5: The alkyl ester in compounds of formula (XXVIII) is hydrolysed, for example under basic conditions e.g. LiOH, MeOH/THF/$H_2O$, to give compounds of formula (III).

Scheme 10: Alternative Synthesis of (XXX) when $R_5$ is $NR_{5b}R_{5c}$ and $R_{5b}$ and $R_{5c}$ are the Same

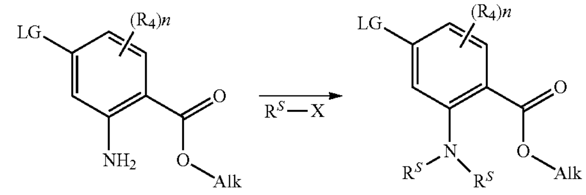

(XXXII)

(XXX)

wherein $R_4$ and n are defined elsewhere herein, $R_S$=$R_{5b}$=$R_{5c}$, Alk is $C_{1-4}$alkyl, LG is a leaving group such as halo e.g. bromo and X is halo, such as chloro or bromo.

Compounds of formula (XXXII) are reacted with $R^S$—X under basic conditions (such as NaH in DMF) to give compounds of formula (XXX).

Scheme 11: Method E for Preparing Compounds of Formula (III) when $R_5$ is an N-Linked Group Such as $NR_{5b}R_{5c}$ or an N-Linked 4-7 Membered Heterocycloalkyl and $R_7$ is Absent

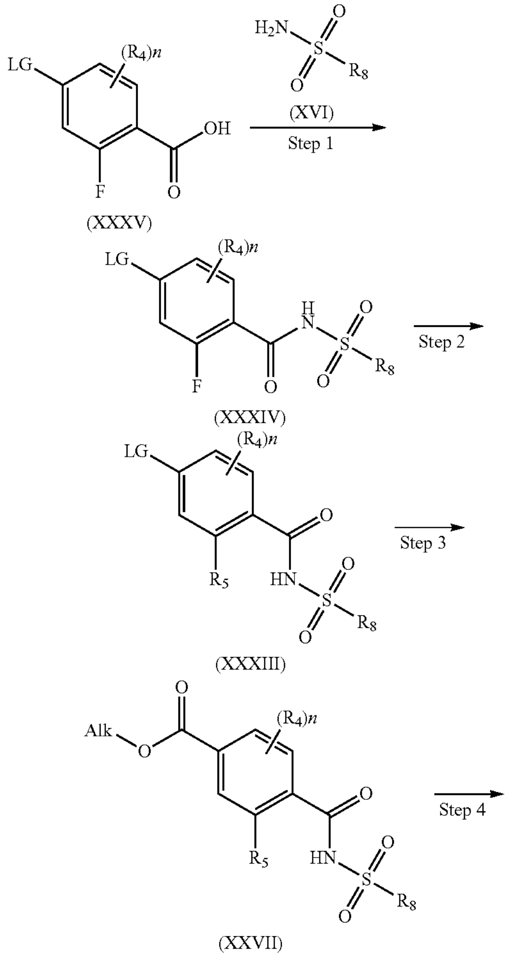

(XXXV)

(XXXIV)

(XXXIII)

(XXVII)

-continued

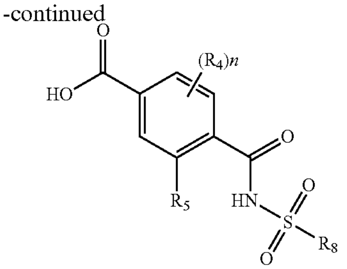

(III)

wherein $R_4$, $R_8$, n are defined elsewhere herein, $R_5$ is an N-linked group such as $NR_{5b}R_{5c}$ or an N-linked 4-7 membered heterocycloalkyl, Alk is $C_{1-4}$alkyl and LG is a leaving group such as halo e.g. bromo.

Step 1: Compounds of formula (XXXV) are coupled with compounds of formula (XVI) under coupling conditions such as HATU, DIPEA, NaH in DMF, or other conditions disclosed herein to give compounds of formula (XXXIV).

Step 2: Compounds of formula (XXXIV) are reacted with $R_5$—H under basic conditions such as $K_2CO_3$ and KI in DMSO (or other conditions disclosed herein), to give compounds of formula (XXXIII).

Step 3: Compounds of formula (XXXIII) can be carbonylated under palladium catalysed reaction conditions (such as Pd catalyst, KOAc, CO and an alcohol such as EtOH) to give compounds of formula (XXVII).

Step 4: The alkyl ester in compounds of formula (XXVII) is hydrolysed, for example under basic conditions e.g. LiOH, MeOH/THF/$H_2O$, to give compounds of formula (III).

Scheme 12: Method F for Preparing Compounds of Formula (III) when $R_5$ is an N-Linked Group Such as $NR_{5b}R_{5c}$ or an N-Linked 4-7 Membered Heterocycloalkyl and $R_7$ is Absent

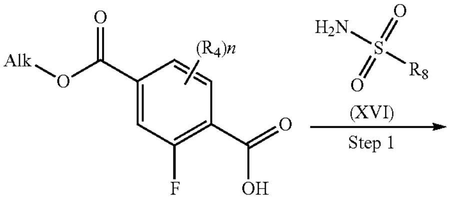

(XXXVII)

-continued

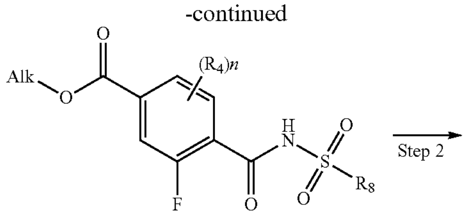

(XXXVI)

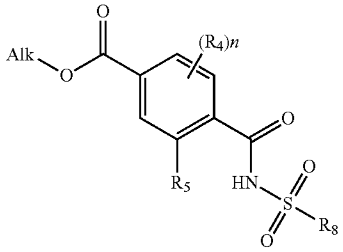

(XXVII)

wherein $R_4$, $R_8$, n are defined elsewhere herein, $R_5$ is an N-linked group such as $NR_{5b}R_{5c}$ or an N-linked 4-7 membered heterocycloalkyl and Alk is $C_{1-4}$alkyl.

Step 1: Compounds of formula (XXXVII) are coupled with compounds of formula (XVI) under coupling conditions such as HATU, DIPEA, NaH in DMF, or other conditions disclosed herein to give compounds of formula (XXXVI).

Step 2: Compounds of formula (XXXVI) are reacted with $R_5$—H under basic conditions such as DIPEA in DMSO or other conditions disclosed herein, to give compounds of formula (XXVII).

Compounds of formula (XXVII) can be converted to compounds of formula (III) as described herein.

Compounds of formula (III) and related intermediates in which $R_7$ is not absent may be prepared by adaptation of Schemes 5, 7, 8, 9, 11 and 12 which is within the knowledge of a skilled person.

Scheme 13: Alternative Synthesis of Compounds of Formula (I) in which $R_7$ is Absent

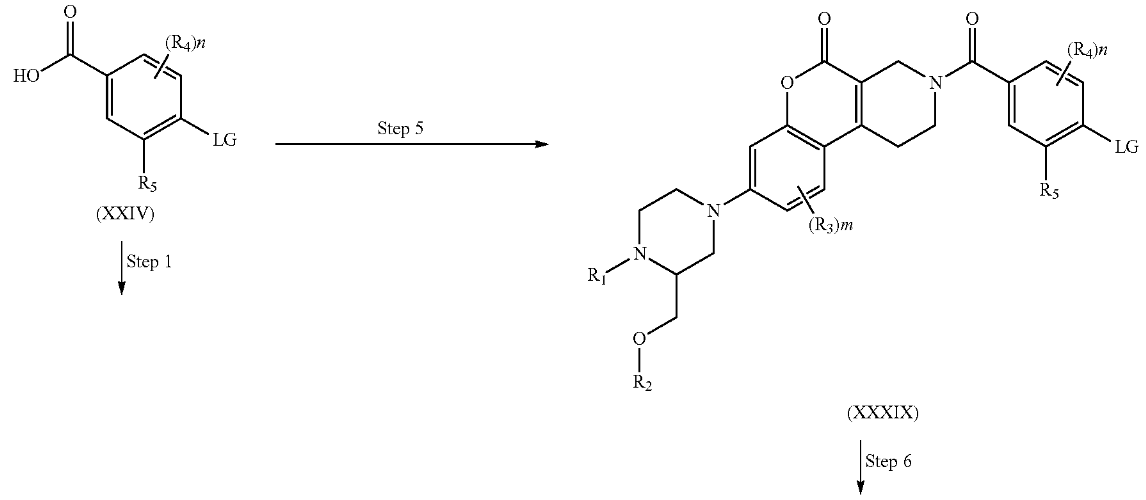

(XXIV)

(XXXIX)

-continued

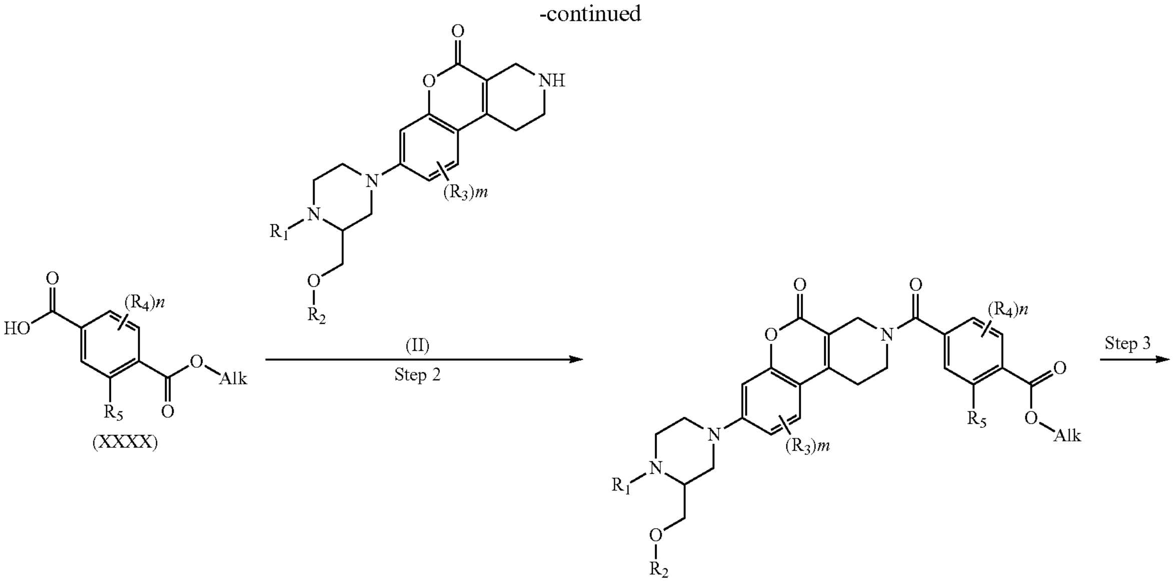

(XXXX)

(XXXIX)

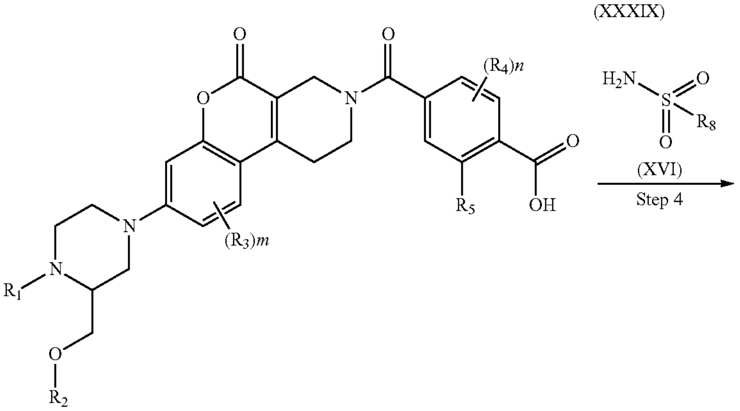

(XXXVIII)

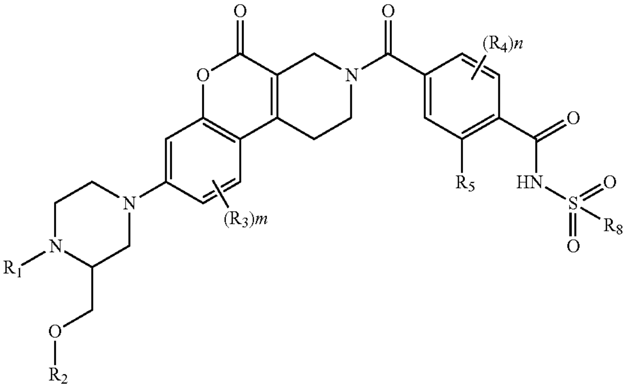

(I)

wherein $R_1$, $R_2$, $R_3$, $R_4$, $R_5$, $R_8$, n and m are defined elsewhere herein, Alk is $C_{1-4}$alkyl and LG is a leaving group such as halo e.g. bromo.

Step 1: Compounds of formula (XXIV) can be carbonylated under palladium catalysed reaction conditions (such as Pd catalyst, TEA, CO, an alcohol such as EtOH and DMA) to give compounds of formula (XXXX).

Step 2: Compounds of formula (XXXX) are coupled with compounds of formula (II) under standard coupling conditions (such as EDCI, HOBt, DIPEA and DCM, or other conditions disclosed herein) to give compounds of formula (XXXIX).

Step 3: The alkyl ester in compounds of formula (XXXIX) is hydrolysed, for example under basic conditions e.g. LiOH, MeOH/THF/$H_2O$, to give compounds of formula (XXXVIII).

Step 4: Compounds of formula (XXXVIII) are coupled with compounds of formula (XVI) under standard coupling conditions (such as EDCI, DMAP and DCM, or other conditions disclosed herein) to give compounds of formula (I).

Alternatively, Steps 5 and 6 can be used to convert compounds of formula (XXIV) to (XXXIX). Step 5 is a coupling reaction as in Steps 2 in Scheme 13, and Step 6 is a carbonylation as is Step 1 in Scheme 13.

Compounds of formula (I) in which $R_7$ is not absent may be prepared by adaptation of Scheme 13 which is within the knowledge of a skilled person.

The invention provides novel intermediates as an aspect of the invention.

Thus, the invention provides a compound of formula (II):

(II)

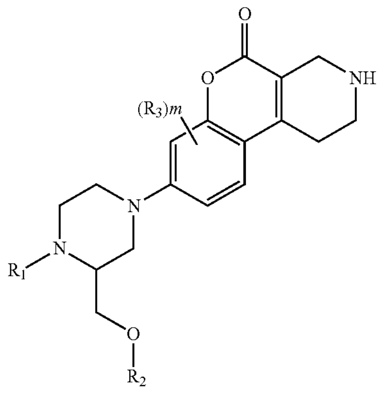

or a salt and/or solvate thereof;

wherein $R_1$, $R_2$, $R_3$ and m are as defined elsewhere herein.

The invention also provides a compound of formula (III):

or a salt and/or solvate thereof;

(III)

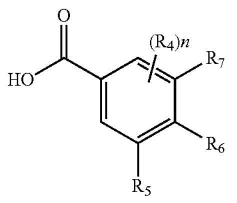

wherein $R_4$, $R_5$, $R_6$, $R_7$ and n are as defined elsewhere herein. In particular, $R_5$ may be an O-linked group such as $C_{1-3}$ alkoxy, $C_{1-3}$ haloalkoxy or $OC_{3-10}$ cycloalkyl, or an N-linked group such as $NR_{5b}R_{5c}$ or N-linked 4-7 membered heterocycloalkyl.

In some suitable compounds of formula (III), the compound of formula (III) has the following structure:

or a salt and/or solvate thereof;

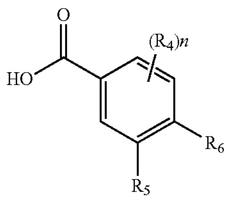

wherein $R_4$, $R_5$, $R_6$ and n are as defined elsewhere herein. In particular, $R_5$ may be an O-linked group such as $C_{1-3}$ alkoxy, $C_{1-3}$ haloalkoxy or $OC_{3-10}$ cycloalkyl, or an N-linked group such as $NR_{5b}R_{5c}$ or N-linked 4-7 membered heterocycloalkyl.

The invention also provides a compound of formula (XXXVIII):

(XXXVIII)

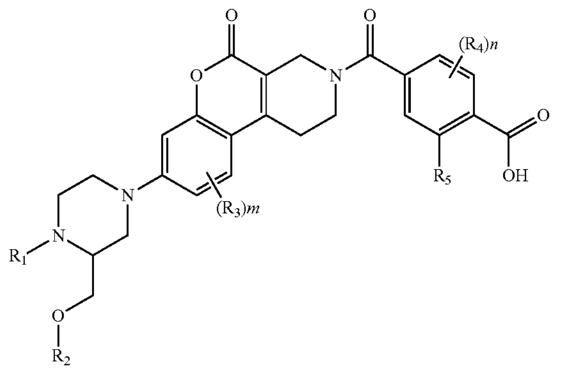

or a salt and/or solvate thereof;

wherein $R_1$, $R_2$, $R_3$, $R_4$, $R_5$, n and m are defined elsewhere herein.

The invention also provides a compound of formula (XXXIX):

(XXXIX)

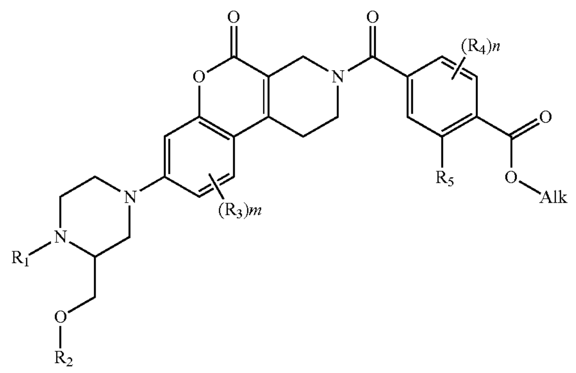

or a salt and/or solvate thereof;

wherein $R_1$, $R_2$, $R_3$, $R_4$, $R_5$, n and m are defined elsewhere herein, and Alk is $C_{1-4}$alkyl.

The invention also provides a compound of formula (XXXXI):

(XXXXI)

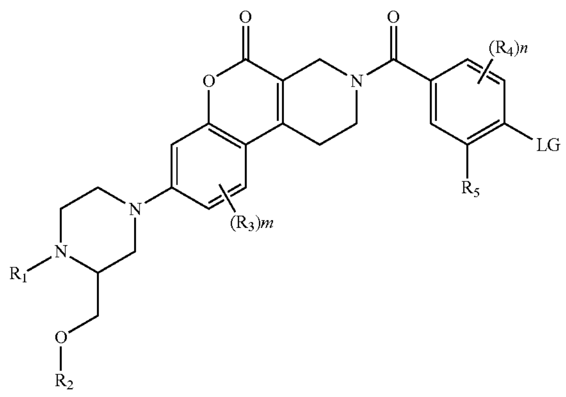

or a salt and/or solvate thereof;

wherein $R_1$, $R_2$, $R_3$, $R_4$, $R_5$, n and m are defined elsewhere herein, and LG is a leaving group such as halo e.g. bromo.

It will be appreciated that for use in therapy the salts of the compounds of formula (I) should be pharmaceutically acceptable. Suitable pharmaceutically acceptable salts will be apparent to those skilled in the art. Pharmaceutically acceptable salts include acid addition salts, suitably salts of compounds of the invention comprising a basic group such as an amino group, formed with inorganic acids, e.g., hydrochloric acid, hydrobromic acid, sulfuric acid, nitric acid or phosphoric acid. Also included are salts formed with organic acids, e.g., succinic acid, maleic acid, acetic acid, fumaric acid, citric acid, tartaric acid, benzoic acid, p-toluenesulfonic acid, methanesulfonic acid, naphthalenesulfonic acid and 1,5-naphthalenedisulfonic acid. Other salts, e.g., oxalates or formates, may be used, for example in the isolation of compounds of formula (I) and are included within the scope of this invention, as are basic addition salts such as sodium, potassium, calcium, aluminium, zinc, magnesium and other metal salts.

Pharmaceutically acceptable salts may also be formed with organic bases such as basic amines, e.g., with ammonia, meglumine, tromethamine, piperazine, arginine, choline, diethylamine, benzathine or lysine.

In one embodiment there is provided a compound of formula (I) in the form of a salt, such as a pharmaceutically acceptable salt. Alternatively, there is provided a compound of formula (I). When the compound contains a basic group as well as the free acid it may be zwitterionic.

Suitably, the compound of formula (I) is not in the form of a salt, e.g., is not in the form of a pharmaceutically acceptable salt.

Suitably, where the compound of formula (I) is in the form of a salt, the pharmaceutically acceptable salt is a basic addition salt such as a carboxylate salt formed with a group 1 metal (e.g., a sodium or potassium salt), a group 2 metal (e.g., a magnesium or calcium salt) or an ammonium salt of a basic amine (e.g., an $NH_4^+$ salt), such as a sodium salt.

The compounds of formula (I) may be prepared in crystalline or non-crystalline form and, if crystalline, may optionally be solvated, e.g., as the hydrate. This invention includes within its scope stoichiometric solvates (e.g., hydrates) as well as compounds containing variable amounts of solvent (e.g., water). Suitably, the compound of formula (I) is not a solvate.

The invention extends to a pharmaceutically acceptable derivative thereof, such as a pharmaceutically acceptable prodrug of compounds of formula (I). Typical prodrugs of compounds of formula (I) which comprise a carboxylic acid include ester (e.g. $C_{1-6}$ alkyl e.g. $C_{1-4}$ alkyl ester) derivatives thereof. Thus, in one embodiment, the compound of formula (I) is provided as a pharmaceutically acceptable prodrug. In another embodiment, the compound of formula (I) is not provided as a pharmaceutically acceptable prodrug.

It is to be understood that the present invention encompasses all isomers of compounds of formula (I) including all geometric, tautomeric and optical forms, and mixtures thereof (e.g. racemic mixtures). In particular, the invention extends to all tautomeric forms of the compounds of formula (I). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The present invention also includes all isotopic forms of the compounds provided herein, whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exists as a mixture of mass numbers. The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant for"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^2H$ or D), carbon-11 ($^{11}C$), carbon-13 ($^{13}C$), carbon-14 ($^{14}C$), nitrogen-13 ($^{13}N$), nitrogen-15 ($^{15}N$), oxygen-15 ($^{15}O$), oxygen-17 ($^{17}O$), oxygen-18 ($^{18}O$), phosphorus-32 ($^{32}P$), sulphur-35 ($^{35}S$), chlorine-36 ($^{36}Cl$), chlorine-37 ($^{37}Cl$), fluorine-18 ($^{18}F$) iodine-123 ($^{123}I$), iodine-125 ($^{125}I$) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Unnatural variant isotopic forms which incorporate deuterium i.e. $^2H$ or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}C$, $^{18}F$, $^{15}O$ and $^{13}N$, and would be useful in positron emission topography (PET) studies for examining substrate receptor occupancy.

In one embodiment, the compounds of formula (I) are provided in a natural isotopic form. In one embodiment, the compounds of formula (I) are provided in an unnatural variant isotopic form. In a specific embodiment, the unnatural variant isotopic form is a form in which deuterium (i.e. $^2H$ or D) is incorporated where hydrogen is specified in the chemical structure in one or more atoms of a compound of formula (I). In one embodiment, the atoms of the compounds of formula (I) are in an isotopic form which is not radioactive. In one embodiment, one or more atoms of the compounds of formula (I) are in an isotopic form which is radioactive. Suitably radioactive isotopes are stable isotopes. Suitably the unnatural variant isotopic form is a pharmaceutically acceptable form.

In one embodiment, a compound of formula (I) is provided whereby a single atom of the compound exists in an unnatural variant isotopic form. In another embodiment, a compound of formula (I) is provided whereby two or more atoms exist in an unnatural variant isotopic form.

Unnatural isotopic variant forms can generally be prepared by conventional techniques known to those skilled in the art or by processes described herein e.g. processes analogous to those described in the accompanying Examples for preparing natural isotopic forms. Thus, unnatural isotopic variant forms could be prepared by using appropriate isotopically variant (or labelled) reagents in place of the normal reagents employed in the Examples. Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the purer forms used in the pharmaceutical compositions.

Therapeutic Indications

Targeting MTHFD2 and optionally additionally MTHFD1 D/C-d with specific inhibitors presents a novel and exciting approach to regulate the 1C pathway in autoimmunity, inflammation and cancer with potential for an enhanced safety profile in comparison to clinically validated agents like MTX that block 1C metabolism more broadly. Inhibiting selectively MTHFD2 represents a particularly attractive option for autoimmunity with the potential to target very specifically the activated lymphocytes that orchestrate inflammation and tissue damage.

Compounds of formula (I) are of use in therapy, particularly for treating or preventing proliferative diseases such as inflammatory, autoimmune or fibrotic diseases, and cancer. Biological Example 1 shows that the compounds of the invention have inhibitory activity against MTHFD2. Certain examples show comparable inhibitory activity against MTHFD2 and MTHFD1 D/C-d therefore certain compounds of formula (I) are expected to have utility in the treatment of diseases where targeting both MTHFD2 and MTHFD1 D/C-d would be beneficial. By comparable activity, this means that the selectivity for targeting MTHFD2 over targeting MTHFD1 D/C-d is less than 3 fold (e.g. as shown by ratio values in Table 1), i.e. the $IC_{50}$ for MTHFD1 D/C-d is less than 3 fold greater than the $IC_{50}$ for MTHFD2. Certain other examples are selective (e.g. 3 to 30 fold selective or >30 fold selective) for MTHFD2 over MTHFD1 D/C-d (e.g. as shown by ratio values in Table 1 i.e. the $IC_{50}$ value for MTHFD1 D/C-d is 3 times or more the $IC_{50}$ value for MTHFD2) and therefore certain compounds of formula (I) are expected to have utility in the treatment of diseases where targeting MTHFD2 over MTHFD1 D/C-d would be beneficial. Certain other examples are selective (e.g. 30 to 600 fold selective) for MTHFD2 over MTHFD1 D/C-d (e.g. as shown by ratio values in Table 1 i.e. the $IC_{50}$ value for MTHFD1 D/C-d is 30 times or more the $IC_{50}$ value for MTHFD2) and therefore certain compounds of formula (I) are expected to have utility in the treatment of diseases where targeting MTHFD2 over MTHFD1 D/C-d would be beneficial. Reference to targeting MTHFD1 throughout is interchangeable with targeting MTHFD1 D/C-d. Biological Example 2 shows that certain examples do not possess off-target effects against the $\alpha4\beta2$ nicotinic receptor, unlike Reference Example 1 as shown in Table 2. Therefore compounds of formula (I) are expected to be more suitable for drug development compared with Reference Example 1.

Thus, in a further aspect, the present invention provides a compound of formula (I) or a pharmaceutically acceptable salt and/or solvate thereof as defined herein, for use as a medicament.

In a further aspect, the present invention provides a compound of formula (I) or a pharmaceutically acceptable salt and/or solvate thereof as defined herein, for use in treating or preventing a disease selected from the group consisting of inflammatory, autoimmune or fibrotic diseases, and cancer.

In a further aspect, the present invention provides a compound of formula (I) or a pharmaceutically acceptable salt and/or solvate thereof as defined herein, for use in treating a disease selected from the group consisting of inflammatory, autoimmune or fibrotic diseases, and cancer.

In a further aspect, the present invention provides a compound of formula (I) or a pharmaceutically acceptable salt and/or solvate thereof as defined herein, for use in preventing a disease selected from the group consisting of inflammatory, autoimmune or fibrotic diseases, and cancer.

In a further aspect, the present invention provides the use of a compound of formula (I) or a pharmaceutically acceptable salt and/or solvate thereof as defined herein, in the manufacture of a medicament for treating or preventing a disease selected from the group consisting of inflammatory, autoimmune or fibrotic diseases, and cancer.

In a further aspect, the present invention provides the use of a compound of formula (I) or a pharmaceutically acceptable salt and/or solvate thereof as defined herein, in the manufacture of a medicament for treating a disease selected from the group consisting of inflammatory, autoimmune or fibrotic diseases, and cancer.

In a further aspect, the present invention provides the use of a compound of formula (I) or a pharmaceutically acceptable salt and/or solvate thereof as defined herein, in the manufacture of a medicament for preventing a disease selected from the group consisting of inflammatory, autoimmune or fibrotic diseases, and cancer.

In a further aspect, the present invention provides a method of treating or preventing a disease selected from the group consisting of inflammatory, autoimmune or fibrotic diseases, and cancer which comprises administering a compound of formula (I) or a pharmaceutically acceptable salt and/or solvate thereof as defined herein.

In a further aspect, the present invention provides a method of treating a disease selected from the group consisting of inflammatory, autoimmune or fibrotic diseases, and cancer which comprises administering a compound of formula (I) or a pharmaceutically acceptable salt and/or solvate thereof as defined herein.

In a further aspect, the present invention provides a method of preventing a disease selected from the group consisting of inflammatory, autoimmune or fibrotic diseases, and cancer which comprises administering a compound of formula (I) or a pharmaceutically acceptable salt and/or solvate thereof as defined herein.

In any one of the above embodiments, the disease is an inflammatory, autoimmune or fibrotic disease. Alternatively, the disease is cancer.

Suitably, the compounds of formula (I) that show comparable inhibitory activity against MTHFD2 and MTHFD1 D/C-d are for use in treating or preventing an inflammatory, autoimmune or fibrotic disease.

Suitably, the compounds of formula (I) that show comparable inhibitory activity against MTHFD2 and MTHFD1 D/C-d are for use in treating or preventing cancer.

Suitably, the compounds of formula (I) that are selective (e.g. 3 to 30 fold selective or >30 fold selective) for MTHFD2 over MTHFD1 D/C-d are for use in treating or preventing an inflammatory, autoimmune or fibrotic disease.

Suitably, the compounds of formula (I) that are selective (e.g. 3 to 30 fold selective or >30 fold selective) for MTHFD2 over MTHFD1 D/C-d are for use in treating or preventing cancer.

Suitably, the inflammatory, autoimmune or fibrotic disease is selected from the group consisting of rheumatoid arthritis, juvenile idiopathic arthritis, psoriatic arthritis, psoriasis, myasthenia gravis (MG), Crohn's disease, multiple sclerosis, sarcoidosis, ulcerative colitis, Celiac's disease, systemic lupus erythematosus (SLE), Sjogren's syndrome, asthma, atopic dermatitis, vitiligo, systemic sclerosis (SSC), graft versus host disease (GvHD), Type 1 diabetes, Hidradenitis suppurativa, idiopathic pulmonary fibrosis (IPF), interstitial lung disease (ILD) and non-alcoholic steatohepatitis (NASH).

The following diseases may be treated using methotrexate, which as stated in the introduction, target enzymes on the one-carbon (1C) metabolism pathway, and has known utility in the treatment of autoimmune diseases (Kozmihski P. et al., 2020; Kerschbaumer A. et al., 2019; Ferrara G. et al., 2018; Gotterer L. et al., 2016; Diaz-Manera J. et al., 2012; Chantam W. 2010; Smolen J S. et al., 2010; Mahr A D. et al., 2007; Baughman R P. et al. 1999). Since the compounds of the invention are expected to work in a similar yet superior way to methotrexate, it is expected that compounds of formula (I) will have utility in the treatment of the same diseases listed below.

Thus, suitably, the inflammatory, autoimmune or fibrotic disease is selected from the group consisting of rheumatoid arthritis, juvenile idiopathic arthritis, psoriatic arthritis, psoriasis, myasthenia gravis (MG), Crohn's disease, multiple sclerosis and sarcoidosis.

The following diseases are linked to the overexpression of MTHFD2 (Aune™. et al., 2017; Sugiura A. et al., 2022), and thus inhibition of MTHFD2 using the compounds of formula (I) represents a strategy for treating the diseases listed below.

Suitably, the inflammatory, autoimmune or fibrotic disease is selected from the group consisting of ulcerative colitis, Celiac's disease, systemic lupus erythematosus (SLE) and Sjogren's syndrome.

The following diseases are linked to T-cell differentiation which as stated in the introduction, $CD4^+$ T-cell subsets Th17 and Th1 that are strongly associated with inflammatory diseases had the highest expression of MTHFD2 (Sun L. et al., 2023; Witte K. et al., 2023; Gaydosik A M. et al., 2021; Karl F. et al., 2021; Raphael I. et al., 2020; Sabat R. et al., 2019). Known MTHFD2 inhibitor DS18561882 greatly decreased the number of Th1 and Th17 cells differentiated in vitro from $CD4^+$ T-cells and expression of the respective Th1 and Th17 cytokines. Thus inhibiting MTHFD2 with the compounds of formula (I) which are superior to DS18561882, as shown in the biological example section, represents a strategy for treating the diseases listed below.

Suitably, the inflammatory, autoimmune or fibrotic disease is selected from the group consisting of asthma, atopic dermatitis, vitiligo, systemic sclerosis (SSC), graft versus host disease (GvHD), Type 1 diabetes and Hidradenitis suppurativa.

The following diseases are linked to fibrosis which shares a number of underlying disease mechanisms with inflammation and autoimmunity (Yanjie G. et al., 2023; Hamanaka R B., et al., 2022; Hiroshi F. et al., 2021). Thus the compounds of formula (I) are expected to have utility in the treatment of the following diseases.

Suitably, the inflammatory, autoimmune or fibrotic disease is selected from the group consisting of idiopathic pulmonary fibrosis (IPF), interstitial lung disease (ILD) and non-alcoholic steatohepatitis (NASH).

The following diseases may be treated using methotrexate, which as stated in the introduction, target enzymes on the one-carbon (1C) metabolism pathway, and has known utility in the treatment of cancer, in particular those listed below (Gong F. et al., 2019; De Wilde V. et al., 2016; Bergner N. et al., 2012; Zhu J J. et al., 2009; Abrão R. et al., 2008; Fahey J B. 2007; Meyers P A. et al., 2005; Batchelor T T. et al., 2003; Khan R B. et al., 2002; Krailo M. et al., 1987; Rizzoli V. et al., 1985; Canello G P., et al., 1981; Nilsson R. et al., 2014). Since the compounds of the invention are expected to work in a similar yet superior way to methotrexate, it is expected that compounds of formula (I) will have utility in the treatment of the same diseases listed below. Furthermore, it is known that MTHFD2 knockdown in tumour cell lines is associated with an anti-proliferative effect (Zhu Z., et al., 2020). Therefore inhibitors of MTHFD2, such as the compounds of formula (I), are expected to have utility in the treatment of cancer.

Suitably, the cancer is selected from the group consisting of acute lymphoblastic leukaemia (ALL), primary central nervous system lymphoma (PCNSL), lymphoma, mycosis fungoides, refectory non-Hodgkin lymphoma (NHL), head and neck squamous cell carcinoma (HNSCC), non-small cell lung cancer (NSCLC), bladder cancer, lymphoma, breast cancer, osteosarcoma, gestational trophoblastic neoplasia (GTN), acute myeloid leukaemia (AML), hepatocellular carcinoma, renal cell carcinoma, colorectal cancer, lung cancer, glioma, ovarian cancer, melanoma, and solid tumours such as cervical, uterine, testicular, stomach, prostate and pancreatic tumours.

Suitably, the cancer is selected from the group consisting of acute lymphoblastic leukaemia (ALL), primary central nervous system lymphoma (PCNSL), lymphoma, mycosis fungoides, refectory non-Hodgkin lymphoma (NHL) and acute myeloid leukaemia (AML).

References providing links between the diseases and MTHFD2 and/or MTHFD1 (D/C-d) are provided in the reference section and above.

Administration

The compound of formula (I) is usually administered as a pharmaceutical composition. Thus, in one embodiment, is provided a pharmaceutical composition comprising a compound of formula (I) and one or more pharmaceutically acceptable diluents or carriers. The present invention also provides a pharmaceutical composition comprising a compound of formula (I) or a pharmaceutically acceptable salt and/or solvate thereof as defined herein, for use as a medicament.

In a further aspect, the present invention provides a pharmaceutical composition comprising a compound of formula (I) or a pharmaceutically acceptable salt and/or solvate thereof as defined herein, for use in treating or preventing a disease selected from the group consisting of inflammatory diseases, autoimmune diseases and cancer.

In a further aspect, the present invention provides a pharmaceutical composition comprising a compound of formula (I) or a pharmaceutically acceptable salt and/or solvate thereof as defined herein, for use in treating a disease selected from the group consisting of inflammatory diseases, autoimmune diseases and cancer.

In a further aspect, the present invention provides a pharmaceutical composition comprising a compound of formula (I) or a pharmaceutically acceptable salt and/or solvate thereof as defined herein, for use in preventing a disease selected from the group consisting of inflammatory diseases, autoimmune diseases and cancer.

The compound of formula (I) may be administered by any convenient method, e.g. by oral, parenteral, buccal, sublingual, nasal, rectal, intrathecal or transdermal administration, and the pharmaceutical compositions adapted accordingly.

The compound of formula (I) may be administered topically to the target organ e.g. topically to the eye, lung, nose or skin. Hence the invention provides a pharmaceutical composition comprising a compound of formula (I) optionally in combination with one or more topically acceptable diluents or carriers.

A compound of formula (I) which is active when given orally can be formulated as a liquid or solid, e.g. as a syrup, suspension, emulsion, tablet, capsule or lozenge.

A liquid formulation will generally consist of a suspension or solution of the compound of formula (I) in a suitable liquid carrier(s). Suitably the carrier is non-aqueous e.g. polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatine capsule; alternatively, a dispersion or suspension can be prepared using any suitable pharmaceutical carrier(s), e.g. aqueous gums, celluloses, silicates or oils and the dispersion or suspension then filled into a soft gelatine capsule.

Typical parenteral compositions consist of a solution or suspension of the compound of formula (I) in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the compound of formula (I) in a pharmaceutically acceptable aqueous or non-aqueous solvent and are usually presented in single or multidose quantities in sterile form in a sealed container which can take the form of a cartridge or refill for use with an atomising device. Alternatively, the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a chlorofluorocarbon (CFC) or a hydrofluorocarbon (HFC). Aerosol dosage forms can also take the form of pump-atomisers.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC).

Topical administration to the lung may also be achieved by use of a non-pressurised formulation such as an aqueous solution or suspension. These may be administered by means of a nebuliser e.g. one that can be hand-held and portable or for home or hospital use (i.e. non-portable). The formulation may comprise excipients such as water, buffers, tonicity adjusting agents, pH adjusting agents, surfactants and co-solvents.

Topical administration to the lung may also be achieved by use of a dry-powder formulation. The formulation will typically contain a topically acceptable diluent such as lactose, glucose or mannitol (preferably lactose).

The compound of the invention may also be administered rectally, for example in the form of suppositories or enemas, which include aqueous or oily solutions as well as suspensions and emulsions and foams. Such compositions are prepared following standard procedures, well known by those skilled in the art. For example, suppositories can be prepared by mixing the active ingredient with a conventional suppository base such as cocoa butter or other glycerides.

In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the compound of the present invention will be about 0.0001 to less than 4.0% (w/w).

Preferably, for topical ocular administration, the compositions administered according to the present invention will be formulated as solutions, suspensions, emulsions and other dosage forms.

The compositions administered according to the present invention may also include various other ingredients, including, but not limited to, tonicity agents, buffers, surfactants, stabilizing polymer, preservatives, co-solvents and viscosity building agents. Suitable pharmaceutical compositions of the present invention include a compound of the invention formulated with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars such as dextrose, fructose, galactose, and/or simply polyols such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g. sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of compound of the present invention. The surfactants function to solubilise the compound and stabilise colloid dispersion, such as micellar solution, microemulsion, emulsion and suspension. Examples of surfactants which may optionally be used include polysorbate, poloxamer, polyosyl 40 stearate, polyoxyl castor oil, tyloxapol, Triton, and sorbitan monolaurate. Preferred surfactants to be employed in the invention have a hydrophile/lipophile/ balance "HLB" in the range of 12.4 to 13.2 and are acceptable for ophthalmic use, such as Triton™ X-114 and tyloxapol.

Additional agents that may be added to the ophthalmic compositions of compounds of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers and Pemulen®, specifically Carbomer 974p (polyacrylic acid), at 0.1-0.5% w/w.

Other compounds may also be added to the ophthalmic compositions of the compound of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family; vinyl polymers; and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

Compositions suitable for buccal or sublingual administration include tablets, lozenges and pastilles where the compound of formula (I) is formulated with a carrier such as sugar and acacia, tragacanth, or gelatine and glycerine.

Compositions suitable for transdermal administration include ointments, gels and patches.

The composition may contain from 0.1% to 100% by weight, for example from 10 to 60% by weight, of the compound of formula (I), depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, such as from 1.0 mg to 50 mg, e.g. about 10 mg of the compound of formula (I), depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide, suitable unit doses may be 0.05 to 1000 mg, more suitably 1.0 to 500 mg, such as from 1.0 mg to 50 mg, e.g. about 10 mg and such unit doses may be administered more than once a day, for example two or three times a day. Such therapy may extend for a number of weeks or months.

In one embodiment of the invention, the compound of formula (I) is used in combination with a further therapeutic agent or agents. When the compound of formula (I) is used in combination with other therapeutic agents, the compounds may be administered either sequentially or simultaneously by any convenient route. Alternatively, the compounds may be administered separately.

Compounds of formula (I) may display, or may be expected to have, one or more of the following desirable properties:

- inhibitory activity against MTHFD1 and MTHFD2;
- selective inhibitory activity against MTHFD2 over MTHFD1;
- no off-target effects such as against the α4β2 nicotinic receptor;
- improved suitability as a potential drug candidate;
- improved oral systemic bioavailability;
- good tolerability, for example, by limiting the side effects showed by other medication targeting broadly the 1C metabolism, such as MTX;
- low toxicity at the relevant therapeutic dose;
- distinct anti-inflammatory profiles;
- disease modifying effect.

The invention may be described by the following clauses:

Clause 1. A compound of formula (I):

(I)

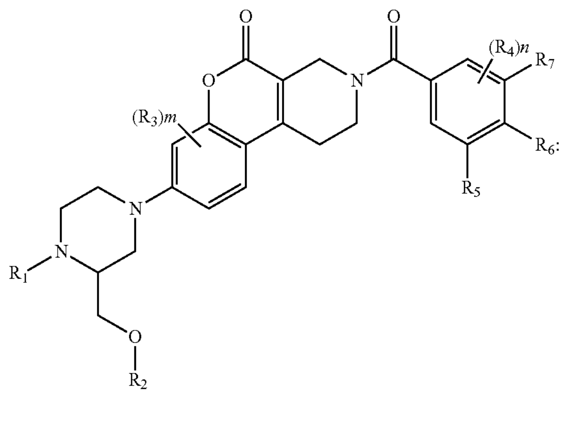

wherein:

$R_1$ is $C_{1-4}$ alkyl or $C_{3-5}$ cycloalkyl;

$R_2$ is $C_{1-4}$ alkyl; or $R_1$ and $R_2$ join to form a 5-7 membered heterocycloalkyl;

$R_3$ is selected from the group consisting of $C_{1-3}$ alkyl and halo;

$R_4$ is selected from the group consisting of $C_{1-3}$ alkyl, halo, $C_{1-3}$ haloalkyl, $C_{1-3}$ alkoxy, $C_{1-3}$ haloalkoxy, $NR_{4a}R_{4b}$ and 4-7 membered heterocycloalkyl;

wherein:

$R_{4a}$ is selected from the group consisting of H and $C_{1-3}$ alkyl;

$R_{4b}$ is selected from the group consisting of H and $C_{1-3}$ alkyl;

m is 0, 1 or 2;

n is 0, 1 or 2;

and $R_5$, $R_6$ and $R_7$ are defined as follows:

(a) $R_6$ is

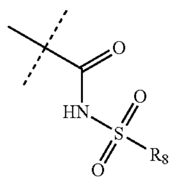

O and $R_7$ is absent;

$R_5$ is selected from the group consisting of H, halo, $C_{1-3}$ alkyl, $C_{1-3}$ haloalkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$ (for example $R_5$ is selected from the group consisting of H, halo, $C_{1-3}$ alkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$);

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{5b}$ is selected from the group consisting of H and $C_{1-3}$ alkyl; and $R_{5c}$ is selected from the group consisting of $C_{1-3}$ alkyl and $C_{3-6}$ cycloalkyl; and $R_8$ is selected from the group consisting of $C_{3-6}$ cycloalkyl, $NR_{8b}R_{8c}$ and 4-10 (e.g. 4-8) membered heterocycloalkyl, wherein the $C_{3-6}$ cycloalkyl and 4-10 (e.g. 4-8) membered heterocycloalkyl are optionally substituted by one or more $R_{8a}$, wherein:

$R_{8a}$ is selected from the group consisting of $C_{1-3}$ alkyl, $C_{1-3}$ alkyl substituted by OH, $C_{1-2}$ alkyl substituted by $OC_{1-2}$ alkyl, $C_{1-3}$ alkoxy, halo and $C_{1-3}$ haloalkyl (for example, $R_{8a}$ is selected from the group consisting of $C_{1-3}$ alkyl, halo and $C_{1-3}$ haloalkyl);

$R_{8b}$ is selected from the group consisting of H, $C_{1-3}$ alkyl and $C_{3-6}$ cycloalkyl;

$R_{8c}$ is selected from the group consisting of H, $C_{1-3}$ alkyl and $C_{3-6}$ cycloalkyl;

or:

(b) $R_7$ is

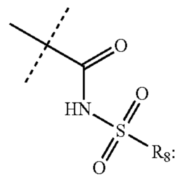

and (i) $R_6$ is H and $R_5$ is selected from the group consisting of H, halo, $C_{1-3}$ alkyl, $C_{1-3}$ haloalkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$ (for example $R_5$ is selected from the group consisting of H, halo, $C_{1-3}$ alkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$);

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring, $R_{5b}$ is selected from the group consisting of H and $C_{1-3}$ alkyl; and $R_{5c}$ is selected from the group consisting of $C_{1-3}$ alkyl and $C_{3-6}$ cycloalkyl;

or (ii) $R_5$ is H and $R_6$ is selected from the group consisting of H, halo, $C_{1-3}$ alkyl, $C_{1-3}$ haloalkyl, $C_{1-3}$ alkoxy, $C_{1-3}$ haloalkoxy, $SC_{1-3}$ alkyl, $SC_{1-3}$ haloalkyl, $OC_3$ cycloalkyl, $NR_{6b}R_{6c}$ and 4-7 membered heterocycloalkyl, wherein the $OC_{3-10}$ cycloalkyl and 4-7 membered heterocycloalkyl are optionally substituted by one or more $R_{6a}$ (for example $R_6$ is selected from the group consisting of H, halo, $C_{1-3}$ alkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{6b}R_{6c}$ and 4-7 membered heterocycloalkyl, wherein the $OC_{3-10}$ cycloalkyl and 4-7 membered heterocycloalkyl are optionally substituted by one or more $R_{6a}$);

wherein:

$R_{6a}$ is selected from the group consisting of halo and $C_{1-3}$ alkyl, or two $R_{6a}$ groups which are attached to the same carbon atom join to form a $C_{3-6}$ cycloalkyl or 4-7 membered heterocycloalkyl ring, $R_{6b}$ is selected from the group consisting of H and $C_{1-3}$ alkyl; and $R_{6c}$ is selected from the group consisting of $C_{1-3}$ alkyl and $C_{3-6}$ cycloalkyl;

or (iii) $R_5$ and $R_6$ join to form a 4-8 membered heterocyclic ring;

and $R_8$ is selected from the group consisting of $C_{3-6}$ cycloalkyl, $NR_{8b}R_{8c}$ and 4-10 (e.g. 4-8) membered heterocycloalkyl, wherein the $C_{3-6}$ cycloalkyl and 4-10 (e.g. 4-8) membered heterocycloalkyl are optionally substituted by one or more $R_{8a}$ wherein:

$R_{8a}$ is selected from the group consisting of $C_{1-3}$ alkyl, $C_{1-3}$ alkyl substituted by OH, $C_{1-2}$ alkyl substituted by $OC_{1-2}$ alkyl, $C_{1-3}$ alkoxy, halo and $C_{1-3}$ haloalkyl (for example, $R_{8a}$ is selected from the group consisting of $C_{1-3}$ alkyl, halo and $C_{1-3}$ haloalkyl);

$R_{8b}$ is selected from the group consisting of H, $C_{1-3}$ alkyl and $C_{3-6}$ cycloalkyl; and $R_{8c}$ is selected from the group consisting of H, $C_{1-3}$ alkyl and $C_{3-6}$ cycloalkyl; or a pharmaceutically acceptable salt and/or solvate thereof.

Clause 2. A compound of formula (I) according to clause 1:

(I)

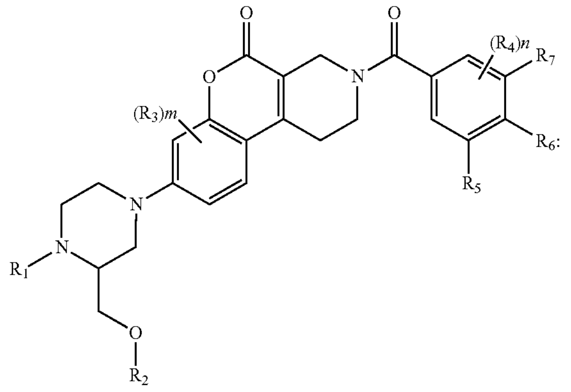

wherein:

$R_1$ is $C_{1-4}$ alkyl or $C_{3-5}$ cycloalkyl;

$R_2$ is $C_{1-4}$ alkyl; or $R_1$ and $R_2$ join to form a 5-7 membered heterocycloalkyl;

$R_3$ is selected from the group consisting of $C_{1-3}$ alkyl and halo;

$R_4$ is selected from the group consisting of $C_{1-3}$ alkyl, halo, $C_{1-3}$ haloalkyl, $C_{1-3}$ alkoxy, $C_{1-3}$ haloalkoxy and 4-7 membered heterocycloalkyl;

$R_6$ is

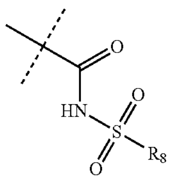

and $R_7$ is absent; or $R_7$ is

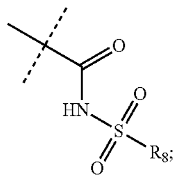

wherein:

when $R_6$ is

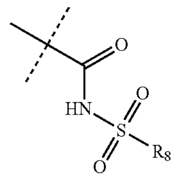

and $R_7$ is absent:

$R_5$ is selected from the group consisting of H, halo, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{5b}$ is selected from the group consisting of H and $C_{1-3}$ alkyl; and $R_{5c}$ is selected from the group consisting of $C_{1-3}$ alkyl and $C_{3-6}$ cycloalkyl; and $R_8$ is selected from the group consisting of $C_{3-6}$ cycloalkyl, $N(C_{1-3}\ alkyl)_2$ and 4-8 membered heterocycloalkyl, wherein the $C_{3-6}$ cycloalkyl and 4-8 membered heterocycloalkyl are optionally substituted by one or more $R_{8a}$, wherein $R_{8a}$ is selected from the group consisting of $C_{1-3}$ alkyl, halo and $C_{1-3}$ haloalkyl;

or:

when $R_7$ is

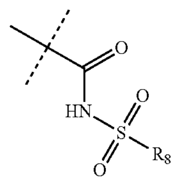

$R_6$ is H and $R_5$ is selected from the group consisting of H, halo, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring, $R_{5b}$ is selected from the group consisting of H and $C_{1-3}$ alkyl; and $R_{5c}$ is selected from the group consisting of $C_{1-3}$ alkyl and $C_{3-6}$ cycloalkyl;

or $R_5$ is H and $R_6$ is selected from the group consisting of H, halo, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{6b}R_{6c}$ and 4-7 membered heterocycloalkyl, wherein the $OC_{3-10}$ cycloalkyl and 4-7 membered heterocycloalkyl are optionally substituted by one or more $R_{6a}$;

wherein:

$R_{6a}$ is selected from the group consisting of halo and $C_{1-3}$ alkyl, or two $R_{6a}$ groups which are attached to the same carbon atom join to form a $C_{3-6}$ cycloalkyl or 4-7 membered heterocycloalkyl ring, $R_{6b}$ is selected from the group consisting of H and $C_{1-3}$ alkyl; and $R_{6c}$ is selected from the group consisting of $C_{1-3}$ alkyl and $C_{3-6}$ cycloalkyl;

or $R_5$ and $R_6$ join to form a 4-8 membered heterocyclic ring; and $R_8$ is selected from the group consisting of $C_{3-6}$ cycloalkyl, $N(C_{1-3}\ alkyl)_2$ and 4-8 membered heterocycloalkyl, wherein the $C_{3-6}$ cycloalkyl and 4-8 membered heterocycloalkyl are optionally substituted by one or more $R_{8a}$ wherein $R_{8a}$ is selected from the group consisting of $C_{1-3}$ alkyl, halo and $C_{1-3}$ haloalkyl;

m is 0, 1 or 2; and n is 0, 1 or 2;

or a pharmaceutically acceptable salt and/or solvate thereof.

Clause 3. The compound or a pharmaceutically acceptable salt and/or solvate thereof according to clause 1 or clause 2 wherein $R_1$ is $C_{1-4}$ alkyl.

Clause 4. The compound or a pharmaceutically acceptable salt and/or solvate thereof according to clause 3 wherein $R_1$ is methyl.

Clause 5. The compound or a pharmaceutically acceptable salt and/or solvate thereof according to clause 1 or clause 2 wherein $R_1$ is $C_{3-5}$ cycloalkyl.

Clause 6. The compound or a pharmaceutically acceptable salt and/or solvate thereof according to clause 5 wherein $R_1$ is cyclopropyl.

Clause 7. The compound or a pharmaceutically acceptable salt and/or solvate thereof according to any one of clauses 1 to 6 wherein $R_2$ is methyl.

Clause 8. The compound or a pharmaceutically acceptable salt and/or solvate thereof according to clause 1 or clause 2 wherein $R_1$ and $R_2$ join to form a 5-7 membered heterocycloalkyl.

Clause 9. The compound or a pharmaceutically acceptable salt and/or solvate thereof according to clause 8 wherein $R_1$ and $R_2$ join to form a 6 membered heterocycloalkyl.

Clause 10. The compound or a pharmaceutically acceptable salt and/or solvate thereof according to any one of clauses 1 to 9 wherein $R_3$ is $C_{1-3}$ alkyl.

Clause 11. The compound or a pharmaceutically acceptable salt and/or solvate thereof according to clause 10 wherein $R_3$ is methyl.

Clause 12. The compound or a pharmaceutically acceptable salt and/or solvate thereof according to any one of clauses 1 to 9 wherein $R_3$ is halo.

Clause 13. The compound or a pharmaceutically acceptable salt and/or solvate thereof according to clause 12 wherein $R_3$ is chloro.

Clause 14. The compound or a pharmaceutically acceptable salt and/or solvate thereof according to any one of clauses 1 to 9 wherein m=0.

Clause 15. The compound or a pharmaceutically acceptable salt and/or solvate thereof according to any one of clauses 1 to 13 wherein m=1.

Clause 16. The compound or a pharmaceutically acceptable salt and/or solvate thereof according to any one of clauses 1 to 13 wherein m=2.

Clause 17. The compound or a pharmaceutically acceptable salt and/or solvate thereof according to any one of clauses 1 to 16 wherein $R_4$ is $C_{1-3}$ alkyl.

Clause 18. The compound or a pharmaceutically acceptable salt and/or solvate thereof according to clause 17 wherein $R_4$ is methyl.

Clause 19. The compound or a pharmaceutically acceptable salt and/or solvate thereof according to any one of clauses 1 to 16 wherein $R_4$ is halo.

Clause 20. The compound or a pharmaceutically acceptable salt and/or solvate thereof according to clause 19 wherein $R_4$ is selected from the group consisting of chloro and fluoro, such as fluoro.

Clause 21. The compound or a pharmaceutically acceptable salt and/or solvate thereof according to any one of clauses 1 to 16 wherein $R_4$ is $C_{1-3}$ haloalkyl.

Clause 22. The compound or a pharmaceutically acceptable salt and/or solvate thereof according to clause 21 wherein $R_4$ is trifluoromethyl.

Clause 23. The compound or a pharmaceutically acceptable salt and/or solvate thereof according to any one of clauses 1 to 16 wherein $R_4$ is $C_{1-3}$ alkoxy.

Clause 24. The compound or a pharmaceutically acceptable salt and/or solvate thereof according to clause 23 wherein $R_4$ is methoxy.

Clause 25. The compound or a pharmaceutically acceptable salt and/or solvate thereof according to any one of clauses 1 to 16 wherein $R_4$ is $C_{1-3}$ haloalkoxy.

Clause 26. The compound or a pharmaceutically acceptable salt and/or solvate thereof according to any one of clauses 1 to 16 wherein $R_4$ is 4-7 membered heterocycloalkyl.

Clause 27. The compound or a pharmaceutically acceptable salt and/or solvate thereof according to clause 26 wherein $R_4$ is pyrrolidinyl.

Clause 28. The compound or a pharmaceutically acceptable salt and/or solvate thereof according to any one of clauses 1 to 16 wherein $R_4$ is $NR_{4a}R_{4b}$.

Clause 29. The compound or a pharmaceutically acceptable salt and/or solvate thereof according to clause 28 wherein $R_{4a}$ is H.

Clause 30. The compound or a pharmaceutically acceptable salt and/or solvate thereof according to clause 28 wherein $R_{4a}$ is $C_{1-3}$ alkyl, such as methyl.

Clause 31. The compound or a pharmaceutically acceptable salt and/or solvate thereof according to clause 28 wherein $R_{4b}$ is H.

Clause 32. The compound or a pharmaceutically acceptable salt and/or solvate thereof according to clause 28 wherein $R_{4b}$ is $C_{1-3}$ alkyl, such as methyl.

Clause 33. The compound or a pharmaceutically acceptable salt and/or solvate thereof according to any one of clauses 1 to 16 wherein n is 0.

Clause 34. The compound or a pharmaceutically acceptable salt and/or solvate thereof according to any one of clauses 1 to 32 wherein n is 1.

Clause 35. The compound or a pharmaceutically acceptable salt and/or solvate thereof according to any one of clauses 1 to 32 wherein n is 2.

Clause 36. The compound or a pharmaceutically acceptable salt and/or solvate thereof according to any one of clauses 1 to 35 wherein:

$R_6$ is

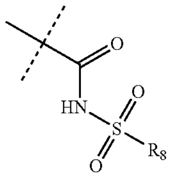

and $R_7$ is absent.

Clause 37. The compound or a pharmaceutically acceptable salt and/or solvate thereof according to clause 36 wherein $R_5$ is H.

Clause 38. The compound or a pharmaceutically acceptable salt and/or solvate thereof according to clause 36 wherein $R_5$ is halo.

Clause 39. The compound or a pharmaceutically acceptable salt and/or solvate thereof according to clause 38 wherein $R_5$ is chloro.

Clause 40. The compound or a pharmaceutically acceptable salt and/or solvate thereof according to clause 36 wherein $R_5$ is $C_{1-3}$alkyl, such as methyl or ethyl.

Clause 41. The compound or a pharmaceutically acceptable salt and/or solvate thereof according to clause 36 wherein $R_5$ is $C_{1-3}$ alkoxy, such as methoxy or ethoxy, e.g. methoxy.

Clause 42. The compound or a pharmaceutically acceptable salt and/or solvate thereof according to clause 36 wherein $R_5$ is $C_{1-3}$ haloalkoxy.

Clause 43. The compound or a pharmaceutically acceptable salt and/or solvate thereof according to clause 36 wherein $R_5$ is $SC_{1-3}$ alkyl.

Clause 44. The compound or a pharmaceutically acceptable salt and/or solvate thereof according to clause 36 wherein $R_5$ is $SC_{1-3}$ haloalkyl.

Clause 45. The compound or a pharmaceutically acceptable salt and/or solvate thereof according to clause 36 wherein $R_5$ is $OC_{3-10}$ cycloalkyl.

Clause 46. The compound or a pharmaceutically acceptable salt and/or solvate thereof according to clause 45 wherein $R_5$ is selected from the group consisting of cyclobutyloxy, cyclopentyloxy, cyclohexyloxy, bicyclo [3.1.0]hexyloxy and 2-adamantanyloxy.

Clause 47. The compound or a pharmaceutically acceptable salt and/or solvate thereof according to clause 36 wherein $R_5$ is 4-7 membered heterocycloalkyl.

Clause 48. The compound or a pharmaceutically acceptable salt and/or solvate thereof according to clause 47 wherein $R_5$ is selected from the group consisting of pyrrolidinyl, piperidinyl, 3-azabicyclo[3.1.0]hexyl, 2-azabicyclo (2.2.1)heptyl and 7-azanorbornanyl.

Clause 49. The compound or a pharmaceutically acceptable salt and/or solvate thereof according to any one of clauses 45 to 48 wherein $R_5$ is unsubstituted.

Clause 50. The compound or a pharmaceutically acceptable salt and/or solvate thereof according to any one of clauses 45 to 48 wherein $R_5$ is substituted by one or more (such as one, two or three, e.g. one) $R_{5a}$.

Clause 51. The compound or a pharmaceutically acceptable salt and/or solvate thereof according to clause 50 wherein $R_{5a}$ is halo.

Clause 52. The compound or a pharmaceutically acceptable salt and/or solvate thereof according to clause 51 wherein $R_{5a}$ is fluoro.

Clause 53. The compound or a pharmaceutically acceptable salt and/or solvate thereof according to clause 50 wherein $R_{5a}$ is $C_{1-3}$ alkyl.

Clause 54. The compound or a pharmaceutically acceptable salt and/or solvate thereof according to clause 53 wherein $R_{5a}$ is methyl.

Clause 55. The compound or a pharmaceutically acceptable salt and/or solvate thereof according to clause 50 wherein $R_5$ is substituted by one methyl group.

Clause 56. The compound or a pharmaceutically acceptable salt and/or solvate thereof according to clause 50 wherein $R_5$ is substituted by two $R_{5a}$ groups selected from the group consisting of methyl and fluoro.

Clause 57. The compound or a pharmaceutically acceptable salt and/or solvate thereof according to clause 50 wherein two $R_{5a}$ groups which are attached to the same carbon atom join to form a $C_{3-6}$ cycloalkyl ring such as a $C_3$ cycloalkyl ring.

Clause 58. The compound or a pharmaceutically acceptable salt and/or solvate thereof according to clause 36 wherein $R_5$ is $NR_{5b}R_{5c}$.

Clause 59. The compound or a pharmaceutically acceptable salt and/or solvate thereof according to clause 58 wherein $R_{5b}$ is H.

Clause 60. The compound or a pharmaceutically acceptable salt and/or solvate thereof according to clause 58 wherein $R_{5b}$ is $C_{1-3}$ alkyl.

Clause 61. The compound or a pharmaceutically acceptable salt and/or solvate thereof according to clause 60 wherein $R_{5b}$ is methyl.

Clause 62. The compound or a pharmaceutically acceptable salt and/or solvate thereof according to any one of clauses 58 to 61 wherein $R_{5c}$ is $C_{1-3}$ alkyl.

Clause 63. The compound or a pharmaceutically acceptable salt and/or solvate thereof according to clause 62 wherein $R_{5c}$ is selected from the group consisting of methyl and isopropyl.

Clause 64. The compound or a pharmaceutically acceptable salt and/or solvate thereof according to any one of clauses 58 to 61 wherein $R_{5c}$ is $C_{3-6}$ cycloalkyl.

Clause 65. The compound or a pharmaceutically acceptable salt and/or solvate thereof according to any one of clauses 1 to 64 wherein $R_8$ is $C_{3-6}$ cycloalkyl.

Clause 66. The compound or a pharmaceutically acceptable salt and/or solvate thereof according to clause 65 wherein $R_8$ is cyclopropyl.

Clause 67. The compound or a pharmaceutically acceptable salt and/or solvate thereof according to any one of clauses 1 to 64 wherein $R_8$ is 4-10 (e.g. 4-8) membered heterocycloalkyl.

Clause 68. The compound or a pharmaceutically acceptable salt and/or solvate thereof according to clause 67 wherein $R_8$ is selected from the group consisting of pyrrolidinyl (e.g. pyrrolidin-1-yl), piperidinyl (e.g. piperidin-1-yl), 7-azanorbornanyl, 3-azabicyclo[3.1.0]hexyl (e.g. 3-azabicyclo[3.1.0]hexan-3-yl), 6-azaspiro[2.5]octyl (e.g. 6-azaspiro[2.5]octan-6-yl) and 3-oxa-6-azabicyclo[3.2.1]octyl (e.g. 3-oxa-8-azabicyclo[3.2.1]octan-8-yl), 7-azabicyclo[2.2.1]heptan-7-yl, (3aR,6aS)-hexahydrocyclopenta[c]pyrrol-2(1H)-yl, octahydro-2H-isoindol-2-yl, 2-azaspiro[3.3]heptan-2-yl, (1 S,4S)-2-oxa-5-azabicyclo[2.2.1]heptan-5-yl), 2-azabicyclo[2.2.1]heptan-2-yl) and 8-azabicyclo[3.2.1]octan-8-yl and for example is selected from the group consisting of pyrrolidinyl (e.g. pyrrolidin-1-yl), piperidinyl (e.g. piperidin-1-yl), 7-azanorbornanyl, 3-azabicyclo[3.1.0]hexyl (e.g. 3-azabicyclo[3.1.0]hexan-3-yl), 6-azaspiro[2.5]octyl (e.g. 6-azaspiro[2.5]octan-6-yl) and 3-oxa-6-azabicyclo[3.2.1]octyl (e.g. 3-oxa-8-azabicyclo[3.2.1]octan-8-yl).

Clause 69. The compound or a pharmaceutically acceptable salt and/or solvate thereof according to any one of clauses 65 to 68 wherein $R_8$ is unsubstituted.

Clause 70. The compound or a pharmaceutically acceptable salt and/or solvate thereof according to any one of clauses 65 to 68 wherein $R_8$ is substituted by one or more (such as one, two or three, e.g. one) $R_{8a}$ groups.

Clause 71. The compound or a pharmaceutically acceptable salt and/or solvate thereof according to clause 70 wherein $R_{8a}$ is $C_{1-3}$ alkyl.

Clause 72. The compound or a pharmaceutically acceptable salt and/or solvate thereof according to clause 71 wherein $R_{8a}$ is methyl.

Clause 73. The compound or a pharmaceutically acceptable salt and/or solvate thereof according to clause 70 wherein $R_{8a}$ is halo.

Clause 74. The compound or a pharmaceutically acceptable salt and/or solvate thereof according to clause 70 wherein $R_{8a}$ is $C_{1-3}$ haloalkyl.

Clause 75. The compound or a pharmaceutically acceptable salt and/or solvate thereof according to clause 70 wherein $R_8$ is substituted by two methyl groups.

Clause 76. The compound or a pharmaceutically acceptable salt and/or solvate thereof according to any one of clauses 1 to 64 wherein $R_8$ is $N(C_{1-3}\ alkyl)_2$.

Clause 77. The compound or a pharmaceutically acceptable salt and/or solvate thereof according to clause 76 wherein $R_8$ is selected from the group consisting of $N(CH_3)_2$ and $N(CH_3)(CH(CH_3)_2)$.

Clause 78. The compound or a pharmaceutically acceptable salt and/or solvate thereof according to any one of clauses 1 to 64 wherein $R_8$ is $NR_{8b}R_{8c}$.

Clause 79. The compound or a pharmaceutically acceptable salt and/or solvate thereof according to clause 78 wherein $R_{8b}$ is H.

Clause 80. The compound or a pharmaceutically acceptable salt and/or solvate thereof according to clause 78 wherein $R_{8b}$ is $C_{1-3}$ alkyl, such as methyl.

Clause 81. The compound or a pharmaceutically acceptable salt and/or solvate thereof according to clause 78 wherein $R_{8b}$ is $C_{3-6}$ cycloalkyl, such as cyclopropyl or cyclopentyl.

Clause 82. The compound or a pharmaceutically acceptable salt and/or solvate thereof according to clause 78 wherein $R_{8c}$ is H.

Clause 83. The compound or a pharmaceutically acceptable salt and/or solvate thereof according to clause 78 wherein $R_{8c}$ is $C_{1-3}$ alkyl, such as methyl.

Clause 84. The compound or a pharmaceutically acceptable salt and/or solvate thereof according to clause 78 wherein $R_{8c}$ is $C_{3-6}$ cycloalkyl, such as cyclopropyl or cyclopentyl.

Clause 85. The compound or a pharmaceutically acceptable salt and/or solvate thereof according to any one of clauses 1 to 43 wherein:

$R_7$ is

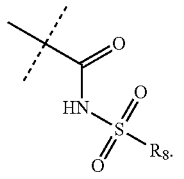

Clause 86. The compound or a pharmaceutically acceptable salt and/or solvate thereof according to clause 85 wherein:

$R_6$ is H and $R_5$ is selected from the group consisting of H, halo, $C_{1-3}$ alkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{5b}$ is selected from the group consisting of H and $C_{1-3}$ alkyl; and $R_{5c}$ is selected from the group consisting of $C_{1-3}$ alkyl and $C_{3-6}$ cycloalkyl.

Clause 87. The compound or a pharmaceutically acceptable salt and/or solvate thereof according to clause 85 wherein:

$R_6$ is H and $R_5$ is selected from the group consisting of H, halo, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring, $R_{5b}$ is selected from the group consisting of H and $C_{1-3}$ alkyl; and $R_{5c}$ is selected from the group consisting of $C_{1-3}$ alkyl and $C_{3-6}$ cycloalkyl.

Clause 88. The compound or a pharmaceutically acceptable salt and/or solvate thereof according to clause 86 or clause 87 wherein $R_5$ is H.

Clause 89. The compound or a pharmaceutically acceptable salt and/or solvate thereof according to clause 86 or clause 87 wherein $R_5$ is halo.

Clause 90. The compound or a pharmaceutically acceptable salt and/or solvate thereof according to clause 86 or clause 87 wherein $R_5$ is $C_{1-3}$alkyl, such as methyl or ethyl.

Clause 91. The compound or a pharmaceutically acceptable salt and/or solvate thereof according to clause 86 or clause 87 wherein $R_5$ is $C_{1-3}$ alkoxy.

Clause 92. The compound or a pharmaceutically acceptable salt and/or solvate thereof according to clause 86 or clause 87 wherein $R_5$ is $C_{1-3}$ haloalkoxy.

Clause 93. The compound or a pharmaceutically acceptable salt and/or solvate thereof according to clause 86 or clause 87 wherein $R_5$ is $SC_{1-3}$ alkyl.

Clause 94. The compound or a pharmaceutically acceptable salt and/or solvate thereof according to clause 86 or clause 87 wherein $R_5$ is $SC_{1-3}$ haloalkyl.

Clause 95. The compound or a pharmaceutically acceptable salt and/or solvate thereof according to clause 86 or clause 87 wherein $R_5$ is $OC_{3-10}$ cycloalkyl.

Clause 96. The compound or a pharmaceutically acceptable salt and/or solvate thereof according to clause 95 wherein $R_5$ is cyclobutyloxy.

Clause 97 The compound or a pharmaceutically acceptable salt and/or solvate thereof according to clause 86 or clause 87 wherein $R_5$ is 4-7 membered heterocycloalkyl.

Clause 98. The compound or a pharmaceutically acceptable salt and/or solvate thereof according to any one of clauses 95 to 96 wherein $R_5$ is unsubstituted.

Clause 99. The compound or a pharmaceutically acceptable salt and/or solvate thereof according to any one of clauses 95 to 97 wherein $R_5$ is substituted by one or more (such as one, two or three e.g. one) $R_{5a}$.

Clause 100. The compound or a pharmaceutically acceptable salt and/or solvate thereof according to clause 99 wherein $R_{5a}$ is halo.

Clause 101. The compound or a pharmaceutically acceptable salt and/or solvate thereof according to clause 99 wherein $R_{5a}$ is $C_{1-3}$ alkyl.

Clause 102. The compound or a pharmaceutically acceptable salt and/or solvate thereof according to clause 99 wherein two $R_{5a}$ groups which are attached to the same carbon atom join to form a $C_{3-6}$ cycloalkyl or 4-7 membered heterocycloalkyl ring.

Clause 103. The compound or a pharmaceutically acceptable salt and/or solvate thereof according to clause 86 or clause 87 wherein $R_5$ is $NR_{5b}R_{5c}$.

Clause 104. The compound or a pharmaceutically acceptable salt and/or solvate thereof according to clause 103 wherein $R_{5b}$ is H.

Clause 105. The compound or a pharmaceutically acceptable salt and/or solvate thereof according to clause 103 wherein $R_{5b}$ is $C_{1-3}$ alkyl.

Clause 106. The compound or a pharmaceutically acceptable salt and/or solvate thereof according to any one of clauses 103 to 105 wherein $R_{5c}$ is $C_{1-3}$ alkyl.

Clause 107. The compound or a pharmaceutically acceptable salt and/or solvate thereof according to any one of clauses 103 to 105 wherein $R_{5c}$ is $C_{3-6}$ cycloalkyl.

Clause 108. The compound or a pharmaceutically acceptable salt and/or solvate thereof according to clause 85 wherein:

$R_5$ is H and $R_6$ is selected from the group consisting of H, halo, $C_{1-3}$ alkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{5b}$ is selected from the group consisting of H and $C_{1-3}$ alkyl; and $R_{5c}$ is selected from the group consisting of $C_{1-3}$ alkyl and $C_{3-6}$ cycloalkyl.

Clause 109. The compound or a pharmaceutically acceptable salt and/or solvate thereof according to clause 85 wherein:

$R_5$ is H and $R_6$ is selected from the group consisting of H, halo, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{6b}R_{6c}$ and 4-7 membered heterocycloalkyl, wherein the $C_{3-10}$ cycloalkyl and 4-7 membered heterocycloalkyl are optionally substituted by one or more $R_{6a}$;

wherein:

$R_{6a}$ is selected from the group consisting of halo and $C_{1-3}$ alkyl, or two $R_{6a}$ groups which are attached to the same carbon atom join to form a $C_{3-6}$ cycloalkyl or 4-7 membered heterocycloalkyl ring, $R_{6b}$ is selected from the group consisting of H and $C_{1-3}$ alkyl; and $R_{6c}$ is selected from the group consisting of $C_{1-3}$ alkyl and $C_{3-6}$ cycloalkyl.

Clause 110. The compound or a pharmaceutically acceptable salt and/or solvate thereof according to clause 108 or clause 109 wherein $R_6$ is H.

Clause 111. The compound or a pharmaceutically acceptable salt and/or solvate thereof according to clause 108 or clause 109 wherein $R_6$ is halo.

Clause 112. The compound or a pharmaceutically acceptable salt and/or solvate thereof according to clause 107 wherein $R_6$ is $C_{1-3}$alkyl, such as methyl or ethyl.

Clause 113. The compound or a pharmaceutically acceptable salt and/or solvate thereof according to clause 108 or clause 109 wherein $R_6$ is $C_{1-3}$ alkoxy.

Clause 114. The compound or a pharmaceutically acceptable salt and/or solvate thereof according to clause 108 or clause 109 wherein $R_6$ is $C_{1-3}$ haloalkoxy.

Clause 115. The compound or a pharmaceutically acceptable salt and/or solvate thereof according to clause 108 or clause 109 wherein $R_6$ is $SC_{1-3}$ alkyl.

Clause 116. The compound or a pharmaceutically acceptable salt and/or solvate thereof according to clause 108 or clause 109 wherein $R_6$ is $SC_{1-3}$ haloalkyl.

Clause 117. The compound or a pharmaceutically acceptable salt and/or solvate thereof according to clause 108 or clause 109 wherein $R_6$ is $OC_{3-10}$ cycloalkyl.

Clause 118. The compound or a pharmaceutically acceptable salt and/or solvate thereof according to clause 117 wherein $R_6$ is cyclobutyloxy.

Clause 119. The compound or a pharmaceutically acceptable salt and/or solvate thereof according to clause 108 or clause 109 wherein $R_6$ is 4-7 membered heterocycloalkyl.

Clause 120. The compound or a pharmaceutically acceptable salt and/or solvate thereof accordingly to clause 119 wherein $R_6$ is pyrrolidinyl.

Clause 121. The compound or a pharmaceutically acceptable salt and/or solvate thereof according to any one of clauses 117 to 120 wherein $R_6$ is unsubstituted.

Clause 122. The compound or a pharmaceutically acceptable salt and/or solvate thereof according to any one of clauses 117 to 120 wherein $R_6$ is substituted by one or more (such as one, two or three e.g. one) $R_{6a}$.

Clause 123. The compound or a pharmaceutically acceptable salt and/or solvate thereof according to clause 122 wherein $R_{6a}$ is halo.

Clause 124. The compound or a pharmaceutically acceptable salt and/or solvate thereof according to clause 122 wherein $R_{6a}$ is $C_{1-3}$ alkyl.

Clause 125. The compound or a pharmaceutically acceptable salt and/or solvate thereof according to clause 122 wherein two $R_{6a}$ groups which are attached to the same carbon atom join to form a $C_{3-6}$ cycloalkyl or 4-7 membered heterocycloalkyl ring.

Clause 126. The compound or a pharmaceutically acceptable salt and/or solvate thereof according to clause 108 or clause 109 wherein $R_6$ is $NR_{6b}R_{6c}$.

Clause 127. The compound or a pharmaceutically acceptable salt and/or solvate thereof according to clause 126 wherein $R_{6b}$ is H.

Clause 128. The compound or a pharmaceutically acceptable salt and/or solvate thereof according to clause 126 wherein $R_{6b}$ is $C_{1-3}$ alkyl.

Clause 129. The compound or a pharmaceutically acceptable salt and/or solvate thereof according to any one of clauses 126 to 128 wherein $R_{6c}$ is $C_{1-3}$ alkyl.

Clause 130. The compound or a pharmaceutically acceptable salt and/or solvate thereof according to any one of clauses 126 to 128 wherein $R_{6c}$ is $C_{3-6}$ cycloalkyl.

Clause 131. The compound or a pharmaceutically acceptable salt and/or solvate thereof according to clause 85 wherein $R_5$ and $R_6$ join to form a 4-8 membered heterocyclic ring.

Clause 132. The compound or a pharmaceutically acceptable salt and/or solvate thereof according to clause 131 wherein $R_5$ and $R_6$ join to form an 8 membered heterocyclic ring.

Clause 133. The compound or a pharmaceutically acceptable salt and/or solvate thereof according to clause 132 wherein $R_5$ and $R_6$ join to form a 5,8-dioxaspiro[3.4]octanyl ring.

Clause 134. The compound or a pharmaceutically acceptable salt and/or solvate thereof according to any one of clauses 1 to 35 and 85 to 133 wherein $R_8$ is $C_{3-6}$ cycloalkyl.

Clause 135. The compound or a pharmaceutically acceptable salt and/or solvate thereof according to any one of clauses 1 to 35 and 85 to 133 wherein $R_8$ is 4-8 membered heterocycloalkyl.

Clause 136. The compound or a pharmaceutically acceptable salt and/or solvate thereof according to clause 135 wherein $R_8$ is pyrrolidinyl.

Clause 137. The compound or a pharmaceutically acceptable salt and/or solvate thereof according to any one of clauses 134 to 136 wherein $R_8$ is unsubstituted.

Clause 138. The compound or a pharmaceutically acceptable salt and/or solvate thereof according to any one of clauses 134 to 136 wherein $R_8$ is substituted by one or more (such as one, two or three, e.g. one) $R_{8a}$.

Clause 139 The compound or a pharmaceutically acceptable salt and/or solvate thereof according to clause 138 wherein $R_{8a}$ is $C_{1-3}$ alkyl.

Clause 140. The compound or a pharmaceutically acceptable salt and/or solvate thereof according to clause 138 wherein $R_{8a}$ is halo.

Clause 141. The compound or a pharmaceutically acceptable salt and/or solvate thereof according to clause 138 wherein $R_{8a}$ is $C_{1-3}$ haloalkyl.

Clause 142. The compound or a pharmaceutically acceptable salt and/or solvate thereof according to any one of clauses 1 to 35 and 85 to 133 wherein $R_8$ is $N(C_{1-3}\ alkyl)_2$.

Clause 143. The compound or a pharmaceutically acceptable salt and/or solvate thereof according to any one of clauses 1 to 35 and 85 to 133 wherein $R_8$ is $NR_{8b}R_{8c}$.

Clause 144. The compound or a pharmaceutically acceptable salt and/or solvate thereof according to clause 143 wherein $R_{8b}$ is H.

Clause 145. The compound or a pharmaceutically acceptable salt and/or solvate thereof according to clause 143 wherein $R_{8b}$ is $C_{1-3}$ alkyl, such as methyl.

Clause 146. The compound or a pharmaceutically acceptable salt and/or solvate thereof according to clause 143 wherein $R_{8b}$ is $C_{3-6}$ cycloalkyl, such as cyclopropyl or cyclopentyl.

Clause 147. The compound or a pharmaceutically acceptable salt and/or solvate thereof according to clause 143 wherein $R_{8c}$ is H.

Clause 148. The compound or a pharmaceutically acceptable salt and/or solvate thereof according to clause 143 wherein $R_{8c}$ is $C_{1-3}$ alkyl, such as methyl.

Clause 149. The compound or a pharmaceutically acceptable salt and/or solvate thereof according to clause 143 wherein $R_{8c}$ is $C_{3-6}$ cycloalkyl, such as cyclopropyl or cyclopentyl.

Clause 150. The compound or a pharmaceutically acceptable salt and/or solvate thereof according to any one of clauses 1 to 149 wherein $R_4$ is 4-7 membered heterocycloalkyl and is attached via a nitrogen atom.

Clause 151. The compound or a pharmaceutically acceptable salt and/or solvate thereof according to any one of clauses 1 to 150 wherein $R_5$ is 4-7 membered heterocycloalkyl and is attached via a nitrogen atom.

Clause 152. The compound or a pharmaceutically acceptable salt and/or solvate thereof according to any one of clauses 1 to 151 wherein $R_6$ is 4-7 membered heterocycloalkyl and is attached via a nitrogen atom.

Clause 153. The compound or a pharmaceutically acceptable salt and/or solvate thereof according any one of clauses 1 to 152 wherein $R_8$ is 4-8 membered heterocycloalkyl and is attached via a nitrogen atom.

Clause 154. The compound or a pharmaceutically acceptable salt and/or solvate thereof according to clause 1 which is selected from the list consisting of:

(R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-cyclobutoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-(cyclopentyloxy)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-(cyclopentyloxy)-N—(N,N-dimethylsulfamoyl)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-(cyclopentyloxy)-3-fluoro-N-(pyrrolidin-1-ylsulfonyl)benzamide;

(R)-2-cyclobutoxy-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

(R)-2-(cyclopentyloxy)-4-(8-(3-(methoxymethyl)-4-methylpiperazin-1-yl)-7-methyl-5-oxo-1,3,4,5-tetrahydro-2H- chromeno[3,4-c]pyridine-3-carbonyl)-N-((1-methylcyclopropyl)sulfonyl)benzamide;

(R)-2-(cyclopentyloxy)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-cyclobutoxy-N-((1-methylcyclopropyl)sulfonyl)benzamide;

2-(((1R,3r,5S)-bicyclo[3.1.0]hexan-3-yl)oxy)-N—(N,N-dimethylsulfamoyl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(cyclopentyloxy)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

2-(((1R,3r,5S)-bicyclo[3.1.0]hexan-3-yl)oxy)-N—(N,N-dimethylsulfamoyl)-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-cyclobutoxy-N-(pyrrolidin-1-ylsulfonyl)benzamide;

(R)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)-2-(pyrrolidin-1-yl)benzamide;

(R)-2-(7-azabicyclo[2.2.1]heptan-7-yl)-N—(N,N-dimethylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-2-(7-azabicyclo[2.2.1]heptan-7-yl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

(R)—N—(N,N-dimethylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-2-(pyrrolidin-1-yl)benzamide;

(R)-2-cyclobutoxy-4-(8-(hexahydropyrazino[2,1-c][1,4]oxazin-8(1H)-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)—N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)benzamide;

(R)-2-cyclobutoxy-4-(8-(hexahydropyrazino[2,1-c][1,4]oxazin-8(1H)-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-(7-azabicyclo[2.2.1]heptan-7-yl)-6-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

(R)-2-(7-azabicyclo[2.2.1]heptan-7-yl)-N—(N,N-dimethylsulfamoyl)-6-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-2-(cyclopentyloxy)-3-fluoro-N—(N-isopropyl-N-methylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-cyclobutoxy-3-fluoro-N—(N-isopropyl-N-methylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-(3-azabicyclo[3.1.0]hexan-3-yl)-6-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

2-(3-azabicyclo[3.1.0]hexan-3-yl)-N—(N,N-dimethylsulfamoyl)-6-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

2-(3-azabicyclo[3.1.0]hexan-3-yl)-N—(N,N-dimethylsulfamoyl)-6-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-(cyclopentyloxy)-3-fluoro-N—(N-isopropyl-N-methylsulfamoyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-cyclobutoxy-3-fluoro-N—(N-isopropyl-N-methylsulfamoyl)benzamide;

(R)—N—(N-isopropyl-N-methylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-2-(pyrrolidin-1-yl)benzamide;

2-(3-azabicyclo[3.1.0]hexan-3-yl)-6-chloro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

2-(3-azabicyclo[3.1.0]hexan-3-yl)-6-chloro-N—(N,N-dimethylsulfamoyl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

2-(3-azabicyclo[3.1.0]hexan-3-yl)-6-chloro-N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-(((1R,3r,5S)-bicyclo[3.1.0]hexan-3-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

2-(((1R,3r,5S)-bicyclo[3.1.0]hexan-3-yl)oxy)-3-fluoro-N—(N-isopropyl-N-methylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-(((1R,3r,5S)-bicyclo[3.1.0]hexan-3-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(cyclobutyl(methyl)amino)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(cyclobutyl(methyl)amino)-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(7-azabicyclo[2.2.1]heptan-7-yl)-6-chloro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

(R)-2-cyclobutoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

(R)-2-(cyclopentyloxy)-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-(cyclopentyloxy)-N—(N,N-dimethylsulfamoyl)-3-fluorobenzamide;

(R)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-(pyrrolidin-1-yl)benzamide;

2-(3-azabicyclo[3.1.0]hexan-3-yl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

2-(3-azabicyclo[3.1.0]hexan-3-yl)-N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(7-azabicyclo[2.2.1]heptan-7-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(7-azabicyclo[2.2.1]heptan-7-yl)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-cyclobutoxy-N—(N,N-dimethylsulfamoyl)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-2-cyclobutoxy-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-cyclobutoxy-N—(N,N-dimethylsulfamoyl)-3-fluorobenzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-cyclobutoxy-3-fluoro-N-(pyrrolidin-1-ylsulfonyl)benzamide;

(R)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)-2-(cyclobutyl(methyl)amino)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-cyclobutoxy-3-fluoro-N—(N-isopropyl-N-methylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-(cyclopentyloxy)-3-fluoro-N-((1-methylcyclopropyl)sulfonyl)benzamide;

(R)-2-(cyclopentyloxy)-3-fluoro-N—(N-isopropyl-N-methylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

2-(((1R,3r,5S)-bicyclo[3.1.0]hexan-3-yl)oxy)-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

2-(((1R,3r,5S)-bicyclo[3.1.0]hexan-3-yl)oxy)-4-(7-chloro-8-((R)-3-(methoxymethyl)-4-methylpiperazin-1-yl)-5-oxo-1,3,4,5-tetrahydro-2H-chromeno[3,4-c]pyridine-3-carbonyl)-3-fluoro-N-((1-methylcyclopropyl)sulfonyl)benzamide;

2-(((1R,3r,5S)-bicyclo[3.1.0]hexan-3-yl)oxy)-4-(7-chloro-8-((R)-3-(methoxymethyl)-4-methylpiperazin-1-yl)-5-oxo-1,3,4,5-tetrahydro-2H-chromeno[3,4-c]pyridine-3-carbonyl)-N—(N,N-dimethylsulfamoyl)-3-fluorobenzamide;

2-(((1R,3r,5S)-bicyclo[3.1.0]hexan-3-yl)oxy)-4-(7-chloro-8-((R)-3-(methoxymethyl)-4-methylpiperazin-1-yl)-5-oxo-1,3,4,5-tetrahydro-2H-chromeno[3,4-c]pyridine-3-carbonyl)-3-fluoro-N-(pyrrolidin-1-ylsulfonyl)benzamide;

2-(((1R,3r,5S)-bicyclo[3.1.0]hexan-3-yl)oxy)-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

2-(((1R,3r,5S)-bicyclo[3.1.0]hexan-3-yl)oxy)-3-fluoro-N—(N-isopropyl-N-methylsulfamoyl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

2-(((1R,3r,5S)-bicyclo[3.1.0]hexan-3-yl)oxy)-4-(7-chloro-8-((R)-3-(methoxymethyl)-4-methylpiperazin-1-yl)-5-oxo-1,3,4,5-tetrahydro-2H-chromeno[3,4-c]pyridine-3-carbonyl)-3-fluoro-N—(N-isopropyl-N-methylsulfamoyl)benzamide;

2-(((1R,3s,5S)-bicyclo[3.1.0]hexan-3-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

2-(((1R,3s,5S)-bicyclo[3.1.0]hexan-3-yl)oxy)-N—(N,N-dimethylsulfamoyl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-(((1R,3s,5S)-bicyclo[3.1.0]hexan-3-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-(pyrrolidin-1-yl)benzamide;

(R)—N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)benzamide;

2-(3-azabicyclo[3.1.0]hexan-3-yl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

2-(3-azabicyclo[3.1.0]hexan-3-yl)-N—(N,N-dimethylsulfamoyl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(7-azabicyclo[2.2.1]heptan-7-yl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(7-azabicyclo[2.2.1]heptan-7-yl)-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(3,3-difluoropiperidin-1-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(3,3-difluoropiperidin-1-yl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(3,3-difluoropiperidin-1-yl)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(3,3-difluoropiperidin-1-yl)-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(7-azabicyclo[2.2.1]heptan-7-yl)-6-chloro-N—(N,N-dimethylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-2-(3,3-difluoropyrrolidin-1-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(3,3-difluoropyrrolidin-1-yl)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(cyclopropyl(methyl)amino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(cyclopropyl(methyl)amino)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-((4,4-difluorocyclohexyl)oxy)-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-((4,4-difluorocyclohexyl)oxy)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(3,3-dimethylpyrrolidin-1-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(3,3-dimethylpyrrolidin-1-yl)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(azetidin-1-yl)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-((adamantan-2-yl)oxy)-N—(N,N-dimethylsulfamoyl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(azetidin-1-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(3,3-difluoropyrrolidin-1-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-N—(N,N-dimethylsulfamoyl)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-((adamantan-2-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

2-(3-azabicyclo[3.1.0]hexan-3-yl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)-N-(pyrrolidin-1-ylsulfonyl)benzamide;

(R)-2-(7-azabicyclo[2.2.1]heptan-7-yl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)-N-(pyrrolidin-1-ylsulfonyl)benzamide;

(R)-2-((4,4-difluorocyclohexyl)oxy)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

2-((adamantan-2-yl)oxy)-N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(cyclopentyloxy)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)-6-(trifluoromethyl)benzamide;

N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-2-((R)-2-methylpyrrolidin-1-yl)benzamide;

N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-2-((S)-2-methylpyrrolidin-1-yl)benzamide;

2-(3-azabicyclo[3.1.0]hexan-3-yl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)-6-(trifluoromethyl)benzamide;

2-(3-azabicyclo[3.1.0]hexan-3-yl)-6-chloro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)—N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-methyl-6-(pyrrolidin-1-yl)benzamide;

(R)-2-(cyclopentyloxy)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;

2-(bicyclo[3.1.0]hexan-3-yloxy)-N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-(bicyclo[3.1.0]hexan-3-yloxy)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(96 yrrolidine-1-ylsulfonyl)benzamide;

(R)-2-(cyclopentyloxy)-N—(N,N-dimethylsulfamoyl)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(cyclopentyloxy)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

2-(3-azabicyclo[3.1.0]hexan-3-yl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;

2-(bicyclo[3.1.0]hexan-3-yloxy)-N—(N,N-dimethylsulfamoyl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

2-(bicyclo[3.1.0]hexan-3-yloxy)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

2-(2-azabicyclo[2.2.1]heptan-2-yl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

2-(2-azabicyclo[2.2.1]heptan-2-yl)-N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(cyclopentyloxy)-N—(N,N-dimethylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-6-(trifluoromethyl)benzamide;

2-(3-azabicyclo[3.1.0]hexan-3-yl)-N—(N,N-dimethylsulfamoyl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-6-(trifluoromethyl)benzamide;

(R)—N—(N,N-dimethylsulfamoyl)-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-6-(pyrrolidin-1-yl)benzamide;

(R)—N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(5-azaspiro[2.5]octan-5-yl)benzamide;

(R)-2-(7-azabicyclo[2.2.1]heptan-7-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-2-((S)-2-methylpyrrolidin-1-yl)-N-(pyrrolidin-1-ylsulfonyl)benzamide;

4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-((R)-2-methylpyrrolidin-1-yl)benzamide;

4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-2-((R)-2-methylpyrrolidin-1-yl)-N-(pyrrolidin-1-ylsulfonyl)benzamide;

4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-((S)-2-methylpyrrolidin-1-yl)benzamide;

2-(3-azabicyclo[3.1.0]hexan-3-yl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-(cyclopentyloxy)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-6-(pyrrolidin-1-yl)benzamide;

(R)-2-(cyclopentyloxy)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-6-(trifluoromethyl)benzamide;

(R)-2-(cyclopentyloxy)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;

(R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-6-(trifluoromethyl)benzamide;

(S)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;

(R)-2-cyclobutoxy-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;

(R)—N—(N,N-dimethylsulfamoyl)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-(dimethylamino)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(dimethylamino)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

(R)-2-(dimethylamino)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-(dimethylamino)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-5-methyl-N-(pyrrolidin-1-ylsulfonyl)benzamide;

(R)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)-N-(pyrrolidin-1-ylsulfonyl)benzamide;

(R)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-(pyrrolidin-1-yl)benzamide;

(R)-2-cyclobutoxy-4-(8-(3-(ethoxymethyl)-4-methylpiperazin-1-yl)-7-methyl-5-oxo-1,3,4,5-tetrahydro-2H-chromeno[3,4-c]pyridine-3-carbonyl)-3-fluoro-N-(pyrrolidin-1-ylsulfonyl)benzamide;

(R)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)—N—(N,N-dimethylsulfamoyl)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)—N—(N,N-dimethylsulfamoyl)-3-fluoro-2-isopropoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-3-fluoro-2-isopropoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-chloro-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-chloro-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-5-(trifluoromethyl)benzamide;

(R)-2-(cyclopentyloxy)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-6-(trifluoromethyl)benzamide;

(R)-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;

(R)—N-((6-azaspiro[2.5]octan-6-yl)sulfonyl)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.1.0]hexan-3-yl)sulfonyl)-3-fluoro-2-methoxy-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-oxa-8-azabicyclo[3.2.1]octan-8-yl)sulfonyl)-3-fluoro-2-methoxy-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-5-(trifluoromethyl)benzamide;

(R)-2-ethoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;

(R)-2-isopropoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;

(R)-2-cyclobutoxy-5-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-3-cyclobutoxy-5-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-6-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)spiro[benzo[d][1,3]dioxole-2,1'-cyclobutane]-4-carboxamide;

(R)—N-((7-azabicyclo[2.2.1]heptan-7-yl)sulfonyl)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-2-cyclobutoxy-4-fluoro-5-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-3-cyclobutoxy-4-fluoro-5-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

2-cyclobutoxy-N-(((2R,5R)-2,5-dimethylpyrrolidin-1-yl)sulfonyl)-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-2-cyclobutoxy-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-3-methyl-N-((1-methylcyclopropyl)sulfonyl)benzamide;

(R)-4-fluoro-5-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)spiro[benzo[d][1,3]dioxole-2,1'-cyclobutane]-7-carboxamide;

(R)-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-5-(trifluoromethyl)benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-2-(trifluoromethoxy)benzamide;

(R)-2-chloro-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-3-fluoro-4-(8-(4-isopropyl-3-(methoxymethyl)piperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)-2-(difluoromethoxy)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-4-(8-(4-ethyl-3-(methoxymethyl)piperazin-1-yl)-7-methyl-5-oxo-1,3,4,5-tetrahydro-2H-chromeno[3,4-c]pyridine-3-carbonyl)-3-fluoro-N-(pyrrolidin-1-ylsulfonyl)benzamide;

(R)-2-cyclobutoxy-4-(8-(4-cyclopropyl-3-(methoxymethyl)piperazin-1-yl)-7-methyl-5-oxo-1,3,4,5-tetrahydro-2H-chromeno[3,4-c]pyridine-3-carbonyl)-3-fluoro-N-(pyrrolidin-1-ylsulfonyl)benzamide;

(S)-2-cyclobutoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide; and (S)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

or a pharmaceutically acceptable salt and/or solvate thereof.

Clause 155. The compound or a pharmaceutically acceptable salt and/or solvate thereof according to clause 1 which is selected from the list consisting of:

N-((3-azabicyclo[3.1.0]hexan-3-yl)sulfonyl)-2-(dimethylamino)-5-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-2-cyclobutoxy-3-fluoro-4-(8-(3-(methoxymethyl)-4-methylpiperazin-1-yl)-5-oxo-1,3,4,5-tetrahydro-2H-chromeno[3,4-c]pyridine-3-carbonyl)-N-(pyrrolidin-1-ylsulfonyl)benzamide;

(R)-2-(cyclopentyloxy)-3-fluoro-4-(8-(3-(methoxymethyl)-4-methylpiperazin-1-yl)-5-oxo-1,3,4,5-tetrahydro-2H-chromeno[3,4-c]pyridine-3-carbonyl)-N-(pyrrolidin-1-ylsulfonyl)benzamide;

(R)-3-chloro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)—N-((7-azabicyclo[2.2.1]heptan-7-yl)sulfonyl)-3-chloro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-cyclobutoxy-3-fluoro-4-(8-(3-(methoxymethyl)-4-methylpiperazin-1-yl)-10-methyl-5-oxo-1,3,4,5-tetrahydro-2H-chromeno[3,4-c]pyridine-3-carbonyl)-N-(pyrrolidin-1-ylsulfonyl)benzamide;

(R)-2-(cyclopentyloxy)-3-fluoro-4-(8-(3-(methoxymethyl)-4-methylpiperazin-1-yl)-10-methyl-5-oxo-1,3,4,5-tetrahydro-2H-chromeno[3,4-c]pyridine-3-carbonyl)-N-(pyrrolidin-1-ylsulfonyl)benzamide;

(R)—N-((7-azabicyclo[2.2.1]heptan-7-yl)sulfonyl)-2-(dimethylamino)-5-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)—N-((6-azaspiro[2.5]octan-6-yl)sulfonyl)-2-(dimethylamino)-5-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)—N-((6-azaspiro[2.5]octan-6-yl)sulfonyl)-5-chloro-2-(dimethylamino)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-2-(dimethylamino)-5-fluoro-4-(8-(3-(methoxymethyl)-4-methylpiperazin-1-yl)-5-oxo-1,3,4,5-tetrahydro-2H-chromeno[3,4-c]pyridine-3-carbonyl)benzamide;

(R)-2-cyclobutoxy-3-fluoro-4-(8-(3-(isopropoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)—N-((7-azabicyclo[2.2.1]heptan-7-yl)sulfonyl)-5-chloro-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(azetidin-1-yl)-5-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-amino-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(piperidin-1-ylsulfonyl)benzamide;

(R)-2-ethoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(piperidin-1-ylsulfonyl)benzamide;

(R)—N—(N-cyclopentyl-N-methylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(cyclobutyl(methyl)amino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(methylamino)-N-(pyrrolidin-1-ylsulfonyl)benzamide;

(R)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

N-((3-azabicyclo[3.1.0]hexan-3-yl)sulfonyl)-2-(azetidin-1-yl)-5-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-3-fluoro-N-((4-fluoropiperidin-1-yl)sulfonyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-propoxy-N-(pyrrolidin-1-ylsulfonyl)benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-2-(2,2,2-trifluoroethoxy)benzamide;

N-((3-azabicyclo[3.1.0]hexan-3-yl)sulfonyl)-2-cyclopropoxy-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.1.0]hexan-3-yl)sulfonyl)-4-(7-chloro-8-((R)-3-(methoxymethyl)-4-methylpiperazin-1-yl)-5-oxo-1,3,4,5-tetrahydro-2H-chromeno[3,4-c]pyridine-3-carbonyl)-2-ethoxy-3-fluorobenzamide;

(R)—N-((7-azabicyclo[2.2.1]heptan-7-yl)sulfonyl)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-ethoxy-3-fluorobenzamide N-(((3aR,6aS)-hexahydrocyclopenta[c]pyrrol-2(1H)-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((octahydro-2H-isoindol-2-yl)sulfonyl)benzamide;

(R)-2-cyclopropoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)—N-((7-azabicyclo[2.2.1]heptan-7-yl)sulfonyl)-2-cyclopropoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.1.0]hexan-3-yl)sulfonyl)-2-ethoxy-4-(7-ethyl-8-((R)-3-(methoxymethyl)-4-methylpiperazin-1-yl)-5-oxo-1,3,4,5-tetrahydro-2H-chromeno[3,4-c]pyridine-3-carbonyl)-3-fluorobenzamide;

(R)—N-((7-azabicyclo[2.2.1]heptan-7-yl)sulfonyl)-2-ethoxy-4-(7-ethyl-8-(3-(methoxymethyl)-4-methylpiperazin-1-yl)-5-oxo-1,3,4,5-tetrahydro-2H-chromeno[3,4-c]pyridine-3-carbonyl)-3-fluorobenzamide;

(R)—N—(N,N-dicyclopropylsulfamoyl)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((3,3-dimethylpyrrolidin-1-yl)sulfonyl)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.1.0]hexan-3-yl)sulfonyl)-2-ethoxy-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((2-azaspiro[3.3]heptan-2-yl)sulfonyl)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-oxa-8-azabicyclo[3.2.1]octan-8-yl)sulfonyl)-2-ethoxy-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-2-(3,3,3-trifluoropropoxy)benzamide;

(R)-3-ethoxy-2-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-fluoro-2-(methoxy-d3)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)—N-((7-azabicyclo[2.2.1]heptan-7-yl)sulfonyl)-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-2-ethoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.1.0]hexan-3-yl)sulfonyl)-2-ethoxy-3-fluoro-4-(8-((R)-3-(methoxymethyl)-4-methylpiperazin- 1-yl)-7,10-dimethyl-5-oxo-1,3,4,5-tetrahydro-2H-chromeno[3,4-c]pyridine-3-carbonyl)benzamide;

N-((2-azabicyclo[2.2.1]heptan-2-yl)sulfonyl)-2-ethoxy-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)—N—(N,N-dicyclopropylsulfamoyl)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-ethoxy-3-fluoro-N-(((3aR,6aS)-hexahydrocyclopenta[c]pyrrol-2(1H)-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((2-azaspiro[3.3]heptan-2-yl)sulfonyl)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((8-azabicyclo[3.2.1]octan-8-yl)sulfonyl)-2-ethoxy-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.2.1]octan-3-yl)sulfonyl)-2-ethoxy-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((8-azabicyclo[3.2.1]octan-8-yl)sulfonyl)-2-ethoxy-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

N-((3-azabicyclo[3.2.1]octan-3-yl)sulfonyl)-2-ethoxy-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)—N—(N-cyclopentyl-N-methylsulfamoyl)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(piperidin-1-ylsulfonyl)benzamide;

(R)-3-fluoro-N-((4-fluoropiperidin-1-yl)sulfonyl)-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-methylbenzamide;

(R)-5-(dimethylamino)-2-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)—N-((7-azabicyclo[2.2.1]heptan-7-yl)sulfonyl)-2-ethyl-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-ethoxy-4-(10-ethyl-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-N-(pyrrolidin-1-ylsulfonyl)benzamide;

(R)-2-(dimethylamino)-4-(10-ethyl-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-N-(pyrrolidin-1-ylsulfonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-(methoxy-d3)-N-(pyrrolidin-1-ylsulfonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(pyrrolidin-1-ylsulfonyl)benzamide;

(R)—N-((7-azabicyclo[2.2.1]heptan-7-yl)sulfonyl)-5-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.1.0]hexan-3-yl)sulfonyl)-5-fluoro-2-methoxy-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-5-fluoro-2-(methoxy-d3)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.1.0]hexan-3-yl)sulfonyl)-5-fluoro-2-(methoxy-d3)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-3-fluoro-2-(methoxy-d3)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((2-azaspiro[3.3]heptan-2-yl)sulfonyl)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-(dimethylamino)-5-fluoro-N—(((S)-3-fluoropyrrolidin-1-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-oxa-8-azabicyclo[3.2.1]octan-8-yl)sulfonyl)-2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N—(N-cyclopropyl-N-methylsulfamoyl)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-3-fluoro-N-(pyrrolidin-1-ylsulfonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluoro-N-(pyrrolidin-1-ylsulfonyl)benzamide;

(R)-4-(10-chloro-8-(3-(methoxymethyl)-4-methylpiperazin-1-yl)-7-methyl-5-oxo-1,3,4,5-tetrahydro-2H-chromeno

[3,4-c]pyridine-3-carbonyl)-2-(dimethylamino)-N—(N,N-dimethylsulfamoyl)-5-fluorobenzamide;

2-ethoxy-5-fluoro-N—(((R)-3-fluoropyrrolidin-1-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-methoxy-N-(pyrrolidin-1-ylsulfonyl)benzamide;

(R)-2-cyclopropoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

N-((3-azabicyclo[3.1.0]hexan-3-yl)sulfonyl)-2-cyclopropoxy-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl) benzamide;

(R)-2-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-fluoro-5-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

N-(((1 S,4S)-2-oxa-5-azabicyclo[2.2.1]heptan-5-yl)sulfonyl)-2-ethoxy-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl) benzamide;

2-ethoxy-5-fluoro-N—(((S)-3-fluoropyrrolidin-1-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N—(N-cyclopropyl-N-methylsulfamoyl)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide; and (R)-2-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-5-methyl-N-(pyrrolidin-1-ylsulfonyl)benzamide;

or a pharmaceutically acceptable salt and/or solvate of any one thereof.

Clause 156. The compound or a pharmaceutically acceptable salt and/or solvate thereof according to clause 1 which is selected from the list consisting of:

(R)—N-((2-oxa-5-azaspiro[3.5]nonan-5-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c] pyridine-3-carbonyl)-2-(dimethylamino)-5-fluorobenzamide;

(R)—N-((2-oxa-6-azaspiro[3.5]nonan-6-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c] pyridine-3-carbonyl)-2-(dimethylamino)-5-fluorobenzamide;

R)—N-((2-oxa-6-azaspiro[3.4]octan-6-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c] pyridine-3-carbonyl)-2-(dimethylamino)-5-fluorobenzamide;

(R)—N-((5-azaspiro[2.4]heptan-5-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c] pyridine-3-carbonyl)-2-(dimethylamino)-5-fluorobenzamide;

R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(piperidin-1-ylsulfonyl)benzamide;

(R)—N—(N,N-dicyclopropylsulfamoyl)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-N—(N,N-dicyclopropylsulfamoyl)-2-(dimethylamino)-5-fluorobenzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N—(((R)-2-(trifluoromethyl)pyrrolidin-1-yl)sulfonyl) benzamide;

(R)—N-((2-azaspiro[3.3]heptan-2-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c] pyridine-3-carbonyl)-2-methoxybenzamide;

N-((3-azabicyclo[3.1.0]hexan-3-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c] pyridine-3-carbonyl)-2-methoxybenzamide;

2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N—(((S)-3-methoxypiperidin-1-yl)sulfonyl)benzamide;

(R)—N-((2-oxa-6-azaspiro[3.3]heptan-6-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-methoxy-N—(((S)-2-(methoxymethyl)pyrrolidin-1-yl)sulfonyl)benzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N—(((S)-3-methoxypyrrolidin-1-yl)sulfonyl)benzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N—(((R)-3-methoxypyrrolidin-1-yl)sulfonyl)benzamide;

2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N—(((R)-3-methoxypiperidin-1-yl)sulfonyl)benzamide;

2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N—(((R)-2-(trifluoromethyl)pyrrolidin-1-yl)sulfonyl) benzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-methoxy-N—(((R)-2-(methoxymethyl)pyrrolidin-1-yl)sulfonyl)benzamide;

(R)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((4-methoxypiperidin-1-yl)sulfonyl)benzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N—(((R)-2-(methoxymethyl)pyrrolidin-1-yl)sulfonyl)benzamide;

(R)-5-chloro-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-N—(N,N-dimethylsulfamoyl)benzamide;

2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N—(((S)-2-(trifluoromethyl)pyrrolidin-1-yl)sulfonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-((4-(trifluoromethyl)piperidin-1-yl)sulfonyl)benzamide;

N-(((1R,4R)-2-oxa-5-azabicyclo[2.2.1]heptan-5-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N—(((S)-2-(trifluoromethyl)pyrrolidin-1-yl)sulfonyl)benzamide;

(R)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((4-(trifluoromethyl)piperidin-1-yl)sulfonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-N—(N,N-dicyclopropylsulfamoyl)-5-fluoro-2-methoxybenzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-N—(N-cyclopropyl-N-methylsulfamoyl)-2-ethoxy-5-fluorobenzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluoro-N-((1-methylcyclopropyl)sulfonyl)benzamide;

(R)—N-((2-azaspiro[3.3]heptan-2-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluorobenzamide;

N-((8-oxa-3-azabicyclo[3.2.1]octan-3-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluorobenzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N—(((S)-3-fluoropyrrolidin-1-yl)sulfonyl)benzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N—(((R)-3-fluoropyrrolidin-1-yl)sulfonyl)benzamide;

(R)—N-((7-azabicyclo[2.2.1]heptan-7-yl)sulfonyl)-2-(dimethylamino)-5-fluoro-4-(10-fluoro-8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-5-fluoro-4-(10-fluoro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-methoxybenzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-cyclopropoxy-N—(N,N-dimethylsulfamoyl)-5-fluorobenzamide;

N-((3-oxa-8-azabicyclo[3.2.1]octan-8-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-cyclopropoxy-5-fluorobenzamide;

(R)-2-(dimethylamino)-5-fluoro-4-(10-fluoro-8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)-5-fluoro-4-(10-fluoro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-methoxy-N-(pyrrolidin-1-ylsulfonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-fluoro-5-methyl-N-(pyrrolidin-1-ylsulfonyl)benzamide;

2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N—(((R)-2-(methoxymethyl)pyrrolidin-1-yl)sulfonyl)benzamide;

2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N—(((S)-2-(methoxymethyl)pyrrolidin-1-yl)sulfonyl)benzamide;

N-(((1 S,4S)-2-oxa-5-azabicyclo[2.2.1]heptan-5-yl)sulfonyl)-2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-(dimethylamino)-5-fluoro-N—(((R)-3-fluoropyrrolidin-1-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.1.0]hexan-3-yl)sulfonyl)-2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

(R)—N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluorobenzamide;

(R)—N-((2-azaspiro[3.3]heptan-2-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

(R)-4-(10-chloro-8-(3-(methoxymethyl)-4-methylpiperazin-1-yl)-7-methyl-5-oxo-1,3,4,5-tetrahydro-2H-chromeno

[3,4-c]pyridine-3-carbonyl)-2-fluoro-5-methoxy-N-(pyrrolidin-1-ylsulfonyl)benzamide;

(R)—N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxybenzamide;

(R)—N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-methoxybenzamide;

N-((3-oxa-8-azabicyclo[3.2.1]octan-8-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-N—(N-cyclopropyl-N-methylsulfamoyl)-2-(dimethylamino)-5-fluorobenzamide;

(R)—N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-methoxybenzamide;

N-((3-azabicyclo[3.1.0]hexan-3-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-methoxybenzamide;

(R)—N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-(methoxy-d3)benzamide;

N-((3-azabicyclo[3.1.0]hexan-3-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-(methoxy-d3)benzamide;

(R)-5-chloro-2-(methoxy-d3)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-chloro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-chloro-2-ethoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide; and (R)—N-((7-azabicyclo[2.2.1]heptan-7-yl)sulfonyl)-2-cyclopropoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

or a pharmaceutically acceptable salt and/or solvate of any one thereof.

Clause 157. The pharmaceutically acceptable salt according to any one of clauses 1 to 156.

Clause 158. The pharmaceutically acceptable solvate according to any one of clauses 1 to 156.

Clause 159. The compound according to any one of clauses 1 to 156.

Clause 160. A pharmaceutical composition comprising a compound or pharmaceutically acceptable salt and/or solvate thereof according to any one of clauses 1 to 159 and one or more pharmaceutically acceptable diluents or carriers.

Clause 161. A compound or pharmaceutically acceptable salt and/or solvate thereof according to any one of clauses 1 to 159 or a pharmaceutical composition according to clause 133 for use as a medicament.

Clause 162. A compound or pharmaceutically acceptable salt and/or solvate thereof according to any one of clauses 1 to 159 or a pharmaceutical composition according to clause 158 for use in the treatment or prevention of a disease selected from the group consisting of inflammatory, autoimmune or fibrotic diseases, and cancer.

Clause 163. Use of a compound or salt and/or solvate thereof according to any one of clauses 1 to 159 or a pharmaceutical composition according to clause 160 in the manufacture of a medicament for treating or preventing a disease selected from inflammatory, autoimmune and fibrotic diseases, and cancer.

Clause 164. A method of treating or preventing a disease selected from inflammatory, autoimmune and fibrotic diseases, and cancer, which comprises administering a compound or salt and/or solvate thereof according to any one of clauses 1 to 159 or a pharmaceutical composition according to clause 160.

Clause 165. The compound for use, composition for use, use or method according to any one of clauses 162 to 164 wherein the inflammatory, autoimmune or fibrotic disease is selected from the group consisting of rheumatoid arthritis, juvenile idiopathic arthritis, psoriatic arthritis, psoriasis, myasthenia gravis (MG), Crohn's disease, multiple sclerosis, sarcoidosis, ulcerative colitis, Celiac's disease, systemic lupus erythematosus (SLE), Sjogren's syndrome, asthma, atopic dermatitis, vitiligo, systemic sclerosis (SSC), graft versus host disease (GvHD), Type 1 diabetes, Hidradenitis suppurativa, idiopathic pulmonary fibrosis (IPF), interstitial lung disease (ILD) and non-alcoholic steatohepatitis (NASH).

Clause 166. The compound for use, composition for use, use or method according to any one of clauses 162 to 164 wherein the cancer is selected from the group consisting of acute lymphoblastic leukaemia (ALL), primary central nervous system lymphoma (PCNSL), lymphoma, mycosis fungoides, refectory non-Hodgkin lymphoma (NHL), head and neck squamous cell carcinoma (HNSCC), non-small cell lung cancer (NSCLC), bladder cancer, lymphoma, breast cancer, osteosarcoma, gestational trophoblastic neoplasia (GTN), acute myeloid leukaemia (AML), hepatocellular carcinoma, renal cell carcinoma, colorectal cancer, lung cancer, glioma, ovarian cancer, melanoma, and solid tumours such as cervical, uterine, testicular, stomach, prostate and pancreatic tumours.

Clause 167. The compound for use, composition for use, use or method according to clause 166 wherein the cancer is selected from the group consisting of acute lymphoblastic leukaemia (ALL), primary central nervous system lymphoma (PCNSL), lymphoma, mycosis fungoides, refectory non-Hodgkin lymphoma (NHL) and acute myeloid leukaemia (AML).

Clause 168. A process for preparing a compound of formula (I), or a salt such as a pharmaceutical acceptable salt thereof, which comprises coupling a compound of formula (II):

(II)

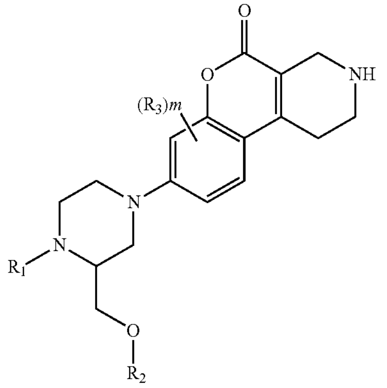

or a salt and/or solvate thereof;

wherein $R_1$, $R_2$, $R_3$ and m are as defined in any one of clauses 1 to 156;

with a compound of formula (III):

or a salt and/or solvate thereof;

(III)

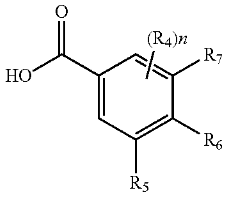

wherein $R_4$, $R_5$, $R_6$, $R_7$ and n are as defined in any one of clauses 1 to 156.

Clause 169. A process for preparing a compound of formula (I), or a salt such as a pharmaceutical acceptable salt thereof, in which $R_7$ is absent which comprises coupling a compound of formula (XXXVIII):

(XXXVIII)

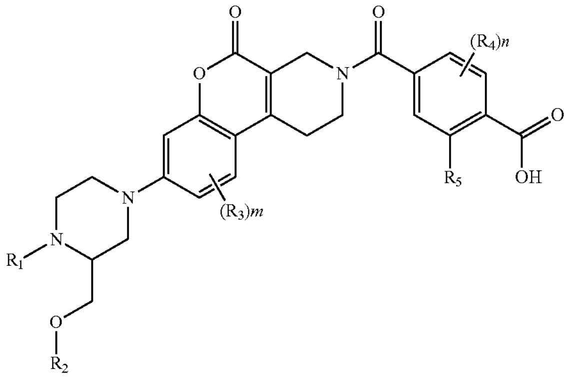

or a salt and/or solvate thereof;

wherein $R_1$, $R_2$, $R_3$, $R_4$, $R_5$, $R_8$, n and m are defined in any one of clauses 1 to 156; with a compound of formula (XVI):

or a salt and/or solvate thereof;

(XVI)

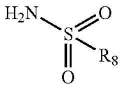

wherein $R_8$ is defined in any in any one of clauses 1 to 156.

Clause 170. A compound of formula (II):

(II)

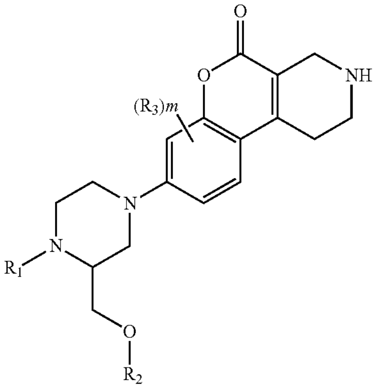

or a salt and/or solvate thereof;

wherein $R_1$, $R_2$, $R_3$ and m are as defined in any one of clauses 1 to 156.

Clause 171. A compound of formula (III):

or a salt and/or solvate thereof;

(III)

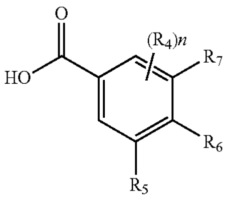

wherein $R_4$, $R_5$, $R_6$, $R_7$ and n are as defined in any one of clauses 1 to 156, such as $R_5$ is an O-linked group such as $C_{1-3}$ alkoxy, $C_{1-3}$ haloalkoxy or $OC_{3-10}$ cycloalkyl, or an N-linked group such as $NR_{5b}R_{5c}$ or N-linked 4-7 membered heterocycloalkyl.

Clause 172. A compound of formula (XXXVIII):

(XXXVIII)

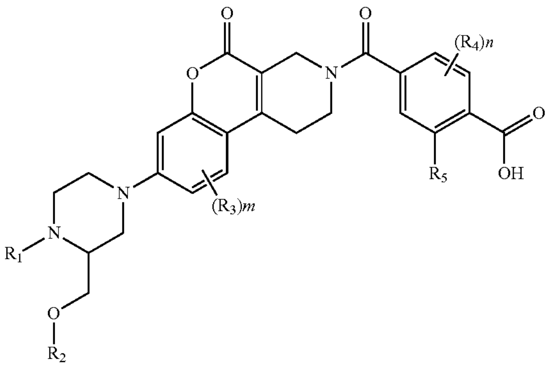

or a salt and/or solvate thereof;

wherein $R_1$, $R_2$, $R_3$, $R_4$, $R_5$, n and m are defined in any one of clauses 1 to 156.

Clause 173. A compound of formula (XXXIX):

(XXXIX)

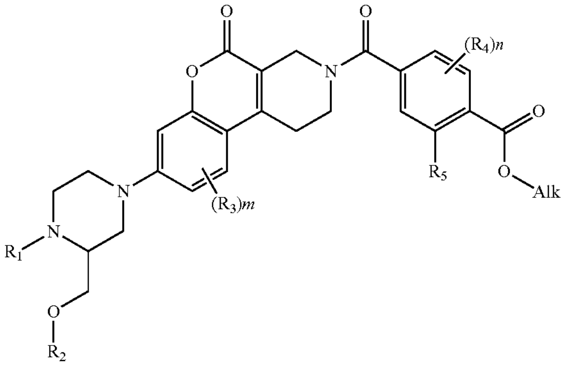

or a salt and/or solvate thereof;

wherein $R_1$, $R_2$, $R_3$, $R_4$, $R_5$, n and m are defined in any one of clauses 1 to 156, and Alk is $C_{1-4}$alkyl.

Clause 174. A compound of formula (XXXXI):

(XXXXI)

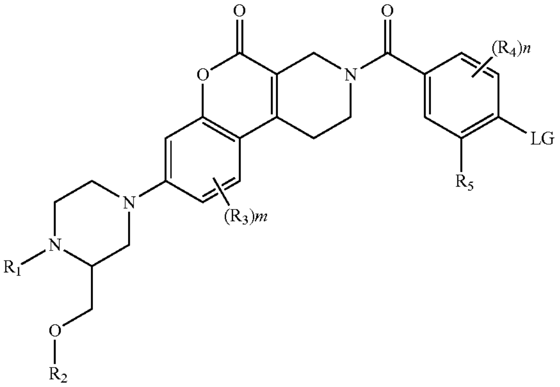

or a salt and/or solvate thereof;

wherein $R_1$, $R_2$, $R_3$, $R_4$, $R_5$, n and m are defined in any one of clauses 1 to 156, and LG is a leaving group such as halo e.g. bromo.

Abbreviations

° C. degrees centigrade
Ac acetyl
AcOH acetic acid
ACN acetonitrile
AO/PI acridine orange/propidium iodide stain
app apparent
aq. aqueous
br s broad singlet
BINAP (±)-(2,2'-bis(diphenylphosphino)-1,1'-binaphthyl)
$Boc_2O$ di-tert-butyldicarbonate
Bn benzyl
Boc tert-butoxycarbonyl
ca. circa
Cbz (benzyloxy)carbonyl
CbzCl benzyl chloroformate
CDI 1,1'-carbonyl diimidazole
CFSE carboxyfluorescein succinimidyl ester
conc. concentrated
cRPMI complete Roswell Park Memorial Institute media
d doublet
DAD diode array detector
DBU 1,8-diazabicyclo[5,4,0]undec-7-ene
DCC N,N'-dicyclohexylcarbodiimide
DCM dichloromethane
dFBS dialysed fetal bovine serum
DMA N,N-dimethylacetamide
DME dimethoxyethene
DIPEA N,N-diisopropylethylamine
DIAD diisopropylazodicarboxylate
DMAP 4-dimethylaminopyridine
DMF N,N-dimethylformamide
DMSO dimethyl sulfoxide
DMSO-d6 deuterated dimethyl sulfoxide
DIPEA N,N-diisopropylethylamine
dPBS Dulbecco's phosphate buffered saline
EDCI N-(3-dimethylaminopropyl)-N'-ethylcarbodiimide hydrochloride
EDTA ethylenediaminetetraacetic acid
Et ethyl
EtOAc ethyl acetate
EtOH ethanol
$ES^+$ electrospray
FA formic acid
FBS fetal bovine serum
g gram(s)
h hour(s)
HATU 1-[bis(dimethylamino)methylene]-1H-1,2,3-triazolo[4,5-b]pyridinium 3-oxide hexafluorophosphate
HPLC high-performance liquid chromatography
LDA lithium diisopropylamide
LCMS liquid chromatography-mass spectrometry
m multiplet
M molar concentration/molar mass
Me methyl
m/z mass to charge ratio
MeCN acetonitrile
MeOH methanol
MHz (mega)hertz
min(s) minute(s)
mL millilitres mmol/mM millimole
MS mass spectrometry
MTBE methyl tert-butyl ether
$Na(Ac)_3BH$ sodium triacetoxyborohydride
NBS N-bromosuccinimide
NIS N-iodosuccinimide
nM nanomolar
NMM 4-methylmorpholine
NMR nuclear magnetic resonance
NMP N-methyl-2-pyrrolidone
p quintet
PBS phosphate buffered saline
PDA photodiode array
$Pd(dppf)Cl_2$ [1,1'-bis(diphenylphosphino)ferrocene]dichloropalladium(II)
PEI polyethylenimine
PMB para-methoxybenzyl
PenStrep mixture of penicillin G and streptomycin
$PPh_3$ triphenylphosphine
q quartet
RPMI Roswell Park Memorial Institute media
rpm revolutions per minute
RT room temperature
s singlet
sat. saturated
t triplet
$tBu_3PHBF_4$ Tri-tert-butylphosphonium tetrafluoroborate
t-BuXPhos 2-Di-tert-butylphosphino-2',4',6'-triisopropylbiphenyl
$^t$BuOH tert-butanol
TBTU 2-(1H-benzotriazole-1-yl)-1,1,3,3-tetramethylaminium tetrafluoroborate
TEA triethylamine
$Tf_2O$ trifluoromethanesulfonic anhydride
Tf trifluoromethanesulfonyl, i.e., $CF_3SO_2$—
TFA trifluoroacetic acid
TFAA trifluoroacetic anhydride
THE tetrahydrofuran
Tris tris(hydroxymethyl)aminomethane hydrochloride
μL microlitre
μM micromolar
UPLC ultra performance liquid chromatography
wt weight
×g times gravity
$ZnEt_2$ diethylzinc

EXAMPLES

Analytical Equipment

Thin layer chromatography (TLC) was performed on silica gel plates (GF254, glass, silica gel size: 400~600 mesh). Spots were visualized by UV light (214 and 254 nm) or colour reagents (iodine, $KMnO_4$ aq.). All evaporations were carried out in vacuo with a rotary evaporator.

Purification by column and flash chromatography was carried out using silica gel (200-300 mesh). Solvent systems are reported as mixtures by volume. NMR spectra were recorded on Bruker 400 MHz Avance III spectrometer fitted with a BBFO 5 mm probe, a Bruker 500 MHz Avance III HD spectrometer equipped with a Bruker 5 mm SmartProbe™, or Jeol ECS400 at rt. $^1H$ chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration.

LCMS/HPLC Instrument Details

| System | Instrument Name | LC Detector | ELS detector | Mass detector |
|---|---|---|---|---|
| 1 (basic) | Agilent LCMS 1200 | G1315D DAD | 380 ELSD | Agilent G6120B |
| 2 (acidic) | Agilent LCMS 1200 | G1315C DAD | 380 ELSD | Agilent G6110A |
| 3 (acid and basic) | Waters Acquity UPLC | Waters Acquity PDA | N/A | Waters Acquity QDa |

LCMS/HPLC Method Details

| Method Name | Solvent System | Column | Gradient | UV range | Mass Range | Column Temp. ° C. | Flow Rate ml/min |
|---|---|---|---|---|---|---|---|
| A (basic LCMS) | A) water + 10 mM $NH_4HCO_3$ B) acetonitrile | Waters X-Bridge C18 (3.5 μm, 50 mm × 4.6 mm) | From 95:5 to 0:100 in 1.6 min, 0:100 for 1.4 min, from 0:100 to 95:5 in 0.1 min, 95:5 for 0.7 min. | 190-400 nm | 100-1800 amu | 40 | 2.0 |
| B (acidic LCMS) | A) water + 0.05% TFA] B) acetonitrile + 0.05% TFA | Waters X-Bridge C18 (3.5 μm, 50 mm × 4.6 mm) | From 95:5 to 0:100 in 1.6 min, 0:100 for 1.4 min, from 0:100 to 95:5 in 0.05 min, 95:5 for 0.7 min | 190-400 nm | 100-1100 amu | 40 | 2.0 |
| C (acidic LCMS) | A) water + 0.05% TFA] B) acetonitrile + 0.05% TFA | Halo C18 (2.7 μm, 30 mm × 4.6 mm) | From 95:5 to 0:100 in 0.8 min, 0:100 for 0.4 min, from 0:100 to 95:5 in 0.01 min, 95:5 for 0.2 min | 190-400 nm | 100-1100 amu | 40 | 3.0 |
| D (basic HPLC) | A) water + 10 mM $NH_4HCO_3$ B) acetonitrile | Waters X-Bridge C18 (3.5 μm, 150 mm × 4.6 mm) | From 95:5 to 0:100 in 10 min, 0:100 for 5 min, from 0:100 to 95:5 in 0.1 min, 95:5 for 5 min. | 190-400 nm | 100-1800 amu | 40 | 1.0 |
| E (acidic HPLC) | A) water + 0.05% TFA B) acetonitrile + 0.05% TFA | L-column2 ODS (5.0 μm, 150 mm × 4.6 mm) | From 95:5 to 0:100 in 10 min, 0:100 for 5 min, from 0:100 to 95:5 in 0.1 min, 95:5 for 5 min | 190-400 nm | 100-1100 amu | 40 | 1.0 |
| F (basic LCMS) | A) water + 10 mM $NH_4HCO_3$ B) acetonitrile | Waters X-Bridge C18 (2.6 μm, 50 mm × 4.6 mm) | From 95:5 to 0:100 in 1.75 min, 0:100 for 0.8 min, from 0:100 to 95:5 in 0.1 min, 95:5 for 0.1 min. | 190-400 nm | 100-1000 amu | 40 | 2.3 |
| G (basic LCMS) | A) water + 10 mM $NH_4HCO_3$ | Waters X-Bridge C18 (3.5 μm, 30 mm × 4.6 mm) | From 95:5 to 5:95 in 1.00 min, 5:95 for 0.35 min, from 5:95 to 95:5 in 0.10 min, 95:5 for 0.05 min. | 190-400 nm | 100-1000 amu | 40 | 3.0 |

-continued

| | | | | | | | |
|---|---|---|---|---|---|---|---|
| H (basic LCMS) | A) water + 10 mM $NH_4HCO_3$ B) acetonitrile | Phenomenex Kinetex EVO (2.6 μm, 30 × 4.6 mm) | From 95:5 to 5:95 in 1.00 min, 5:95 for 0.35 min, from 5:95 to 95:5 in 0.10 min, 95:5 for 0.05 min. | 190-400 nm | 100-1000 amu | 40 | 3.0 |
| I (basic LCMS) | A) NH4HCO3 10 mM aq. (pH 9, adjusted with NH3) B) acetonitrile | Waters BEH C18 (50 × 2.1 mm, 1.7 μm) | 95:5 for 0.05 min, 95:5 to 5:95 in 1.55 min, 5:95 for 0.65 min | 210-400 nm | 120-1000 amu | 50 | 0.6 |
| J (acidic LCMS) | A) water + 0.1% FA B) acetonitrile | Waters BEH C18 (50 × 2.1 mm, 1.7 μm) | 95:5 for 0.05 min, 95:5 to 5:95 in 1.55 min, 5:95 for 0.65 min | 210-400 nm | 120-1000 amu | 50 | 0.6 |
| K (basic LCMS) | A) $NH_4HCO_3$ 10 mM aq. (pH 9, adjusted with $NH_3$) B) acetonitrile | Waters Acquity CSH C18 (1.7 μm, 100 × 2.1 mm) | From 95:5 for to 5:95 in 6.5 min, 5:95 for 2.5 min. | 210-400 nm | 120-1250 | 50 | 0.35 |
| L (acidic LCMS) | A) water + 0.1% FA B) acetonitrile | Waters Acquity CSH C18 (1.7 μm, 100 × 2.1 mm) | From 95:5 for to 5:95 in 6.5 min, 5:95 for 2.5 min. | 210-400 nm | 120-1250 | 50 | 0.35 |

Commercial Materials

All starting materials are commercially available unless otherwise stated.

SYNTHESIS OF INTERMEDIATES

Intermediate 1: (R)-2-(methoxymethyl)-1-methylpiperazine

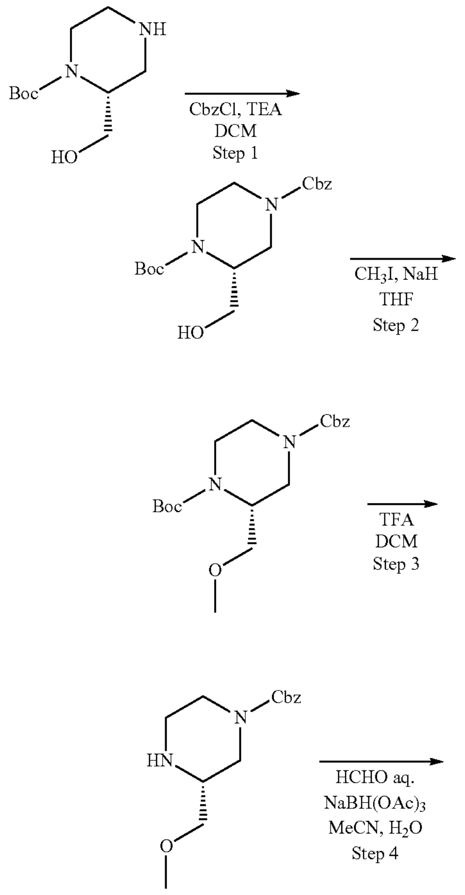

-continued

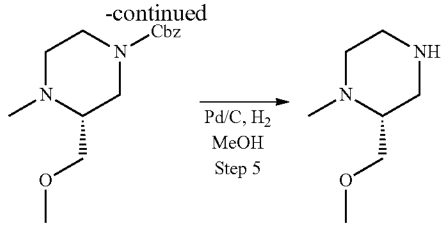

Step 1

Benzylchloroformate (47.4 g, 277 mmol) was added dropwise to a solution of (R)-tert-butyl 2-(hydroxymethyl) piperazine-1-carboxylate (50.0 g, 231 mmol) and TEA (56.0 g, 555 mmol) in DCM (1.1 L) at 0° C. The mixture was stirred at RT for 3 h. Ice water (800 mL) was added and the mixture was extracted with DCM (3×1 L). The organic layers were combined, dried ($Na_2SO_4$), filtered and concentrated under reduced pressure. The residue was purified by column chromatography on silica gel (20-50% EtOAc/ petroleum ether) to afford (R)-4-benzyl 1-tert-butyl 2-(hydroxymethyl)piperazine-1,4-dicarboxylate (72.0 g, 205 mmol) as a colourless oil. LCMS (System 1, Method F) Rt=1.59 min, m/z 251.0 $(M-100+H)^+$, 295 $(M-56+H)^+$ $(ES^+)$. $^1$H NMR (400 MHz, $CDCl_3$) δ: 7.38-7.29 (m, 5H), 5.15 (br s, 2H), 4.17-4.08 (m, 2H), 4.00 (s, 1H), 3.86-3.83 (m, 1H), 3.57 (m, 2H), 2.99 (m, 3H), 1.48-1.41 (s, 9H).

Step 2

Sodium hydride (60% dispersion in mineral oil, 16.4 g, 411 mmol) was added in small portions to a solution of (R)-4-benzyl 1-tert-butyl 2-(hydroxymethyl)piperazine-1,4-dicarboxylate (72.0 g, 205 mmol) in THE (822 mL) at −10° C. The mixture was stirred at this temperature for 30 min, iodomethane (64.2 g, 452 mmol) was added and the reaction was stirred for 2 h at −10° C. The mixture was poured into $NH_4Cl$ aq. sat. (500 mL), and the mixture was extracted with MTBE (3×800 mL). The combined organic layers were washed with brine, dried ($Na_2SO_4$), filtered and concentrated under reduced pressure. The residue was purified by column chromatography on silica gel (20-30% MTBE/ petroleum ether) to afford (R)-4-benzyl 1-tert-butyl 2-(methoxymethyl)piperazine-1,4-dicarboxylate (41.0 g, 113 mmol) as a pale-yellow oil. LCMS (System 1, Method F) Rt=1.77 min, m/z 309.0 $(M-56+H)^+$ $(ES^+)$. $^1H$ NMR (400 MHz, $CDCl_3$) δ: 7.35-7.27 (m, 5H), 5.19-5.09 (m, 2H), 4.19-3.85 (m, 4H), 3.39-3.26 (m, 5H), 3.04-2.94 (m, 3H), 1.49-1.29 (s, 9H).

Step 3

To a solution of (R)-4-benzyl 1-tert-butyl 2-(methoxymethyl)piperazine-1,4-dicarboxylate (41.0 g, 113 mmol) in DCM (500 mL) was added TFA (100 mL) at RT. The reaction mixture was stirred at RT for 4 h. TFA was evaporated and the residue was partitioned between DCM (500 mL) and $NaHCO_3$ aq. sat. (300 mL). The aqueous layer was extracted with DCM (2×500 mL). The combined organic layers were washed with brine, dried ($Na_2SO_4$), filtered and concentrated under reduced pressure to afford (R)-benzyl 3-(methoxymethyl)piperazine-1-carboxylate (29.0 g, 110 mmol) as a yellow oil. LCMS (System 1, Method F) Rt=1.33 min, m/z 265.2 $(M+H)^+$ $(ES^+)$.

Step 4

To a solution of (R)-benzyl 3-(methoxymethyl)piperazine-1-carboxylate (29.0 g, 110 mmol) in ACN (400 mL) and water (133 mL) was added formaldehyde aq. (37%, 27.8 g, 340 mmol), the mixture was stirred at RT for 2 h. Sodium triacetoxyborohydride (46.5 g, 219 mmol) was added at 0° C., and the mixture was stirred at RT overnight. The pH of the mixture was taken to 8 by adding $NaHCO_3$ aq. sat., ACN was evaporated under reduced pressure and the resulting aqueous solution was extracted with DCM (3×400 mL). The combined organic layers were washed with brine, dried ($Na_2SO_4$), filtered and concentrated under reduced pressure. The crude product was purified by column chromatography on silica gel (1-5% MeOH/DCM) to afford (R)-benzyl 3-(methoxymethyl)-4-methylpiperazine-1-carboxylate (27.0 g, 97 mmol) as a yellow oil. LCMS (System 1, Method F) Rt=1.45 min, m/z 279.2 $(M+H)^+$ $(ES^+)$.

Step 5

Pd/C (10%, 2.70 g) was added to a solution of (R)-benzyl 3-(methoxymethyl)-4-methylpiperazine-1-carboxylate (27.0 g, 97.0 mmol) in MeOH (750 mL), and the mixture was stirred at RT overnight under $H_2$. The mixture was filtered through celite and the filtrate was concentrated under reduced pressure to afford (R)-2-(methoxymethyl)-1-methylpiperazine (14 g, 97.0 mmol) as a yellow oil. $^1H$ NMR (400 MHz, DMSO-$d_6$) δ: 3.44 (dd, J=10.0, 5.6 Hz, 1H), 3.45-3.41 (m, 4H), 2.96-2.85 (m, 2H), 2.72-2.63 (m, 2H), 2.48-2.42 (m, 1H), 2.18-2.09 (m, 5H).

Alternative Procedure

Step 1

Five batches were carried out in parallel: 4×1.49 kg and a 1.0 kg.

To a solution of tert-butyl (R)-3-(hydroxymethyl)piperazine-1-carboxylate (1.49 kg, 6.89 mol, 1.0 eq) in THE (14.9 L) was added portionwise NaH (303 g, 7.58 mol, 60%, 1.1 eq) at 20° C. The mixture was stirred at 20° C. for 0.5 h. Methyl iodide (1.08 kg, 7.58 mol, 472 mL, 1.1 eq) was added dropwise into the mixture at 20-30° C. The mixture was stirred at 20° C. for 0.5 h. More NaH (386 g, 9.65 mol, 60%, 1.4 eq) was slowly added into the mixture at 20° C., the mixture was stirred at 20-30° C. for 0.5 hr. More methyl iodide (1.37 kg, 9.65 mol, 600 mL, 1.4 eq) was added dropwise to the mixture at 20° C. The resulting mixture was stirred at 20° C. for 12 h. The reaction mixture was quenched by addition sat. aq. $NH_4Cl$ (1.49 L) at 0° C., diluted with more sat. aq. $NH_4Cl$ (13.41 L) then extracted with EtOAc (14.9 L, 7.45 L). The combined organic layers were washed with brine (14.9 L), dried over $Na_2SO_4$, filtered and concentrated under reduced pressure to give a residue. Material from 5 batches were combined. Compound tert-butyl (R)-3-(methoxymethyl)-4-methylpiperazine-1-carboxylate (5.80 kg, 23.7 mol, 86.1% yield) was obtained as a yellow oil.

Step 2

Three batches were carried out in parallel.

To a solution of tert-butyl (R)-3-(methoxymethyl)-4-methylpiperazine-1-carboxylate (1.93 kg, 7.90 mol, 1.0 eq) in EtOAc (3.86 L) was added to HCl/EtOAc (4 M, 15.4 L, 7.82 eq) at 20° C., the mixture was stirred at 20° C. for 3 h. The reaction mixture was filtered and concentrated under reduced pressure to give a residue. Material from 3 batches were combined. (R)-2-(methoxymethyl)-1-methylpiperazine hydrochloride (5.44 kg) was obtained as a yellow solid.

Step 3

Two batches were carried out in parallel.

To a solution of (R)-2-(methoxymethyl)-1-methylpiperazine hydrochloride (2.72 kg, 15.1 mol, 1.0 eq) in MeOH (13.6 L) was added $K_2CO_3$ (2.29 kg, 16.6 mol, 1.1 eq) at 10-20° C. The mixture was stirred at 20-30° C. for 3 h. The reaction mixture was filtered, and the filtrate was concentrated at 35° C. under reduced pressure to give a residue. Residue was dissolved with DCM (13.6 L) and stirred at 20-30° C. for 0.5 h, solid was filtered and the filtrate was concentrated under reduced pressure to give a residue. The residue was dissolved with DCM (10 L) and $Na_2SO_4$ added, suspension stirred at 20-30° C. for 0.5 h, filtered and the filtrate was concentrated under reduced pressure to give the product. Material from 3 batches were combined. (R)-2-(methoxymethyl)-1-methylpiperazine hydrochloride (2.90 kg, 20.1 mol) was obtained as brown oil.

Intermediate 2: tert-butyl 7-methyl-5-oxo-8-(((trifluoromethyl)sulfonyl)oxy)-1,5-dihydro-2H-chromeno[3,4-c]pyridine-3(4H)-carboxylate

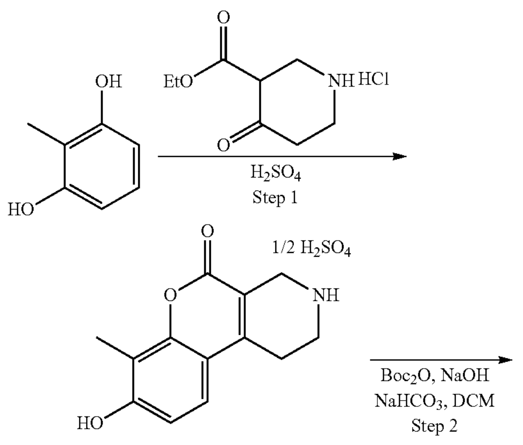

-continued

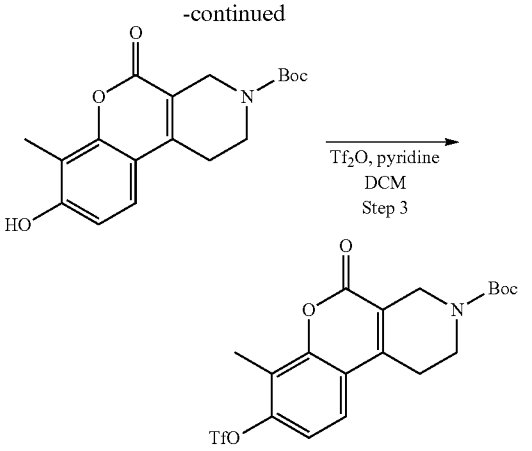

Step 1

A mixture of 2-methylbenzene-1,3-diol (25.0 g, 202 mmol) and ethyl 4-oxopiperidine-3-carboxylate hydrochloride (41.7 g, 202 mmol) in sulfuric acid (64%, 200 mL) was stirred at RT overnight. The reaction was quenched by adding ice water (300 mL) and the mixture was stirred at RT for 2 h. The precipitate was collected by filtration, washed with water and hexane, and dried under reduced pressure to afford 8-hydroxy-7-methyl-1,2,3,4-tetrahydro-5H-chromeno[3,4-c]pyridin-5-one hemisulfate (46.0 g, 164 mmol) as an off-white solid. LCMS (System 2, Method B) Rt 0.38 min, m/z 232.2 $(M+H)^+$ $(ES^+)$.

Step 2

Sodium hydroxide aq. 1 M (115 mL, 115 mmol) was added to a mixture of 8-hydroxy-7-methyl-1,2,3,4-tetrahydro-5H-chromeno[3,4-c]pyridin-5-one hemisulfate (30.0 g, 107 mmol) in DCM (500 mL) and the reaction was stirred at RT for 30 min. Then $NaHCO_3$ aq. sat. (200 mL) and di-tert-butyl dicarbonate (25.7 g, 118 mmol) were added and the reaction was stirred at RT overnight. The organic solvent was evaporated and the resulting precipitate was recovered by filtration, washed with water, hexane, and dried to afford tert-butyl 7-chloro-8-hydroxy-5-oxo-1,5-dihydro-2H-chromeno[3,4-c]pyridine-3(4H)-carboxylate (25.0 g, 75.5 mmol) as an off-white solid. LCMS (System 2, Method B) Rt=1.74 min, m/z 354.0 $(M+Na)^+$ $(ES^+)$.

Step 3

A mixture tert-butyl 7-chloro-8-hydroxy-5-oxo-1,5-dihydro-2H-chromeno[3,4-c]pyridine-3(4H)-carboxylate (25.0 g, 75.5 mmol) in DCM (400 mL) was added pyridine (11.9 g, 151 mmol), the mixture was cooled to 0° C. then trifluoromethanesulfonic anhydride (21.3 g, 75.5 mmol) was added dropwise. The solution was allowed to warm to RT and stirred for 1 h. Water (300 mL) was added, and the organic phase was separated, washed with HCl aq. 0.1N (50 mL) and brine (200 mL), dried ($Na_2SO_4$) and concentrated under reduced pressure. The crude product was purified by column chromatography on silica gel (0-2% MeOH/DCM) to afford tert-butyl 7-methyl-5-oxo-8-(((trifluoromethyl)sulfonyl)oxy)-1,5-dihydro-2H-chromeno[3,4-c]pyridine-3(4H)-carboxylate (30.0 g, 64.8 mmol) as a pale-yellow solid. LCMS: (System 2, Method B). Rt=2.14 min, m/z 486.1 $(M+Na)^+$ $(ES^+)$.

Alternative Procedure

Step 1

2×500 g batches were carried out in parallel.

To a solution of 2-methylbenzene-1,3-diol (500 g, 4.03 mol, 1.0 eq) in sulfuric acid (5.0 L, 75%) was added ethyl 4-oxopiperidine-3-carboxylate hydrochloride (920 g, 4.43 mol, 1.1 eq) at 20° C., the reaction mixture was stirred at 30° C. for 12 h. The reaction mixture was added to ice water (20 L). The precipitate was collected by filtration, washed with water (5.0 L) and hexane (3.0 L). The filter cake was dried under reduced pressure. The crude product was used to the next step without further purification. The materials from the two batches were combined. 8-hydroxy-7-methyl-1,2,3,4-tetrahydro-5H-chromeno[3,4-c]pyridin-5-one hemisulfate (3.50 kg, crude) was obtained as a white solid.

Step 2

To a suspension of 8-hydroxy-7-methyl-1,2,3,4-tetrahydro-5H-chromeno[3,4-c]pyridin-5-one hemisulfate (3.15 kg, 6.42 mol, 1.0 eq) in THE (19 L) was added NaOH (1.0 M, 3.71 L) and the mixture was stirred at 25° C. for 0.5 h. $NaHCO_3$ aq. sat. (165 mL) and di-tert-butyl dicarbonate (1.40 kg, 6.42 mol, 1.0 eq) were added to the mixture. The reaction mixture was stirred at 25° C. for 12 h. The reaction mixture was concentrated at 35° C. under reduced pressure to remove THF, the residue was filtered and washed with water (2.0 L) and hexane (4.0 L). The crude product was triturated with n-hexane/acetone 1/1 (4.0 L) at 20° C. for 12 h. tert-butyl 7-chloro-8-hydroxy-5-oxo-1,5-dihydro-2H-chromeno[3,4-c]pyridine-3(4H)-carboxylate (2.14 kg, 5.76 mol, 89.7% yield) was obtained as a white solid.

Step 3

7 batches were carried out in parallel: 5×330 g batches, a 290 g batch and a 200 g batch.

To a solution of tert-butyl 7-chloro-8-hydroxy-5-oxo-1,5-dihydro-2H-chromeno[3,4-c]pyridine-3(4H)-carboxylate (330 g, 996 mmol, 1.0 eq) in DCM (1.65 L) was added pyridine (197 g, 2.49 mol, 201 mL, 2.5 eq) at −10-0° C., then trifluoromethanesulfonic anhydride (421 g, 1.49 mol, 246 mL, 1.5 eq) was added dropwise into the mixture at the same temperature. The mixture was stirred at −10-0° C. for 0.5 h until the reaction was completed by HPLC. The reaction mixture was quenched by adding water (1.65 L) at −10-0° C. then the organic phase was separated, washed with HCl (0.1 M, 0.9 L) and brine (1.65 L), dried over anhydrous $Na_2SO_4$, and concentrated at 35° C. under reduced pressure to give the crude product. Seven batches were combined for further purification. The crude product was triturated with n-heptane (5.0 L) at 20° C. for 1 h. The solid was filtered and the filter cake was dried at 35° C. to obtained tert-butyl 7-methyl-5-oxo-8-(((trifluoromethyl)sulfonyl)oxy)-1,5-dihydro-2H-chromeno[3,4-c]pyridine-3(4H)-carboxylate (2.64 kg, 99.0% purity, 88.2% yield) as a pale yellow solid.

Intermediate 3: tert-butyl 7,10-dimethyl-5-oxo-8-(((trifluoromethyl)sulfonyl)oxy)-1,5-dihydro-2H-chromeno[3,4-c]pyridine-3(4H)-carboxylate

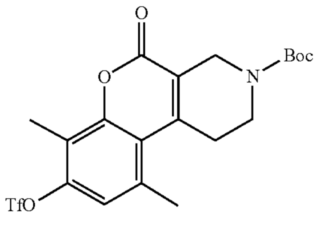 [SMILES: Cc1c(OS(=O)(=O)C(F)(F)F)cc(C)c2c3c(c(=O)oc12)CN(C(=O)OC(C)(C)C)CC3]

Prepared by an analogous method to tert-butyl 7-methyl-5-oxo-8-(((trifluoromethyl)sulfonyl)oxy)-1,5-dihydro-2H-chromeno[3,4-c]pyridine-3(4H)-carboxylate (Intermediate 2) starting from 2,5-dimethylbenzene-1,3-diol (10.0 g, 73 mmol). Yield: 9.3 g, 19.5 mmol. White solid. LCMS: (System 1, Method A) Rt=2.47 min, m/z 422.2 $(M-56+H)^+$ $(ES^+)$.

Alternative Procedure

Step 1

3 batches were carried out in parallel: 50.0 g and 2×225 g.

A mixture of 2,5-dimethylbenzene-1,3-diol (225 g, 1.63 mol, 1.0 eq), ethyl 4-oxopiperidine-3-carboxylate hydrochloride (371 g, 1.79 mol, 1.1 eq, HCl), in $H_2SO_4$ (75%, 2250 mL) was degassed and purged with nitrogen for 3 times, and then the mixture was stirred at 30° C. for 96 h under nitrogen atmosphere. The three batched were combined and poured into ice water (6750 mL) at 0-10° C., and the solid was recovered by filtration and washed with water (2×120 mL). The filter cake was dried under reduced pressure. The crude product was used to the next step without further purification. 8-hydroxy-7,10-dimethyl-1,2,3,4-tetrahydro-5H-chromeno[3,4-c]pyridin-5-one hemisulfate (1.27 kg, crude) was obtained as a white solid.

Step 2

A mixture of 8-hydroxy-7,10-dimethyl-1,2,3,4-tetrahydro-5H-chromeno[3,4-c]pyridin-5-one hemisulfate (1.15 kg, 3.58 mol, 1.0 eq) tert-butyl carbonate (687 g, 3.15 mol, 723 mL, 0.88 eq), $NaHCO_3$ (1.14 M, 890 mL, 0.28 eq) and NaOH (1.0 M, 4.30 L, 1.2 eq) in THE (16.5 L) was degassed and purged with nitrogen for 3 times, and then the mixture was stirred at 15-25° C. for 12 h under nitrogen atmosphere. The solid was filtered and the filtrate concentrated under reduced pressure to give a residue. The crude product was purified by re-crystallization from 1000 mL of 1/1 acetone/n-hexane. tert-butyl 8-hydroxy-7,10-dimethyl-5-oxo-1,5-dihydro-2H-chromeno[3,4-c]pyridine-3(4H)-carboxylate (489 g, 1.42 mol, 39.5% yield) was obtained as a white solid.

Step 3

Two 239.5 g batches were carried out in parallel.

To a mixture of tert-butyl 8-hydroxy-7,10-dimethyl-5-oxo-1,5-dihydro-2H-chromeno[3,4-c]pyridine-3(4H)-carboxylate (239.5 g, 693 mmol, 1.0 eq) in DCM (2.40 L) was added pyridine (137 g, 1.73 mol, 140 mL, 2.5 eq) at −10-0° C., followed by trifluoromethanesulfonic anhydride (293 g, 1.04 mol, 172 mL, 1.5 eq) at −10-0° C. The mixture was stirred at −10-0° C. for 0.5 hr. The mixture was quenched by addition of water (1.12 L) at −10-0° C., the organic phase was separated and extracted with DCM (718 mL). The combined organic phase was washed with HCl (1.0 M, 3×718 mL) and brine (1.12 L), dried over anhydrous $Na_2SO_4$, filtered and concentrated under reduced pressure to give a residue. Two batches were combined for further purification. The crude product was triturated with n-heptane (1.5 L) at 25° C. for 1 hr, filtered and concentrated under reduced pressure. tert-butyl 7,10-dimethyl-5-oxo-8-(((trifluoromethyl)sulfonyl)oxy)-1,5-dihydro-2H-chromeno[3,4-c]pyridine-3(4H)-carboxylate (459 g, 959 mmol, 69.2% yield, 99.8% purity) was obtained as a light-yellow solid.

Intermediate 4: tert-butyl 7-chloro-5-oxo-8-(((trifluoromethyl)sulfonyl)oxy)-1,5-dihydro-2H-chromeno[3,4-c]pyridine-3(4H)-carboxylate

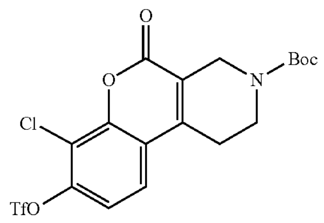 [SMILES: CC(C)(C)OC(=O)N1CCc2c(c(=O)oc3c(Cl)c(OS(=O)(=O)C(F)(F)F)ccc23)C1]

Prepared by an analogous method to tert-butyl 7-methyl-5-oxo-8-(((trifluoromethyl)sulfonyl)oxy)-1,5-dihydro-2H-chromeno[3,4-c]pyridine-3(4H)-carboxylate (Intermediate 2) starting from 2-chlorobenzene-1,3-diol (20.0 g, 139 mmol). Yield: 31.0 g, mmol. Pale-yellow solid. LCMS: (System 1, Method F) Rt=1.97 min, m/z 428.0 $(M-56+H)^+$ $(ES^+)$.

Intermediate 5: (R)-8-(3-(methoxymethyl)-4-methylpiperazin-1-yl)-7-methyl-1,2,3,4-tetrahydro-5H-chromeno[3,4-c]pyridin-5-one

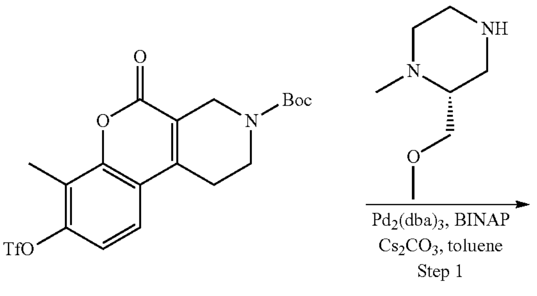

-continued

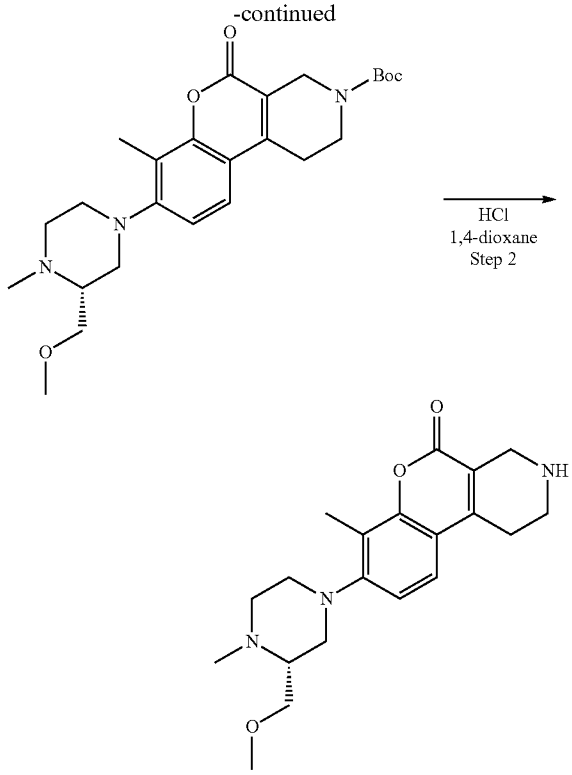

Step 1

A mixture of (R)-2-(methoxymethyl)-1-methylpiperazine (Intermediate 1, 3.73 g, 25.9 mmol), tert-butyl 7-methyl-5-oxo-8-(((trifluoromethyl)sulfonyl)oxy)-1,5-dihydro-2H-chromeno[3,4-c]pyridine-3(4H)-carboxylate (Intermediate 2, 8.0 g, 17.3 mmol), $Cs_2CO_3$ (11.2 g, 34.6 mmol), tris (dibenzylideneacetone)dipalladium(0) (1.58 g, 1.73 mmol) and BINAP (2.16 g, 3.46 mmol) in toluene (87 mL) was stirred at 100° C. for 16 h under nitrogen atmosphere. The reaction mixture was cooled to RT, EtOAc was added and the mixture was filtered, the filtrate was concentrated under reduced pressure. The crude product was purified by column chromatography on silica gel (20-80% EtOAc/petroleum ether then 1-5% MeOH/DCM) to afford (R)-tert-butyl 8-(3-(methoxymethyl)-4-methylpiperazin-1-yl)-7-methyl-5-oxo-4,5-dihydro-1H-chromeno[3,4-c]pyridine-3(2H)-carboxylate (7.8 g, 17.0 mmol) as a yellow solid. LCMS: (System 1, Method A). Rt=2.19 min, 458.2 $(M+H)^+$ $(ES^+)$.

Step 2

To a solution of (R)-tert-butyl 8-(3-(methoxymethyl)-4-methylpiperazin-1-yl)-7-methyl-5-oxo-4,5-dihydro-1H-chromeno[3,4-c]pyridine-3(2H)-carboxylate (7.8 g, 17.0 mmol) in MeOH (100 mL) was added HCl 4 M solution in 1,4-dioxane (100 mL). The reaction mixture was stirred at RT overnight. The mixture was concentrated under reduced pressure and the residue was diluted with water (50 mL) and washed with DCM (2×20 mL). The pH of the aqueous layer was adjusted to pH=7-8 by adding $NaHCO_3$ aq. sat. and washed with DCM (20 mL). The pH of the water layer was adjusted to pH=10-11 with $Na_2CO_3$ aq. sat. and extracted with DCM (3×30 mL). The combined organic layers were dried ($Na_2SO_4$), filtered and concentrated under reduced pressure to afford (R)-8-(3-(methoxymethyl)-4-methylpiperazin-1-yl)-7-methyl-1,2,3,4-tetrahydro-5H-chromeno[3,4-c]pyridin-5-one (3.5 g, 9.8 mmol) as a yellow solid. LCMS: (System 1, Method A). Rt=1.48 min, 358.4 $(M+H)^+$ $(ES^+)$. $^1H$ NMR (400 MHz, DMSO-$d_6$) δ: 7.49 (d, J=7.2 Hz, 1H), 7.03 (d, J=8.8 Hz, 1H), 3.59-3.53 (m, 3H), 3.36-3.30 (m, 2H), 3.26 (s, 3H), 3.13-3.10 (m, 1H), 3.03-3.00 (m, 3H), 2.84-2.81 (m, 2H), 2.79-2.73 (m, 2H), 2.62-2.57 (m, 1H), 2.41-2.38 (m, 2H), 2.29-2.26 (m, 6H).

Intermediate 6: (R)-8-(3-(methoxymethyl)-4-methylpiperazin-1-yl)-7,10-dimethyl-1,2,3,4-tetrahydro-5H-chromeno[3,4-c]pyridin-5-one

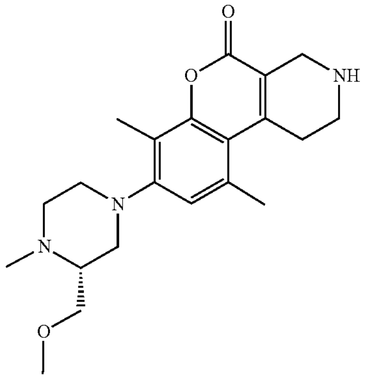 [SMILES: COC[C@H]1CN(c2cc(C)c3c4c(c(=O)oc3c2C)CNCC4)CCN1C]

Prepared by an analogous method to Intermediate 5 starting from (R)-2-(methoxymethyl)-1-methylpiperazine (Intermediate 1, 3.6 g, 25.2 mmol) and tert-butyl 7,10-dimethyl-5-oxo-8-(((trifluoromethyl)sulfonyl)oxy)-1,5-dihydro-2H-chromeno[3,4-c]pyridine-3(4H)-carboxylate (Intermediate 3, 8.0 g, 16.8 mmol). Yield: 4.4 g, 11.8 mmol. Yellow solid. LCMS: (System 1, Method F) Rt=1.34 min, m/z 372.0 $(M+H)^+$ $(ES^+)$. $^1H$ NMR (400 MHz, DMSO-$d_6$) δ: 6.80 (s, 1H), 3.58-3.53 (m, 3H), 3.34-3.30 (m, 2H), 3.26 (s, 3H), 3.11-3.08 (m, 1H), 3.01-2.94 (m, 3H), 2.90-2.88 (m, 2H), 2.82-2.77 (m, 2H), 2.65 (s, 3H), 2.61-2.56 (m, 1H), 2.39-2.35 (m, 2H), 2.28 (s, 3H), 2.20 (s, 3H)

Specific Procedure

Step 1

A solution of tert-butyl 7,10-dimethyl-5-oxo-8-(trifluoromethylsulfonyloxy)-4,5-dihydro-1H-chromeno[3,4-c]pyridine-3(2H)-carboxylate (40.0 g, 83.9 mmol) in toluene (850 mL) was added $Cs_2CO_3$ (54.7 g, 167.7 mmol), $Pd_2(dba)_3$ (7.7 g, 8.39 mmol), BINAP (10.4 g, 16.77 mmol) and (R)-2-(methoxymethyl)-1-methylpiperazine (15.7 g, 109.0 mmol). The reaction mixture was stirred at 100° C. overnight under nitrogen atmosphere. The reaction mixture was cooled to room temperature, ethyl acetate was added and the resulting solid was filtered off. The filtrate was concentrated at 45° C. under reduced pressure and purified by silica gel column chromatography (20-80% EtOAc/petroleum ether then 1-5% MeOH/DCM) to give (R)-tert-butyl8-(3-(methoxymethyl)-4-methylpiperazin-1-yl)-7,10-dimethyl-5-oxo-4,5-dihydro-1H-chromeno[3,4-c]pyridine-3(2H)-carboxylate (30.0 g, 92.4% purity, 76% yield) as a yellow solid. LCMS: (System 1, Method A) Rt=2.14 min, m/z 472.2 $(M+H)^+$ $(ES^+)$.

Step 2

To a solution of (R)-tert-butyl 8-(3-(methoxymethyl)-4-methylpiperazin-1-yl)-7,10-dimethyl-5-oxo-4,5-dihydro-1H-chromeno[3,4-c]pyridine-3(2H)-carboxylate (30.0 g, 63.7 mmol) in dioxane (120 mL) was added HCl in dioxane (4 M, 120 mL). The reaction mixture was stirred at room temperature overnight. The mixture was concentrated at 45° C. under reduced pressure. Water was added (200 mL) and the aqueous phase washed by DCM (2×80 mL). DMC layer was discarded. The pH was adjusted to 7-8 with $NaHCO_3$ and the aqueous phase washed by DCM (80 mL). DMC layer was discarded. The pH was adjusted to 10-11 with $Na_2CO_3$ and aqueous phase extracted with DCM (3×120 mL). The organic layers were dried over anhydrous $Na_2SO_4$, filtered and concentrated at 35° C. under reduced pressure to give (R)-8-(3-(methoxymethyl)-4-methylpiperazin-1-yl)-7,10-dimethyl-3,4-dihydro-1H-chromeno[3,4-c]pyridin-5(2H)-one (21.0 g, >95% purity, 89% yield) as a yellow solid.

Intermediate 7: (R)-7-chloro-8-(3-(methoxymethyl)-4-methylpiperazin-1-yl)-1,2,3,4-tetrahydro-5H-chromeno[3,4-c]pyridin-5-one

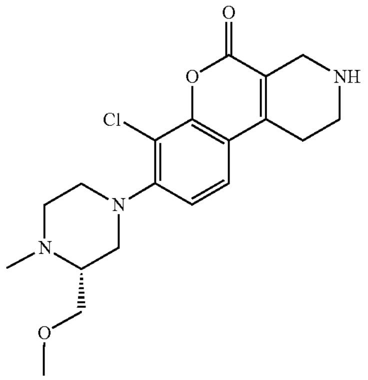 [SMILES: COC[C@H]1CN(c2ccc3c4c(c(=O)oc3c2Cl)CNCC4)CCN1C]

Prepared by an analogous method to Intermediate 5 starting from (R)-2-(methoxymethyl)-1-methylpiperazine (Intermediate 1, 671 mg, 4.7 mmol) and tert-butyl 7-chloro-5-oxo-8-(((trifluoromethyl)sulfonyl)oxy)-1,5-dihydro-2H-chromeno[3,4-c]pyridine-3(4H)-carboxylate (Intermediate 4, 1.5 g, 3.1 mmol). Yield: 330 mg, 0.87 mmol. Yellow solid. LCMS: (System 1, Method F) Rt=1.31 min, m/z 377.2 $(M+H)^+$ $(ES^+)$. $^1H$ NMR (400 MHz, DMSO-$d_6$) δ: 7.61 (d, J=8.8 Hz, 1H), 7.13 (d, J=8.4 Hz, 1H), 3.60-3.55 (m, 3H), 3.44-3.32 (m, 4H), 3.26 (s, 3H), 3.01 (br s, 2H), 2.94-2.82 (m, 2H), 2.74 (br s, 2H), 2.68-2.63 (m, 1H), 2.41-2.36 (m, 2H), 2.28 (s, 3H).

Intermediate 8: (R)-8-(hexahydropyrazino[2,1-c][1,4]oxazin-8(1H)-yl)-7-methyl-1,2,3,4-tetrahydro-5H-chromeno[3,4-c]pyridin-5-one

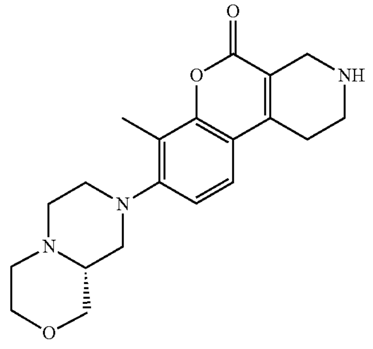 [SMILES: Cc1c(N2CCN3CCOC[C@H]3C2)ccc2c3c(c(=O)oc12)CNCC3]

Prepared by an analogous method to Intermediate 5 starting from (R)-octahydropyrazino[2,1-c][1,4]oxazine (936 mg, 5.89 mmol) and tert-butyl 7-methyl-5-oxo-8-(((trifluoromethyl)sulfonyl)oxy)-1,5-dihydro-2H-chromeno[3,4-c]pyridine-3(4H)-carboxylate(Intermediate 2, 2.1 g, 5.54 mmol). Yield: 900 mg, 2.53 mmol. Yellow solid. LCMS: (System 2, Method F) Rt=1.23 min, m/z 355.9 $(M+H)^+$ $(ES^+)$.

Intermediate 9: (R)-8-(hexahydropyrazino[2,1-c][1,4]oxazin-8(1H)-yl)-7,10-dimethyl-1,2,3,4-tetrahydro-5H-chromeno[3,4-c]pyridin-5-one

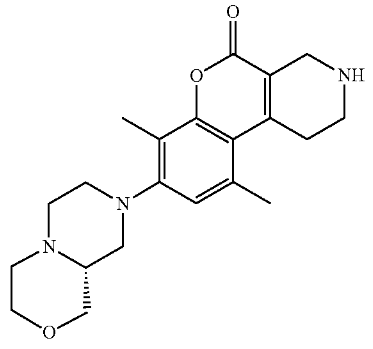 [SMILES: Cc1c(N2CCN3CCOC[C@H]3C2)cc(C)c2c3c(c(=O)oc12)CNCC3]

Prepared by an analogous method to Intermediate 5 starting from (R)-octahydropyrazino[2,1-c][1,4]oxazine (233 mg, 1.63 mmol) and tert-butyl 7,10-dimethyl-5-oxo-8-(((trifluoromethyl)sulfonyl)oxy)-1,5-dihydro-2H-chromeno[3,4-c]pyridine-3(4H)-carboxylate (Intermediate 3, 600 mg, 1.26 mmol). Yield: 31.0 g, mmol. Pale-yellow solid. LCMS: (System 1, Method F) Rt=1.97 min, m/z 428.0 $(M-56+H)^+$ $(ES^+)$.

Intermediate 10: 3-cyclobutoxy-4-((pyrrolidin-1-ylsulfonyl)carbamoyl)benzoic acid

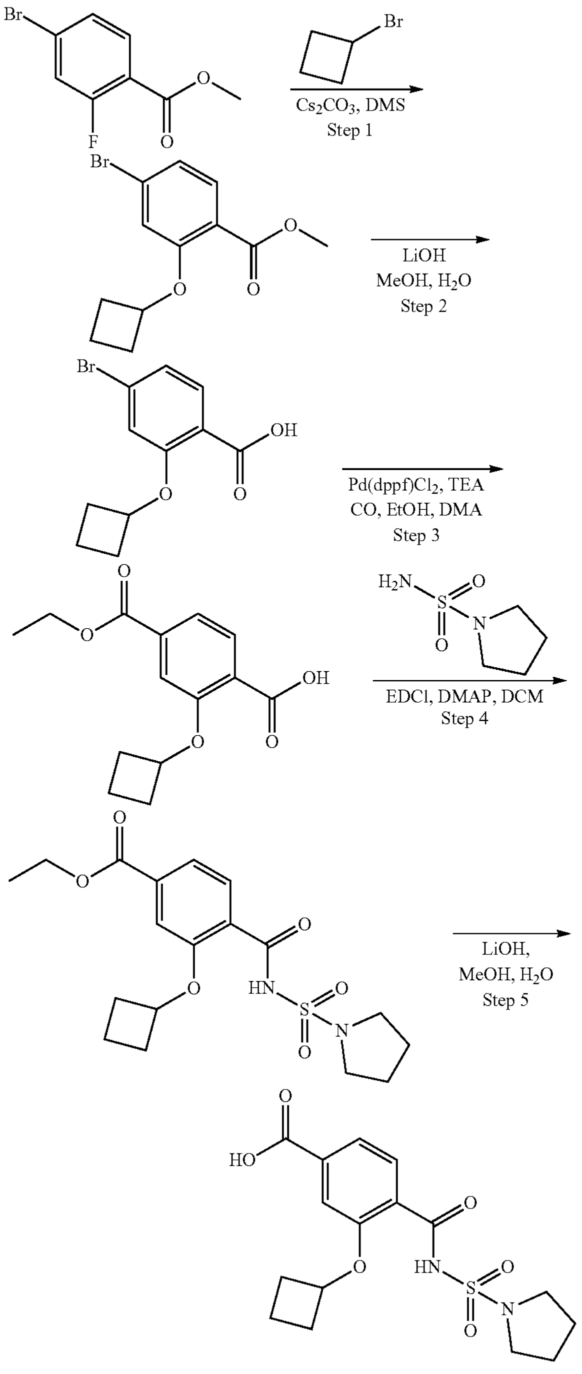

Step 1

A mixture of 4-bromo-2-hydroxybenzoate (3.0 g, 13.0 mmol), bromocyclobutane (3.5 g, 26.0 mmol) and $Cs_2CO_3$ (8.5 g, 26.0 mmol) in DMA (30 mL) was stirred at 80° C. overnight. The reaction was cooled to RT, diluted with water (150 mL) and extracted with EtOAc (3×100 mL). The combined organic layers were washed with brine, dried ($Na_2SO_4$) and concentrated under reduced pressure. The crude product was purified by chromatography on silica gel (1-10% EtOAc/petroleum ether) to afford methyl 4-bromo-2-cyclobutoxybenzoate (3.0 g, 10.6 mmol) as a colourless oil. LCMS: (System 2, Method B) Rt=2.02 min, m/z 285.0 $(M+H)^+$ $(ES^+)$.

Step 2

A mixture of methyl 4-bromo-2-cyclobutoxybenzoate (3.0 g, 10.5 mmol) and LiOH·$H_2O$ (1.3 g, 31.6 mmol) in MeOH (20 mL) and water (10 mL) was stirred at RT overnight. The organic solvent was removed under reduced pressure, then the pH of the mixture was adjusted to pH=3 by adding HCl aq. 1N The precipitate was recovered by filtration, washed with water and hexane, and dried under reduce pressure to afford 4-bromo-2-cyclobutoxybenzoic acid (2.50 g, 9.30 mmol) as an off-white solid. LCMS: (System 1, Method A) Rt=1.25 min, m/z 271.2 $(M+H)^+$ $(ES^+)$.

Step 3

A mixture of 4-bromo-2-cyclobutoxybenzoic acid (1.4 g, 5.16 mmol), [1,1'-bis(diphenylphosphino)ferrocene]dichloropalladium(II) (0.8 g, 1.04 mmol) and triethylamine (2.6 g, 25.7 mmol) in DMA (8 mL) and EtOH (30 mL) was stirred at 90° C. overnight under CO atmosphere. The reaction was cooled to RT, diluted with water (80 mL) and washed with EtOAc (3×40 mL). Then the pH of the aqueous layer was adjusted to pH=3 by adding HCl aq. 1N and it was extracted with EtOAc (3×40 mL). The combined organic layers were washed with brine, dried ($Na_2SO_4$) and concentrated under reduced pressure to afford 2-cyclobutoxy-4-(ethoxycarbonyl)benzoic acid (1.1 g, 4.16 mmol) as a brown solid which was used without further purification in the next step. LCMS: (System 1, Method A) Rt=1.27 min, m/z 265.3 $(M+H)^+$ $(ES^+)$.

Step 4

A mixture of 2-cyclobutoxy-4-(ethoxycarbonyl)benzoic acid (600 mg, 2.27 mmol), EDCI (871 mg, 4.54 mmol), pyrrolidine-1-sulfonamide (512 mg, 3.41 mmol) and DMAP (549 mg, 4.49 mmol) in DCM (20 mL) was stirred at RT overnight. The reaction was diluted with water (20 mL) and the mixture was extracted with DCM (3×20 mL). The combined organic layers were dried ($Na_2SO_4$), filtered and concentrated under reduced pressure. The crude product was purified by column chromatography on silica gel (1-50% EtOAc/petroleum ether) to afford ethyl 3-cyclobutoxy-4-(pyrrolidin-1-ylsulfonylcarbamoyl)benzoate (880 mg, 2.22 mmol) as a colourless oil. LCMS: (System 1, Method A) Rt=1.65 min, m/z 397.3 $(M+H)^+$ $(ES^+)$.

Step 5

A mixture of ethyl 3-cyclobutoxy-4-(pyrrolidin-1-ylsulfonylcarbamoyl)benzoate (400 mg, 1.0 mmol) and LiOH·$H_2O$ (127 mg, 3.03 mmol) in MeOH (10 mL) and water (5 mL) was stirred at RT overnight. The organic solvent was removed under reduced pressure and the pH of the resulting aqueous solution was adjusted to pH=3 by adding HCl aq. 1N, the resulting solution was extracted with EtOAc (3×20 mL). The combined organic layers were washed with brine, dried ($Na_2SO_4$) and concentrated under reduced pressure to afford 3-cyclobutoxy-4-(pyrrolidin-1-ylsulfonylcarbamoyl)

benzoic acid (330 mg, 0.90 mmol) as a white solid. LCMS: (System 1, Method A) Rt=1.13 min, m/z 369.2 $(M+H)^+$ $(ES^+)$.

Intermediate 11: 3-cyclobutoxy-4-(1-methylcyclopropylsulfonylcarbamoyl)benzoic Acid

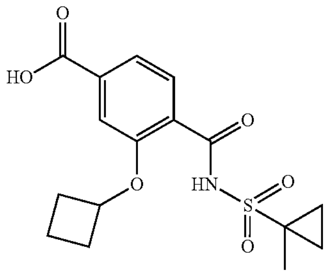 [SMILES: CC1(S(=O)(=O)NC(=O)c2ccc(C(=O)O)cc2OC2CCC2)CC1]

Prepared by an analogous method to Intermediate 10 starting from 4-bromo-2-hydroxybenzoate (3.0 g, 13.0 mmol) and bromocyclobutane (3.5 g, 26.0 mmol) except the Step 4 was carried out with 1-methylcyclopropane-1-sulfonamide in place of pyrrolidine-1-sulfonamide. Yield: 310 mg, 0.88 mmol. White solid. LCMS: (System 1, Method A) Rt=0.95 min, m/z 354.2 $(M+H)^+$ $(ES^+)$.

Intermediate 12: 3-(cyclopentyloxy)-4-(((1-methylcyclopropyl)sulfonyl)carbamoyl)benzoic acid

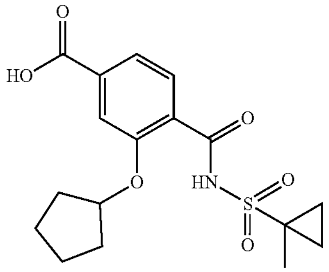 [SMILES: CC1(S(=O)(=O)NC(=O)c2ccc(C(=O)O)cc2OC2CCCC2)CC1]

Prepared by an analogous method to Intermediate 10 starting from 4-bromo-2-hydroxybenzoate (5.0 g, 21.6 mmol) and bromocyclopentane (12.9 g, 86.6 mmol) except the Step 4 was carried out with 1-methylcyclopropane-1-sulfonamide in place of pyrrolidine-1-sulfonamide. Yield: 1.0 g, 2.72 mmol. White solid. LCMS: (System 1, Method A) Rt=1.07 min, m/z 366.0 $(M-H)^-$ $(ES^-)$.

Intermediate 13: 3-cyclobutoxy-2-fluoro-4-((pyrrolidin-1-ylsulfonyl)carbamoyl)benzoic acid

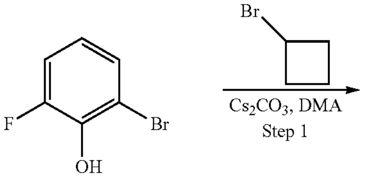

-continued

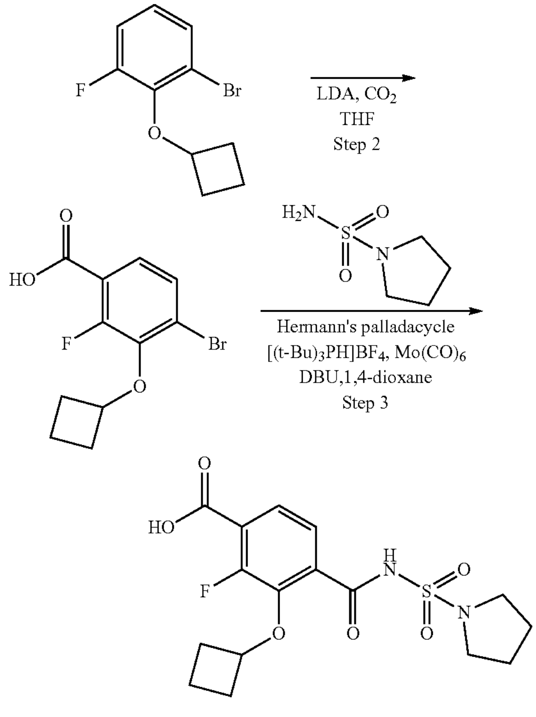

Step 1

A mixture of 2-bromo-6-fluorophenol (2.0 g, 10.5 mmol), bromocyclobutane (2.8 g, 20.9 mmol) and $Cs_2CO_3$ (10.2 g, 31.4 mmol) in DMA (50 mL) was stirred at RT overnight. The mixture was diluted with water (150 mL) and extracted with EtOAc (3×100 mL). The combined organic layers were washed with brine, dried ($Na_2SO_4$), filtered and concentrated under reduced pressure. The crude product was purified by column chromatography on silica gel (1-10% EtOAc/petroleum ether) to afford 1-bromo-2-cyclobutoxy-3-fluorobenzene (2.2 g, 8.98 mmol) as a pale-yellow oil. $^1H$ NMR (400 MHz, $CD_3OD$) δ: 7.35 (dd, J=8.0, 1.2 Hz, 1H), 7.14-7.10 (m, 1H), 7.00-6.94 (m, 1H), 4.70-4.63 (m, 1H), 2.32-2.20 (m, 4H), 1.81-1.72 (m, 1H), 1.58-1.49 (m, 1H).

Step 2

To a solution of 1-bromo-2-cyclobutoxy-3-fluorobenzene (2.20 g, 8.98 mmol) in THF (70 mL) was slowly added LDA 2 M (5.4 mL, 10.8 mmol) at −70° C. and stirred for 1 h, then dry ice (10 g) was added slowly and the mixture was stirred at RT overnight. The reaction was quenched with $NH_4Cl$ aq. sat. (100 mL) and partitioned with EtOAc (3×60 mL). The combined organic layers were washed with brine, dried ($Na_2SO_4$), filtered and concentrated under reduced pressure to afford 4-bromo-3-cyclobutoxy-2-fluorobenzoic acid (1.6 g, 5.53 mmol) as a white solid. LCMS: (System 1, Method A) Rt=1.36 min, m/z 287.0 $(M-H)^-$ $(ES^-)$.

Step 3

A mixture of 4-bromo-3-cyclobutoxy-2-fluorobenzoic acid (650 mg, 2.25 mmol), pyrrolidine-1-sulfonamide (1.01 g, 6.75 mmol), trans-bis(acetato)bis[o-(di-o-tolylphosphino)-benzyl]dipalladium (II) (Herrmann's palladacycle, 216 mg, 0.23 mmol), tri-tert-butylphosphonium tetrafluoroborate (133 mg, 0.46 mmol), molybdenum hexacarbonyl (891 mg, 3.38 mmol) and DBU (1.03 g, 6.75 mmol) in 1,4-dioxane (20 mL) was stirred at 140° C. for 15 minutes under microwave irradiation. The mixture was concentrated under reduced pressure, the residue was taken in $K_2CO_3$ aq. 2 M (40 mL) and washed with EtOAc (3×40 mL). The pH of the aqueous layer was adjusted to pH=4 by adding HCl aq. 1N, then it was extracted with EtOAc (3×40 mL). The combined organic layers were dried ($Na_2SO_4$), filtered and concentrated under reduced pressure. The crude product was purified by column chromatography on silica gel (1-5% MeOH/DCM) to afford 3-cyclobutoxy-2-fluoro-4-((pyrrolidin-1-ylsulfonyl)carbamoyl)benzoic acid (200 mg, 0.52 mmol) as a colourless oil. LCMS: (System 1, Method A) Rt=0.99 min, m/z 385.0 $(M-H)^-$ $(ES^-)$.

Intermediate 14: 3-(cyclopentyloxy)-2-fluoro-4-((pyrrolidin-1-ylsulfonyl)carbamoyl)benzoic acid

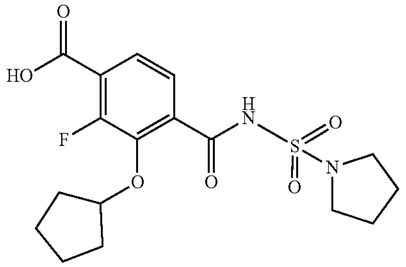

Prepared by an analogous method to Intermediate 13 starting from of 2-bromo-6-fluorophenol (50.0 g, 263 mmol) and bromocyclopentane (78.0 g, 526 mmol). Yield: 32.0 g, 79.9 mmol. White solid. LCMS: (System 1, Method A) Rt=1.11 min, m/z $(M-H)^-$ $(ES^-)$.

Intermediate 15: 3-(cyclopentyloxy)-4-((N,N-dimethylsulfamoyl)carbamoyl)-2-fluorobenzoic acid

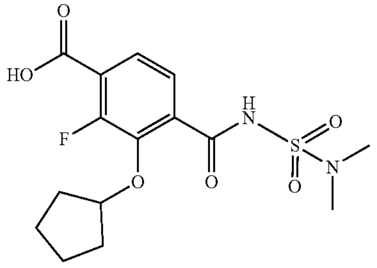

Prepared by an analogous method to Intermediate 14 except the Step 3 was carried out with N,N-dimethylsulfamide in place of pyrrolidine-1-sulfonamide. Yield: 410 mg, 1.10 mmol. Pale-yellow solid. LCMS: (System 1, Method A) Rt=0.96 min, m/z 373.0 $(M-H)^-$ $(ES^-)$.

Intermediate 16: 3-(cyclopentyloxy)-2-fluoro-4-(((1-methylcyclopropyl)sulfonyl)carbamoyl)benzoic Acid

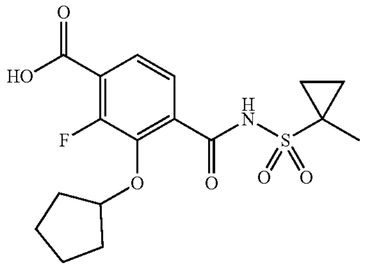 [SMILES: CC1(S(=O)(=O)NC(=O)c2ccc(C(=O)O)c(F)c2OC2CCCC2)CC1]

Prepared by an analogous method to Intermediate 14 except the Step 3 was carried out with 1-methylcyclopropane-1-sulfonamide in place of pyrrolidine-1-sulfonamide. Yield: 440 mg, 1.14 mmol. Pale-yellow solid. LCMS: (System 1, Method A) Rt=1.01 min, m/z 384.2 $(M-H)^-$ $(ES^-)$.

Intermediate 17: 3-(cyclopentyloxy)-2-fluoro-4-(N-isopropyl-N-methylsulfamoylcarbamoyl)benzoic Acid

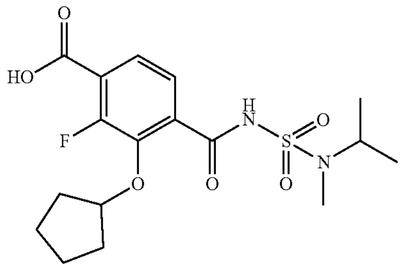 [SMILES: CC(C)N(C)S(=O)(=O)NC(=O)c1ccc(C(=O)O)c(F)c1OC1CCCC1]

Prepared by an analogous method to Intermediate 14 except the Step 3 was carried out with N-methyl-N-isopropylsulfamoyl amide in place of pyrrolidine-1-sulfonamide. Yield: 220 mg, 0.55 mmol. White solid. LCMS: (System 1, Method F) Rt=0.99 min, m/z 401.0 $(M-H)^-$ $(ES^-)$.

Intermediate 18: 3-cyclobutoxy-2-fluoro-4-((N-isopropyl-N-methylsulfamoyl)carbamoyl)benzoic acid

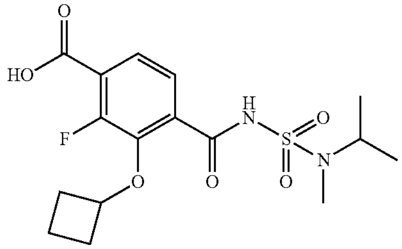 [SMILES: CC(C)N(C)S(=O)(=O)NC(=O)c1ccc(C(=O)O)c(F)c1OC1CCC1]

Prepared by an analogous method to Intermediate 13 except the Step 3 was carried out with N-methyl-N-isopropylsulfamoyl amide in place of pyrrolidine-1-sulfonamide.

Yield: 240 mg, 0.62 mmol. White solid. LCMS: (System 1, Method F) Rt=0.94 min, m/z 387.0 $(M-H)^-$ $(ES^-)$.

Intermediate 19: 3-cyclobutoxy-2-fluoro-4-(1-methylcyclopropylsulfonylcarbamoyl)benzoic acid

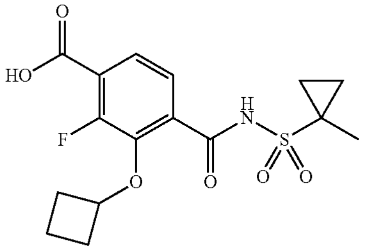 [SMILES: CC1(S(=O)(=O)NC(=O)c2ccc(C(=O)O)c(F)c2OC2CCC2)CC1]

Prepared by an analogous method to Intermediate 13 except the Step 3 was carried out with 1-methylcyclopropane-1-sulfonamide in place of pyrrolidine-1-sulfonamide. Yield: 500 mg, 1.35 mmol. White solid. LCMS: (System 1, Method A) Rt=0.85 min, m/z 370.0 $(M-H)^-$ $(ES^-)$.

Intermediate 20: 3-cyclobutoxy-4-(N,N-dimethylsulfamoylcarbamoyl)-2-fluorobenzoic Acid

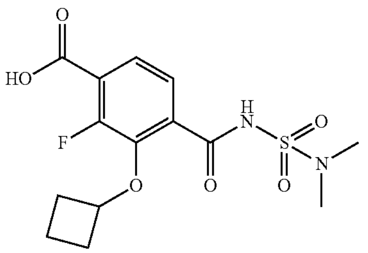 [SMILES: CN(C)S(=O)(=O)NC(=O)c1ccc(C(=O)O)c(F)c1OC1CCC1]

Prepared by an analogous method to Intermediate 13 except the Step 3 was carried out with N,N-dimethylsulfamide in place of pyrrolidine-1-sulfonamide. Yield: 670 mg, 1.86 mmol. White solid. LCMS: (System 2, Method B) Rt=1.61 min, m/z 361.1 $(M-H)^-$ $(ES^-)$.

Intermediate 21: (1R,3r,5S)-3-(2-bromo-6-fluorophenoxy)bicyclo[3.1.0]hexane

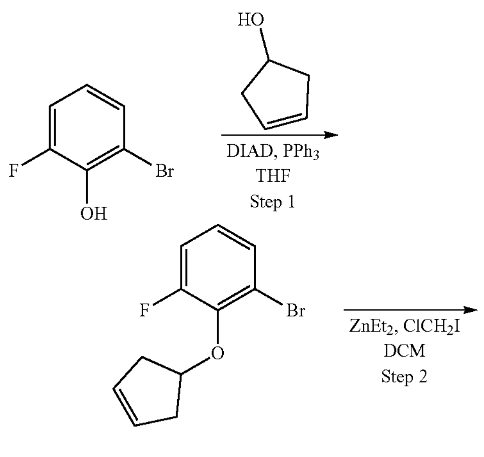

-continued

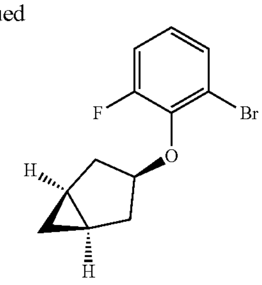

Step 1

DIAD (6.8 g, 33.7 mmol) was added to a solution of 2-bromo-6-fluorophenol (3.2 g, 16.8 mmol), $PPh_3$ (8.8 g, 33.7 mmol) and cyclopent-3-en-1-ol (2.1 g, 25.3 mmol) in THF (150 mL) at 0° C., the reaction mixture was stirred at RT overnight. The mixture was diluted with water (100 mL) and extracted with EtOAc (3×100 mL). The combined organic layers were washed with brine, dried ($Na_2SO_4$), filtered and concentrated under reduced pressure. The crude product was purified by column chromatography on silica gel (1% EtOAc/petroleum ether) to afford 1-bromo-2-(cyclopent-3-en-1-yloxy)-3-fluorobenzene (2.1 g, 8.17 mmol) as a pale-yellow oil. $^1H$ NMR (400 MHz, DMSO-$d_6$) δ: 7.47-7.45 (m, 1H), 7.35-7.30 (m, 1H), 7.10-7.05 (m, 1H), 5.77 (s, 2H), 5.06-5.03 (m, 1H), 2.67-2.50 (m, 4H).

Step 2

A solution of diethylzinc 1 M in heptane (24.6 mL, 24.6 mmol) in DCM (80 mL) was slowly added to a solution of chloroiodomethane (11.6 g, 65.6 mmol) in DCM (20 mL) at 0° C. and the mixture was stirred at this temperature for 1 h. Then, a solution of 1-bromo-2-(cyclopent-3-en-1-yloxy)-3-fluorobenzene (2.1 g, 8.2 mmol) in DCM (10 mL) was added and the mixture was allowed to reach RT and stirred overnight. The reaction was quenched by adding $NH_4Cl$ aq. (50 mL) and extracted with DCM (3×50 mL). The combined organic layers were washed with brine, dried ($Na_2SO_4$), filtered and concentrated under reduced pressure. The crude product was purified by column chromatography on silica gel (1% EtOAc/petroleum ether) to afford (1R,3r,5S)-3-(2-bromo-6-fluorophenoxy)bicyclo[3.1.0]hexane (1.7 g, 6.27 mmol) as a pale-yellow oil. $^1H$ NMR (400 MHz, DMSO-$d_6$) δ: 7.46-7.43 (m, 1H), 7.33-7.27 (m, 1H), 7.08-7.02 (m, 1H), 4.81-4.78 (m, 1H), 2.18-2.11 (m, 2H), 2.05-2.01 (m, 2H), 1.36-1.30 (m, 2H), 0.86-0.83 (m, 1H), 0.54-0.50 (m, 1H).

Intermediate 22: 3-(((1R,3r,5S)-bicyclo[3.1.0]hexan-3-yl)oxy)-2-fluoro-4-((pyrrolidin-1-ylsulfonyl)carbamoyl)benzoic acid

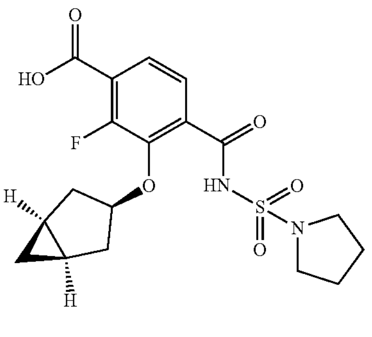 [SMILES: O=C(O)c1ccc(C(=O)NS(=O)(=O)N2CCCC2)c(O[C@@H]2C[C@@H]3C[C@@H]3C2)c1F]

Prepared by an analogous method to Intermediate 13 (Step 2 and Step 3 only) starting from (1R,3r,5S)-3-(2-bromo-6-fluorophenoxy)bicyclo[3.1.0]hexane (Intermediate 21, 1.2 g, 3.8 mmol) in Step 2. Yield: 370 mg, 0.90 mmol. Pale-yellow solid. LCMS: (System 1, Method A) Rt=1.10 min, m/z 410.9 $(M-H)^-$ $(ES^-)$.

Intermediate 23: 3-(((1R,3r,5S)-bicyclo[3.1.0]hexan-3-yl)oxy)-4-((N,N-dimethylsulfamoyl)carbamoyl)-2-fluorobenzoic acid

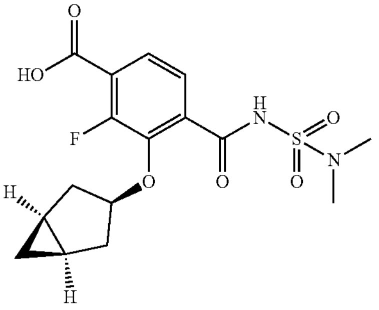 [SMILES: CN(C)S(=O)(=O)NC(=O)c1ccc(C(=O)O)c(F)c1O[C@@H]1C[C@@H]2C[C@@H]2C1]

Prepared by an analogous method to Intermediate 22 except the Step 3 was carried out with N,N-dimethylsulfamide in place of pyrrolidine-1-sulfonamide. Yield: 600 mg, 1.55 mmol. Yellow solid. LCMS: (System 1, Method F) Rt=0.83 min, m/z 385.4 $(M-H)^-$ $(ES^-)$.

Intermediate 24: 3-(((1R,3r,5S)-bicyclo[3.1.0]hexan-3-yl)oxy)-2-fluoro-4-((N-isopropyl-N-methylsulfamoyl)carbamoyl)benzoic acid

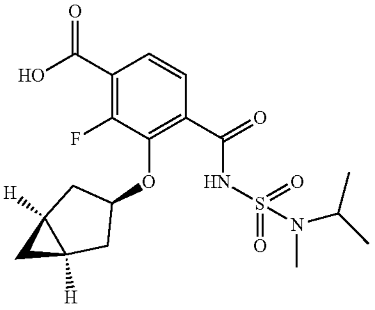 [SMILES: CC(C)N(C)S(=O)(=O)NC(=O)c1ccc(C(=O)O)c(F)c1O[C@@H]1C[C@@H]2C[C@@H]2C1]

Prepared by an analogous method to Intermediate 22 except the Step 3 was carried out with N-methyl-N-isopropylsulfamoyl amide in place of pyrrolidine-1-sulfonamide. Yield: 356 mg, 0.86 mmol. Pale-yellow solid. LCMS: (System 1, Method A) Rt=1.21 min, m/z 412.8 $(M-H)^-$ $(ES^-)$.

Intermediate 25: 3-(((1R,3r,5S)-bicyclo[3.1.0]hexan-3-yl)oxy)-2-fluoro-4-(((1-methylcyclopropyl)sulfonyl)carbamoyl)benzoic acid

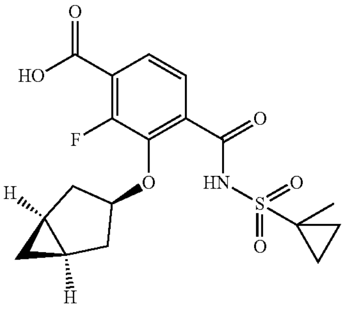 [SMILES: CC1(S(=O)(=O)NC(=O)c2ccc(C(=O)O)c(F)c2O[C@@H]2C[C@@H]3C[C@@H]3C2)CC1]

Prepared by an analogous method to Intermediate 22 except the Step 3 was carried out with 1-methylcyclopropane-1-sulfonamide in place of pyrrolidine-1-sulfonamide. Yield: 364 mg, 0.92 mmol. Pale-yellow solid. LCMS: (System 1, Method A) Rt=1.06 min, m/z 395.9 $(M-H)^-$ $(ES^-)$.

Intermediate 26: (1R,3s,5S)-3-(2-bromo-6-fluorophenoxy)bicyclo[3.1.0]hexane

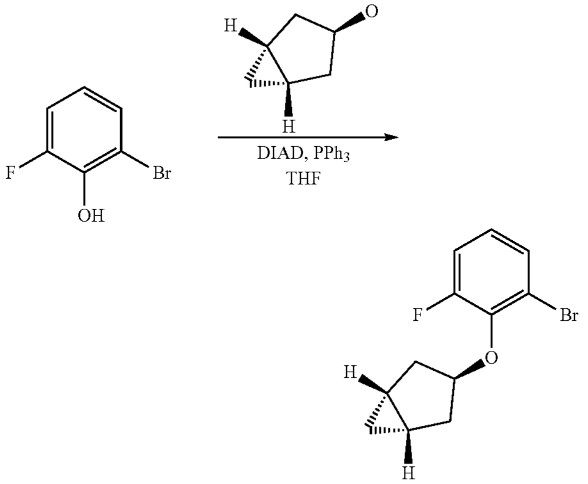

DIAD (6.4 g, 31.6 mmol) was added to a mixture of 2-bromo-6-fluorophenol (2.0 g, 10.5 mmol), (1R,3r,5S)-bicyclo[3.1.0]hexan-3-ol (1.0 g, 10.5 mmol) and $PPh_3$ (8.3 g, 31.6 mmol) in THE (50 mL). The reaction was stirred at RT overnight. The reaction mixture was quenched with water (50 mL) and extracted with EtOAc (3x50 mL). The combined organic layers were washed with brine, dried ($Na_2SO_4$), filtered and concentrated under reduced pressure. The crude product was purified by column chromatography on silica gel (1-10% EtOAc/petroleum ether) to afford (1R,3s,5S)-3-(2-bromo-6-fluorophenoxy)bicyclo[3.1.0]hexane (1.9 g, 7.0 mmol) as a white solid. $^1H$ NMR (400 MHz, DMSO-$d_6$) δ: 7.46-7.43 (m, 1H), 7.33-7.28 (m, 1H), 7.10-7.04 (m, 1H), 4.43-4.35 (m, 1H), 2.17-2.13 (m, 2H), 2.03-1.98 (m, 2H), 1.34-1.30 (m, 2H), 0.37-0.32 (m, 1H), 0.07-0.04 (m, 1H).

Intermediate 27: 1-bromo-2-((4,4-difluorocyclohexyl)oxy)-3-fluorobenzene

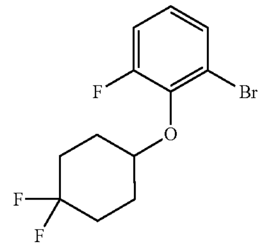 [SMILES: Fc1cccc(Br)c1OC1CCC(F)(F)CC1]

Prepared by an analogous method to Intermediate 26 starting from 2-bromo-6-fluorophenol (500 mg, 2.62 mmol) and 4,4-difluorocyclohexanol (535 mg, 3.93 mmol). Yield: 650 mg, 2.1 mmol. White solid. LCMS: (System 3, Method I). Rt=2.14 min.

Intermediate 28: 2-(2-bromo-6-fluorophenoxy)adamantane

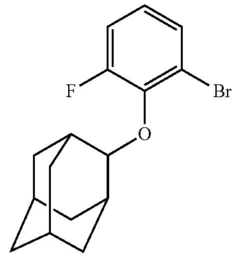 [SMILES: Fc1cccc(Br)c1OC1C2CC3CC(C2)CC1C3]

Prepared by an analogous method to Intermediate 26 starting from 2-bromo-6-fluorophenol (1.0 g, 5.24 mmol) and 2-adamantanol (1.2 g, 7.85 mmol). Yield: 700 mg, 2.2 mmol. White solid. LCMS: (System 3, Method I). Rt=2.21 min.

Intermediate 29: 3-((1R,3s,5S)-bicyclo[3.1.0]hexan-3-yloxy)-2-fluoro-4-(pyrrolidin-1-ylsulfonylcarbamoyl)benzoic acid

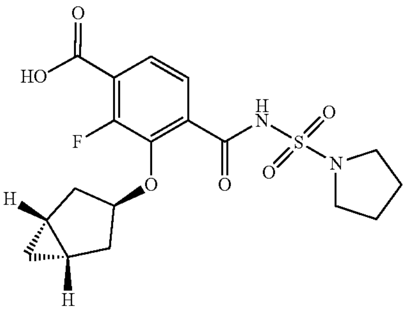 [SMILES: O=C(O)c1ccc(C(=O)NS(=O)(=O)N2CCCC2)c(O[C@H]2C[C@@H]3C[C@@H]3C2)c1F]

Prepared by an analogous method to Intermediate 13 (Step 2 and Step 3 only) starting from (1R,3s,5S)-3-(2-bromo-6-fluorophenoxy)bicyclo[3.1.0]hexane (Intermediate 26, 1.9 g, 16.7 mmol) in Step 2. Yield: 250 mg, 0.61 mmol. Pale-yellow solid. LCMS: (System 1, Method F) Rt=0.91 min, m/z 411.0 $(M-H)^-$ $(ES^-)$.

Intermediate 30: 3-((1R,3s,5S)-bicyclo[3.1.0]hexan-3-yloxy)-2-fluoro-4-(pyrrolidin-1-ylsulfonylcarbamoyl)benzoic acid

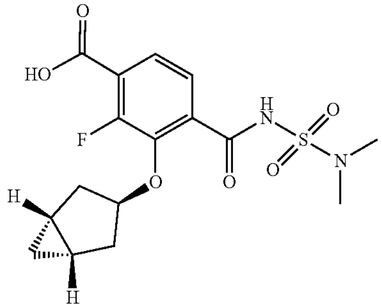 [SMILES: CN(C)S(=O)(=O)NC(=O)c1ccc(C(=O)O)c(F)c1O[C@H]1C[C@@H]2C[C@@H]2C1]

Prepared by an analogous method to Intermediate 29 except the Step 3 was carried out with N,N-dimethylsulfamide in place of pyrrolidine-1-sulfonamide. Yield: 230 mg, 0.60 mmol. White solid. LCMS: (System 1, Method A) Rt=1.01 min, m/z 384.8 $(M-H)^-$ $(ES^-)$ Intermediate 31: 3-(((1R,3s,5S)-bicyclo[3.1.0]hexan-3-yl)oxy)-2-fluoro-4-(((1-methylcyclopropyl)sulfonyl)carbamoyl)benzoic acid

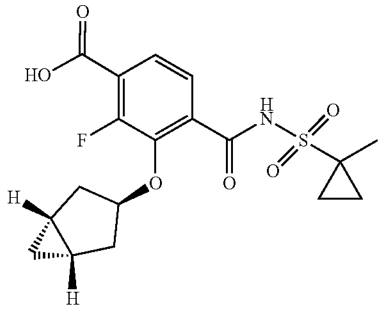 [SMILES: CC1(S(=O)(=O)NC(=O)c2ccc(C(=O)O)c(F)c2O[C@H]2C[C@@H]3C[C@@H]3C2)CC1]

Prepared by an analogous method to Intermediate 29 except the Step 3 was carried out with 1-methylcyclopropane-1-sulfonamide in place of pyrrolidine-1-sulfonamide. Yield: 240 mg, 0.60 mmol. White solid. LCMS: (System 1, Method F) Rt=0.85 min, m/z 396.0 $(M-H)^-$ $(ES^-)$ Intermediate 32: 3-(4,4-difluorocyclohexoxy)-4-(dimethylsulfamoylcarbamoyl)-2-fluoro-benzoic Acid

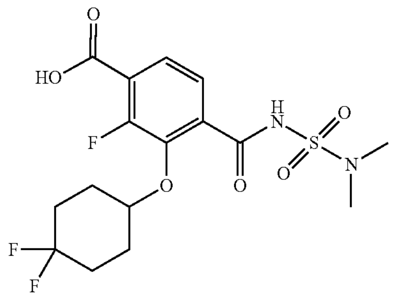 [SMILES: CN(C)S(=O)(=O)NC(=O)c1ccc(C(=O)O)c(F)c1OC1CCC(F)(F)CC1]

Prepared by an analogous method to Intermediate 13 (Step 2 and Step 3 only) starting from 1-bromo-2-((4,4-difluorocyclohexyl)oxy)-3-fluorobenzene (Intermediate 27, 650 mg, 2.10 mmol) in Step 2. Step 3 was carried out with N,N-dimethylsulfamide in place of pyrrolidine-1-sulfonamide. Yield: 190 mg, 0.45 mmol. White solid. LCMS: (System 3, Method I) Rt=0.80 min, m/z 423.2 $(M-H)^-$ $(ES^-)$ Intermediate 33: 3-(4,4-difluorocyclohexoxy)-2-fluoro-4-[(1-methylcyclopropyl)sulfonylcarbamoyl] benzoic Acid

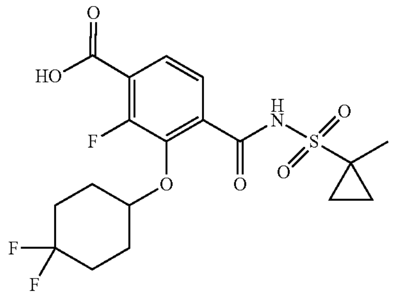 [SMILES: CC1(S(=O)(=O)NC(=O)c2ccc(C(=O)O)c(F)c2OC2CCC(F)(F)CC2)CC1]

Prepared by an analogous method to Intermediate 32 except the Step 3 was carried out with 1-methylcyclopropane-1-sulfonamide in place of pyrrolidine-1-sulfonamide. Yield: 165 mg, 0.38 mmol. Yellow solid. LCMS: (System 3, Method I) Rt=0.98 min, m/z 434.3 $(M-H)^-$ $(ES^-)$ Intermediate 34: 3-((adamantan-2-yl)oxy)-2-fluoro-4-((pyrrolidin-1-ylsulfonyl)carbamoyl)benzoic Acid

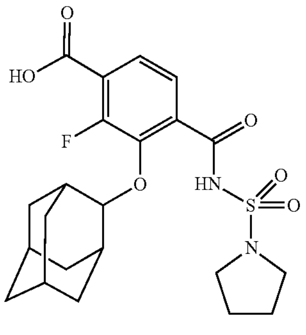 [SMILES: O=C(O)c1ccc(C(=O)NS(=O)(=O)N2CCCC2)c(OC2C3CC4CC(C3)CC2C4)c1F]

Prepared by an analogous method to Intermediate 13 (Step 2 and Step 3 only) starting from 2-(2-bromo-6-fluorophenoxy)adamantane (Intermediate 28, 700 mg, 2.15 mmol) in Step 2. Yield: 16 mg, 0.03 mmol. Yellow solid. LCMS: (System 3, Method I) Rt=1.19 min, m/z 467.2 $(M+H)^+$ $(ES^+)$ Intermediate 35: 3-((adamantan-2-yl)oxy)-4-((N,N-dimethylsulfamoyl)carbamoyl)-2-fluorobenzoic Acid

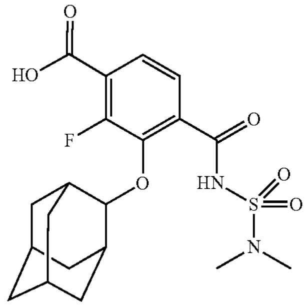 [SMILES: CN(C)S(=O)(=O)NC(=O)c1ccc(C(=O)O)c(F)c1OC1C2CC3CC(C2)CC1C3]

Prepared by an analogous method to Intermediate 34 except the Step 3 was carried out with N,N-dimethylsulfamide in place of pyrrolidine-1-sulfonamide. Yield: 27 mg, 0.06 mmol. White solid. LCMS: (System 3, Method J) Rt=1.84 min, m/z 439.0 $(M-H)^-$ $(ES^-)$ Intermediate 36: 5-cyclobutoxy-4-((N,N-dimethylsulfamoyl)carbamoyl)-2-fluorobenzoic Acid

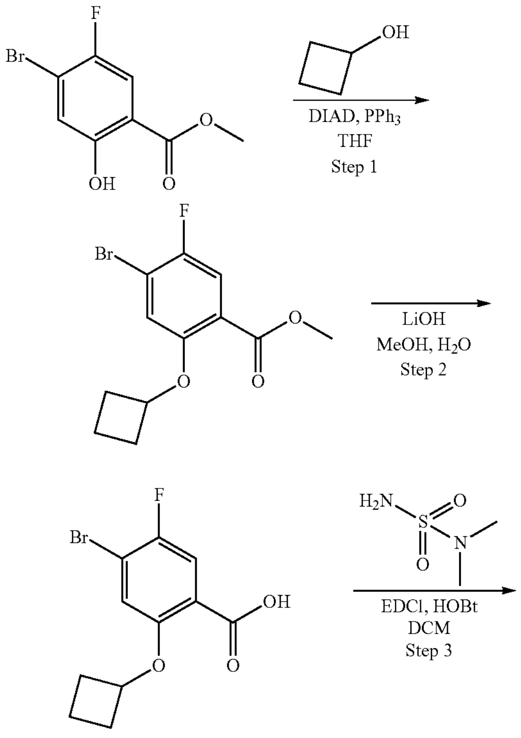

-continued

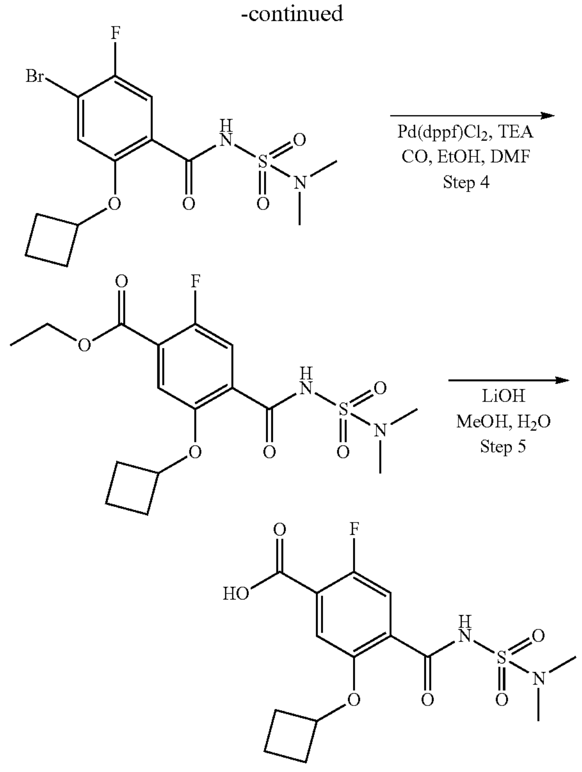

Step 1

DIAD (1.3 mL, 6.42 mmol) was added to a mixture of methyl 4-bromo-5-fluoro-2-hydroxybenzoate (800 mg, 3.21 mmol), $PPh_3$ (1685 mg, 6.42 mmol) and cyclobutanol (0.38 mL, 4.82 mmol) in THE (25 mL) at 0° C. and the mixture was stirred at RT overnight. The reaction was diluted with water (50 mL) and extracted with EtOAc (3×50 mL). The combined organic layers were washed with brine, dried ($Na_2SO_4$), filtered and concentrated under reduced pressure. The crude product was purified by column chromatography on silica gel (1-10% EtOAc/iso-hexane) to afford methyl 4-bromo-2-cyclobutoxy-5-fluorobenzoate (619 mg, 2.04 mmol) as a pale-yellow oil. $^1$H NMR (400 MHz, $CDCl_3$) δ: 7.57 (d, J=8.7 Hz, 1H), 6.97 (d, J=5.5 Hz, 1H), 4.64 (p, J=7.1 Hz, 1H), 3.88 (s, 3H), 2.51-2.43 (m, 2H), 2.29-2.19 (m, 2H), 1.93-1.84 (m, 1H), 1.75-1.64 (m, 1H).

Step 2

A mixture of methyl 4-bromo-2-cyclobutoxy-5-fluorobenzoate (619 mg, 2.04 mmol) and LiOH aq. 2N (2.0 mL, 4.00 mmol) in MeOH (2 mL) was stirred at RT overnight. The organic solvent was removed under reduced pressure, then the pH of the mixture was adjusted to 3 by adding 1N HCl aq. The precipitate was recovered by filtration, washed with water and hexane, and dried under reduce pressure to afford 4-bromo-2-cyclobutoxy-5-fluorobenzoic acid (424 mg, 1.47 mmol) as an off-white solid. LCMS: (System 3, Method I) Rt=1.24 min, m/z 287.0 $(M-H)^-$ $(ES^-)$

Step 3

A mixture of 4-bromo-2-cyclobutoxy-5-fluorobenzoic acid (212 mg, 0.73 mmol), EDCI (290 mg, 1.51 mmol), pyrrolidine-1-sulfonamide (276 mg, 2.23 mmol) and DMAP (185 mg, 1.51 mmol) in DCM (4 mL) was stirred at RT overnight. The reaction was diluted with water (15 mL) and the mixture was extracted with DCM (3×15 mL). The combined organic layers were dried ($Na_2SO_4$), filtered and concentrated under reduced pressure. The crude product was purified by column chromatography on silica gel (20-100% EtOAc/iso-hexane) to afford 4-bromo-2-cyclobutoxy-N—(N,N-dimethylsulfamoyl)-5-fluorobenzamide (175 mg, 0.43 mmol) as a white solid. LCMS: (System 3, Method I) Rt=1.43 min, m/z 393.1 $(M-H)^-$ $(ES^-)$.

Step 4

A mixture of 4-bromo-2-cyclobutoxy-N—(N,N-dimethylsulfamoyl)-5-fluorobenzamide (175 mg, 0.43 mmol), [1,1'-bis(diphenylphosphino)ferrocene]dichloropalladium (II) (16 mg, 0.02 mmol) and triethylamine (216 mg, 2.14 mmol) in DMF (3.5 mL) and EtOH (2 mL) was stirred at 100° C. overnight under CO atmosphere. The reaction was cooled to RT, diluted with water (20 mL) and extracted with EtOAc (3×40 mL). The combined organic layers were washed with brine, dried ($Na_2SO_4$) and concentrated under reduced pressure. The crude product was purified by column chromatography on silica gel (20-80% EtOAc/iso-hexane then 1%-10% MeOH/DCM) to afford ethyl 5-cyclobutoxy-4-((N,N-dimethylsulfamoyl)carbamoyl)-2-fluorobenzoate (102 mg, 0.25 mmol) as a brown solid. LCMS: (System 3, Method I) Rt=1.36 min, m/z 387.2 $(M-H)^-$ $(ES^-)$.

Step 5

$LiOH{\cdot}H_2O$ (1.2 mL, 2.46 mmol) was added to a solution of ethyl 5-(cyclobutoxy)-2-fluoro-4-(pyrrolidin-1-ylsulfonylcarbamoyl)benzoate (102 mg, 0.25 mmol) in MeOH (3.0 mL) and the reaction was stirred at RT for 1 h. The organic solvent was removed under reduced pressure and the crude product was purified by column chromatography on $C_{18}$ (0-100% ACN/0.1% FA in water) to afford 5-cyclobutoxy-4-((N,N-dimethylsulfamoyl)carbamoyl)-2-fluorobenzoic acid (41 mg, 0.11 mmol) as an off-white solid. LCMS: (System 3, Method J) Rt=1.64 min, m/z 359.2 $(M-H)^-$ $(ES^-)$.

Intermediate 37: (S)-2-(methoxymethyl)-1-methylpiperazine

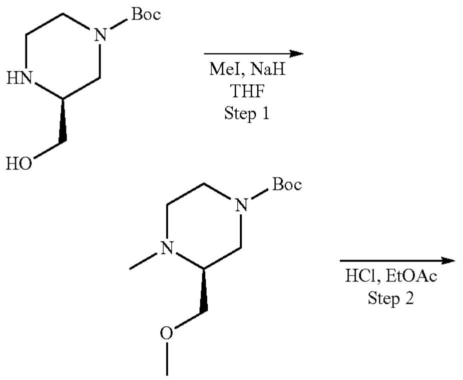

-continued

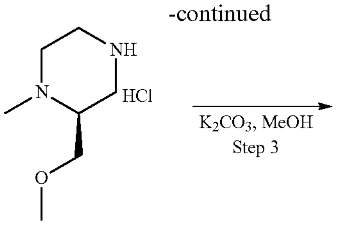

Step 1

Sodium hydride (60% dispersion in mineral oil, 2.3 g, 57.8 mmol) was added portion wise to a solution of tert-butyl (S)-3-(hydroxymethyl)piperazine-1-carboxylate (5.0 g, 23.1 mmol) in THE (50 mL) at 0° C. for 1 h. Then iodomethane (8.2 g, 57.8 mmol) was added dropwise at 0° C. and the mixture was stirred at RT for 12 h. The reaction was quenched by adding $NH_4Cl$ aq. sat. (30 mL) at 0° C., the resulting aqueous layer was extracted with EtOAc (3×10 mL). The combined organic layers were washed with brine, dried ($Na_2SO_4$), filtered and concentrated under reduced pressure to afford tert-butyl (S)-3-(methoxymethyl)-4-methylpiperazine-1-carboxylate (6.2 g, 25.4 mmol) as a white solid which was used in the next step without further purification. $^1H$ NMR (400 MHz, $CDCl_3$) δ 3.87-3.84 (m, 2H), 3.52-3.41 (m, 2H), 3.31 (s, 3H), 3.06-2.67 (m, 3H), 2.34 (s, 3H), 2.22-2.01 (m, 2H), 1.44 (s, 9H).

Step 2

A mixture of tert-butyl (S)-3-(methoxymethyl)-4-methylpiperazine-1-carboxylate (5.7 g, 23.1 mmol, 1.0 eq) and HCl 4N solution in EtOAc (25 mL) in EtOAc (25 mL) was stirred at RT for 12 h. The mixture was concentrated under reduced pressure to afford (S)-2-(methoxymethyl)-1-methylpiperazine hydrochloride (3.00 g, 16.60 mmol) as a brown solid which was used in the next step without further purification. LCMS: (System 3, Method J) Rt=0.33 min, m/z 145.1 $(M+H)^+$ $(ES^+)$ Step 3

A mixture of (S)-2-(methoxymethyl)-1-methylpiperazine hydrochloride (1.50 g, 8.30 mmol) and $K_2CO_3$ (1.26 g, 9.13 mmol, 1.1 eq) in MeOH (7.50 mL) was stirred at RT for 1 h. The reaction was partitioned between water (10 mL) and DCM (3×10 mL). The combined organic layers were washed with brine, dried ($Na_2SO_4$), filtered and concentrated under reduced pressure to afford (S)-2-(methoxymethyl)-1-methylpiperazine (1.1 g, 7.63 mmol) as a black solid. $^1H$ NMR (400 MHz, DMSO-$d_6$) δ: 3.44-3.48 (m, 1H), 3.30-3.35 (m, 1H), 3.24 (s, 3H), 3.10-3.14 (m, 2H), 2.78-2.85 (m, 2H), 2.63-2.69 (m, 1H), 2.39-2.46 (m, 2H), 2.22 (s, 3H), Intermediate 38: 3-(bicyclo[3.1.0]hexan-3-yloxy)-4-((N,N-dimethylsulfamoyl)carbamoyl)benzoic Acid

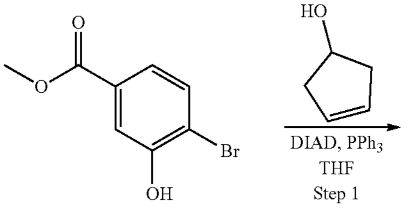

-continued

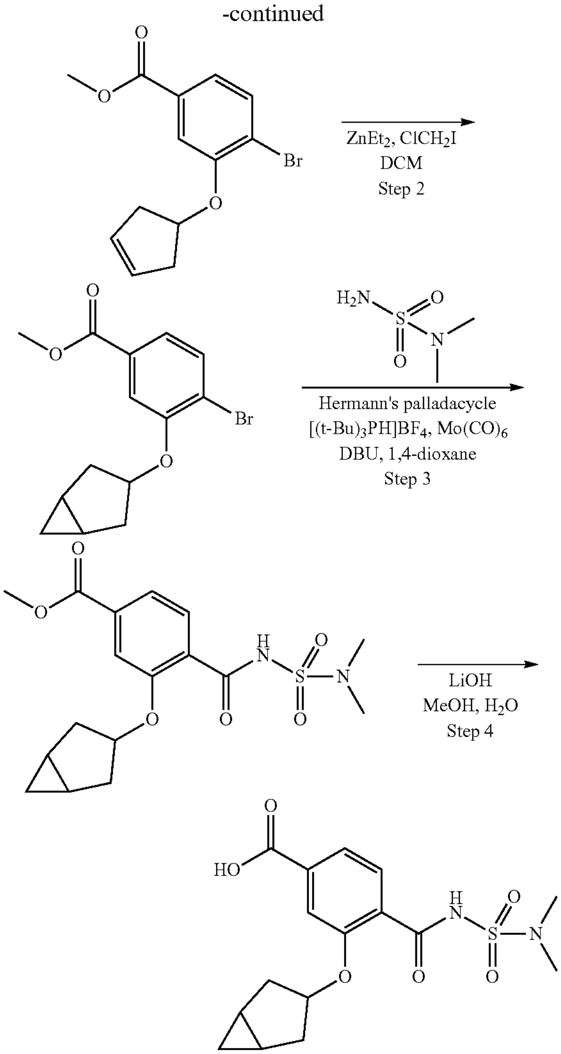

Step 1

DIAD (15.9 g, 77.9 mmol) was added to a mixture of methyl 4-bromo-3-hydroxybenzoate (6.0 g, 26.0 mmol), cyclopent-3-enol (6.6 g, 78.0 mmol) and $PPh_3$ (20.4 g, 77.9 mmol) in THE (300 mL) and the mixture was stirred at RT overnight. Water (300 mL) was added, and the mixture was extracted with EtOAc (3×300 mL). The combined organic layers were washed with brine, dried ($Na_2SO_4$), filtered and concentrated under reduced pressure. The crude product was purified by column chromatography on silica gel (1-10% EtOAc/petroleum ether) to afford methyl 4-bromo-3-(cyclopent-3-en-1-yloxy)benzoate (6.0 g, 20.2 mmol) as a brown solid. LCMS: (System 2, Method C) Rt=0.86 min, m/z 297.1 2 $(M+H)^+$ $(ES^+)$.

Step 2

Chloroiodomethane (23.6 g, 133 mmol) was added dropwise to a solution of diethylzinc 1 M in heptane (67.5 mL) in DCM (75 mL) at 0° C., the mixture was stirred at this temperature for 30 min, then solution of methyl 4-bromo-3-(cyclopent-3-en-1-yloxy)benzoate (6.0 g, 20.2 mmol) in DCM (75 mL) was added. The mixture was stirred at RT overnight. The reaction was quenched with $NH_4Cl$ aq. sat. (200 mL) and extracted with DCM (3×200 mL). The combined organics layers were washed with brine, dried ($Na_2SO_4$), filtered and concentrated under reduced pressure. The crude product was purified by column chromatography on silica gel (1-10% EtOAc/petroleum ether) to afford methyl 3-(bicyclo[3.1.0]hexan-3-yloxy)-4-bromobenzoate (4.5 g, 14.5 mmol) as a colorless oil. LCMS: (System 2, Method C) Rt=0.92 min, m/z 311.2 $(M+H)^+$ $(ES^+)$.

Step 3

A mixture of methyl 3-(bicyclo[3.1.0]hexan-3-yloxy)-4-bromobenzoate (2.0 g, 6.45 mmol), tri-tert-butylphosphonium tetrafluoroborate (377 mg, 1.3 mmol), trans-bis(acetato)bis[o-(di-o-tolylphosphino)benzyl]dipalladium(II) (Herrmann's palladacycle, 610 mg, 0.65 mmol), molybdenum hexacarbonyl (2.6 g, 9.67 mmol), DBU (2.9 g, 19.35 mmol) and methanesulfonamide (2.4 g, 19.4 mmol) in 1,4-dioxane (50 mL) was stirred at 100° C. overnight. The reaction mixture was cooled to RT, diluted with DCM/water (5:1, 120 mL) and filtered through celite. The filtrate was concentrated under reduced pressure and the crude product was purified by column chromatography on silica gel (0-5% MeOH/DCM) to afford methyl 3-(bicyclo[3.1.0]hexan-3-yloxy)-4-((N,N-dimethylsulfamoyl)carbamoyl)benzoate (1.3 g, 3.40 mmol) as a pale-yellow solid. LCMS: (System 2, Method F) Rt=1.31 min, m/z 383.2 $(M+H)^+$ $(ES^+)$.

Step 4

A mixture of 3-(bicyclo[3.1.0]hexan-3-yloxy)-4-((N,N-dimethylsulfamoyl)carbamoyl)benzoate (1.0 g, 2.62 mmol) in MeOH (20 mL) and water (5 mL) was added $LiOH \cdot H_2O$ (660 mg, 15.7 mmol), then the mixture was stirred at RT overnight. The organic solvent was removed under reduced pressure, then the pH of the mixture was adjusted to ca. 5 by adding HCl aq. 1N and extracted with EtOAc (3×20 mL). The combined organic layers were dried ($Na_2SO_4$), filtered and concentrated under reduced pressure to afford 3-(bicyclo[3.1.0]hexan-3-yloxy)-4-((N,N-dimethylsulfamoyl)carbamoyl)benzoic acid (849 mg, 2.30 mmol) as a white solid which was used in the next step without further purification. LCMS: (System 1, Method A) Rt=1.14 min, m/z 366.8 $(M-H)^-$ $(ES^-)$.

Intermediate 39: 3-(bicyclo[3.1.0]hexan-3-yloxy)-4-((pyrrolidin-1-ylsulfonyl)carbamoyl)benzoic Acid

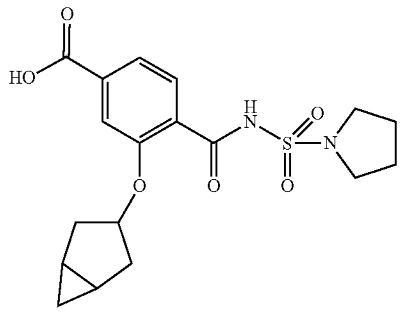 [SMILES: O=C(O)c1ccc(C(=O)NS(=O)(=O)N2CCCC2)c(OC2CC3CC3C2)c1]

Prepared by an analogous method to Intermediate 38 starting from 4-bromo-3-hydroxybenzoate (6.0 g, 26.0 mmol) except the Step 3 was carried out with pyrrolidine-1-sulfonamide in place of N,N-dimethylsulfamide. Yield: 1.3 g, 3.30 mmol. Pale-yellow solid. LCMS: (System 2, Method F) Rt=1.31 min, m/z 409.2 $(M+H)^+$ $(ES^+)$.

Intermediate 40: 3-((4,4-difluorocyclohexyl)oxy)-4-((pyrrolidin-1-ylsulfonyl)carbamoyl)benzoic Acid

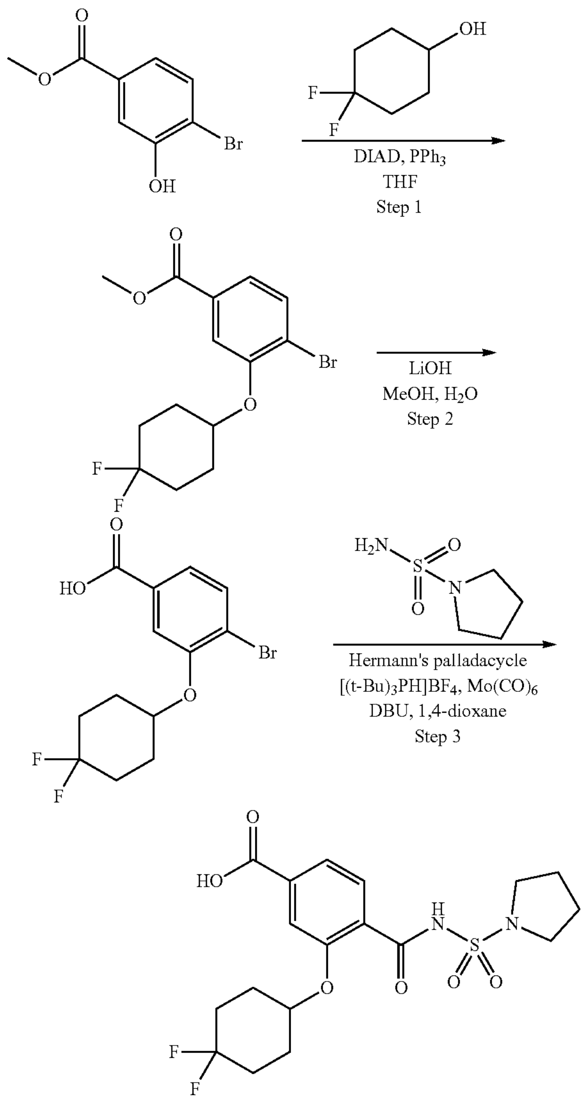

Step 1

DIAD (963 mg, 4.76 mmol) was added to a mixture of methyl 4-bromo-3-hydroxybenzoate (500 mg, 2.38 mmol), 4,4-difluorocyclohexanol (487 mg, 3.57 mmol) and $PPh_3$ (1.25 g, 4.76 mmol) in THE (12 mL) and the mixture was stirred at RT overnight. Water (50 mL) was added, and the mixture was extracted with EtOAc (3×50 mL). The combined organic layers were washed with brine, dried ($Na_2SO_4$), filtered and concentrated under reduced pressure. The crude product was purified by column chromatography on silica gel (1-10% EtOAc/petroleum ether) to afford methyl 4-bromo-3-((4,4-difluorocyclohexyl)oxy)benzoate (810 mg, 2.32 mmol) as a pale-yellow solid. LCMS: (System 3, Method I) Rt=2.07 min.

Step 2

A solution of LiOH aq. 2 M (3.5 mL, 7.0 mmol) was added to a solution of methyl 4-bromo-3-((4,4-difluorocyclohexyl)oxy)benzoate (810 mg, 2.32 mmol) in MeOH (3.5 mL). The reaction mixture was stirred at 40° C. overnight. The reaction mixture was cooled to RT, and after adjusting pH to ca. 3 with HCl aq. 1N, extracted with EtOAc (2×30 mL). The combined organic layers were dried ($MgSO_4$), filtered and concentrated under reduced pressure to afford 4-bromo-3-(4,4-difluorocyclohexoxy)benzoic acid (530 mg, 1.58 mmol) as pale-yellow solid. LCMS: (System 3, Method I) Rt=1.38 min, m/z 334.9 $(M-H)^-$ $(ES^-)$.

Step 3

A mixture of DBU (0.39 mL, 2.64 mmol), 4-bromo-3-(4,4-difluorocyclohexoxy)benzoic acid (295 mg, 0.88 mmol), molybdenum hexacarbonyl (594 mg, 1.32 mmol), pyrrolidine-1-sulfonamide (397 mg, 2.64 mmol), trans-bis(acetato)bis[o-(di-o-tolylphosphino)benzyl]dipalladium(II) (Herrmann palladacycle, 83 mg, 0.09 mmol) and tri-tert-butylphosphoniumtetrafluoroborate (51 mg, 0.18 mmol) in 1,4-dioxane (4.7 mL) was stirred at 140° C. for 30 min under microwave irradiation. The mixture was dissolved in MeOH (20 mL) and concentrated under reduced pressure. The residue was diluted with $K_2CO_3$ aq. 2 M (30 mL) and washed with EtOAc (3×30 mL). The resulting aqueous layer was acidified to pH 1-2 by adding HCl aq. 2N and extracted with EtOAc (3×30 mL). The combined organic layers were dried ($MgSO_4$), filtered and concentrated under reduced pressure to afford 3-(4,4-difluorocyclohexoxy)-4-(pyrrolidin-1-ylsulfonylcarbamoyl)benzoic acid (33 mg, 0.08 mmol) as a white solid which was used in the next step without further purification. LCMS: (System 3, Method I) Rt=1.71 min, m/z 431.2 $(M-H)^-$ $(ES^-)$.

Intermediate 41: 3-((adamantan-2-yl)oxy)-4-((pyrrolidin-1-ylsulfonyl)carbamoyl)benzoic acid

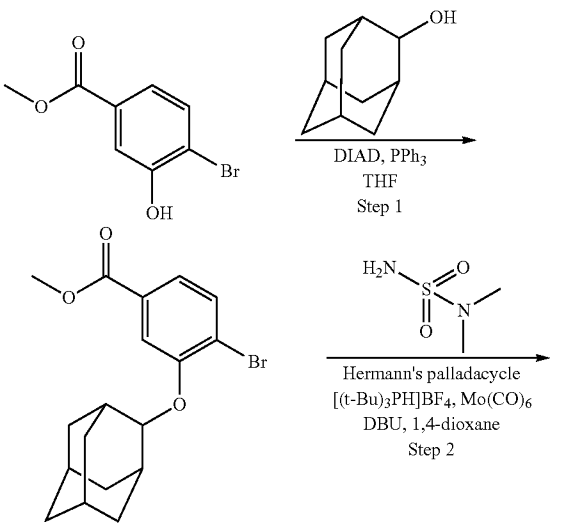

-continued

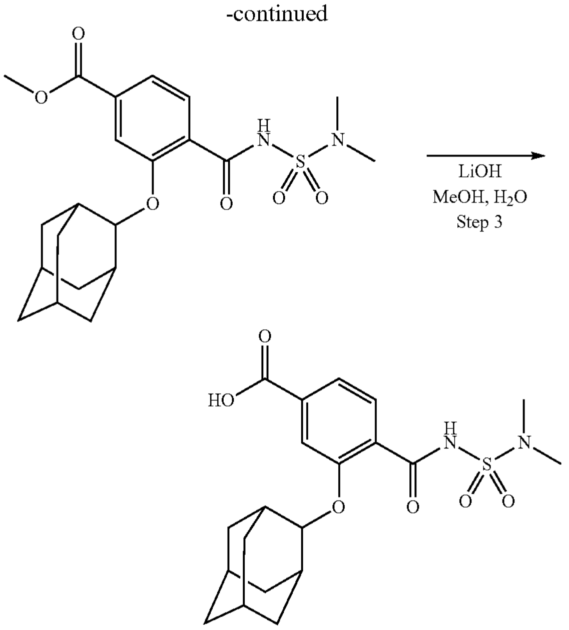

Step 1

DIAD (2.1 mL, 10.5 mmol) was added to a mixture of methyl 4-bromo-3-hydroxybenzoate (1.2 g, 5.24 mmol), adamantan-2-ol (1.2 g, 7.85 mmol) and $PPh_3$ (2.7 g, 10.5 mmol) in THE (25 mL) and the mixture was stirred at RT overnight. Water (50 mL) was added, and the mixture was extracted with EtOAc (3×50 mL). The combined organic layers were washed with brine, dried ($Na_2SO_4$), filtered and concentrated under reduced pressure. The crude product was purified by column chromatography on silica gel (1-10% EtOAc/petroleum ether) to afford methyl 3-((adamantan-2-yl)oxy)-4-bromobenzoate (49 mg, 0.12 mmol) as a pale-yellow solid. LCMS: (System 3, Method I) Rt=1.21 min, m/z 421.1 $(M-H)^-$ $(ES^-)$.

Step 2

A mixture of DBU (0.31 mL, 0.68 mmol), methyl 3-((adamantan-2-yl)oxy)-4-bromobenzoate (249 mg, 0.68 mmol), molybdenum hexacarbonyl (459 mg, 1.02 mmol), N,N-dimethylsulfamide (253 mg, 2.04 mmol), trans-bis(acetato)bis[o-(di-o-tolylphosphino)benzyl]dipalladium(II) (Herrmann palladacycle, 128 mg, 0.14 mmol), tri-tert-butylphosphoniumtetrafluoroborate (79 mg, 0.27 mmol) in 1,4-dioxane (4.5 mL) was stirred at 140° C. for 30 min under microwave irradiation. The mixture was dissolved in MeOH (20 mL) and concentrated under reduced pressure. The crude product was purified by column chromatography on silica gel (10-90% EtOAc/iso-hexane) to afford methyl 3-((adamantan-2-yl)oxy)-4-((N,N-dimethylsulfamoyl)carbamoyl) benzoate (124 mg, 0.28 mmol) as a yellow solid. LCMS: (System 3, Method I) Rt=1.62 min, m/z 435.1 $(M-H)^-$ $(ES^-)$.

Step 3

A mixture of methyl 3-((adamantan-2-yl)oxy)-4-((N,N-dimethylsulfamoyl)carbamoyl)benzoate (124 mg, 0.284 mmol) and LiOH aq. 2 M (0.43 mL, 0.85) in THE (0.4 mL) and MeOH (0.4 mL) was stirred at 40° C. overnight. The mixture was acidified to pH 1-2 by adding HCl aq. 2N (10 mL) and extracted with EtOAc (2×30 mL). Then combined organic layers were dried ($MgSO_4$), filtered and concentrated under reduced pressure to afford 3-(2-adamantyloxy)-4-(dimethylsulfamoylcarbamoyl)benzoic acid (49 mg, 0.12 mmol) as a pale-yellow solid which was used in the next step without further purification. LCMS: (System 3, method I) Rt=1.21 min, m/z 421.1 $(M-H)^-$ $(ES^-)$.

Intermediate 42: 4-(ethoxycarbonyl)-2-fluoro-6-(trifluoromethyl)benzoic acid

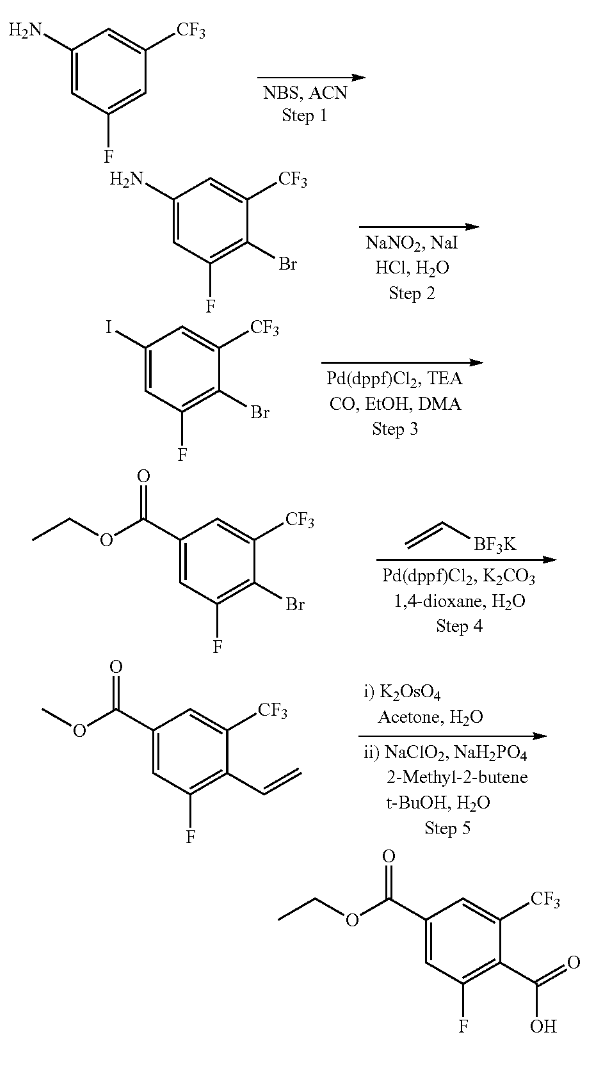

Step 1

N-Bromosuccinimide (24.8 g, 140 mmol) was added portionwise to a solution of 3-fluoro-5-(trifluoromethyl) aniline (25.0 g, 140 mmol) in ACN (500 mL) at 0° C., then the reaction was stirred at 0° C. for 2 h. The reaction was concentrated under reduced pressure and the crude product was purified by column chromatography on silica gel (10% DCM/petroleum ether) to afford 4-bromo-3-fluoro-5-(trifluoromethyl)aniline (25.0 g, 96.9) as a white solid. $^1H$ NMR (400 MHz, $CDCl_3$) δ: 6.81-6.80 (m, 1H), 6.59 (dd, J=9.8, 2.6 Hz, 1H), 4.00 (br s, 2H).

Step 2

A solution of $NaNO_2$ (7.4 g, 107 mmol) in water (125 mL) was added to a solution of 4-bromo-3-fluoro-5-(trifluoromethyl)aniline (25.0 g, 96.9 mmol) in HCl aq. conc. (250 mL) at 0° C., and the mixture was stirred at 0° C. for 1 h. Then NaI (16.0 g, 107 mmol) was added portionwise and the reaction mixture was stirred at 0° C. for 2 h. The reaction mixture was quenched with $Na_2S_2O_3$ aq. sat. (500 mL) and extracted with EtOAc (3×500 mL). The combined organic layers were dried ($Na_2SO_4$), filtered and concentrated under reduced pressure. The crude product was purified by column chromatography on silica gel (10% DCM/petroleum ether) to afford 2-bromo-1-fluoro-5-iodo-3-(trifluoromethyl)benzene (21.8 g, 59.1 mmol) as a brown solid. $^1H$ NMR (400 MHz, $CDCl_3$) δ: 7.81 (s, 1H), 7.65 (dd, J=7.2, 1.6 Hz, 1H).

Step 3

A mixture of 2-bromo-1-fluoro-5-iodo-3-(trifluoromethyl)benzene (21.8 g, 59.1 mmol), TEA (29.9 g, 295 mmol) and [1,1'-bis(diphenylphosphino)ferrocene]dichloropalladium(II) (8.7 g, 11.8 mmol) in EtOH (600 mL) was stirred at 80° C. overnight under CO atmosphere. The reaction mixture was allowed to reach RT and concentrated under reduced pressure. The crude product was purified by column chromatography on silica gel (4% DCM/petroleum ether) to afford ethyl 4-bromo-3-fluoro-5-(trifluoromethyl)benzoate (13.1 g, 41.6 mmol) as a brown solid. $^1H$ NMR (400 MHz, $CDCl_3$) δ: 8.17 (s, 1H), 7.95 (dd, J=8.2, 2.2 Hz, 1H), 4.43 (q, J=7.1 Hz, 2H), 1.42 (t, J=7.2 Hz, 3H).

Step 4

A mixture of ethyl 4-bromo-3-fluoro-5-(trifluoromethyl) benzoate (8.0 g, 25.4 mmol), potassium vinyltrifluoroborate (10.2 g, 76.2 mmol), [1,1'-bis(diphenylphosphino)ferrocene] dichloropalladium(II) (1.9 g, 2.5 mmol) and $K_2CO_3$ (7.0 g, 50.8 mmol) in 1,4-dioxane (200 mL) and water (50 mL) was stirred at 100° C. overnight under nitrogen atmosphere. The reaction was allowed to reach RT and partitioned between water (300 mL) and EtOAc (3×300 mL). The combined organic layers were dried ($Na_2SO_4$), filtered and concentrated under reduced pressure. The crude product was purified by column chromatography on silica gel (10% DCM/petroleum ether) to afford ethyl 3-fluoro-5-(trifluoromethyl)-4-vinylbenzoate (5.0 g, 19.2 mmol) as a brown oil. $^1H$ NMR (400 MHz, $CDCl_3$) δ: 8.07 (s, 1H), 7.86 (d, J=10.8 Hz, 1H), 6.76-6.68 (m, 1H), 5.93 (d, J=17.6 Hz, 1H), 5.75-5.71 (m, 1H), 4.35 (q, J=7.1 Hz, 2H), 1.35 (t, J=7.2 Hz, 3H).

Step 5

To a solution of ethyl 3-fluoro-5-(trifluoromethyl)-4-vinylbenzoate (5.0 g, 19.2 mmol) in acetone (150 mL) and water (150 mL) was added potassium osmate(VI) dehydrate (1.4 g, 3.8 mmol), followed by $NaIO_4$ (16.41 g, 76.74 mmol) and the reaction mixture was stirred at RT for 2 h. The reaction mixture was quenched with $Na_2S_2O_3$ aq. sat. and extracted with EtOAc (3×200 mL). The combined organic layers were dried ($Na_2SO_4$), filtered and concentrated under reduced pressure. The residue was dissolved in $^t$BuOH (75 mL) and water (75 mL), and $NaH_2PO{\cdot}2H_2O$ (6.9 g, 57.6 mmol) was added, followed by $NaClO_2$ (5.2 g, 57.6 mmol) and 2-methylbut-2-ene (15 mL). The reaction mixture was stirred at RT overnight. Then, $^t$BuOH was removed under reduced pressure, and pH of the mixture was adjusted to ca. 3 with HCl aq. 1N. The aqueous solution was extracted with DCM (3×100 mL), the combined organic layers were dried ($Na_2SO_4$), filtered and concentrated under reduced pressure to afford 4-(ethoxycarbonyl)-2-fluoro-6-(trifluoromethyl) benzoic acid (2.5 g, 8.92 mmol) as a white solid. $^1H$ NMR (400 MHz, DMSO-$d_6$) δ: 14.67 (br s, 1H), 8.16 (d, J=9.2 Hz, 1H), 8.08 (s, 1H), 4.38 (q, J=7.1 Hz, 2H), 1.35 (t, J=7.2 Hz, 3H).

Intermediate 43: 3-(cyclopentyloxy)-4-(((1-methylcyclopropyl)sulfonyl)carbamoyl)-5-(trifluoromethyl) benzoic acid PGP-161 $C_3$

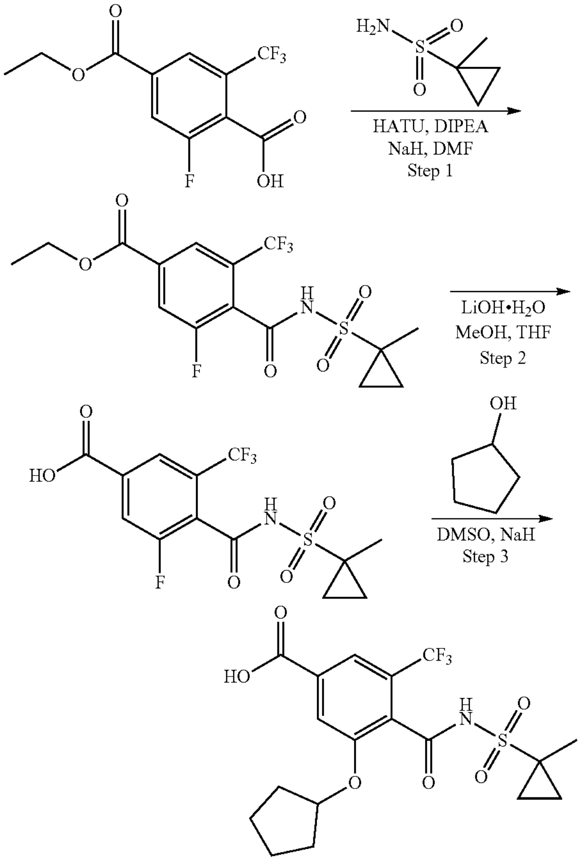

Step 1

A mixture of 4-(ethoxycarbonyl)-2-fluoro-6-(trifluoromethyl)benzoic acid (Intermediate 42, 1.6 g, 5.7 mmol), HATU (2.6 g, 6.9 mmol) and DIPEA (3.0 g, 22.8 mmol) in DMF (50 mL) was stirred at RT for 1.5 h. After this time, 1-methylcyclopropane-1-sulfonamide (2.3 g, 17.1 mmol) was added, followed by sodium hydride (60% in mineral oil, 914 mg, 22.8 mmol). The reaction was stirred at RT overnight then poured into $NH_4Cl$ aq. sat. (150 mL). HCl aq. 1N (20 mL) was added and the mixture was extracted with EtOAc (3×150 mL). The combined organic layers were washed with brine, dried ($Na_2SO_4$), filtered and concentrated under reduced pressure. The crude product was purified by column chromatography on silica gel (1-10% EtOAc/petroleum ether) to afford ethyl 3-fluoro-4-(((1-methylcyclopropyl)sulfonyl)carbamoyl)-5-(trifluoromethyl) benzoate (1.5 g, 3.8 mmol) as a brown oil. LCMS: (System 1, Method A) Rt=1.81 min, m/z 398.0 $(M+H)^+$ $(ES^+)$.

Step 2

A mixture of ethyl 3-fluoro-4-(((1-methylcyclopropyl) sulfonyl)carbamoyl)-5-(trifluoromethyl)benzoate (500 mg, 1.26 mmol), $LiOH{\cdot}H_2O$ (207 mg, 5.04 mmol) in THE (16 mL), MeOH (4 mL) and water (4 mL) was stirred at RT overnight. The organic solvent was removed under reduced pressure, then pH of the mixture was adjusted to ca. 3 by adding HCl aq. 1N. The precipitate was collected by filtration, washed with water then hexane and dried to afford 3-fluoro-4-(((1-methylcyclopropyl)sulfonyl)carbamoyl)-5-(trifluoromethyl)benzoic acid (400 mg, 1.08 mmol) as a brown solid. LCMS: (System 1, Method A) Rt=0.61 min, m/z 387.0 $(M+NH_4)+(ES^+)$.

Step 3

Sodium hydride (60% in mineral oil, 867 mg, 21.7 mmol) was added in small portions to a solution of 3-fluoro-4-(((1-methylcyclopropyl)sulfonyl)carbamoyl)-5-(trifluoromethyl) benzoic acid (400.0 mg, 1.08 mmol) in DMSO (15 mL). Then cyclopentanol (932 mg, 10.84 mmol) was added and the mixture was stirred at 100° C. for 30 min. The reaction mixture was allowed to reach RT and poured into $NH_4Cl$ aq. sat. (45 mL). The pH of the solution was adjusted to ca. 8 by adding HCl aq. 1N. The aqueous solution was extracted with EtOAc (3×60 mL), the combined organic layers were washed with brine, dried ($Na_2SO_4$), filtered and concentrated under reduced pressure to afford 3-(cyclopentyloxy)-4-(((1-methylcyclopropyl)sulfonyl)carbamoyl)-5-(trifluoromethyl)benzoic acid (275 mg, 0.63) as a brown solid. LCMS: (System 1, Method A) Rt=1.08 min, m/z 453.0 $(M+NH_4)+(ES^+)$.

Intermediate 44: 3-(cyclopentyloxy)-4-((pyrrolidin-1-ylsulfonyl)carbamoyl)-5-(trifluoromethyl)benzoic acid

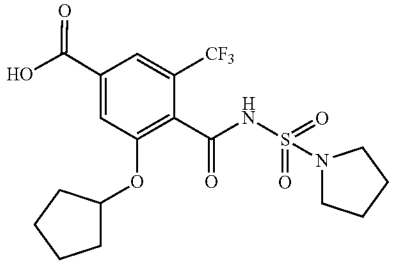 [SMILES: O=C(O)c1cc(OC2CCCC2)c(C(=O)NS(=O)(=O)N2CCCC2)c(C(F)(F)F)c1]

Prepared by an analogous method to Intermediate 43 starting from 4-(ethoxycarbonyl)-2-fluoro-6-(trifluoromethyl)benzoic acid (Intermediate 42, 1.6 g, 5.7 mmol) except the Step 1 was carried out with pyrrolidine-1-sulfonamide in place of 1-methylcyclopropane-1-sulfonamide. Yield: 255 mg, 0.57 mmol. Brown solid. LCMS: (System 1, Method G) Rt=0.45 min, m/z 451.1 $(M+H)^+$ $(ES^+)$.

Intermediate 45: 3-(cyclopentyloxy)-4-((N,N-dimethylsulfamoyl)carbamoyl)-5-(trifluoromethyl)benzoic acid

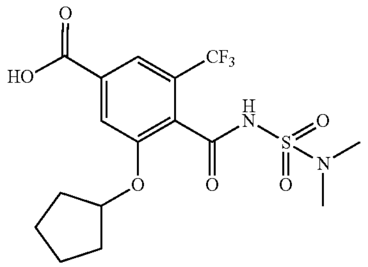 [SMILES: CN(C)S(=O)(=O)NC(=O)c1c(OC2CCCC2)cc(C(=O)O)cc1C(F)(F)F]

Prepared by an analogous method to Intermediate 43 starting from 4-(ethoxycarbonyl)-2-fluoro-6-(trifluoromethyl)benzoic acid (Intermediate 42, 1.6 g, 5.7 mmol) except the Step 1 was carried out with N,N-dimethylsulfamide in place of 1-methylcyclopropane-1-sulfonamide. Yield: 400 mg, 0.94 mmol. Brown solid. LCMS: (System 1, Method A) Rt=1.00 min, m/z 422.8 $(M-H)^-$ $(ES^-)$.

Intermediate 46: 4-(((1-methylcyclopropyl)sulfonyl)carbamoyl)-3-(pyrrolidin-1-yl)benzoic acid

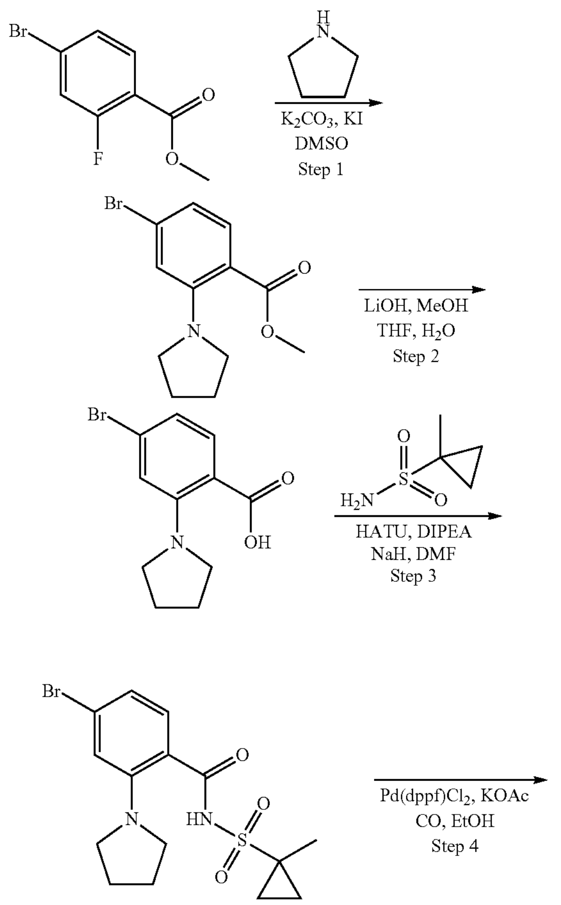

-continued

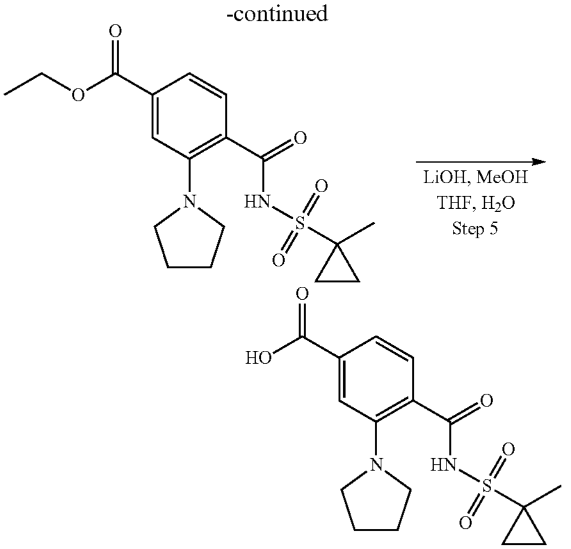

Step 1

A mixture of methyl 4-bromo-2-fluorobenzoate (5.0 g, 21.6 mmol), $K_2CO_3$ (8.9 g, 64.7 mmol), KI (1.8 g, 10.8 mmol) and pyrrolidine (2.3 g, 32.3 mmol) in DMSO (100 mL) was stirred at 100° C. overnight. The reaction was allowed to reach RT and partitioned between water (200 mL) and EtOAc (3×200 mL). The combined organic layers were washed with brine, dried ($Na_2SO_4$), filtered and concentrated under reduced pressure. The crude product was purified by column chromatography on silica gel (35% DCM/petroleum ether) to afford methyl 4-bromo-2-(pyrrolidin-1-yl)benzoate (5.0 g, 17.7 mmol) as a white solid. LCMS: (System 1, Method F) Rt=1.88 min, m/z 283.8 $(M-H)^-$ $(ES^-)$.

Step 2

A mixture of methyl 4-bromo-2-(pyrrolidin-1-yl)benzoate (5.0 g, 17.7 mmol) and $LiOH \cdot H_2O$ (2.9 g, 70.7 mmol) in THF (60 mL), MeOH (15 mL) and water (15 mL) was stirred at 65° C. overnight. The reaction was cooled to RT and the organic solvents were removed under reduced pressure. The pH of the resulting aqueous solution was set to ca. 3 by adding HCl aq. 1N. The precipitate was recovered by filtration, washed with water and hexane, and dried under reduced pressure to afford 4-bromo-2-(pyrrolidin-1-yl)benzoic acid (4.0 g, 14.8 mmol) as a white solid. LCMS: (System 1, Method F) Rt=1.09 min, m/z 269.8 $(M+H)^+$ $(ES^+)$.

Step 3

A mixture of 4-bromo-2-(pyrrolidin-1-yl)benzoic acid (1.1 g, 4.09 mmol), HATU (1.86 g, 4.91 mmol) and DIPEA (2.11 g, 16.36 mmol) in DMF (20 mL) was stirred at RT for 1 h, then 1-methylcyclopropane-1-sulfonamide (1.7 g, 12.3 mmol) and sodium hydride (60% dispersion in mineral oil, 655 mg, 16.4 mmol) were added, and the reaction was stirred at RT overnight. The pH of the crude mixture was adjusted to ca. 4 by adding HCl aq. 1N and the mixture was extracted with EtOAc (3×25 mL). The combined organic layers were dried ($Na_2SO_4$), filtered and concentrated under reduced pressure. The crude product was purified by column chromatography on silica gel (1-10% MeOH/DCM) to afford 4-bromo-N-(1-methylcyclopropylsulfonyl)-2-(pyrrolidin-1-yl)benzamide (700 mg, 1.81 mmol) as a white solid. LCMS: (System 1, Method F) Rt=1.24 min, m/z 387.3 $(M+H)^+$ $(ES^+)$.

Step 4

A mixture of 4-bromo-N-(1-methylcyclopropylsulfonyl)-2-(pyrrolidin-1-yl)benzamide (700 mg, 1.81 mmol), [1,1'-bis(diphenylphosphino)ferrocene]dichloropalladium(II) (265 mg, 0.36 mmol) and potassium acetate (532 mg, 5.43 mmol) in EtOH (15 mL) was stirred at 90° C. overnight under CO atmosphere. The mixture was dissolved in MeOH (20 mL) and concentrated under reduced pressure. The residue was dissolved in $K_2CO_3$ aq. 2 M (30 mL) and washed with EtOAc (3×15 mL). The resulting aqueous layer was acidified to pH 2-3 by adding HCl aq. 1N and extracted with EtOAc (3×15 mL). The combined organic layers were washed with brine, dried ($Na_2SO_4$), filtered and concentrated under reduced pressure to afford ethyl 4-(1-methylcyclopropylsulfonylcarbamoyl)-3-(pyrrolidin-1-yl)benzoate (600 mg, 1.58 mmol) as yellow oil. LCMS: (System 1, Method A) Rt=1.42 min, m/z 381.4 $(M+H)^+$ $(ES^+)$.

Step 5

A mixture of ethyl 4-(1-methylcyclopropylsulfonylcarbamoyl)-3-(pyrrolidin-1-yl)benzoate (600 mg, 1.58 mmol) and $LiOH{\cdot}H_2O$ (259 mg, 6.32 mmol) in THE (12 mL), MeOH (3 mL) and water (3 mL) was stirred at RT overnight. The organic solvents were removed under reduced pressure. The pH of the resulting aqueous solution was set to ca. 3 by adding HCl aq. 1N. The precipitate was recovered by filtration, washed with water and hexane, and dried under reduced pressure to afford 4-(1-methylcyclopropylsulfonylcarbamoyl)-3-(pyrrolidin-1-yl)benzoic acid (500 mg, 1.42 mmol) as a yellow solid. LCMS: (System 1, Method A) Rt=0.73 min, m/z 353.0 $(M+H)^+$ $(ES^+)$.

Intermediate 47: 4-((N,N-dimethylsulfamoyl)carbamoyl)-3-(pyrrolidin-1-yl)benzoic acid

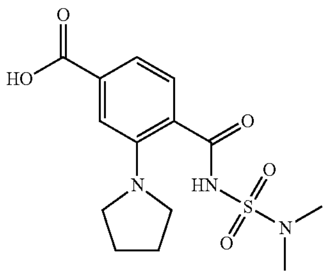 [SMILES: CN(C)S(=O)(=O)NC(=O)c1ccc(C(=O)O)cc1N1CCCC1]

Prepared by analogous method to Intermediate 46 starting except the Step 3 was carried out with N,N-dimethylsulfamide in place of 1-methylcyclopropane-1-sulfonamide. Yield: 320 mg, 0.94 mmol. Yellow solid. LCMS: (System 1, Method H) Rt=0.12 min, m/z 342.1 $(M+H)^+$ $(ES^+)$.

Intermediate 48: 3-(pyrrolidin-1-yl)-4-((pyrrolidin-1-ylsulfonyl)carbamoyl)benzoic acid

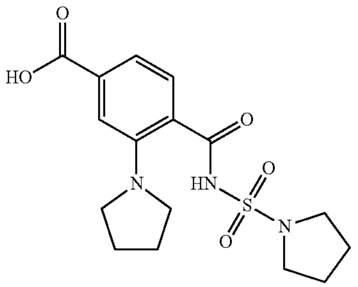 [SMILES: O=C(O)c1ccc(C(=O)NS(=O)(=O)N2CCCC2)c(N2CCCC2)c1]

Prepared by analogous method to Intermediate 46 except the Step 3 was carried out with pyrrolidine-1-sulfonamide in place of 1-methylcyclopropane-1-sulfonamide. Yield: 370 mg, 1.01 mmol. Yellow solid. LCMS: (System 1, Method F) Rt=0.72 min, m/z 368.2 $(M+H)^+$ $(ES^+)$.

Intermediate 49: 4-((N-isopropyl-N-methylsulfamoyl)carbamoyl)-3-(pyrrolidin-1-yl)benzoic acid

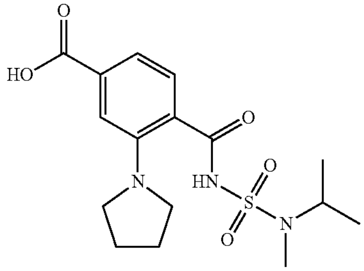 [SMILES: CC(C)N(C)S(=O)(=O)NC(=O)c1ccc(C(=O)O)cc1N1CCCC1]

Prepared by analogous method to Intermediate 46 starting except the Step 3 was carried out with N-methyl-N-isopropylsulfamoyl amide in place of 1-methylcyclopropane-1-sulfonamide. Yield: 820 mg, 2.22 mmol. Yellow solid. LCMS: (System 1, Method H) Rt=0.94 min, m/z 369.8 $(M+H)^+$ $(ES^+)$.

Intermediate 50: 3-(7-azabicyclo[2.2.1]heptan-7-yl)-4-(((1-methylcyclopropyl)sulfonyl)carbamoyl)benzoic acid

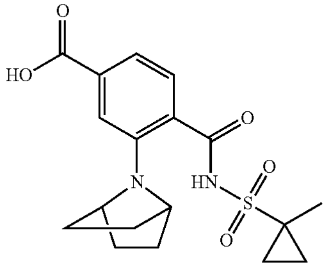 [SMILES: CC1(S(=O)(=O)NC(=O)c2ccc(C(=O)O)cc2N2C3CCC2CC3)CC1]

Prepared by analogous method to Intermediate 46 starting from methyl 4-bromo-2-fluorobenzoate (1.5 g, 6.44 mmol) and 7-azabicyclo[2.2.1]heptane (1.25 g, 12.9 mmol). Yield:

164 mg, 0.43 mmol. Yellow solid. LCMS: (System 1, Method F) Rt=0.65 min, m/z 377.2 $(M-H)^-$ $(ES^-)$.

Intermediate 51: 3-(7-azabicyclo[2.2.1]heptan-7-yl)-4-((N,N-dimethylsulfamoyl)carbamoyl)benzoic acid

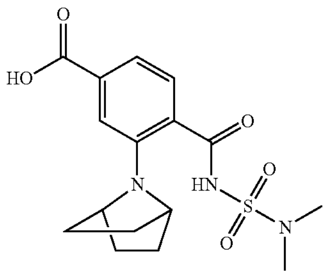 [SMILES: CN(C)S(=O)(=O)NC(=O)c1ccc(C(=O)O)cc1N1C2CCC1CC2]

Prepared by analogous method to Intermediate 50 except the Step 3 was carried out with N,N-dimethylsulfamide in place of 1-methylcyclopropane-1-sulfonamide. Yield: 215 mg, 0.59 mmol. Yellow solid. LCMS: (System 1, Method F) Rt=0.59 min, m/z 366.2 $(M-H)^-$ $(ES^-)$.

Intermediate 52: 3-(3-azabicyclo[3.1.0]hexan-3-yl)-4-(((1-methylcyclopropyl)sulfonyl)carbamoyl)benzoic acid

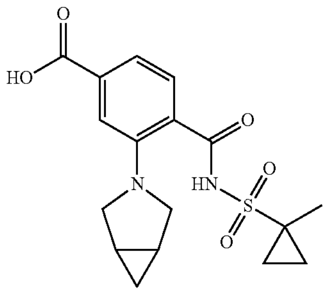 [SMILES: CC1(S(=O)(=O)NC(=O)c2ccc(C(=O)O)cc2N2CC3CC3C2)CC1]

Prepared by analogous method to Intermediate 46 starting from methyl 4-bromo-2-fluorobenzoate (2.0 g, 8.62 mmol) and 3-azabicyclo[3.1.0]hexane (2.15 g, 25.9 mmol). Yield: 430 mg, 1.18 mmol. Yellow solid. LCMS: (System 1, Method F) Rt=0.27 min, m/z 363.2 $(M-H)^-$ $(ES^-)$.

Intermediate 53: 3-(3-azabicyclo[3.1.0]hexan-3-yl)-4-((N,N-dimethylsulfamoyl)carbamoyl)benzoic acid

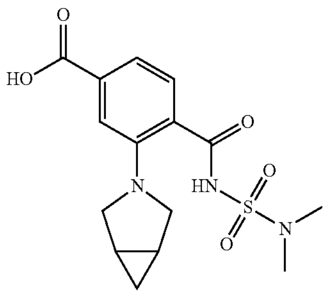 [SMILES: CN(C)S(=O)(=O)NC(=O)c1ccc(C(=O)O)cc1N1CC2CC2C1]

Prepared by analogous method to Intermediate 52 except the Step 3 was carried out with N,N-dimethylsulfamide in place of 1-methylcyclopropane-1-sulfonamide. Yield: 440 mg, 1.25 mmol. Yellow solid. LCMS: (System 1, Method F) Rt=0.27 min, m/z 352.3 $(M-H)^-$ $(ES^-)$.

Intermediate 54: 3-(3,3-difluoropiperidin-1-yl)-4-(((1-methylcyclopropyl)sulfonyl)carbamoyl)benzoic acid

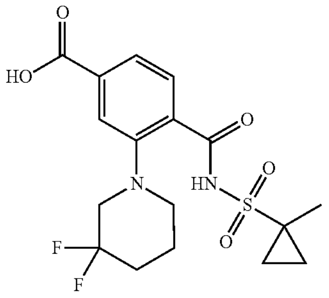 [SMILES: CC1(S(=O)(=O)NC(=O)c2ccc(C(=O)O)cc2N2CCCC(F)(F)C2)CC1]

Prepared by analogous method to Intermediate 46 starting from methyl 4-bromo-2-fluorobenzoate (3.0 g, 12.9 mmol) and 3,3-difluoropiperidine (4.1 g, 25.8 mmol). Yield: 250 mg, 0.62 mmol. Yellow solid. LCMS: (System 1, Method F) Rt=0.91 min, m/z 403.0 $(M-H)^-$ $(ES^-)$.

Intermediate 55: 3-(3,3-difluoropiperidin-1-yl)-4-((N,N-dimethylsulfamoyl)carbamoyl)benzoic acid

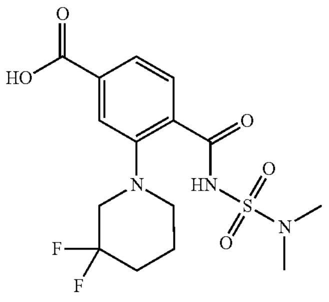 [SMILES: CN(C)S(=O)(=O)NC(=O)c1ccc(C(=O)O)cc1N1CCCC(F)(F)C1]

Prepared by analogous method to Intermediate 54 except the Step 3 was carried out with N,N-dimethylsulfamide in place of 1-methylcyclopropane-1-sulfonamide. Yield: 295 mg, 0.76 mmol. Yellow solid. LCMS: (System 1, Method F) Rt=0.92 min, m/z 392.0 $(M+H)^+$ $(ES^+)$.

Intermediate 56: 3-(3,3-difluoropyrrolidin-1-yl)-4-(((1-methylcyclopropyl)sulfonyl)carbamoyl)benzoic acid

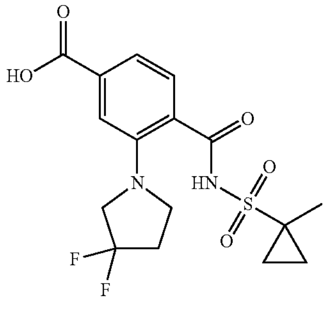 [SMILES: CC1(S(=O)(=O)NC(=O)c2ccc(C(=O)O)cc2N2CCC(F)(F)C2)CC1]

Prepared by analogous method to Intermediate 46 starting from methyl 4-bromo-2-fluorobenzoate (2.0 g, 8.58 mmol) and 3,3-difluoropyrrolidine hydrochloride (3.7 g, 25.8 mmol). Yield: 102 mg, 0.26 mmol. Yellow solid. LCMS: (System 2, Method B) Rt=1.58 min, m/z 389.0 $(M+H)^+$ $(ES^+)$. Intermediate 57: 3-(3,3-difluoropyrrolidin-1-yl)-4-((N,N-dimethylsulfamoyl)carbamoyl)benzoic acid

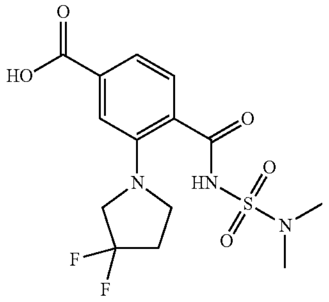 [SMILES: CN(C)S(=O)(=O)NC(=O)c1ccc(C(=O)O)cc1N1CCC(F)(F)C1]

Prepared by analogous method to Intermediate 56 except the Step 3 was carried out with N,N-dimethylsulfamide in place of 1-methylcyclopropane-1-sulfonamide. Yield: 111 mg, 0.29 mmol. Yellow solid. LCMS: (System 2, Method B) Rt=1.54 min, m/z 378.1 $(M-H)^-$ $(ES^-)$.

Intermediate 58: 3-(3,3-difluoropyrrolidin-1-yl)-4-((pyrrolidin-1-ylsulfonyl)carbamoyl)benzoic acid

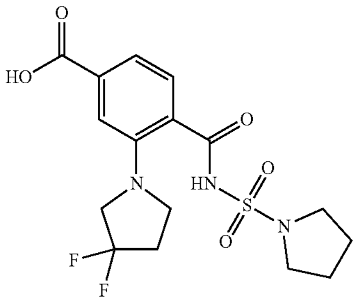 [SMILES: O=C(O)c1ccc(C(=O)NS(=O)(=O)N2CCCC2)c(N2CCC(F)(F)C2)c1]

Prepared by analogous method to Intermediate 56 starting except the Step 3 was carried out with pyrrolidine-1-sulfonamide in place of 1-methylcyclopropane-1-sulfonamide. Yield: 130 mg, 0.32 mmol. Yellow solid. LCMS: (System 2, Method B) Rt=1.61 min, m/z 404.2 $(M+H)^+$ $(ES^+)$.

Intermediate 59: 3-(cyclopropyl(methyl)amino)-4-(((1-methylcyclopropyl)sulfonyl)carbamoyl)benzoic acid

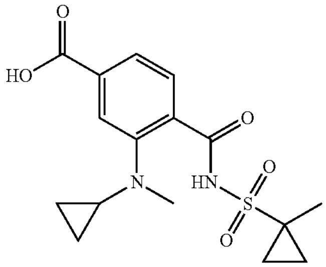 [SMILES: CN(c1cc(C(=O)O)ccc1C(=O)NS(=O)(=O)C1(C)CC1)C1CC1]

Prepared by analogous method to Intermediate 46 starting from methyl 4-bromo-2-fluorobenzoate (1.6 g, 6.4 mmol) and N-methylcyclopropanamine (1.36 g, 19.2 mmol). Yield: 215 mg, 0.61 mmol. Yellow solid. LCMS: (System 1, Method F) Rt=0.80 min, m/z 353.2 $(M+H)^+$ $(ES^+)$.

Intermediate 60: 3-(cyclopropyl(methyl)amino)-4-((N,N-dimethylsulfamoyl)carbamoyl)benzoic acid

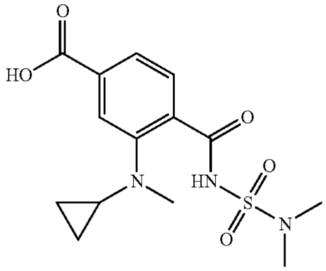 [SMILES: CN(c1cc(C(=O)O)ccc1C(=O)NS(=O)(=O)N(C)C)C1CC1]

Prepared by analogous method to Intermediate 59 except the Step 3 was carried out with N,N-dimethylsulfamide in place of 1-methylcyclopropane-1-sulfonamide. Yield: 192 mg, 0.56 mmol. Yellow solid. LCMS: (System 1, Method F) Rt=0.80 min, m/z 342.2 $(M+H)^+$ $(ES^+)$.

Intermediate 61: 3-(3,3-dimethylpyrrolidin-1-yl)-4-(((1-methylcyclopropyl)sulfonyl)carbamoyl)benzoic acid

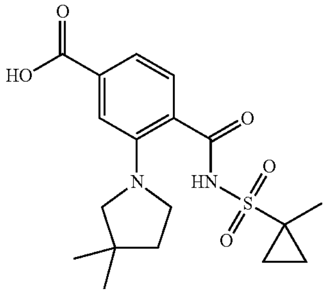 [SMILES: CC1(C)CCN(c2cc(C(=O)O)ccc2C(=O)NS(=O)(=O)C2(C)CC2)C1]

Prepared by analogous method to Intermediate 46 starting from methyl 4-bromo-2-fluorobenzoate (2.1 g, 8.40 mmol) and 3,3-dimethylpyrrolidine (2.5 g, 25.2 mmol). Yield: 430 mg, 1.18 mmol. Yellow solid. LCMS: (System 1, Method F) Rt=0.27 min, m/z 363.2 $(M-H)^-$ $(ES^-)$.

Intermediate 62: 3-(3,3-dimethylpyrrolidin-1-yl)-4-((N,N-dimethylsulfamoyl)carbamoyl)benzoic acid

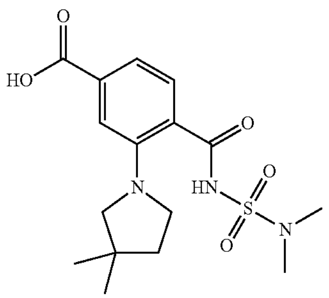 [SMILES: CN(C)S(=O)(=O)NC(=O)c1ccc(C(=O)O)cc1N1CCC(C)(C)C1]

Prepared by analogous method to Intermediate 61 except the Step 3 was carried out with N,N-dimethylsulfamide in place of 1-methylcyclopropane-1-sulfonamide. Yield: 310 mg, 0.84 mmol. Yellow solid. LCMS: (System 1, Method F) Rt=0.90 min, m/z 370.2 $(M+H)^+$ $(ES^+)$.

Intermediate 63: 3-(azetidin-1-yl)-4-(((1-methylcyclopropyl)sulfonyl)carbamoyl)benzoic acid

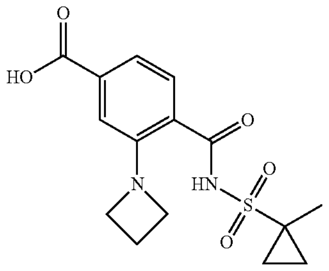 [SMILES: CC1(S(=O)(=O)NC(=O)c2ccc(C(=O)O)cc2N2CCC2)CC1]

Prepared by analogous method to Intermediate 46 starting from methyl 4-bromo-2-fluorobenzoate (2.1 g, 8.40 mmol) and azetidine (1.44 g, 25.2 mmol). Yield: 200 mg, 0.59 mmol. Yellow solid. LCMS: (System 1, Method F) Rt=0.31 min, m/z 377.0 $(M+H)^+$ $(ES^+)$.

Intermediate 64: 3-(azetidin-1-yl)-4-((N,N-dimethylsulfamoyl)carbamoyl)benzoic acid

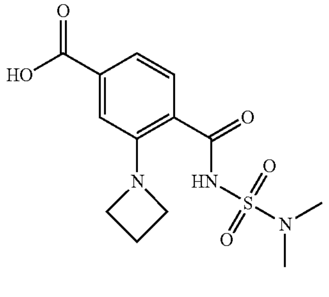 [SMILES: CN(C)S(=O)(=O)NC(=O)c1ccc(C(=O)O)cc1N1CCC1]

Prepared by analogous method to Intermediate 63 except the Step 3 was carried out with N,N-dimethylsulfamide in place of 1-methylcyclopropane-1-sulfonamide. Yield: 205 mg, 0.63 mmol. Yellow solid. LCMS: (System 1, Method F) Rt=0.25 min, m/z 328.2 $(M+H)^+$ $(ES^+)$.

Intermediate 65: (R)-4-((N,N-dimethylsulfamoyl)carbamoyl)-3-(2-methylpyrrolidin-1-yl)benzoic acid

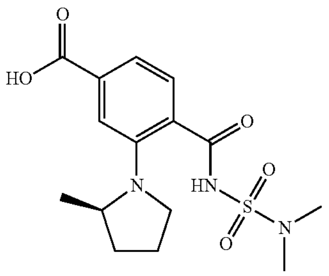 [SMILES: C[C@@H]1CCCN1c1cc(C(=O)O)ccc1C(=O)NS(=O)(=O)N(C)C]

Prepared by analogous method to Intermediate 46 starting from methyl 4-bromo-2-fluorobenzoate (1.5 g, 6.4 mmol) and (R)-2-methylpyrrolidine hydrochloride (1.6 g, 12.9 mmol) except the Step 3 was carried out with N,N-dimethylsulfamide in place of 1-methylcyclopropane-1-sulfonamide. Yield: 355 mg, 1.18 mmol. Yellow solid. LCMS: (System 1, Method F) Rt=0.84 min, m/z 356.2 $(M+H)^+$ $(ES^+)$.

Intermediate 66: (S)-4-((N,N-dimethylsulfamoyl)carbamoyl)-3-(2-methylpyrrolidin-1-yl)benzoic acid

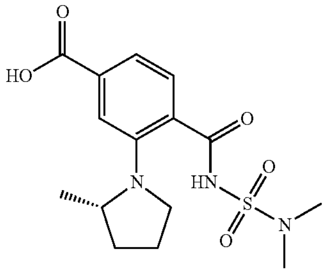 [SMILES: C[C@H]1CCCN1c1cc(C(=O)O)ccc1C(=O)NS(=O)(=O)N(C)C]

Prepared by analogous method to Intermediate 65 starting from methyl 4-bromo-2-fluorobenzoate (1.9 g, 7.60 mmol) and (S)-2-methylpyrrolidine (1.9 g, 22.8 mmol). Yield: 270 mg, 0.76 mmol. Yellow solid. LCMS: (System 1, Method F) Rt=0.83 min, m/z 356.2 $(M+H)^+$ $(ES^+)$.

Intermediate 67: 3-(2-azabicyclo[2.2.1]heptan-2-yl)-4-((pyrrolidin-1-ylsulfonyl)carbamoyl)benzoic acid

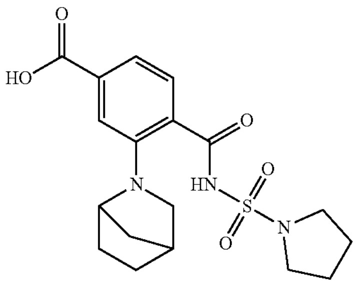 [SMILES: O=C(O)c1ccc(C(=O)NS(=O)(=O)N2CCCC2)c(N2CC3CCC2C3)c1]

Prepared by analogous method to Intermediate 46 starting from methyl 4-bromo-2-fluorobenzoate (2.5 g, 10.0 mmol) and 2-azabicyclo[2.2.1]heptane (2.9 g, 30 mmol) except the Step 3 was carried out with pyrrolidine-1-sulfonamide in place of 1-methylcyclopropane-1-sulfonamide. Yield: 460 mg, 1.17 mmol. Yellow solid. LCMS: (System 1, Method F) Rt=0.83 min, m/z 394.2 $(M+H)^+$ $(ES^+)$.

Intermediate 68: 3-(2-azabicyclo[2.2.1]heptan-2-yl)-4-((N,N-dimethylsulfamoyl)carbamoyl)benzoic acid

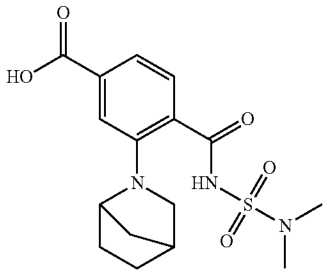 [SMILES: CN(C)S(=O)(=O)NC(=O)c1ccc(C(=O)O)cc1N1CC2CCC1C2]

Prepared by analogous method to Intermediate 67 except the Step 3 was carried out with N,N-dimethylsulfamide in place of 1-methylcyclopropane-1-sulfonamide. Yield: 440 mg, 1.20 mmol. Yellow solid. LCMS: (System 1, Method A) Rt=0.91 min, m/z 368.2 $(M+H)^+$ $(ES^+)$.

Intermediate 69: 4-((N,N-dimethylsulfamoyl)carbamoyl)-3-(5-azaspiro[2.5]octan-5-yl)benzoic acid

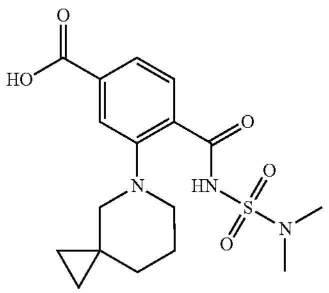 [SMILES: CN(C)S(=O)(=O)NC(=O)c1ccc(C(=O)O)cc1N1CCCC2(CC2)C1]

Prepared by analogous method to Intermediate 46 starting from methyl 4-bromo-2-fluorobenzoate (1.3 g, 5.00 mmol) and 5-azaspiro[2.5]octane (1.7 g, 15 mmol) except the Step 3 was carried out with N,N-dimethylsulfamide in place of 1-methylcyclopropane-1-sulfonamide. Yield: 600 mg, 1.57 mmol. Yellow solid. LCMS: (System 1, Method F) Rt=1.21 min, m/z 382.4 $(M+H)^+$ $(ES^+)$.

Intermediate 70: 2-fluoro-4-(((1-methylcyclopropyl)sulfonyl)carbamoyl)-3-(pyrrolidin-1-yl)benzoic acid

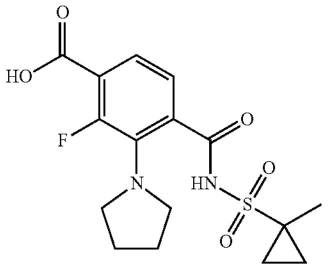 [SMILES: CC1(S(=O)(=O)NC(=O)c2ccc(C(=O)O)c(F)c2N2CCCC2)CC1]

Prepared by analogous method to Intermediate 46 starting from methyl 4-bromo-2,3-difluorobenzoate (3.0 g, 12.2 mmol) and pyrrolidine (1.74 g, 24.5 mmol). Yield: 483 mg, 1.30 mmol. White solid. LCMS: (System 1, Method F) Rt=1.06 min, m/z 371.2 $(M+H)^+$ $(ES^+)$.

Intermediate 71: 4-((N,N-dimethylsulfamoyl)carbamoyl)-2-fluoro-3-(pyrrolidin-1-yl)benzoic acid

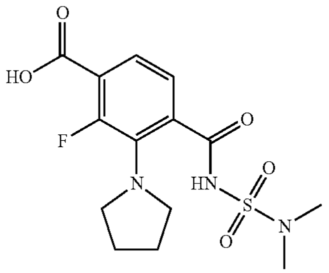 [SMILES: CN(C)S(=O)(=O)NC(=O)c1ccc(C(=O)O)c(F)c1N1CCCC1]

Prepared by analogous method to Intermediate 70 except the Step 3 was carried out with N,N-dimethylsulfamide in place of 1-methylcyclopropane-1-sulfonamide. Yield: 496 mg, 1.38 mmol. White solid. LCMS: (System 1, Method A) Rt=1.01 min, m/z 360.2 $(M+H)^+$ $(ES^+)$.

Intermediate 72: 2-fluoro-3-(pyrrolidin-1-yl)-4-((pyrrolidin-1-ylsulfonyl)carbamoyl)benzoic acid

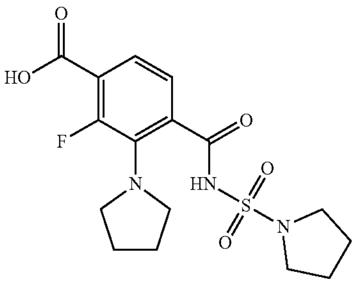 [SMILES: O=C(O)c1ccc(C(=O)NS(=O)(=O)N2CCCC2)c(N2CCCC2)c1F]

Prepared by analogous method to Intermediate 70 except the Step 3 was carried out with pyrrolidine-1-sulfonamide in place of 1-methylcyclopropane-1-sulfonamide. Yield: 400 mg, 1.08 mmol. Yellow solid. LCMS: (System 1, Method F) Rt=0.96 min, m/z 386.2 $(M+H)^+$ $(ES^+)$.

Intermediate 73: 3-(3-azabicyclo[3.1.0]hexan-3-yl)-2-fluoro-4-(((1-methylcyclopropyl)sulfonyl)carbamoyl)benzoic acid

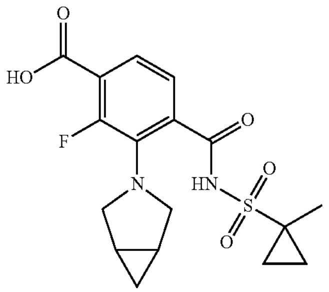 [SMILES: CC1(S(=O)(=O)NC(=O)c2ccc(C(=O)O)c(F)c2N2CC3CC3C2)CC1]

Prepared by analogous method to Intermediate 46 starting from methyl 4-bromo-2,3-difluorobenzoate (3.0 g, 12.2 mmol) and 3-azabicyclo[3.1.0]hexane (2.9 g, 24.5 mmol). Yield: 260 mg, 0.68 mmol. White solid. LCMS: (System 1, Method A) Rt=1.10 min, m/z 381.2 $(M-H)^-$ $(ES^-)$.

Intermediate 74: 3-(3-azabicyclo[3.1.0]hexan-3-yl)-4-((N,N-dimethylsulfamoyl)carbamoyl)-2-fluorobenzoic acid

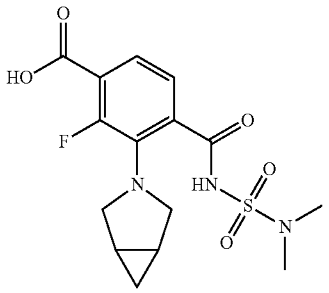 [SMILES: CN(C)S(=O)(=O)NC(=O)c1ccc(C(=O)O)c(F)c1N1CC2CC2C1]

Prepared by analogous method to Intermediate 73 except the Step 3 was carried out with N,N-dimethylsulfamide in place of 1-methylcyclopropane-1-sulfonamide. Yield: 280 mg, 0.75 mmol. White solid. LCMS: (System 1, Method A) Rt=1.09 min, m/z 370.2 $(M-H)^-$ $(ES^-)$.

Intermediate 75: 3-(3-azabicyclo[3.1.0]hexan-3-yl)-2-fluoro-4-((pyrrolidin-1-ylsulfonyl)carbamoyl)benzoic acid

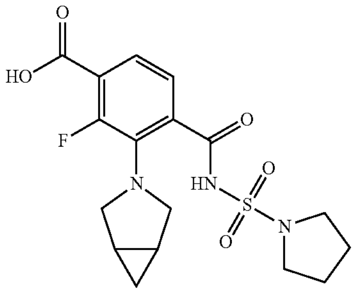 [SMILES: O=C(O)c1ccc(C(=O)NS(=O)(=O)N2CCCC2)c(N2CC3CC3C2)c1F]

Prepared by analogous method to Intermediate 73 except the Step 3 was carried out with pyrrolidine-1-sulfonamide in place of 1-methylcyclopropane-1-sulfonamide. Yield: 214 mg, 0.54 mmol. Yellow solid. LCMS: (System 1, Method F) Rt=1.01 min, m/z 398.2 $(M+H)^+$ $(ES^+)$.

Intermediate 76: 3-(7-azabicyclo[2.2.1]heptan-7-yl)-2-fluoro-4-(((1-methylcyclopropyl)sulfonyl)carbamoyl)benzoic acid

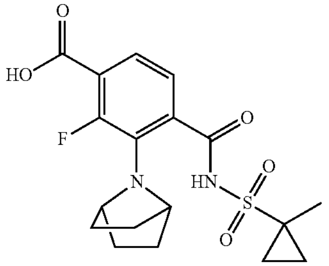 [SMILES: CC1(S(=O)(=O)NC(=O)c2ccc(C(=O)O)c(F)c2N2C3CCC2CC3)CC1]

Prepared by analogous method to Intermediate 46 starting from methyl 4-bromo-2,3-difluorobenzoate (3.1 g, 12.4 mmol) and 7-azabicyclo[2.2.1]heptane (3.61 g, 37.2 mmol). Yield: 230 mg, 0.58 mmol. Yellow solid. LCMS: (System 1, Method F) Rt=0.70 min, m/z 397.0 $(M+H)^+$ $(ES^+)$.

Intermediate 77: 3-(7-azabicyclo[2.2.1]heptan-7-yl)-4-((N,N-dimethylsulfamoyl)carbamoyl)-2-fluorobenzoic acid

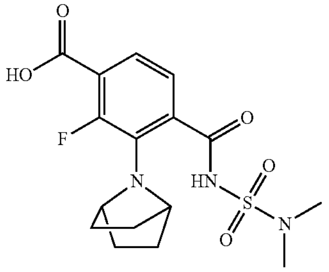 [SMILES: CN(C)S(=O)(=O)NC(=O)c1ccc(C(=O)O)c(F)c1N1C2CCC1CC2]

Prepared by analogous method to Intermediate 76 except the Step 3 was carried out with N,N-dimethylsulfamide in place of 1-methylcyclopropane-1-sulfonamide. Yield: 275 mg, 0.71 mmol. Yellow solid. LCMS: (System 1, Method F) Rt=0.48 min, m/z 386.0 $(M+H)^+$ $(ES^+)$.

Intermediate 78: 3-(7-azabicyclo[2.2.1]heptan-7-yl)-2-fluoro-4-((pyrrolidin-1-ylsulfonyl)carbamoyl)benzoic acid

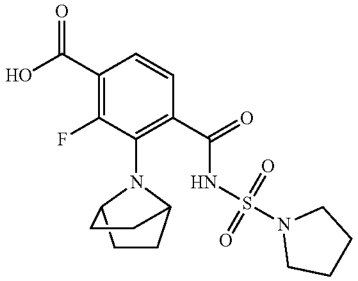 [SMILES: O=C(O)c1ccc(C(=O)NS(=O)(=O)N2CCCC2)c(N2C3CCC2CC3)c1F]

Prepared by analogous method to Intermediate 76 except the Step 3 was carried out with pyrrolidine-1-sulfonamide in place of 1-methylcyclopropane-1-sulfonamide. Yield: 320 mg, 0.78 mmol. Yellow solid. LCMS: (System 1, Method F) Rt=0.83 min, m/z 412.2 $(M+H)^+$ $(ES^+)$.

Intermediate 79: 3-(3,3-difluoropiperidin-1-yl)-2-fluoro-4-(((1-methylcyclopropyl)sulfonyl)carbamoyl)benzoic acid

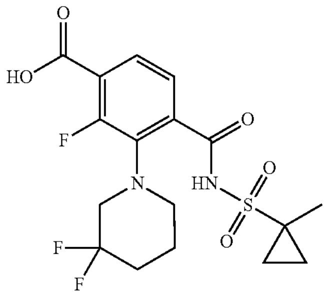 [SMILES: CC1(S(=O)(=O)NC(=O)c2ccc(C(=O)O)c(F)c2N2CCCC(F)(F)C2)CC1]

Prepared by analogous method to Intermediate 46 starting from methyl 4-bromo-2,3-difluorobenzoate (2.0 g, 7.97 mmol) and 3,3-difluoropiperidine hydrochloride (3.8 g, 23.9 mmol). Yield: 180 mg, 0.43 mmol. Yellow solid. LCMS: (System 2, Method B) Rt=1.65 min, m/z 421.1 $(M+H)^+$ $(ES^+)$.

Intermediate 80: 3-(3,3-difluoropiperidin-1-yl)-4-((N,N-dimethylsulfamoyl)carbamoyl)-2-fluorobenzoic acid

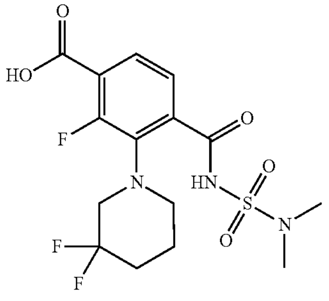 [SMILES: CN(C)S(=O)(=O)NC(=O)c1ccc(C(=O)O)c(F)c1N1CCCC(F)(F)C1]

Prepared by analogous method to Intermediate 79 except the Step 3 was carried out with N,N-dimethylsulfamide in place of 1-methylcyclopropane-1-sulfonamide. Yield: 165 mg, 0.40 mmol. Yellow solid. LCMS: (System 2, Method B) Rt=1.62 min, m/z 410.1 $(M+H)^+$ $(ES^+)$.

Intermediate 81: methyl 4-bromo-2-(dimethylamino)benzoate

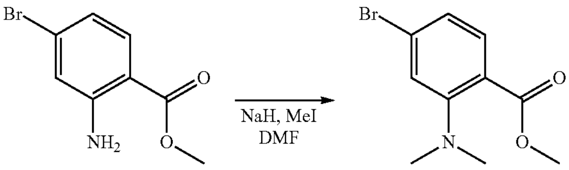

Sodium hydride (60% in mineral oil, 1.56 g, 39.12 mmol) was added to a solution of methyl 2-amino-4-bromobenzoate (1.5 g, 6.5 mmol) in DMF (14 mL) and the reaction was stirred at RT for 10 min. Iodomethane (5.6 g, 39.1 mmol) was added and the mixture was stirred at RT overnight. The reaction mixture was poured into water (100 mL) and extracted with EtOAc (3×100 mL). The combined organic layers were washed with brine (3×100 mL), dried ($Na_2SO_4$) and concentrated under reduced pressure to afford methyl 4-bromo-2-(dimethylamino)benzoate (365 mg, 1.41 mmol) as a yellow oil. LCMS: (System 2, Method B), Rt=1.48 min, m/z 258.0 $(M+H)^+$ $(ES^+)$.

Intermediate 82: 3-(dimethylamino)-4-(((1-methylcyclopropyl)sulfonyl)carbamoyl)benzoic acid

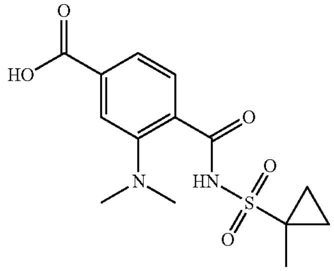 [SMILES: CN(C)c1cc(C(=O)O)ccc1C(=O)NS(=O)(=O)C1(C)CC1]

Prepared by analogous method to Intermediate 46 (Steps 2 to 5) starting at Step 2 from methyl 4-bromo-2-(dimethylamino)benzoate (Intermediate 81, 340 mg, 1.39 mmol). Yield: 150 mg, 0.46 mmol. Yellow solid. LCMS: (System 2, Method B) Rt=1.27 min, m/z 327.1 $(M+H)^+$ $(ES^+)$.

Intermediate 83: 3-(cyclobutyl(methyl)amino)-4-((N,N-dimethylsulfamoyl)carbamoyl)benzoic acid

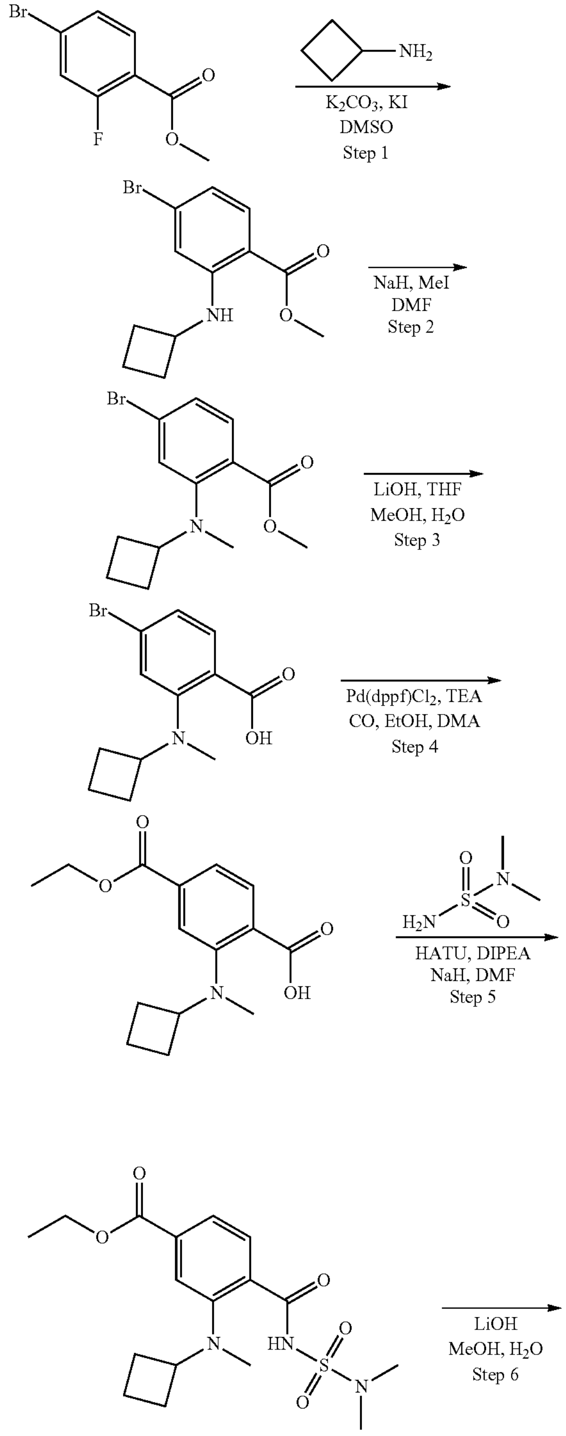

-continued

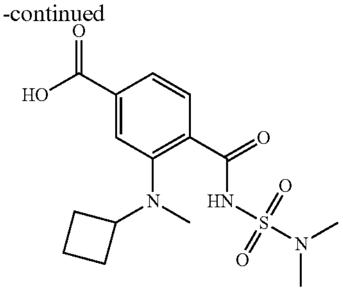

Step 1

A mixture of methyl 4-bromo-2-fluorobenzoate (1.0 g, 4.29 mmol), $K_2CO_3$ (1.8 g, 12.9 mmol), KI (356 mg, 2.15 mmol) and cyclobutanamine (610 mg, 8.58 mmol) in DMSO (20 mL) was stirred at 100° C. overnight. The reaction mixture was allowed to reach RT and was partitioned between water (80 mL) and EtOAc (3×80 mL). The combined organic layers were washed with brine, dried ($Na_2SO_4$), filtered and concentrated under reduced pressure. The crude product was purified by column chromatography on silica gel (35% DCM/petroleum ether) to afford methyl 4-bromo-2-(cyclobutylamino)benzoate (1.0 g, 3.52 mmol) as a colourless oil. LCMS: (System 1, Method A) Rt=2.69 min, m/z 284.2 $(M+H)^+$ $(ES^+)$.

Step 2

Sodium hydride (60% dispersion in mineral oil, 422 mg, 17.6 mmol) was added in small portions to a solution of methyl 4-bromo-2-(cyclobutylamino)benzoate (1.0 g, 3.52 mmol) in DMF (15 mL) and the mixture was stirred at RT for 1 h. Iodomethane (3.5 g, 24.6 mmol) was added and the mixture was stirred at RT overnight. The mixture was poured into $NH_4Cl$ aq. sat. (50 mL) and extracted with EtOAc (3×50 mL). The combined organic layers were washed with brine, dried ($Na_2SO_4$), filtered and concentrated under reduced pressure. The crude product was purified by column chromatography on silica gel (DCM) to afford methyl 4-bromo-2-(cyclobutyl(methyl)amino)benzoate (950 mg, 3.19 mmol) as a pale-yellow oil. LCMS: (System 1, Method F) Rt=2.01 min, m/z 298.2 $(M+H)^+$ $(ES^+)$.

Step 3

A mixture of 4-bromo-2-(cyclobutyl(methyl)amino)benzoate (950 mg, 3.19 mmol) and $LiOH{\cdot}H_2O$ (668 mg, 15.9 mmol) in THE (20 mL), MeOH (5 mL) and water (5 mL) was stirred at 60° C. overnight. Organic solvents were removed under reduced pressure, then the pH of the mixture was adjusted to ca. 3 by adding HCl aq. 1N. The precipitate was recovered by filtration, washed with water and hexane, and dried under reduced pressure to afford 4-bromo-2-(cyclobutyl(methyl)amino)benzoic acid (815 mg, 2.87 mmol) as a yellow solid. LCMS: (System 1, Method A) Rt=1.45 min, m/z 284.1 $(M+H)^+$ $(ES^+)$.

Step 4

A mixture of 4-bromo-2-(cyclobutyl(methyl)amino)benzoic acid (815 mg, 2.87 mmol), [1,1'-bis(diphenylphosphino)ferrocene]dichloropalladium(II) (420 mg, 0.57 mmol) and TEA (1.45 g, 14.34 mmol) in DMA (5 mL) and EtOH (20 mL) was stirred at 90° C. overnight under CO atmosphere. The reaction mixture was allowed to reach RT and $Na_2CO_3$ aq. sat. (20 mL) was added. The reaction mixture was washed with EtOAc (3×20 mL), and after adjusting the pH of the aqueous layer to ca. 3 with HCl aq. 1N, extracted with EtOAc (3×20 mL). The combined organic layers were washed with brine, dried ($Na_2SO_4$), filtered and concentrated under reduced pressure to afford 2-(cyclobutyl(methyl)amino)-4-(ethoxycarbonyl)benzoic acid (600 mg, 2.16 mmol) as a brown solid. LCMS: (System 1, Method F) Rt=1.23 min, m/z 276.1 $(M-H)^-$ $(ES^-)$.

Step 5

A mixture of 2-(cyclobutyl(methyl)amino)-4-(ethoxycarbonyl)benzoic acid (600 mg, 2.16 mmol), EDCI (830 mg, 4.33 mmol), DMAP (529 mg, 4.33 mmol) N,N-dimethylsulfamide (537 mg, 4.33 mmol) in DCM (20 mL) was stirred at RT overnight. The reaction mixture was partitioned between water (20 mL) and DCM (3×20 mL). The combined organic layers were dried ($Na_2SO_4$), filtered and concentrated under reduced pressure. The crude product was purified by column chromatography on silica gel (1-10% MeOH/DCM) to afford ethyl 3-(cyclobutyl(methyl)amino)-4-((N,N-dimethylsulfamoyl)carbamoyl)benzoate (320 mg, 0.83 mmol) as a brown oil. LCMS: (System 1, Method A) Rt=2.02 min, m/z $(M+H)^+$ $(ES^+)$.

Step 6

A mixture of ethyl 3-(cyclobutyl(methyl)amino)-4-((N,N-dimethylsulfamoyl)carbamoyl)benzoate (320 mg, 0.83 mmol) and $LiOH \cdot H_2O$ (175 mg, 4.17 mmol) in MeOH (16 mL) and in water (4 mL) was stirred at RT overnight. The organic solvent was removed under reduced pressure, and the 10 pH of the resulting aqueous solution was adjusted to ca. 3 by adding HCl aq. 1N. The precipitate was recovered by filtration, washed with water and hexane, and dried under reduced pressure to afford 3-(cyclobutyl(methyl)amino)-4-((N,N-dimethylsulfamoyl)carbamoyl)benzoic acid (200 mg, 0.56 mmol) as a brown solid. LCMS: (System 1, Method A) Rt=1.14 min, m/z 354.2 $(M-H)^-$ $(ES^-)$.

Intermediate 84: 3-(cyclobutyl(methyl)amino)-4-((N,N-dimethylsulfamoyl)carbamoyl)-2-fluorobenzoic acid

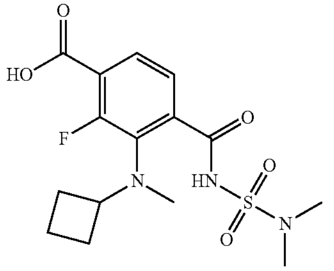 [SMILES: CN(c1c(C(=O)NS(=O)(=O)N(C)C)ccc(C(=O)O)c1F)C1CCC1]

Prepared by analogous method to Intermediate 83 starting from methyl 4-bromo-2,3-difluorobenzoate (25.0 g, 106 mmol). Yield: 450 mg, 1.21 mmol. White solid. LCMS: (System 1, Method F) Rt=1.01 min, m/z 372.3 $(M-H)^-$ $(ES^-)$.

Intermediate 85: 3-(cyclobutyl(methyl)amino)-2-fluoro-4-(((1-methylcyclopropyl)sulfonyl)carbamoyl)benzoic acid

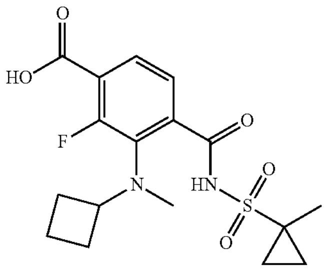 [SMILES: CN(c1c(C(=O)NS(=O)(=O)C2(C)CC2)ccc(C(=O)O)c1F)C1CCC1]

Prepared by analogous method to Intermediate 83 except the Step 5 was carried out with 1-methylcyclopropane-1-sulfonamide in place of N,N-dimethylsulfamide. Yield: 450 mg, 1.17 mmol. White solid. LCMS: (System 1, Method F) Rt=1.10 min, m/z 383.3 $(M-H)^-$ $(ES^-)$.

Intermediate 86: 3-(7-azabicyclo[2.2.1]heptan-7-yl)-5-fluoro-4-(((1-methylcyclopropyl)sulfonyl)carbamoyl)benzoic acid

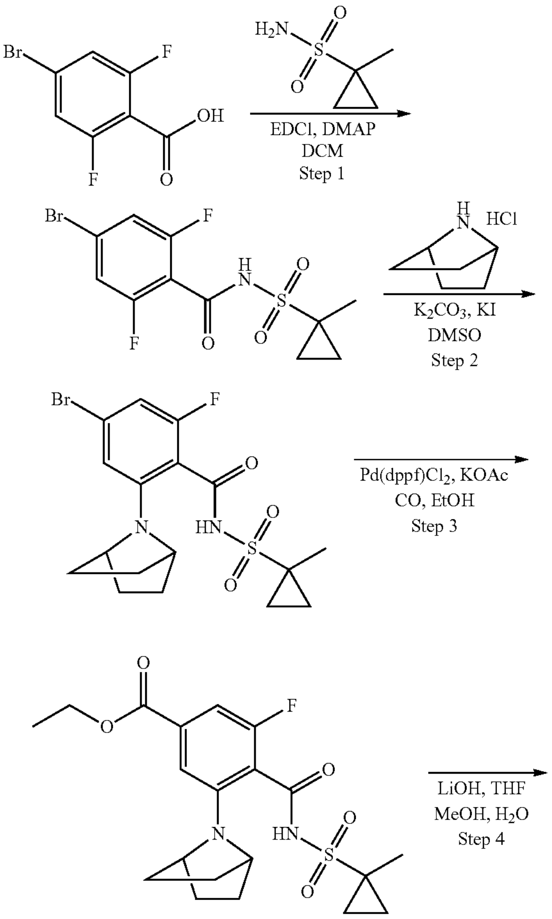

-continued

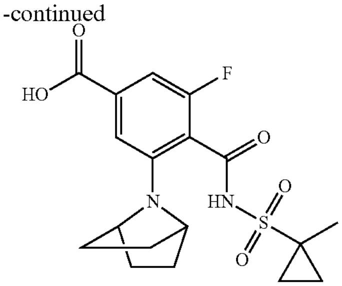

Step 1

A mixture of 4-bromo-2,6-difluorobenzoic acid (1.0 g, 4.22 mmol), 1-methylcyclopropane-1-sulfonamide (1.14 g, 8.44 mmol), EDCI (1.62 g, 8.44 mmol) and DMAP (1.03 g, 8.44 mmol) in DCM (40 mL) was stirred at RT overnight. The reaction mixture was partitioned between water (40 mL) and DCM (3×40 mL). The combined organic layers were dried ($Na_2SO_4$), filtered and concentrated under reduced pressure. The crude product was purified by column chromatography on silica gel (1-3% MeOH/DCM) to afford 4-bromo-2,6-difluoro-N-((1-methylcyclopropyl)sulfonyl) benzamide (1.1 g, 3.00 mmol) as a white solid. LCMS: (System 1, Method F) Rt=1.07 min, m/z 353.6 $(M+H)^+$ $(ES^+)$.

Step 2

A mixture of 4-bromo-2,6-difluoro-N-((1-methylcyclopropyl)sulfonyl)benzamide (1.06 g, 2.99 mmol), $K_2CO_3$ (1.24 g, 8.98 mmol), KI (248 mg, 1.50 mmol) and 7-azabicyclo[2.2.1]heptane hydrochloride (800 mg, 5.99 mmol) in DMSO (15 mL) was stirred at 120° C. overnight. The reaction mixture was partitioned between water (60 mL) and EtOAc (3×60 mL). The combined organic layers were washed with brine, dried ($Na_2SO_4$), filtered and concentrated under reduced pressure. The crude product was purified by column chromatography on silica gel (1-5% MeOH/DCM) to afford 2-(7-azabicyclo[2.2.1]heptan-7-yl)-4-bromo-6-fluoro-N-((1-methylcyclopropyl)sulfonyl) benzamide (800 mg, 1.85 mmol) as a white solid. LCMS: (System 1, Method F) Rt=1.24 min, m/z 430.7 $(M+H)^+$ $(ES^+)$.

Step 3

A mixture of 2-(7-azabicyclo[2.2.1]heptan-7-yl)-4-bromo-6-fluoro-N-((1-methylcyclopropyl)sulfonyl)benzamide (500 mg, 1.16 mmol), [1,1'-bis(diphenylphosphino) ferrocene]dichloropalladium(II) (170 mg, 0.23 mmol) and KOAc (341 mg, 3.48 mmol) in EtOH (15 mL) was stirred at 80° C. for 5 h under CO atmosphere. The mixture was concentrated under reduced pressure and the crude product was purified by column chromatography on silica gel (1-3% MeOH/DCM) to afford ethyl 3-(7-azabicyclo[2.2.1]heptan-7-yl)-5-fluoro-4-(((1-methylcyclopropyl)sulfonyl)carbamoyl)benzoate (300 mg, 0.71 mmol) as a brown oil. LCMS: (System 1, Method F) Rt=1.22 min, m/z 425.0 $(M+H)^+$ $(ES^+)$.

Step 4

A mixture of ethyl 3-(7-azabicyclo[2.2.1]heptan-7-yl)-5-fluoro-4-(((1-methylcyclopropyl)sulfonyl)carbamoyl)benzoate (300 mg, 0.71 mmol) and $LiOH \cdot H_2O$ (148 mg, 3.53 mmol) in THE (12 mL), MeOH (3 mL) and water (3 mL) was stirred at RT overnight. The pH of the mixture was adjusted to ca. 8 by adding HCl aq. 1N. Then the organic solves were evaporated under reduced pressure and the pH of the resulting aqueous phase was adjusted to ca. 3 by adding HCl aq. 1N. The precipitate was collected by filtration, washed with water then hexane and dried to afford 3-(7-azabicyclo[2.2.1]heptan-7-yl)-5-fluoro-4-(((1-methylcyclopropyl)sulfonyl)carbamoyl)benzoic acid (215 mg, 0.54 mmol) as a brown solid. LCMS: (System 1, Method F) Rt=0.55 min, m/z 395.4 $(M-H)^-$ $(ES^-)$.

Intermediate 87: 3-(7-azabicyclo[2.2.1]heptan-7-yl)-4-((N,N-dimethylsulfamoyl)carbamoyl)-5-fluorobenzoic acid

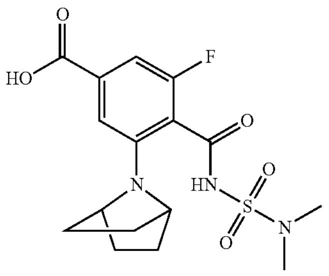 [SMILES: CN(C)S(=O)(=O)NC(=O)c1c(F)cc(C(=O)O)cc1N1C2CCC1CC2]

Prepared by analogous method to Intermediate 86 starting from 4-bromo-2,6-difluorobenzoic acid (1.0 g, 4.22 mmol) and N,N-dimethylsulfamide (1.05 g, 8.44 mmol). Yield: 335 mg, 0.87 mmol. Brown solid. LCMS: (System 1, Method F) Rt=0.38 min, m/z 384.4 $(M-H)^-$ $(ES^-)$.

Intermediate 88: 3-(3-azabicyclo[3.1.0]hexan-3-yl)-5-fluoro-4-(((1-methylcyclopropyl)sulfonyl)carbamoyl)benzoic acid

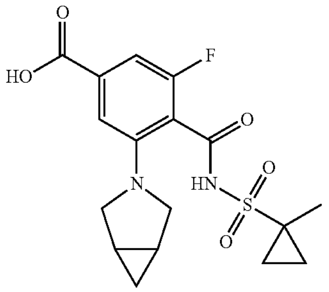 [SMILES: CC1(S(=O)(=O)NC(=O)c2c(F)cc(C(=O)O)cc2N2CC3CC3C2)CC1]

Prepared by analogous method to Intermediate 86 starting except the Step 2 was carried out with 3-azabicyclo[3.1.0] hexane hydrochloride in place of 7-azabicyclo[2.2.1]heptane hydrochloride. Yield: 265 mg, 0.69 mmol. Brown solid. LCMS: (System 1, Method F) Rt=0.43 min, m/z 381.3 $(M-H)^-$ $(ES^-)$.

Intermediate 89: 3-(3-azabicyclo[3.1.0]hexan-3-yl)-4-((N,N-dimethylsulfamoyl)carbamoyl)-5-fluorobenzoic acid

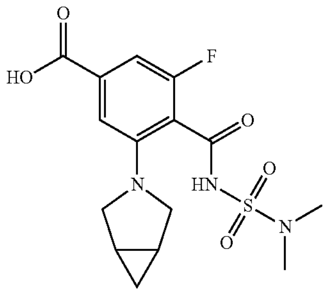 [SMILES: CN(C)S(=O)(=O)NC(=O)c1c(F)cc(C(=O)O)cc1N1CC2CC2C1]

Prepared by analogous method to Intermediate 86 starting from 4-bromo-2,6-difluorobenzoic acid (2.0 g, 8.44 mmol) and N,N-dimethylsulfamide (2.1 g, 16.9 mmol) except the Step 2 was carried out with 3-azabicyclo[3.1.0]hexane hydrochloride in place of 7-azabicyclo[2.2.1]heptane hydrochloride. Yield: 636 mg, 1.71 mmol. Brown solid. LCMS: (System 1, Method F) Rt=0.25 min, m/z 370.3 $(M-H)^-$ $(ES^-)$.

Intermediate 90: 3-(3-azabicyclo[3.1.0]hexan-3-yl)-5-chloro-4-(((1-methylcyclopropyl)sulfonyl)carbamoyl)benzoic acid

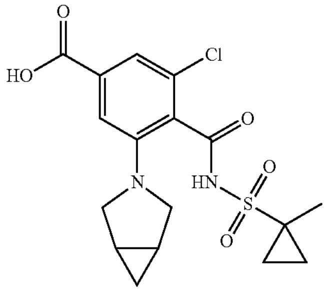 [SMILES: CC1(S(=O)(=O)NC(=O)c2c(Cl)cc(C(=O)O)cc2N2CC3CC3C2)CC1]

Prepared by analogous method to Intermediate 86 starting from 4-bromo-2-chloro-6-fluorobenzoic acid (2.0 g, 7.94 mmol) and 1-methylcyclopropane-1-sulfonamide (2.1 g, 15.8 mmol) except the Step 2 was carried out with 3-azabicyclo[3.1.0]hexane hydrochloride in place of 7-azabicyclo[2.2.1]heptane hydrochloride. Yield: 394 mg, 0.99 mmol. White solid. LCMS: (System 1, Method F) Rt=0.52 min, m/z 397.0 $(M-H)^-$ $(ES^-)$.

Intermediate 91: 3-(3-azabicyclo[3.1.0]hexan-3-yl)-5-chloro-4-((N,N-dimethylsulfamoyl)carbamoyl)benzoic acid

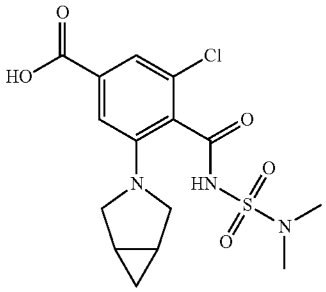 [SMILES: CN(C)S(=O)(=O)NC(=O)c1c(Cl)cc(C(=O)O)cc1N1CC2CC2C1]

Prepared by analogous method to Intermediate 86 starting from 4-bromo-2-chloro-6-fluorobenzoic acid (2.0 g, 7.94 mmol) and N,N-dimethylsulfamide (2.10 g, 15.8 mmol) except the Step 2 was carried out with 3-azabicyclo[3.1.0]hexane hydrochloride in place of 7-azabicyclo[2.2.1]heptane hydrochloride. Yield: 349 mg, 0.90 mmol. White solid. LCMS: (System 1, Method F) Rt=0.39 min, m/z 386.0 $(M-H)^-$ $(ES^-)$.

Intermediate 92: 3-(3-azabicyclo[3.1.0]hexan-3-yl)-5-chloro-4-(((1-methylcyclopropyl)sulfonyl)carbamoyl)benzoic acid

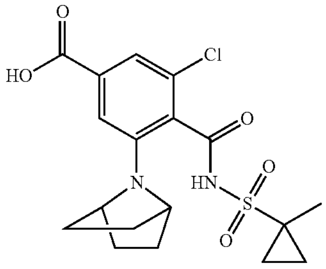 [SMILES: CC1(S(=O)(=O)NC(=O)c2c(Cl)cc(C(=O)O)cc2N2C3CCC2CC3)CC1]

Prepared by analogous method to Intermediate 86 starting from 4-bromo-2-chloro-6-fluorobenzoic acid (1.4 g, 5.52 mmol) and 1-methylcyclopropane-1-sulfonamide (1.5 g, 11.01 mmol). Yield: 172 mg, 0.42 mmol. Brown solid. LCMS: (System 1, Method F) Rt=0.59 min, m/z 411.1 $(M-H)^-$ $(ES^-)$.

Intermediate 93: 3-(7-azabicyclo[2.2.1]heptan-7-yl)-5-chloro-4-((N,N-dimethylsulfamoyl)carbamoyl)benzoic acid

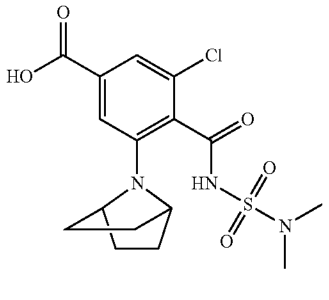 [SMILES: CN(C)S(=O)(=O)NC(=O)c1c(Cl)cc(C(=O)O)cc1N1C2CCC1CC2]

Prepared by analogous method to Intermediate 86 starting from 4-bromo-2-chloro-6-fluorobenzoic acid (3.0 g, 11.8 mmol) and N,N-dimethylsulfamide (2.9 g, 23.7 mmol). Yield: 235 mg, 0.58 mmol. Brown solid. LCMS: (System 1, Method A) Rt=0.77 min, m/z 399.6 $(M-H)^-$ (ES Intermediate 94: 3-(7-azabicyclo[2.2.1]heptan-7-yl)-5-chloro-4-((pyrrolidin-1-ylsulfonyl)carbamoyl)benzoic acid

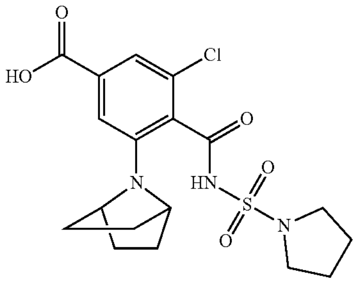 [SMILES: O=C(O)c1cc(Cl)c(C(=O)NS(=O)(=O)N2CCCC2)c(N2C3CCC2CC3)c1]

Prepared by analogous method to Intermediate 86 starting from 4-bromo-2-chloro-6-fluorobenzoic acid (600 mg, 2.37 mmol) and pyrrolidine-1-sulfonamide (1.1 g, 7.10 mmol). Yield: 340 mg, 0.54 mmol. Brown solid. LCMS: (System 1, Method F) Rt=0.74 min, m/z 412.0 $(M-H)^-$ $(ES^-)$.

Intermediate 95: 4-((N,N-dimethylsulfamoyl)carbamoyl)-3-methoxy-5-(pyrrolidin-1-yl)benzoic acid

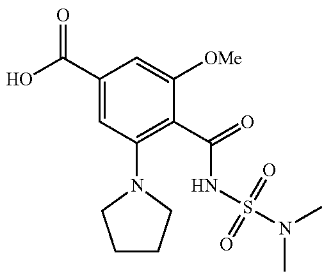 [SMILES: COc1cc(C(=O)O)cc(N2CCCC2)c1C(=O)NS(=O)(=O)N(C)C]

Prepared by analogous method to Intermediate 86 starting from 4-bromo-2-fluoro-6-methoxybenzoic acid (2.1 g, 8.40 mmol) and N,N-dimethylsulfamide (3.12 g, 25.2 mmol) except the Step 2 was carried out with pyrrolidine in place of 7-azabicyclo[2.2.1]heptane hydrochloride. Yield: 700 mg, 1.88 mmol. Yellow solid. LCMS: (System 1, Method A) Rt=0.54 min, m/z 372.2 $(M+H)^+$ $(ES^+)$.

Intermediate 96: 4-((N,N-dimethylsulfamoyl)carbamoyl)-3-methyl-5-(pyrrolidin-1-yl)benzoic acid

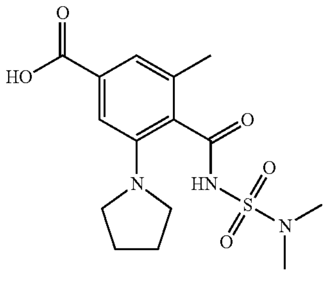 [SMILES: Cc1cc(C(=O)O)cc(N2CCCC2)c1C(=O)NS(=O)(=O)N(C)C]

Prepared by analogous method to Intermediate 86 starting from 4-bromo-2-fluoro-6-methylbenzoic acid (1.6 g, 6.90 mmol) and N,N-dimethylsulfamide (2.57 g, 20.7 mmol) except the Step 2 was carried out with pyrrolidine in place of 7-azabicyclo[2.2.1]heptane hydrochloride. Yield: 1.5 g, 4.22 mmol. White solid. LCMS: (System 1, Method A) Rt=1.30 min, m/z 339.2 $(M+H)^+$ $(ES^+)$.

Intermediate 97: 3-(3-azabicyclo[3.1.0]hexan-3-yl)-4-(((1-methylcyclopropyl)sulfonyl)carbamoyl)-5-(trifluoromethyl)benzoic acid

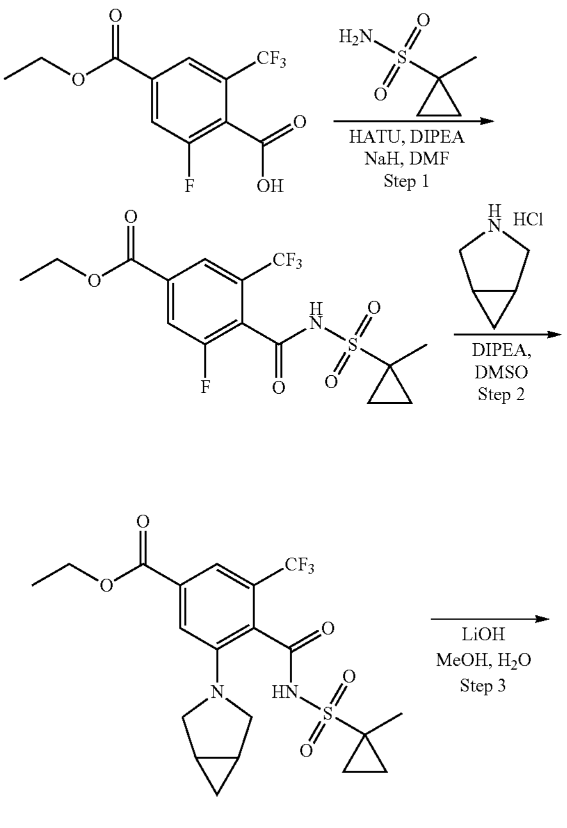

-continued

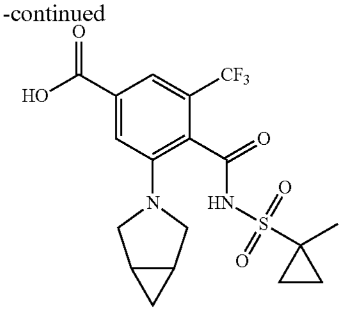

Step 1

A mixture of 4-(ethoxycarbonyl)-2-fluoro-6-(trifluoromethyl)benzoic acid (1.6 g, 5.71 mmol), HATU (2.6 g, 6.85 mmol) and DIPEA (3.0 g, 22.8 mmol) in DMF (50 mL) was stirred at RT for 1.5 h. 1-methylcyclopropane-1-sulfonamide (2.31 g, 17.13 mmol) was added, followed by sodium hydride (60% dispersion in mineral oil, 914 mg, 22.84 mmol) and the reaction mixture was stirred at RT overnight. The mixture was poured into $NH_4Cl$ aq. sat. (150 mL), HCl aq. 1N (20 mL) and was added and the mixture was extracted with EtOAc (3×150 mL). The combined organic layers were washed with brine, dried ($Na_2SO_4$), filtered and concentrated under reduced pressure. The crude product was purified by column chromatography on silica gel (1-10% EtOAc/petroleum ether) to afford ethyl 3-fluoro-4-(((1-methylcyclopropyl)sulfonyl)carbamoyl)-5-(trifluoromethyl) benzoate (1.5 g, 3.78 mmol) as a brown oil. LCMS: (System 1, Method A) Rt=1.81 min, m/z 398.0 $(M+H)^+$ $(ES^+)$.

Step 2

A mixture of 3-fluoro-4-(((1-methylcyclopropyl)sulfonyl) carbamoyl)-5-(trifluoromethyl)benzoate (630.0 mg, 1.59 mmol), DIPEA (1.02 g, 7.93 mmol) and 3-azabicyclo[3.1.0] hexane (263 mg, 3.17 mmol) in DMSO (3 mL) was stirred at 100° C. in a sealed vial for 48 h. The reaction mixture was allowed to reach RT and partitioned between water (10 ml) and EtOAc (3×10 mL). The combined organic layers were washed with brine, dried ($Na_2SO_4$), filtered and concentrated under reduced pressure to afford ethyl 3-(3-azabicyclo [3.1.0]hexan-3-yl)-4-(((1-methylcyclopropyl)sulfonyl)carbamoyl)-5-(trifluoromethyl)benzoate (220 mg, 0.48 mmol) as a brown solid which was used in the next step without further purification. LCMS: (System 1, Method F) Rt=1.30 min, 461.2 $(M+NH_4)+(ES^+)$.

Step 3

A mixture of ethyl 3-(3-azabicyclo[3.1.0]hexan-3-yl)-4-(((1-methylcyclopropyl)sulfonyl)carbamoyl)-5-(trifluoromethyl)benzoate (220 mg, 0.48 mmol) and $LiOH \cdot H_2O$ (78 mg, 1.91 mmol) in THE (16 mL), MeOH (4 mL) and water (4 mL) was stirred at RT overnight. The organic solvents were removed under reduced pressure, then the pH of the resulting aqueous layer was adjusted to ca. 3 by adding HCl aq. 1N. The precipitate was recovered by filtration, washed with water and hexane, and dried under reduced pressure to afford 3-(3-azabicyclo[3.1.0]hexan-3-yl)-4-(((1-methylcyclopropyl)sulfonyl)carbamoyl)-5-(trifluoromethyl)benzoic acid (180 mg, 0.42 mmol) as a brown solid. LCMS: (System 1, Method A) Rt=0.99 min, 433.3 $(M+NH_4)+(ES^+)$.

Intermediate 98: 3-(3-azabicyclo[3.1.0]hexan-3-yl)-4-((pyrrolidin-1-ylsulfonyl)carbamoyl)-5-(trifluoromethyl)benzoic acid

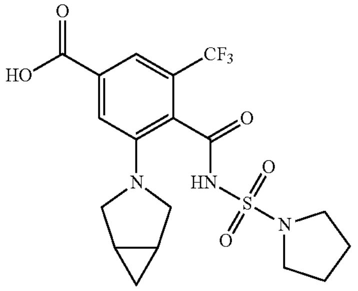 [SMILES: O=C(O)c1cc(N2CC3CC3C2)c(C(=O)NS(=O)(=O)N2CCCC2)c(C(F)(F)F)c1]

Prepared by analogous method to Intermediate 97 starting from 4-(ethoxycarbonyl)-2-fluoro-6-(trifluoromethyl)benzoic acid (Intermediate 42, 1.6 g, 6.90 mmol) and pyrrolidine-1-sulfonamide (2.6 g, 17.13 mmol). Yield: 170 mg, 0.38 mmol. Brown solid. LCMS: (System 1, Method A) Rt=1.09 min, m/z 448.2 $(M+H)^+$ $(ES^+)$.

Intermediate 99: 3-(3-azabicyclo[3.1.0]hexan-3-yl)-4-((N,N-dimethylsulfamoyl)carbamoyl)-5-(trifluoromethyl)benzoic acid

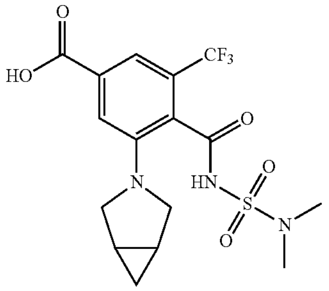 [SMILES: CN(C)S(=O)(=O)NC(=O)c1c(N2CC3CC3C2)cc(C(=O)O)cc1C(F)(F)F]

Prepared by analogous method to Intermediate 97 starting from Intermediate 42 (1.6 g, 6.90 mmol) and N,N-dimethylsulfamide (2.57 g, 20.7 mmol). Yield: 1.5 g, 4.22 mmol. White solid. LCMS: (System 1, Method A) Rt=1.30 min, m/z 339.2 $(M+H)^+$ $(ES^+)$.

Intermediate 100: 3-methoxy-4-((pyrrolidin-1-ylsulfonyl)carbamoyl)-5-(trifluoromethyl)benzoic acid

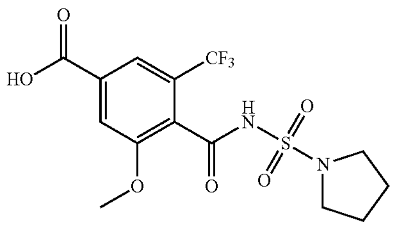 [SMILES: COc1cc(C(=O)O)cc(C(F)(F)F)c1C(=O)NS(=O)(=O)N1CCCC1]

Prepared by an analogous method to Intermediate 43 starting from 4-(ethoxycarbonyl)-2-fluoro-6-(trifluoromethyl)benzoic acid (Intermediate 42, 1.6 g, 5.71 mmol) except the Step 1 was carried out with pyrrolidine-1-sulfonamide in place of 1-methylcyclopropane-1-sulfonamide and the Step 3 was carried out with MeOH instead of cyclopentanol. Yield: 260 mg, 0.57 mmol. White solid. LCMS: (System 1, Method A) Rt=0.60 min, m/z 395.0 $(M-H)^-$ $(ES^-)$.

Intermediate 101: 3-ethoxy-4-((pyrrolidin-1-ylsulfonyl)carbamoyl)-5-(trifluoromethyl)benzoic acid

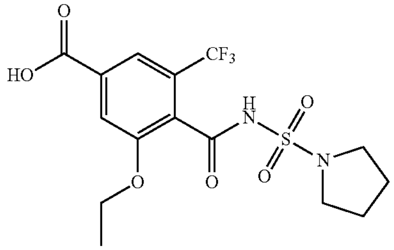 [SMILES: CCOc1cc(C(=O)O)cc(C(F)(F)F)c1C(=O)NS(=O)(=O)N1CCCC1]

Prepared by an analogous method to Intermediate 100 except Step 3 was carried out with EtOH instead of MeOH. Yield: 270 mg, 0.66 mmol. White solid. LCMS: (System 1, Method A) Rt=0.80 min, m/z 409.2 $(M-H)^-$ $(ES^-)$.

Intermediate 102: 3-isopropoxy-4-((pyrrolidin-1-ylsulfonyl)carbamoyl)-5-(trifluoromethyl)benzoic acid

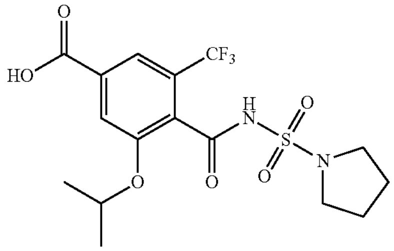 [SMILES: CC(C)Oc1cc(C(=O)O)cc(C(F)(F)F)c1C(=O)NS(=O)(=O)N1CCCC1]

Prepared by an analogous method to Intermediate 100 except the Step 3 was carried out with isopropanol instead of MeOH. Yield: 280 mg, 0.66 mmol. White solid. LCMS: (System 1, Method A) Rt=0.98 min, m/z 423.0 $(M-H)^-$ $(ES^-)$.

Intermediate 103: methyl 4-bromo-2-(dimethylamino)-3-fluorobenzoate

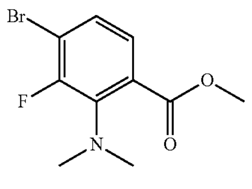

Prepared by an analogous method to Intermediate 81 starting from methyl 2-amino-4-bromo-3-fluorobenzoate (6.4 g, 160 mmol). Yield: 3.6 g, 13.1 mmol. Yellow oil. LCMS: (System 1, Method F) Rt=1.84 min, m/z 276.0 $(M+H)^+$ $(ES^+)$.

Intermediate 104: 3-(dimethylamino)-2-fluoro-4-(((1-methylcyclopropyl)sulfonyl)carbamoyl)benzoic acid

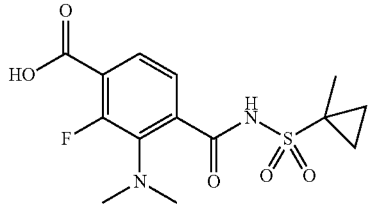 [SMILES: CN(C)c1c(C(=O)NS(=O)(=O)C2(C)CC2)ccc(C(=O)O)c1F]

Prepared by an analogous method to Intermediate 82 starting from 2-amino-4-bromo-3-fluorobenzoic acid (Intermediate 103, 3.6 g, 13.1 mmol). Yield: 340 mg, 0.99 mmol. Yellow solid. LCMS: (System 1, Method A) Rt=0.52 min, m/z 342.8 $(M-H)^-$ $(ES^-)$.

Intermediate 105: 3-(dimethylamino)-2-fluoro-4-((pyrrolidin-1-ylsulfonyl)carbamoyl)benzoic acid

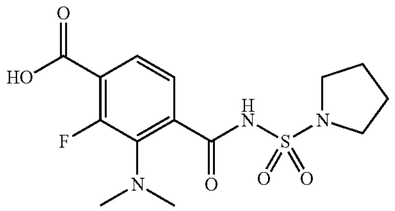 [SMILES: CN(C)c1c(C(=O)NS(=O)(=O)N2CCCC2)ccc(C(=O)O)c1F]

Prepared by an analogous method to Intermediate 82 starting from 2-amino-4-bromo-3-fluorobenzoic acid (Intermediate 103, 3.6 g, 13.1 mmol). Yield: 430 mg, 1.20 mmol. Yellow solid. LCMS: (System 1, Method A) Rt=1.76 min, m/z 394.0 $(M+H)^+$ $(ES^+)$.

Intermediate 106: (S)-8-(3-(methoxymethyl)-4-methylpiperazin-1-yl)-7-methyl-1,2,3,4-tetrahydro-5H-chromeno[3,4-c]pyridin-5-one

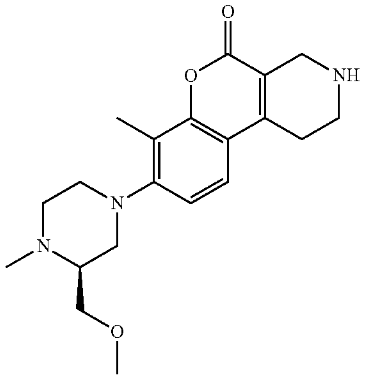 [SMILES: COC[C@@H]1CN(c2ccc3c4c(c(=O)oc3c2C)CNCC4)CCN1C]

Prepared by an analogous method to Intermediate 5 starting from (S)-2-(methoxymethyl)-1-methylpiperazine (Intermediate 37, 205 mg, 1.43 mmol) and tert-butyl 7-methyl-5-oxo-8-(((trifluoromethyl)sulfonyl)oxy)-1,5-dihydro-2H-chromeno[3,4-c]pyridine-3(4H)-carboxylate (Intermediate 2, 550 mg, 1.19 mmol). Yield: 205 mg, 0.57 mmol. Yellow solid. LCMS: (System 1, Method A) Rt=1.51 min, m/z 358.4 $(M+H)^+$ $(ES^+)$.

Intermediate 107: methyl 2-amino-4-bromo-5-(trifluoromethyl)benzoate

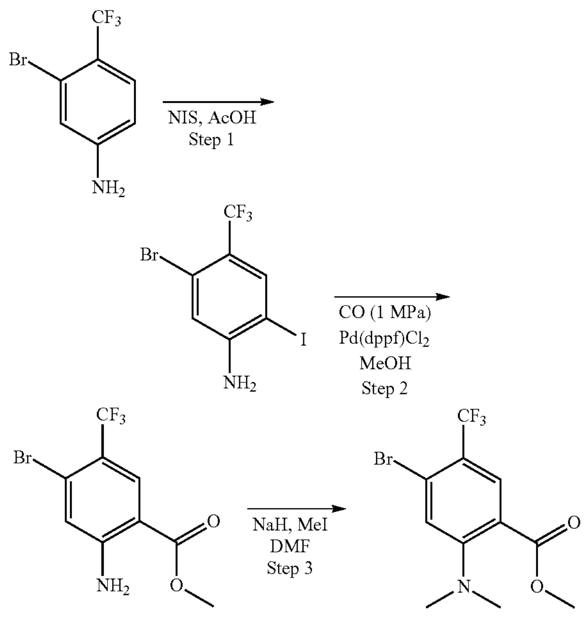

Step 1

NIS (5.7 g, 25.1 mmol) was added to a solution of 3-bromo-4-(trifluoromethyl)aniline (5.0 g, 20.9 mmol) in AcOH (50 mL) and the reaction was stirred at RT overnight. The mixture was partitioned between water (50 mL) and EtOAc (3×50 mL). The combined organic layers were dried $(Na_2SO_4)$, filtered and concentrated under reduced pressure. The crude product was purified by column chromatography on silica gel (1-30% EtOAc/petroleum ether) to afford 5-bromo-2-iodo-4-(trifluoromethyl)aniline (5.6 g, 15.3 mmol) as yellow oil. $^1H$ NMR (400 MHz, DMSO-$d_6$) δ: 7.82 (s, 1H), 7.07 (s, 1H), 6.20 (s, 2H).

Step 2

A solution of 5-bromo-2-iodo-4-(trifluoromethyl)aniline (5.6 g, 15.3 mmol), [1,1'-bis(diphenylphosphino)ferrocene]dichloropalladium(II) (2.2 g, 3.07 mmol) and KOAc (4.5 g, 46.0 mmol) in MeOH (100 mL) was stirred at 30° C. overnight under CO (1 Mpa) atmosphere. The reaction mixture was partitioned between $Na_2CO_3$ aq. sat. (15 mL) and EtOAc (3×100 mL). The pH of the aqueous layer was adjusted to pH ca. 3 with HCl aq. 1N and the aqueous layer extracted with EtOAc (3×100 mL). The combined organic layers were washed with brine, dried $(Na_2SO_4)$, filtered and concentrated under reduced pressure to afford methyl 2-amino-4-bromo-5-(trifluoromethyl)benzoate (2.8 g, 9.43 mmol) as a black solid which was used in the next step without further purification. LCMS: (System 1, Method G). Rt=0.99 min, m/z 296.0 $(M-H)^-$ $(ES^-)$.

Step 3

Sodium hydride (60% dispersion in mineral oil, 2.7 g, 56.6 mmol) was added to a solution of methyl 2-amino-4-bromo-5-(trifluoromethyl)benzoate (2.8 g, 9.43 mmol) in DMF (30 mL) and the reaction was stirred at RT for 10 min. Iodomethane (10.7 g, 75.4 mmol) was added and the mixture was stirred at RT overnight. The reaction was partitioned between water (100 mL) and EtOAc (3×30 mL). The combined organic layers were washed with brine (3×30 mL), dried $(Na_2SO_4)$, filtered and concentrated under reduced pressure to afford methyl 4-bromo-2-(dimethylamino)-5-(trifluoromethyl)benzoate (2.0 g, 6.2 mmol) as yellow oil. LCMS: (System 1, Method A), Rt=2.10 min, m/z 326.2 $(M+H)^+$ $(ES^+)$.

Intermediate 108: 5-(dimethylamino)-4-((pyrrolidin-1-ylsulfonyl)carbamoyl)-2-(trifluoromethyl)benzoic acid

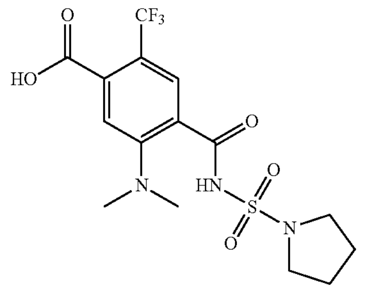 [SMILES: CN(C)c1cc(C(=O)O)c(C(F)(F)F)cc1C(=O)NS(=O)(=O)N1CCCC1]

Prepared by analogous method to Intermediate 46 (Steps 2 to 5) from Intermediate 107 (2.0 g, 6.2 mmol) except the Step 3 was carried out with pyrrolidine-1-sulfonamide in place of 1-methylcyclopropane-1-sulfonamide. Yield: 360 mg, 0.88 mmol. Yellow solid. LCMS: (System 1, Method F) Rt=0.24 min, m/z 408.0 $(M-H)^-$ $(ES^-)$.

Intermediate 109: 5-(dimethylamino)-4-(((1-methylcyclopropyl)sulfonyl)carbamoyl)-2-(trifluoromethyl)benzoic acid

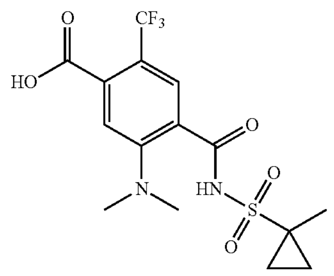 [SMILES: CN(C)c1cc(C(=O)O)c(C(F)(F)F)cc1C(=O)NS(=O)(=O)C1(C)CC1]

Prepared by analogous method to Intermediate 46 (steps 2 to 5) from Intermediate 107 (2.0 g, 6.2 mmol). Yield: 370 mg, 0.94 mmol. Yellow solid. LCMS: (System 1, Method A) Rt=0.36 min, m/z 393.0 $(M-H)^-$ $(ES^-)$.

Intermediate 110: methyl 4-bromo-5-chloro-2-(diethylamino)benzoate

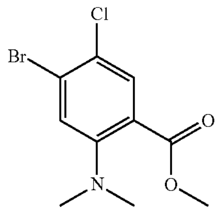

Prepared by analogous method to Intermediate 81 starting from 2-amino-4-bromo-5-chlorobenzoic acid (5.0 g, 22.1 mmol). Yield: 4.5 g, 14.4 mmol. Yellow oil. LCMS: (System 1, Method G) Rt=1.04 min, m/z 292.0 $(M+H)^+$ $(ES^+)$.

Intermediate 111: 2-chloro-5-(dimethylamino)-4-((pyrrolidin-1-ylsulfonyl)carbamoyl)benzoic acid

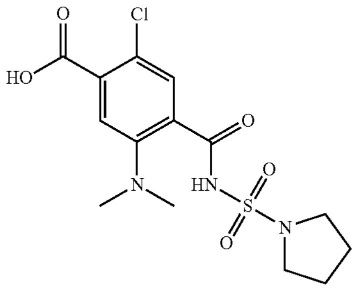 [SMILES: CN(C)c1cc(C(=O)O)c(Cl)cc1C(=O)NS(=O)(=O)N1CCCC1]

Prepared by analogous method to Intermediate 46 (steps 2 to 5) from methyl 4-bromo-5-chloro-2-(dimethylamino) benzoate (Intermediate 110, 2.5 g, 8.59 mmol) except the Step 3 was carried out with pyrrolidine-1-sulfonamide in place of 1-methylcyclopropane-1-sulfonamide. Yield: 540 mg, 1.44 mmol. Yellow solid. LCMS: (System 1, Method F) Rt=0.41 min, m/z 374.0 $(M-H)^-$ (ES Intermediate 112: 2-chloro-5-(dimethylamino)-4-(((1-methylcyclopropyl)sulfonyl)carbamoyl)benzoic acid

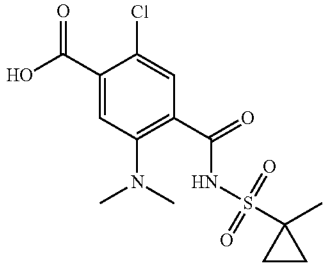 [SMILES: CN(C)c1cc(C(=O)O)c(Cl)cc1C(=O)NS(=O)(=O)C1(C)CC1]

Prepared by analogous method to Intermediate 46 (steps 2 to 5) from methyl 4-bromo-5-chloro-2-(dimethylamino) benzoate (Intermediate 110, 2.5 g, 8.59 mmol). Yield: 510 mg, 1.41 mmol. Yellow solid. LCMS: (System 1, Method F) Rt=0.23 min, m/z 359.0 $(M-H)^-$ $(ES^-)$.

Intermediate 113: 4-cyclobutoxy-3-((pyrrolidin-1-ylsulfonyl)carbamoyl)benzoic acid

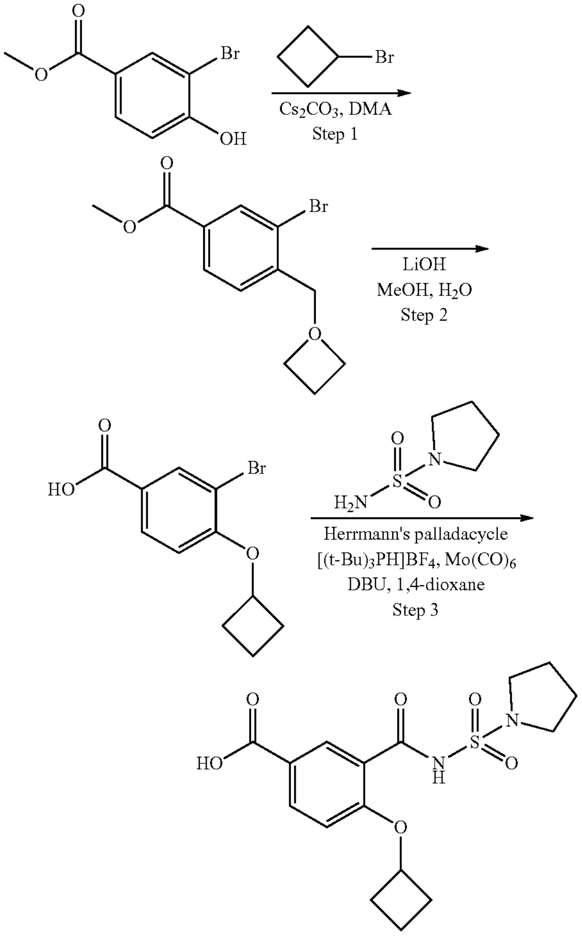

Step 1

Bromocyclobutane (2.6 g, 19.6 mmol) was added to a solution of methyl 3-bromo-4-hydroxybenzoate (3.0 g, 13.0 mmol) and $K_2CO_3$ (3.6 g, 26.1 mmol) in DMF (30 mL) and the reaction was stirred at 80° C. overnight. The mixture was partitioned between water (100 mL) and EtOAc (3×60 mL). The combined organic layers were washed with brine, dried ($Na_2SO_4$), filtered and concentrated under reduced pressure. The crude product was purified by column chromatography on silica gel (1-10% EtOAc/petroleum ether) to afford methyl 3-bromo-4-cyclobutoxybenzoate (3.5 g, 12.3 mmol) as a white solid. LCMS: (System 2, Method B) Rt=2.09 min, m/z 285.0 $(M+H)^+$ $(ES^+)$.

Step 2

A solution of methyl 3-bromo-4-cyclobutoxybenzoate (3.5 g, 12.3 mmol) and $LiOH \cdot H_2O$ (2.6 g, 61.6 mmol) in MeOH (100 mL) and water (30 mL) was stirred at RT overnight. The pH of the mixture was adjusted to pH ca. 3 by adding HCl aq. 1N. The organic solvent was evaporated under reduced pressure and the resulting precipitate was recovered by filtration, washed with water, hexane, and dried to afford 3-bromo-4-cyclobutoxybenzoic acid (3.1 g, 11.4 mmol) as a white solid. LCMS: (System 2, Method B) Rt=1.81 min, 271.0 $(M+H)^+$ $(ES^+)$.

Step 3

A solution of 3-bromo-4-cyclobutoxybenzoic acid (1.0 g, 3.7 mmol), pyrrolidine-1-sulfonamide (1.5 g, 11 mmol), trans-bis(acetato)bis[o-(di-o-tolylphosphino)benzyl]dipalladium(II) (Herrmann's palladacycle, 341 mg, 0.4 mmol), tri-tert-butylphosphonium tetrafluoroborate (217 mg, 0.70 mmol), molybdenum hexacarbonyl (968 mg, 5.5 mmol) and DBU (1.7 g, 11.0 mmol) in 1,4-dioxane (30 mL) was stirred at 100° C. for 15 minutes under microwave irradiation. Once the reaction was cooled down to RT, MeOH (30 mL) was added and solvents were removed under reduced pressure. $K_2CO_3$ aq. 2 M (30 mL) was added and reaction mixture washed with EtOAc (3×40 mL). The pH of the aqueous layer was adjusted to pH ca. 4-5 by adding HCl aq. 1N, and reaction mixture extracted with EtOAc (3×30 mL). The combined organic layers were dried ($Na_2SO_4$), filtered and concentrated under reduced pressure. The crude product was purified by column chromatography on silica gel (1-5% MeOH/DCM) to afford 4-cyclobutoxy-3-((pyrrolidin-1-ylsulfonyl)carbamoyl)benzoic acid (700 mg, 1.90 mmol) as a white solid. LCMS: (System 1, Method A) Rt=1.24 min, m/z 366.8 $(M-H)^-$ $(ES^-)$.

Intermediate 114: 3-cyclobutoxy-5-((pyrrolidin-1-ylsulfonyl)carbamoyl)benzoic acid

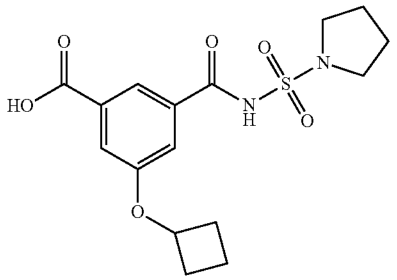 [SMILES: O=C(O)c1cc(OC2CCC2)cc(C(=O)NS(=O)(=O)N2CCCC2)c1]

Prepared by analogous method to Intermediate 113 from methyl 3-bromo-5-hydroxybenzoate (3.0 g, 13.0 mmol). Yield: 410 mg, 1.11 mmol. White solid. LCMS: (System 1, Method A) Rt=1.14 min, m/z 366.8 $(M-H)^-$ $(ES^-)$.

Intermediate 115: methyl 5-bromo-2-fluoro-4-hydroxybenzoate

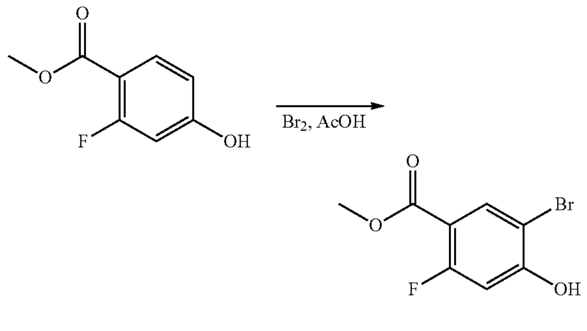

A mixture of methyl 2-fluoro-4-hydroxybenzoate (2.0 g, 11.8 mmol) in AcOH (30 mL) was stirred at 0° C. for 10 min, then bromine (1.9 g, 35.3 mmol) was added and the reaction was allowed to reach RT and stirred overnight. The mixture was partitioned between water (100 mL) and EtOAc (3×60 mL). The combined organic layers were washed with brine, dried ($Na_2SO_4$), filtered and concentrated under reduced pressure. The crude product was purified by column chromatography on silica gel (1-10% EtOAc/petroleum ether) to afford methyl 5-bromo-2-fluoro-4-hydroxybenzoate (800 mg, 3.23 mmol) as a white solid. LCMS: (System 1, Method F) Rt=1.00 min, 247.0 $(M-H)^-$ $(ES^-)$.

Intermediate 116: 4-cyclobutoxy-2-fluoro-5-((pyrrolidin-1-ylsulfonyl)carbamoyl)benzoic acid

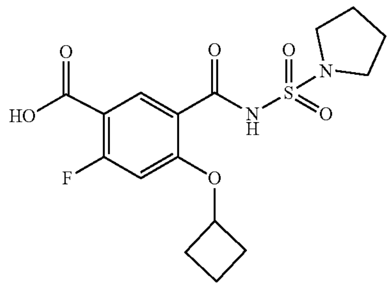 [SMILES: O=C(O)c1cc(C(=O)NS(=O)(=O)N2CCCC2)c(OC2CCC2)cc1F]

Prepared by analogous method to Intermediate 113 from methyl 5-bromo-2-fluoro-4-hydroxybenzoate (Intermediate 115, 800 g, 3.23 mmol). Yield: 215 mg, 0.56 mmol. White solid.

LCMS: (System 1, Method A) Rt=1.20 min, m/z 387.3 $(M+H)^+$ $(ES^+)$.

Intermediate 117: 3-bromo-5-cyclobutoxy-4-fluorobenzoic acid

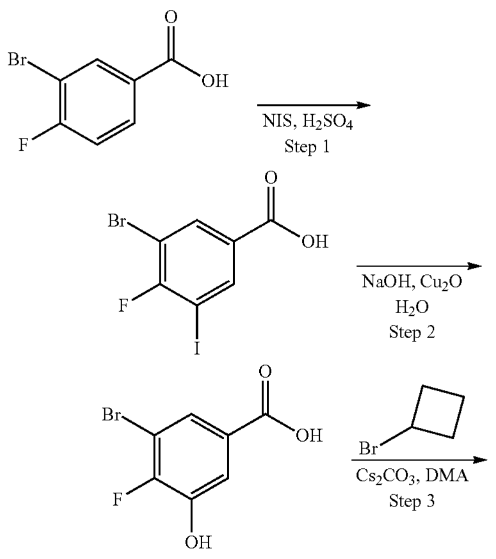

-continued

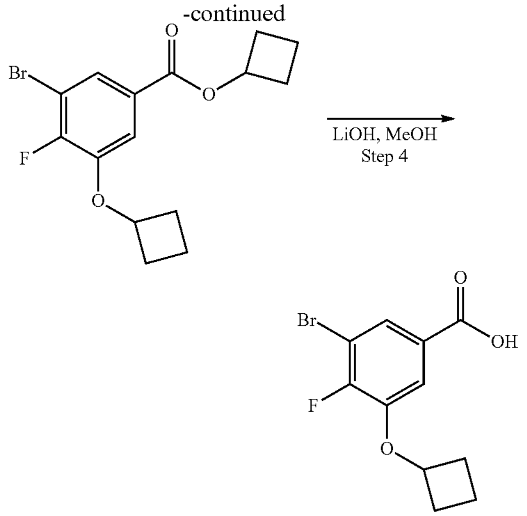

Step 1

NIS (2.3 g, 10.1 mmol) was added to a suspension of 3-bromo-4-fluorobenzoic acid (2.0 g, 9.17 mmol) in $H_2SO_4$ (40 mL) at 0° C. and the mixture was stirred at RT overnight. The reaction was poured into ice water (50 mL) and extracted with EtOAc (3×50 mL). The combined organic layers were dried ($Na_2SO_4$), filtered and concentrated under reduced pressure to afford 3-bromo-4-fluoro-5-iodobenzoic acid (2.2 g, 6.40 mmol) as a white solid which was used in the next step without further purification. LCMS: (System 1, Method B) Rt=1.14 min, m/z 342.8 $(M+H)^+$ $(ES^+)$.

Step 2

Copper(I) oxide (1.8 g, 12.80 mmol) was added to a solution of 3-bromo-4-fluoro-5-iodobenzoic acid (2.2 g, 6.40 mmol) and NaOH (1.0 g, 25.6 mmol) in water (30 mL) and the mixture was stirred at 100° C. overnight. The pH of the mixture was adjusted to ca. 3 with HCl aq. 1N and this aqueous phase was extracted with EtOAc (3×330 mL). The combined organic layers were dried ($Na_2SO_4$), filtered and concentrated under reduced pressure to afford 3-bromo-4-fluoro-5-hydroxybenzoic acid (900 mg, 3.95 mmol) as a white solid which was used in the next step without further purification. LCMS: (System 1, Method A) Rt=0.91 min, m/z 232.8 $(M-H)^-$ $(ES^-)$.

Step 3

A mixture of 3-bromo-4-fluoro-5-hydroxybenzoic acid (900 mg, 3.85 mmol), $Cs_2CO_3$ (2.5 g, 7.69 mmol) and bromocyclobutane (2.1 g, 15.4 mmol) in DMA (20 mL) was stirred at 60° C. overnight. The reaction was partitioned between water (60 mL) and EtOAc (3×30 mL) and the combined organic layers were washed with brine, dried ($Na_2SO_4$), filtered and concentrated under reduced pressure. The crude product was purified by column chromatography on silica gel (1-10% EtOAc/petroleum ether) to afford cyclobutyl 3-bromo-5-cyclobutoxy-4-fluorobenzoate (1.1 g, 3.21 mmol) as a white solid. LCMS: (System 1, Method A) Rt=2.41 min, m/z 343.0 $(M+H)^+$ $(ES^+)$.

Step 4

A mixture of cyclobutyl 3-bromo-5-cyclobutoxy-4-fluorobenzoate (1.1 g, 3.21 mmol) and $LiOH\cdot H_2O$ (811 mg, 19.3 mmol) in MeOH (20 mL) and water (5 mL) was stirred at RT overnight. The organic solvent was removed under reduced pressure and the pH of the mixture was adjusted to ca. 5 with HCl aq. 1N and the resulting solution was extracted with EtOAc (3×20 mL). The combined organic layers were dried ($Na_2SO_4$), filtered and concentrated under reduced pressure to afford 3-bromo-5-cyclobutoxy-4-fluorobenzoic acid (900 mg, 3.11 mmol) as a white solid. LCMS: (System 1, Method A) Rt=1.41 min, m/z 286.8 $(M-H)^-$ $(ES^-)$.

Intermediate 118: 3-cyclobutoxy-2-fluoro-5-((pyrrolidin-1-ylsulfonyl)carbamoyl)benzoic

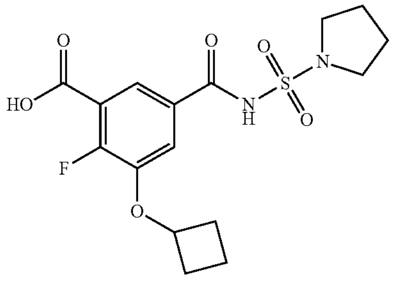 [SMILES: O=C(NS(=O)(=O)N1CCCC1)c1cc(OC2CCC2)c(F)c(C(=O)O)c1]

Prepared by an analogous method to Intermediate 36 (Steps 3 to 5 only) starting from 3-bromo-5-cyclobutoxy-4-fluorobenzoic acid (Intermediate 117, 900 mg, 3.11 mmol) except the Step 3 was carried out with pyrrolidine-1-sulfonamide in place N,N-dimethylsulfamide. Yield: 245 mg, 0.63 mmol. Brown solid. LCMS: (System 1, Method A) Rt=1.15 min, m/z 384.7 $(M-H)^-$ $(ES^-)$.

Intermediate 119: methyl 4-bromospiro[benzo[d][1,3]dioxole-2,1'-cyclobutane]-6-carboxylate

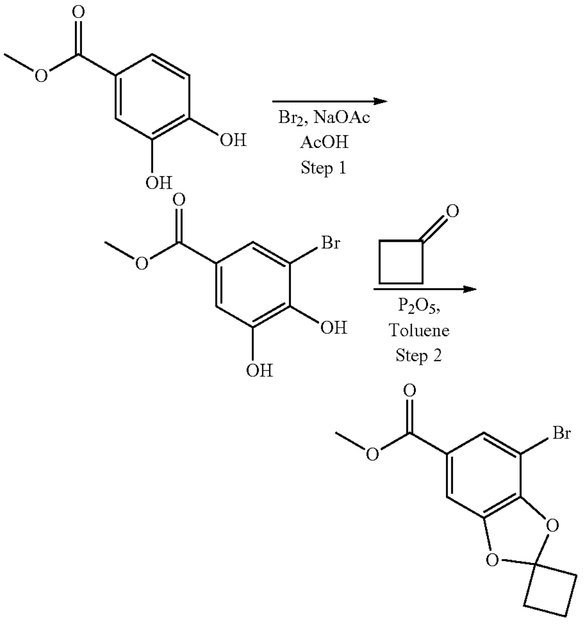

Step 1

A mixture of methyl 3,4-dihydroxybenzoate (3.0 g, 17.9 mmol) and sodium acetate (2.9 g, 35.7 mmol) in AcOH (30 mL) was stirred at 0° C. for 10 min, then bromine (8.6 g, 53.6 mmol) was added and the reaction was allowed to reach RT and stirred overnight. The mixture was partitioned between water (100 mL) and EtOAc (3×60 mL) and the combined organic layers were washed with brine, dried ($Na_2SO_4$), filtered and concentrated under reduced pressure. The crude product was purified by column chromatography on silica gel (1-10% EtOAc/petroleum ether) to afford methyl 3-bromo-4,5-dihydroxybenzoate (3.0 g, 12.2 mmol) as a white solid. LCMS: (System 2, Method B) Rt=1.49 min, m/z 247.0 $(M+H)^+$ $(ES^+)$.

Step 2

A mixture of methyl 3-bromo-4,5-dihydroxybenzoate (3.0 g, 12.2 mmol), cyclobutanone (1.3 g, 18.3 mmol) and phosphorus pentoxide (8.3 g, 58.6 mmol) in toluene (40 mL) was stirred at 75° C. overnight. The mixture was poured into water and extracted with EtOAc (3×50 mL). The combined organic layers were washed with brine, dried ($Na_2SO_4$), filtered and concentrated under reduced pressure. The crude product was purified by column chromatography on silica gel (0-30% EtOAc/petroleum ether) to afford methyl 4-bromospiro[benzo[d][1,3]dioxole-2,1'-cyclobutane]-6-carboxylate (1.5 g, 4.85 mmol) as yellow oil. LCMS: (System 2, Method B) Rt=2.10 min, m/z 299.0 $(M+H)^+$ $(ES^+)$.

Intermediate 120: 4-((pyrrolidin-1-ylsulfonyl)carbamoyl)spiro[benzo[d][1,3]dioxole-2,1'-cyclobutane]-6-carboxylic acid

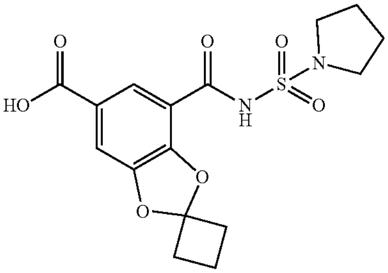 [SMILES: O=C(O)c1cc2c(c(C(=O)NS(=O)(=O)N3CCCC3)c1)OC1(CCC1)O2]

Prepared by an analogous method to Intermediate 38 (Step 3 and Step 4 only) starting from methyl 4-bromospiro[benzo[d][1,3]dioxole-2,1'-cyclobutane]-6-carboxylate (Intermediate 119, 1.5 g, 4.85 mmol) except the Step 3 was carried out with pyrrolidine-1-sulfonamide in place of N,N-dimethylsulfamide. Yield: 255 mg, 0.67 mmol. White solid. LCMS: (System 2, Method F) Rt=0.89 min, m/z 383.0 $(M+H)^+$ $(ES^+)$.

Intermediate 121: ethyl 7-bromo-4-fluorospiro[benzo[d][1,3]dioxole-2,1'-cyclobutane]-5-carboxylate

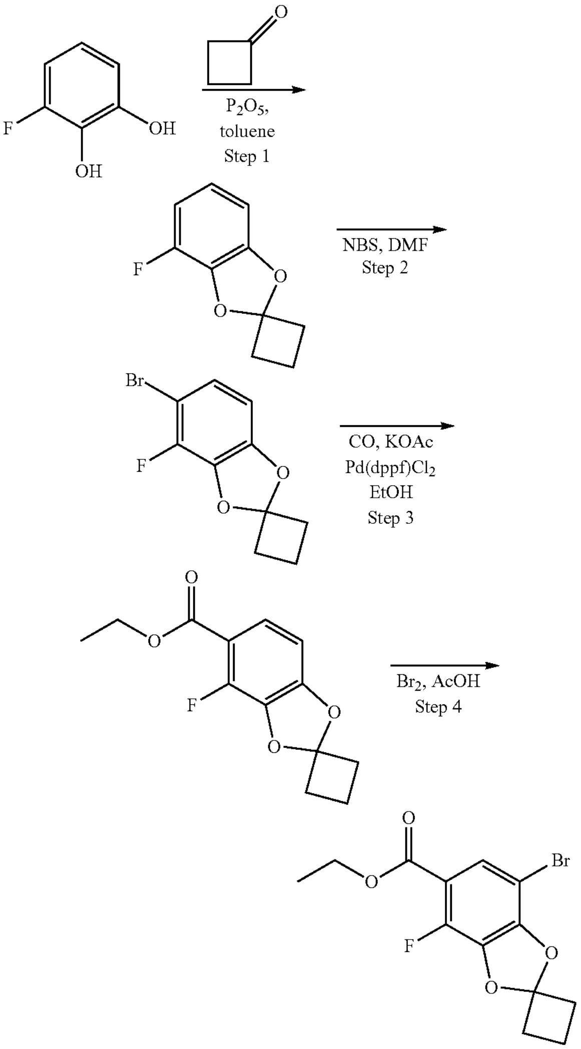

Step 1

A mixture of 3-fluorobenzene-1,2-diol (6.0 g, 46.8 mmol), cyclobutanone (4.9 g, 70.2 mmol), phosphorus pentoxide (26.6 g, 187.2 mmol) in toluene (200 mL) was stirred at 75° C. overnight. The mixture was poured into ice-water (50 mL) and extracted with EtOAc (3×50 mL). The combined organic layers were washed with brine, dried ($Na_2SO_4$), filtered and concentrated under reduced pressure. The crude product was purified by column chromatography on silica gel (0-30% EtOAc/petroleum ether) to afford 4-fluorospiro[benzo[d][1,3]dioxole-2,1'-cyclobutane](2.5 g, 13.9) as a yellow oil. $^1H$ NMR (400 MHz, DMSO-$d_6$) δ: 6.86-6.77 (m, 3H), 2.65-2.57 (m, 4H), 1.85-1.77 (m, 2H).

Step 2

A mixture of 4-fluorospiro[benzo[d][1,3]dioxole-2,1'-cyclobutane](2.2 g, 12.21 mmol), NBS (2.4 g, 13.4 mmol) in DMF (50 mL) was stirred at RT overnight. The reaction mixture was partitioned between water (150 mL) and EtOAc (3×100 mL). The combined organic layers were dried ($Na_2SO_4$), filtered and concentrated under reduced pressure. The crude product was purified by column chromatography on silica gel (20-50% EtOAc/petroleum ether) to afford 4-bromo-7-fluorospiro[benzo[d][1,3]dioxole-2,1'-cyclobutane](2.1 g, 8.14 mmol) as a white solid. $^1H$ NMR (400 MHz, DMSO-$d_6$) δ: 7.20 (dd, J=8.4, 2.8 Hz, 1H), 7.34 (dd, J=8.4, 0.8 Hz, 1H), 2.73-2.66 (m, 4H), 1.91-1.83 (m, 2H).

Step 3

A mixture of 5-bromo-4-fluorospiro[benzo[d][1,3]dioxole-2,1'-cyclobutane] (2.1 g, 8.14 mmol), [1,1'-bis(diphenylphosphino)ferrocene]dichloropalladium(II) (1.20 g, 1.63 mmol) and KOAc (2.40 g, 24.4 mmol) in EtOH (40 mL) was stirred at 80° C. for 5 h under CO atmosphere. The reaction was allowed to reach RT and partitioned between water (40 mL) and EtOAc (3×40 mL). The combined organic layers were dried ($Na_2SO_4$), filtered and concentrated under reduced pressure. The crude product was purified by column chromatography on silica gel (20-50% EtOAc/petroleum ether) to afford ethyl 4-fluorospiro[benzo[d][1,3]dioxole-2,1'-cyclobutane]-5-carboxylate (1.6 g, 6.35 mmol) as a white solid. LCMS: (System 1, Method A) Rt=2.11 min, m/z 253.4 $(M+H)^+$ $(ES^+)$.

Step 4

A mixture of bromine (4.1 g, 25.4 mmol), ethyl 4-fluorospiro[benzo[d][1,3]dioxole-2,1'-cyclobutane]-5-carboxylate (1.6 g, 6.35 mmol) in AcOH (20 mL) and DMF (1 mL) was stirred at 50° C. for 5 h under nitrogen atmosphere. The reaction was partitioned between water (20 mL) and EtOAc (3×10 mL). The combined organic layers were dried ($Na_2SO_4$), filtered and concentrated under reduced pressure. The crude product was purified by column chromatography on silica gel (20-50% EtOAc/petroleum ether) to afford ethyl 7-bromo-4-fluorospiro[benzo[d][1,3]dioxole-2,1'-cyclobutane]-5-carboxylate (1.6 g, 4.80 mmol) as a white solid. LCMS: (System 1, Method A) Rt=2.03 min, m/z 331.0 $(M+H)^+$ $(ES^+)$.

Intermediate 122: 4-fluoro-7-((pyrrolidin-1-ylsulfonyl)carbamoyl)spiro[benzo[d][1,3]dioxole-2,1'-cyclobutane]-5-carboxylic acid

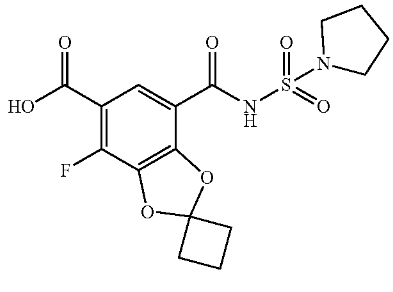 [SMILES: O=C(O)c1cc(C(=O)NS(=O)(=O)N2CCCC2)c2c(c1F)OC1(CCC1)O2]

Prepared by an analogous method to Intermediate 120 starting from ethyl 7-bromo-4-fluorospiro[benzo[d][1,3]dioxole-2,1'-cyclobutane]-5-carboxylate (Intermediate 121, 1.6 g, 4.80 mmol). Yield: 180 mg, 0.45 mmol. White solid. LCMS: (System 1, Method A) Rt=1.14 min, m/z 401.0 $(M+H)^+$ $(ES^+)$.

Intermediate 123: 3-(7-azabicyclo[2.2.1]heptan-7-yl)-4-((pyrrolidin-1-ylsulfonyl)carbamoyl)benzoic acid

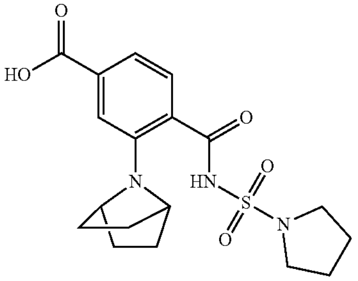 [SMILES: O=C(O)c1ccc(C(=O)NS(=O)(=O)N2CCCC2)c(N2C3CCC2CC3)c1]

Prepared by analogous method to Intermediate 51 except the Step 3 was carried out with pyrrolidine-1-sulfonamide in place of 1-methylcyclopropane-1-sulfonamide. Yield: 293 mg, 0.74 mmol. Yellow solid. LCMS: (System 1, Method A) Rt=1.23 min, m/z 391.9 $(M-H)^-$ $(ES^-)$.

Intermediate 124: (S)-3-(2-methylpyrrolidin-1-yl)-4-((pyrrolidin-1-ylsulfonyl)carbamoyl)benzoic acid

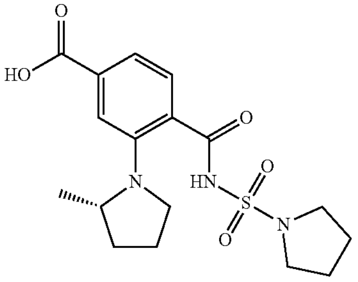 [SMILES: C[C@H]1CCCN1c1cc(C(=O)O)ccc1C(=O)NS(=O)(=O)N1CCCC1]

Prepared by analogous method to Intermediate 46 starting from methyl 4-bromo-2-fluorobenzoate (1.5 g, 6.4 mmol) and (S)-2-methylpyrrolidine hydrochloride (1.6 g, 12.9 mmol) except the Step 3 was carried out with pyrrolidine-1-sulfonamide in place of 1-methylcyclopropane-1-sulfonamide. Yield: 320 mg, 0.84 mmol. Yellow solid. LCMS: (System 1, Method F) Rt=0.97 min, m/z 382.2 $(M+H)^+$ $(ES^+)$.

Intermediate 125: (S)-4-(((1-methylcyclopropyl)sulfonyl)carbamoyl)-3-(2-methylpyrrolidin-1-yl)benzoic acid

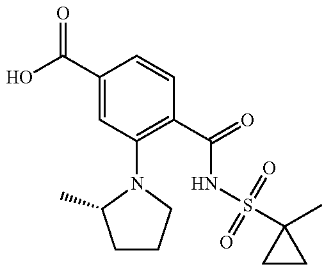 [SMILES: C[C@H]1CCCN1c1cc(C(=O)O)ccc1C(=O)NS(=O)(=O)C1(C)CC1]

Prepared by analogous method to Intermediate 46 starting from methyl 4-bromo-2-fluorobenzoate (1.5 g, 6.4 mmol) and (S)-2-methylpyrrolidine hydrochloride (1.6 g, 12.9 mmol). Yield: 300 mg, 0.82 mmol. Yellow solid. LCMS: (System 1, Method F) Rt=0.88 min, m/z 367.2 $(M+H)^+$ $(ES^+)$.

Intermediate 126: (R)-3-(2-methylpyrrolidin-1-yl)-4-((pyrrolidin-1-ylsulfonyl)carbamoyl)benzoic acid

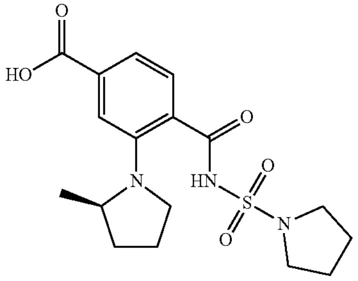 [SMILES: C[C@@H]1CCCN1c1cc(C(=O)O)ccc1C(=O)NS(=O)(=O)N1CCCC1]

Prepared by analogous method to Intermediate 46 starting from methyl 4-bromo-2-fluorobenzoate (1.5 g, 6.4 mmol) and (R)-2-methylpyrrolidine hydrochloride (1.6 g, 12.9 mmol) except the Step 3 was carried out with pyrrolidine-1-sulfonamide in place of 1-methylcyclopropane-1-sulfonamide. Yield: 330 mg, 0.87 mmol. White solid. LCMS: (System 1, Method F) Rt=0.97 min, m/z 382.2 $(M+H)^+$ $(ES^+)$.

Intermediate 127: (R)-4-(((1-methylcyclopropyl)sulfonyl)carbamoyl)-3-(2-methylpyrrolidin-1-yl)benzoic acid

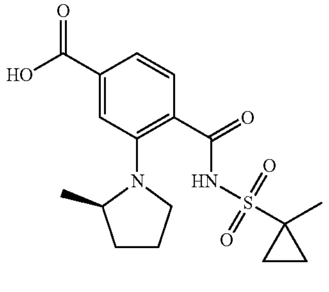 [SMILES: C[C@@H]1CCCN1c1cc(C(=O)O)ccc1C(=O)NS(=O)(=O)C1(C)CC1]

Prepared by analogous method to Intermediate 46 starting from methyl 4-bromo-2-fluorobenzoate (1.5 g, 6.4 mmol) and (R)-2-methylpyrrolidine hydrochloride (1.6 g, 12.9 mmol). Yield: 310 mg, 0.84 mmol. White solid. LCMS: (System 1, Method F) Rt=0.88 min, m/z 367.0 $(M+H)^+$ $(ES^+)$.

Intermediate 128: 3-(3-azabicyclo[3.1.0]hexan-3-yl)-4-((pyrrolidin-1-ylsulfonyl)carbamoyl)benzoic acid

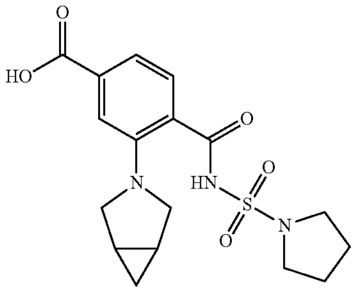 [SMILES: O=C(O)c1ccc(C(=O)NS(=O)(=O)N2CCCC2)c(N2CC3CC3C2)c1]

Prepared by analogous method to Intermediate 46 starting from methyl 4-bromo-2-fluorobenzoate (2.0 g, 8.62 mmol) and 3-azabicyclo[3.1.0]hexane (2.15 g, 25.9 mmol) except the Step 3 was carried out with pyrrolidine-1-sulfonamide in place of 1-methylcyclopropane-1-sulfonamide. Yield: 390 mg, 1.03 mmol. Yellow solid. LCMS: (System 1, Method F) Rt=0.83 min, m/z 378.0 $(M-H)^-$ $(ES^-)$.

Intermediate 129: 3-cyclobutoxy-4-(((1-methylcyclopropyl)sulfonyl)carbamoyl)-5-(trifluoromethyl)benzoic acid

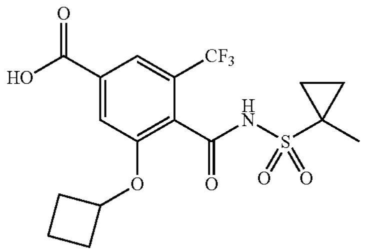 [SMILES: CC1(S(=O)(=O)NC(=O)c2c(OC3CCC3)cc(C(=O)O)cc2C(F)(F)F)CC1]

Prepared by an analogous method to Intermediate 43 starting from 4-(ethoxycarbonyl)-2-fluoro-6-(trifluoromethyl)benzoic acid (Intermediate 42, 1.6 g, 5.7 mmol) except the Step 3 was carried out with cyclobutanol in place of cyclopentanol. Yield: 250 mg, 0.60 mmol. Brown solid. LCMS: (System 1, Method A) Rt=1.07 min, m/z 419.8 $(M+H)^+$ $(ES^+)$.

Intermediate 130: 3-cyclobutoxy-4-((pyrrolidin-1-ylsulfonyl)carbamoyl)-5-(trifluoromethyl)benzoic acid

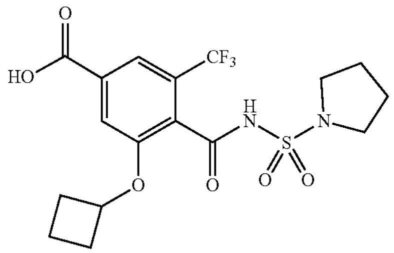 [SMILES: O=C(O)c1cc(OC2CCC2)c(C(=O)NS(=O)(=O)N2CCCC2)c(C(F)(F)F)c1]

Prepared by an analogous method to Intermediate 43 starting from 4-(ethoxycarbonyl)-2-fluoro-6-(trifluoromethyl)benzoic acid (Intermediate 42, 1.6 g, 5.7 mmol) except the Step 1 was carried out with pyrrolidine-1-sulfonamide in place of 1-methylcyclopropane-1-sulfonamide and the Step 3 was carried out with cyclobutanol in place of cyclopentanol. Yield: 600 mg, 1.38 mmol. Brown solid. LCMS: (System 1, Method A) Rt=1.05 min, m/z 434.6 $(M-H)^-$ $(ES^-)$.

Intermediate 131: 3-(cyclopentyloxy)-4-((N,N-dimethylsulfamoyl)carbamoyl)-5-(pyrrolidin-1-yl)benzoic acid

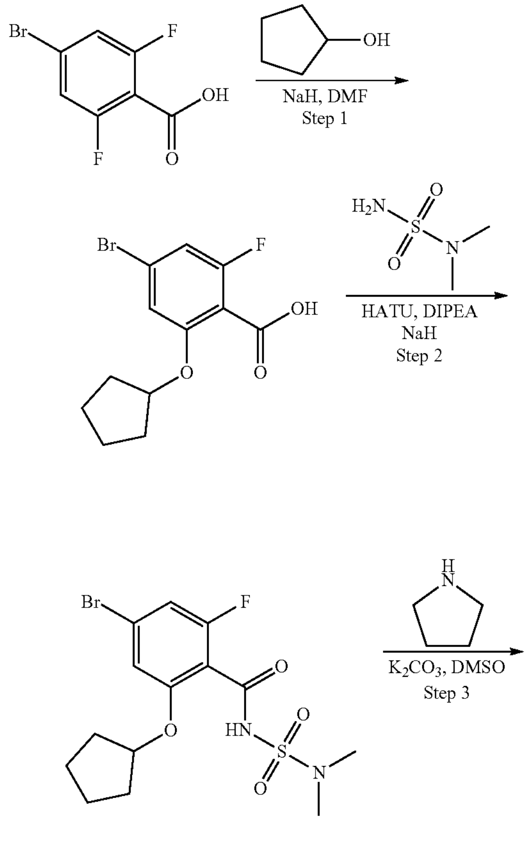

-continued

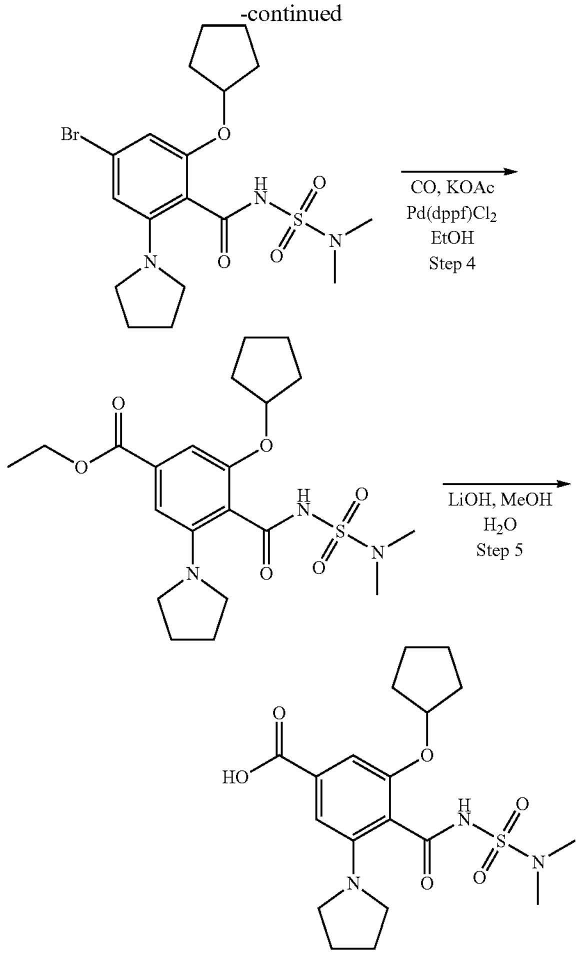

Step 1

Sodium hydride (60% dispersion in mineral oil, 628 mg, 15.7 mmol) was added in small portions to a solution of 4-bromo-2,6-difluorobenzoic acid (3.1 g, 13.1 mmol) in DMF (50 mL). Cyclopentanol (1.2 g, 14.4 mmol) was added and the reaction was stirred at 100° C. for 2 h. The mixture was quenched with $NH_4Cl$ aq. sat. (150 mL) and partitioned with EtOAc (3×150 mL). The combined organics were washed with brine, dried ($Na_2SO_4$), filtered and concentrated under reduced pressure. The crude product was purified by reverse phase column chromatography ($C_{18}$, 35% $ACN/H_2O$) to afford 4-bromo-2-(cyclopentyloxy)-6-fluorobenzoic acid (1.6 g, 5.28 mmol) as a brown solid. LCMS: (System 1, Method A) Rt=1.35 min, m/z 300.8 $(M-H)^-$ $(ES^-)$.

Step 2

A mixture of 4-bromo-2-(cyclopentyloxy)-6-fluorobenzoic acid (1.6 g, 5.28 mmol), HATU (2.4 g, 6.33 mmol) and DIPEA (2.7 g, 21.1 mmol) in DMF (40 mL) was stirred at RT for 1.5 h. After this time, N,N-dimethylsulfamide (2.0 g, 15.8 mmol) was added, followed by sodium hydride (60% dispersion in mineral oil, 844 mg, 21.1 mmol), and the reaction mixture was stirred at RT overnight. The reaction mixture was poured into $NH_4Cl$ aq. sat. (120 mL), acidified with HCl aq. 1N (15 mL) and extracted with EtOAc (3×120 mL). The combined organic layers were washed with brine, dried ($Na_2SO_4$), filtered, concentrated under reduced pressure. The crude product was purified by silica gel column chromatography (1-3% MeOH/DCM) to afford 4-bromo-2-(cyclopentyloxy)-N—(N,N-dimethylsulfamoyl)-6-fluorobenzamide (1.0 g, 2.44 mmol) as a white solid. LCMS: (System 1, Method A) Rt=1.64 min, m/z 409.0 $(M+H)^+$ $(ES^+)$.

Step 3

A mixture of 4-bromo-2-(cyclopentyloxy)-N—(N,N-dimethylsulfamoyl)-6-fluorobenzamide (1.0 g, 2.44 mmol), $K_2CO_3$ (1.0 g, 7.33 mmol) and pyrrolidine (869 mg, 12.2 mmol) in DMSO (14 mL) was stirred at 120° C. overnight. The reaction mixture was partitioned between water (50 mL) and EtOAc (3×50 mL). The combined organic layers were washed with brine, dried ($Na_2SO_4$), filtered and concentrated under reduced pressure. The crude product was purified by column chromatography on silica gel (1-2% MeOH/DCM) to afford 4-bromo-2-(cyclopentyloxy)-N—(N,N-dimethylsulfamoyl)-6-(pyrrolidin-1-yl)benzamide (500 mg, 1.09 mmol) as a white solid. LCMS: (System 1, Method A) Rt=2.14 min, m/z 460.0 $(M+H)^+$ $(ES^+)$.

Step 4

A mixture of 4-bromo-2-(cyclopentyloxy)-N—(N,N-dimethylsulfamoyl)-6-(pyrrolidin-1-yl)benzamide (500 mg, 1.09 mmol), [1,1'-bis(diphenylphosphino)ferrocene]dichloropalladium(II) (159 mg, 0.22 mmol) and potassium acetate (320 mg, 3.26 mmol) in EtOH (15 mL) was stirred at 80° C. for 5 h under CO atmosphere. The mixture was concentrated under reduced pressure. The crude product was purified by column chromatography on silica gel (1-3% MeOH/DCM) to afford ethyl 3-(cyclopentyloxy)-4-((N,N-dimethylsulfamoyl)carbamoyl)-5-(pyrrolidin-1-yl)benzoate (455 mg, 1.00 mmol) as a brown oil. LCMS: (System 1, Method F) Rt=1.58 min, 454.2 $(M+H)^+$ $(ES^+)$.

Step 5

A solution of $LiOH \cdot H_2O$ (210 mg, 5.02 mmol) in water (3 mL) was added to a solution of ethyl 3-(cyclopentyloxy)-4-((N,N-dimethylsulfamoyl)carbamoyl)-5-(pyrrolidin-1-yl) benzoate (455 mg, 1.00 mmol) in MeOH (12 mL). The reaction mixture was stirred at RT overnight. Organic solvents were removed under reduced pressure, then the pH of the mixture was adjusted to ca. 3 with HCl aq. 1N. The formed precipitate was collected by filtration, washed with water then hexane and dried under reduced pressure to afford 3-(cyclopentyloxy)-4-((N,N-dimethylsulfamoyl)carbamoyl)-5-(pyrrolidin-1-yl)benzoic acid (385 mg, 0.85 mmol) as a yellow solid. LCMS: (System 1, Method A) Rt=1.23 min, 454.2 $(M-H)^-$ $(ES^-)$.

Intermediate 132: 3-cyclobutoxy-2-fluoro-6-methyl-4-((pyrrolidin-1-ylsulfonyl)carbamoyl)benzoic acid

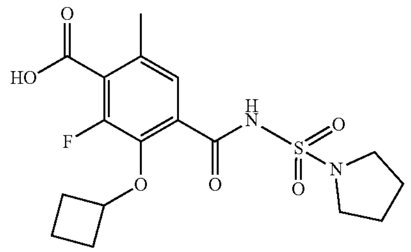

Prepared by an analogous method to Intermediate 13 starting from of 2-bromo-6-fluoro-4-methylphenol (2.0 g, 10 mmol) and bromocyclobutane (2.7 g, 20 mmol). Yield: 230 mg, 0.58 mmol. White solid. LCMS: (System 1, Method A) Rt=1.02 min, m/z 398.8 $(M-H)^-$ $(ES^-)$.

Intermediate 133: methyl 4-bromo-2-(dimethylamino)-5-fluorobenzoate

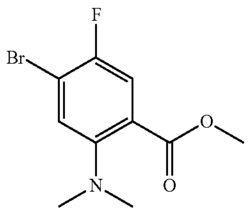

Prepared by an analogous method to Intermediate 81 starting from 2-amino-4-bromo-5-fluorobenzoic acid (5.2 g, 22.3 mmol). Yield: 2.8 g, 10.2 mmol. Yellow oil. LCMS: (System 1, Method F) Rt=1.78 min, m/z 276.0 $(M+H)^+$ $(ES^+)$.

Specific Procedure

To a solution of 2-amino-4-bromo-5-fluorobenzoic acid (5.2 g, 22.32 mmol) in DMF (50 mL), was added NaH (60%, 5.36 g, 133.91 mmol), and the reaction mixture was stirred at room temperature for 10 min. Methyl iodide (25.4 g, 178.54 mmol) was added and the reaction mixture was stirred at room temperature overnight. The reaction mixture was poured into water (100 mL) and extracted with ethyl acetate (3×100 mL). The combined ethyl acetate extracts were washed with brine (3×100 mL), dried over $Na_2SO_4$ and concentrated to give methyl 4-bromo-2-(dimethylamino)-5-fluorobenzoate (2.8 g, 46% yield) as yellow oil. LCMS: (System 1, Method F) Rt=1.78 min, m/z 276.0 $(M+H)^+$.

Intermediate 134: 5-(dimethylamino)-2-fluoro-4-((pyrrolidin-1-ylsulfonyl)carbamoyl)benzoic acid

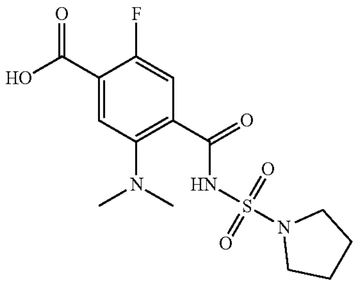 [SMILES: CN(C)c1cc(C(=O)O)c(F)cc1C(=O)NS(=O)(=O)N1CCCC1]

Prepared by analogous method to Intermediate 46 (Steps 2 to 5) from methyl 4-bromo-2-(dimethylamino)-5-fluorobenzoate (Intermediate 133, 2.8 g, 10.2 mmol) except the Step 3 was carried out with pyrrolidine-1-sulfonamide in place of 1-methylcyclopropane-1-sulfonamide. Yield: 430 mg, 1.20 mmol. Yellow solid. LCMS: (System 1, Method A) Rt=0.93 min, m/z 360.3 $(M+H)^+$ $(ES^+)$.

Specific Procedure

Step 1

To a solution of methyl 4-bromo-2-(dimethylamino)-5-fluorobenzoate (Intermediate 133, 2.8 g, 10.18 mmol) in THF/MeOH/water (16 mL/16 mL/4 mL) was added LiOH (1.7 g, 40.73 mmol), and the reaction mixture was stirred at 60° C. for 4 h. The pH of the mixture was adjusted to 8 with 1N HCl, MeOH and THE were removed at 35° C. under reduced pressure. The pH was adjusted to 3 with 1N HCl. The formed precipitate was collected by filtration, washed with water then hexane and dried at 35° C. under reduced pressure to give 4-bromo-2-(dimethylamino)-5-fluorobenzoic acid (2.6 g, 98% yield) as a yellow solid. LCMS: (System 1, Method A) Rt=1.25 min, m/z 262.2 $(M+H)^+$.

Step 2

A solution of 4-bromo-2-(dimethylamino)-5-fluorobenzoic acid (900 mg, 3.45 mmol) HATU (1.57 g, 4.14 mmol), TEA (1.39 g, 13.79 mmol) in DMF (20 mL) was stirred at room temperature 1 h. Pyrrolidine-1-sulfonamide (1.55 g, 10.34 mmol) and NaH (60%, 552 mg, 13.79 mmol) were added and the reaction mixture was stirred at room temperature overnight. The pH of the mixture was adjusted to 4 with 1N HCl and the mixture was extracted with ethyl acetate (3x25 mL). The combined organic layers were dried over $Na_2SO_4$, filtered and concentrated at 35° C. under reduced pressure to give crude material, which was purified by silica gel column chromatography (1-10% MeOH/DCM) to give 4-bromo-2-(dimethylamino)-5-fluoro-N-(pyrrolidin-1-ylsulfonyl)benzamide (700 mg, 52% yield) as yellow oil. LCMS: (System 1, Method A), Rt=1.88 min, m/z 394.0 $(M+H)^+$.

Step 3

To a solution of 4-bromo-2-(dimethylamino)-5-fluoro-N-(pyrrolidin-1-ylsulfonyl)benzamide (700 mg, 1.78 mmol) in EtOH (15 mL) was added $Pd(dppf)Cl_2$ (260 mg, 0.36 mmol) and KOAc (524 mg, 5.34 mmol), then the mixture was stirred at 80° C. for 5 hours under CO atmosphere. Sat. aq. $Na_2CO_3$ (15 mL) was added, and the reaction mixture was extracted with EtOAc (3x15 mL). The pH of the aqueous layer was adjusted to 3 with 1N HCl aq. and aqueous layer extracted again with EtOAc (3x15 mL). The combined organic layers were washed with brine, dried over $Na_2SO_4$ and filtered. The filtrate was concentrated at 35° C. under reduced pressure to give ethyl 5-(dimethylamino)-2-fluoro-4-((pyrrolidin-1-ylsulfonyl)carbamoyl)benzoate (500 mg, 73% yield) as a black solid. LCMS: (System 1, Method F). Rt=1.33 min, m/z 388.0 $(M+H)^+$.

Step 4

To a solution of ethyl 5-(dimethylamino)-2-fluoro-4-((pyrrolidin-1-ylsulfonyl)carbamoyl)benzoate (500 mg, 1.29 mmol) in THE (12 mL) and MeOH (3 mL) was added a solution of LiOH $H_2O$ (212 mg, 5.17 mmol) in water (3 mL). The reaction mixture was stirred at room temperature overnight. The pH of the mixture was adjusted to 8 with 1N HCl, MeOH and THE were removed at 35° C. under reduced pressure, then pH of the mixture was adjusted to 3 with 1N HCl. The formed precipitate was collected by filtration, washed with water, hexane and dried at 35° C. under reduced pressure to give 5-(dimethylamino)-2-fluoro-4-((pyrrolidin-1-ylsulfonyl)carbamoyl)benzoic acid (430 mg, 93% yield) as a yellow solid.

LCMS: (System 1, Method A). Rt=0.93 min, m/z 360.3 $(M+H)^+$ $(ES^+)$.

Intermediate 135: 5-(dimethylamino)-2-fluoro-4-(((1-methylcyclopropyl)sulfonyl)carbamoyl)benzoic acid

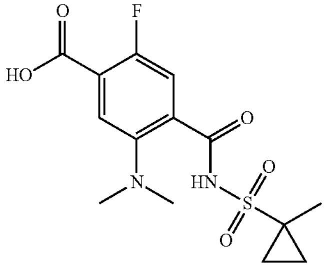 [SMILES: CN(C)c1cc(C(=O)O)c(F)cc1C(=O)NS(=O)(=O)C1(C)CC1]

Prepared by analogous method to Intermediate 46 (Steps 2 to 5) from methyl 4-bromo-2-(dimethylamino)-5-fluorobenzoate (Intermediate 133, 2.5 g, 8.59 mmol). Yield: 400 mg, 1.16 mmol. Yellow solid. LCMS: (System 1, Method F) Rt=0.35 min, m/z 345.0 $(M+H)^+$ $(ES^+)$.

Intermediate 136: 2-fluoro-4-(((1-methylcyclopropyl)sulfonyl)carbamoyl)-5-(pyrrolidin-1-yl)benzoic acid

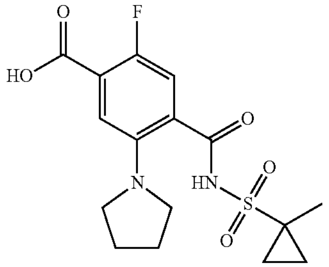 [SMILES: CC1(S(=O)(=O)NC(=O)c2cc(F)c(C(=O)O)cc2N2CCCC2)CC1]

Prepared by analogous method to Intermediate 46 starting from methyl 4-bromo-2,5-difluorobenzoate (2.5 g, 10.0 mmol) and pyrrolidine (2.13 g, 30.0 mmol). Yield: 280 mg, 0.76 mmol. Yellow solid. LCMS: (System 1, Method F) Rt=0.69 min, m/z 369.0 $(M+H)^+$ $(ES^+)$.

Intermediate 137: 2-fluoro-4-(((1-methylcyclopropyl)sulfonyl)carbamoyl)-5-(pyrrolidin-1-yl)benzoic acid

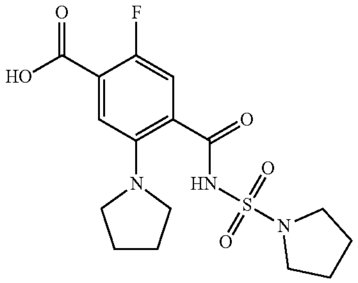

Prepared by analogous method to Intermediate 136 except the Step 3 was carried out with pyrrolidine-1-sulfonamide in place of 1-methylcyclopropane-1-sulfonamide. Yield: 330 mg, 0.89 mmol. White solid. LCMS: (System 1, Method F) Rt=0.66 min, m/z 371.2 $(M+H)^+$ $(ES^+)$.

Intermediate 138: 2-fluoro-4-((pyrrolidin-1-ylsulfonyl)carbamoyl)-3-(trifluoromethoxy)benzoic acid

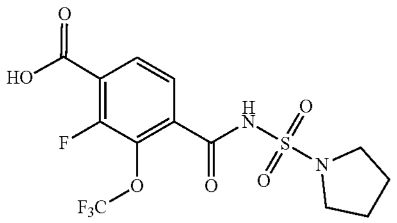 [SMILES: O=C(O)c1ccc(C(=O)NS(=O)(=O)N2CCCC2)c(OC(F)(F)F)c1F]

Prepared by an analogous method to Intermediate 13 (Step 3 only) starting from 4-bromo-2-fluoro-3-(trifluoromethoxy)benzoic acid (577 mg, 1.91 mmol). Yield: 160 mg, 0.40 mmol. Pale-yellow solid. LCMS: (System 1, Method I) Rt=0.95 min, m/z 399.0 $(M+H)^+$ $(ES^+)$.

Intermediate 139: (R)-2-(ethoxymethyl)-1-methylpiperazine

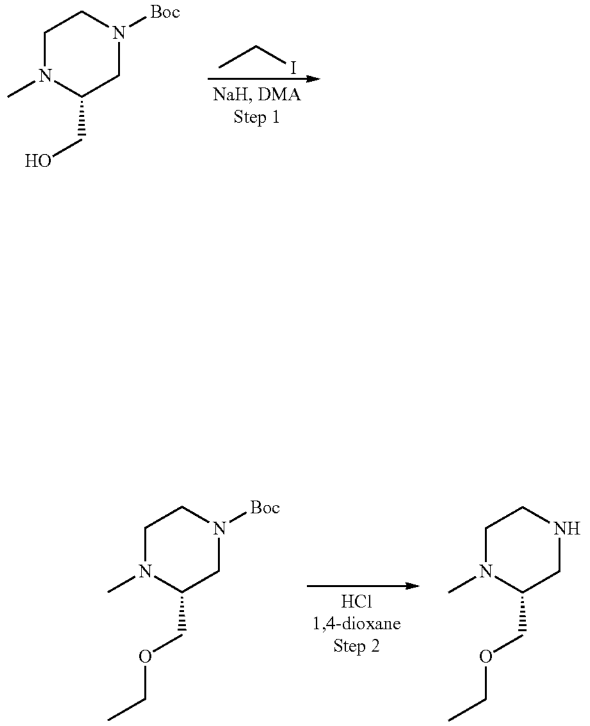

Step 1

Sodium hydride (60% dispersion in mineral oil, 208 mg, 5.21 mmol) was added in small portions to a solution of (R)-tert-butyl 3-(hydroxymethyl)-4-methylpiperazine-1-carboxylate (1.0 g, 4.34 mmol) in DMA (20 mL) at 0° C. and the mixture was stirred at this temperature for 30 min. Iodoethane (677 mg, 4.34 mmol) was added and the reaction was stirred at RT overnight. The mixture was partitioned between ice-water (60 mL) and EtOAc (3×60 mL). The combined organic layers were washed with brine, dried ($Na_2SO_4$), filtered and concentrated under reduced pressure. The crude product was purified by column chromatography on silica gel (1-20% EtOAc/petroleum ether) to afford (R)-tert-butyl 3-(ethoxymethyl)-4-methylpiperazine-1-carboxylate (500 mg, 1.94 mmol) as a colorless oil. LCMS: (System 1, Method F) Rt=1.50 min, m/z 259.2 $(M+H)^+$ $(ES^+)$.

Step 2

HCl 4N in 1,4-dioxane (5 mL, 20 mmol) was added to a solution of (R)-tert-butyl 3-(ethoxymethyl)-4-methylpiperazine-1-carboxylate (500 mg, 1.94 mmol) in 1,4-dioxane (5 mL) and the reaction was stirred at RT overnight. The mixture was concentrated under reduced pressure to afford (R)-2-(ethoxymethyl)-1-methylpiperazine which was used without further purification. LCMS: (System 1, Method H) Rt=0.73 min, m/z 159.3 $(M+H)^+$ $(ES^+)$.

Intermediate 140: (R)-8-(3-(ethoxymethyl)-4-methylpiperazin-1-yl)-7-methyl-1,2,3,4-tetrahydro-5H-chromeno[3,4-c]pyridin-5-one

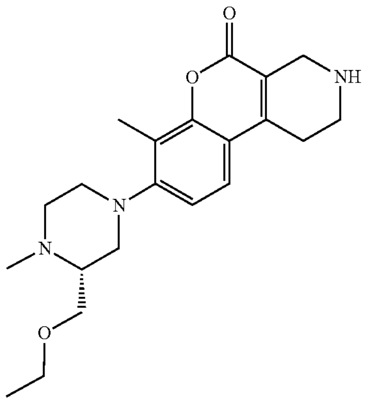 [SMILES: CCOC[C@H]1CN(c2ccc3c4c(c(=O)oc3c2C)CNCC4)CCN1C]

Prepared by an analogous method to Intermediate 5 starting from (R)-2-(ethoxymethyl)-1-methylpiperazine (Intermediate 139) and tert-butyl 7-methyl-5-oxo-8-(((trifluoromethyl)sulfonyl)oxy)-1,5-dihydro-2H-chromeno[3,4-c]pyridine-3(4H)-carboxylate (Intermediate 2, 897 mg, 1.94 mmol). Yield: 235 mg, 0.63 mmol. Brown solid. LCMS: (System 1, Method A) Rt=1.70 min, m/z 372.2 $(M+H)^+$ $(ES^+)$.

Intermediate 141: 3-(difluoromethoxy)-2-fluoro-4-((pyrrolidin-1-ylsulfonyl)carbamoyl)benzoic acid

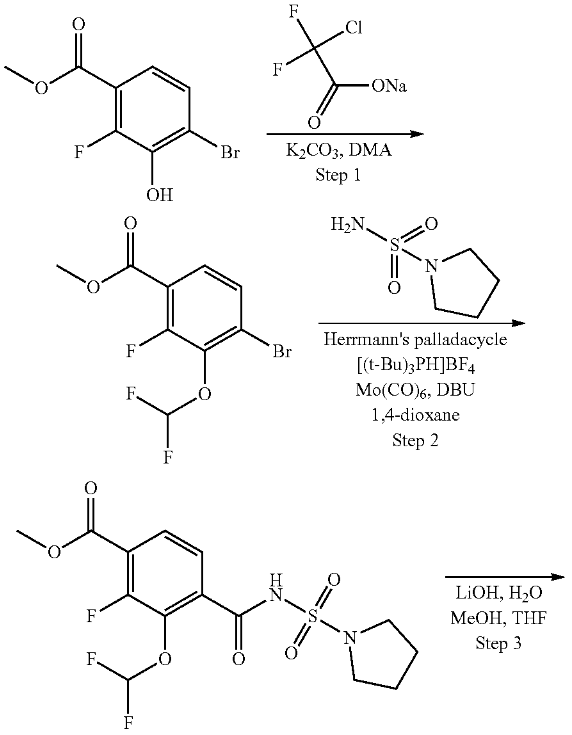

-continued

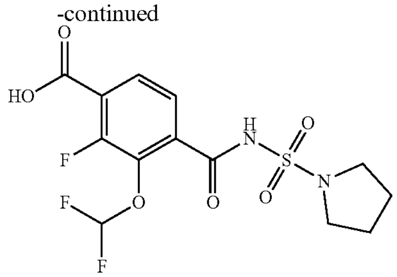

Step 1

A mixture of methyl 4-bromo-2-fluoro-3-hydroxybenzoate (1.0 g, 4.03 mmol), $K_2CO_3$ (1.7 g, 12.1 mmol) and sodium 2-chloro-2,2-difluoroacetate (1.8 g, 12.1 mmol) in DMA (20 mL) was stirred at 100° C. overnight. The reaction was cooled down to RT and partitioned between water (30 mL) and EtOAc (3×30 mL). The combined organic layers were washed with brine, dried ($Na_2SO_4$), filtered and concentrated under reduce pressure. The crude product was purified by column chromatography on silica gel (1% MeOH/DCM) to afford methyl 4-bromo-3-(difluoromethoxy)-2-fluorobenzoate (880 mg, 2.95 mmol) as a white solid. $^1H$ NMR (400 MHz, $CDCl_3$) δ: 7.73 (dd, J=8.8, 7.2 Hz, 1H), 7.48 (dd, J=8.4, 2.0 Hz, 1H), 6.62 (t, J=73.6 Hz, 1H), 3.93 (s, 3H).

Step 2

A mixture of methyl 4-bromo-3-(difluoromethoxy)-2-fluorobenzoate (880 mg, 2.95 mmol), [(t-tri-tert-butylphosphonium tetrafluoroborate (170 mg, 0.59 mmol), trans-bis(acetato)bis[o-(di-o-tolylphosphino)benzyl]dipalladium(II) (Herrmann's palladacycle, 277 mg, 0.30 mmol), molybdenum hexacarbonyl (1.2 g, 4.43 mmol), DBU (1.3 g, 8.85 mmol) and pyrrolidine-1-sulfonamide (1.3 g, 8.85 mmol) in dioxane (25 mL) was stirred at 100° C. for 16 h under nitrogen atmosphere. The reaction mixture was cooled to RT, DCM/water (5:1, 120 mL) was added and the mixture was filtered over celite. The filtrate was concentrated under reduced pressure. The crude product was purified by column chromatography on silica gel (0-5% MeOH/DCM) to afford methyl 3-(difluoromethoxy)-2-fluoro-4-((pyrrolidin-1-ylsulfonyl)carbamoyl)benzoate (250 mg, 0.63 mmol) as a pale-yellow solid. LCMS: (System 2, Method A) Rt=1.38 min, m/z 397.3 $(M+H)^+$ $(ES^+)$.

Step 3

A mixture of methyl 3-(difluoromethoxy)-2-fluoro-4-((pyrrolidin-1-ylsulfonyl)carbamoyl)benzoate (250 mg, 0.63 mmol) and $LiOH \cdot H_2O$ (159 mg, 3.78 mmol) in MeOH (8 mL), water (2 mL) and THE (2 mL) was stirred at RT overnight. Organic solvents were removed under reduced pressure and the pH of the mixture was adjusted to ca. 5 with HCl aq. 1N. This aqueous layer was extracted with EtOAc (3×15 mL) and the combined organic layers were dried ($Na_2SO_4$), filtered and concentrated under reduced pressure to afford 3-(difluoromethoxy)-2-fluoro-4-((pyrrolidin-1-ylsulfonyl)carbamoyl)benzoic acid (190 mg, 0.50 mmol) as a white solid which was used in the next step without further purification. LCMS: (System 1, Method A) Rt=0.67 min, m/z 381.2 $(M-H)^-$ $(ES^-)$.

Intermediate 142: (R)-1-ethyl-2-(methoxymethyl)piperazine

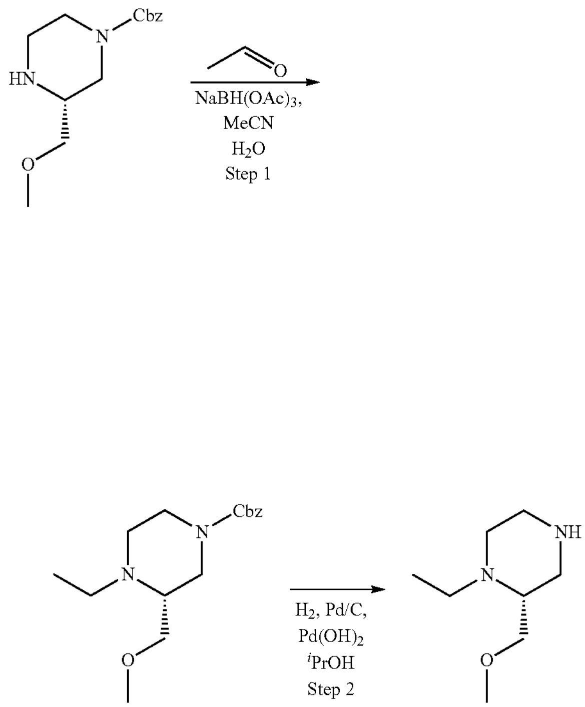

Step 1

Acetaldehyde (600 mg, 13.6 mmol) was added to a solution of (R)-benzyl 3-(methoxymethyl)piperazine-1-carboxylate (Step 3 Intermediate 1, 1.2 g, 4.55 mmol) in ACN/water (20 mL/5 mL) and the mixture was stirred at RT for 2 h. Sodium triacetoxyborohydride (1.9 g, 9.1 mmol) was added at 0° C., and the reaction was stirred at RT overnight. The pH of the mixture was adjusted to ca.8 with $NaHCO_3$ aq. sat. and the organic solvents were removed under reduced pressure. The resulting aqueous phase was extracted with DCM (3×20 mL) and the combined organic layers were washed with brine, dried ($Na_2SO_4$), filtered and concentrated under reduced pressure. The crude product was purified by column chromatography on silica gel (1-5% MeOH/DCM) to afford (R)-benzyl 4-ethyl-3-(methoxymethyl)piperazine-1-carboxylate (460 mg, 1.58 mmol) as a yellow oil. LCMS: (System 1, Method F) Rt=1.55 min, m/z 293.2 $(M+H)^+$ $(ES^+)$.

Step 2

A mixture of (R)-benzyl 4-ethyl-3-(methoxymethyl)piperazine-1-carboxylate (460 mg, 1.58 mmol), Pd/C (20%, 92 mg), $Pd(OH)_2$ (20%, 92 mg) in isopropanol (10 mL) was stirred at RT for 2 days under $H_2$ atmosphere. The mixture was filtered and the filtrate was concentrated under reduced pressure to afford (R)-1-ethyl-2-(methoxymethyl)piperazine (210 mg, 1.33 mmol) as a yellow oil. LCMS: (System 1, Method A) Rt=0.86 min, m/z 159.4 $(M+H)^+$ $(ES^+)$.

Intermediate 143: (R)-8-(4-ethyl-3-(methoxymethyl)piperazin-1-yl)-7-methyl-1,2,3,4-tetrahydro-5H-chromeno[3,4-c]pyridin-5-one

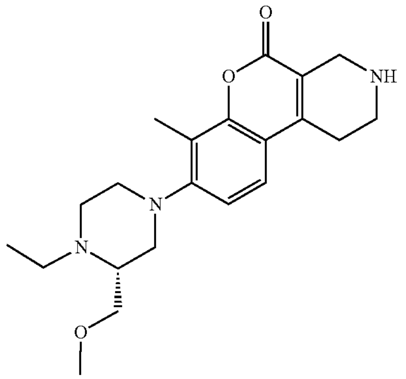 [SMILES: CCN1CCN(c2ccc3c4c(c(=O)oc3c2C)CNCC4)C[C@@H]1COC]

Prepared by an analogous method to Intermediate 5 starting from (R)-1-ethyl-2-(methoxymethyl)piperazine (Intermediate 142, 210 mg, 1.33 mmol) and 7-methyl-5-oxo-8-(((trifluoromethyl)sulfonyl)oxy)-1,5-dihydro-2H-chromeno[3,4-c]pyridine-3(4H)-carboxylate (Intermediate 2, 410 mg, 0.89 mmol). Yield: 160 mg, 0.43 mmol. Yellow solid. LCMS: (System 1, Method A) Rt=1.60 min, m/z 372.4 $(M+H)^+$ $(ES^+)$.

Intermediate 144: (R)-1-isopropyl-2-(methoxymethyl)piperazine

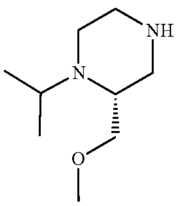

Prepared by an analogous method to Intermediate 142 starting from (R)-benzyl 3-(methoxymethyl)piperazine-1-carboxylate (Step 3 Intermediate 1, 1.2 g, 4.55 mmol) and acetone (791 mg, 13.6 mmol). Yield: 460 mg, 2.67 mmol. Yellow oil. LCMS: (System 1, Method F) Rt=0.76 min, m/z 173.3 $(M+H)^+$ $(ES^+)$.

Intermediate 145: (R)-8-(4-isopropyl-3-(methoxymethyl)piperazin-1-yl)-7-methyl-1,2,3,4-tetrahydro-5H-chromeno[3,4-c]pyridin-5-one

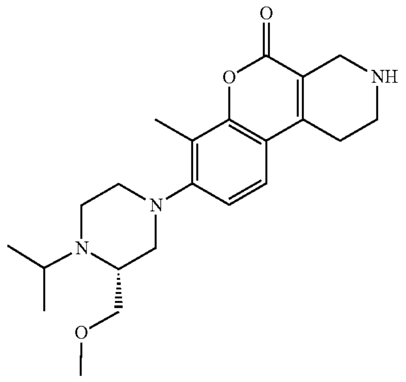 [SMILES: COC[C@H]1CN(c2ccc3c4c(c(=O)oc3c2C)CNCC4)CCN1C(C)C]

Prepared by an analogous method to Intermediate 5 starting from (R)-1-isopropyl-2-(methoxymethyl)piperazine (Intermediate 144, 460 mg, 2.67 mmol) and 7-methyl-5-oxo-8-(((trifluoromethyl)sulfonyl)oxy)-1,5-dihydro-2H-chromeno[3,4-c]pyridine-3(4H)-carboxylate (Intermediate 2, 820 mg, 1.78 mmol). Yield: 380 mg, 0.99 mmol. Yellow solid. LCMS: (System 1, Method A) Rt=1.72 min, m/z 386.4 $(M+H)^+$ $(ES^+)$.

Intermediate 146: (R)-1-cyclopropyl-2-(methoxymethyl)piperazine

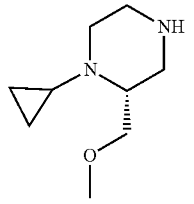

Prepared by an analogous method to Intermediate 142 starting from (R)-benzyl 3-(methoxymethyl)piperazine-1-carboxylate (Step 3 Intermediate 1, 1.2 g, 4.55 mmol) and (1-ethoxycyclopropoxy)trimethylsilane (2.4 g, 13.6 mmol) except in Step 1 sodium cyanoborohydride was used instead of sodium triacetoxyborohydride and the reaction was stirred for 2 h at 70° C. instead of overnight at RT. Yield: 500 mg, 2.94 mmol. Yellow oil. LCMS: (System 1, Method A) Rt 20=1.27 min, m/z 171.4 $(M+H)^+$ $(ES^+)$.

Intermediate 147: (R)-8-(4-cyclopropyl-3-(methoxymethyl)piperazin-1-yl)-7-methyl-1,2,3,4-tetrahydro-5H-chromeno[3,4-c]pyridin-5-one

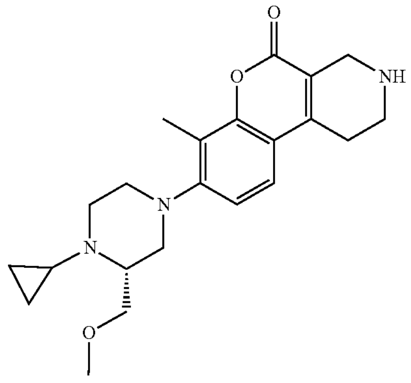 [SMILES: COC[C@H]1CN(c2ccc3c4c(c(=O)oc3c2C)CNCC4)CCN1C1CC1]

Prepared by an analogous method to Intermediate 5 starting from (R)-1-cyclopropyl-2-(methoxymethyl)piperazine (Intermediate 146, 500 mg, 2.94 mmol) and 7-methyl-5-oxo-8-(((trifluoromethyl)sulfonyl)oxy)-1,5-dihydro-2H-chromeno[3,4-c]pyridine-3(4H)-carboxylate (Intermediate 2, 903 mg, 1.96 mmol). Yield: 350 mg, 0.91 mmol. Yellow solid. LCMS: (System 1, Method A) Rt=1.74 min, m/z 384.2 $(M+H)^+$ $(ES^+)$.

Intermediate 148: 7-azabicyclo[2.2.1]heptane-7-sulfonamide

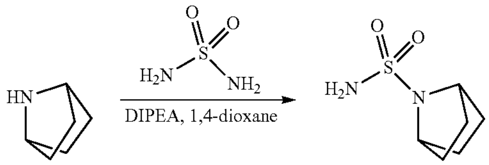 [SMILES: C1CC2CCC1N2 ; NS(N)(=O)=O ; NS(=O)(=O)N1C2CCC1CC2]

A mixture of 7-azabicyclo[2.2.1]heptane hydrochloride (6.0 g, 62.0 mmol), sulfuric diamide (8.9 g, 93 mmol) and TEA (19.1 g, 189 mmol) in DME (50 mL) was stirred at 100° C. overnight. The reaction mixture was partitioned between water (50 mL) and DCM (3×50 mL). The combined organic layers were dried ($Na_2SO_4$), filtered and concentrated under reduced pressure. The crude product was purified by column chromatography on silica gel (40-60% EtOAc/petroleum ether) to afford 7-azabicyclo[2.2.1]heptane-7-sulfonamide (1.2 g, 6.82 mmol) as a light-yellow oil. $^1H$ NMR (400 MHz, DMSO-$d_6$) δ: 6.86 (s, 2H), 4.00-3.97 (m, 2H), 1.85-1.83 (m, 4H), 1.38-1.35 (m, 4H).

Intermediate 149: 3-cyclobutoxy-4-(ethoxycarbonyl)-2-fluorobenzoic acid

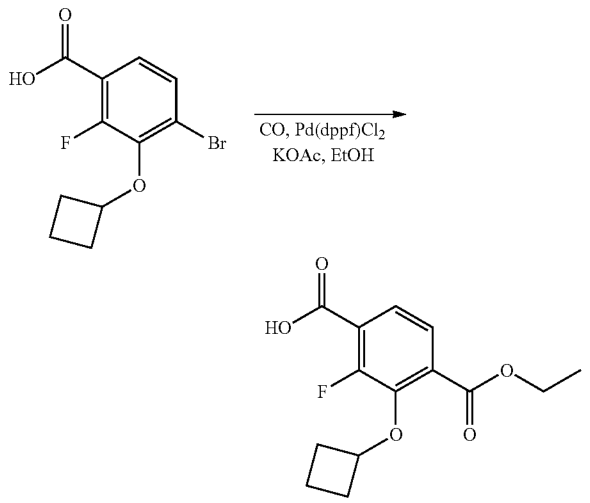

A mixture of 4-bromo-3-cyclobutoxy-2-fluorobenzoic acid (Step 2 Intermediate 13, 1.0 g, 3.48 mmol), [1,1'-bis (diphenylphosphino)ferrocene]dichloropalladium(II) (509 mg, 0.70 mmol) and potassium acetate (1.02 g, 10.5 mmol) in EtOH (20 mL) was stirred at 90° C. overnight under CO atmosphere. The reaction mixture diluted with $Na_2CO_3$ aq. sat. (20 mL) and washed with EtOAc (3×20 mL). Then, the pH of the resulting aqueous layer was adjusted to ca. 3 with HCl aq. 1N and the aqueous layer extracted with EtOAc (3×20 mL). The combined organic layers were washed with brine, dried ($Na_2SO_4$), filtered and concentrated under reduced pressure to afford 3-cyclobutoxy-4-(ethoxycarbonyl)-2-fluorobenzoic acid (720 mg, 2.55 mmol) as yellow oil which was used in the next step without further purification. LCMS: (System 1, Method F) Rt=1.11 min, m/z 283.0 $(M+H)^+$ $(ES^+)$.

Intermediate 150: 3-chloro-4-(ethoxycarbonyl)-2-fluorobenzoic acid

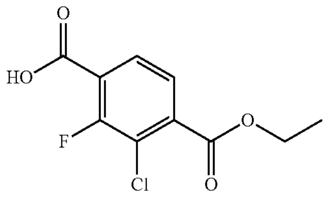 [SMILES: CCOC(=O)c1ccc(C(=O)O)c(F)c1Cl]

Prepared by an analogous method to Intermediate 149 starting from 4-bromo-3-chloro-2-fluorobenzoic acid (1.0 g, 3.95 mmol). Yield: 820 mg, 3.32 mmol. Pale-yellow solid. LCMS: (System 1, Method A) Rt=1.26 min, m/z 245.0 $(M+H)^+$ $(ES^+)$.

Intermediate 151: 4-bromo-3-cyclobutoxy-2-methylbenzoic acid

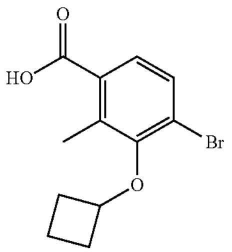 [SMILES: Cc1c(C(=O)O)ccc(Br)c1OC1CCC1]

Prepared by an analogous method to Intermediate 40 (Steps 1 to 2 only) starting from methyl 4-bromo-3-methoxy-2-methylbenzoate (500 g, 2.04 mmol) and cyclobutanol (184 mg, 2.45 mmol). Yield: 494 mg, 3.32 mmol. White solid. LCMS: (System 3, Method I) Rt=1.32 min, m/z 283.0 $(M-H)^-$ $(ES^-)$.

Intermediate 152: 4-(((7-azabicyclo[2.2.1]heptan-7-yl)sulfonyl)carbamoyl)-2-fluoro-3-methoxybenzoic acid

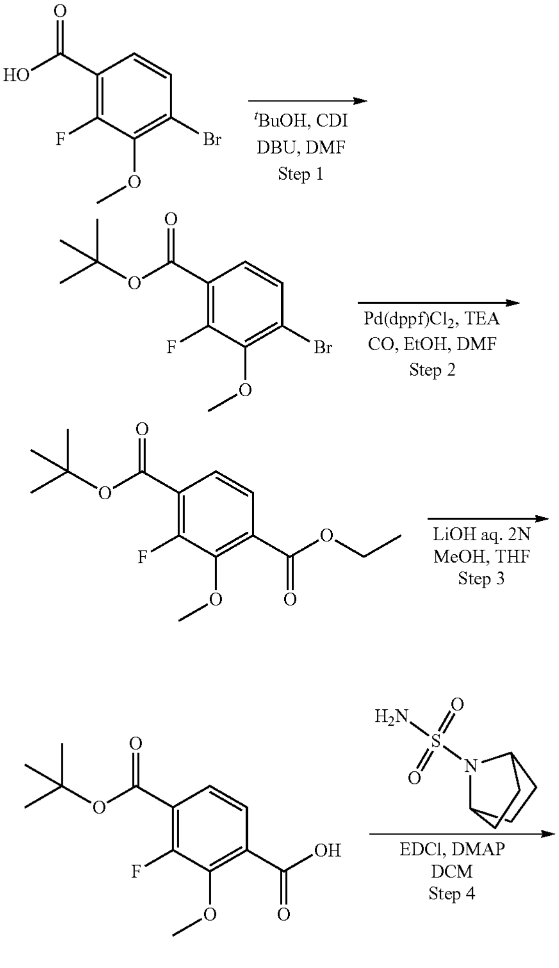

-continued

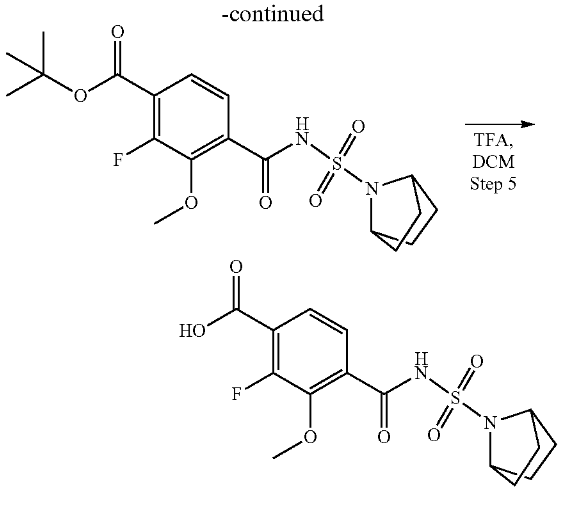

Step 1

A mixture of 4-bromo-2-fluoro-3-methoxybenzoic acid (2.7 g, 10.6 mmol) and CDI (2.6 g, 16.0 mmol) in DMF (15 mL) was stirred for 1 h at 40° C. Then tert-butanol (2.0 mL, 21.3 mmol) and DBU (1.6 mL, 10.6 mmol) were added and the mixture was stirred overnight at 40° C. The organic solvents were removed under reduced pressure. The crude product was purified by column chromatography on C18-modified silica (0-100% ACN/$NH_4OH$ 10 mM aq.) to afford tert-butyl 4-bromo-2-fluoro-3-methoxy-benzoate (1.6 g, 5.08 mmol) as a pale-brown oil. LCMS: (System 3, Method I) Rt=2.10 min.

Step 2

A mixture of tert-butyl 4-bromo-2-fluoro-3-methoxy-benzoate (260 mg, 0.85 mmol), TEA (0.60 mL, 4.28 mmol) and [1,1'-bis(diphenylphosphino)ferrocene]dichloropalladium (II) (31 mg, 0.04 mmol) in EtOH (0.9 mL) and DMF (0.9 mL) was stirred at 100° C. overnight under CO atmosphere.

Organic solvents were removed under reduced pressure. The crude product was purified by column chromatography on C18-modified silica (0-100% ACN/$NH_4OH$ aq. 10 mM) to afford 1-(tert-butyl) 4-ethyl 2-fluoro-3-methoxyterephthalate (165 mg, 0.55 mmol) as a brown oil. LCMS: (System 3, Method I) Rt=1.95 min.

Step 3

LiOH aq. 2N (0.3 mL) was added to solution of 1-(tert-butyl) 4-ethyl 2-fluoro-3-methoxyterephthalate (723 mg, 2.42 mmol) THE (6.1 mL) and MeOH (6.1 mL) and the reaction was stirred at RT for 2 h. Then the solvents were removed, and the crude product was purified by column chromatography on C18-modified silica (0-100% ACN/0.1% FA in water) to afford 4-tert-butoxycarbonyl-3-fluoro-2-methoxy-benzoic acid (116 mg, 0.43 mmol) as a yellow solid. LCMS: (System 3, Method I) Rt=1.24 min, m/z 269.0 $(M-H)^-$ $(ES^-)$.

Step 4

A mixture of 4-tert-butoxycarbonyl-3-fluoro-2-methoxy-benzoic acid (30 mg, 0.11 mmol), 7-azabicyclo[2.2.1]heptane-7-sulfonamide (Intermediate 148, 23 mg, 0.133 mmol), EDCI (43 mg, 0.22 mmol), DMAP (27 mg, 0.22 mmol) in DCM (1.1 mL) was stirred at RT overnight. The organic solvent was removed under reduced pressure and the crude product was purified by column chromatography on C18-modified silica (0-100% ACN, 0.1% FA in water) to afford tert-butyl 4-(((7-azabicyclo[2.2.1]heptan-7-yl)sulfonyl)carbamoyl)-2-fluoro-3-methoxybenzoate (22 mg, 0.05 mmol) as a yellow solid. LCMS: (System 3, Method J) Rt=1.96, m/z 427.4 $(M-H)^-$ $(ES^-)$.

Step 5

A mixture of tert-butyl 4-(((7-azabicyclo[2.2.1]heptan-7-yl)sulfonyl)carbamoyl)-2-fluoro-3-methoxybenzoate and TFA (0.50 mL, 6.53 mmol) in DCM (1.0 mL) was stirred at RT for 1 h. The organic solvents were removed under reduced pressure and the crude product was purified by column chromatography on C18-modified silica (0-100% ACN/0.1% FA in water) to afford 4-(7-azabicyclo[2.2.1]heptan-7-ylsulfonylcarbamoyl)-2-fluoro-3-methoxy-benzoic acid (16 mg, 0.04 mmol) as a pale-yellow solid. LCMS (System 3, Method I) Rt=0.28 min, m/z 373.1 $(M-H)^-$ $(ES^-)$.

Intermediate 153: 4-((N,N-dimethylsulfamoyl)carbamoyl)-2-fluoro-3-methoxybenzoic acid

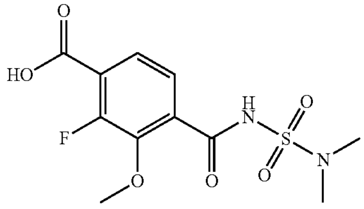 [SMILES: COc1c(C(=O)NS(=O)(=O)N(C)C)ccc(C(=O)O)c1F]

Prepared by analogous method to Intermediate 152 except the Step 4 was carried out with N,N-dimethylsulfamide in place of 7-azabicyclo[2.2.1]heptane-7-sulfonamide. Yield: 41 mg, 0.13 mmol. White solid. LCMS: (System 3, Method J) Rt=1.36 min, m/z 319.1 $(M-H)^-$ $(ES^-)$.

Intermediate 154: 2-fluoro-3-methoxy-4-((pyrrolidin-1-ylsulfonyl)carbamoyl)benzoic acid

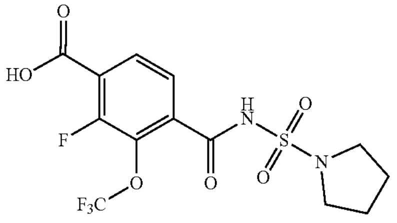 [SMILES: O=C(O)c1ccc(C(=O)NS(=O)(=O)N2CCCC2)c(OC(F)(F)F)c1F]

Prepared by analogous method to Intermediate 152 except the Step 4 was carried out with pyrrolidine-1-sulfonamide in place of 7-azabicyclo[2.2.1]heptane-7-sulfonamide. Yield: 43 mg, 0.12 mmol. White solid. LCMS: (System 3, Method J) Rt=1.47 min, m/z 345.1 $(M-H)^-$ $(ES^-)$.

Intermediate 155: 4-(((6-azaspiro[2.5]octan-6-yl)sulfonyl)carbamoyl)-2-fluoro-3-methoxybenzoic acid

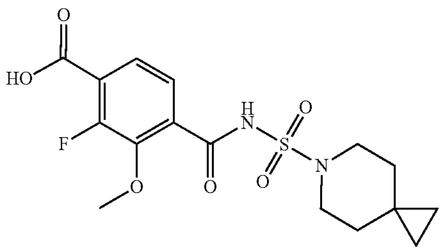 [SMILES: COc1c(C(=O)NS(=O)(=O)N2CCC3(CC2)CC3)ccc(C(=O)O)c1F]

Prepared by analogous method to Intermediate 152 except the Step 4 was carried out with 6-azaspiro[2.5]octane-6-sulfonamide in place of 7-azabicyclo[2.2.1]heptane-7-sulfonamide. Yield: 16 mg, 0.04 mmol. White solid. LCMS: (System 3, Method J) Rt=1.70 min, m/z 385.2 $(M-H)^-$ (ES Intermediate 156: 4-(((3-azabicyclo[3.1.0]hexan-3-yl)sulfonyl)carbamoyl)-2-fluoro-3-methoxybenzoic acid

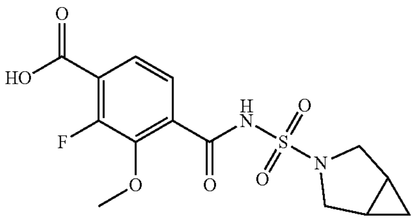 [SMILES: COc1c(C(=O)NS(=O)(=O)N2CC3CC3C2)ccc(C(=O)O)c1F]

Prepared by analogous method to Intermediate 152 except the Step 4 was carried out with 3-azabicyclo[3.1.0]hexane-3-sulfonamide in place of 7-azabicyclo[2.2.1]heptane-7-sulfonamide. Yield: 20 mg, 0.06 mmol. White solid. LCMS: (System 3, Method J) Rt=1.52 min, m/z 357.2 $(M-H)^-$ $(ES^-)$.

Intermediate 157: 4-(((3-oxa-8-azabicyclo[3.2.1]octan-8-yl)sulfonyl)carbamoyl)-2-fluoro-3-methoxybenzoic acid

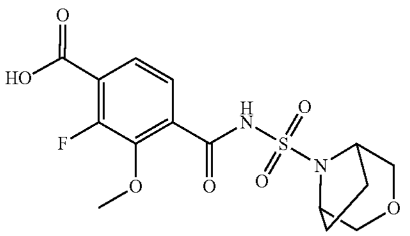 [SMILES: COc1c(C(=O)NS(=O)(=O)N2C3CCC2COC3)ccc(C(=O)O)c1F]

Prepared by analogous method to Intermediate 152 except the Step 4 was carried out with 3-oxa-8-azabicyclo[3.2.1]octane-8-sulfonamide in place of 7-azabicyclo[2.2.1]heptane-7-sulfonamide. Yield: 14 mg, 0.04 mmol. Pale-brown solid. LCMS: (System 3, Method J) Rt=1.38 min, m/z 389.1 $(M+H)^+$ $(ES^+)$.

Intermediate 158: 4-bromo-2-fluoro-3-isopropoxybenzoic acid

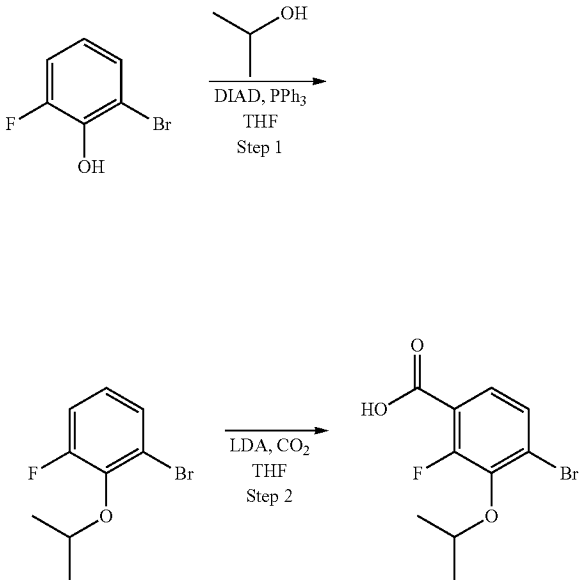

Step 1

DIAD (1.0 mL, 5.24 mmol) was added to a mixture of 2-bromo-6-fluorophenol (500 mg, 2.62 mmol), $PPh_3$ (1.4 mg, 5.24 mmol) and anhydrous isopropanol (0.30 mL, 3.93 mmol) in tetrahydrofuran (13 mL) at 0° C. and the reaction was stirred at RT overnight. The mixture was partitioned between water (20 mL) and EtOAc (3×20 mL). The combined organic layers were washed with brine, dried $(Na_2SO_4)$, filtered and concentrated under reduced pressure. The crude product was purified by column chromatography on silica gel (1-10% EtOAc/iso-hexene) to afford 1-bromo-3-fluoro-2-isopropoxy-benzene (490 mg, 2.10 mmol) as pale-yellow oil. LCMS (System 3, Method I) Rt=2.04 min.

Step 2

LDA (468 mg, 4.37 mmol) was added dropwise to a solution of 1-bromo-3-fluoro-2-isopropoxy-benzene (509 mg, 2.18 mmol) in tetrahydrofuran (21 mL) at −78° C. and the reaction was stirred at this temperature for 1 h under nitrogen atmosphere. Dry ice pellets were added at −78° C. and the resultant mixture was allowed to reach RT and stirred overnight. The reaction was quenched with $NaHCO_3$ aq. sat. (20 mL) and the resulting aqueous layer was extracted with EtOAc (3×30 mL). Then the pH of aqueous layer was adjusted to ca. 1-2 with HCl aq. 1N and the aqueous layer extracted with EtOAc (3×20 mL). The combined organic layers were washed with brine (50 mL), dried $(MgSO_4)$, filtered and concentrated under reduced pressure. The crude product was triturated with hexane, isolated by filtration and dried under reduced pressure to afford 4-bromo-2-fluoro-3-isopropoxy-benzoic acid (456 mg, 1.65 mmol) as off-white solid. LCMS (System 3, Method I) Rt=1.20 min, m/z 276.9 $(M+H)^+$ $(ES^+)$.

Intermediate 159: 4-bromo-3-ethoxy-2-fluorobenzoic acid

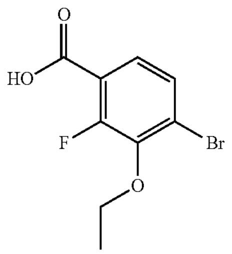

Prepared by analogous method to Intermediate 158 (only Step 2) starting from 1-bromo-2-ethoxy-3-fluorobenzene (2.7 g, 10.6 mmol). Yield: 1.6 g, 6.1 mmol. White solid. LCMS: (System 3, Method J) Rt=1.75 min, m/z 262.8 $(M+H)^+$ $(ES^+)$.

Intermediate 160: 4-((N,N-dimethylsulfamoyl)carbamoyl)-3-ethoxy-2-fluorobenzoic acid

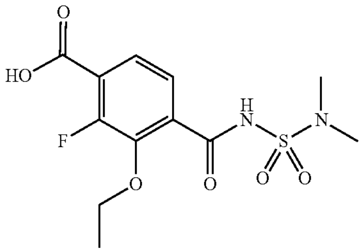 [SMILES: CCOc1c(C(=O)NS(=O)(=O)N(C)C)ccc(C(=O)O)c1F]

Prepared by analogous method to Intermediate 152 starting from 4-bromo-3-ethoxy-2-fluorobenzoic acid (Intermediate 159, 451 mg, 1.71 mmol) except the Step 4 was carried out with N,N-dimethylsulfamide in place of 7-azabicyclo[2.2.1]heptane-7-sulfonamide. Yield: 21 mg, 0.06 mmol. Yellow solid. LCMS: (System 3, Method J) Rt=1.45 min, m/z 333.1 $(M-H)^-$ $(ES^-)$.

Intermediate 161: 3-ethoxy-2-fluoro-4-((pyrrolidin-1-ylsulfonyl)carbamoyl)benzoic acid

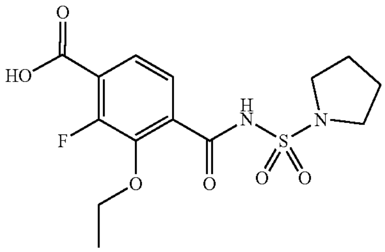 [SMILES: CCOc1c(C(=O)NS(=O)(=O)N2CCCC2)ccc(C(=O)O)c1F]

Prepared by analogous method to Intermediate 152 starting from 4-bromo-3-ethoxy-2-fluorobenzoic acid (Intermediate 159, 451 mg, 1.71 mmol) except the Step 4 was carried out with pyrrolidine-1-sulfonamide in place of 7-azabicyclo[2.2.1]heptane-7-sulfonamide. Yield: 22 mg, 0.06 mmol. Off-white solid. LCMS: (System 3, Method J) Rt=1.54 min, m/z 359.2 $(M-H)^-$ $(ES^-)$.

Intermediate 162: 4-((N,N-dimethylsulfamoyl)carbamoyl)-2-fluoro-3-isopropoxybenzoic acid

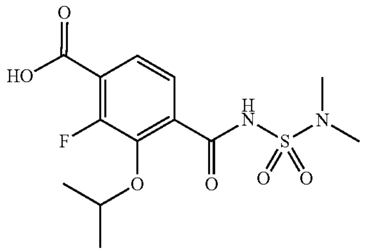 [SMILES: CC(C)Oc1c(C(=O)NS(=O)(=O)N(C)C)ccc(C(=O)O)c1F]

Prepared by analogous method to Intermediate 152 starting from 4-bromo-2-fluoro-3-isopropoxybenzoic acid (Intermediate 158, 456 mg, 1.65 mmol) except the Step 4 was carried out with N,N-dimethylsulfamide in place of 7-azabicyclo[2.2.1]heptane-7-sulfonamide. Yield: 12 mg, 0.03 mmol. White solid. LCMS: (System 3, Method J) Rt=1.52 min, m/z 347.2 $(M-H)^-$ $(ES^-)$.

Intermediate 163: 2-fluoro-3-isopropoxy-4-((pyrrolidin-1-ylsulfonyl)carbamoyl)benzoic acid

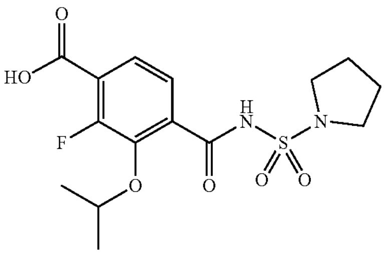 [SMILES: CC(C)Oc1c(C(=O)NS(=O)(=O)N2CCCC2)ccc(C(=O)O)c1F]

Prepared by analogous method to Intermediate 152 starting from 4-bromo-2-fluoro-3-isopropoxybenzoic acid (Intermediate 158, 456 mg, 1.65 mmol) except the Step 4 was carried out with pyrrolidine-1-sulfonamide in place of 7-azabicyclo[2.2.1]heptane-7-sulfonamide. Yield: 13 mg, 0.03 mmol. White solid. LCMS: (System 3, Method J) Rt=1.61 min, m/z 373.2 $(M-H)^-$ $(ES^-)$.

Intermediate 164: 5-(cyclopentyloxy)-4-((N,N-dimethylsulfamoyl)carbamoyl)-2-fluorobenzoic acid

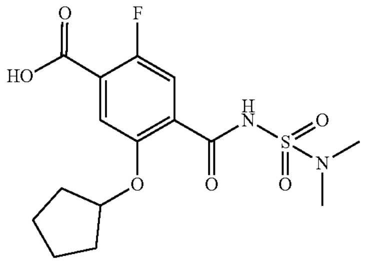 [SMILES: CN(C)S(=O)(=O)NC(=O)c1cc(F)c(C(=O)O)cc1OC1CCCC1]

Prepared by an analogous method to Intermediate 36 starting from methyl 4-bromo-5-fluoro-2-hydroxybenzoate (800 mg, 3.21 mmol) and cyclopentanol (415 mg, 4.82 mmol). Yield: 65 mg, 0.17 mmol. White solid. LCMS: (System 3, Method I) Rt=0.30 min, m/z 373.2 $(M-H)^-$ $(ES^-)$.

Intermediate 165: 5-(cyclopentyloxy)-2-fluoro-4-((pyrrolidin-1-ylsulfonyl)carbamoyl)benzoic acid

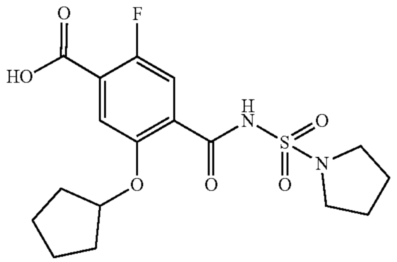 [SMILES: O=C(O)c1cc(OC2CCCC2)c(C(=O)NS(=O)(=O)N2CCCC2)cc1F]

Prepared by an analogous method to Intermediate 164 except the Step 3 was carried out with pyrrolidine-1-sulfonamide in place of N,N-dimethylsulfamide. Yield: 45 mg, 0.11 mmol. White solid. LCMS: (System 3, Method I) Rt=0.59 min, m/z 399.2 $(M-H)^-$ $(ES^-)$.

Intermediate 166: (S)-8-(3-(methoxymethyl)-4-methylpiperazin-1-yl)-7,10-dimethyl-1,2,3,4-tetrahydro-5H-chromeno[3,4-c]pyridin-5-one

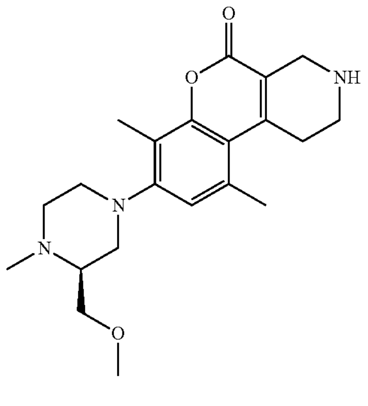 [SMILES: COC[C@@H]1CN(c2cc(C)c3c4c(c(=O)oc3c2C)CNCC4)CCN1C]

Prepared by an analogous method to Intermediate 5 starting from (S)-2-(methoxymethyl)-1-methylpiperazine (Intermediate 37, 187 mg, 1.3 mmol) and tert-butyl 7,10-dimethyl-5-oxo-8-(trifluoromethylsulfonyloxy)-4,5-dihydro-1H-chromeno[3,4-c]pyridine-3(2H)-carboxylate (Intermediate 3, 480 mg, 1.00 mmol). Yield: 200 mg, 0.54 mmol. Yellow solid. LCMS: (System 1, Method A) Rt=1.48 min, m/z 372.3 $(M+H)^+$ $(ES^+)$.

Intermediate 167: 2-fluoro-4-((pyrrolidin-1-ylsulfonyl)carbamoyl)benzoic acid

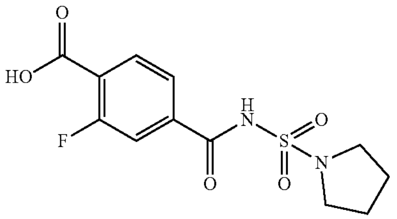 [SMILES: O=C(NS(=O)(=O)N1CCCC1)c1ccc(C(=O)O)c(F)c1]

Prepared by an analogous method to Intermediate 36 (Steps 3 to 5 only) starting from 4-bromo--3-fluorobenzoic acid (1.50 g, 6.85 mmol) except the Step 3 was carried out with pyrrolidine-1-sulfonamide in place N,N-dimethylsulfamide. Yield: 114 mg, 0.36 mmol. Off-white solid. LCMS: (System 3, Method J) Rt=1.38 min, m/z 315.2 $(M-H)^-$ $(ES^-)$ Intermediate 168: 3-azabicyclo[3.1.0]hexane-3-sulfonamide

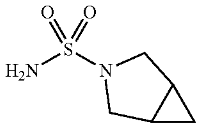

Prepared by an analogous method to Intermediate 148 starting from 3-azabicyclo[3.1.0]hexane (5.4 g, 64.6 mmol), sulfuric diamide (6.2 g, 64.6 mmol). Yield: 2.1 g, 0.91 mmol. Colourless oil. $^1H$ NMR (400 MHz, DMSO-$d_6$) δ: 6.72 (s, 2H), 3.19-3.14 (m, 4H), 1.55-1.53 (m, 2H), 0.58-0.53 (m, 1H), 0.41-0.38 (m, 1H).

Intermediate 169: 4-(((3-azabicyclo[3.1.0]hexan-3-yl)sulfonyl)carbamoyl)-5-(dimethylamino)-2-fluorobenzoic acid

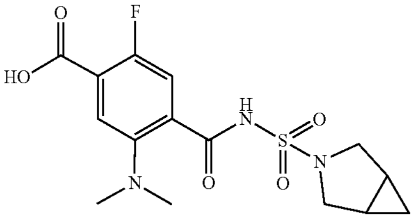 [SMILES: CN(C)c1cc(C(=O)O)c(F)cc1C(=O)NS(=O)(=O)N1CC2CC2C1]

Prepared by analogous method to Intermediate 134 specific procedure except the Step 2 was carried out with 3-azabicyclo[3.1.0]hexane-3-sulfonamide (Intermediate 168) in place of pyrrolidine-1-sulfonamide. Yield: 400 mg, 1.08 mmol. Yellow solid. LCMS: (System 1, Method F) Rt=1.02 min, m/z 372.0 $(M+H)^+$ $(ES^+)$.

Intermediate 170: 4-(((7-azabicyclo[2.2.1]heptan-7-yl)sulfonyl)carbamoyl)-5-(dimethylamino)-2-fluorobenzoic acid

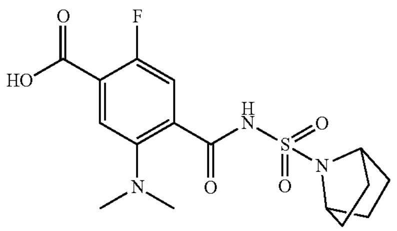 [SMILES: CN(C)c1cc(C(=O)O)c(F)cc1C(=O)NS(=O)(=O)N1C2CCC1CC2]

Prepared by analogous method to Intermediate 134 specific procedure except the Step 2 was carried out with 7-azabicyclo[2.2.1]heptane-7-sulfonamide (Intermediate 148) in place of pyrrolidine-1-sulfonamide. Yield: 130 mg, 0.34 mmol. Yellow solid. LCMS: (System 1, Method A) Rt=1.06 min, m/z 386.0 $(M+H)^+$ $(ES^+)$.

Intermediate 171: 6-azaspiro[2.5]octane-6-sulfonamide

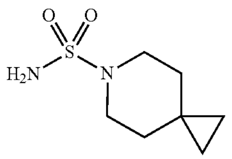 [SMILES: NS(=O)(=O)N1CCC2(CC1)CC2]

Prepared by an analogous method to Intermediate 148 starting from 6-azaspiro[2.5]octane hydrochloride (5.0 g, 45.0 mmol) and sulfuric diamide (6.5 g, 67.6 mmol). Yield: 2.5 g, 0.91 mmol. Pale-yellow oil. $^1H$ NMR (400 MHz, $CD_3OD$) δ: 6.69 (s, 2H), 3.01-2.99 (m, 4H), 1.41 (t, J=5.4 Hz, 4H), 0.31 (s, 4H).

Intermediate 172: 4-(((6-azaspiro[2.5]octan-6-yl)sulfonyl)carbamoyl)-5-(dimethylamino)-2-fluorobenzoic acid

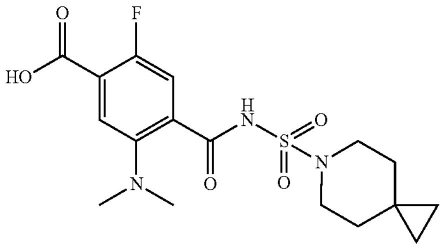 [SMILES: CN(C)c1cc(C(=O)O)c(F)cc1C(=O)NS(=O)(=O)N1CCC2(CC1)CC2]

Prepared by analogous method to Intermediate 134 specific procedure except the Step 2 was carried out with 6-azaspiro[2.5]octane-6-sulfonamide (Intermediate 171) in place of pyrrolidine-1-sulfonamide. Yield: 350 mg, 0.88 mmol. Yellow solid. LCMS: (System 1, Method A) Rt=1.23 min, m/z 400.0 $(M+H)^+$ $(ES^+)$.

Intermediate 173. 4-(((6-azaspiro[2.5]octan-6-yl)sulfonyl)carbamoyl)-2-chloro-5-(dimethylamino)benzoic acid

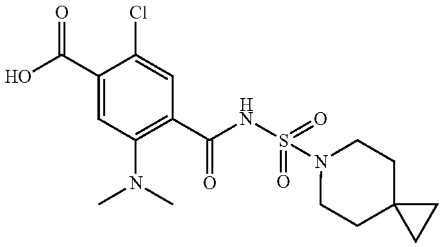 [SMILES: CN(C)c1cc(C(=O)O)c(Cl)cc1C(=O)NS(=O)(=O)N1CCC2(CC1)CC2]

Prepared by analogous method to Intermediate 111 except the Step 3 was carried out with 6-azaspiro[2.5]octane-6-sulfonamide (Intermediate 171) in place of pyrrolidine-1-sulfonamide. Yield: 380 mg, 0.91 mmol. Yellow solid. LCMS: (System 1, Method B) Rt=1.01 min, m/z 414.0 $(M-H)^-$ $(ES^-)$.

Intermediate 174: 4-(((7-azabicyclo[2.2.1]heptan-7-yl)sulfonyl)carbamoyl)-2-chloro-5-(dimethylamino)benzoic acid

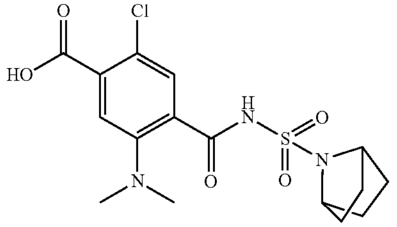 [SMILES: CN(C)c1cc(C(=O)O)c(Cl)cc1C(=O)NS(=O)(=O)N1C2CCC1CC2]

Prepared by an analogous method to Intermediate 111 except the Step 3 was carried out with 7-azabicyclo[2.2.1]heptane-7-sulfonamide (Intermediate 148) in place of pyrrolidine-1-sulfonamide. Yield: 340 mg, 0.85 mmol. Yellow solid. LCMS: (System 1, Method A) Rt=1.02 min, m/z 402.0 $(M+H)^+$ $(ES^+)$.

Intermediate 175: 5-amino-2-fluoro-4-((pyrrolidin-1-ylsulfonyl)carbamoyl)benzoic acid

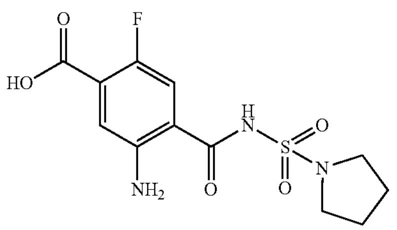 [SMILES: Nc1cc(C(=O)O)c(F)cc1C(=O)NS(=O)(=O)N1CCCC1]

Prepared by analogous method to Intermediate 46 (Steps 3 to 5) from 2-amino-4-bromo-5-fluorobenzoic acid (1.0 g, 4.29 mmol) except the Step 3 was carried out with pyrrolidine-1-sulfonamide in place of 1-methylcyclopropane-1-sulfonamide. Yield: 440 mg, 1.32 mmol. Yellow solid. LCMS: (System 1, Method B) Rt=0.24 min, m/z 330.0 $(M-H)^-$ $(ES^-)$.

Intermediate 176: 2-fluoro-5-(methylamino)-4-((pyrrolidin-1-ylsulfonyl)carbamoyl)benzoic acid

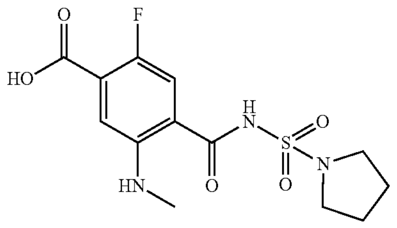 [SMILES: CNc1cc(C(=O)O)c(F)cc1C(=O)NS(=O)(=O)N1CCCC1]

Prepared by analogous method to Intermediate 46 starting from methyl 4-bromo-2,5-difluorobenzoate (2.1 g, 8.4 mmol) and methylamine hydrochloride (1.7 g, 25.2 mmol) except the Step 3 was carried out with pyrrolidine-1-sulfonamide in place of 1-methylcyclopropane-1-sulfonamide. Yield: 200 mg, 0.58 mmol. Yellow solid. LCMS: (System 1, Method A) Rt=0.35 min, m/z 346.3 $(M+H)^+$ $(ES^+)$.

Intermediate 177: 5-(azetidin-1-yl)-2-fluoro-4-((pyrrolidin-1-ylsulfonyl)carbamoyl)benzoic acid

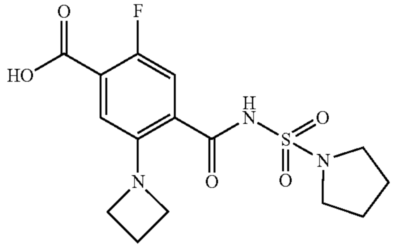 [SMILES: O=C(O)c1cc(N2CCC2)c(C(=O)NS(=O)(=O)N2CCCC2)cc1F]

Prepared by analogous method to Intermediate 46 starting from methyl 4-bromo-2,5-difluorobenzoate (2.1 g, 8.4 mmol) and azetidine (1.4 g, 25.0 mmol) except the Step 3 was carried out with pyrrolidine-1-sulfonamide in place of 1-methylcyclopropane-1-sulfonamide. Yield: 200 mg, 0.58 mmol. Yellow solid. LCMS: (System 1, Method A) Rt=0.35 min, m/z 346.3 $(M+H)^+$ $(ES^+)$.

Intermediate 178: 4-(((3-azabicyclo[3.1.0]hexan-3-yl)sulfonyl)carbamoyl)-5-(azetidin-1-yl)-2-fluorobenzoic acid

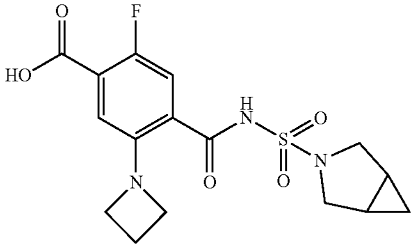 [SMILES: O=C(O)c1cc(N2CCC2)c(C(=O)NS(=O)(=O)N2CC3CC3C2)cc1F]

Prepared by analogous method to Intermediate 177 except the Step 3 was carried out with 3-azabicyclo[3.1.0]hexane-3-sulfonamide (Intermediate 168) in place of 1-methylcyclopropane-1-sulfonamide. Yield: 200 mg, 0.58 mmol. Yellow solid. LCMS: (System 1, Method A) Rt=0.35 min, m/z 346.3 $(M+H)^+$ $(ES^+)$.

Intermediate 179: 3-(cyclobutyl(methyl)amino)-2-fluoro-4-(((1-methylcyclopropyl)sulfonyl)carbamoyl)benzoic acid

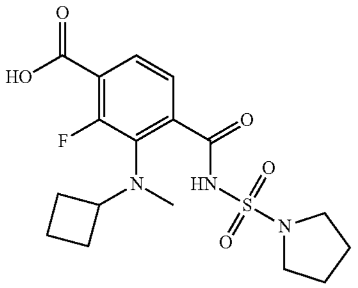 [SMILES: CN(c1c(C(=O)NS(=O)(=O)N2CCCC2)ccc(C(=O)O)c1F)C1CCC1]

Prepared by analogous method to Intermediate 83 except the Step 5 was carried out with pyrrolidine-1-sulfonamide in place of N,N-dimethylsulfamide. Yield: 450 mg, 1.17 mmol. White solid. LCMS: (System 1, Method F) Rt=1.10 min, m/z 383.3 $(M-H)^-$ $(ES^-)$.

Intermediate 180: N,N-dicyclopropylsulfamide

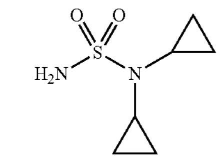 [SMILES: NS(=O)(=O)N(C1CC1)C1CC1]

Prepared by an analogous method to Intermediate 148 starting from dicyclopropylamine hydrochloride (1.0 g, 7.48 mmol), sulfuric diamide (863 mg, 8.98 mmol). Yield: 986 mg, 5.59 mmol. Off-white solid. $^1H$ NMR (400 MHz, DMSO-$d_6$) δ 6.89 (s, 2H), 2.31-2.25 (m, 2H), 0.72-0.67 (m, 4H), 0.66-0.59 (m, 4H).

Intermediate 181: 4-((N,N-dicyclopropylsulfamoyl)carbamoyl)-5-ethoxy-2-fluorobenzoic acid

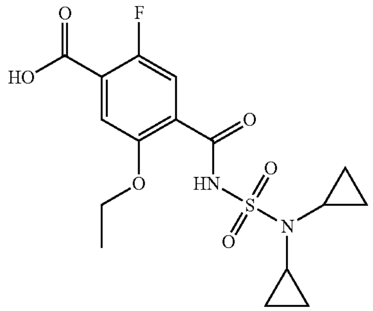

Prepared by an analogous method to Intermediate 10 starting from methyl 4-bromo-5-fluoro-2-hydroxybenzoate (3.0 g, 13.0 mmol) and iodoethane (3.5 g, 26.0 mmol) except the Step 4 was carried out with N,N-dicyclopropylsulfamide (Intermediate 180) in place of pyrrolidine-1-sulfonamide. Yield: 109 mg, 0.28 mmol. White solid. LCMS: (System 3, Method J) Rt=1.71 min, m/z 385.0 $(M-H)^-$ $(ES^-)$.

Intermediate 182: 3,3-dimethylpyrrolidine-1-sulfonamide

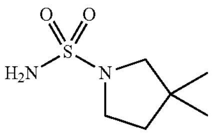

Prepared by an analogous method to Intermediate 148 starting from 3,3-dimethylpyrrolidine hydrochloride (1.0 g, 7.37 mmol), sulfuric diamide (850 mg, 8.85 mmol). Yield: 650 mg, 3.65 mmol. Brown solid. $^1H$ NMR (400 MHz, DMSO-$d_6$) δ 6.68 (s, 2H), 3.20 (t, J=7.1 Hz, 2H), 2.86 (s, 2H), 1.60 (t, J=7.1 Hz, 2H), 1.05 (s, 6H).

Intermediate 183: 4-(((3,3-dimethylpyrrolidin-1-yl) sulfonyl)carbamoyl)-5-ethoxy-2-fluorobenzoic acid

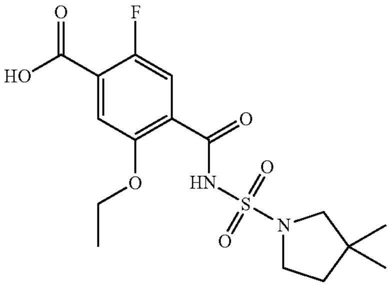 [SMILES: CCOc1cc(C(=O)O)c(F)cc1C(=O)NS(=O)(=O)N1CCC(C)(C)C1]

Prepared by an analogous method to Intermediate 181 except the Step 4 was carried out with 3,3-dimethylpyrrolidine-1-sulfonamide (Intermediate 182) in place of N,N-dicyclopropylsulfamide. Yield: 111 mg, 0.29 mmol. Off-white solid. LCMS: (System 3, Method J) Rt=1.74 min, m/z 387.0 $(M-H)^-$ $(ES^-)$.

Intermediate 184: 4-(((7-azabicyclo[2.2.1]heptan-7-yl)sulfonyl)carbamoyl)-5-ethoxy-2-fluorobenzoic acid

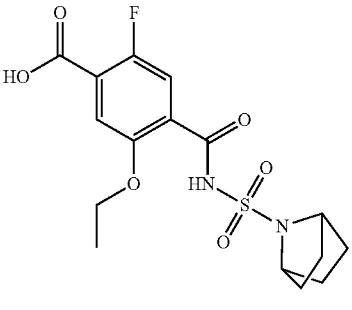 [SMILES: CCOc1cc(C(=O)O)c(F)cc1C(=O)NS(=O)(=O)N1C2CCC1CC2]

Prepared by an analogous method to Intermediate 181 except the Step 4 was carried out with 7-azabicyclo[2.2.1] heptane-7-sulfonamide (Intermediate 148) in place of N,N-dicyclopropylsulfamide. Yield: 52 mg, 0.14 mmol. Off-white solid. LCMS: (System 3, Method J) Rt=1.63 min, m/z 385.0 $(M-H)^-$ $(ES^-)$.

Intermediate 185: 4-(((3-azabicyclo[3.1.0]hexan-3-yl)sulfonyl)carbamoyl)-5-ethoxy-2-fluorobenzoic acid

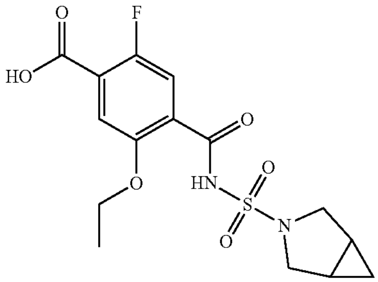 [SMILES: CCOc1cc(C(=O)O)c(F)cc1C(=O)NS(=O)(=O)N1CC2CC2C1]

Prepared by an analogous method to Intermediate 181 except the Step 4 was carried out with 3-azabicyclo[3.1.0] hexane-3-sulfonamide (Intermediate 168) in place of N,N-dicyclopropylsulfamide. Yield: 120 mg, 0.32 mmol. Off-white solid. LCMS: (System 3, Method I) Rt=0.42 min, m/z 371.2 $(M-H)^-$ $(ES^-)$.

Intermediate 186: 2-azaspiro[3.3]heptane-2-sulfonamide

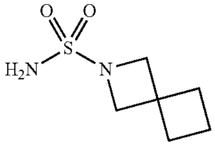 [SMILES: NS(=O)(=O)N1CC2(CCC2)C1]

Prepared by an analogous method to Intermediate 148 starting from 2-azaspiro[3.3]heptane hydrochloride (1.0 g, 7.48 mmol), sulfuric diamide (1510 mg, 15 mmol). Yield: 1000 mg, 3.65 mmol. Off-white solid. $^1H$ NMR (400 MHz, DMSO-$d_6$) δ 6.79 (s, 2H), 3.63 (s, 4H), 2.08 (t, J=7.6 Hz, 4H), 1.76-1.76 (m, 2H).

Intermediate 187: 4-(((2-azaspiro[3.3]heptan-2-yl) sulfonyl)carbamoyl)-5-ethoxy-2-fluorobenzoic acid

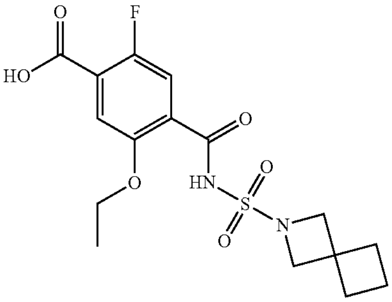 [SMILES: CCOc1cc(C(=O)O)c(F)cc1C(=O)NS(=O)(=O)N1CC2(CCC2)C1]

Prepared by an analogous method to Intermediate 181 except the Step 4 was carried out with 3-2-azaspiro[3.3]heptane-2-sulfonamide (Intermediate 186) in place of N,N-dicyclopropylsulfamide. Yield: 120 mg, 0.31 mmol. Off-white solid. LCMS: (System 3, Method J) Rt=1.72 min, m/z 385.0 $(M-H)^-$ $(ES^-)$.

Intermediate 188: 3-oxa-8-azabicyclo[3.2.1]octane-8-sulfonamide

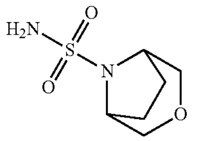

Prepared by an analogous method to Intermediate 148 starting from 3-oxa-8-azabicyclo[3.2.1]octane hydrochloride (1.5 g, 16.0 mmol), sulfuric diamide (2.0 g, 13.4 mmol). Yield: 1.6 g, 8.11 mmol. Off-white solid. $^1H$ NMR (400 MHz, DMSO-$d_6$) δ 6.85 (s, 2H), 3.90-3.85 (m, 2H), 3.54 (s, 4H), 2.06-1.99 (m, 2H), 1.80-1.75 (m, 2H).

Intermediate 189: 4-(((3-oxa-8-azabicyclo[3.2.1]octan-8-yl)sulfonyl)carbamoyl)-5-ethoxy-2-fluorobenzoic acid

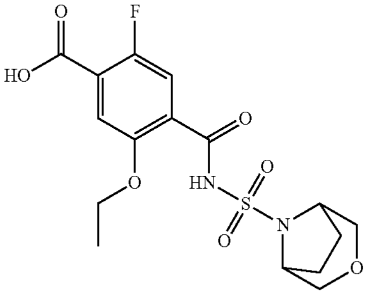 [SMILES: CCOc1cc(C(=O)O)c(F)cc1C(=O)NS(=O)(=O)N1C2CCC1COC2]

Prepared by an analogous method to Intermediate 181 except the Step 4 was carried out with 3-oxa-8-azabicyclo[3.2.1]octane-8-sulfonamide (Intermediate 188) in place of N,N-dicyclopropylsulfamide. Yield: 177 mg, 0.44 mmol. Off-white solid. LCMS: (System 3, Method I) Rt=1.51 min, m/z 401.0 $(M-H)^-$ $(ES^-)$.

Intermediate 190: 2-chloro-4-((pyrrolidin-1-ylsulfonyl)carbamoyl)benzoic acid

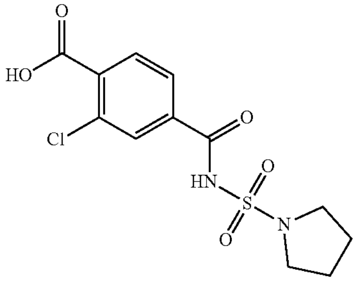 [SMILES: O=C(NS(=O)(=O)N1CCCC1)c1ccc(C(=O)O)c(Cl)c1]

Prepared by an analogous method to Intermediate 10 (Steps 4 to 5 only) starting from 3-chloro-4-(methoxycarbonyl)benzoic acid (1.50 g, 6.85 mmol). Yield: 61 mg, 0.18 mmol. Light-brown solid. LCMS: (System 3, Method J) Rt=1.41 min, m/z 331.2 $(M-H)^-$ $(ES^-)$.

Intermediate 191: 4-(((7-azabicyclo[2.2.1]heptan-7-yl)sulfonyl)carbamoyl)-2-chlorobenzoic acid

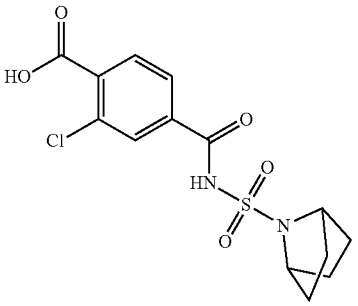 [SMILES: O=C(NS(=O)(=O)N1C2CCC1CC2)c1ccc(C(=O)O)c(Cl)c1]

Prepared by an analogous method to Intermediate 190 except the Step 4 was carried out with 7-azabicyclo[2.2.1]heptane-7-sulfonamide (Intermediate 148) in place of N,N-dimethylsulfamide. Yield: 61 mg, 0.18 mmol. Pale-brown oil. LCMS: (System 3, Method J) Rt=1.41 min, m/z 331.2 $(M-H)^-$ $(ES^-)$.

Intermediate 192: 4-((pyrrolidin-1-ylsulfonyl)carbamoyl)benzoic acid

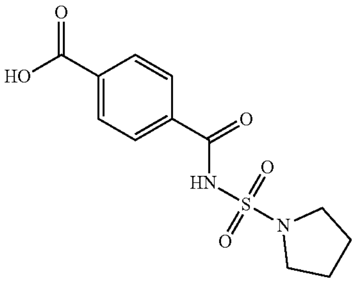 [SMILES: O=C(O)c1ccc(C(=O)NS(=O)(=O)N2CCCC2)cc1]

Prepared by an analogous method to Intermediate 10 (Steps 4 to 5 only) starting from 4-(methoxycarbonyl)benzoic acid (0.60 g, 3.33 mmol). Yield: 540 mg, 1.81 mmol. Yellow solid. LCMS: (System 1, Method B) Rt=0.24 min, m/z 297.0 $(M-H)^-$ $(ES^-)$.

Intermediate 193: (3aR,6aS)-hexahydrocyclopenta[c]pyrrole-2(1H)-sulfonamide

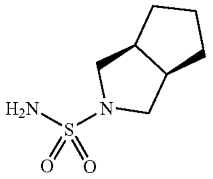 [SMILES: NS(=O)(=O)N1C[C@H]2CCC[C@H]2C1]

Prepared by an analogous method to Intermediate 148 starting from (3aR,6aS)-octahydrocyclopenta[c]pyrrole hydrochloride (1.0 g, 6.77 mmol), sulfuric diamide (781 mg, 13.5 mmol). Yield: 1.0 g, 5.36 mmol. Pale-yellow solid. $^1H$ NMR (400 MHz, DMSO-$d_6$) δ 6.78-6.68 (m, 2H), 3.19-3.11 (m, 2H), 2.73-2.70 (m, 2H), 2.68-2.59 (m, 2H), 1.54-1.81 (m, 3H), 1.28-1.54 (m, 3H).

Intermediate 194: 4-((((3aR,6aS)-hexahydrocyclopenta[c]pyrrol-2(1H)-yl)sulfonyl)carbamoyl)benzoic acid

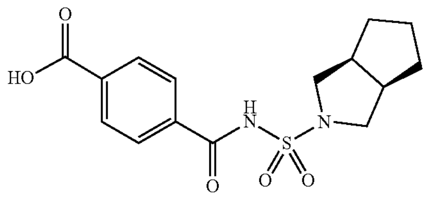 [SMILES: O=C(O)c1ccc(C(=O)NS(=O)(=O)N2C[C@H]3CCC[C@H]3C2)cc1]

Prepared by an analogous method to Intermediate 192 except the Step 4 was carried out with (3aR,6aS)-hexahydrocyclopenta[c]pyrrole-2(1H)-sulfonamide (Intermediate 193) in place of N,N-dimethylsulfamide. Yield: 268 mg, 0.79 mmol. White solid. LCMS: (System 3, Method I) Rt=0.93 min, m/z 337.1 $(M-H)^-$ $(ES^-)$.

Intermediate 195: octahydro-2H-isoindole-2-sulfonamide

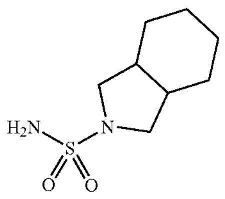 [SMILES: NS(=O)(=O)N1CC2CCCCC2C1]

Prepared by an analogous method to Intermediate 148 starting from octahydro-1H-isoindole hydrochloride (1.9 g, 15.1 mmol), sulfuric diamide (1.7 g, 18.2 mmol). Yield: 2.3 g, 11.5 mmol. Off-white solid. $^1H$ NMR (400 MHz, DMSO-$d_6$) δ 6.59 (s, 2H), 4.07-3.98 (m, 1H), 2.55 (s, 3H), 1.77-1.38 (in, 8H)

Intermediate 196: 4-(((octahydro-2H-isoindol-2-yl)sulfonyl)carbamoyl)benzoic acid

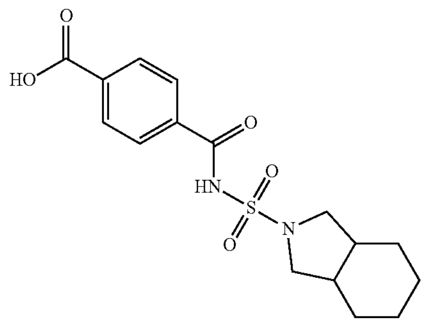 [SMILES: O=C(O)c1ccc(C(=O)NS(=O)(=O)N2CC3CCCCC3C2)cc1]

Prepared by an analogous method to Intermediate 192 except the Step 4 was carried out with octahydro-2H-isoindole-2-sulfonamide (Intermediate 195) in place of N,N-dimethylsulfamide. Yield: 215 mg, 0.61 mmol. White solid. LCMS: (System 3, Method I) Rt=0.99 min, m/z 351.1 $(M-H)^-$ $(ES^-)$.

Intermediate 197: N-cyclopentyl-N-methyl-sulfamide

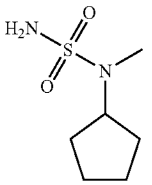

Prepared by an analogous method to Intermediate 148 starting from cyclopentylmethylamine (1.0 g, 10.1 mmol), sulfuric diamide (1.5 g, 15.1 mmol). Yield: 1.5 g, 8.2 mmol. Off-white solid. $^1H$ NMR (400 MHz, DMSO-$d_6$) δ 6.59 (s, 2H), 4.07-3.98 (m, 1H), 2.55 (s, 3H), 1.77-1.38 (m, 8H).

Intermediate 198: 4-((N-cyclopentyl-N-methylsulfamoyl)carbamoyl)-2-fluorobenzoic Acid

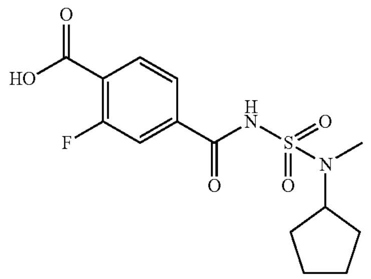 [SMILES: CN(C1CCCC1)S(=O)(=O)NC(=O)c1ccc(C(=O)O)c(F)c1]

Prepared by an analogous method to Intermediate 167 except the Step 3 was carried out with N-cyclopentyl-N-methyl-sulfamide (Intermediate 197) in place of pyrrolidine-1-sulfonamide. Yield: 61 mg, 0.18 mmol. Pale-brown oil. LCMS: (System 3, Method I) Rt=0.84 min, m/z 343.0 $(M-H)^-$ $(ES^-)$.

Intermediate 199: 4-fluoropiperidine-1-sulfonamide

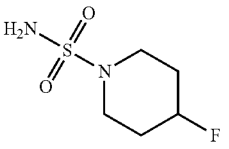 [SMILES: NS(=O)(=O)N1CCC(F)CC1]

Prepared by an analogous method to Intermediate 148 starting from 4-fluoropiperidine (1.0 g, 9.7 mmol), sulfuric diamide (1.4 g, 14.5 mmol). Yield: 1.1 g, 6.2 mmol. Off-white solid. $^1H$ NMR (400 MHz, DMSO-$d_6$) δ 6.77 (s, 2H), 4.88-4.71 (m, 1H), 3.05-3.05 (m, 4H), 1.97-1.76 (m, 4H)

Intermediate 200: 2-fluoro-4-(((4-fluoropiperidin-1-yl)sulfonyl)carbamoyl)benzoic Acid

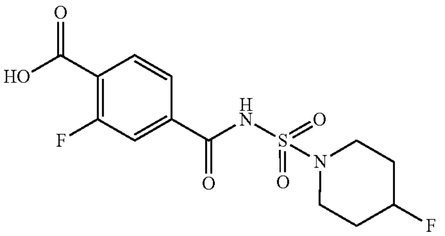 [SMILES: O=C(NS(=O)(=O)N1CCC(F)CC1)c1ccc(C(=O)O)c(F)c1]

Prepared by an analogous method to Intermediate 167 except the Step 3 was carried out with 4-fluoropiperidine-1-sulfonamide (Intermediate 199) in place of pyrrolidine-1-sulfonamide. Yield: 104 mg, 0.30 mmol. Light-brown oil. LCMS: (System 3, Method J) Rt=1.40 min, m/z 347.2 $(M-H)^-$ $(ES^-)$.

Intermediate 201: 5-ethoxy-2-fluoro-4-((pyrrolidin-1-ylsulfonyl)carbamoyl)benzoic Acid

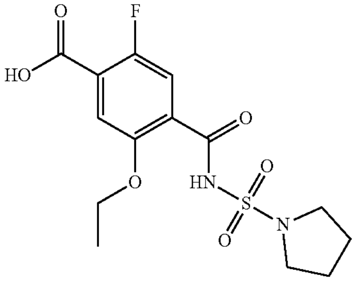 [SMILES: CCOc1cc(C(=O)O)c(F)cc1C(=O)NS(=O)(=O)N1CCCC1]

Prepared by an analogous method to Intermediate 181 except the Step 4 was carried out with pyrrolidine-1-sulfonamide in place of N,N-dicyclopropylsulfamide. Yield: 181 mg, 0.50 mmol. White solid. LCMS: (System 1, Method A) Rt=0.72 min, m/z 361.0 $(M+H)^+$ $(ES^+)$.

Intermediate 202: 3-ethoxy-2-fluoro-4-((piperidin-1-ylsulfonyl)carbamoyl)benzoic Acid

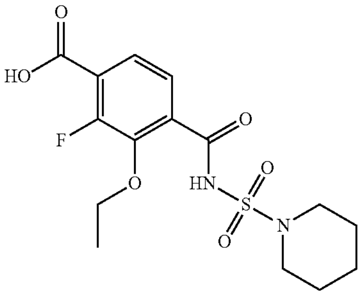 [SMILES: CCOc1c(C(=O)NS(=O)(=O)N2CCCCC2)ccc(C(=O)O)c1F]

Prepared by an analogous method to Intermediate 13 starting from of 2-bromo-6-fluorophenol (6.0 g, 31.6 mmol) and iodoethane (9.9 g, 63.2 mmol) except the Step 4 was carried out with piperidine-1-sulfonamide in place of pyrrolidine-1-sulfonamide. Yield: 600 mg, 1.60 mmol. Off-white solid. LCMS: (System 1, Method A) Rt=1.00 min, m/z 373.2 $(M-H)^-$ $(ES^-)$.

Intermediate 203: 2-fluoro-3-propoxy-4-((pyrrolidin-1-ylsulfonyl)carbamoyl)benzoic Acid

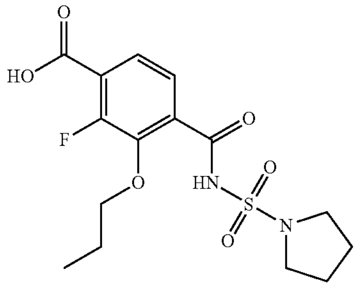 [SMILES: CCCOc1c(C(=O)NS(=O)(=O)N2CCCC2)ccc(C(=O)O)c1F]

Prepared by an analogous method to Intermediate 13 starting from of 2-bromo-6-fluorophenol (4.0 g, 21.1 mmol) and iodopropane (7.2 g, 42.1 mmol). Yield: 600 mg, 1.6 mmol. White solid. LCMS: (System 1, Method A) Rt=0.93 min, m/z 373.0 $(M-H)^-$ $(ES^-)$.

Intermediate 204: 4-(((3-azabicyclo[3.1.0]hexan-3-yl)sulfonyl)carbamoyl)-3-cyclopropoxy-2-fluorobenzoic Acid

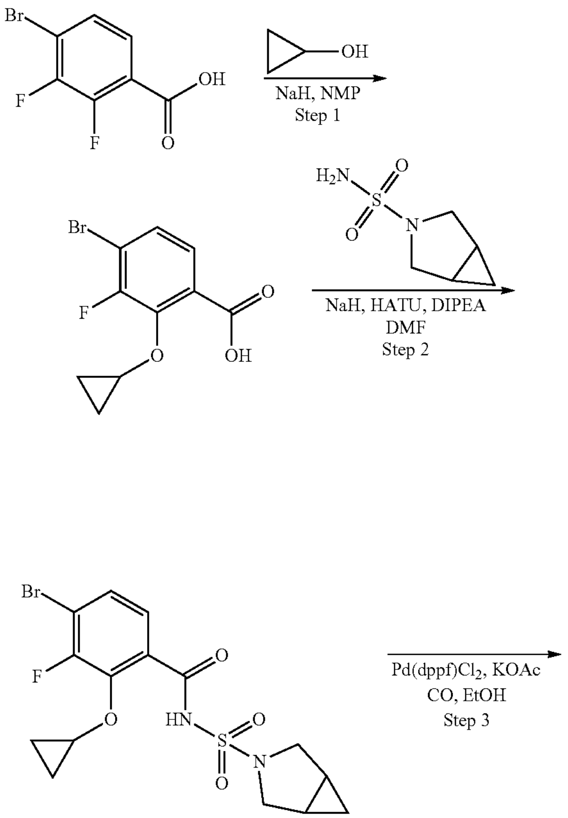

-continued

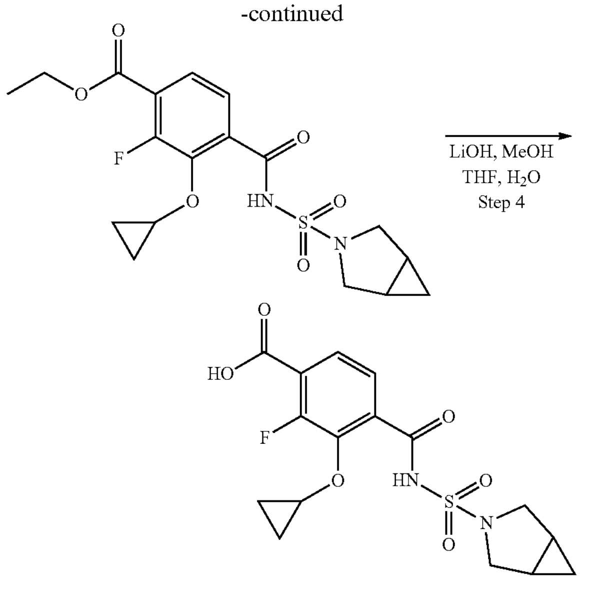

Step 1

Sodium hydride (60% dispersion in mineral oil, 3.9 g, 84.8 mmol) was added in small portions to a solution of 4-bromo-2,3-difluorobenzoic acid (5.0 g, 21.19 mmol) in NMP (150 mL) at RT. Then cyclopropanol (4.90 g, 84.75 mmol) was added and the mixture was stirred at RT overnight. The reaction was quenched with $NH_4Cl$ aq. sat. (450 mL), then the pH of the mixture was adjusted to ca. 4 by adding HCl aq. 1N. The resulting aqueous phase was extracted with EtOAc (3×200 mL). The combined organic layers were washed by brine, dried ($Na_2SO_4$), filtered and concentrated under reduced pressure to afford 4-bromo-2-cyclopropoxy-3-fluorobenzoic acid (3.6 g, 13.1 mmol) as an off-white solid. LCMS: (System 1, Method A) Rt=1.27, m/z 273 $(M-H)^-$ $(ES^-)$.

Step 2

A mixture of 4-bromo-2-cyclopropoxy-3-fluorobenzoic acid (1.5 g, 5.5 mmol), HATU (2.5 g, 6.6 mmol) and DIPEA (2.82 g, 21.90 mmol) in DMF (50 mL) was stirred for 1 h at RT, 3-azabicyclo[3.1.0]hexane-3-sulfonamide (Intermediate 168, 2.7 g, 16.4 mmol) and sodium hydride (60% dispersion in mineral oil, 876 mg, 21.9 mmol) were added and the reaction was stirred overnight at RT. The mixture was quenched with $NH_4Cl$ aq. sat. (150 mL), then the pH of the resulting aqueous layer was adjusted to ca. 4 with HCl aq. 1N. the reaction mixture was extracted with EtOAc (3×100 mL) and the combined organic layers were dried ($Na_2SO_4$), filtered and concentrated under reduced pressure. The crude product was purified by column chromatography on silica gel (1-25% EtOAc/petroleum ether) to afford N-(3-azabicyclo[3.1.0]hexan-3-ylsulfonyl)-4-bromo-2-cyclopropoxy-3-fluorobenzamide (850 mg, 2.03 mmol) as yellow oil. LCMS: (System 1, Method A) Rt=1.50 min, m/z 418.9 $(M+H)^+$ $(ES^+)$.

Step 3

To a mixture of N-(3-azabicyclo[3.1.0]hexan-3-ylsulfonyl)-4-bromo-2-cyclopropoxy-3-fluorobenzamide (836 mg, 2.00 mmol) in EtOH (20 mL) was added [1,1'-bis(diphenylphosphino)ferrocene]dichloropalladium(II) (146 mg, 0.20 mmol) and potassium acetate (588 mg, 6.00 mmol), then the mixture was stirred for 2 h at 80° C. under CO atmosphere. The reaction mixture was concentrated under reduced pressure and the crude product was purified by column chromatography on silica gel (1-50% EtOAc/petroleum ether) to afford ethyl 4-((3-azabicyclo[3.1.0]hexan-3-ylsulfonyl)carbamoyl)-3-cyclopropoxy-2-fluorobenzoate (659 mg, 1.60 mmol) as a white solid. LCMS: (System 1, Method A) Rt=1.46 min, m/z 413.0 $(M+H)^+$ $(ES^+)$.

Step 4

A mixture of ethyl 4-((3-azabicyclo[3.1.0]hexan-3-ylsulfonyl)carbamoyl)-3-cyclopropoxy-2-fluorobenzoate (412 mg, 1.00 mmol) and $LiOH \cdot H_2O$ (252 mg, 6.00 mmol) in water (3 mL) and MeOH (10 mL) was stirred for 3 h at RT. The pH of the mixture was adjusted to ca. 8 by adding HCl aq. 1N and the organic solvents were removed under reduced pressure. The pH of the resulting aqueous phase was adjusted to ca. 3 with HCl aq. 1N. The formed precipitate was collected by filtration, washed with water then hexane and dried under reduced pressure to afford 4-((3-azabicyclo[3.1.0]hexan-3-ylsulfonyl)carbamoyl)-3-cyclopropoxy-2-fluorobenzoic acid (360 mg, 0.94 mmol) as a yellow solid. LCMS: (System 1, Method A) Rt=0.91 min, 383.0 $(M-H)^-$ (ES Intermediate 205: 2-fluoro-4-((pyrrolidin-1-ylsulfonyl)carbamoyl)-3-(2,2,2-trifluoroethoxy)benzoic Acid

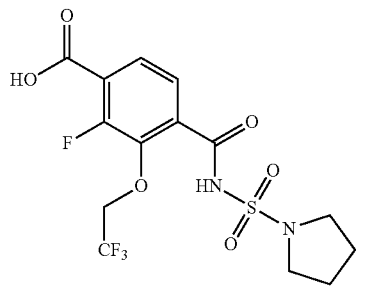 [SMILES: O=C(O)c1ccc(C(=O)NS(=O)(=O)N2CCCC2)c(OCC(F)(F)F)c1F]

Prepared by an analogous method to Intermediate 204 starting from of 4-bromo-2,3-difluorobenzoic acid (1.1 g, 4.66 mmol) and 2,2,2-trifluoroethanol (2.14 g, 46.6 mmol) except the Step 2 was carried out with pyrrolidine-1-sulfonamide in place of 3-azabicyclo[3.1.0]hexane-3-sulfonamide. Yield: 230 mg, 0.56 mmol. Off-white solid. LCMS: (System 1, Method A) Rt=0.99 min, m/z 415.0 $(M-H)^-$ $(ES^-)$.

Intermediate 206: 4-(((3-azabicyclo[3.1.0]hexan-3-yl)sulfonyl)carbamoyl)-3-ethoxy-2-fluorobenzoic acid

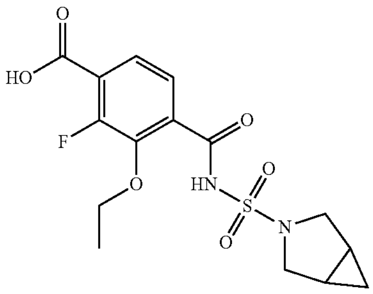 [SMILES: CCOc1c(C(=O)NS(=O)(=O)N2CC3CC3C2)ccc(C(=O)O)c1F]

Prepared by an analogous method to Intermediate 204 starting from of 4-bromo-2,3-difluorobenzoic acid (11.0 g, 46.6 mmol) and ethanol (21.4 g, 466 mmol). Yield: 1.0 g, 2.69 mmol. Yellow solid. LCMS: (System 1, Method A) Rt=0.76 min, m/z 372.0 $(M-H)^-$ $(ES^-)$.

Intermediate 207: 4-(((7-azabicyclo[2.2.1]heptan-7-yl)sulfonyl)carbamoyl)-3-ethoxy-2-fluorobenzoic Acid

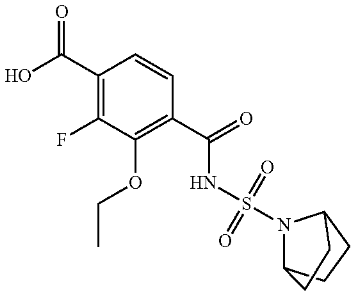 [SMILES: CCOc1c(C(=O)NS(=O)(=O)N2C3CCC2CC3)ccc(C(=O)O)c1F]

Prepared by an analogous method to Intermediate 204 starting from of 4-bromo-2,3-difluorobenzoic acid (11.0 g, 46.6 mmol) and ethanol (21.4 g, 466 mmol) except the Step 2 was carried out with 7-azabicyclo[2.2.1]heptane-7-sulfonamide (Intermediate 148) in place of 3-azabicyclo[3.1.0]hexane-3-sulfonamide. Yield: 1.1 g, 2.72 mmol. White solid. LCMS: (System 1, Method A) Rt=0.95 min, m/z 385.0 $(M-H)^-$ $(ES^-)$.

Intermediate 208: 3-cyclopropoxy-2-fluoro-4-((pyrrolidin-1-ylsulfonyl)carbamoyl)benzoic Acid

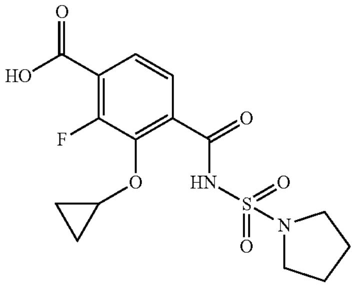 [SMILES: O=C(O)c1ccc(C(=O)NS(=O)(=O)N2CCCC2)c(OC2CC2)c1F]

Prepared by an analogous method to Intermediate 204 starting from of 4-bromo-2,3-difluorobenzoic acid (5.0 g, 21.2 mmol) and cyclopropanol (4.9 g, 84.8 mmol) except the Step 2 was carried out with pyrrolidine-1-sulfonamide in place of 3-azabicyclo[3.1.0]hexane-3-sulfonamide. Yield: 300 g, 0.81 mmol. Yellow solid. LCMS: (System 1, Method A) Rt=0.62 min, m/z 370.9 $(M-H)^-$ $(ES^-)$.

Intermediate 209: 4-(((7-azabicyclo[2.2.1]heptan-7-yl)sulfonyl)carbamoyl)-3-cyclopropoxy-2-fluorobenzoic acid

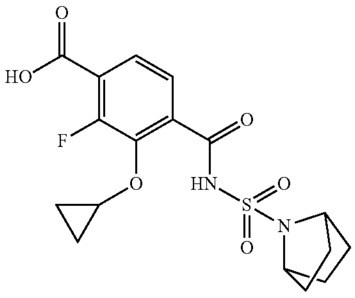 [SMILES: O=C(O)c1ccc(C(=O)NS(=O)(=O)N2C3CCC2CC3)c(OC2CC2)c1F]

Prepared by an analogous method to Intermediate 204 starting from of 4-bromo-2,3-difluorobenzoic acid (5.0 g, 21.2 mmol) and cyclopropanol (4.9 g, 84.8 mmol) except the Step 2 was carried out with 7-azabicyclo[2.2.1]heptane-7-sulfonamide (Intermediate 148) in place of 3-azabicyclo[3.1.0]hexane-3-sulfonamide. Yield: 300 g, 0.75 mmol. White solid. LCMS: (System 1, Method A) Rt=1.00 min, m/z 398.8 $(M+H)^+$ $(ES^+)$.

Intermediate 210: 2-fluoro-4-((pyrrolidin-1-ylsulfonyl)carbamoyl)-3-(3,3,3-trifluoropropoxy)benzoic Acid

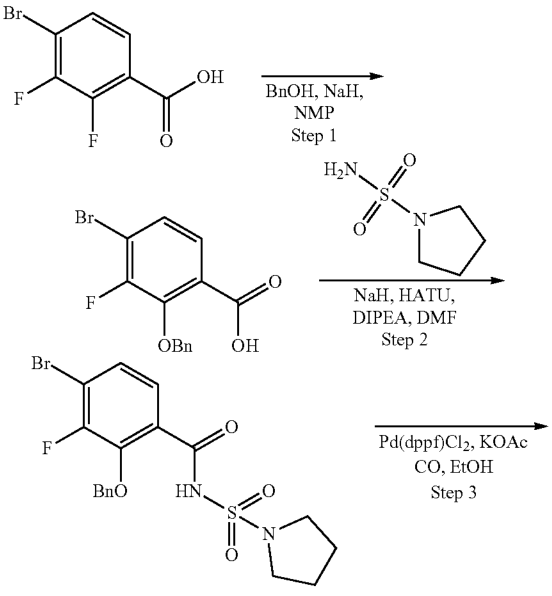

-continued

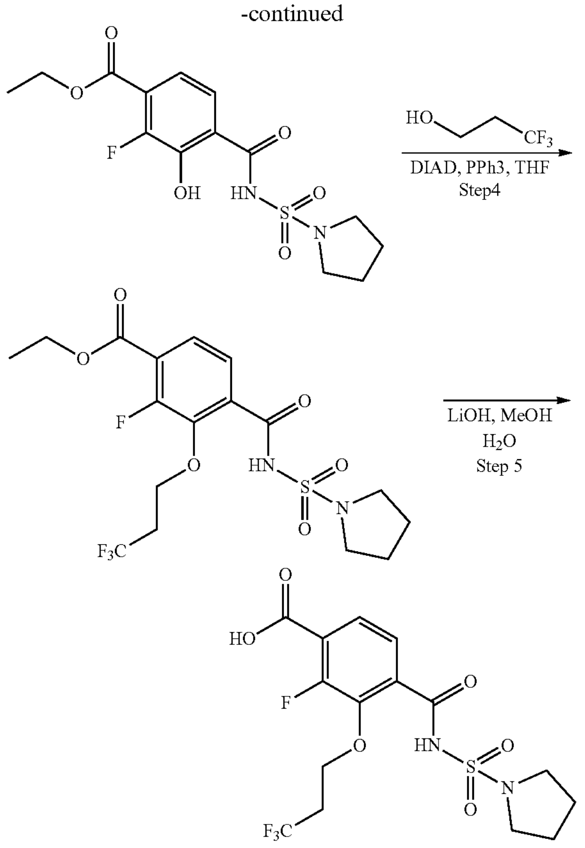

Step 1

Sodium hydride (60% dispersion in mineral oil, 2.2 g, 54.9 mmol) was added portionwise to a solution of 4-bromo-2,3-difluorobenzoic acid (2.6 g, 11.0 mmol) in NMP (40 mL) at 0° C., then benzyl alcohol (7.1 g, 65.8 mmol) was added and the reaction was stirred at RT overnight. The mixture was poured into $NH_4Cl$ aq. sat. (120 mL) and extracted with EtOAc (3×100 mL). The combined organic layers were washed with brine, dried ($Na_2SO_4$) filtered and concentrated under reduced pressure. The crude product was purified by column chromatography on silica gel (1-10% EtOAc/Petroleum ether) to afford 2-(benzyloxy)-4-bromo-3-fluorobenzoic acid (2.5 g, 7.69 mmol) as a white solid. LCMS: (System 1, Method A) Rt=1.39 min, m/z 324.6 $(M+H)^+$ $(ES^+)$.

Step 2

A mixture of 2-(benzyloxy)-4-bromo-3-fluorobenzoic acid (2.4 g, 7.38 mmol), HATU (3.4 g, 8.86 mmol) and DIPEA (3.8 g, 29.5 mmol) in DMF (50 mL) was stirred at RT for 1 h, pyrrolidine-1-sulfonamide (3.3 g, 22.2 mmol) and sodium hydride (60% dispersion in mineral oil, 1.2 g, 29.5 mmol) was added, then the reaction mixture was stirred at RT for 2 h. The mixture was poured into $NH_4Cl$ aq. sat. (150 mL), then the pH of the resulting aqueous layer was adjusted to ca. 5 with HCl aq. 1N and extracted with EtOAc (3×120 mL). The combined organic layers were washed by brine, dried ($Na_2SO_4$), filtered and concentrated under reduced pressure. The crude product was purified by column chromatography on silica gel (1-25% EtOAc/petroleum ether) to afford 2-(benzyloxy)-4-bromo-3-fluoro-N-(pyrrolidin-1-ylsulfonyl)benzamide (1.0 g, 2.2 mmol) as a white solid. LCMS: (System 1, Method A) Rt=1.61 min, m/z 457.0 $(M+H)^+$ $(ES^+)$.

Step 3

A mixture of 2-(benzyloxy)-4-bromo-3-fluoro-N-(pyrrolidin-1-ylsulfonyl)benzamide (1.0 g, 2.2 mmol), [1,1'-bis(diphenylphosphino)ferrocene]dichloropalladium(II) (160 mg, 0.22 mmol) and potassium acetate (644 mg, 6.57 mmol) in EtOH (22 mL) was stirred at 80° C. for 5 h under CO atmosphere. The organic solvent was removed under reduced pressure and the residue partitioned between water (20 mL) and EtOAc (3×20 mL). The combined organic layers were dried ($Na_2SO_4$), filtered and concentrated under reduced pressure. The crude product was purified by column chromatography on silica gel column (1-50% EtOAc/Petroleum ether) to afford ethyl 2-fluoro-3-hydroxy-4-((pyrrolidin-1-ylsulfonyl)carbamoyl)benzoate (600 mg, 1.67 mmol) as a brown solid. LCMS: (System 1, Method A) Rt=1.55 min, m/z 361.0 $(M+H)^+$ $(ES^+)$.

Step 4

A mixture of ethyl 2-fluoro-3-hydroxy-4-((pyrrolidin-1-ylsulfonyl)carbamoyl)benzoate (360 mg, 1.00 mmol), 3,3,3-trifluoropropan-1-ol (171 mg, 1.50 mmol), $PPh_3$ (786 mg, 3.00 mmol) and DIAD (606 mg, 3.00 mmol) in THE (10 mL) was stirred at RT overnight under $N_2$ atmosphere. The mixture was partitioned between water (30 mL) and EtOAc (3×30 mL). The combined organic layers were dried ($Na_2SO_4$), filtered and concentrated under reduced pressure. The crude product was purified by column chromatography on silica gel (1-50% ethyl acetate/petroleum ether) to afford ethyl 2-fluoro-4-((pyrrolidin-1-ylsulfonyl)carbamoyl)-3-(3,3,3-trifluoropropoxy)benzoate (41k-6, 400 mg, 0.80 mmol) as a yellow solid. LCMS: (System 1, Method A). Rt=1.72 min, m/z 456.7 $(M+H)^+$ $(ES^+)$.

Step 5

A solution of $LiOH{\cdot}H_2O$ (184 mg, 4.38 mmol) and ethyl 2-fluoro-4-((pyrrolidin-1-ylsulfonyl)carbamoyl)-3-(3,3,3-trifluoropropoxy)benzoate (400 mg, 0.88 mmol) in MeOH (10 mL) and water (2.5 mL) was stirred at RT overnight. The pH of the mixture was adjusted to ca. 8 by adding HCl aq. 1N and the organic solvents was removed under reduced pressure. The aqueous residue was washed with EtOAc (3×10 mL), and the pH of the resulting aqueous layer was adjusted to ca. 3 by adding HCl aq. 1N. the mixture was extracted with EtOAc (3×10 mL) and the combined organic layers were dried ($Na_2SO_4$), filtered and concentrated under reduced pressure to afford 2-fluoro-4-((pyrrolidin-1-ylsulfonyl)carbamoyl)-3-(3,3,3-trifluoropropoxy)benzoic acid (45 mg, 0.11 mmol) as a white solid. LCMS: (System 1, Method A). Rt=1.03 min, m/z 426.8 $(M-H)^-$ $(ES^-)$.

Intermediate 211: 2-ethoxy-3-fluoro-4-((pyrrolidin-1-ylsulfonyl)carbamoyl)benzoic Acid

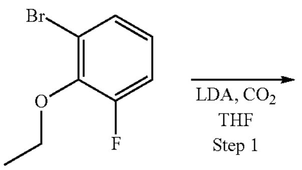

-continued

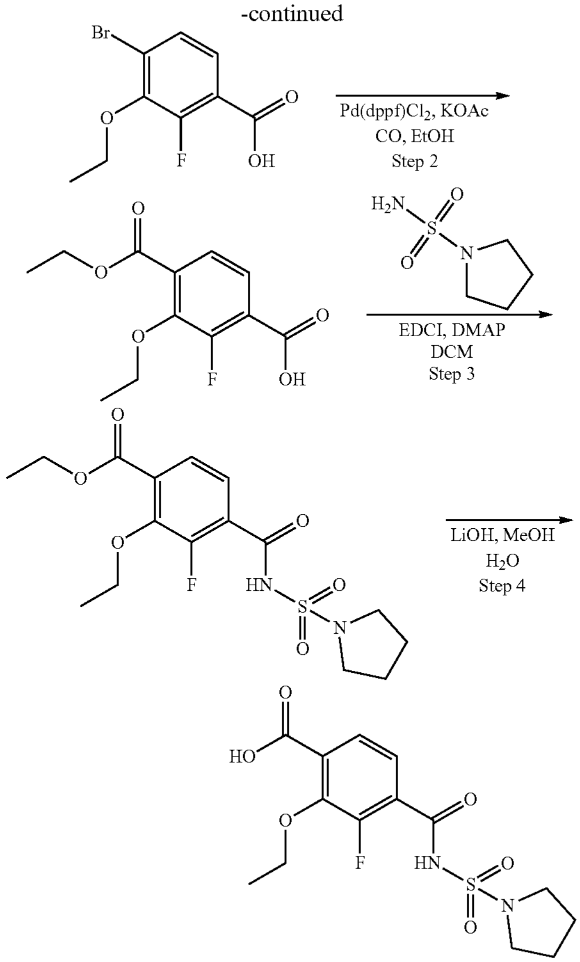

Step 1

LDA 2N in THE (23 mL) was added to a solution of 1-bromo-2-ethoxy-3-fluorobenzene (2.5 g, 11.4 mmol) in THE (23 mL) at −78° C. and the reaction mixture was stirred at this temperature for 1 h under $N_2$. Dry ice pellets were added under $N_2$ at −78° C. and the mixture was stirred at RT overnight. The reaction was quenched with $NH_4Cl$ aq. sat. (20 mL), the pH of the resulting aqueous layer adjusted to ca. 2 with HCl aq. 1N and the mixture extracted with EtOAc (3×20 mL). The combined organic layers were washed with brine (50 mL), dried ($MgSO_4$), filtered and concentrated under reduced pressure. The crude material was triturated with hexane to afford 4-bromo-3-ethoxy-2-fluoro-benzoic acid (1.6 g, 6.08 mmol) as an off-white solid. LCMS: (System 3, Method J) Rt=1.75 min, m/z 262.8 $(M-H)^-$ $(ES^-)$.

Step 2

A mixture of 4-bromo-3-ethoxy-2-fluoro-benzoic acid (1.9 g, 7.15 mmol), [1,1'-bis(diphenylphosphino)ferrocene] dichloropalladium(II) (1.1 g, 1.43 mmol) and potassium acetate (2.1 g, 21.4 mmol) in EtOH (16 mL) was stirred under CO atmosphere at 80° C. overnight. The mixture was allowed to reach RT, filtered through a pad of celite and concentrated under reduced pressure. The residue was partitioned between EtOAc (20 mL) and HCl aq. 4N (10 mL). The aqueous layer was extracted with EtOAc (2×20 mL) and the combined organic layers were dried ($MgSO_4$), filtered and concentrated under reduced pressure to afford 3-ethoxy-4-(ethoxycarbonyl)-2-fluorobenzoic acid (1.7 g, 6.63 mmol) as a red oil which was used without further purification in the next step. LCMS: (System 3, Method J) Rt=1.79 min, m/z 255.0 $(M-H)^-$ $(ES^-)$.

Step 3

A mixture of 3-ethoxy-4-(ethoxycarbonyl)-2-fluorobenzoic acid (250 mg, 0.98 mmol), EDCI (281 mg, 1.46 mmol), DMAP (477 mg, 3.90 mmol) and pyrrolidine-1-sulfonamide (440 mg, 2.93 mmol) in DCM (4.9 mL) was stirred at RT overnight. The reaction mixture was partitioned between $NaHCO_3$ aq. sat. (20 mL) and DCM (10 mL). The aqueous layer was extracted with DCM (2×15 mL). The combined organic layers were washed with brine (30 mL), dried ($Na_2SO_4$), filtered and concentrated under reduced pressure. The crude product was purified by column chromatography on $C_{18}$ (0-100% ACN/0.1% formic acid in water) to afford ethyl 2-ethoxy-3-fluoro-4-(227yrrolidine-1-ylsulfonylcarbamoyl)benzoate (262 mg, 0.68 mmol) as an off-white solid. LCMS: (System 3, Method J) Rt=1.89 min, m/z 387.3 $(M-H)^-$ $(ES^-)$.

Step 4

A mixture of ethyl 2-ethoxy-3-fluoro-4-(227yrrolidine-1-ylsulfonylcarbamoyl)benzoate (262 mg, 0.68 mmol) and LiOH aq. 2N (2.7 mL) in MeOH (1.2 mL) and THE (1.2 mL) was stirred at RT for 1 h. Then the reaction was quenched with HCl aq. 1N (20 mL) and the aqueous phase was extracted with EtOAc (2×20 mL). The combined organic layers were dried ($MgSO_4$), filtered and concentrated under reduced pressure to afford 2-ethoxy-3-fluoro-4-(227 yrrolidine-1-ylsulfonylcarbamoyl)benzoic acid (208 mg, 0.58 mmol) as an off-white solid. LCMS: (System 3, Method J) Rt=1.57 min, m/z 359.2 $(M-H)^-$ $(ES^-)$.

Intermediate 212: methyl 4-bromo-5-fluoro-2-methoxybenzoate

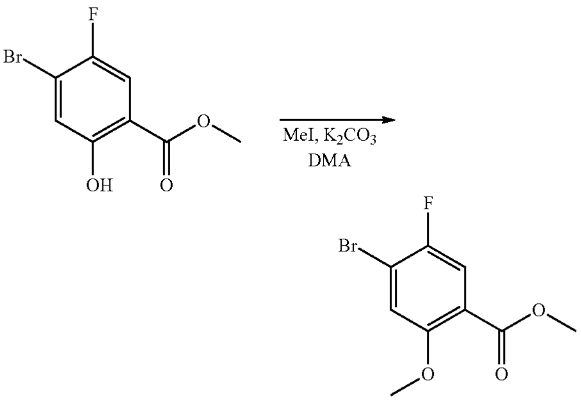

Iodomethane (1.71 g, 12.05 mmol) was added to a mixture of methyl 4-bromo-5-fluoro-2-hydroxybenzoate (2.0 g, 8.03 mmol) and $K_2CO_3$ (2.2 g, 16.1 mmol) in DMA (40 mL) and the mixture was stirred at RT overnight. The reaction mixture was poured into ice-water (120 mL) and extracted with ethyl acetate (3×100 mL). The combined organic layers were washed with brine, dried ($Na_2SO_4$), filtered and concentrated under reduced pressure. The crude product was purified by column chromatography on silica gel (1-10% EtOAc/petroleum ether) to afford methyl 4-bromo-5-fluoro-2-methoxybenzoate (2.0 g, 7.60 mmol) as a yellow oil. LCMS: (System 1, Method A) Rt=1.85 min, m/z 262.8 $(M+H)^+$ (ES)+.

Intermediate 213: 2-fluoro-5-methoxy-4-((pyrrolidin-1-ylsulfonyl)carbamoyl)benzoic acid

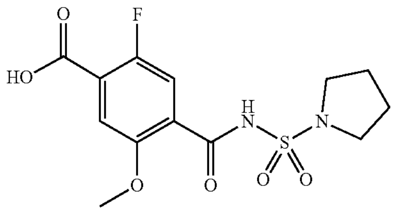 [SMILES: COc1cc(C(=O)O)c(F)cc1C(=O)NS(=O)(=O)N1CCCC1]

Prepared by an analogous method to Intermediate 36 (Steps 2 to 5) starting from methyl 4-bromo-5-fluoro-2-methoxybenzoate (Intermediate 212) except the Step 3 was carried out with pyrrolidine-1-sulfonamide in place of 1-methylcyclopropane-1-sulfonamide. Yield: 320 mg, 0.92 mmol. Yellow solid. LCMS: (System 1, Method A) Rt=0.42 min, m/z 346.17 $(M+H)^+$ $(ES^+)$.

Intermediate 214: methyl 4-bromo-5-fluoro-2-(methoxy-$d_3$)benzoate

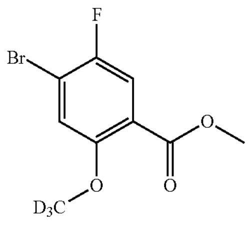 [SMILES: [2H]C([2H])([2H])Oc1cc(Br)c(F)cc1C(=O)OC]

Prepared by an analogous method to Intermediate 212 starting from of methyl 4-bromo-5-fluoro-2-hydroxybenzoate (2.0 g, 8.1 mmol) and iodomethane-$d_3$ (1.7 g, 12.1 mmol). Yield: 1.9 g, 7.17 mmol. White solid. LCMS: (System 1, Method A) Rt=1.87 min, m/z 266.1 $(M+H)^+$ $(ES^+)$.

Intermediate 215: 2-fluoro-5-(methoxy-$d_3$)-4-((pyrrolidin-1-ylsulfonyl)carbamoyl)benzoic Acid

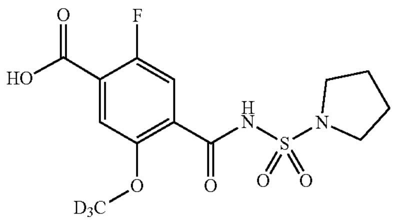 [SMILES: [2H]C([2H])([2H])Oc1cc(C(=O)O)c(F)cc1C(=O)NS(=O)(=O)N1CCCC1]

Prepared by an analogous method to Intermediate 213 starting from methyl 4-bromo-5-fluoro-2-(methoxy-$d_3$)benzoate (Intermediate 214). Yield: 300 mg, 0.86 mmol. White solid. LCMS: (System 1, Method A) Rt=0.35 min, m/z 348.0 $(M-H)^-$ $(ES^-)$.

Intermediate 216: 4-(((7-azabicyclo[2.2.1]heptan-7-yl)sulfonyl)carbamoyl)-3-methoxybenzoic Acid

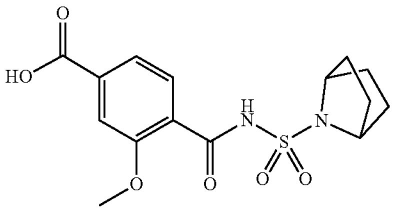 [SMILES: COc1cc(C(=O)O)ccc1C(=O)NS(=O)(=O)N1C2CCC1CC2]

Prepared by an analogous method to Intermediate 213 starting from methyl 4-bromo-2-methoxybenzoate except the Step 3 was carried out with 7-azabicyclo[2.2.1]heptane-7-sulfonamide (Intermediate 148) in place of pyrrolidine-1-sulfonamide. Yield: 280 mg, 0.79 mmol. White solid. LCMS: (System 1, Method A) Rt=0.73 min, m/z 355.0 $(M+H)^+$ $(ES^+)$.

Intermediate 217: 4-(((7-azabicyclo[2.2.1]heptan-7-yl)sulfonyl)carbamoyl)-3-ethoxybenzoic Acid

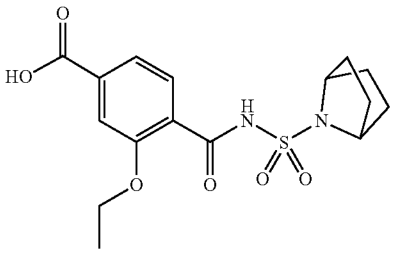 [SMILES: CCOc1cc(C(=O)O)ccc1C(=O)NS(=O)(=O)N1C2CCC1CC2]

Prepared by an analogous method to Intermediate 213 starting from methyl 4-bromo-2-ethoxybenzoate except the Step 3 was carried out with 7-azabicyclo[2.2.1]heptane-7-sulfonamide (Intermediate 148) in place of pyrrolidine-1-sulfonamide. Yield: 290 mg, 0.79 mmol. White solid. LCMS: (System 1, Method A) Rt=1.05 min, m/z 369.0 $(M+H)^+$ $(ES^+)$.

Intermediate 218: 3-azabicyclo[3.2.1]octane-3-sulfonamide

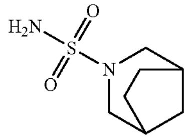 [SMILES: NS(=O)(=O)N1CC2CCC(C2)C1]

Prepared by an analogous method to Intermediate 148 starting from 3-azabicyclo[3.2.1]octane (1.0 g, 9.0 mmol), sulfuric diamide (1.3 g, 13.5 mmol). Yield: 1.3 g, 6.8 mmol.

Off-white solid. $^1H$ NMR (400 MHz, DMSO-$d_6$) δ 6.57 (s, 2H), 3.16-3.13 (m, 2H), 2.63 (d, J=10.4 Hz, 2H), 2.24 (br s, 2H), 1.61-1.43 (m, 5H), 1.34-1.31 (m, 1H).

Intermediate 219: 4-(ethoxycarbonyl)-2-fluoro-3-methoxybenzoic Acid

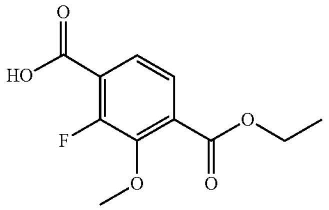 [SMILES: CCOC(=O)c1ccc(C(=O)O)c(F)c1OC]

Prepared by an analogous method to Intermediate 149 starting from 4-bromo-2-fluoro-3-methoxybenzoic acid (5.4 g, 21.8 mmol). Yield: 4.4 g, 18.0 mmol. Pale-yellow solid. LCMS: (System 1, Method A) Rt=1.14 min, m/z 241.2 $(M-H)^-$ $(ES^-)$.

Intermediate 220: 4-(ethoxycarbonyl)-2-fluoro-3-methylbenzoic Acid

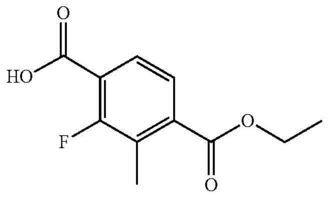 [SMILES: CCOC(=O)c1ccc(C(=O)O)c(F)c1C]

Prepared by an analogous method to Intermediate 149 starting from 4-bromo-2-fluoro-3-methylbenzoic acid (1.0 g, 4.29 mmol). Yield: 700 mg, 3.1 mmol. Pale-yellow solid. LCMS: (System 1, Method A) Rt=1.18 min, m/z 225.3 $(M-H)^-$ $(ES^-)$.

Intermediate 221: 4-(ethoxycarbonyl)-3-ethyl-2-fluorobenzoic Acid

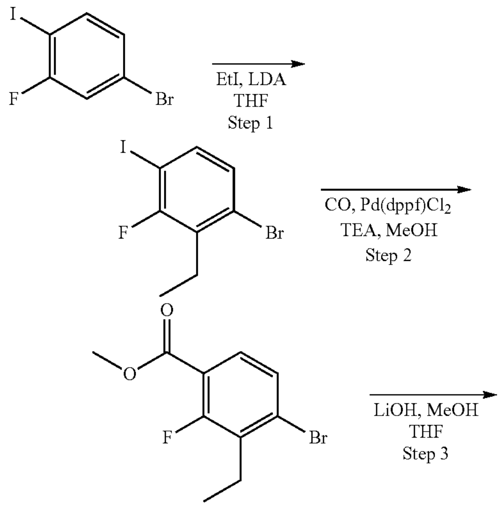

-continued

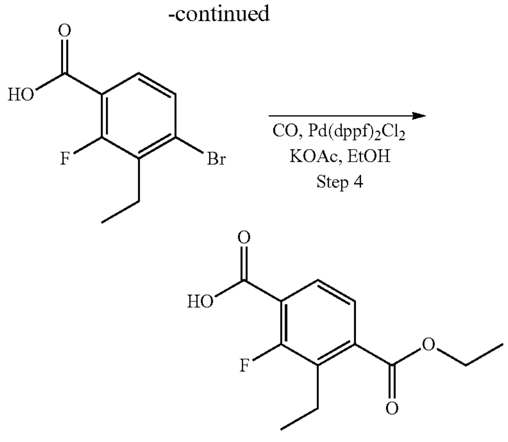

Step 1

To a solution of 4-bromo-2-fluoro-1-iodobenzene (5 g, 16.7 mmol) in THE (34 mL) was slowly added LDA (2M in THF, 16.67 mL, 33.3 mmol) at −78° C. under $N_2$. The reaction was slowly warmed to −20° C. and stirred at this temperature for 0.5 h, then it was cooled to −78° C. Iodoethane (8.67 g, 55.5 mmol) was added and the mixture was stirred at room temperature overnight. Saturated $NH_4Cl$ aq. (100 mL) was added, and the mixture was extracted with EtOAc (3×100 mL). The combined organic layers were washed by brine, dried over $Na_2SO_4$ and filtered. The filtrate was concentrated under reduced pressure and the crude product was purified by column chromatography on silica gel (10% EtOAc/petroleum ether) to afford 1-bromo-2-ethyl-3-fluoro-4-iodobenzene (2 g, 6.08 mmol) as a white solid. $^1H$ NMR (400 MHz, DMSO-$d_6$) δ: 7.62 (dd, J=8.2, 7.0 Hz, 1H), 7.27 (dd, J=8.4, 1.2 Hz, 1H), 2.80-2.74 (m, 2H), 1.11 (t, J=7.4 Hz, 3H).

Step 2

To a solution of 1-bromo-2-ethyl-3-fluoro-4-iodobenzene (1 g, 3.05 mmol) in MeOH (30 mL) was added Pd(dppf)$Cl_2$ (223 mg, 0.31 mmol) and TEA (1.85 g, 18.3 mmol), then the mixture was stirred at room temperature overnight under CO (1 MPa). The mixture was concentrated under reduced pressure, water (30 mL) was added and the mixture was extracted with EtOAc (3×30 mL). The combined organic layers were washed by brine, dried over $Na_2SO_4$ and filtered. The filtrate was concentrated under reduced pressure and the crude product was purified by column chromatography on silica gel (1-10% EtOAc/petroleum ether) to afford ethyl methyl 4-bromo-3-ethyl-2-fluorobenzoate (550 mg, 2.11 mmol) as a white solid. $^1H$ NMR (400 MHz, DMSO-d6) δ: 7.65 (d, J=8.2, 7.6 Hz, 1H), 7.59 (dd, J=8.2, 0.8 Hz, 1H), 3.86 (s, 3H), 2.83-2.77 (m, 2H), 1.12 (t, J=7.6 Hz, 3H).

Step 3

To a solution of methyl 4-bromo-3-ethyl-2-fluorobenzoate (550 mg, 2.11 mmol) in MeOH (20 mL) was added a solution of LiOH·$H_2O$ (534 mg, 12.7 mmol) in water (5 mL). The reaction mixture was stirred at room temperature overnight. The pH was adjusted to ca. 8 with HCl aq. 1N. MeOH was removed under reduced pressure, and pH was further adjusted to pH=3 with HCl aq. 1N.

The formed precipitate was collected by filtration, washed with water and hexane to afford 4-bromo-3-ethyl-2-fluorobenzoic acid (400 mg, 1.63 mmol) as a white solid. LCMS: (System 1, Method A). Rt=1.30 min. m/z 245.4 $(M-H)^-$ $(ES^-)$.

Step 4

To a solution of 4-bromo-3-ethyl-2-fluorobenzoic acid (400 mg, 1.63 mmol) in EtOH (20 mL) was added Pd(dppf)$Cl_2$ (117 mg, 0.16 mmol) and potassium acetate (479 mg, 4.89 mmol), and the mixture was stirred at 80° C. overnight under CO atmosphere (1 atm). The solvent was removed under reduced pressure and $K_2CO_3$ aq. 2M (15 mL) was added. The aqueous layer was washed with EtOAc (3×15 ml) and the pH was adjusted to ca. 4-5 with HCl aq. 1N. The aqueous layer was extracted with EtOAc (3×15 ml) and the combined organic layers were dried over $Na_2SO_4$ and filtered. The solvent was removed under reduced pressure to afford 4-(ethoxycarbonyl)-3-ethyl-2-fluorobenzoic acid (330 mg, 1.37 mmol) as an off-white solid. LCMS: (System 1, Method A). Rt=1.29 min. m/z 239.2 $(M-H)^-$ $(ES^-)$ Intermediate 222: 2-(dimethylamino)-4-(ethoxycarbonyl)-5-fluorobenzoic Acid

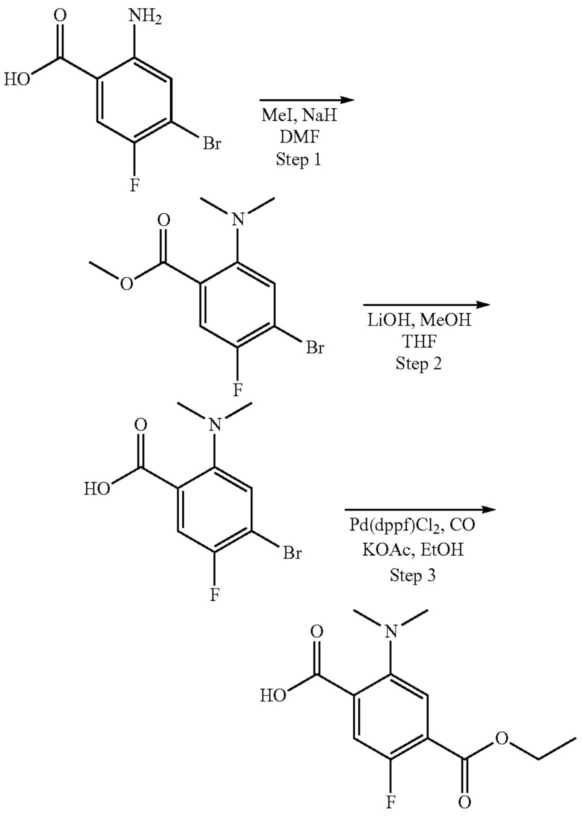

Step 1

Sodium hydride (60% dispersion in mineral oil, 615 mg, 25.6 mmol) was added portionwise to a solution of 2-amino-4-bromo-5-fluorobenzoic acid (1.0 g, 4.27 mmol) in DMF (9.5 mL) at 0° C. and the reaction was stirred at this temperature for 30 min. Iodomethane (2.1 mL, 34.2 mmol) was added and the reaction was stirred for 2 h at RT. The reaction was poured into water (20 mL) and extracted with EtOAc (3×20 mL). The combined organic layers were washed with brine, dried ($MgSO_4$) and concentrated under reduced pressure to afford 4-bromo-2-(dimethylamino)-5-fluorobenzoate (1.0 g, 3.62 mmol) as a yellow oil which was used in the next step without further purification. LCMS: (System 3, Method J) Rt=1.78 min, m/z 276.0 $(M-H)^-$ $(ES^-)$.

Step 2

LiOH aq. 2N (7.3 mL, 14.5 mmol) was added to a mixture of methyl 4-bromo-2-(dimethylamino)-5-fluoro-benzoate (1.0 g, 3.62 mmol) in methanol (3.6 mL) and tetrahydrofuran (3.6 mL), and the solution was stirred at RT for 1 h. The solvents were removed, and the crude product was purified by column chromatography on $C_{18}$ (0-100% ACN/0.1% FA in water) to afford 4-bromo-2-(dimethylamino)-5-fluorobenzoic acid (240 mg, 0.92 mmol) as a yellow solid. LCMS: (System 3, Method J) Rt=1.18 min, m/z 262.0 $(M-H)^-$ $(ES^-)$.

Step 3

A solution of 4-bromo-2-(dimethylamino)-5-fluorobenzoic acid (2.7 g, 10.3 mmol), [1,1'-bis(diphenylphosphino)ferrocene]dichloropalladium(II) (758 mg, 1.03 mmol) and potassium acetate (3.1 g, 30.9 mmol) in EtOH (52 mL) was stirred at 80° C. overnight under CO atmosphere. The reaction mixture was allowed to reach RT, filtered through a celite pad and concentrated under reduce pressure. The crude product was purified by column chromatography on $C_{18}$ (0-100% ACN/0.1% formic acid in water) to afford 2-(dimethylamino)-4-ethoxycarbonyl-5-fluorobenzoic acid (750 mg, 2.94 mmol) as a yellow solid. LCMS: (System 3, Method J) Rt=1.20 min, m/z 254.0 $(M-H)^-$ $(ES^-)$.

Intermediate 223: tert-butyl 5-oxo-8-(((trifluoromethyl)sulfonyl)oxy)-1,5-dihydro-2H-chromeno[3,4-c]pyridine-3(4H)-carboxylate

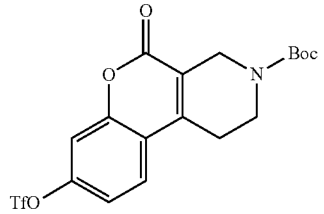 [SMILES: CC(C)(C)OC(=O)N1CCc2c(c(=O)oc3cc(OS(=O)(=O)C(F)(F)F)ccc23)C1]

Prepared by an analogous method to Intermediate 2 starting from resorcinol (4.4 g, 40.4 mmol). Yield: 6.5 g, 14.5 mmol. Pale-yellow solid. LCMS: (System 1, Method F) Rt=2.11 min, m/z 394.2 $(M-56+H)^+$ $(ES^+)$.

Intermediate 224: (R)-8-(3-(methoxymethyl)-4-methylpiperazin-1-yl)-1,2,3,4-tetrahydro-5H-chromeno[3,4-c]pyridin-5-one

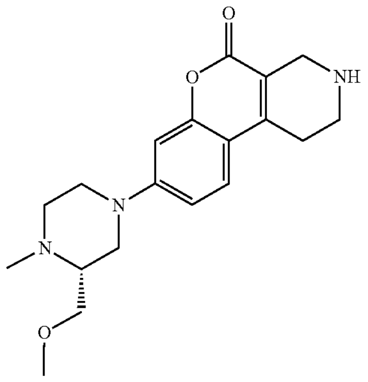 [SMILES: COC[C@H]1CN(c2ccc3c4c(c(=O)oc3c2)CNCC4)CCN1C]

Prepared by an analogous method to Intermediate 5 starting from (R)-2-(methoxymethyl)-1-methylpiperazine (Intermediate 1, 1.9 g, 13.0 mmol) and tert-butyl 5-oxo-8-(((trifluoromethyl)sulfonyl)oxy)-1,5-dihydro-2H-chromeno[3,4-c]pyridine-3(4H)-carboxylate (Intermediate 223, 3.9 g, 8.65 mmol). Yield: 1.9 g, 5.54 mmol. Yellow solid. LCMS: (System 1, Method A) Rt=1.34 min, m/z 344.2.0 $(M+H)^+$ $(ES^+)$.

Intermediate 225: tert-butyl 10-methyl-5-oxo-8-(((trifluoromethyl)sulfonyl)oxy)-1,5-dihydro-2H-chromeno[3,4-c]pyridine-3(4H)-carboxylate

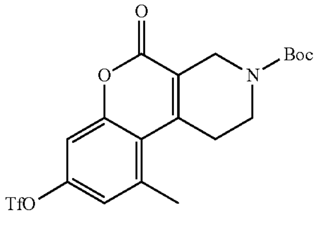 [SMILES: Cc1cc(OS(=O)(=O)C(F)(F)F)cc2oc(=O)c3c(c12)CCN(C(=O)OC(C)(C)C)C3]

Prepared by an analogous method to Intermediate 2 starting from 5-methylresorcinol (5.0 g, 40.4 mmol). Yield: 10.0 g, 21.6 mmol. Pale-yellow solid. LCMS: (System 1, Method A) Rt=2.16 min, m/z 408.3 $(M-56+H)^+$ $(ES^+)$.

Intermediate 226: (R)-8-(3-(methoxymethyl)-4-methylpiperazin-1-yl)-10-methyl-1,2,3,4-tetrahydro-5H-chromeno[3,4-c]pyridin-5-one

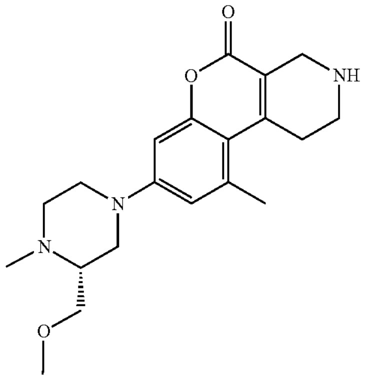 [SMILES: COC[C@H]1CN(c2cc(C)c3c4c(c(=O)oc3c2)CNCC4)CCN1C]

Prepared by an analogous method to Intermediate 5 starting from (R)-2-(methoxymethyl)-1-methylpiperazine (Intermediate 1, 1.9 g, 13 mmol) and tert-butyl 10-methyl-5-oxo-8-(((trifluoromethyl)sulfonyl)oxy)-1,5-dihydro-2H-chromeno[3,4-c]pyridine-3(4H)-carboxylate (Intermediate 225, 4.0 g, 8.7 mmol). Yield: 1.9 g, 5.32 mmol. Yellow solid. LCMS: (System 1, Method A) Rt=1.46 min, m/z 358.2 $(M+H)^+$ $(ES^+)$.

Intermediate 227: 2-ethylresorcinol

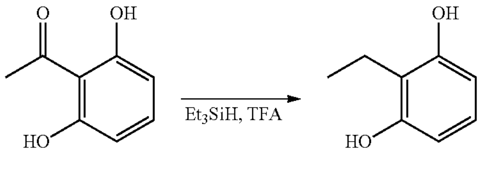

Triethylsilane (25.2 g, 217.1 mmol) was added dropwise to a solution of 1-(2,6-dihydroxyphenyl)ethanone (11.0 g, 72.4 mmol) in TFA (200 mL) at 0° C., the reaction was stirred at RT overnight. The mixture was poured into ice-water (400 mL) and extracted with DCM (3×400 mL). The combined organic layers were washed with brine, dried ($Na_2SO_4$), filtered and concentrated under reduced pressure. The crude product was purified by column chromatography on silica gel (1% EtOAc/Petroleum ether) to afford 2-ethylbenzene-1,3-diol (8.0 g, 57.9 mmol) as a colourless oil. LCMS: (System 1, Method A) Rt=1.30 min, m/z 137.3 $(M-H)^-$ $(ES^-)$.

Intermediate 228: tert-butyl 7-ethyl-5-oxo-8-(((trifluoromethyl)sulfonyl)oxy)-1,5-dihydro-2H-chromeno[3,4-c]pyridine-3(4H)-carboxylate

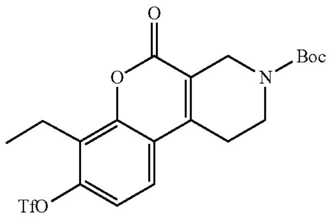 [SMILES: CCc1c(OS(=O)(=O)C(F)(F)F)ccc2c3c(c(=O)oc12)CN(C(=O)OC(C)(C)C)CC3]

Prepared by an analogous method to Intermediate 2 starting from 2-ethylresorcinol (Intermediate 227, 5.2 g, 37.68 mmol). Yield: 3.0 g, 6.20 mmol. Pale-yellow solid. LCMS: (System 1, Method A) Rt=2.54 min, m/z 422.0 $(M-56+H)^+$ $(ES^+)$.

Intermediate 229: (R)-7-ethyl-8-(3-(methoxymethyl)-4-methylpiperazin-1-yl)-1,2,3,4-tetrahydro-5H-chromeno[3,4-c]pyridin-5-one

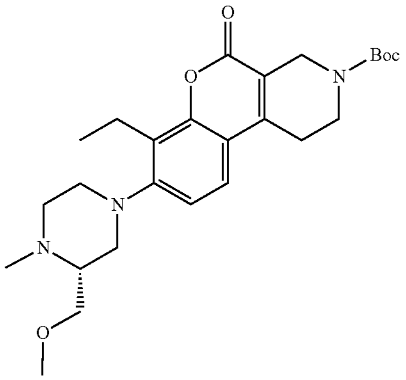 [SMILES: CCc1c(N2CCN(C)[C@@H](COC)C2)ccc2c3c(c(=O)oc12)CN(C(=O)OC(C)(C)C)CC3]

Prepared by an analogous method to Intermediate 5 starting from (R)-2-(methoxymethyl)-1-methylpiperazine (Intermediate 1, 671 mg, 4.65 mmol) and tert-butyl 7-ethyl-5-oxo-8-(((trifluoromethyl)sulfonyl)oxy)-1,5-dihydro-2H-chromeno[3,4-c]pyridine-3(4H)-carboxylate (Intermediate 228, 1.5 g, 3.10 mmol). Yield: 0.6 g, 1.62 mmol. Brown solid. LCMS: (System 1, Method A) Rt=1.63 min, m/z 372.2 $(M+H)^+$ $(ES^+)$.

Intermediate 230: (R)-3-(isopropoxymethyl)-1-methylpiperazine

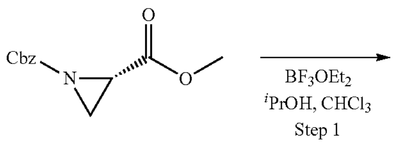

-continued

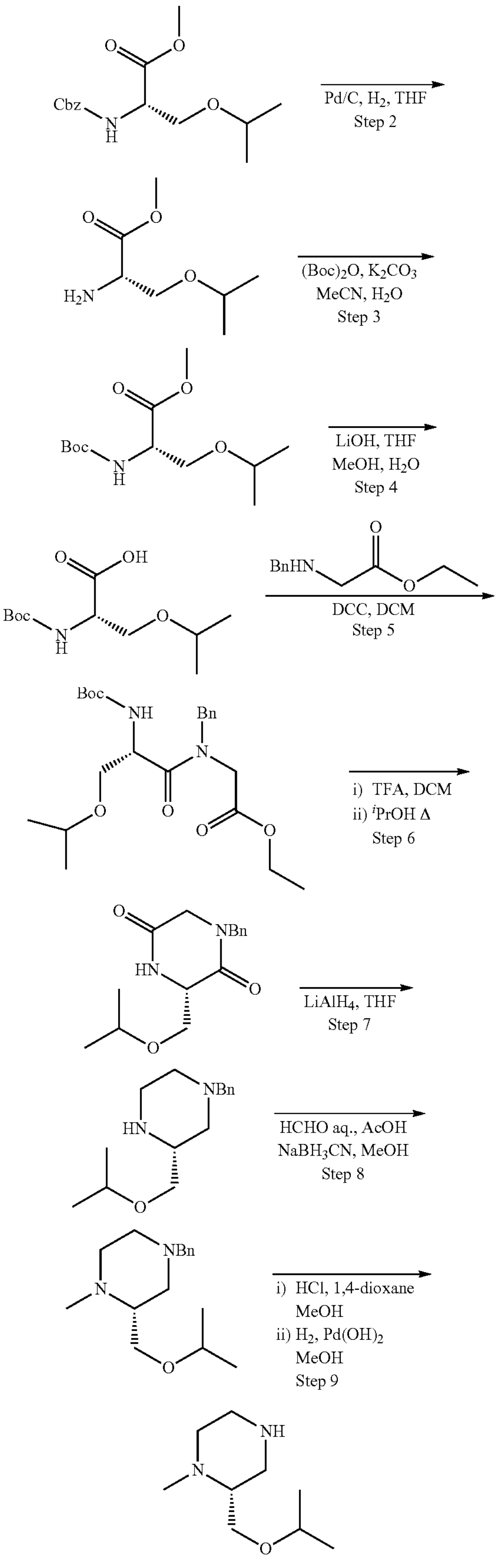

Step 1

Boron trifluoride diethyl etherate (22 mL) was added dropwise to a solution of (S)-1-benzyl 2-methyl aziridine-1,2-dicarboxylate (5.0 g, 21.3 mmol) in chloroform (106 mL) and isopropanol (106 mL) and the reaction was stirred at RT overnight. The mixture was partitioned between water (200 mL) and DCM (3×200 mL). The combined organic layers were dried ($Na_2SO_4$), filtered and concentrated under reduced pressure. The crude product was purified by column chromatography on silica gel (1-10% EtOAc/petroleum ether) to afford (S)-methyl 2-(((benzyloxy)carbonyl)amino)-3-isopropoxypropanoate (5.0 g, 16.9 mmol) as a yellow oil. LCMS: (System 1, Method A) Rt=1.88 min, m/z 296.4 $(M+H)^+$ $(ES^+)$.

Step 2

A mixture of (S)-methyl 2-(((benzyloxy)carbonyl)amino)-3-isopropoxypropanoate (5.0 g, 16.9 mmol) and Pd/C (10%, 1.5 g) in THE (170 mL) was stirred at RT overnight under $H_2$. The mixture was filtered and the filtrate was concentrated under reduced pressure to afford (S)-methyl 2-amino-3-isopropoxypropanoate (2.5 g, 15.5 mmol) as a yellow oil which was used in the next step without further purification. LCMS: (System 1, Method A) Rt=1.23 min, m/z 162.4 $(M+H)^+$ $(ES^+)$.

Step 3

A mixture of (S)-methyl 2-amino-3-isopropoxypropanoate (2.5 g, 15.51 mmol), $K_2CO_3$ (4.3 g, 31.0 mmol) and $Boc_2O$ (4.1 g, 18.6 mmol) in ACN (70 mL) and water (70 mL) was stirred at RT overnight. The reaction mixture was partitioned with EtOAc (3×100 mL) and the combined organic layers were dried ($Na_2SO_4$), filtered and concentrated under reduced pressure. The crude product was purified by column chromatography on silica gel (1-10% EtOAc/petroleum ether) to afford (S)-methyl 2-((tert-butoxycarbonyl)amino)-3-isopropoxypropanoate (3.0 g, 11.5 mmol) as a colourless oil. LCMS: (System 1, Method A) Rt=1.84 min, m/z 206.2 $(M-56+H)^+$ $(ES^+)$.

Step 4

A solution LiOH·$H_2O$ (2.4 g, 57.4 mmol) in water (20 mL) was added to a solution of (S)-methyl 2-((tert-butoxycarbonyl)amino)-3-isopropoxypropanoate (3.0 g, 11.5 mmol) in THE (80 mL) and MeOH (20 mL). The reaction mixture was stirred at RT overnight. The pH of the mixture was adjusted to ca. 8 by adding HCl aq. 1N and the organic solvents were removed under reduced pressure. The pH of the resulting aqueous layer was adjusted to ca. 5 by adding HCl aq. 1N and the aqueous layer extracted with EtOAc (3×40 mL). The combined organic layers were dried ($Na_2SO_4$), filtered and concentrated under reduced pressure to afford (S)-2-((tert-butoxycarbonyl)amino)-3-isopropoxypropanoic acid (2.3 g, 9.30 mmol) as a brown oil which was used in the next step without further purification. LCMS: (System 1, Method A) Rt=1.21 min, m/z 246.2 $(M-H)^-$ $(ES^-)$.

Step 5

A mixture of (S)-2-((tert-butoxycarbonyl)amino)-3-isopropoxypropanoic acid (2.3 g, 9.30 mmol), ethyl 2-(benzylamino)acetate (1.8 g, 9.30 mmol) and DCC (1.9 g, 9.30 mmol) in DCM (90 mL) was stirred at RT for 2 h. The mixture was concentrated under reduced pressure. The residue was suspended in MTBE/Petroleum ether (v/v 3/1, 3×20 mL) and the solid filtered off. The filtrate was concentrated under reduced pressure to afford (S)-ethyl 2-(N-benzyl-2-((tert-butoxycarbonyl)amino)-3-isopropoxypropanamido)acetate (3.1 g, 7.34 mmol) as a yellow oil. LCMS: (System 1, Method A) Rt=2.31 min, m/z 423.2 $(M+H)^+$ $(ES^+)$.

Step 6

TFA (15 mL) was added to a mixture of (S)-ethyl 2-(N-benzyl-2-((tert-butoxycarbonyl)amino)-3-isopropoxypropanamido)acetate (3.1 g, 7.34 mmol) in DCM (60 mL) and the reaction mixture was stirred at RT overnight. The mixture was concentrated under reduced pressure and the residue dissolved in isopropanol (60 mL) and stirred at 80° C. for 2 h. The organic solvent was removed under reduced pressure and water (30 mL) was added to the residue. The pH of the resulting aqueous layer was adjusted to ca. 9 by adding 15% NaOH aq. The formed precipitate was filtered and dried under reduced pressure to afford (S)-1-benzyl-3-(isopropoxymethyl)piperazine-2,5-dione (1.6 g 5.79 mmol) as a white solid. LCMS: (System 1, Method A) Rt=1.51 min, m/z 277.4 $(M+H)^+$ $(ES^+)$.

Step 7

Lithium aluminium hydride 2.5N in THE (7 mL, 17.5 mmol) was added dropwise to a solution of (S)-1-benzyl-3-(isopropoxymethyl)piperazine-2,5-dione (1.6 g, 5.79 mmol) in THE (60 mL) at 0° C. and the reaction mixture was stirred at 60° C. for 2 h. $Na_2SO_4 \cdot 10H_2O$ was added portionwise and the mixture was stirred at RT for 15 min. The reaction was filtered and the filtrate was concentrated under reduced pressure to afford (R)-1-benzyl-3-(isopropoxymethyl)piperazine (1.28 g, 5.15 mmol) as a pale-yellow oil which was used in the next step without further purification. LCMS: (System 1, Method A) Rt=1.61 min, 249.3 $(M+H)^+$ $(ES^+)$.

Step 8

A mixture of (R)-1-benzyl-3-(isopropoxymethyl)piperazine (1.3 g, 5.15 mmol), formaldehyde (37% aq. solution, 4.2 g, 51.54 mmol) and AcOH (309 mg, 5.15 mmol) in MeOH (40 mL) was stirred at RT for 30 min, then sodium cyanoborohydride (648 mg, 10.3 mmol) was added and the reaction mixture was stirred at RT overnight. The mixture was poured into $NaHCO_3$ aq. sat. (40 mL) and extracted with DCM (4×40 mL). The combined organics layers were washed by brine, dried ($Na_2SO_4$), filtered and concentrated under reduced pressure. The crude product was purified by column chromatography on silica gel (1-10% MeOH/DCM) to afford (R)-4-benzyl-2-(isopropoxymethyl)-1-methylpiperazine (750 mg, 2.86 mmol) as a yellow oil. LCMS: (System 1, Method C) Rt=0.83 min, m/z 263.3 $(M+H)^+$ $(ES^+)$.

Step 9

HCl 4N in 1,4-dioxane (10 mL, 40 mmol) was added to (R)-4-benzyl-2-(isopropoxymethyl)-1-methylpiperazine (750 mg, 2.86 mmol) and the reaction was stirred at RT overnight. The mixture was concentrated under reduced pressure. The residue dissolved in MeOH (20 mL), $Pd(OH)_2$ (20%, 225 mg) was added and the reaction mixture was stirred at 50° C. overnight under $H_2$ (1.2 MPa). The mixture was filtered and the filtrate was concentrated under reduced pressure to afford (R)-2-(isopropoxymethyl)-1-methylpiperazine (430 mg, 2.50 mmol) as a brown oil. LCMS: (System 1, Method A) Rt=1.08 min, m/z 173.4 $(M+H)^+$ $(ES^+)$.

Intermediate 231: (R)-8-(3-(isopropoxymethyl)-4-methylpiperazin-1-yl)-7-methyl-1,2,3,4-tetrahydro-5H-chromeno[3,4-c]pyridin-5-one

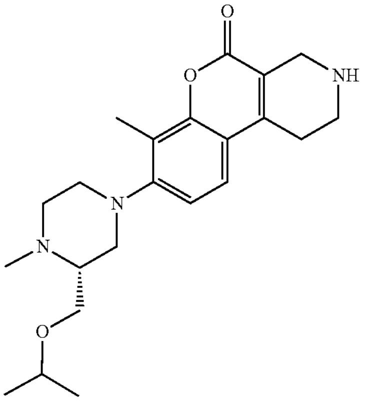 [SMILES: Cc1c(N2CCN(C)[C@@H](COC(C)C)C2)ccc2c3c(c(=O)oc12)CNCC3]

Prepared by an analogous method to Intermediate 5 starting from (R)-3-(isopropoxymethyl)-1-methylpiperazine (Intermediate 230, 430 mg, 2.50 mmol) and (Intermediate 2, 850 mg, 1.78 mmol). Yield: 288 mg, 0.75 mmol. Brown solid. LCMS: (System 1, Method C) Rt=0.76 min, m/z 386.2 $(M+H)^+$ $(ES^+)$.

Intermediate 232: 4-(((7-azabicyclo[2.2.1]heptan-7-yl)sulfonyl)carbamoyl)-2-fluoro-5-methoxybenzoic Acid

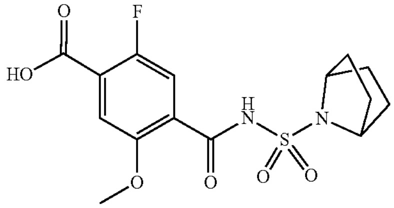 [SMILES: COc1cc(C(=O)O)c(F)cc1C(=O)NS(=O)(=O)N1C2CCC1CC2]

Prepared by analogous method to Intermediate 213 starting from methyl 4-bromo-5-fluoro-2-methoxybenzoate (Intermediate 212) except the Step 3 was carried out with 7-azabicyclo[2.2.1]heptane-7-sulfonamide (Intermediate 148) in place of pyrrolidine-1-sulfonamide. Yield: 300 mg, 0.81 mmol. White solid. LCMS: (System 1, Method A) Rt=0.72 min, m/z 371.2 $(M-H)^-$ $(ES^-)$.

Intermediate 233: 4-(((3-azabicyclo[3.1.0]hexan-3-yl)sulfonyl)carbamoyl)-2-fluoro-5-methoxybenzoic Acid

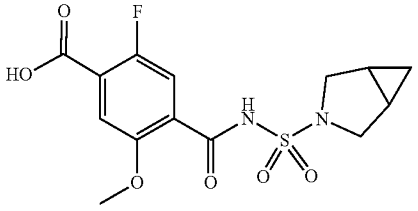 [SMILES: COc1cc(C(=O)O)c(F)cc1C(=O)NS(=O)(=O)N1CC2CC2C1]

Prepared by analogous method to Intermediate 213 starting from methyl 4-bromo-5-fluoro-2-methoxybenzoate (Intermediate 212) except the Step 3 was carried out with 3-azabicyclo[3.1.0]hexane-3-sulfonamide (Intermediate 168) in place of pyrrolidine-1-sulfonamide. Yield: 290 mg, 0.81 mmol. White solid. LCMS: (System 1, Method A) Rt=0.55 min, m/z 357.2 $(M-H)^-$ $(ES^-)$.

Intermediate 234: 4-(((7-azabicyclo[2.2.1]heptan-7-yl)sulfonyl)carbamoyl)-2-fluoro-5-(methoxy-$d_3$) benzoic Acid

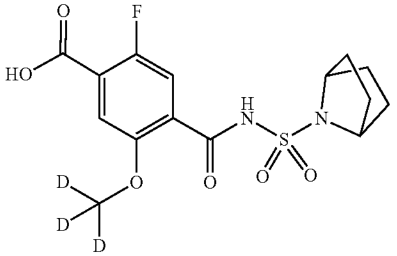 [SMILES: [2H]C([2H])([2H])Oc1cc(C(=O)O)c(F)cc1C(=O)NS(=O)(=O)N1C2CCC1CC2]

Prepared by analogous method to Intermediate 213 starting from methyl 4-bromo-5-fluoro-2-(methoxy-$d_3$)benzoate (Intermediate 214) except the Step 3 was carried out with 7-azabicyclo[2.2.1]heptane-7-sulfonamide (Intermediate 148) in place of pyrrolidine-1-sulfonamide. Yield: 280 mg, 0.75 mmol. White solid. LCMS: (System 1, Method A) Rt=0.61 min, m/z 375.6 $(M+H)^+$ $(ES^+)$.

Intermediate 235: 4-(((3-azabicyclo[3.1.0]hexan-3-yl)sulfonyl)carbamoyl)-2-fluoro-5-(methoxy-$d_3$) benzoic Acid

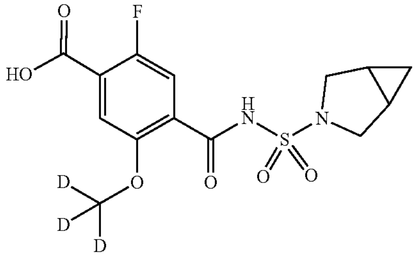 [SMILES: [2H]C([2H])([2H])Oc1cc(C(=O)O)c(F)cc1C(=O)NS(=O)(=O)N1CC2CC2C1]

Prepared by analogous method to Intermediate 213 starting from methyl 4-bromo-5-fluoro-2-(methoxy-$d_3$)benzoate (Intermediate 214) except the Step 3 was carried out with 3-azabicyclo[3.1.0]hexane-3-sulfonamide (Intermediate 168) in place of pyrrolidine-1-sulfonamide. Yield: 285 mg, 0.79 mmol. White solid. LCMS: (System 1, Method A) Rt=0.51 min, m/z 361.6 $(M+H)^+$ $(ES^+)$.

Intermediate 236: 3-fluoro-4-((pyrrolidin-1-ylsulfonyl)carbamoyl)benzoic

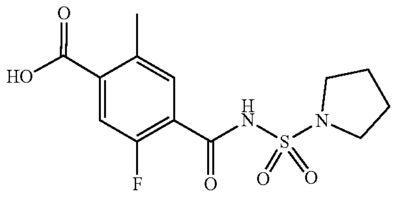 [SMILES: Cc1cc(C(=O)NS(=O)(=O)N2CCCC2)c(F)cc1C(=O)O]

Prepared by analogous method to Intermediate 36 (Steps 3 to 5) starting from 4-bromo-2-fluorobenzoic acid (542 mg, 2.49 mmol) except the Step 3 was carried out with pyrrolidine-1-sulfonamide in place of 1-methylcyclopropane-1-sulfonamide. Yield: 205 mg, 0.65 mmol. White solid. LCMS: (System 1, Method A) Rt=0.32 min, m/z 317.0 $(M+H)^+$ $(ES^+)$.

Intermediate 237: 4-(((7-azabicyclo[2.2.1]heptan-7-yl)sulfonyl)carbamoyl)-2-fluoro-3-(methoxy-$d_3$) benzoic Acid

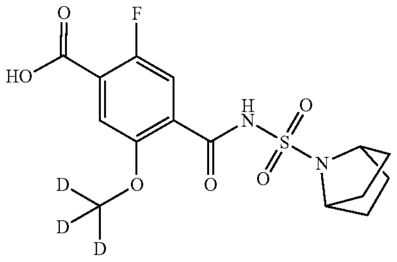 [SMILES: [2H]C([2H])([2H])Oc1cc(C(=O)O)c(F)cc1C(=O)NS(=O)(=O)N1C2CCC1CC2]

Prepared by an analogous method to Intermediate 204 starting from of 4-bromo-2,3-difluorobenzoic acid (0.5 g, 2.13 mmol) and methanol-$d_3$ (383 mg, 10.6 mmol) except the Step 2 was carried out with 7-azabicyclo[2.2.1]heptane-7-sulfonamide (Intermediate 148) in place of 3-azabicyclo [3.1.0]hexane-3-sulfonamide. Yield: 250 mg, 0.67 mmol. Off-white solid. LCMS: (System 1, Method A) Rt=0.39 min, m/z 374.0 $(M-H)^-$ $(ES^-)$.

Intermediate 238: (S)-3-fluoropyrrolidine-1-sulfonamide

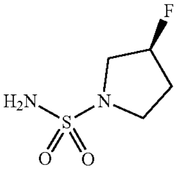

Prepared by an analogous method to Intermediate 148 starting from (S)-3-fluoropyrrolidine hydrochloride (1.0 g, 8.0 mmol), sulfuric diamide (918 mg, 9.6 mmol). Yield: 608 mg, 3.6 mmol. Off-white solid. $^1$H-NMR (400 MHz, DMSO-$d_6$) δ: 6.78 (s, 2H), 5.35-5.19 (m, 1H), 3.37-3.30 (m, 1H), 3.26-3.12 (m, 3H), 2.12-1.91 (m, 2H).

Intermediate 239: (S)-5-ethoxy-2-fluoro-4-(((3-fluoropyrrolidin-1-yl)sulfonyl)carbamoyl)benzoic Acid

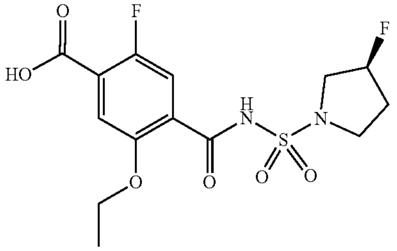 [SMILES: CCOc1cc(C(=O)O)c(F)cc1C(=O)NS(=O)(=O)N1CC[C@H](F)C1]

Prepared by an analogous method to Intermediate 181 except the Step 4 was carried out with (S)-3-fluoropyrrolidine-1-sulfonamide (Intermediate 238) in place of N,N-dicyclopropylsulfamide. Yield: 244 mg, 0.65 mmol. Off-white solid. LCMS: (System 3, Method J) Rt=1.53 min, m/z 377.2 $(M-H)^-$ $(ES^-)$.

Intermediate 240: (R)-3-fluoropyrrolidine-1-sulfonamide

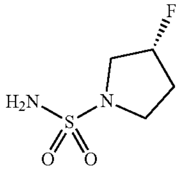

Prepared by an analogous method to Intermediate 148 starting from (R)-3-fluoropyrrolidine hydrochloride (2.35 g, 18.7 mmol), sulfuric diamide (1.5 g, 15.6 mmol). Yield: 1.5 g, 8.7 mmol. White solid. $^1$H NMR (400 MHz, DMSO-$d_6$) δ 6.82 (br s, 2H), 5.31 (dq, J=57.1, 2.2 Hz, 1H), 3.41-3.17 (m, 5H), 2.12-1.95 (m, 2H).

Intermediate 241: (R)-5-ethoxy-2-fluoro-4-(((3-fluoropyrrolidin-1-yl)sulfonyl)carbamoyl)benzoic Acid

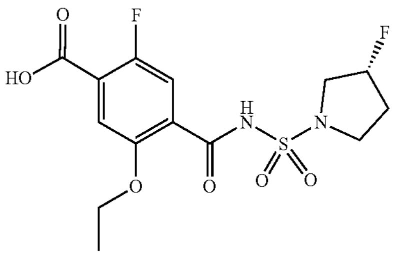 [SMILES: CCOc1cc(C(=O)O)c(F)cc1C(=O)NS(=O)(=O)N1CC[C@@H](F)C1]

Prepared by an analogous method to Intermediate 181 except the Step 4 was carried out with (R)-3-fluoropyrrolidine-1-sulfonamide (Intermediate 240) in place of N,N-dicyclopropylsulfamide. Yield: 280 mg, 0.74 mmol. White solid. LCMS: (System 3, Method J) Rt=1.54 min, m/z 377.0 $(M-H)^-$ $(ES^-)$.

Intermediate 242: (1S,4S)-2-oxa-5-azabicyclo[2.2.1]heptane-5-sulfonamide

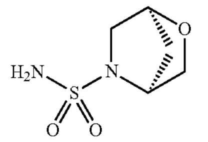

Prepared by an analogous method to Intermediate 148 starting from (1 S,4S)-2-oxa-5-azabicyclo[2.2.1]heptane hydrochloride (1.0 g, 7.4 mmol), sulfuric diamide (1.1 g, 11.1 mmol). Yield: 0.9 g, 5.1 mmol. Off-white solid. $^1$H-NMR (400 MHz, DMSO-D6) δ 6.85 (s, 2H), 4.55 (s, 1H), 4.18 (d, J=18.8 Hz, 1H), 3.85-3.78 (m, 1H), 3.63-3.57 (m, 1H), 3.24-3.16 (m, 1H), 3.10-3.05 (m, 1H), 1.86 (dd, J=10.1, 2.3 Hz, 1H), 1.70-1.67 (m, 1H).

Intermediate 243: 4-((((1S,4S)-2-oxa-5-azabicyclo[2.2.1]heptan-5-yl)sulfonyl)carbamoyl)-5-ethoxy-2-fluorobenzoic Acid

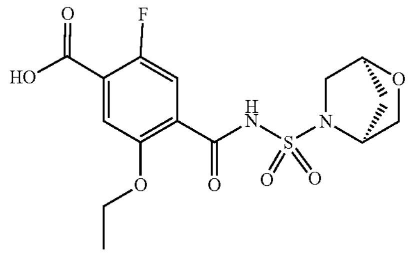

Prepared by an analogous method to Intermediate 181 except the Step 4 was carried out with (1 S,4S)-2-oxa-5-azabicyclo[2.2.1]heptane-5-sulfonamide (Intermediate 242) in place of N,N-dicyclopropylsulfamide. Yield: 289 mg, 0.7 mmol. White solid. LCMS: (System 3, Method J) Rt=1.41 min, m/z 387.0 $(M-H)^-$ $(ES^-)$.

Intermediate 244: 5-cyclopropoxy-2-fluoro-4-((pyrrolidin-1-ylsulfonyl)carbamoyl)benzoic Acid

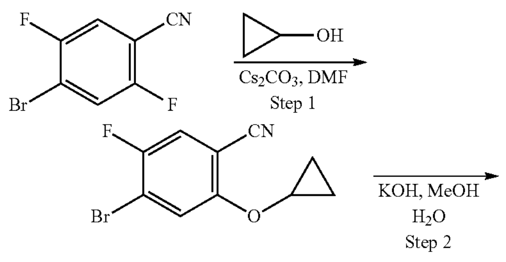

-continued

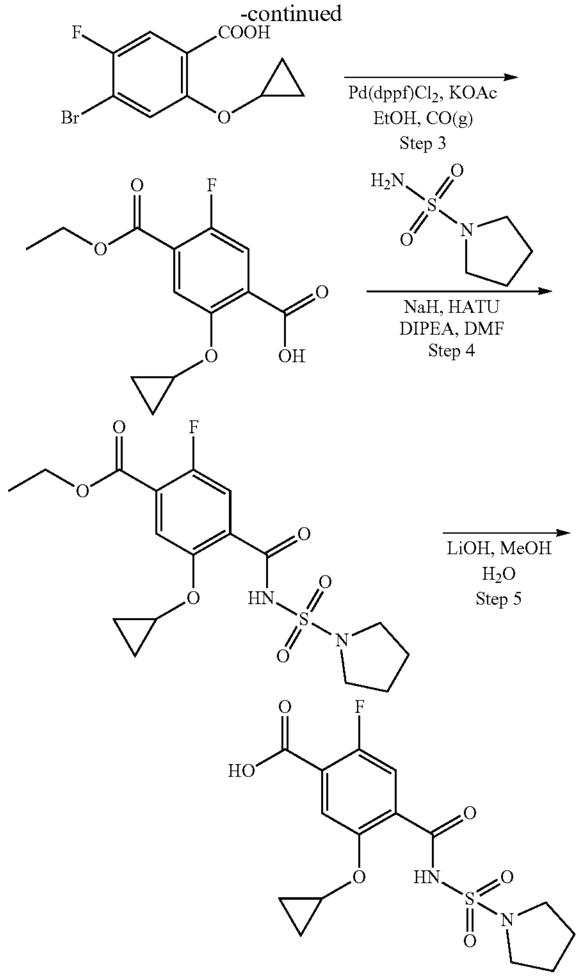

Step 1

To a solution of 4-bromo-2,5-difluorobenzonitrile (5.1 g, 23.5 mmol) in DMF (100 mL) was added $Cs_2CO_3$ (23.0 g, 70.5 mmol) and cyclopropanol (1.64 g, 28.2 mmol). The reaction mixture was stirred at 50° C. overnight, then cooled at RT, poured into water (300 mL) and extracted with ethyl acetate (3×300 mL). The combined organic layers were washed with brine (3×50 mL), dried over $Na_2SO_4$, filtered and concentrated under reduced pressure. The crude product was purified by column chromatography on silica gel (1-10% EtOAc/petroleum ether) to afford 4-bromo-2-cyclopropoxy-5-fluorobenzonitrile (4.07 g, 15.9 mmol) as yellow oil. $^1$H NMR (400 MHz, DMSO-$d_6$) δ: 7.97 (d, J=8.0 Hz, 1H), 7.82 (d, J=5.6 Hz, 1H), 4.14-4.11 (m, 1H), 0.90-0.85 (m, 2H), 0.78-0.74 (m, 2H).

Step 2

To a solution of 4-bromo-2-cyclopropoxy-5-fluorobenzonitrile (4.07 g, 15.9 mmol) in MeOH/water (32 mL/8 mL) was added KOH (3.58 g, 63.8 mmol), then the reaction mixture was stirred at 80° C. overnight. The pH was adjusted to ca. 8 with HCl aq. 1N and the organic solvents were removed under reduced pressure. The pH was then adjusted to ca. 3 with HCl aq. 1N. The formed precipitate was collected by filtration, washed with water then hexane to afford 4-bromo-2-cyclopropoxy-5-fluorobenzoic acid (3.8 g, 13.8 mmol) as a yellow solid. LCMS: (System 1, Method A), Rt=1.25 min. m/z 273.0 $[M-H]^-$ $(ES^-)$.

Step 3

To a solution of 4-bromo-2-cyclopropoxy-5-fluorobenzoic acid (3.8 g, 13.8 mmol) in EtOH (50 mL) was added Pd(dppf)$Cl_2$ (2.03 g, 2.77 mmol) and potassium acetate (4.08 g, 41.6 mmol), and the mixture was stirred at 80° C. for 5 hours under CO atmosphere (1 atm). EtOH was removed at 45° C. under reduced pressure, saturated $Na_2CO_3$ aq. (50 mL) was added and the reaction mixture was extracted with EtOAc (3×50 mL). The pH of the aqueous layer was adjusted to ca. 3 with HCl aq. 1N and the aqueous layer extracted with EtOAc (3×50 mL). The combined organic layers were washed with brine, dried over $Na_2SO_4$ and filtered. The solvent was removed under reduced pressure to afford 2-cyclopropoxy-4-(ethoxycarbonyl)-5-fluorobenzoic acid (2.4 g, 8.94 mmol) as a yellow solid. LCMS: (System 1, Method A). Rt=1.23 min. m/z 269.1 $[M+H]^+$ $(ES^+)$.

Step 4

A solution of 2-cyclopropoxy-4-(ethoxycarbonyl)-5-fluorobenzoic acid (600 mg, 2.24 mmol), HATU (1.02 g, 2.69 mmol) and DIPEA (1.16 g, 9 mmol) in DMF (10 mL) was stirred at room temperature for 1 h. Pyrrolidine-1-sulfonamide (672 mg, 4.48 mmol) and NaH (60% in mineral oil, 358 mg, 9 mmol) were added and the reaction mixture was stirred at room temperature for 2 h. The mixture was poured into sat $NH_4Cl$ aq. (30 mL), then the pH was adjusted to ca. 4 with HCl aq. 1N and extracted with ethyl acetate (3×30 mL). The combined organic layers were washed with brine (3×20 mL), dried over $Na_2SO_4$, filtered and concentrated under reduced pressure. The crude product was purified by column chromatography on silica gel (1-25% EtOAc/petroleum ether) to afford ethyl 5-cyclopropoxy-2-fluoro-4-((pyrrolidin-1-ylsulfonyl)carbamoyl)benzoate (500 mg, 1.25 mmol) as a white solid. LCMS: (System 1, Method A), Rt=1.44 min. m/z 401.0 [M+H]+$(ES^+)$.

Step 5

To a solution of ethyl 5-cyclopropoxy-2-fluoro-4-((pyrrolidin-1-ylsulfonyl)carbamoyl)benzoate (500 mg, 1.25 mmol) in MeOH (12 mL) was added a solution of LiOH·$H_2O$ (205 mg, 5.00 mmol) in water (3 mL). The reaction mixture was stirred at room temperature overnight and the pH was adjusted to ca. 8 with HCl aq. 1N. The organic solvents were removed under reduced pressure and the pH was adjusted to ca. 3 with HCl aq. 1N. The formed precipitate was collected by filtration, washed with water then hexane to afford 5-cyclopropoxy-2-fluoro-4-((pyrrolidin-1-ylsulfonyl)carbamoyl)benzoic acid (370 mg, 0.99 mmol) as a yellow solid. LCMS: (System 1, Method A). Rt=0.70 min. m/z 370.6 $[M-H]^-$ $(ES^-)$. Step 1

Intermediate 245: 4-(((3-azabicyclo[3.1.0]hexan-3-yl)sulfonyl)carbamoyl)-5-cyclopropoxy-2-fluorobenzoic Acid

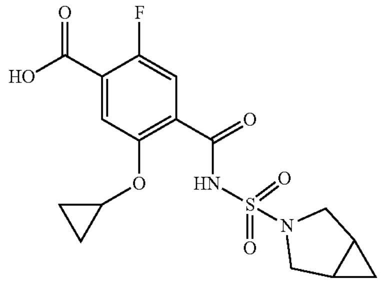 [SMILES: O=C(O)c1cc(OC2CC2)c(C(=O)NS(=O)(=O)N2CC3CC3C2)cc1F]

Prepared by an analogous method to Intermediate 245 except the Step 4 was carried out with 3-azabicyclo[3.1.0]hexane-3-sulfonamide (Intermediate 168) in place of pyrrolidine-1-sulfonamide. Yield: 93 mg, 0.24 mmol. Off-white solid. LCMS: (System 3, Method J) Rt=1.45 min, m/z 384.0 $(M-H)^-$ $(ES^-)$.

Intermediate 246: 4-(((2-azaspiro[3.3]heptan-2-yl)sulfonyl)carbamoyl)-5-(dimethylamino)-2-fluorobenzoic Acid

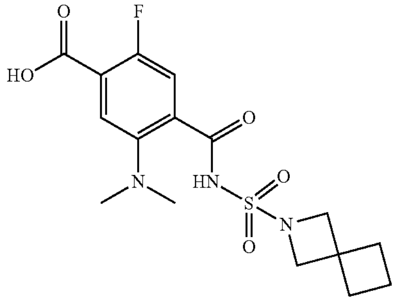 [SMILES: CN(C)c1cc(C(=O)O)c(F)cc1C(=O)NS(=O)(=O)N1CC2(CCC2)C1]

Prepared by an analogous method to Intermediate 134 specific procedure except the Step 2 was carried out with 2-azaspiro[3.3]heptane-2-sulfonamide (Intermediate 186) in place of pyrrolidine-1-sulfonamide. Yield: 93 mg, 0.24 mmol. Off-white solid. LCMS: (System 3, Method J) Rt=1.45 min, m/z 384.0 $(M-H)^-$ $(ES^-)$.

Intermediate 247: (S)-5-(dimethylamino)-2-fluoro-4-(((3-fluoropyrrolidin-1-yl)sulfonyl)carbamoyl) benzoic Acid

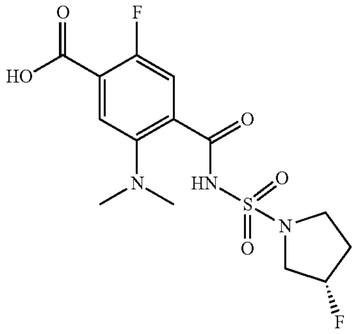 [SMILES: CN(C)c1cc(C(=O)O)c(F)cc1C(=O)NS(=O)(=O)N1CC[C@H](F)C1]

Prepared by an analogous method to Intermediate 134 specific procedure except the Step 2 was carried out with (S)-3-fluoropyrrolidine-1-sulfonamide (Intermediate 238) in place of pyrrolidine-1-sulfonamide. Yield: 40 mg, 0.11 mmol. Off-white solid. LCMS: (System 3, Method J) Rt=1.24 min, m/z 376.0 $(M-H)^-$ $(ES^-)$.

Intermediate 248: 4-(((3-oxa-8-azabicyclo[3.2.1] octan-8-yl)sulfonyl)carbamoyl)-5-(dimethylamino)-2-fluorobenzoic Acid

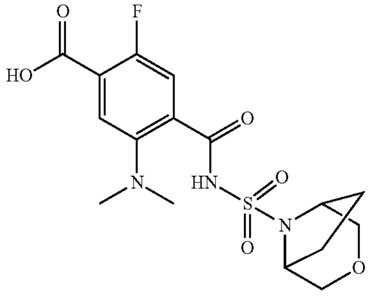 [SMILES: CN(C)c1cc(C(=O)O)c(F)cc1C(=O)NS(=O)(=O)N1C2CCC1COC2]

Prepared by an analogous method to Intermediate 134 specific procedure except the Step 2 was carried out with 3-oxa-8-azabicyclo[3.2.1]octane-8-sulfonamide (Intermediate 188) in place of pyrrolidine-1-sulfonamide. Yield: 42 mg, 0.11 mmol. Off-white. LCMS: (System 3, Method J) Rt=1.23 min, m/z 400.0 $(M-H)^-$ $(ES^-)$.

Intermediate 249: N-cyclopropyl-N-methylsulfamide

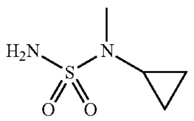

Prepared by an analogous method to Intermediate 148 starting from N-methylcyclopropanamine hydrochloride (1.5 g, 13.9 mmol), sulfuric diamide (1.6 g, 16.7 mmol). Yield: 0.8 g, 5.3 mmol. Off-white solid. $^1H$ NMR (400 MHz, DMSO-$d_6$) δ: 7.16 (s, 2H), 3.68 (s, 1H), 2.98 (s, 3H), 0.97-0.95 (m, 4H).

Intermediate 250: 4-((N-cyclopropyl-N-methylsulfamoyl)carbamoyl)-5-(dimethylamino)-2-fluorobenzoic acid

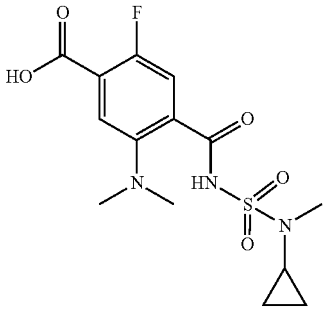 [SMILES: CN(C)c1cc(C(=O)O)c(F)cc1C(=O)NS(=O)(=O)N(C)C1CC1]

Prepared by an analogous method to Intermediate 134 specific procedure except the Step 2 was carried out with N-cyclopropyl-N-methylsulfamide (Intermediate 249) in place of pyrrolidine-1-sulfonamide. Yield: 36 mg, 0.10 mmol. Off-white solid. LCMS: (System 3, Method J) Rt=1.39 min, m/z 358.0 $(M-H)^-$ $(ES^-)$.

Intermediate 251: 5-(dimethylamino)-4-((N,N-dimethylsulfamoyl)carbamoyl)-2-fluorobenzoic Acid

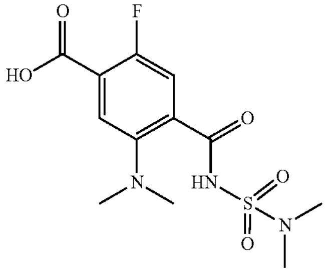 [SMILES: CN(C)c1cc(C(=O)O)c(F)cc1C(=O)NS(=O)(=O)N(C)C]

Prepared by an analogous method to Intermediate 134 specific procedure except the Step 2 was carried out with N,N-dimethylsulfamide in place of pyrrolidine-1-sulfonamide. Yield: 280 mg, 0.84 mmol. Yellow solid. LCMS: (System 1, Method A) Rt=0.46 min, m/z 332.0 $[M-H]^-$ $(ES^-)$.

Intermediate 252: 5-fluoro-2-methoxy-4-((pyrrolidin-1-ylsulfonyl)carbamoyl)benzoic Acid

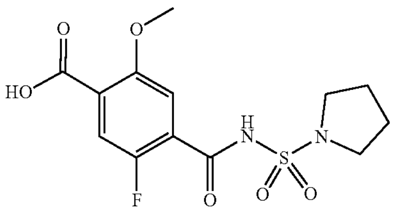 [SMILES: COc1cc(C(=O)NS(=O)(=O)N2CCCC2)c(F)cc1C(=O)O]

Prepared by an analogous method to Intermediate 40 starting from methyl 4-bromo-5-fluoro-2-methoxybenzoate (Intermediate 212, 2.0 g, 7.64 mmol). Yield: 500 mg, 1.44 mmol. White solid. LCMS: (System 1, Method A) Rt=0.35 min, m/z 345.0 $[M-H]^-$ $(ES^-)$.

Intermediate 253: 5-ethyl-2-methylbenzene-1,3-diol

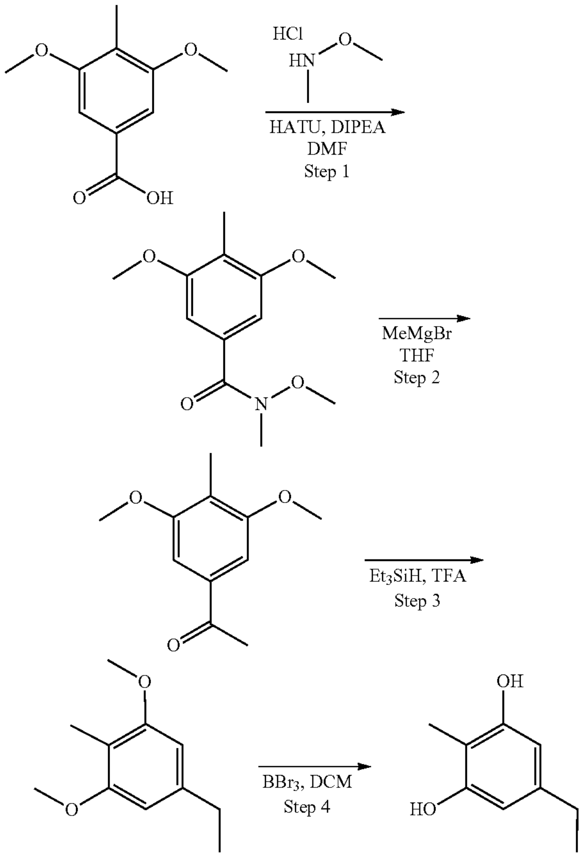

Step 1

To a solution of 3,5-dimethoxy-4-methylbenzoic acid (4 g, 20.4 mmol) in DMF (60 mL) was added HATU (8.53 g, 22.4 mmol), DIPEA (10.5 g, 81.6 mmol) and N,O-dimethylhydroxylamine hydrochloride (3.96 g, 40.8 mmol) at 0° C., then the mixture was stirred at room temperature for 4 hours. Water (180 mL) was added and the mixture was extracted with EtOAc (2×150 ml), the combined organic layers were washed with brine twice, dried over $Na_2SO_4$, filtered and concentrated under reduced pressure. The crude product was purified by column chromatography on silica gel (1-2% EtOAc/petroleum ether) to afford N,3,5-trimethoxy-N,4-dimethylbenzamide (4 g, 18.2 mmol) as a white solid. LCMS: (System 1, Method A). Rt=1.70 min. m/z 239.9 [M+H]+$(ES^+)$.

Step 2

To a solution of N,3,5-trimethoxy-N,4-dimethylbenzamide (4 g, 16.7 mmol) in THE (160 mL) was added Methylmagnesium bromide (3N in THF, 16.7 mL) at 0° C., then the mixture was stirred at 0° C. for 2 h under $N_2$ atmosphere. Sat. $NH_4Cl$ aq. (160 mL) was added slowly and the mixture was extracted with EtOAc (3×200 mL). The combined organic layers were dried over $Na_2SO_4$, filtered and concentrated under reduced pressure. The crude product was purified by column chromatography on silica gel (1-5% EtOAc/petroleum ether) to afford 1-(3,5-dimethoxy-4-methylphenyl)ethanone (3.2 g, 16.5 mmol) as a white solid. LCMS: (System 1, Method A). Rt=1.84 min. m/z 194.9 [M+H]+$(ES^+)$.

Step 3

To a solution of 1-(3,5-dimethoxy-4-methylphenyl)ethanone (3.2 g, 16.5 mmol) in TFA (50 mL) was added triethylsilane (5.8 g, 49.4 mmol) dropwise at 0° C. The solution was allowed to warm to room temperature and stirred at room temperature for 3 hours. The mixture was poured into ice-water (200 mL) slowly and extracted with DCM (3×200 mL). The combined organic layers were dried over $Na_2SO_4$, filtered and concentrated under reduced pressure. The crude product was purified by column chromatography on silica gel (1-5% EtOAc/petroleum ether) to afford 5-ethyl-1,3-dimethoxy-2-methylbenzene (2.25 g, 12.5 mmol) as a pale yellow solid. 1H NMR (400 MHz, DMSO-$d_6$) δ: 6.45 (s, 2H), 3.75 (s, 6H), 2.57-2.55 (m, 2H), 1.94 (s, 3H), 1.18 (t, J=7.6 Hz, 3H).

Step 4

To a solution of 5-ethyl-1,3-dimethoxy-2-methylbenzene (2.25 g, 12.5 mmol) in dichloromethane (60 mL) was added $BBr_3$ (1N in DCM, 62.4 mL) dropwise at 0° C. The mixture was allowed to warm to room temperature and stirred at room temperature overnight. The mixture was poured into ice-water (150 mL) slowly and extracted with DCM (3×150 mL); the combined organic layers were dried over $Na_2SO_4$, filtered and concentrated reduced pressure. The crude product was purified by column chromatography on silica gel (1-40% EtOAc/petroleum ether) to afford 5-ethyl-2-methylbenzene-1,3-diol (1.5 g, 9.86 mmol) as a white solid. LCMS: (System 1, Method A). Rt=1.46 min. m/z 151.4 $[M-H]^-$ $(ES^-)$.

Intermediate 254: tert-butyl 10-ethyl-7-methyl-5-oxo-8-(((trifluoromethyl)sulfonyl)oxy)-1,5-dihydro-2H-chromeno[3,4-c]pyridine-3(4H)-carboxylate

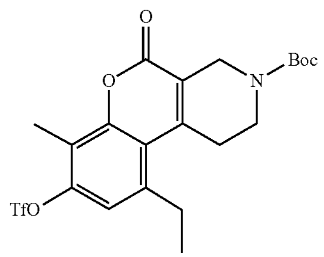 [SMILES: CCc1cc(OS(=O)(=O)C(F)(F)F)c(C)c2oc(=O)c3c(c12)CCN(C(=O)OC(C)(C)C)C3]

Prepared by an analogous method to Intermediate 2 starting from 5-ethyl-2-methylbenzene-1,3-diol (Intermediate 253, 1.46 g, 9.61 mmol). Yield: 530 mg, 1.08 mmol. Pale-yellow solid. LCMS: (System 1, Method A) Rt=2.61 min, m/z 436.0 $(M-56+H)^+$ $(ES^+)$.

Intermediate 255: (R)-10-ethyl-8-(3-(methoxymethyl)-4-methylpiperazin-1-yl)-7-methyl-1,2,3,4-tetrahydro-5H-chromeno[3,4-c]pyridin-5-one

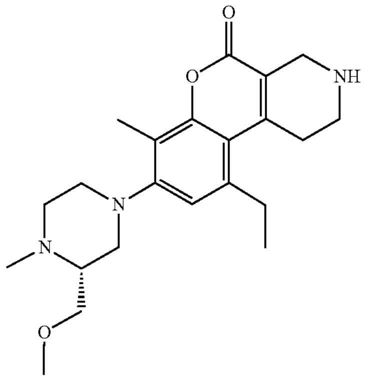 [SMILES: CCc1cc(N2CCN(C)[C@@H](COC)C2)c(C)c2oc(=O)c3c(c12)CCNC3]

Prepared by an analogous method to Intermediate 5 starting from (R)-2-(methoxymethyl)-1-methylpiperazine (Intermediate 1, 235 mg, 1.63 mmol) and tert-butyl 10-ethyl-7-methyl-5-oxo-8-(((trifluoromethyl)sulfonyl)oxy)-1,5-dihydro-2H-chromeno[3,4-c]pyridine-3(4H)-carboxylate (Intermediate 254, 530 mg, 1.08 mmol). Yield: 210 mg, 0.54 mmol. Brown solid. LCMS: (System 1, Method A) Rt=1.56 min, m/z 386.2 $(M+H)^+$ $(ES^+)$.

Intermediate 256: 5-chloro-2-methylbenzene-1,3-diol

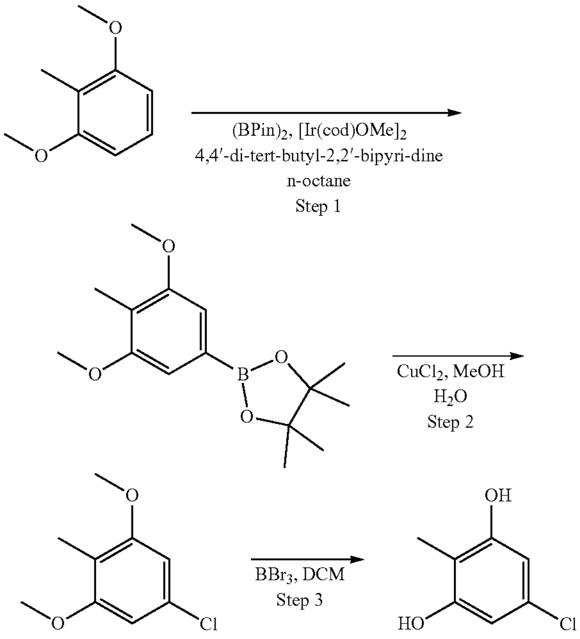

Step 1

A solution of (1,5-cyclooctadiene)(methoxy)iridium(I) dimer ($[Ir(cod)OMe]_2$, 185 mg, 0.28 mmol), 4,4'-di-tert-butyl-2,2'-bipyridine (148 mg, 0.55 mmol) and 4,4,4',4',5,5,5',5'-octamethyl-2,2'-bi(1,3,2-dioxaborolane) $(BPin)_2$, 10.0 g, 39.5 mmol) in n-octane (395 mL) was stirred at RT for 15 min, then 1,3-dimethoxy-2-methylbenzene (6.0 g, 39.47 mmol) was added and the mixture was stirred at 125° C. for 3 days under $N_2$ atmosphere. The mixture was cooled to RT and partitioned between water (300 mL) and EtOAc (300 mL×3). The combined organic layers were dried ($Na_2SO_4$), filtered and concentrated under reduced pressure. The crude product was purified by column chromatography on silica gel (n-hexane) to afford 2-(3,5-dimethoxy-4-methylphenyl)-4,4,5,5-tetramethyl-1,3,2-dioxaborolane (4.0 g, 14.39 mmol) as a white solid. LCMS: (System 1, Method A) Rt=2.18 min, m/z 279.2 $(M+H)^+$ $(ES^+)$.

Step 2

A mixture of 2-(3,5-dimethoxy-4-methylphenyl)-4,4,5,5-tetramethyl-1,3,2-dioxaborolane (4.0 g, 14.39 mmol) and copper(II) chloride (5.8 g, 43.2 mmol) in MeOH (80 mL) and water (80 ml) was stirred at 80° C. for 5 h under air atmosphere. MeOH was removed under reduced pressure, and the aqueous mixture was extracted with EtOAc (3×80 mL). The combined organic layers were dried over ($Na_2SO_4$), filtered and concentrated under reduced pressure. The crude product was purified by column chromatography on silica gel (1-5% EtOAc/Petroleum ether) to afford 5-chloro-1,3-dimethoxy-2-methylbenzene (2.0 g, 10.8 mmol) as a white solid. $^1H$ NMR (400 MHz, DMSO-$d_6$) δ: 6.69 (s, 2H), 3.78 (s, 6H), 1.95 (s, 3H).

Step 3

Boron tribromide 1N solution in DCM (54 mL) was added dropwise to a solution of 5-chloro-1,3-dimethoxy-2-methylbenzene in DCM (100 mL) at 0° C. The solution was allowed to reach RT and stirred at this temperature overnight. The mixture was slowly poured into ice-water (200 mL) and extracted with EtOAc (3×200 mL). The combined organic layers were dried ($Na_2SO_4$), filtered and concentrated under reduced pressure. The crude product was purified by column chromatography on silica gel (1-50% EtOAc/petroleum ether) to afford 5-chloro-2-methylbenzene-1,3-diol (1.6 g, 10.1 mmol) as a pale-yellow solid. LCMS: (System 1, Method A) Rt=1.45 min, m/z 157.2 $(M-H)^-$ $(ES^-)$.

Alternative Procedure

To a solution of 1,3-dibromo-5-chloro-2-methylbenzene (40.0 g, 141.8 mmol) in dioxane (700 mL) and water (700 mL) was added NaOH (56.7 g, 1418 mmol), $Pd_2(dba)_3$ (3.25 g, 3.55 mmol) and t-BuXPhos (3.01 g, 7.09 mmol). The reaction mixture was stirred at 110° C. for 3 h under nitrogen atmosphere. The reaction mixture was washed with DCM (3×700 mL), the pH of the aqueous layer was adjusted 5 with 1N HCl and extracted with EtOAc (3×700 mL). The combined organic layers were dried over anhydrous $Na_2SO_4$, filtered and concentrated at 35° C. under reduced pressure to give the crude product, which was purified by silica gel column chromatography (20-80% EtOAc/petroleum ether) to give 5-chloro-2-methylbenzene-1,3-diol (20.0 g, 89% yield) as a white solid.

Intermediate 257: tert-butyl 10-chloro-7-methyl-5-oxo-8-(((trifluoromethyl)sulfonyl)oxy)-1,5-dihydro-2H-chromeno[3,4-c]pyridine-3(4H)-carboxylate

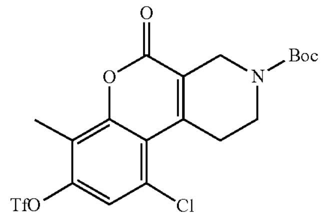 [SMILES: Cc1c(OS(=O)(=O)C(F)(F)F)cc(Cl)c2c3c(c(=O)oc12)CN(C(=O)OC(C)(C)C)CC3]

Prepared by an analogous method to Intermediate 2 starting from 5-chloro-2-methylbenzene-1,3-diol (Intermediate 256, 1.0 g, 10.13 mmol). Yield: 2.0 g, 4.0 mmol. Pale-yellow solid. LCMS: (System 1, Method A) Rt=2.29 min, m/z 497.0 $(M-56+H)^+$ $(ES^+)$.

Specific Method

Step 1

A solution of 5-chloro-2-methylbenzene-1,3-diol (16.0 g, 101.3 mmol) and ethyl 4-oxopiperidine-3-carboxylate hydrochloride (17.3 g, 101.3 mmol) in sulfuric acid (64%, 200 mL) was stirred at room temperature overnight. Ice water (500 mL) was added and the mixture was stirred at room temperature for 1 h. The precipitate was collected by filtration, washed with water then hexane, dried under reduced pressure to give 10-chloro-8-hydroxy-7-methyl-3,4-dihydro-1H-chromeno[3,4-c]pyridin-5(2H)-one (16.0 g, 60% yield) as an off-white solid. LCMS: (System 1, Method A). Rt=1.213 min, m/z 266.4 $(M+H)^+$ $(ES^+)$.

Step 2

To a suspension of 10-chloro-8-hydroxy-7-methyl-3,4-dihydro-1H-chromeno[3,4-c]pyridin-5(2H)-one (16.0 g, 60.4 mmol) in THE (500 mL) was added sat. aq. $NaHCO_3$ (500 mL) and di-tert-butyl dicarbonate (14.5 g, 66.4 mmol). The reaction mixture was stirred at room temperature overnight. The reaction mixture was extracted with ethyl acetate (3×500 mL), the organic phase was dried over anhydrous $Na_2SO_4$, concentrated at 35° C. under reduced pressure to give the crude product which was dried under reduced pressure to give tert-butyl 10-chloro-8-hydroxy-7-methyl-5-oxo-4,5-dihydro-1H-chromeno[3,4-c]pyridine-3(2H)-carboxylate (18.0 g, 82% yield) as an off-white solid. LCMS: (System 1, Method A). Rt=1.85 min, m/z 310.0 $(M-56+H)^+$ $(ES^+)$.

Step 3

To a suspension of tert-butyl 10-chloro-8-hydroxy-7-methyl-5-oxo-4,5-dihydro-1H-chromeno[3,4-c]pyridine-3(2H)-carboxylate (18.0 g, 49.3 mmol) in dichloromethane (500 mL) was added pyridine (15.6 g, 197.2 mmol), the mixture was cooled to 0° C. then $Tf_2O$ (27.8 g, 98.6 mmol) was added dropwise at 0° C. The solution was allowed to warm to room temperature and stirred at room temperature for 1 h. Water (500 mL) was added. The organic phase was separated, washed with aq. $CuSO_4$ (3×500 mL), dried over anhydrous $Na_2SO_4$, concentrated at 35° C. under reduced pressure to give the crude product, which was purified by silica gel column chromatography (1-5% MeOH/DCM) to give tert-butyl 10-chloro-7-methyl-5-oxo-8-(((trifluoromethyl)sulfonyl)oxy)-4,5-dihydro-1H-chromeno[3,4-c]pyridine-3(2H)-carboxylate (20.0 g, 55% yield) as a pale yellow solid. LCMS: (System 1, Method A). Rt=2.29 min. m/z 442.0 $(M-56+H)^+$ $(ES^+)$.

Intermediate 258: (R)-10-chloro-8-(3-(methoxymethyl)-4-methylpiperazin-1-yl)-7-methyl-1,2,3,4-tetrahydro-5H-chromeno[3,4-c]pyridin-5-one

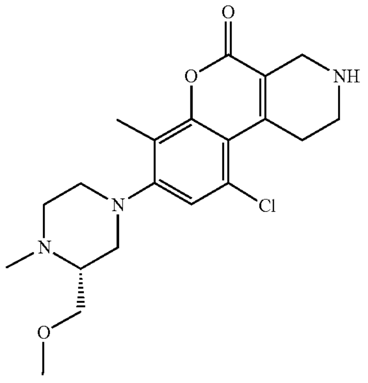 [SMILES: COC[C@H]1CN(c2cc(Cl)c3c4c(c(=O)oc3c2C)CNCC4)CCN1C]

Prepared by an analogous method to Intermediate 5 starting from (R)-2-(methoxymethyl)-1-methylpiperazine (Intermediate 1, 871 mg, 6.0 mmol) and tert-butyl 10-chloro-7-methyl-5-oxo-8-(((trifluoromethyl)sulfonyl)oxy)-1,5-dihydro-2H-chromeno[3,4-c]pyridine-3(4H)-carboxylate (Intermediate 257, 2.0 g, 4.0 mmol). Yield: 500 mg, 1.28 mmol. Brown solid. LCMS: (System 1, Method A) Rt=1.58 min, m/z 392.2 $(M+H)^+$ $(ES^+)$.

Intermediate 259: 4-((N-cyclopropyl-N-methylsulfamoyl)carbamoyl)-5-ethoxy-2-fluorobenzoic acid

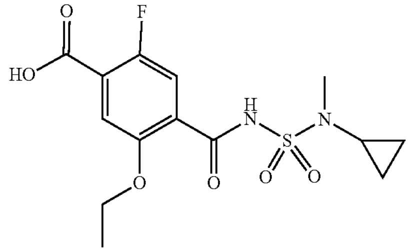 [SMILES: CCOc1cc(C(=O)O)c(F)cc1C(=O)NS(=O)(=O)N(C)C1CC1]

Prepared by an analogous method to Intermediate 181 except the Step 4 was carried out with N-cyclopropyl-N-methylsulfamide (Intermediate 249) in place of N,N-dicyclopropylsulfamide. Yield: 123 mg, 0.34 mmol. Off-white solid. LCMS: (System 3, Method J) Rt=1.24 min, m/z 376.0 $(M-H)^-$ $(ES^-)$.

Intermediate 260: 5-fluoro-2-methyl-4-((pyrrolidin-1-ylsulfonyl)carbamoyl)benzoic Acid

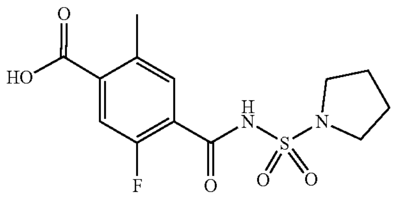 [SMILES: Cc1cc(C(=O)NS(=O)(=O)N2CCCC2)c(F)cc1C(=O)O]

Prepared by an analogous method to Intermediate 10 (Step 3 to Step 5 only) starting from 4-bromo-2-fluoro-5-methylbenzoic acid (1.0 g, 4.29 mmol). Yield: 179 mg, 0.54 mmol. Off-White solid. LCMS: (System 3, Method J) Rt=1.50 min, m/z 329.2 $(M-H)^-$ $(ES^-)$ Intermediate 261: 2-oxa-5-azaspiro[3.5]nonane-5-sulfonamide

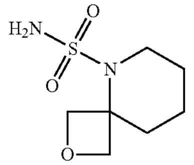 [SMILES: NS(=O)(=O)N1CCCCC12COC2]

Prepared by an analogous method to Intermediate 148 starting from 2-oxa-5-azaspiro[3.5]nonane hemioxalate (2.0 g, 5.81 mmol), sulfuric diamide (0.84 g, 8.72 mmol). Yield: 0.8 g, 3.88 mmol. Off-white solid. $^1$H NMR (400 MHz, DMSO-$d_6$) δ: 6.94 (s, 2H), 4.79 (d, J=6.8 Hz, 2H), 4.18 (d, J=6.8 Hz, 2H), 3.10-3.06 (m, 2H), 1.98-1.95 (m, 2H), 1.69-1.66 (m, 2H), 1.52-1.49 (m, 2H).

Intermediate 262: 4-(((2-oxa-5-azaspiro[3.5]nonan-5-yl)sulfonyl)carbamoyl)-5-(dimethylamino)-2-fluorobenzoic Acid

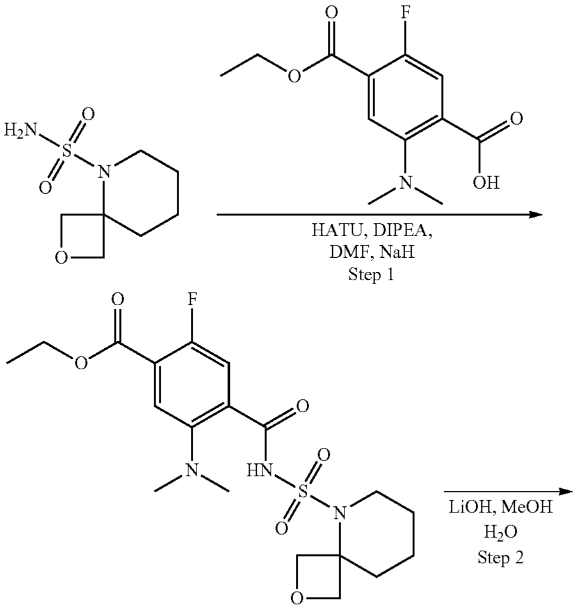

-continued

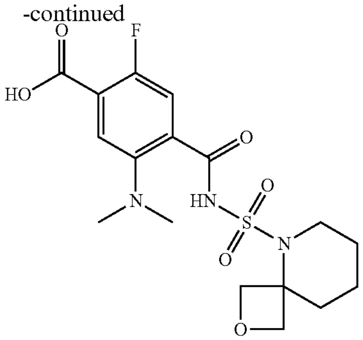

Step 1

A solution of 2-(dimethylamino)-4-(ethoxycarbonyl)-5-fluorobenzoic acid (400 mg, 1.57 mmol), HATU (715 mg, 1.88 mmol), DIPEA (810 mg, 6.28 mmol) in DMF (15 mL) was stirred at room temperature for 1 h, then 2-oxa-5-azaspiro[3.5]nonane-5-sulfonamide (647 mg, 3.14 mmol) and NaH (60%, 251 mg, 6.28 mmol) were added and the reaction mixture was stirred at room temperature overnight. The pH of the mixture was adjusted to 4 with 1N HCl aq. and the mixture was extracted with ethyl acetate (3×15 mL). The combined organic layers were dried over $Na_2SO_4$, filtered and concentrated at 35° C. under reduced pressure to give the crude materials, which was purified by column chromatography on silica gel (1-25% EtOAc/petroleum ether) to afford ethyl 4-((2-oxa-5-azaspiro[3.5]nonan-5-ylsulfonyl)carbamoyl)-5-(dimethylamino)-2-fluorobenzoate (200 mg, 0.45 mmol) as yellow oil. LCMS: (System 1, Method A) Rt=1.47 min, m/z 444.0 $(M+H)^+$ $(ES^+)$.

Step 2

To a solution of ethyl 4-((2-oxa-6-azaspiro[3.5]nonan-6-ylsulfonyl)carbamoyl)-5-(dimethylamino)-2-fluorobenzoate (200 mg, 0.45 mmol) in THE (5 mL) and MeOH (2 mL) was added a solution of $LiOH{\cdot}H_2O$ (76 mg, 1.80 mmol) in water (1 mL). The reaction mixture was stirred at room temperature for 3 h. The pH of the mixture was adjusted to 8 with 1N HCl aq., MeOH and THE was removed at 35° C. under reduced pressure, and the pH of the mixture was adjusted to 3 with 1N HCl aq. The formed precipitate was collected by filtration, washed with water then hexane and dried at 35° C. under reduced pressure to give 4-((2-oxa-5-azaspiro[3.5]nonan-5-ylsulfonyl)carbamoyl)-5-(dimethylamino)-2-fluorobenzoic acid (150 mg, 0.36 mmol) as a yellow solid. LCMS: (System 1, Method A) Rt=1.08 min, m/z 414.0 $(M-H)^-$ $(ES^-)$.

Intermediate 263: 2-oxa-6-azaspiro[3.5]nonane-6-sulfonamide

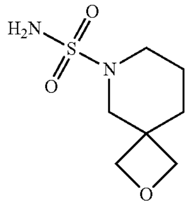 [SMILES: NS(=O)(=O)N1CCCC2(COC2)C1]

Prepared by an analogous method to Intermediate 148 starting from 2-oxa-6-azaspiro[3.5]nonane (1 g, 7.87 mmol), sulfuric diamide (1.13 g, 11.8 mmol). Yield: 1.3 g, 6.31 mmol. White solid. $^1$H NMR (400 MHz, DMSO-$d_6$) δ: 6.79 (s, 2H), 4.27 (d, J=6.0 Hz, 2H), 4.21 (d, J=6.0 Hz, 2H), 3.12 (s, 2H), 2.86 (t, J=5.6 Hz, 2H), 1.69 (t, J=6.0 Hz, 2H), 1.52-1.47 (m, 2H).

Intermediate 264: 4-(((2-oxa-6-azaspiro[3.5]nonan-6-yl)sulfonyl)carbamoyl)-5-(dimethylamino)-2-fluorobenzoic acid

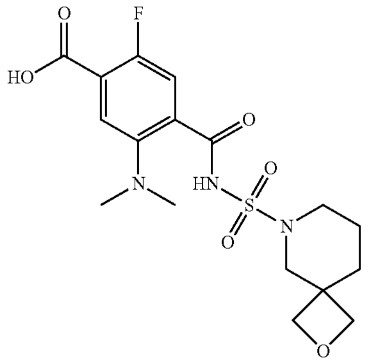 [SMILES: CN(C)c1cc(C(=O)O)c(F)cc1C(=O)NS(=O)(=O)N1CCCC2(COC2)C1]

Prepared by analogous method to Intermediate 262 except the Step 1 was carried out with 2-oxa-6-azaspiro[3.5]nonane-6-sulfonamide (Intermediate 263, 400 mg, 1.57 mmol) in place of 2-oxa-5-azaspiro[3.5]nonane-5-sulfonamide. Yield: 330 mg, 0.80 mmol. White solid. LCMS: (System 1, Method A) Rt=0.98 min, m/z 414.0 $(M+H)^+$ $(ES^+)$.

Intermediate 265: 2-oxa-6-azaspiro[3.4]octane-6-sulfonamide

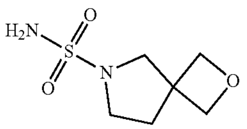 [SMILES: NS(=O)(=O)N1CCC2(COC2)C1]

Prepared by an analogous method to Intermediate 148 starting from 2-oxa-6-azaspiro[3.4]octane (1 g, 8.85 mmol), sulfuric diamide (1 g, 10.6 mmol). Yield: 1.2 g, 6.25 mmol. Yellow solid. $^1$H NMR (400 MHz, DMSO-$d_6$) δ: 6.75 (s, 2H), 5.54 (d, J=6.0 Hz, 2H), 4.44 (d, J=6.0 Hz, 2H), 3.34 (s, 2H), 3.10 (t, J=6.8 Hz, 2H), 2.11 (d, J=6.8 Hz, 2H).

Intermediate 266: 4-(((2-oxa-6-azaspiro[3.4]octan-6-yl)sulfonyl)carbamoyl)-5-(dimethylamino)-2-fluorobenzoic Acid

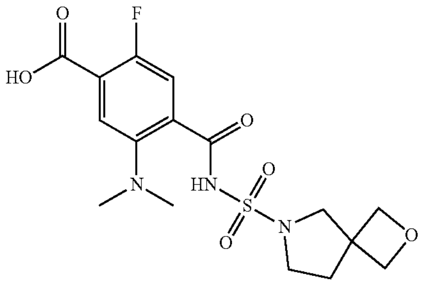 [SMILES: CN(C)c1cc(C(=O)O)c(F)cc1C(=O)NS(=O)(=O)N1CCC2(COC2)C1]

Prepared by analogous method to Intermediate 262 except the Step 1 was carried out with 2-oxa-6-azaspiro[3.4]octane-6-sulfonamide (Intermediate 265, 602 mg, 3.14 mmol) in place of 2-oxa-5-azaspiro[3.5]nonane-5-sulfonamide. Yield: 320 mg, 0.79 mmol. Yellow solid. LCMS: (System 1, Method A) Rt=0.52 min, m/z 401.7 $(M+H)^+$ $(ES^+)$.

Intermediate 267: 5-azaspiro[2.4]heptane-5-sulfonamide

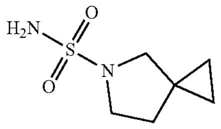 [SMILES: NS(=O)(=O)N1CCC2(CC2)C1]

Prepared by an analogous method to Intermediate 148 starting from 5-azaspiro[2.4]heptane hydrochloride (1 g, 7.52 mmol), sulfuric diamide (1.08 g, 11.3 mmol). Yield: 0.7 g, 3.98 mmol. White solid. $^1$H NMR (400 MHz, DMSO-$d_6$) δ: 6.72 (s, 2H), 3.25 (t, J=7.2 Hz, 2H), 3.01 (s, 2H), 1.76 (t, J=7.2 Hz, 2H), 0.61-0.52 (m, 4H).

Intermediate 268: 4-((5-azaspiro[2.4]heptan-5-ylsulfonyl)carbamoyl)-5-(dimethylamino)-2-fluorobenzoic Acid

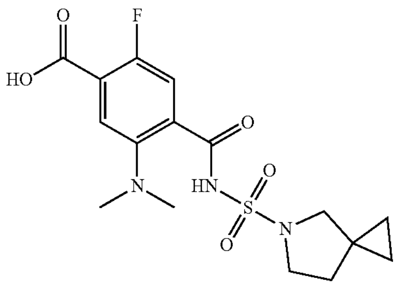 [SMILES: CN(C)c1cc(C(=O)O)c(F)cc1C(=O)NS(=O)(=O)N1CCC2(CC2)C1]

Prepared by analogous method to Intermediate 262 except the Step 1 was carried out with 5-azaspiro[2.4]heptane-5-sulfonamide (Intermediate 267, 691 mg, 3.93 mmol) in place of 2-oxa-5-azaspiro[3.5]nonane-5-sulfonamide. Yield: 300 mg, 0.79 mmol. Yellow solid. LCMS: (System 1, Method A) Rt=0.52 min, m/z 401.7 $(M+H)^+$ $(ES^+)$.

Intermediate 269: 5-(dimethylamino)-2-fluoro-4-((piperidin-1-ylsulfonyl)carbamoyl)benzoic Acid

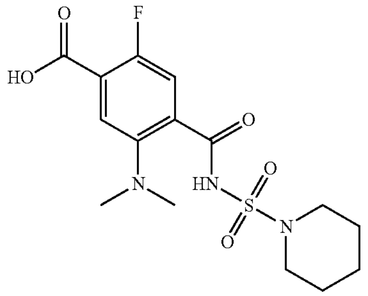 [SMILES: CN(C)c1cc(C(=O)O)c(F)cc1C(=O)NS(=O)(=O)N1CCCCC1]

Prepared by analogous method to Intermediate 262 except the Step 1 was carried out with piperidine-1-sulfonamide (385 mg, 2.35 mmol) in place of 2-oxa-5-azaspiro[3.5]nonane-5-sulfonamide. Yield: 360 mg, 0.97 mmol. Yellow solid. LCMS: (System 1, Method A) Rt=1.13 min, m/z 372.2 $(M+H)^+$ $(ES^+)$.

Intermediate 270: 4-((N,N-dicyclopropylsulfamoyl)carbamoyl)-5-(dimethylamino)-2-fluorobenzoic Acid

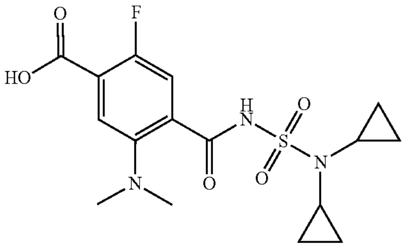 [SMILES: CN(C)c1cc(C(=O)O)c(F)cc1C(=O)NS(=O)(=O)N(C1CC1)C1CC1]

Prepared by analogous method to Intermediate 262 except the Step 1 was carried out with N,N-dicyclopropylsulfamide (Intermediate 180, 963 mg, 5.47 mmol) in place of 2-oxa-5-azaspiro[3.5]nonane-5-sulfonamide. Yield: 500 mg, 1.30 mmol. Yellow solid. LCMS: (System 1, Method A) Rt=1.75 min, m/z 414.3 $(M+H)^+$ $(ES^+)$.

Intermediate 271: (R)-2-(trifluoromethyl)pyrrolidine-1-sulfonamide

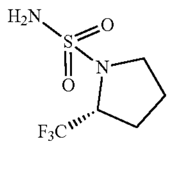

Prepared by an analogous method to Intermediate 148 starting from (R)-2-(trifluoromethyl)pyrrolidine hydrochloride (1.0 g, 5.75 mmol), sulfuric diamide (732 mg, 7.47 mmol). Yield: 0.7 g, 3. 21 mmol. White solid. $^1H$ NMR (400 MHz, DMSO) δ: 7.03 (s, 2H), 4.31-4.26 (m, 1H), 3.44-3.38 (m, 1H), 3.24-3.19 (m, 1H), 2.07-1.84 (m, 4H).

Intermediate 272: (R)-5-(dimethylamino)-2-fluoro-4-(((2-(trifluoromethyl)pyrrolidin-1-yl)sulfonyl)carbamoyl)benzoic Acid

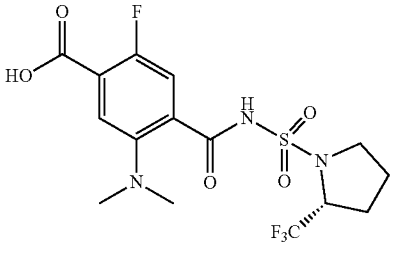 [SMILES: CN(C)c1cc(C(=O)O)c(F)cc1C(=O)NS(=O)(=O)N1CCC[C@@H]1C(F)(F)F]

Prepared by analogous method to Intermediate 262 except the Step 1 was carried out (R)-2-(trifluoromethyl)pyrrolidine-1-sulfonamide (Intermediate 271, 513 mg, 2.35 mmol) in place of 2-oxa-5-azaspiro[3.5]nonane-5-sulfonamide. Yield: 350 mg, 0.78 mmol. Yellow solid. LCMS: (System 1, Method A) Rt=1.72 min, m/z 456.3 $(M+H)^+$ $(ES^+)$.

Intermediate 273: 4-((2-azaspiro[3.3]heptan-2-ylsulfonyl)carbamoyl)-3-methoxybenzoic Acid

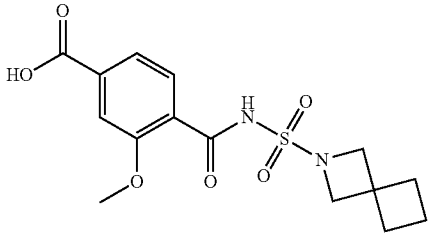 [SMILES: COc1cc(C(=O)O)ccc1C(=O)NS(=O)(=O)N1CC2(CCC2)C1]

Prepared by an analogous method to Intermediate 213 starting from methyl 4-bromo-2-methoxybenzoate except the Step 3 was carried out with 2-azaspiro[3.3]heptane-2-sulfonamide (Intermediate 186, 473 mg, 2.69 mmol) in place of pyrrolidine-1-sulfonamide. Yield: 280 mg, 0.79 mmol. White solid. LCMS: (System 1, Method A) Rt=0.83 min, m/z 353.0 $(M-H)^-$ $(ES^-)$.

Intermediate 274: 4-((2-azaspiro[3.3]heptan-2-ylsulfonyl)carbamoyl)-3-methoxybenzoic Acid

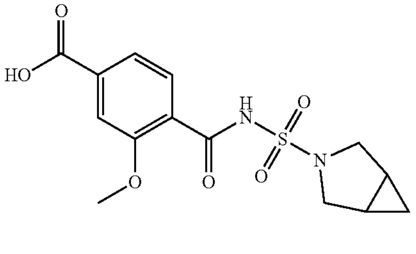 [SMILES: COc1cc(C(=O)O)ccc1C(=O)NS(=O)(=O)N1CC2CC2C1]

Prepared by an analogous method to Intermediate 213 starting from methyl 4-bromo-2-methoxybenzoate except the Step 3 was carried out with 3-azabicyclo[3.1.0]hexane-3-sulfonamide (Intermediate 168, 473 mg, 2.69 mmol) in place of pyrrolidine-1-sulfonamide. Yield: 280 mg, 0.88 mmol. White solid. LCMS: (System 1, Method A) Rt=0.61 min, m/z 339.0 $(M-H)^-$ $(ES^-)$.

Intermediate 275: (S)-3-methoxypiperidine-1-sulfonamide

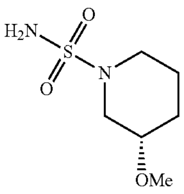 [SMILES: CO[C@H]1CCCN(S(N)(=O)=O)C1]

Prepared by an analogous method to Intermediate 148 starting from (S)-3-methoxypiperidine hydrochloride (1 g, 6.59 mmol), sulfuric diamide (824 mg, 8.57 mmol) Yield: 0.7 g, 3.60 mmol. White solid. $^1H$ NMR (400 MHz, DMSO-$d_6$) δ: 6.74 (s, 2H), 3.35-3.28 (m, 2H), 3.26 (s, 3H), 3.14-3.09 (m, 1H), 2.69-2.63 (m, 1H), 2.59-2.54 (m, 1H), 1.86-1.82 (m, 1H), 1.77-1.71 (m, 1H), 1.49-1.42 (m, 1H), 1.30-1.24 (m, 1H).

Intermediate 276: (S)-5-(dimethylamino)-2-fluoro-4-(((3-methoxypiperidin-1-yl)sulfonyl)carbamoyl) benzoic Acid

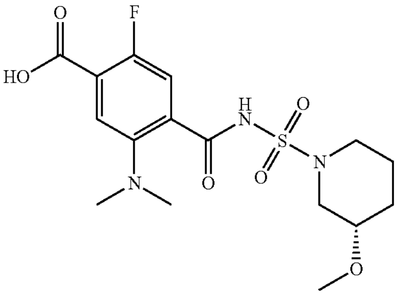 [SMILES: CO[C@H]1CCCN(S(=O)(=O)NC(=O)c2cc(F)c(C(=O)O)cc2N(C)C)C1]

Prepared by analogous method to Intermediate 262 except the Step 1 was carried out (S)-3-methoxypiperidine-1-sulfonamide (Intermediate 275, 457 mg, 2.35 mmol) in place of 2-oxa-5-azaspiro[3.5]nonane-5-sulfonamide. Yield: 320 mg, 0.79 mmol. White solid. LCMS: (System 1, Method A) Rt=0.94 min, m/z 402.2 $(M-H)^-$ $(ES^-)$.

Intermediate 277: 2-oxa-6-azaspiro[3.3]heptane-6-sulfonamide

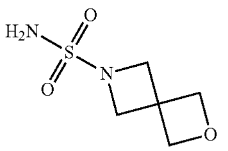 [SMILES: NS(=O)(=O)N1CC2(COC2)C1]

Prepared by an analogous method to Intermediate 148 starting from 2-Oxa-6-azaspiro[3.3]heptane hemioxalate (5.0 g, 17.4 mmol), sulfuric diamide (4.2 g, 43.4 mmol. Yield: 0.7 g, 4 mmol. Light yellow solid. $^1H$ NMR (400 MHz, DMSO-d6) δ: 6.89 (s, 2H), 4.63 (s, 4H), 3.86 (s, 4H).

Intermediate 278: 4-(((2-oxa-6-azaspiro[3.3]heptan-6-yl)sulfonyl)carbamoyl)-5-(dimethylamino)-2-fluorobenzoic Acid

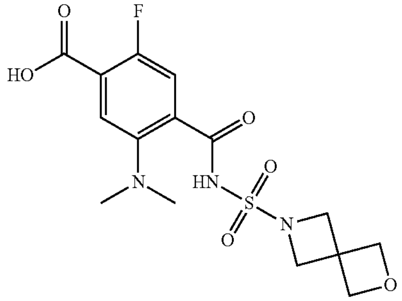 [SMILES: CN(C)c1cc(C(=O)O)c(F)cc1C(=O)NS(=O)(=O)N1CC2(COC2)C1]

Prepared by analogous method to Intermediate 262 except the Step 1 was carried out with 2-oxa-6-azaspiro[3.3]heptane-6-sulfonamide (Intermediate 277, 419 mg, 2.35 mmol) in place of 2-oxa-5-azaspiro[3.5]nonane-5-sulfonamide. Yield: 300 mg, 0.77 mmol. White solid. LCMS: (System 1, Method A) Rt=0.31 min, m/z 387.8 $(M+H)^+$ $(ES^+)$.

Intermediate 279: (S)-2-(methoxymethyl)pyrrolidine-1-sulfonamide

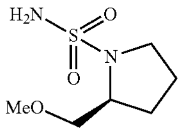

Prepared by an analogous method to Intermediate 148 starting from (S)-2-(methoxymethyl)pyrrolidine (2.0 g, 17.39 mmol) and sulfuric diamide (2.04 g, 20.87 mmol) Yield: 2.0 g, 10.3 mmol. White solid. $^1H$ NMR (400 MHz, DMSO) δ: 6.75 (s, 2H), 3.69-3.66 (m, 1H), 3.41-3.38 (m, 1H), 3.25 (s, 3H), 3.19-3.09 (m, 3H), 1.81-1.75 (m, 4H).

Intermediate 280: (S)-2-(methoxymethyl)pyrrolidine-1-sulfonamide

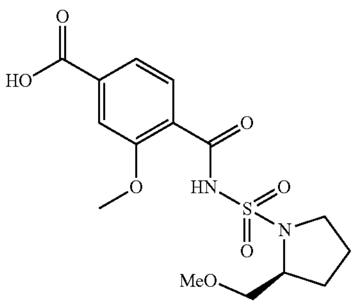 [SMILES: COC[C@@H]1CCCN1S(=O)(=O)NC(=O)c1ccc(C(=O)O)cc1OC]

Prepared by an analogous method to Intermediate 213 starting from methyl 4-bromo-2-methoxybenzoate except the Step 3 was carried out with (S)-2-(methoxymethyl) pyrrolidine-1-sulfonamide (Intermediate 279, 520 mg, 2.68 mmol) in place of pyrrolidine-1-sulfonamide. Yield: 320 mg, 0.86 mmol. White solid. LCMS: (System 1, Method A) Rt=0.87 min, m/z 371.0 $(M-H)^-$ $(ES^-)$.

Intermediate 281: (S)-3-methoxypyrrolidine-1-sulfonamide

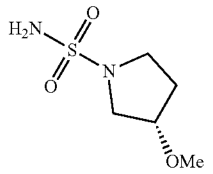 [SMILES: CO[C@H]1CCN(S(N)(=O)=O)C1]

Prepared by an analogous method to Intermediate 148 starting from (S)-3-methoxypyrrolidine hydrochloride (2 g, 14.60 mmol), sulfuric diamide (2.10 g, 21.90 mmol). Yield: 1.2 g, 6.67 mmol. White solid. $^1H$ NMR (400 MHz, DMSO) δ: 6.73 (s, 2H), 3.97-3.94 (m, 1H), 3.26-3.21 (m, 4H), 3.15-3.07 (m, 3H), 1.94-1.86 (m, 2H).

Intermediate 282: (S)-5-(dimethylamino)-2-fluoro-4-(((3-methoxypyrrolidin-1-yl)sulfonyl)carbamoyl) benzoic Acid

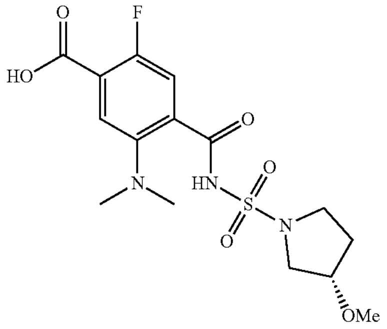 [SMILES: CO[C@H]1CCN(S(=O)(=O)NC(=O)c2cc(F)c(C(=O)O)cc2N(C)C)C1]

Prepared by analogous method to Intermediate 262 except the Step 1 was carried out with (S)-3-methoxypyrrolidine-1-sulfonamide (Intermediate 281, 425 mg, 2.36 mmol) in place of 2-oxa-5-azaspiro[3.5]nonane-5-sulfonamide. Yield: 310 mg, 0.80 mmol. White solid. LCMS: (System 1, Method A) Rt=0.74 min, m/z 388.0 $(M+H)^+$ $(ES^+)$.

Intermediate 283: (R)-3-methoxypyrrolidine-1-sulfonamide

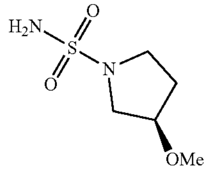 [SMILES: CO[C@@H]1CCN(S(N)(=O)=O)C1]

Prepared by an analogous method to Intermediate 148 starting from (R)-3-methoxypyrrolidine hydrochloride (2 g, 14.60 mmol), sulfuric diamide (2.10 g, 21.90 mmol). Yield: 1.8 g, 10.0 mmol. White solid. $^1H$ NMR (400 MHz, DMSO) δ: 6.73 (s, 2H), 3.97-3.94 (m, 1H), 3.26-3.21 (m, 4H), 3.15-3.07 (m, 3H), 1.94-1.86 (m, 2H)

Intermediate 284: (R)-5-(dimethylamino)-2-fluoro-4-(((3-methoxypyrrolidin-1-yl)sulfonyl)carbamoyl) benzoic Acid

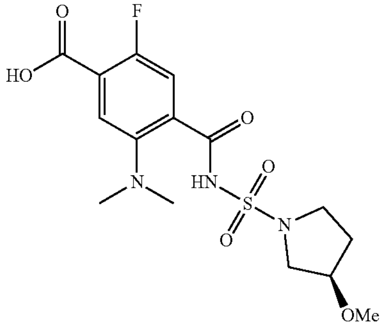 [SMILES: CO[C@@H]1CCN(S(=O)(=O)NC(=O)c2cc(F)c(C(=O)O)cc2N(C)C)C1]

Prepared by analogous method to Intermediate 262 except the Step 1 was carried out with (R)-3-methoxypyrrolidine-1-sulfonamide (Intermediate 283, 425 mg, 2.36 mmol) in place of 2-oxa-5-azaspiro[3.5]nonane-5-sulfonamide. Yield: 325 mg, 0.83 mmol. Yellow solid. LCMS: (System 1, Method A) Rt=0.86 min m/z 387.8 $(M+H)^+$ $(ES^+)$.

Intermediate 285: (R)-3-methoxypiperidine-1-sulfonamide

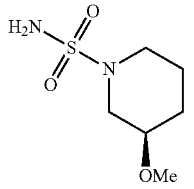 [SMILES: CO[C@@H]1CCCN(S(N)(=O)=O)C1]

Prepared by an analogous method to Intermediate 148 starting from (R)-3-methoxypiperidine hydrochloride (1 g, 6.67 mmol), sulfuric diamide (1.28 g, 13.3 mmol). Yield: 800 mg, 4.11 mmol. White solid. $^1H$ NMR (400 MHz, DMSO) δ: 6.74 (s, 2H), 3.35-3.28 (i, 2H), 3.26 (s, 3H), 3.14-3.09 (m, 1H), 2.69-2.63 (m, 1H), 2.59-2.54 (m, 1H), 1.86-1.82 (m, 1H), 1.77-1.71 (m, 1H), 1.51-1.41 (M, 1H), 1.31-1.22 (min, 1H).

Intermediate 286: (R)-5-(dimethylamino)-2-fluoro-4-(((3-methoxypiperidin-1-yl)sulfonyl)carbamoyl) benzoic Acid

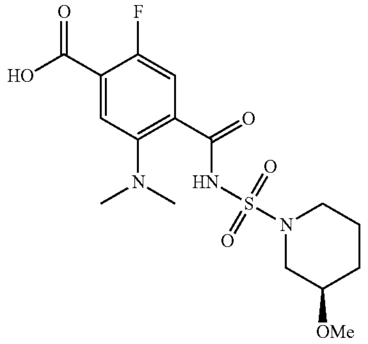 [SMILES: CO[C@@H]1CCCN(S(=O)(=O)NC(=O)c2cc(F)c(C(=O)O)cc2N(C)C)C1]

Prepared by analogous method to Intermediate 262 except the Step 1 was carried out with (R)-3-methoxypiperidine-1-sulfonamide (Intermediate 285, 457 mg, 2.36 mmol) in place of 2-oxa-5-azaspiro[3.5]nonane-5-sulfonamide. Yield: 320 mg, 0.72 mmol. Yellow oil. LCMS: (System 1, Method A) Rt=1.01 min, m/z 402.0 $(M-H)^-$ $(ES^-)$.

Intermediate 287: (R)-2-(methoxymethyl)pyrrolidine-1-sulfonamide

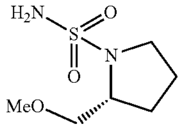 [SMILES: COC[C@H]1CCCN1S(N)(=O)=O]

Prepared by an analogous method to Intermediate 148 starting from (R)-2-(methoxymethyl)pyrrolidine (1 g, 8.68 mmol), sulfuric diamide (0.97 g, 10 mmol). Yield: 670 mg, 3.45 mmol. White solid. $^1$H NMR (400 MHz, DMSO-D6) δ 6.77 (s, 2H), 3.70 (s, 1H), 3.45-3.42 (m, 1H), 3.29 (s, 3H), 3.23-3.13 (m, 3H), 1.87-1.78 (m, 4H)

Intermediate 288: (R)-2-(methoxymethyl)pyrrolidine-1-sulfonamide

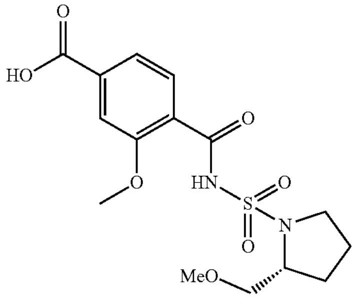 [SMILES: COC[C@H]1CCCN1S(=O)(=O)NC(=O)c1ccc(C(=O)O)cc1OC]

Prepared by analogous method to Intermediate 262 except the Step 1 was carried out with (R)-2-(methoxymethyl) pyrrolidine-1-sulfonamide (Intermediate 287, 400 mg, 1 mmol) in place of 2-oxa-5-azaspiro[3.5]nonane-5-sulfonamide. Yield: 340 mg, 0.92 mmol. Off-white solid. LCMS: (System 1, Method A) Rt=0.69 min, m/z 371.0 $(M-H)^-$ $(ES^-)$.

Intermediate 289: 4-methoxypiperidine-1-sulfonamide

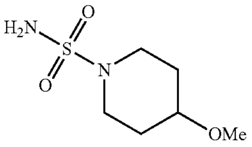 [SMILES: COC1CCN(S(N)(=O)=O)CC1]

Prepared by an analogous method to Intermediate 148 starting from 4-methoxypiperidine (2 g, 17.4 mmol), sulfuric diamide (2 g, 20.9 mmol). Yield: 2 g, 3.45 mmol. Light-yellow solid. $^1$H NMR (400 MHz, DMSO-d6) δ: 6.71 (s, 2H), 3.31-3.27 (m, 1H), 3.24 (s, 3H), 3.18-3.12 (m, 2H), 3.82-3.77 (m, 2H), 1.87-1.81 (m, 2H), 1.58-1.51 (m, 2H)

Intermediate 290: 5-(dimethylamino)-2-fluoro-4-(((4-methoxypiperidin-1-yl)sulfonyl)carbamoyl) benzoic Acid

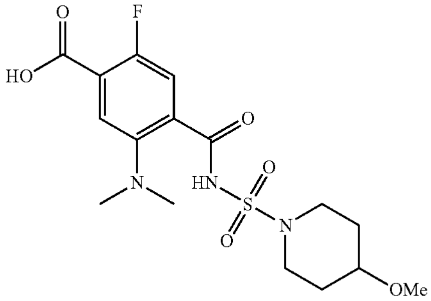 [SMILES: COC1CCN(S(=O)(=O)NC(=O)c2cc(F)c(C(=O)O)cc2N(C)C)CC1]

Prepared by analogous method to Intermediate 262 except the Step 1 was carried out with 4-methoxypiperidine-1-sulfonamide (Intermediate 289, 609 mg, 3.14 mmol) in place of 2-oxa-5-azaspiro[3.5]nonane-5-sulfonamide. Yield: 300 mg, 0.70 mmol. Yellow solid. LCMS: (System 1, Method A) Rt=1.50 min, m/z 431.8 $(M+H)^+$ $(ES^+)$.

Intermediate 291: (R)-5-(dimethylamino)-2-fluoro-4-(((2-(methoxymethyl)pyrrolidin-1-yl)sulfonyl) carbamoyl)benzoic Acid

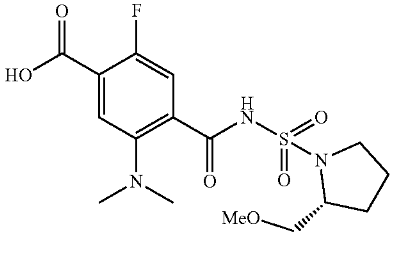 [SMILES: COC[C@H]1CCCN1S(=O)(=O)NC(=O)c1cc(F)c(C(=O)O)cc1N(C)C]

Prepared by analogous method to Intermediate 262 except the Step 1 was carried out with (R)-2-(methoxymethyl)

pyrrolidine-1-sulfonamide (Intermediate 287, 456 mg, 2.35 mmol) in place of 2-oxa-5-azaspiro[3.5]nonane-5-sulfonamide. Yield: 300 mg, 0.75 mmol. Yellow solid. LCMS: (System 1, Method A) Rt=1.06 min, m/z 402.0 $(M-H)^-$ $(ES^-)$.

Intermediate 292: 2-chloro-5-(dimethylamino)-4-((N,N-dimethylsulfamoyl)carbamoyl) benzoic Acid

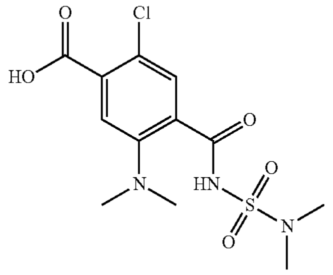 [SMILES: CN(C)c1cc(C(=O)O)c(Cl)cc1C(=O)NS(=O)(=O)N(C)C]

Prepared by an analogous method to Intermediate 111 except the Step 3 was carried out with N,N-dimethyl sulfamide (367 mg, 2.96 mmol) in place of pyrrolidine-1-sulfonamide. Yield: 250 mg, 0.72 mmol. Yellow solid. LCMS: (System 1, Method A) Rt=0.35 min, m/z 348.0 $(M-H)^-$ $(ES^-)$.

Intermediate 293: (S)-2-(trifluoromethyl)pyrrolidine-1-sulfonamide

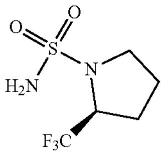 [SMILES: NS(=O)(=O)N1CCC[C@H]1C(F)(F)F]

Prepared by an analogous method to Intermediate 148 starting from (S)-2-(trifluoromethyl)pyrrolidine (0.8 g, 5.75 mmol), sulfuric diamide (0.66 g, 6.9 mmol). Yield: 640 mg, 2.93 mmol. Off-white solid. $^1$H NMR (400 MHz, DMSO-D6) b 7.06 (s, 2H), 4.37-4.28 (m, 1H), 3.48-3.42 (m, 1H), 3.28-3.22 (m, 1H), 2.11-1.85 (m, 4H).

Intermediate 294: (S)-5-(dimethylamino)-2-fluoro-4-(((2-(trifluoromethyl)pyrrolidin-1-yl)sulfonyl)carbamoyl)benzoic Acid

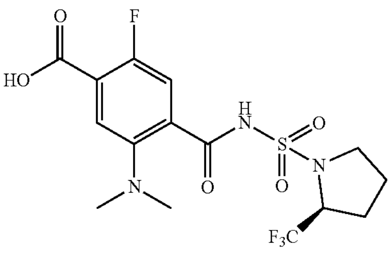 [SMILES: CN(C)c1cc(C(=O)O)c(F)cc1C(=O)NS(=O)(=O)N1CCC[C@H]1C(F)(F)F]

Prepared by analogous method to Intermediate 262 except the Step 1 was carried out with (S)-2-(trifluoromethyl)pyrrolidine-1-sulfonamide (Intermediate 293, 577 mg, 2.65 mmol) in place of 2-oxa-5-azaspiro[3.5]nonane-5-sulfonamide. Yield: 360 mg, 0.79 mmol. Yellow solid. LCMS: (System 1, Method A) Rt=1.58 min, m/z 456.0 $(M+H)^+$ $(ES^+)$.

Intermediate 295: 4-(trifluoromethyl)piperidine-1-sulfonamide

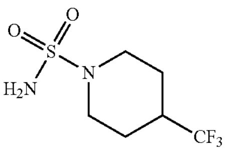 [SMILES: NS(=O)(=O)N1CCC(C(F)(F)F)CC1]

Prepared by an analogous method to Intermediate 148 starting from 4-(trifluoromethyl)piperidine (2 g, 13.1 mmol), sulfuric diamide (1.51 g, 15.1 mmol). Yield: 1.91 g, 8.22 mmol. Off-white solid. $^1$H NMR (400 MHz, DMSO-D6) δ 6.85 (s, 2H), 3.60 (d, J=11.9 Hz, 2H), 3.24-3.41 (1H), 2.60 (d, J=9.6 Hz, 1H), 2.48 (s, 1H), 1.93 (d, J=11.4 Hz, 2H), 1.57-1.47 (m, 2H).

Intermediate 296: 5-(dimethylamino)-2-fluoro-4-(((4-(trifluoromethyl)piperidin-1-yl)sulfonyl)carbamoyl)benzoic Acid

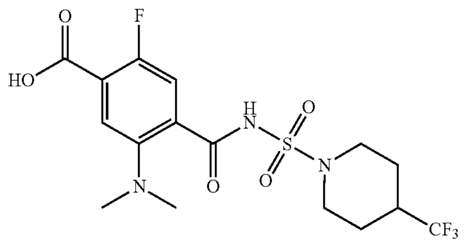 [SMILES: CN(C)c1cc(C(=O)O)c(F)cc1C(=O)NS(=O)(=O)N1CCC(C(F)(F)F)CC1]

Prepared by analogous method to Intermediate 262 except the Step 1 was carried out with 4-(trifluoromethyl)piperidine-1-sulfonamide (Intermediate 295, 1.27 g, 5.49 mmol) in place of 2-oxa-5-azaspiro[3.5]nonane-5-sulfonamide. Yield: 1.91 g, 8.22 mmol. Yellow solid. LCMS: (System 1, Method A) Rt=1.26 min, m/z 440.0 $(M-H)^-$ $(ES^-)$.

Intermediate 297: (1R,4R)-2-oxa-5-azabicyclo[2.2.1]heptane-5-sulfonamide

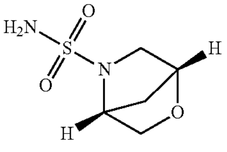 [SMILES: NS(=O)(=O)N1C[C@H]2C[C@@H]1CO2]

Prepared by an analogous method to Intermediate 148 starting from (1R,4R)-2-oxa-5-azabicyclo[2.2.1]heptane hydrochloride (2.95 g, 21.7 mmol), sulfuric diamide (1.9 g, 19.8 mmol). Yield: 2.68 g, 15 mmol. Off-white solid. $^1$H NMR (400 MHz, DMSO-D6) δ 6.88 (s, 2H), 4.58 (s, 1H), 4.24 (s, 1H), 3.87 (d, J=7.3 Hz, 1H), 3.63 (d, J=7.8 Hz, 1H), 3.22-3.09 (m, 2H), 1.89 (dd, J=10.1, 2.3 Hz, 1H), 1.72 (dt, J=10.1, 1.1 Hz, 1H).

Intermediate 298: 4-((((1R,4R)-2-oxa-5-azabicyclo[2.2.1]heptan-5-yl)sulfonyl)carbamoyl)-5-(dimethylamino)-2-fluorobenzoic Acid

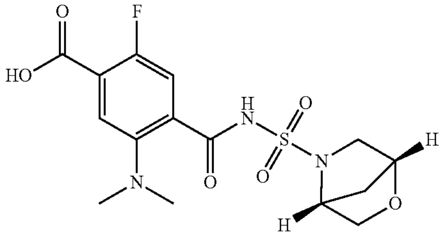 [SMILES: CN(C)c1cc(C(=O)O)c(F)cc1C(=O)NS(=O)(=O)N1C[C@H]2C[C@@H]1CO2]

Prepared by analogous method to Intermediate 262 except the Step 1 was carried out with (1R,4R)-2-oxa-5-azabicyclo[2.2.1]heptane-5-sulfonamide (Intermediate 297, 698 mg, 3.92 mmol) in place of 2-oxa-5-azaspiro[3.5]nonane-5-sulfonamide. Yield: 330 mg, g, 0.86 mmol. Light-yellow solid. LCMS: (System 1, Method A) Rt=0.43 min, m/z 386.2 $(M-H)^-$ $(ES^-)$.

Intermediate 299: 4-((N,N-dicyclopropylsulfamoyl)carbamoyl)-2-fluoro-5-methoxybenzoic Acid

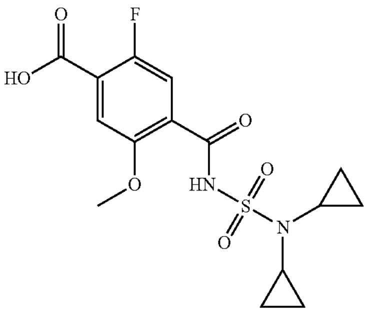 [SMILES: COc1cc(C(=O)O)c(F)cc1C(=O)NS(=O)(=O)N(C1CC1)C1CC1]

Prepared by analogous method to Intermediate 213 except the Step 3 was carried out with N,N-dicyclopropylsulfamide (Intermediate 180, 704 mg, 4 mmol) in place of pyrrolidine-1-sulfonamide. Yield: 200 mg, 0.53 mmol. White solid. LCMS: (System 1, Method A) Rt=0.91 min, m/z 371.0 $(M-H)^-$ $(ES^-)$.

Intermediate 300: 5-ethoxy-2-fluoro-4-(((1-methylcyclopropyl)sulfonyl)carbamoyl)benzoic Acid

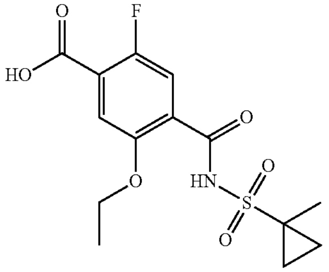 [SMILES: CCOc1cc(C(=O)O)c(F)cc1C(=O)NS(=O)(=O)C1(C)CC1]

Prepared by an analogous method to Intermediate 181 except the Step 4 was carried out with methylcyclopropane-1-sulfonamide (540 mg, 4 mmol) in place of N,N-dicyclopropylsulfamide. Yield: 210 mg, 0.61 mmol. White solid. LCMS: (System 1, Method A) Rt=0.48 min, m/z 346.1 $(M+H)^+$ $(ES^+)$.

Intermediate 301: 8-oxa-3-azabicyclo[3.2.1]octane-3-sulfonamide

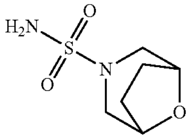

Prepared by an analogous method to Intermediate 148 starting from 8-oxa-3-azabicyclo[3.2.1]octane hydrochloride (2.0 g, 13.5 mmol), sulfuric diamide (1.95 g, 20.3 mmol). Yield: 1.5 g, 7.81 mmol. Off-white solid. $^1H$ NMR (400 MHz, DMSO-$d_6$) δ: 6.75 (s, 2H), 4.37 (s, 2H), 3.04-3.01 (m, 2H), 2.78-2.74 (m, 2H), 1.78-1.77 (m, 4H).

Intermediate 302: 4-((8-oxa-3-azabicyclo[3.2.1]octan-3-ylsulfonyl)carbamoyl)-5-ethoxy-2-fluorobenzoic Acid

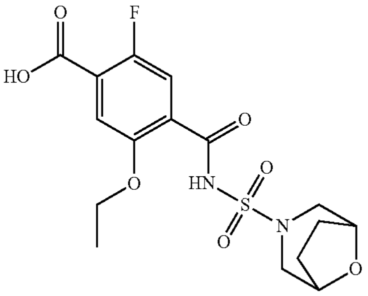 [SMILES: CCOc1cc(C(=O)O)c(F)cc1C(=O)NS(=O)(=O)N1CC2CCC(C1)O2]

Prepared by an analogous method to Intermediate 181 except the Step 4 was carried out with 8-oxa-3-azabicyclo[3.2.1]octane-3-sulfonamide (Intermediate 301, 768 mg, 4 mmol) in place of N,N-dicyclopropylsulfamide. Yield: 290 mg, 0.72 mmol. Yellow solid. LCMS: (System 1, Method A) Rt=0.46 min, m/z 403.1 $(M+H)^+$ $(ES^+)$.

Intermediate 303: (S)-3-fluoropyrrolidine-1-sulfonamide

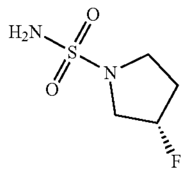

Prepared by an analogous method to Intermediate 148 starting from (S)-3-fluoro-pyrrolidine hydrochloride (3.0 g, 24.0 mmol), sulfuric diamide (3.45 g, 36 mmol). Yield: 1.9 g, 11.2 mmol. Light yellow oil. $^1$H NMR (400 MHz, DMSO-$d_6$) δ: 6.84 (s, 2H), 5.32 (d, J=52.8 Hz, 1H), 3.38-3.34 (m, 1H), 3.30-3.17 (m, 3H), 2.12-1.98 (m, 2H).

Intermediate 304: (S)-5-(dimethylamino)-2-fluoro-4-(((3-fluoropyrrolidin-1-yl)sulfonyl) carbamoyl) benzoic Acid

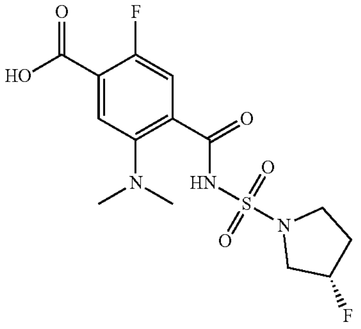 [SMILES: CN(C)c1cc(C(=O)O)c(F)cc1C(=O)NS(=O)(=O)N1CC[C@H](F)C1]

Prepared by analogous method to Intermediate 262 except the Step 1 was carried out with (S)-3-fluoropyrrolidine-1-sulfonamide (Intermediate 303, 605 mg, 3.6 mmol) in place of 2-oxa-5-azaspiro[3.5]nonane-5-sulfonamide. Yield: 270 mg, g, 0.89 mmol. Yellow solid. LCMS: (System 1, Method A) Rt=0.75 min, m/z 376.0 $(M-H)^-$ $(ES^-)$.

Intermediate 305: (R)-3-fluoropyrrolidine-1-sulfonamide

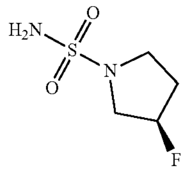

Prepared by an analogous method to Intermediate 148 starting from (R)-3-fluoro-pyrrolidine hydrochloride (3.0 g, 24.0 mmol), sulfuric diamide (3.45 g, 36 mmol). Yield: 2 g, 11.8 mmol. Light yellow oil. $^1$H NMR (400 MHz, DMSO-$d_6$) δ: 6.84 (s, 2H), 5.32 (d, J=52.8 Hz, 1H), 3.38-3.34 (m, 1H), 3.30-3.17 (m, 3H), 2.12-1.98 (m, 2H).

Intermediate 306: (R)-5-(dimethylamino)-2-fluoro-4-(((3-fluoropyrrolidin-1-yl)sulfonyl) carbamoyl) benzoic Acid

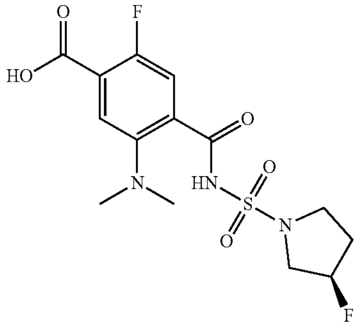 [SMILES: CN(C)c1cc(C(=O)O)c(F)cc1C(=O)NS(=O)(=O)N1CC[C@@H](F)C1]

Prepared by analogous method to Intermediate 262 except the Step 1 was carried out with (R)-3-fluoropyrrolidine-1-sulfonamide (Intermediate 303, 672 mg, 4 mmol) in place of 2-oxa-5-azaspiro[3.5]nonane-5-sulfonamide. Yield: 400, g, 1.06 mmol. Yellow solid. LCMS: (System 1, Method A) Rt=0.67 min, m/z 375. $(M-H)^-$ $(ES^-)$.

Intermediate 307: 5-fluoro-2-methylbenzene-1,3-diol

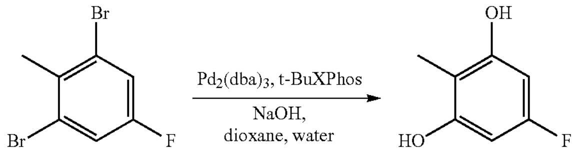

To a solution of 1,3-dibromo-5-fluoro-2-methylbenzene (5 g, 18.66 mmol) in dioxane (90 mL) and water (90 mL), was added NaOH (7.46 g, 186.62 mmol), $Pd_2(dba)_3$ (427 mg, 0.47 mmol) and t-BuXPhos (396 mg, 0.93 mmol). The reaction mixture was stirred at 110° C. for 3 h under nitrogen atmosphere. The reaction mixture was washed with DCM (3×150 mL). The pH of the aqueous layer was adjusted to 3 with 1N HCl. and the aqueous layer extracted with EtOAc (3×200 mL). The organic layers were dried over anhydrous $Na_2SO_4$, filtered and concentrated under reduced pressure to give the crude material, which was purified by silica gel column chromatography (20-80% EtOAc/petroleum ether) to give 5-fluoro-2-methylbenzene-1,3-diol (2.3 g, 37.5 mmol) as a white solid. LCMS: (System 1, Method A). Rt=1.321 min. m/z 141.2 $(M-H)^-$ $(ES^-)$.

Intermediate 308: tert-butyl 10-fluoro-7-methyl-5-oxo-8-(((trifluoromethyl)sulfonyl)oxy)-4,5-dihydro-1H-chromeno[3,4-c]pyridine-3(2H)-carboxylate

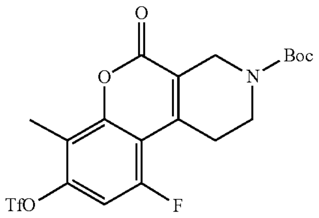 [SMILES: Cc1c(OS(=O)(=O)C(F)(F)F)cc(F)c2c3c(c(=O)oc12)CN(C(=O)OC(C)(C)C)CC3]

Prepared by an analogous method to Intermediate 2 starting from 5-fluoro-2-methylbenzene-1,3-diol (Intermediate 307, 2.3 g, 37.5 mmol) Yield: 1.8 g, 3.8 mmol. Pale yellow solid. LCMS: (System 1, Method A) Rt=2.43 min, m/z 475.3 $(M+H)^+$ $(ES^+)$.

Intermediate 309: (R)-10-fluoro-8-(3-(methoxymethyl)-4-methylpiperazin-1-yl)-7-methyl-3,4-dihydro-1H-chromeno[3,4-c]pyridin-5(2H)-one

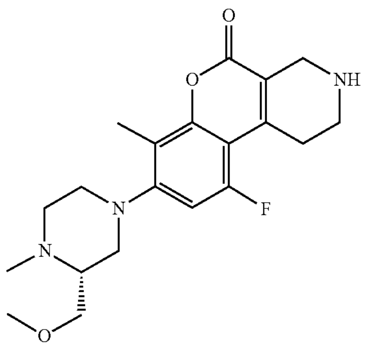 [SMILES: COC[C@H]1CN(c2cc(F)c3c4c(c(=O)oc3c2C)CNCC4)CCN1C]

Prepared by an analogous method to Intermediate 5 starting from (R)-2-(methoxymethyl)-1-methylpiperazine (Intermediate 1, 449 mg, 3.12 mmol) and tert-butyl 10-fluoro-7-methyl-5-oxo-8-(((trifluoromethyl)sulfonyl)oxy)-4,5-dihydro-1H-chromeno[3,4-c]pyridine-3(2H)-carboxylate (Intermediate 308, 1 g, 2.08 mmol). Yield: 380 mg, 1.10 mmol. Brown solid. LCMS: (System 1, Method A) Rt=1.60 min, m/z 376.4 $(M+H)^+$ $(ES^+)$.

Intermediate 310: 5-cyclopropoxy-4-((N,N-dimethylsulfamoyl)carbamoyl)-2-fluorobenzoic Acid

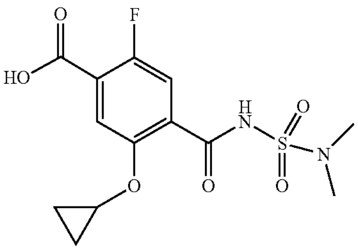 [SMILES: CN(C)S(=O)(=O)NC(=O)c1cc(F)c(C(=O)O)cc1OC1CC1]

Prepared by analogous method to Intermediate 244 except the Step 4 was carried out with N,N-dimethyl sulfamide (741 mg, 5.96 mmol) in place of pyrrolidine-1-sulfonamide. Yield: 400, g, 1.06 mmol. White solid. LCMS: (System 1, Method A) Rt=1.36 min, m/z 372.9 $(M-H)^-$ $(ES^-)$.

Intermediate 311: 4-((3-oxa-8-azabicyclo[3.2.1]octan-8-ylsulfonyl)carbamoyl)-5-cyclopropoxy-2-fluorobenzoic Acid

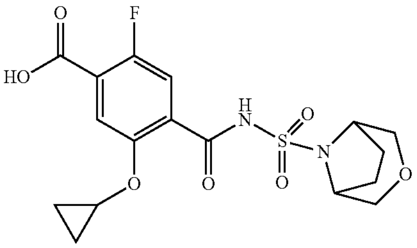 [SMILES: O=C(O)c1cc(OC2CC2)c(C(=O)NS(=O)(=O)N2C3CCC2COC3)cc1F]

Prepared by analogous method to Intermediate 244 except the Step 4 was carried out with 3-oxa-8-azabicyclo[3.2.1]octane-8-sulfonamide (Intermediate 188, 860 mg, 4.47 mmol) in place of pyrrolidine-1-sulfonamide. Yield: 0.5 g, 1.21 mmol. White solid. LCMS: (System 1, Method A) Rt=0.53 min, m/z 412.8 $(M-H)^-$ $(ES^-)$.

Intermediate 312: 5-(dimethylamino)-2-fluoro-4-[(2S)-2-(methoxymethyl)pyrrolidin-1-yl]sulfonylcarbamoyl]benzoic Acid

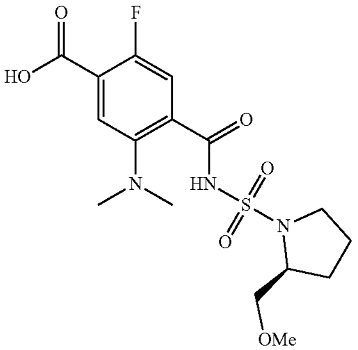 [SMILES: COC[C@@H]1CCCN1S(=O)(=O)NC(=O)c1cc(F)c(C(=O)O)cc1N(C)C]

Prepared by analogous method to Intermediate 262 except the Step 1 was carried out with (2S)-2-(methoxymethyl)pyrrolidine-1-sulfonamide (Intermediate 279, 152 mg, 0.78 mmol) in place of 2-oxa-5-azaspiro[3.5]nonane-5-sulfonamide. Yield: 87.8 mg, g, 0.22 mmol. White solid. LCMS: (System 1, Method A) Rt=1.45 min, m/z 402.1 $(M-H)^-$ $(ES^-)$.

Intermediate 313: 4-((((1S,4S)-2-oxa-5-azabicyclo[2.2.1]heptan-5-yl)sulfonyl)carbamoyl)-5-(dimethylamino)-2-fluorobenzoic Acid

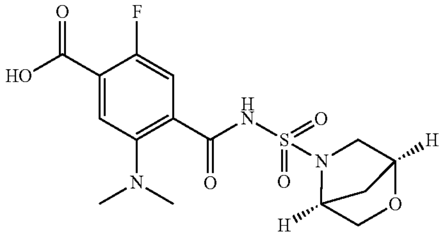 [SMILES: CN(C)c1cc(C(=O)O)c(F)cc1C(=O)NS(=O)(=O)N1C[C@@H]2C[C@H]1CO2]

Prepared by analogous method to Intermediate 262 except the Step 1 was carried out with (1S,4S)-2-oxa-5-azabicyclo[2.2.1]heptane-5-sulfonamide (Intermediate 242, 140 mg, 0.78 mmol) in place of 2-oxa-5-azaspiro[3.5]nonane-5-sulfonamide. Yield: 55.9 mg, g, 0.14 mmol. Light brown oil. LCMS: (System 1, Method A) Rt=1.15 min, m/z 386.1 $(M+H)^+$ $(ES^+)$.

Intermediate 314: 4-(((3-azabicyclo[3.1.0]hexan-3-yl)sulfonyl)carbamoyl)-5-(dimethylamino)-2-fluorobenzoic Acid

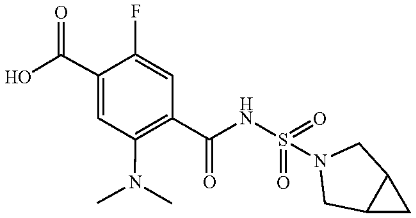

Prepared by analogous method to Intermediate 262 except the Step 1 was carried out with 3-azabicyclo[3.1.0]hexane-3-sulfonamide (Intermediate 168, 127 mg, 0.78 mmol) in place of 2-oxa-5-azaspiro[3.5]nonane-5-sulfonamide. Yield: 128 mg, g, 0.34 mmol. Light-brown oil. LCMS: (System 1, Method A) Rt=1.47 min, m/z 370.1 $(M+H)^+$ $(ES^+)$.

Intermediate 315: 4-bromo-5-chloro-2-(methoxy-d3)benzoic Acid

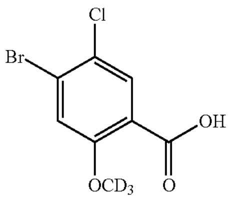

To a solution of 4-bromo-5-chloro-2-hydroxybenzoic acid (620 mg, 2.48 mmol) in DMA (20 mL), was added $CD_3OD$ (794 mg, 24.8 mmol) and NaH (60%, 496 mg, 12.4 mmol). The reaction mixture was stirred at 80° C. for 20 min, poured into water (20 mL) and extracted with ethyl acetate (3×20 mL). The combined ethyl acetate extracts were washed with brine three times, dried over $Na_2SO_4$, filtered and concentrated to give crude material, which was purified by column chromatography on silica gel (1-10% EtOAc/petroleum ether) to give 4-bromo-5-chloro-2-(methoxy-d3)benzoic acid (505 mg, 1.90 mmol) as yellow oil. LCMS: (System 1, Method A) Rt=1.21 min, m/z 266.1 $(M-H)^-$ $(ES^-)$.

Intermediate 316: 2-chloro-5-(methoxy-d3)-4-((pyrrolidin-1-ylsulfonyl)carbamoyl)benzoic acid

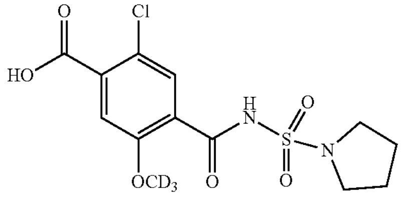

Prepared by an analogous method to Intermediate 213 starting from 4-bromo-5-chloro-2-(methoxy-d3)benzoic acid (Intermediate 315). Yield: 250 mg, 0.86 mmol. White solid. LCMS: (System 1, Method A) Rt=0.45 min, m/z 366.0 $(M+H)^+$ $(ES^+)$.

Intermediate 317: 2-chloro-5-methoxy-4-((pyrrolidin-1-ylsulfonyl)carbamoyl)benzoic Acid

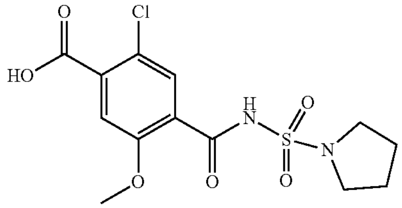 [SMILES: COc1cc(C(=O)O)c(Cl)cc1C(=O)NS(=O)(=O)N1CCCC1]

Prepared by an analogous method to Intermediate 213 starting from 4-bromo-5-chloro-2-methoxy benzoic acid (620 mg, 2.48 mmol). Yield: 260 mg, 0.86 mmol. Yellow solid. LCMS: (System 1, Method A) Rt=0.47 min, m/z 363.0 $(M+H)^+$ $(ES^+)$.

Intermediate 318: 2-chloro-5-ethoxy-4-((pyrrolidin-1-ylsulfonyl)carbamoyl)benzoic Acid

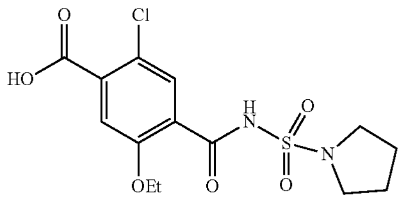 [SMILES: CCOc1cc(C(=O)O)c(Cl)cc1C(=O)NS(=O)(=O)N1CCCC1]

Prepared by an analogous method to Intermediate 213 starting from 4-bromo-5-chloro-2-methoxy benzoic acid (620 mg, 2.48 mmol) and ethanol (1.14 g, 24.8 mmol) in Step 1. Yield: 270 mg, 0.72 mmol. Yellow solid. LCMS: (System 1, Method A) Rt=0.59 min, m/z 377 $(M+H)^+$ $(ES^+)$.

Intermediate 319: 4-((7-azabicyclo[2.2.1]heptan-7-ylsulfonyl)carbamoyl)-5-cyclopropoxy-2-fluorobenzoic Acid

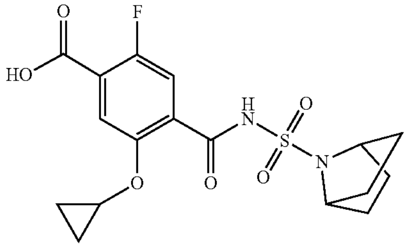 [SMILES: O=C(O)c1cc(OC2CC2)c(C(=O)NS(=O)(=O)N2C3CCC2CC3)cc1F]

Prepared by analogous method to Intermediate 244 except the Step 4 was carried out with 7-azabicyclo[2.2.1]heptane-7-sulfonamide (Intermediate 148, 788 mg, 4.48 mmol in place of pyrrolidine-1-sulfonamide. Yield: 0.34 g, 0.85 mmol. White solid. LCMS: (System 1, Method A) Rt=1.024 min, m/z 399.0 $(M+H)^+$ $(ES^+)$.

Example 1: (R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide

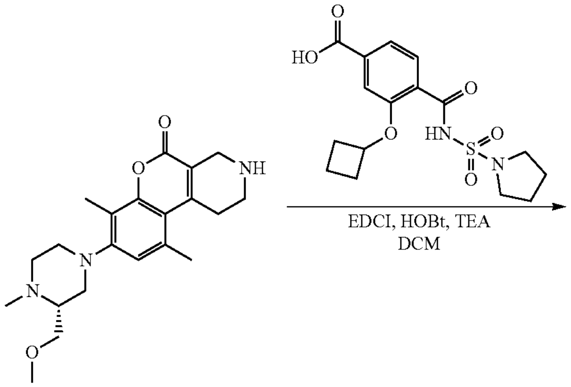

-continued

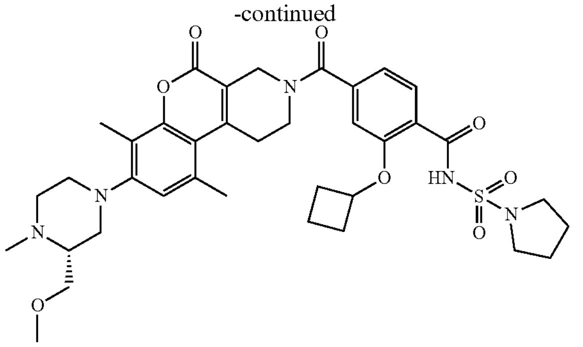

A mixture of (R)-8-(3-(methoxymethyl)-4-methylpiperazin-1-yl)-7,10-dimethyl-1,2,3,4-tetrahydro-5H-chromeno[3,4-c]pyrrolid-5-one (Intermediate 6, 3.5 g, 9.4 mmol), EDCI (2.7 g, 14.1 mmol), HOBt (1.9 g, 14.1 mmol), TEA (3.8 g, 37.5 mmol) and 3-cyclobutoxy-4-((pyrrolidin-1-ylsulfonyl)carbamoyl)benzoic acid (Intermediate 10, 3.8 g, 10.3 mmol) in DCM (100 mL) was stirred at RT overnight. Water (10 mL) was added and the mixture was extracted with DCM (3×100 mL). The combined organic layers were dried ($Na_2SO_4$), filtered and concentrated under reduced pressure. The crude product was purified by column chromatography on silica gel (1-5% MeOH/DCM) and by reverse phase column chromatography (C18-modified silica, 40-60% ACN/water) to afford (R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide (3.3 g, 4.6 mmol) as a white solid. HPLC: (System 1, Method D) Rt=8.12 min, m/z 722.0 $(M+H)^+$ $(ES^+)$. $^1$H NMR (400 MHz, DMSO-$d_6$) δ: 11.34 (br s, 1H), 7.56-7.54 (m, 1H), 7.13-7.08 (m, 1H), 7.03-6.99 (m, 1H), 6.84 (s, 1H), 4.89-4.82 (m, 1H), 4.48 (br s, 1H), 4.28 (br s, 1H), 3.83 (br s, 1H), 3.55 (dd, J=10.0, 4.0 Hz, 1H), 3.49-3.43 (m, 5H), 3.35-3.31 (m, 1H), 3.26 (br s, 3H), 3.20 (br s, 2H), 3.14-3.11 (m, 1H), 3.04-3.01 (m, 1H), 2.84-2.79 (m, 2H), 2.68-2.59 (m, 4H), 2.43-2.40 (m, 4H), 2.32 (s, 3H), 2.23-2.19 (m, 3H), 2.09 (br s, 2H), 1.87-1.84 (m, 5H), 1.65-1.63 (m, 1H). Mixture of rotamers.

The following examples were prepared by analogous method to Example 1:

| Example No. | Name/Structure/Intermediates | LCMS/$^1$H NMR data |
|---|---|---|
| Example 2 | (R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 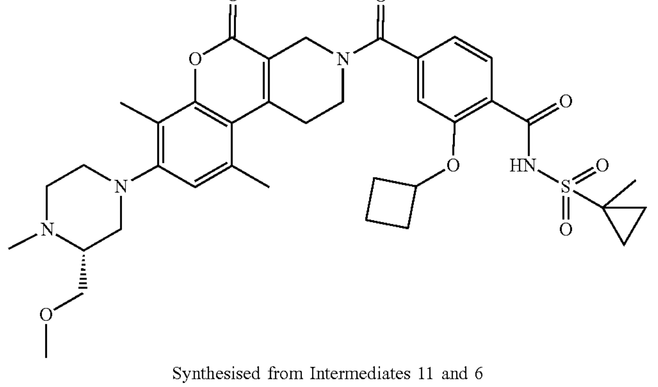 Synthesised from Intermediates 11 and 6 | HPLC: (System 1, Method D) Rt = 7.07 min, m/z 707.3 $(M + H)^+$ $(ES^+)$. $^1$H NMR (400 MHz, DMSO-$d_6$) δ: 11.40 (br s, 1H), 7.53-7.51 (m, 1H), 7.13-7.08 (m, 1H), 7.02-6.99 (m, 1H), 6.85 (s, 1H), 4.86-4.81 (m, 1H), 4.48 (br s, 1H), 4.29 (br s, 1H), 3.83 (br s, 1H), 3.57-3.50 (m, 2H), 3.34 (br s, 5H), 3.21 (br s, 2H), 3.15-3.13 (m, 1H), 3.06-3.03 (m, 1H), 2.88-2.80 (m, 2H), 2.69-2.61 (m, 4H), 2.45 (br s, 3H), 2.33 (s, 3H), 2.24-2.19 (m, 3H), 2.14-2.09 (m, 2H), 1.82-1.80 (m, 1H), 1.65-1.62 (m, 1H), 1.54 (s, 3H), 1.46-1.43 (m, 2H), 0.96-0.94 (m, 2H). Mixture of rotamers. |

-continued

| Example No. | Name/Structure/Intermediates | LCMS/$^1$H NMR data |
|---|---|---|
| Example 3 | (R)-2-cyclobutoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 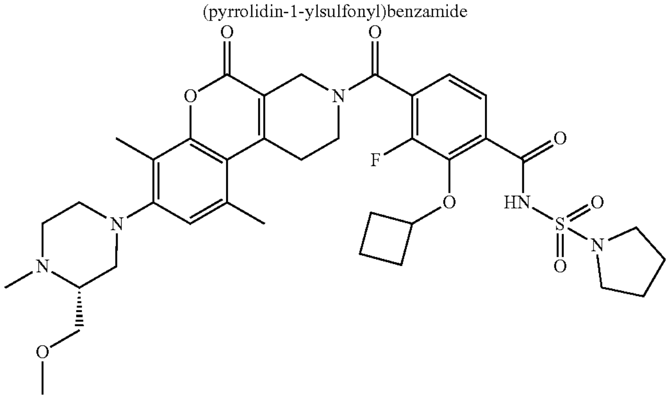 Synthesised from Intermediates 13 and 6 | HPLC: (System 1, Method D) Rt = 7.86 min, m/z 740.3 $(M + H)^+$ $(ES^+)$. $^1$H NMR (400 MHz, DMSO-$d_6$) δ: 11.58 (br s, 1H), 7.35-7.33 (m, 1H), 7.25-7.16 (m, 1H), 6.86-6.84 (m, 1H), 4.73-4.66 (m, 1H), 4.50 (br s, 1H), 4.17 (s, 1H), 3.88-3.86 (m, 1H), 3.57-3.54 (m, 1H), 3.45-3.37 (m, 7H), 3.27 (br s, 3H), 3.23 (br s, 1H), 3.16-3.13 (m, 2H), 3.07-3.04 (m, 1H), 2.90-2.81 (m, 2H), 2.69-2.62 (m, 4H), 2.49-2.46 (m, 1H), 2.35 (s, 3H), 2.30-2.20 (m, 5H), 2.15-2.07 (m, 2H), 1.87-1.84 (m, 4H), 1.71-1.66 (m, 1H), 1.50-1.41 (m, 1H). Mixture of rotamers. |
| Example 4 | (R)-2-(cyclopentyloxy)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 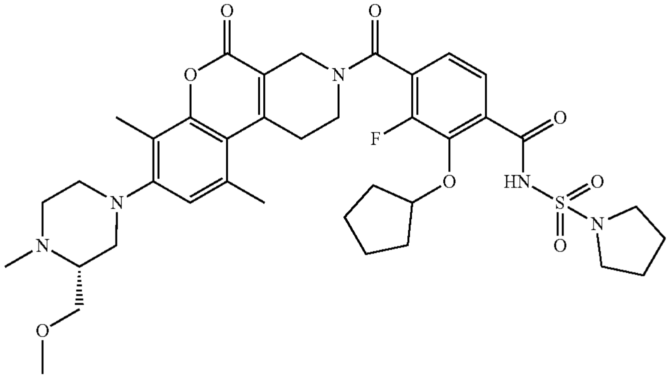 [SMILES: COC[C@H]1CN(c2cc(C)c3c4c(c(=O)oc3c2C)CN(C(=O)c2ccc(C(=O)NS(=O)(=O)N3CCCC3)c(OC3CCCC3)c2F)CC4)CCN1C] Synthesised from Intermediates 14 and 6 | HPLC: (System 1, Method D) Rt = 7.63 min, m/z 754.0 $(M + H)^+$ $(ES^+)$. $^1$H NMR (400 MHz, DMSO-$d_6$) δ: 11.51 (br s, 1H), 7.36-7.33 (m, 1H), 7.25-7.15 (m, 1H), 6.86-.684 (m, 1H), 4.87-4.82 (m, 1H), 4.50 (br s, 1H), 4.18 (s, 1H), 3.87 (br s, 1H), 3.57-3.54 (m, 1H), 3.45-3.44 (m, 1H), 3.41-3.38 (m, 5H), 3.27 (s, 3H), 3.27-3.23 (m, 1H), 3.16-3.14 (m, 2H), 3.07-3.04 (m, 1H), 2.90-2.80 (m, 2H), 2.69-2.62 (m, 4H), 2.51 (br s, 1H),2.50 (br s, 1H), 2.35 (s, 3H), 2.23-2.19 (m, 3H), 1.86-1.74 (m, 10H), 1.59-1.55 (m, 2H). Mixture of rotamers. |
| Example 5 | (R)-2-(cyclopentyloxy)-N-(N,N-dimethylsulfamoyl)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide 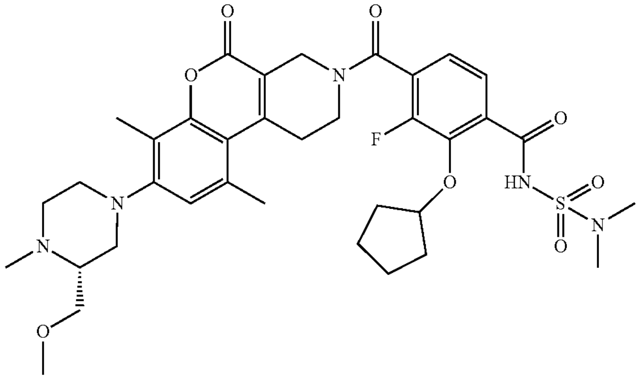 Synthesised from Intermediates 15 and 5 | HPLC: (System 1, Method D) Rt = 7.02 min, m/z 714.4 $(M + H)^+$ $(ES^+)$. $^1$H NMR (400 MHz, DMSO-$d_6$) δ: 11.39 (br s, 1H), 7.59-7.50 (m, 1H), 7.34-7.32 (m, 1H), 7.21-7.14 (m, 1H), 7.10-7.06 (m, 1H), 4.88-4.82 (m, 1H), 4.53 (br s, 1H), 4.18 (s, 1H), 3.99-3.96 (m, 1H), 3.59-3.54 (m, 2H), 3.43-3.39 (m, 1H), 3.28 (s, 3H), 3.19-3.16 (m, 1H), 3.09-3.06 (m, 1H), 3.00-2.87 (m, 4H), 2.84-2.83 (m, 6H), 2.71-2.67 (m, 1H), 2.62-2.56 (m, 2H), 2.40 (s, 3H), 2.30-2.26 (m, 3H), 1.84-1.72 (m, 6H), 1.57-1.55 (m, 2H). Mixture of rotamers. |

-continued

| Example No. | Name/Structure/Intermediates | LCMS/$^1$H NMR data |
|---|---|---|
| Example 6 | (R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-(cyclopentyloxy)-3-fluoro-N-(pyrrolidin-1-ylsulfonyl)benzamide 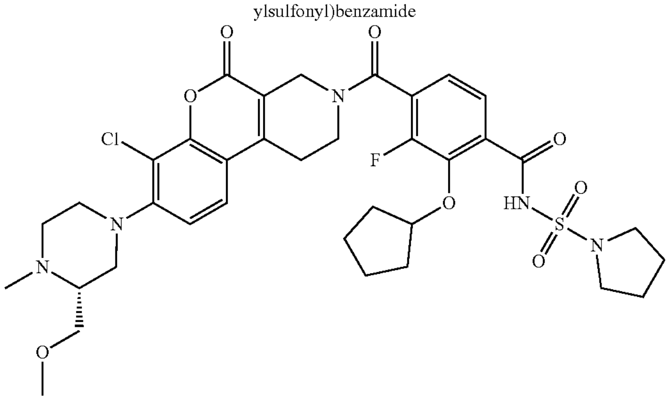 Synthesised from Intermediates 14 and 7 | HPLC: (System 1, Method D) Rt = 7.44 min, m/z 760.2 (M + H)$^+$ (ES$^+$). $^1$H NMR (400 MHz, DMSO-d$_6$) δ: 11.57 (br s, 1H), 7.70-7.68 (m, 1H), 7.36-7.33 (m, 1H), 7.23-7.15 (m, 2H), 4.87-4.82 (m, 1H), 4.54 (br s, 1H), 4.19 (s, 1H), 3.99-3.96 (m, 1H), 3.59-3.54 (m, 2H), 3.45-3.36 (m, 7H), 3.29-3.27 (m, 4H), 3.01-2.87 (m, 4H), 2.70 (t, J = 10.4 Hz, 1H), 2.46-2.43 (m, 1H), 2.33 (s, 3H), 1.85-1.74 (m, 10H), 1.57-1.55 (m, 2H). Mixture of rotamers. |
| Example 7 | (R)-2-cyclobutoxy-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide 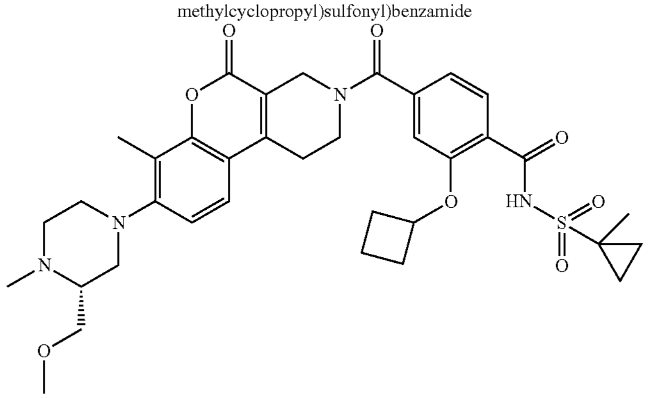 Synthesised from Intermediates 5 and 11 | HPLC: (System 1, Method D) Rt = 7.50 min, m/z 693.5 (M + H)$^+$ (ES$^+$). $^1$H NMR (400 MHz, DMSO-d$_6$) δ: 11.41 (br s, 1H), 7.59-7.50 (m, 2H), 7.09-7.07 (m, 2H), 6.99-6.97 (m, 1H), 4.84-4.82 (m, 1H), 4.49 (s, 1H), 4.28 (s, 1H), 3.93-3.90 (m, 1H), 3.58-3.54 (m, 2H), 3.38-3.36 (m, 2H), 3.27 (s, 3H), 3.16-3.14 (m, 1H), 3.06-3.04 (m, 1H), 2.96-2.95(m, 2H), 2.88-2.82(m, 2H), 2.67-2.61 (m, 1H), 2.49-2.43 (m, 3H), 2.33 (s, 3H), 2.30-2.23 (m, 3H), 2.14-2.08 (m, 2H), 1.81-1.77 (m, 1H), 1.67-1.61 (m, 1H), 1.54 (s, 3H), 1.46-1.43 (m, 2H), 0.97-0.94 (s, 2H). Mixture of rotamers. |
| Example 8 | (R)-2-(cyclopentyloxy)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide 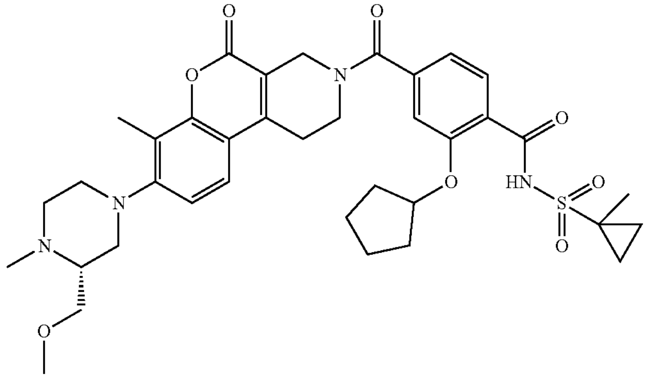 [SMILES: COC[C@H]1CN(c2ccc3c4c(c(=O)oc3c2C)CN(C(=O)c2ccc(C(=O)NS(=O)(=O)C3(C)CC3)c(OC3CCCC3)c2)CC4)CCN1C] Synthesised from Intermediates 12 and 5 | HPLC: (System 1, Method D) Rt = 7.97 min, m/z 707.4 (M + H)$^+$ (ES$^+$). $^1$H NMR (400 MHz, DMSO-d$_6$) δ: 11.23 (br s, 1H), 7.59-7.52 (m, 2H), 7.20-7.17 (m, 1H), 7.09-7.07 (m, 2H), 5.03-4.96 (m, 1H), 4.50 (s, 1H), 4.29 (s, 1H), 3.94-3.93 (m, 1H), 3.60-3.54 (m, 2H), 3.36-3.33 (m, 1H), 3.26 (s, 3H), 3.16-3.13 (m, 1H), 3.06-3.03 (m, 1H), 2.97 (br s, 2H), 2.87-2.82 (m, 2H), 2.67-2.60 (m, 1H), 2.47-2.40 (m, 2H), 2.32 (s, 3H), 2.25-2.23 (m, 3H), 1.90 (br s, 2H), 1.80-1.73 (m, 4H), 1.59-1.58 (m, 2H), 1.51 (s, 3H), 1.46-1.43 (m, 2H), 0.96-0.94 (m, 2H). Mixture of rotamers. |

-continued

| Example No. | Name/Structure/Intermediates | LCMS/$^1$H NMR data |
|---|---|---|
| Example 9 | (R)-2-(cyclopentyloxy)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide 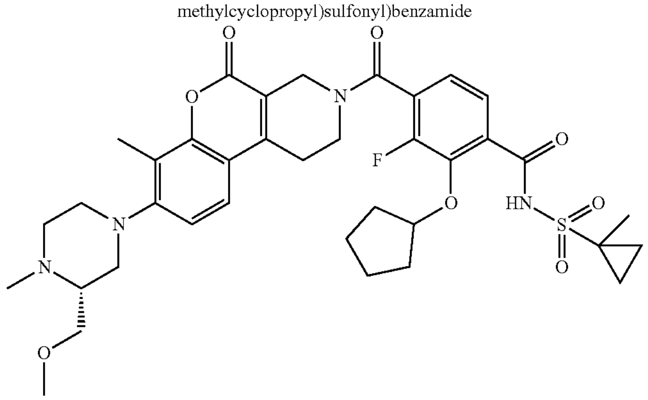 Synthesised from Intermediates 16 and 5 | HPLC: (System 1, Method D) Rt = 7.11 min, m/z 725.2 $(M + H)^+$ $(ES^+)$. $^1$H NMR (400 MHz, DMSO-$d_6$) δ: 7.59-7.50 (m, 1H), 7.32-7.30 (m, 1H), 7.20-7.13 (m, 1H), 7.10-7.06 (m, 1H), 4.88-4.82 (m, 1H), 4.53 (br s, 1H), 4.18 (s, 1H), 3.98 (t, J = 5.6 Hz,1H), 3.59-3.54 (m, 2H), 3.46-3.42 (m, 1H), 3.29 (s, 3H), 3.20-3.18 (m, 1H), 3.09 (m, 1H), 3.00-2.98 (m, 2H), 2.91-2.86 (m, 2H), 2.73-2.64 (m, 3H), 2.45 (s, 3H), 2.30-2.26 (m, 3H), 1.83-1.72 (m, 6H), 1.56-1.54 (m, 2H), 1.48 (s, 3H), 1.40-1.39 (m, 2H), 0.88-0.84 (m, 2H). One exchangeable proton not visible. Mixture of rotamers. |
| Example 10 | (R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-cyclobutoxy-N-((1-methylcyclopropyl)sulfonyl)benzamide 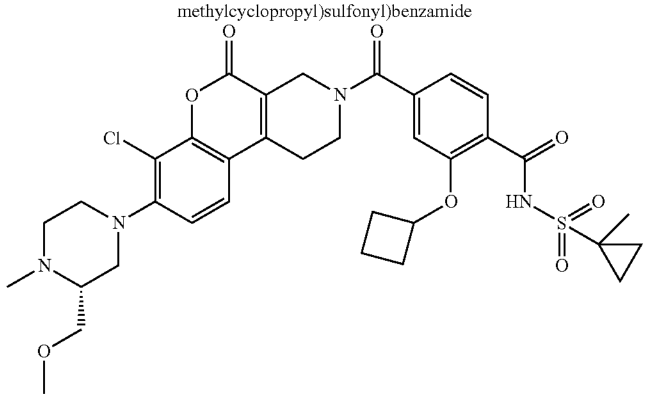 Synthesised from Intermediates 11 and 7 | HPLC: (System 1, Method D) Rt = 6.95 min, m/z 713.3 $(M + H)^+$ $(ES^+)$. $^1$H NMR (400 MHz, DMSO-$d_6$) δ: 11.38 (br s, 1H), 7.69-7.62 (m, 1H), 7.52 (d, J = 7.6 Hz, 1H), 7.17 (d, J = 8.8 Hz, 1H), 7.09 (d, J = 7.2 Hz, 1H), 7.00 (s, 1H), 4.84-4.83 (m, 1H), 4.50 (s, 1H), 4.29 (br s, 1H), 3.94 (br s, 1H), 3.59-3.55 (m, 2H), 3.44-3.31 (m, 7H), 2.96-2.87 (m, 4H), 2.70 (t, J = 10.0 Hz, 1H), 2.45-2.43 (m, 3H), 2.32 (s, 3H), 2.14-2.09 (m, 2H), 1.82-1.79 (m, 1H), 1.65-1.61 (m, 1H), 1.55 (s, 3H), 1.47-1.44 (m, 2H), 0.98-0.95 (m, 2H). |
| Example 11 | 2-(((1R,3r,5S)-bicyclo[3.1.0]hexan-3-yl)oxy)-N-(N,N-dimethylsulfamoyl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 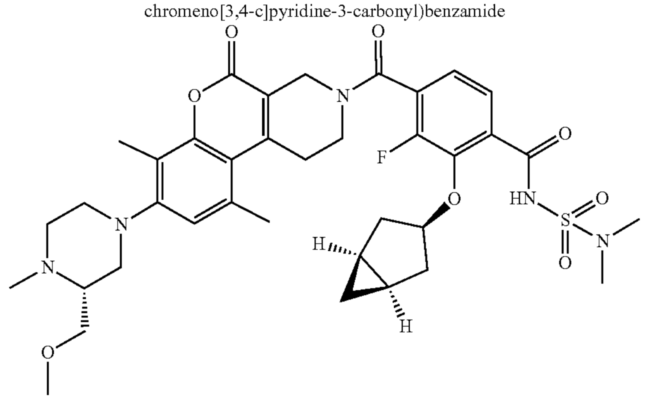 Synthesised from Intermediates 23 and 6 | HPLC: (System 1, Method D) Rt = 7.23 min, m/z 740.6 $(M + H)^+$ $(ES^+)$. $^1$H NMR (400 MHz, DMSO-$d_6$) δ: 11.41 (br s, 1H), 7.32-7.30 (m, 1H), 7.21-7.12 (m, 1H), 6.87-6.85 (m, 1H), 4.82-4.73 (m, 1H), 4.50 (br s, 1H), 4.17 (s, 1H), 3.87 (br s, 1H), 3.58-3.55 (m, 1H), 3.46-3.39 (m, 2H), 3.33 (s, 3H), 3.28-3.06 (m, 4H), 2.96-2.93 (m, 1H), 2.88-2.84 (m, 7H), 2.72-2.54 (m, 6H), 2.40 (s, 3H), 2.20-2.24 (m, 3H), 2.11-2.08 (m, 2H), 2.01-1.95 (m, 2H), 1.30 (br s, 2H), 0.70-0.63 (m, 1H), 0.47-0.43 (m, 1H). Mixture of rotamers. |

-continued

| Example No. | Name/Structure/Intermediates | LCMS/$^1$H NMR data |
|---|---|---|
| Example 12 | (R)-2-(cyclopentyloxy)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide 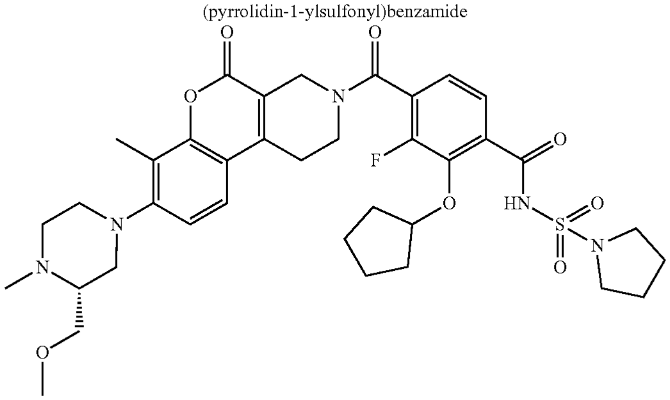 Synthesised from Intermediates 14 and 5 | HPLC: (System 1, Method D) Rt = 7.44 min, m/z 740.4 $(M + H)^+$ $(ES^+)$. $^1$H NMR (400 MHz, DMSO-$d_6$) δ: 11.48 (br s, 1H), 7.60-7.51 (dd, J = 28.0, 8.8 Hz, 1H), 7.36-7.33 (m, 1H), 7.23-7.15 (m, 1H), 7.10-7.06 (m, 1H), 4.87-4.81 (m, 1H), 4.53 (br s, 1H), 4.18 (s, 1H), 3.98 (t, J = 5.6 Hz, 1H), 3.58-3.55 (m, 2H), 2.40-3.39 (m, 5H), 3.27 (s, 3H), 3.18-3.16 (m, 1H), 3.08-3.06 (m, 1H), 3.00 (br s, 1H), 2.92-2.84 (m, 3H), 2.67 (t, J = 10.4 Hz, 1H), 2.55-2.51 (m, 2H), 2.37 (s, 3H), 2.30-2.26 (m, 3H), 1.85-1.73 (m, 10 H), 1.57-1.54 (m, 2H). Mixture of rotamers. |
| Example 13 | 2-(((1R,3r,5S)-bicyclo[3.1.0]hexan-3-yl)oxy)-N-(N,N-dimethylsulfamoyl)-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide 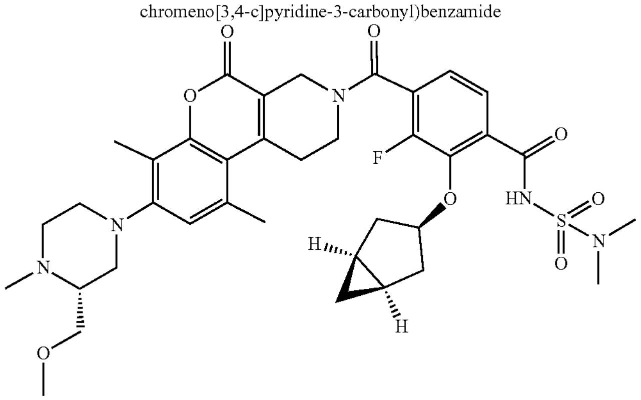 Synthesised from Intermediates 23 and 5 | HPLC: (System 1, Method D) Rt = 7.29 min, m/z 726.3 $(M + H)^+$ $(ES^+)$. $^1$H NMR (400 MHz, DMSO-$d_6$) δ: 11.42 (br s, 1H), 7.59-7.50 (m, 1H), 7.30 (d, J = 8.0 Hz, 1H), 7.18-7.06 (m, 2H), 4.82-4.73 (m, 1H), 4.53 (br s, 1H), 4.17 (s, 1H), 3.98-3.96 (m, 1H), 3.59-3.54 (m, 2H), 3.43-3.40 (m, 1H), 3.28 (s, 3H), 3.19-3.17 (m, 1H), 3.10-3.07 (m, 1H), 2.99-2.87 (m, 4H), 2.84-2.83 (m, 6H), 2.71-2.57 (m, 3H), 2.40 (s, 3H), 2.30-2.26 (m, 3H), 2.12-2.07 (m, 2H), 2.01-1.95 (m, 2H), 1.32-1.28 (m, 2H), 0.69-0.63 (m, 1H), 0.46-0.42 (m, 1H). Mixture of rotamers. |
| Example 14 | (R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-cyclobutoxy-N-(pyrrolidin-1-ylsulfonyl)benzamide 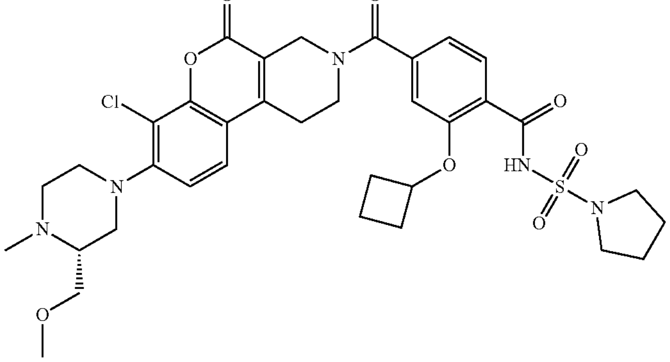 Synthesised from Intermediates 10 and 7 | HPLC: (System 1, Method D) Rt = 7.90 min, m/z 728.2 $(M + H)^+$ $(ES^+)$. $^1$H NMR (400 MHz, DMSO-$d_6$) δ: 11.39 (br s, 1H), 7.71-7.63 (m, 1H), 7.57-7.55 (m, 1H), 7.18-7.16 (m, 1H), 7.11-7.09 (m, 1H), 6.98 (br s, 1H), 4.86-4.83 (m, 1H), 4.50 (s, 1H), 4.28 (br s, 1H), 3.93 (br s, 1H), 3.58-3.55 (m, 2H), 3.47-3.41 (m, 5H), 3.31-3.36 (m, 5H), 2.96-2.84 (m, 4H), 2.68 (t, J = 10.8 Hz, 1H), 2.43-2.38 (m, 4H), 2.30 (s, 3H), 2.08-2.07 (m, 2H), 1.87-1.80 (m, 5H), 1.66-1.61 (m, 1H). |

-continued

| Example No. | Name/Structure/Intermediates | LCMS/$^1$H NMR data |
|---|---|---|
| Example 15 | (R)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)-2-(pyrrolidin-1-yl)benzamide 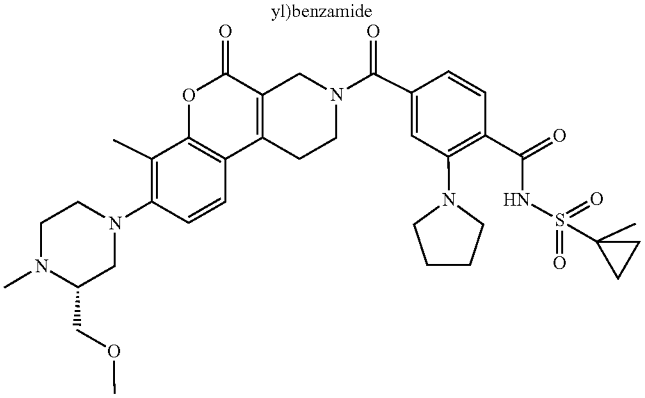 Synthesised from Intermediates 46 and 5 | HPLC: (System 1, Method D) Rt = 6.64 min, m/z 692.4 (M + H)$^+$ (ES$^+$). $^1$H NMR (400 MHz, DMSO-$d_6$) δ: 11.87 (br s, 1H), 7.55-7.49 (m, 1H), 7.34 (d, J = 7.6 Hz, 1H), 7.05 (d, J = 8.8 Hz, 1H), 6.73-6.71 (m, 2H), 4.45 (br s, 1H), 4.27 (br s, 1H), 3.89 (br s, 1H), 3.58-3.51 (m, 2H), 3.35-3.31 (m, 1H), 3.24 (s, 3H), 3.17-3.11 (m, 5H), 3.03-3.00 (m, 1H), 2.93 (br s, 2H), 2.86-2.79 (m, 2H), 2.63-2.58 (m, 1H), 2.48-2.43 (m, 2H), 2.30-2.22 (m, 6H), 1.88 (s, 4H), 1.48 (s, 3H), 1.45-1.43 (m, 2H), 0.90 (br s, 2H). |
| Example 16 | (R)-2-(7-azabicyclo[2.2.1]heptan-7-yl)-N-(N,N-dimethylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide 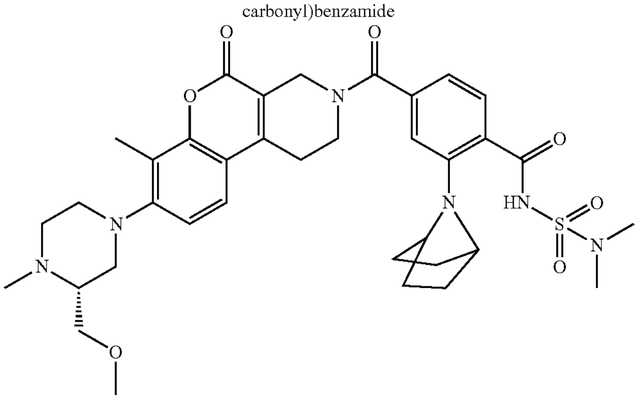 Synthesised from Intermediates 51 and 5 | HPLC: (System 1, Method D) Rt = 7.12 min, m/z 707.0 (M + H)$^+$ (ES$^+$). $^1$H NMR (400 MHz, DMSO-$d_6$) δ: 11.64 (br s, 1H), 7.53-7.48 (m, 1H), 7.39 (d, J = 7.6 Hz, 1H), 7.04 (d, J = 8.8 Hz, 1H), 7.01-7.00 (m, 1H), 6.92-6.88 (m, 1H), 4.45 (br s, 1H), 4.24 (br s, 1H), 4.08-4.06 (m, 2H), 3.89 (br s, 1H), 3.55-3.51 (m, 2H), 3.34-3.30 (m, 1H), 3.24 (s, 3H), 3.13-3.11 (m, 1H), 3.03-3.00 (m, 1H), 2.93 (br s, 2H), 2.85-2.79 (m, 8H), 2.63-2.58 (m, 1H), 2.45-2.40 (m, 2H), 2.30 (s, 3H), 2.26-2.22 (m, 3H), 1.69 (br s, 4H), 1.40 (br s, 4H). Mixture of rotamers. |
| Example 17 | (R)-2-(7-azabicyclo[2.2.1]heptan-7-yl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide 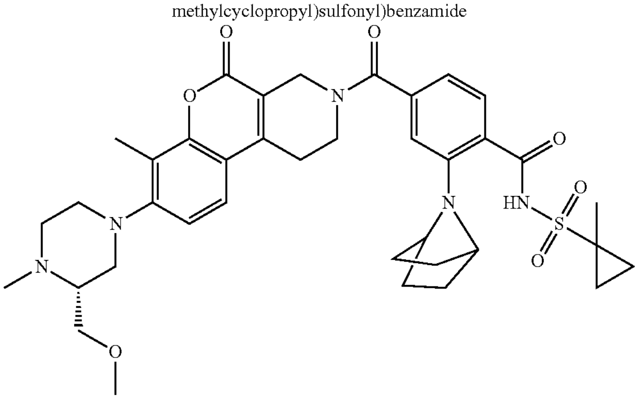 Synthesised from Intermediates 50 and 5 | HPLC: (System 1, Method D) Rt = 6.83 min, m/z 718.4 (M + H)$^+$ (ES$^+$). $^1$H NMR (400 MHz, DMSO-$d_6$) δ: 11.67 (br s, 1H), 7.56-7.51 (m, 1H), 7.37 (d, J = 7.6 Hz, 1H), 7.07 (d, J = 7.6 Hz, 1H), 7.02 (br s, 1H), 6.92-6.91 (m, 1H), 4.47 (br s, 1H), 4.27 (br s, 1H), 4.12-4.10 (m, 2H), 3.92 (br s, 1H), 3.57-3.54 (m, 2H), 3.37-3.33 (m, 4H), 3.16-3.13 (m, 1H), 3.06-3.03 (m, 1H), 2.95 (br s, 2H), 2.88-2.82 (m, 2H), 2.66-2.62 (m, 1H), 2.49-2.43 (m, 2H), 2.33 (s, 3H), 2.29-2.24 (m, 3H), 1.72 (br s, 4H), 1.48 (s, 3H), 1.46-1.41 (m, 6H), 0.94-0.91 (m, 2H). |

-continued

| Example No. | Name/Structure/Intermediates | LCMS/$^1$H NMR data |
|---|---|---|
| Example 18 | (R)-N-(N,N-dimethylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-2-(pyrrolidin-1-yl)benzamide 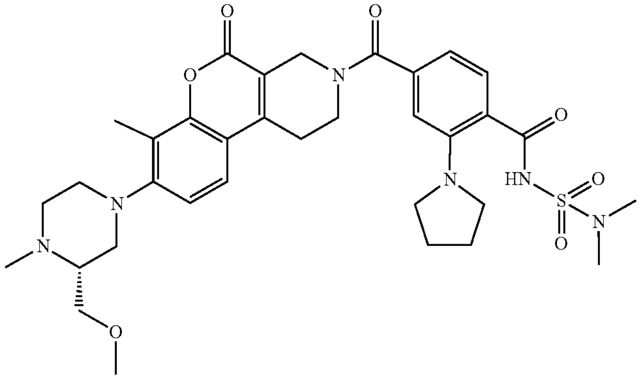 Synthesised from Intermediates 47 and 5 | HPLC: (System 1, Method D) Rt = 6.61 min, m/z 681.4 $(M + H)^+$ $(ES^+)$. $^1$H NMR (400 MHz, DMSO-$d_6$) δ: 11.80 (br s, 1H), 7.54-7.49 (m, 1H), 7.34 (d, J = 7.6 Hz, 1H), 7.05 (d, J = 8.4 Hz, 1H), 6.73-6.70 (m, 2H), 4.45 (br s, 1H), 4.27 (br s, 1H), 3.89 (br s, 1H), 3.58-3.52 (m, 2H), 3.32 (br s, 1H), 3.24 (s, 3H), 3.17-3.11 (m, 5H), 3.03-3.00 (m, 1H), 2.92 (br s, 2H), 2.86 (s, 6H), 2.86-2.79 (m, 2H), 2.63-2.57 (m, 1H), 2.47-2.41 (m, 2H), 2.29-2.22 (m, 6H), 1.88 (s, 4H). |
| Example 19 | (R)-2-cyclobutoxy-4-(8-(hexahydropyrazino[2,1-c][1,4]oxazin-8(1H)-yl)-7-methyl-5-oxo-1,3,4,5-tetrahydro-2H-chromeno[3,4-c]pyridine-3-carbonyl)-N-(pyrrolidin-1-ylsulfonyl)benzamide 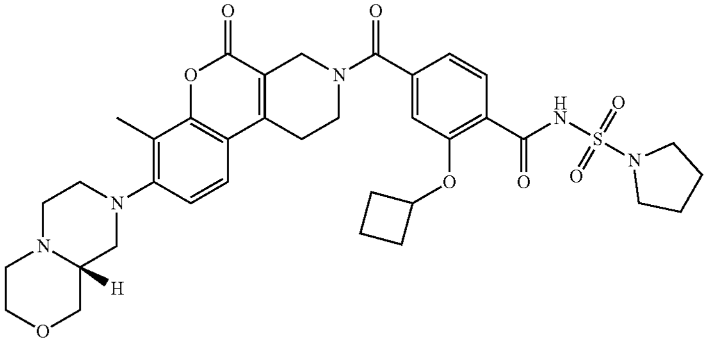 [SMILES: Cc1c(N2CCN3CCOC[C@H]3C2)ccc2c3c(c(=O)oc12)CN(C(=O)c1ccc(C(=O)NS(=O)(=O)N2CCCC2)c(OC2CCC2)c1)CC3] Synthesised from Intermediates 10 and 8 | HPLC: (System 1, Method D) Rt = 7.91 min, m/z 706.1 $(M + H)^+$ $(ES^+)$. $^1$H NMR (400 MHz, DMSO-$d_6$) δ: 11.41 (br s, 1H), 7.56-7.48 (m, 2H), 7.06-7.04 (m, 2H), 6.97-6.95 (m, 1H), 4.84-4.77 (m, 1H), 4.46 (br s, 1H), 4.24 (br s, 1H), 3.90 (br s, 1H), 3.76-3.74 (m, 1H), 3.69-3.66 (m, 1H), 3.54-3.48 (m, 2H), 3.44-3.42 (m, 4H), 3.16-3.06 (m, 2H), 2.94-2.92 (m, 3H), 2.86-2.77 (m, 2H), 2.67-2.64 (m, 1H), 2.43-2.39 (m, 4H), 2.36-2.23 (m, 5H), 2.06 (br s, 2H), 1.85-1.74 (m, 5H), 1.65-1.58 (m, 1H). |
| Example 20 | (R)-N-(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)benzamide 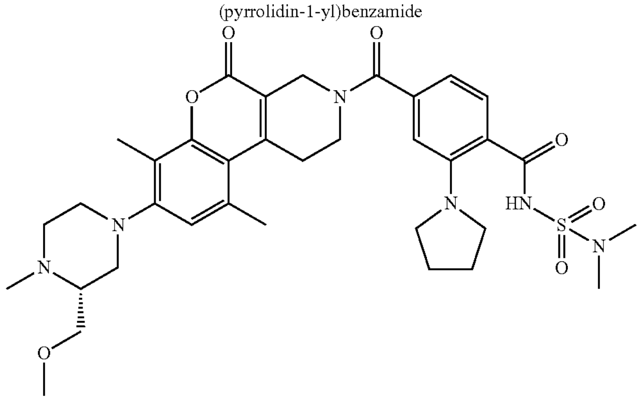 Synthesised from Intermediates 47 and 6 | HPLC: (System 1, Method D) Rt = 6.80 min, m/z 695.0 $(M + H)^+$ $(ES^+)$. $^1$H NMR (400 MHz, DMSO-$d_6$) δ: 11.82 (br s, 1H), 7.34 (d, J = 7.6 Hz, 1H), 6.82 (s, 1H), 6.76-6.69 (m, 2H), 4.43 (br s, 1H), 4.27 (br s, 1H), 3.79 (br s, 1H), 3.54-3.49 (m, 2H), 3.31 (br s, 1H), 3.23 (s, 3H), 3.17 (br s, 6H), 3.12-3.09 (m, 1H), 3.02-2.99 (m, 1H), 2.85 (s, 6H), 2.81-2.76 (m, 2H), 2.66-2.57 (m, 4H), 2.41-2.39 (m, 2H), 2.28 (s, 3H), 2.20-2.16 (m, 3H), 1.88 (br s, 4H). |

-continued

| Example No. | Name/Structure/Intermediates | LCMS/$^1$H NMR data |
|---|---|---|
| Example 21 | (R)-2-cyclobutoxy-4-(8-(hexahydropyrazino[2,1-c][1,4]oxazin-8(1 H)-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 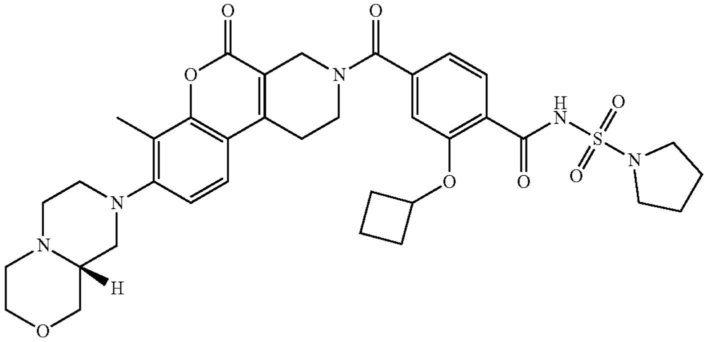 Synthesised from Intermediates 10 and 9 | HPLC: (System 1, Method D) Rt = 7.80 min, m/z 720.2 $(M + H)^+$ $(ES^+)$. $^1$H NMR (400 MHz, DMSO-$d_6$) δ: 11.38 (br s, 1H), 7.50 (d, J = 7.2 Hz, 1H), 7.10-7.07 (m, 1H), 6.99-6.95 (m, 1H), 6.82 (s, 1H), 4.85-4.78 (m, 1H), 4.45 (br s, 1H), 4.25 (br s, 1H), 3.80 (br s, 1H), 3.76-3.73 (m, 1H), 3.69-3.66 (m, 1H), 3.53-3.50 (m, 1H), 3.48-3.41 (m, 5H), 3.17-3.06 (m, 4H), 2.93-2.90 (m, 1H), 2.83-2.76 (m, 2H), 2.65-2.61 (m, 4H), 2.44-2.37 (m, 3H), 2.34-2.25 (m, 3H), 2.22-2.18 (m, 3H), 2.08-2.05 (m, 2H), 1.84-1.75 (m, 5H), 1.62-1.60 (m, 1H). |
| Example 22 | (R)-2-(7-azabicyclo[2.2.1]heptan-7-yl)-6-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide 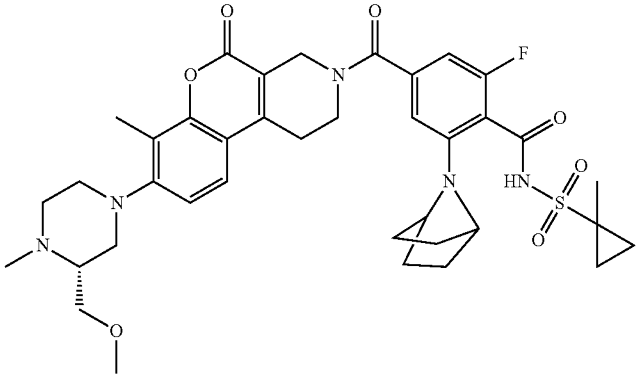 [SMILES: COC[C@H]1CN(c2ccc3c4c(c(=O)oc3c2C)CN(C(=O)c2cc(F)c(C(=O)NS(=O)(=O)C3(C)CC3)c(N3C5CCC3CC5)c2)CC4)CCN1C] Synthesised from Intermediates 86 and 5 | HPLC: (System 1, Method D) Rt = 7.18 min, m/z 736.2 $(M + H)^+$ $(ES^+)$. $^1$H NMR (400 MHz, DMSO-$d_6$) δ: 7.56-7.50 (m, 1H), 7.05 (d, J = 8.8 Hz, 1H), 6.78 (s, 1H), 6.72-6.70 (m, 1H), 4.44 (br s, 1H), 4.25 (br s, 3H), 3.88 (br s, 1H), 3.56-3.53 (m, 2H), 3.43-3.37 (m, 1H), 3.32 (s, 3H), 3.16-3.14 (m, 1H), 3.07-3.04 (m, 1H), 2.93 (br s, 3H), 2.87-2.82 (m, 1H), 2.69-2.56 (m, 3H), 2.38 (s, 3H), 2.27-2.23 (m, 3H), 1.66 (br s, 4H), 1.46 (s, 3H), 1.38-1.37 (m, 6H), 0.86 (br s, 2H). One exchangeable proton not visible. Mixture of rotamers. |
| Example 23 | (R)-2-(7-azabicyclo[2.2.1]heptan-7-yl)-N-(N,N-dimethylsulfamoyl)-6-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide 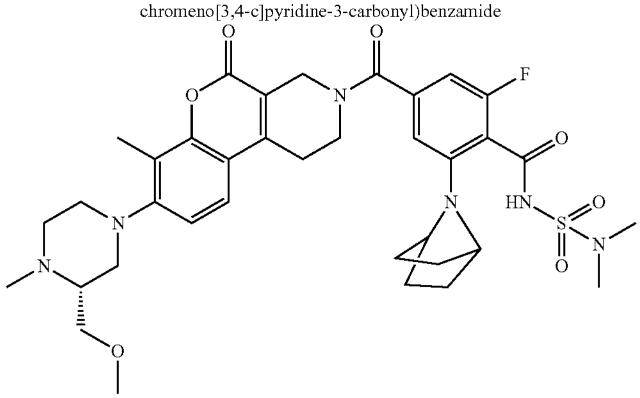 Synthesised from Intermediates 87 and 5 | HPLC: (System 1, Method D) Rt = 6.70 min, m/z 725.0 $(M + H)^+$ $(ES^+)$. $^1$H NMR (400 MHz, DMSO-$d_6$) δ: 11.83 (br s, 1H), 7.54-7.49 (m, 1H), 7.05 (d, J = 8.8 Hz, 1H), 6.79 (s, 1H), 6.73-6.71 (m, 1H), 4.43 (br s, 1H), 4.25 (br s, 3H), 3.87 (br s, 1H), 3.56-3.52 (m, 2H), 3.38-3.35 (m, 1H), 3.25 (s, 3H), 3.15-3.13 (m, 1H), 3.06-3.03 (m, 1H), 2.93-2.83 (m, 4H), 2.81 (s, 6H), 2.67-2.62 (m, 1H), 2.54-2.51 (m, 2H), 2.35 (s, 3H), 2.27-2.23 (m, 3H), 1.65 (br s, 4H), 1.39-1.38 (m, 4H). |

-continued

| Example No. | Name/Structure/Intermediates | LCMS/$^1$H NMR data |
|---|---|---|
| Example 24 | (R)-2-(cyclopentyloxy)-3-fluoro-N-(N-isopropyl-N-methylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 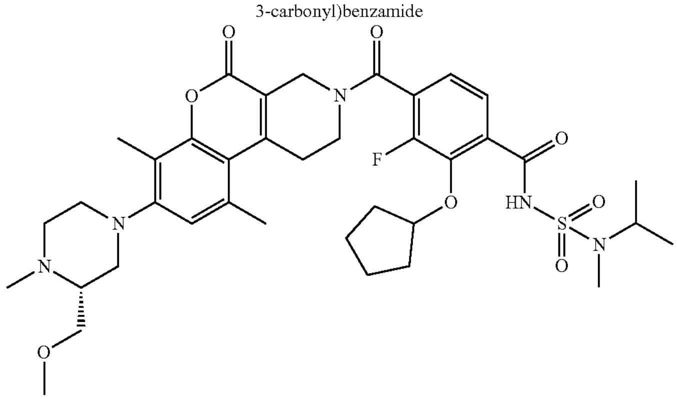 Synthesised from Intermediates 17 and 6 | HPLC: (System 1, Method D) Rt = 8.29 min, m/z 756.4 $(M + H)^+$ $(ES^+)$. $^1$H NMR (400 MHz, DMSO-$d_6$) δ: 11.61 (br s, 1H), 7.32-7.29 (m, 1H), 7.26-7.16 (m, 1H), 6.86-8.84 (m, 1H), 4.85-4.80 (m, 1H), 4.46 (br s, 1H), 4.18 (s, 1H), 4.11-4.06 (m, 1H), 3.87 (br s, 1H), 3.57-3.54 (m, 1H), 3.45-3.44 (m, 1H), 3.37-3.36 (m, 1H), 3.27-3.23 (m, 4H), 3.15-3.13 (m, 2H), 3.05-3.03 (m, 1H), 2.88-2.80 (m, 5H), 2.69-2.62 (m, 4H), 2.42 (br s, 2H), 2.33 (s, 3H), 2.23-2.19 (m, 3H), 1.83-1.74 (m, 6H), 1.59-1.55 (m, 2H), 1.13-1.09 (m, 6H). Mixture of rotamers. |
| Example 25 | (R)-2-cyclobutoxy-3-fluoro-N-(N-isopropyl-N-methylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 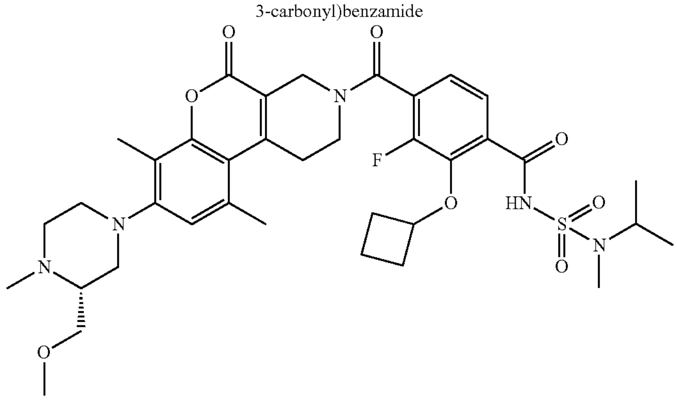 Synthesised from Intermediates 18 and 6 | HPLC: (System 1, Method D) Rt = 7.92 min, m/z 742.4 $(M + H)^+$.$(ES^+)$ $^1$H NMR (400 MHz, DMSO-$d_6$) δ: 11.60 (br s, 1H), 7.32-7.29 (m, 1H), 7.26-7.17 (m, 1H), 6.86-6.84 (d, J = 7.2 Hz, 1H), 4.72-4.53 (m, 1H), 4.50 (br s, 1H), 4.17 (s, 1H), 4.14-4.07 (m, 1H), 3.88-3.86 (m, 1H), 3.57-3.54 (m, 1H), 3.45 (br s, 1H), 3.38-3.34 (m, 1H), 3.27-3.23 (m, 4H), 3.15-3.13 (m, 2H), 3.06-3.03 (m, 1H), 2.88-2.81 (m, 5H), 2.69-2.59 (m, 4H), 2.46-2.41 (m, 2H), 2.33 (s, 3H), 2.30-2.19 (m, 5H), 2.16-2.08 (m, 2H), 1.71-1.66 (m, 1H), 1.50-1.41 (m, 1H), 1.15-1.12 (m, 6H). Mixture of rotamers. |
| Example 26 | 2-(3-azabicyclo[3.1.0]hexan-3-yl)-6-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide 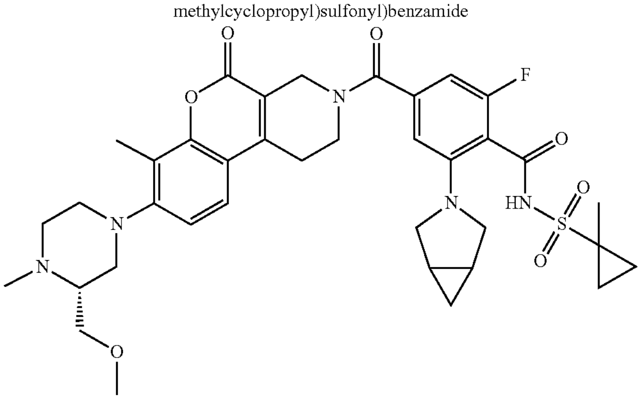 Synthesised from Intermediates 88 and 5 | HPLC: (System 1, Method D) Rt = 6.71 min, m/z 722.4 $(M + H)^+$ $(ES^+)$. $^1$H NMR (400 MHz, DMSO-$d_6$) δ: 11.76 (br s, 1H), 7.56-7.53 (m, 1H), 7.08 (d, J = 8.8 Hz, 1H), 6.61 (d, J = 9.2 Hz, 1H), 6.50 (s, 1H), 4.45 (br s, 1H), 4.29 (br s, 1H), 3.90 (br s, 1H), 3.59-3.56 (m, 4H), 3.42-3.41 (m, 1H), 3.34 (br s, 2H), 3.28 (s, 3H), 3.19-3.17 (m, 1H), 3.10-3.07 (m, 1H), 2.96 (br s, 3H), 2.90-2.85 (m, 1H), 2.72-2.51 (m, 3H), 2.41 (s, 3H), 2.30-2.26 (m, 3H), 1.66-1.64 (m, 2H), 1.49 (s, 3H), 1.41 (br s, 2H), 0.89 (br s, 2H), 0.69-0.65 (m, 1H), 0.20 (br s, 1H). |

-continued

| Example No. | Name/Structure/Intermediates | LCMS/$^1$H NMR data |
|---|---|---|
| Example 27 | 2-(3-azabicyclo[3.1.0]hexan-3-yl)-N-(N,N-dimethylsulfamoyl)-6-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide 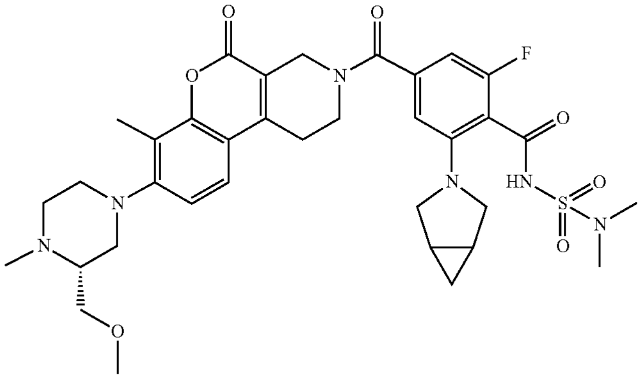 Synthesised from Intermediates 89 and 5 | HPLC: (System 1, Method D) Rt = 6.65 min, m/z 711.3 (M + H)$^+$ (ES$^+$). $^1$H NMR (400 MHz, DMSO-d$_6$) δ: 11.80 (br s, 1H), 7.58-7.53 (m, 1H), 7.08 (d, J = 8.8 Hz, 1H), 6.62 (d, J = 8.8 Hz, 1H), 6.50 (s, 1H), 4.45 (br s, 1H), 4.28 (br s, 1H), 3.89 (br s, 1H), 3.58-3.55 (m, 4H), 3.42-3.41 (m, 1H), 3.32 (br s, 2H), 3.28 (s, 3H), 3.18-3.16 (m, 1H), 3.09-3.06 (m, 1H), 2.95-2.92 (m, 3H), 2.89-2.84 (m, 7H), 2.70-2.51 (m, 3H), 2.38 (s, 3H), 2.29-2.26 (m, 3H), 1.67-1.65 (m, 2H), 0.70-0.66 (m, 2H). |
| Example 28 | 2-(3-azabicyclo[3.1.0]hexan-3-yl)-N-(N,N-dimethylsulfamoyl)-6-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 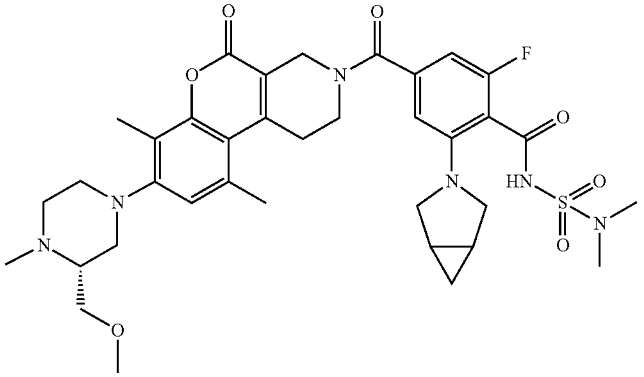 Synthesised from Intermediates 89 and 6 | HPLC: (System 1, Method D) Rt = 6.89 min, m/z 725.4 (M + H)$^+$ (ES$^+$). $^1$H NMR (400 MHz, DMSO-d$_6$) δ: 11.80 (br s, 1H), 6.85 (s, 1H), 6.66-6.61 (m, 1H), 6.52 (s, 1H), 4.44 (br s, 1H), 4.29 (br s, 1H), 3.79 (br s, 1H), 3.58-3.54 (m, 4H), 3.41-3.38 (m, 3H), 3.27 (s, 3H), 3.19-3.14 (m, 3H), 3.07-3.05 (m, 1H), 2.92-2.90 (m, 1H), 2.85-2.81 (m, 7H), 2.67-2.65 (m, 4H), 2.55 (br s, 2H), 2.37 (s, 3H), 2.23-2.20 (m, 3H), 1.67-1.66 (m, 2H), 0.70-0.66 (m, 1H), 0.20 (br s, 1H). |
| Example 29 | (R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-(cyclopentyloxy)-3-fluoro-N-(N-isopropyl-N-methylsulfamoyl)benzamide 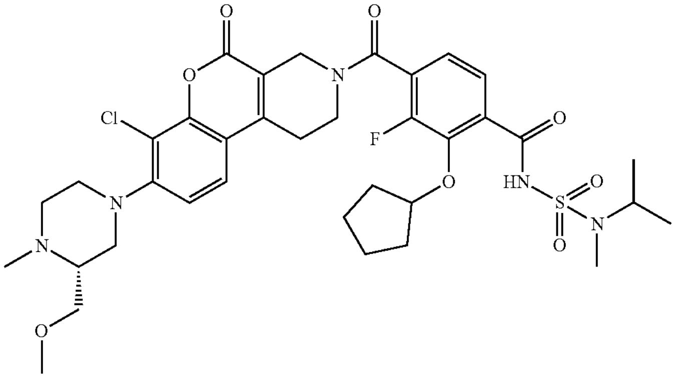 [SMILES: COC[C@H]1CN(c2ccc3c4c(c(=O)oc3c2Cl)CN(C(=O)c2ccc(C(=O)NS(=O)(=O)N(C)C(C)C)c(OC3CCCC3)c2F)CC4)CCN1C] Synthesised from Intermediates 17 and 7 | HPLC: (System 1, Method D) Rt = 8.22 min, m/z 762.3 (M + H)$^+$ (ES$^+$). $^1$H NMR (400 MHz, DMSO-d$_6$) δ: 11.66 (br s, 1H), 7.71-7.61 (m, 1H), 7.32-7.28 (m, 1H), 7.24-7.16 (m, 2H), 4.85-4.80 (m, 1H), 4.56 (br s, 1H), 4.19 (s, 1H), 4.11-4.08 (m, 1H), 3.98 (br s, 1H), 3.58-3.55 (m, 2H), 3.45-3.42 (m, 1H), 3.34-3.27 (m, 5H), 3.01-2.86 (m, 4H), 2.81 (s, 3H), 2.72-2.67 (m, 1H), 2.50 (br s, 2H), 2.32 (s, 3H), 1.79-1.74 (m, 6H), 1.56-1.51 (m, 2H), 1.13-1.06 (m, 6H). Mixture of rotamers. |

-continued

| Example No. | Name/Structure/Intermediates | LCMS/$^1$H NMR data |
|---|---|---|
| Example 30 | (R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-cyclobutoxy-3-fluoro-N-(N-isopropyl-N-methylsulfamoyl)benzamide 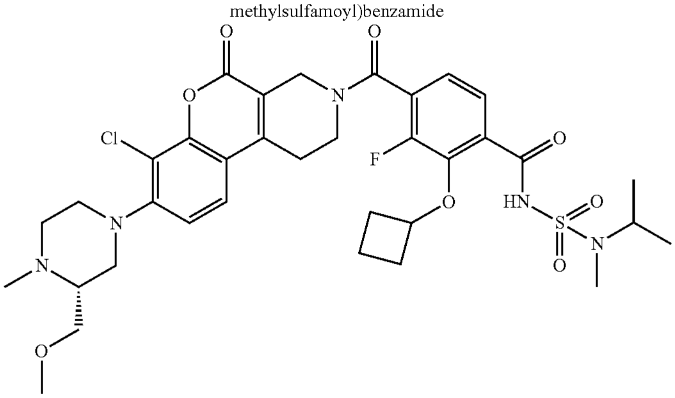 Synthesised from Intermediates 18 and 7 | HPLC: (System 1, Method D) Rt = 7.75 min, m/z 748.3 (M + H)$^+$ (ES$^+$). $^1$H NMR (400 MHz, DMSO-$d_6$) δ: 11.67 (br s, 1H), 7.71-7.62 (m, 1H), 7.32-7.25 (m, 1H), 7.23-7.16 (m, 2H), 4.72-4.64 (m, 1H), 4.55 (br s, 1H), 4.18 (s, 1H), 4.14-4.07 (m, 1H), 3.97-3.96 (m, 1H), 3.59-3.53 (m, 2H), 3.45-3.42 (m, 1H), 3.37 (br s, 1H), 3.28-3.27 (m, 1H), 3.25 (s, 3H), 3.01-2.85 (m, 4H), 2.82 (s, 3H), 2.72-2.67 (m, 1H), 2.45 (br s, 2H), 2.32 (s, 3H), 2.27-2.19 (m, 2H), 2.16-2.08 (m, 2H), 1.71-1.66 (m, 1H), 1.51-1.43 (m, 1H), 1.15-1.13 (m, 6H). Mixture of rotamers. |
| Example 31 | (R)-N-(N-isopropyl-N-methylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-2-(pyrrolidin-1-yl)benzamide 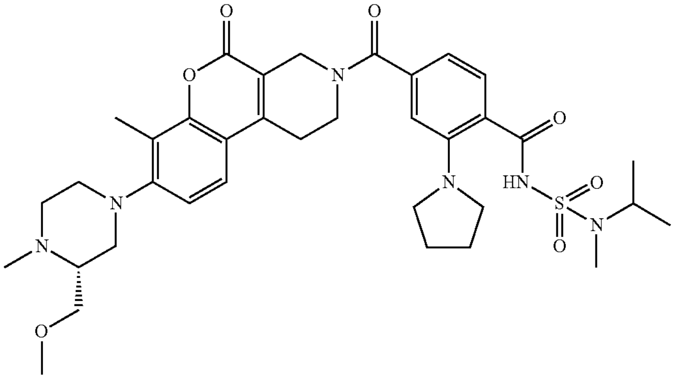 [SMILES: COC[C@H]1CN(c2ccc3c4c(c(=O)oc3c2C)CN(C(=O)c2ccc(C(=O)NS(=O)(=O)N(C)C(C)C)c(N3CCCC3)c2)CC4)CCN1C] Synthesised from Intermediates 49 and 5 | HPLC: (System 1, Method D) Rt = 7.84 min, m/z 709.4 (M + H)$^+$ (ES$^+$). $^1$H NMR (400 MHz, DMSO-$d_6$) δ: 11.87 (br s, 1H), 7.58-7.51 (m, 1H), 7.29 (d, J = 7.6 Hz, 1H), 7.07 (d, J = 8.8 Hz, 1H), 6.75 (br s, 2H), 4.47 (br s, 1H), 4.29 (br s, 1H), 4.14-4.09 (m, 1H), 3.92 (br s, 1H), 3.60-3.54 (m, 2H), 3.31 (br s, 1H), 3.26 (s, 3H), 3.19-3.12 (m, 5H), 3.05-3.02 (m, 1H), 2.95 (br s, 2H), 2.86-2.81 (m, 5H), 2.64-2.59 (m, 1H), 2.43-2.40 (m, 2H), 2.30-2.25 (m, 6H), 1.90 (br s, 4H), 1.13 (d, J = 6.4 Hz, 6H). |
| Example 32 | 2-(3-azabicyclo[3.1.0]hexan-3-yl)-6-chloro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide 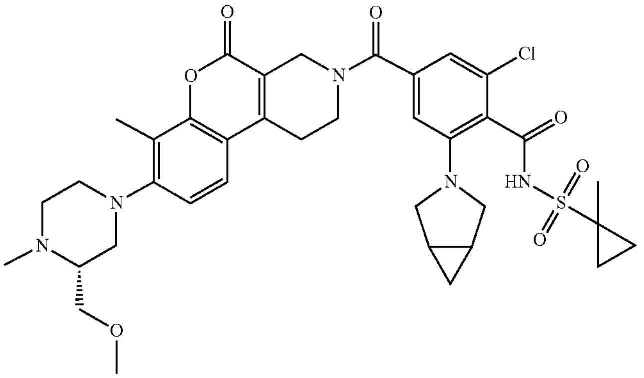 [SMILES: COC[C@H]1CN(c2ccc3c4c(c(=O)oc3c2C)CN(C(=O)c2cc(Cl)c(C(=O)NS(=O)(=O)C3(C)CC3)c(N3CC5CC5C3)c2)CC4)CCN1C] Synthesised from Intermediates 90 and 5 | HPLC: (System 1, Method D) Rt = 6.84 min, m/z 738.3 (M + H)$^+$ (ES$^+$). $^1$H NMR (400 MHz, DMSO-$d_6$) δ: 11.82 (br s, 1H), 7.56-7.54 (m, 1H), 7.08 (d, J = 8.4 Hz, 1H), 6.82 (s, 1H), 6.65 (s, 1H), 4.45 (br s, 1H), 4.29 (br s, 1H), 3.89 (br s, 1H), 3.61-3.55 (m, 4H), 3.45-3.40 (m, 2H), 3.34 (br s, 1H), 3.28 (s, 3H), 3.19-3.16 (m, 1H), 3.09-3.06 (m, 1H), 2.95 (br s, 3H), 2.90-2.84 (m, 1H), 2.71-2.56 (m, 3H), 2.39 (s, 3H), 2.29-2.26 (m, 3H), 1.64-1.62 (m, 2H), 1.52 (s, 3H), 1.42 (br s, 2H), 0.87 (br s, 2H), 0.67-0.62 (m, 1H), 0.24 (br s, 1H). |

-continued

| Example No. | Name/Structure/Intermediates | LCMS/$^1$H NMR data |
|---|---|---|
| Example 33 | 2-(3-azabicyclo[3.1.0]hexan-3-yl)-6-chloro-N-(N,N-dimethylsulfamoyl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide 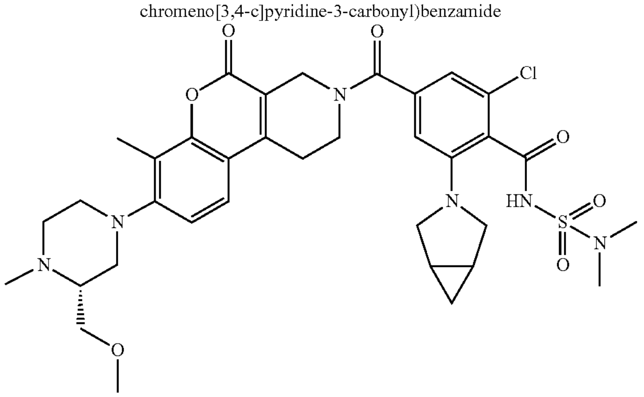 Synthesised from Intermediates 91 and 5 | HPLC: (System 1, Method D) Rt = 6.79 min, m/z 727.3 (M + H)$^+$ (ES$^+$). $^1$H NMR (400 MHz, DMSO-d$_6$) δ: 11.84 (br s, 1H), 7.56-7.54 (m, 1H), 7.08 (d, J = 8.4 Hz, 1H), 6.84 (s, 1H), 6.65 (s, 1H), 4.46 (br s, 1H), 4.29 (br s, 1H), 3.89 (br s, 1H), 3.60-3.55 (m, 4H), 3.41-3.38 (m, 1H), 3.34 (br s, 2H), 3.27 (s, 3H), 3.18-3.15 (m, 1H), 3.08-3.05 (m, 1H), 2.95-2.83 (m, 10H), 2.69-2.64 (m, 1H), 2.55 (br s, 2H), 2.37 (s, 3H), 2.29-2.26 (m, 3H), 1.65-1.64 (m, 2H), 0.68-0.63 (m, 1H), 0.23 (br s, 1H). |
| Example 34 | 2-(3-azabicyclo[3.1.0]hexan-3-yl)-6-chloro-N-(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 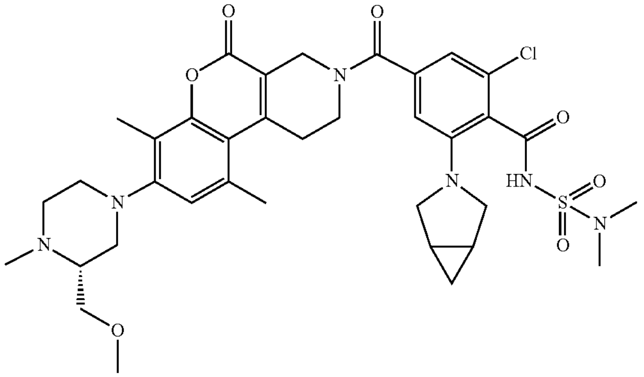 Synthesised from Intermediates 91 and 6 | HPLC: (System 1, Method D) Rt = 6.93 min, 741.4 (M + H)$^+$ (ES$^+$). $^1$H NMR (400 MHz, DMSO-d$_6$) δ: 11.82 (br s, 1H), 6.85 (s, 2H), 6.67 (s, 1H), 4.45 (br s, 1H), 4.29 (br s, 1H), 3.79 (br s, 1H), 3.61-3.51 (m, 4H), 3.40-3.38 (m, 1H), 3.34 (br s, 2H), 3.27 (s, 3H), 3.24-3.14 (m, 3H), 3.09-3.05 (m, 1H), 2.88-2.81 (m, 8H), 2.68-2.64 (m, 4H), 2.51 (br s, 2H), 2.37 (s, 3H), 2.23-2.20 (m, 3H), 1.66-1.64 (m, 2H), 0.68-0.63 (m, 1H), 0.23 (br s, 1H). |
| Example 35 | 2-(((1R,3r,5S)-bicyclo[3.1.0]hexan-3-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 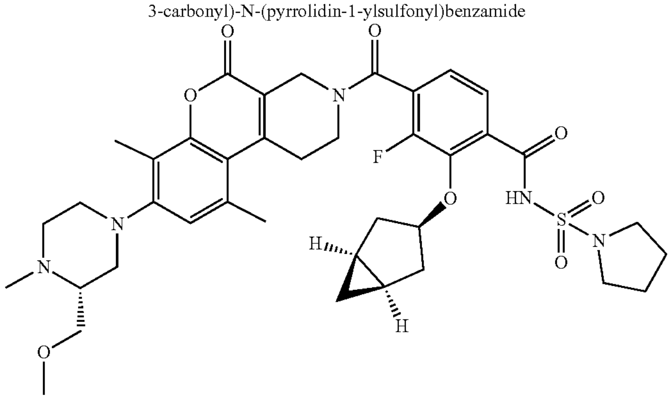 Synthesised from Intermediates 22 and 6 | HPLC: (System 1, Method D) Rt = 7.58 min, m/z 766.4 (M + H)$^+$ (ES$^+$). $^1$H NMR (400 MHz, DMSO-d$_6$) δ: 11.59 (br s, 1H), 7.30-7.28 (m, 1H), 7.21-7.12 (m, 1H), 6.86-8.84 (m, 1H), 4.80-4.72 (m, 1H), 4.49 (br s, 1H), 4.17 (s, 1H), 3.88-3.85 (m, 1H), 3.57-3.54 (m, 1H), 3.46-3.44 (m, 1H), 3.41-3.38 (m, 2H), 3.36-3.35 (m, 3H), 3.27 (s, 3H), 3.23 (br s, 1H), 3.16-3.13 (m, 2H), 3.06-3.04 (m, 1H), 2.89-2.80 (m, 2H), 2.69-2.62 (m, 4H), 2.48-2.46 (m, 2H), 2.34 (s, 3H), 2.23-2.20 (m, 3H), 2.13-2.08 (m, 2H), 2.02-1.95 (m, 2H), 1.87-1.84 (m, 4H), 1.32-1.29 (m, 2H), 0.67-0.60 (m, 1H), 0.47-0.40 (m, 1H). Mixture of rotamers. |

-continued

| Example No. | Name/Structure/Intermediates | LCMS/$^1$H NMR data |
|---|---|---|
| Example 36 | 2-(((1R,3r,5S)-bicyclo[3.1.0]hexan-3-yl)oxy)-3-fluoro-N-(N-isopropyl-N-methylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 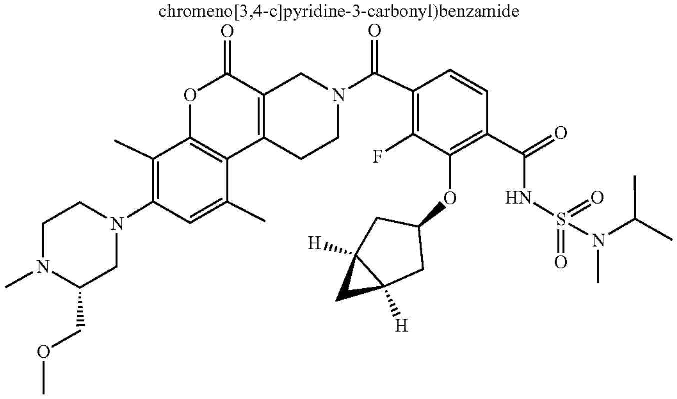 Synthesised from Intermediates 24 and 6 | HPLC: (System 1, Method D) Rt = 8.10 min, m/z 768.4 (M + H)$^+$ (ES$^+$). $^1$H NMR (400 MHz, DMSO-d$_6$) δ: 11.67 (br s, 1H), 7.28-7.25 (m, 1H), 7.23-7.14 (m, 1H), 6.86-6.84 (m, 1H), 4.78-4.69 (m, 1H), 4.51 (br s, 1H), 4.17 (s, 1H), 4.12-4.08 (m, 1H), 3.88-3.85 (m, 1H), 3.57-3.55 (m, 1H), 3.45-3.44 (m, 1H), 3.38-3.34 (m, 1H), 3.27 (s, 3H), 3.23 (br s, 1H), 3.15-3.13 (m, 2H), 3.06-3.03 (m, 1H), 2.88-2.83 (m, 2H), 2.80 (s, 3H), 2.69-2.62 (m, 4H), 2.50-2.49 (m, 2H), 2.33 (s, 3H), 2.23-2.20 (m, 3H), 2.14-2.08 (m, 2H), 2.02-1.95 (m, 2H), 1.32-1.28 (m, 2H), 1.14-1.11 (m, 6H), 0.68-0.61 (m, 1H), 0.47-0.40 (m, 1H). Mixture of rotamers. |
| Example 37 | 2-(((1R,3r,5S)-bicyclo[3.1.0]hexan-3-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 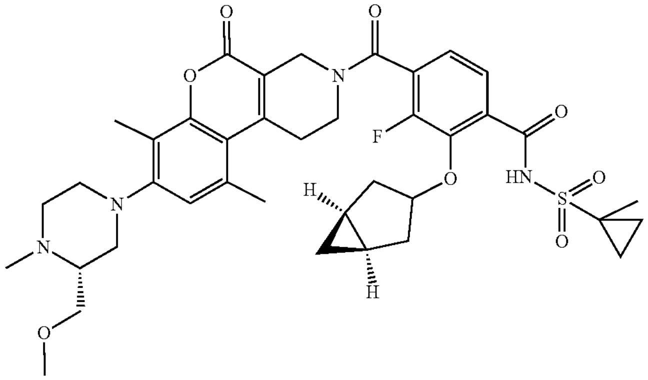 [SMILES: COC[C@H]1CN(c2cc(C)c3c4c(c(=O)oc3c2C)CN(C(=O)c2ccc(C(=O)NS(=O)(=O)C3(C)CC3)c(OC3C[C@@H]5C[C@@H]5C3)c2F)CC4)CCN1C] Synthesised from Intermediates 25 and 6 | HPLC: (System 1, Method D) Rt = 7.29 min, m/z 751.4 (M + H)$^+$ (ES$^+$). $^1$H NMR (400 MHz, DMSO-d$_6$) δ: 11.25 (br s, 1H), 7.29-7.27 (m, 1H), 7.19-7.11 (m, 1H), 6.87-6.85 (m, 1H), 4.84-4.75 (m, 1H), 4.50 (br s, 1H), 4.18 (s, 1H), 3.87 (br s, 1H), 3.59-3.56 (m, 1H), 3.46-3.45 (m, 2H), 3.28 (s, 3H), 3.23-3.08 (m, 4H), 2.99-2.97 (m, 1H), 2.89-2.84 (m, 1H), 2.75-2.62 (m, 6H), 2.44 (s, 3H), 2.24-2.20 (m, 3H), 2.09-2.06 (m, 2H), 2.01-1.95 (m, 2H), 1.48 (s, 3H), 1.46-1.37 (m, 2H), 1.31-1.29 (m, 2H), 0.85-0.83 (m, 2H), 0.72-0.65 (m, 1H), 0.46-0.39 (m, 1H). Mixture of rotamers. |
| Example 38 | (R)-2-(cyclobutyl(methyl)amino)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 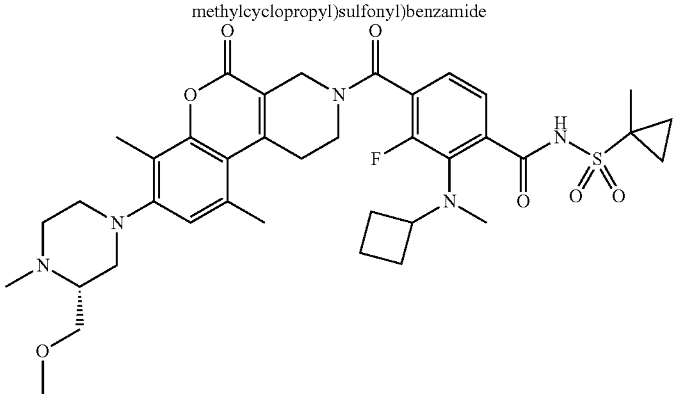 Synthesised from Intermediates 85 and 6 | HPLC: (System 1, Method D) Rt = 8.63 min, m/z 738.4 (M + H)$^+$ (ES$^+$). $^1$H NMR (400 MHz, DMSO-d$_6$) δ: 13.85 (br s, 1H), 7.77-7.71 (m, 1H), 7.50-7.39 (m, 1H), 6.85 (d, J = 7.2 Hz, 1H), 4.48 (br s, 1H), 4.16 (s, 1H), 3.89-3.81 (m, 2H), 3.57-3.54 (m, 1H), 3.44 (br s, 1H), 3.38 (br s, 1H), 3.27 (s, 3H), 3.24 (br s, 1H), 3.15-3.13 (m, 2H), 3.06-3.03 (m, 1H), 2.89-2.80 (m, 2H), 2.75-2.73 (m, 3H), 2.71-2.67 (m, 2H), 2.64-2.61 (m, 2H), 2.46 (br s, 2H), 2.33 (s, 3H), 2.23-2.18 (m, 3H), 2.02 (br s, 2H), 1.94-1.85 (m, 2H), 1.68-1.59 (m, 2H), 1.55 (s, 3H), 1.50-1.48 (m, 2H), 0.97 (br s, 2H). Mixture of rotamers. |

-continued

| Example No. | Name/Structure/Intermediates | LCMS/$^1$H NMR data |
|---|---|---|
| Example 39 | (R)-2-(cyclobutyl(methyl)amino)-N-(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 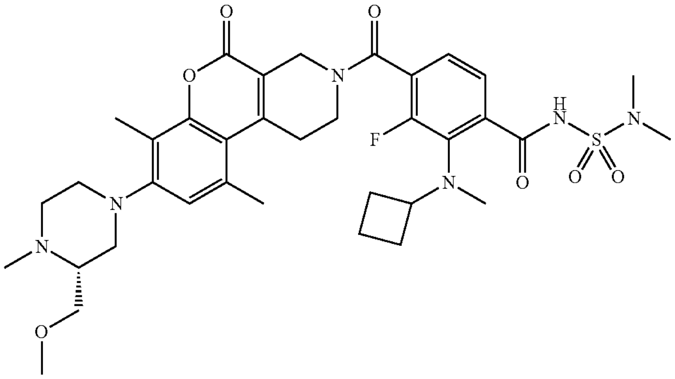 Synthesised from Intermediates 84 and 6 | HPLC: (System 1, Method D) Rt = 9.05 min, m/z 727.0 $(M + H)^+$ $(ES^+)$. $^1$H NMR (400 MHz, DMSO-$d_6$) δ: 13.75 (br s, 1H), 7.78-7.73 (m, 1H), 7.50-7.40 (m, 1H), 6.86-6.84 (m, 1H), 4.59-4.42 (m, 1H), 4.15 (s, 1H), 3.89-3.80 (m, 2H), 3.57-3.54 (m, 1H), 3.43 (br s, 1H), 3.37 (br s, 1H), 3.26-3.24 (m, 4H), 3.15-3.12 (m, 2H), 3.05-3.03 (m, 1H), 2.91 (s, 6H), 2.87-2.79 (m, 2H), 2.74-2.66 (m, 5H), 2.63-2.61 (m, 2H), 2.462.44 (m, 2H), 2.32 (s, 3H), 2.23-2.19 (m, 3H), 2.02 (br s, 2H), 1.92-1.83 (m, 2H), 1.68-1.59 (m, 2H). Mixture of rotamers. |
| Example 40 | (R)-2-(7-azabicyclo[2.2.1]heptan-7-yl)-6-chloro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide 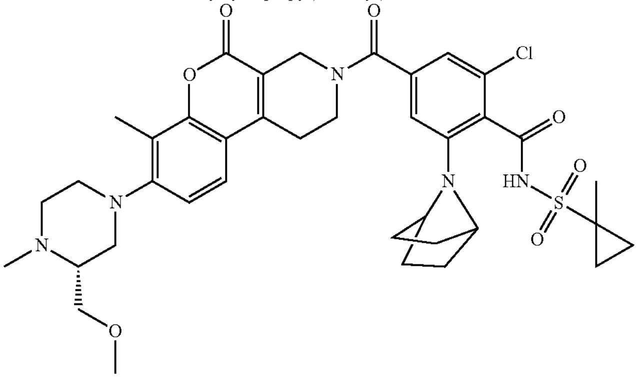 Synthesised from Intermediates 92 and 5 | HPLC: (System 1, Method D) Rt = 7.02 min, m/z 752.3 $(M + H)^+$ $(ES^+)$. $^1$H NMR (400 MHz, DMSO-$d_6$) δ: 11.84 (br s, 1H), 7.58-7.53 (m, 1H), 7.08 (d, J = 8.8 Hz, 1H), 0.95 (s, 2H), 4.47 (br s, 1H), 4.28 (br s, 3H), 3.90 (br s, 1H), 3.59-3.55 (m, 2H), 3.42-3.39 (m, 1H), 3.28 (s, 3H), 3.19-3.16 (m, 1H), 3.09-3.06 (m, 1H), 2.96-2.84 (m, 4H), 2.70-2.65 (m, 1H), 2.57 (br s, 2H), 2.39 (s, 3H), 2.33-2.26 (m, 3H), 1.69 (br s, 4H), 1.51 (s, 3H), 1.48-1.39 (m, 6H), 0.89 (m, 2H). |
| Example 41 | (R)-2-cyclobutoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 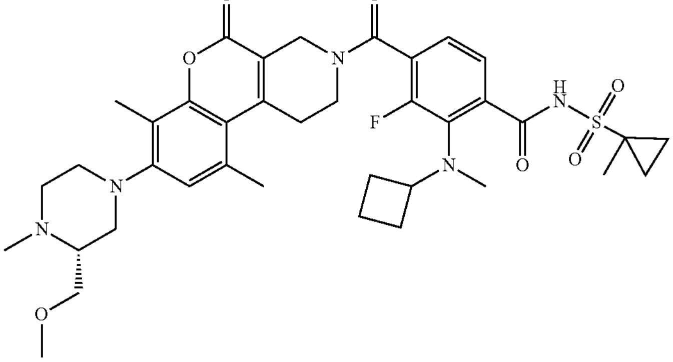 Synthesised from Intermediates 19 and 6 | HPLC: (System 1, Method D) Rt = 6.98 min, m/z 725.4 $(M + H)^+$ $(ES^+)$. $^1$H NMR (400 MHz, DMSO-$d_6$) δ: 11.32 (br s, 1H), 7.31-7.29 (m, 1H), 7.22-7.13 (m, 1H), 6.87-6.85 (m, 1H), 4.74-4.67 (m, 1H), 4.50 (br s, 1H), 4.18 (s, 1H), 3.87 (br s, 1H), 3.58-3.56 (m, 1H), 3.46-3.44 (m, 2H), 3.28 (s, 3H), 3.23-3.07 (m, 4H), 2.98-2.95 (m, 1H), 2.89-2.83 (m, 1H), 2.74-2.62 (m, 6H), 2.43 (s, 3H), 2.27-2.20 (m, 5H), 2.16-2.08 (m, 2H), 1.70-1.65 (m, 1H), 1.50 (s, 3H), 1.46-1.39 (m, 3H), 0.86-0.84 (m, 2H). Mixture of rotamers. |

-continued

| Example No. | Name/Structure/Intermediates | LCMS/$^1$H NMR data |
|---|---|---|
| Example 42 | (R)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide 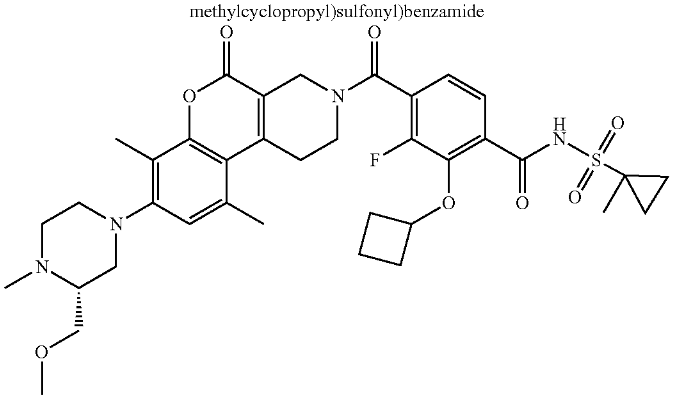 Synthesised from Intermediates 19 and 5 | HPLC: (System 1, Method D) Rt = 6.84 min, m/z 711.4 $(M + H)^+$ $(ES^+)$. $^1$H NMR (400 MHz, DMSO-$d_6$) δ: 11.28 (br s, 1H), 7.60-7.51 (m, 1H), 7.31-7.29 (m, 1H), 7.20-7.13 (m, 1H), 7.11-7.09 (m, 1H), 4.74-4.66 (m, 1H), 4.53 (br s, 1H), 4.18 (s, 1H), 3.97 (t, J = 6.0 Hz, 1H), 3.59-3.54 (m, 2H), 3.45-3.43 (m, 1H), 3.29 (s, 3H), 3.21-3.18 (m, 1H), 3.11-3.08 (m, 1H), 3.00-2.91 (m, 2H), 2.89-2.86 (m, 2H), 2.74-2.63 (m, 3H), 2.44 (s, 3H), 2.30-2.28 (m, 3H), 2.26-2.07 (m, 4H), 1.70-1.65 (m, 1H), 1.50 (s, 3H), 1.46-1.39 (m, 3H), 0.87-0.85 (m, 2H). Mixture of rotamers. |
| Example 43 | (R)-2-(cyclopentyloxy)-N-(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 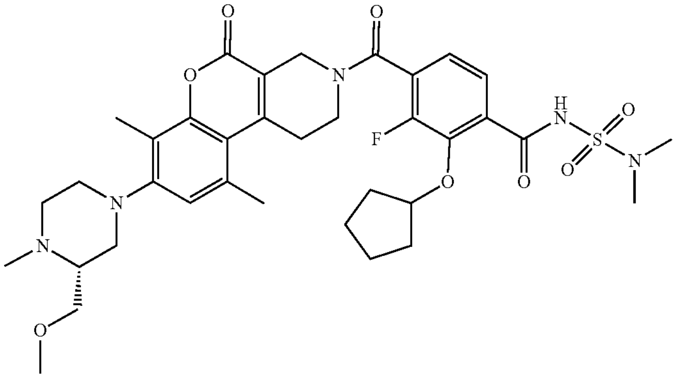 Synthesised from Intermediates 15 and 6 | HPLC: (System 1, Method D) Rt = 7.18 min, m/z 728.4 $(M + H)^+$ $(ES^+)$. $^1$H NMR (400 MHz, DMSO-$d_6$) δ: 11.40 (br s, 1H), 7.34 (d, J = 6.0 Hz, 1H), 7.23-7.14 (m, 1H), 6.86 (d, J = 7.2 Hz, 1H), 4.88-4.83 (m, 1H), 4.51 (br s, 1H), 4.18 (s, 1H), 3.87 (br s, 1H), 3.58-3.55 (m, 1H), 3.46-3.38 (m, 2H), 3.28 (s, 3H), 3.24 (br s, 1H), 3.18-3.15 (m, 2H), 3.09-3.06 (m, 1H), 2.94-2.92 (m, 1H), 2.87-2.83 (m, 7H), 2.71-2.56 (m, 6H), 2.39 (s, 3H), 2.24-2.20 (m, 3H), 1.84-1.73 (m, 6H), 1.56-1.54 (m, 2H). |
| Example 44 | (R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-(cyclopentyloxy)-N-(N,N-dimethylsulfamoyl)-3-fluorobenzamide 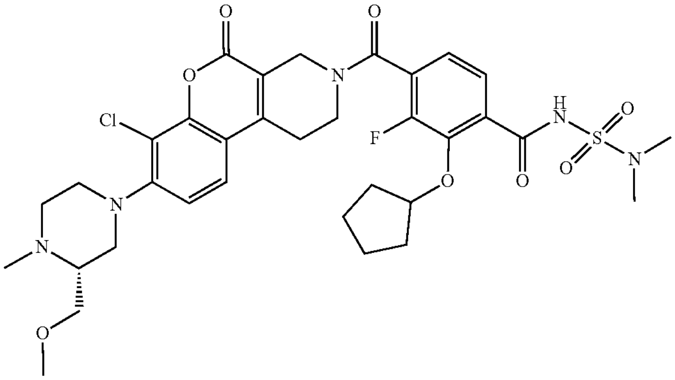 Synthesised from Intermediates 15 and 7 | HPLC: (System 1, Method D) Rt = 7.06 min, m/z 734.3 $(M + H)^+$ $(ES^+)$. $^1$H NMR (400 MHz, DMSO-$d_6$) δ: 11.49 (br s, 1H), 7.71-7.62 (m, 1H), 7.36-7.34 (m, 1H), 7.22-7.15 (m, 2H), 4.87-4.82 (m, 1H), 4.54 (br s, 1H), 4.19 (s, 1H), 3.98 (br s, 1H), 3.59-3.54 (m, 2H), 3.46-3.44 (m, 1H), 3.39-3.31 (m, 2H), 3.28 (s, 3H), 3.01-2.92 (m, 4H), 2.84 (s, 6H), 2.76-2.71 (m, 1H), 2.57-2.51 (m, 2H), 2.37 (s, 3H), 1.83-1.73 (m, 6H), 1.59-1.56 (m, 2H). Mixture of rotamers. |

-continued

| Example No. | Name/Structure/Intermediates | LCMS/$^1$H NMR data |
|---|---|---|
| Example 45 | (R)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-(pyrrolidin-1-yl)benzamide 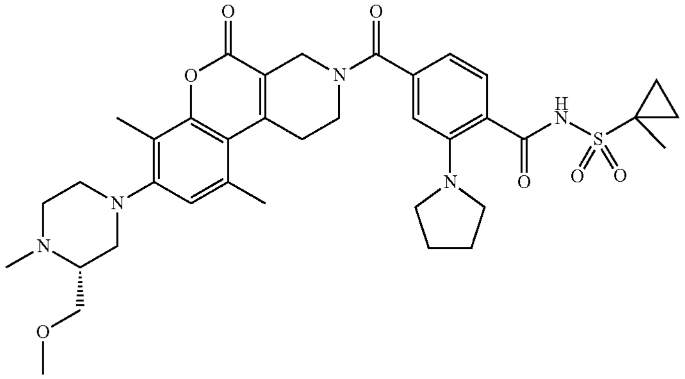 [SMILES: COC[C@H]1CN(c2cc(C)c3c4c(c(=O)oc3c2C)CN(C(=O)c2ccc(C(=O)NS(=O)(=O)C3(C)CC3)c(N3CCCC3)c2)CC4)CCN1C] Synthesised from Intermediates 46 and 6 | HPLC: (System 1, Method D) Rt = 6.74 min, m/z 706.4 $(M + H)^+$ $(ES^+)$. $^1$H NMR (400 MHz, DMSO-$d_6$) δ: 11.84 (br s, 1H), 7.38 (m, 1H), 6.85 (s, 1H), 6.80-6.73 (m, 2H), 4.46 (br s, 1H), 4.30 (br s, 1H), 3.82 (br s, 1H), 3.57-3.52 (m, 2H), 3.38 (br s, 2H), 3.27 (s, 3H), 3.20-3.13 (m, 7H), 3.06-3.04 (m, 1H), 2.89-2.80 (m, 2H), 2.69-2.62 (m, 4H), 2.50 (br s, 1H), 2.34 (s, 3H), 2.23-2.19 (m, 3H), 1.91 (br s, 4H), 1.51 (s, 3H), 1.49-1.46 (m, 2H), 0.95-0.92 (m, 2H). |
| Example 46 | 2-(3-azabicyclo[3.1.0]hexan-3-yl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 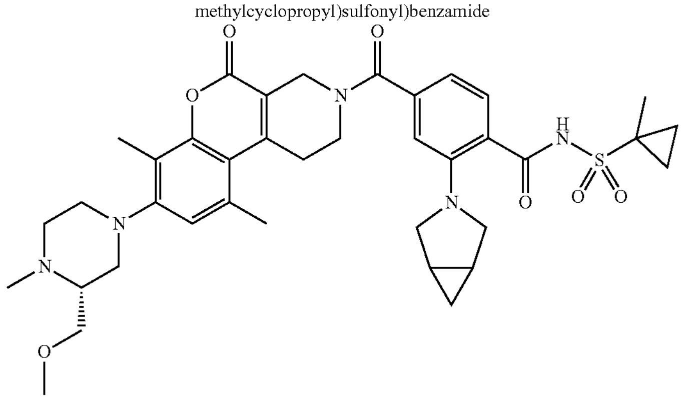 Synthesised from Intermediates 52 and 6 | HPLC: (System 1, Method D) Rt = 6.88 min, m/z 718.0 $(M + H)^+$ $(ES^+)$. $^1$H NMR (400 MHz, DMSO-$d_6$) δ: 11.85 (br s, 1H), 7.30 (d, J = 8.0 Hz, 1H), 6.85-6.82 (m, 3H), 4.46 (br s, 1H), 4.29 (br s, 1H), 3.82 (br s, 1H), 3.57-3.46 (m, 4H), 3.38 (br s, 1H), 3.27-3.25 (m, 5H), 3.19-3.13 (m, 3H), 3.06-3.03 (m, 1H), 2.89-2.80 (m, 2H), 2.68-2.62 (m, 4H), 2.49 (br s, 2H), 2.34 (s, 3H), 2.23-2.20 (m, 3H), 1.65-1.63 (m, 2H), 1.51 (s, 3H), 1.47-1.44 (m, 2H), 0.93 (br s, 2H), 0.66-0.61 (m, 1H), 0.30 (br s, 1H). |
| Example 47 | 2-(3-azabicyclo[3.1.0]hexan-3-yl)-N-(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 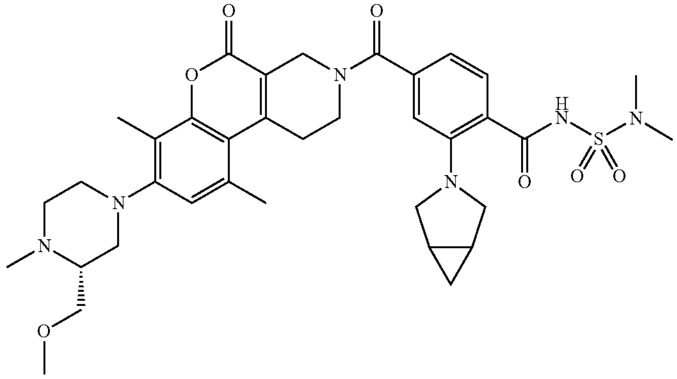 Synthesised from Intermediates 53 and 6 | HPLC: (System 1, Method D) Rt = 6.93 min, m/z 707.0 $(M + H)^+$ $(ES^+)$. $^1$H NMR (400 MHz, DMSO-$d_6$) δ: 11.78 (br s, 1H), 7.30 (d, J = 8.0 Hz, 1H), 6.85-6.81 (m, 3H), 4.46 (br s, 1H), 4.29 (br s, 1H), 3.81 (br s, 1H), 3.57-3.45 (m, 4H), 3.37 (br s, 1H), 3.27-3.24 (m, 5H), 3.19-3.12 (m, 3H), 3.06-3.03 (m, 1H), 2.88-2.79 (m, 8H), 2.68-2.61 (m, 4H), 2.45-2.43 (m, 2H), 2.33 (s, 3H), 2.23-2.19 (m, 3H), 1.64-1.63 (m, 2H), 0.64-0.63 (m, 1H), 0.30 (br s, 1H). |

-continued

| Example No. | Name/Structure/Intermediates | LCMS/$^1$H NMR data |
|---|---|---|
| Example 48 | (R)-2-(7-azabicyclo[2.2.1]heptan-7-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 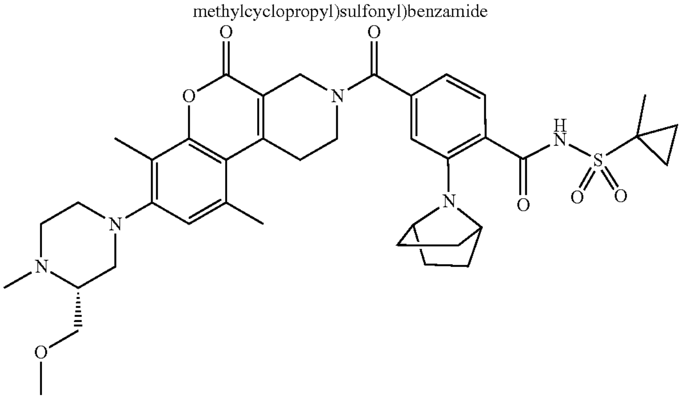 Synthesised from Intermediates 50 and 6 | HPLC: (System 1, Method D) Rt = 7.03 min, m/z 732.5 $(M + H)^+$ $(ES^+)$. $^1$H NMR (400 MHz, DMSO-$d_6$) δ: 11.68 (br s, 1H), 7.38 (d, J = 7.6 Hz, 1H), 7.06-7.03 (m, 1H), 6.96-6.91 (m, 1H), 6.85 (s, 1H), 4.47 (br s, 1H), 4.28 (br s, 1H), 4.14-4.10 (m, 2H), 3.82 (br s, 1H), 3.57-3.54 (m, 1H), 3.48 (br s, 1H), 3.38 (br s, 1H), 3.27 (s, 3H), 3.21 (br s, 2H), 3.15-3.13 (m, 1H), 3.06-3.03 (m, 1H), 2.88-2.80 (m, 2H), 2.68-2.61 (m, 4H), 2.50-2.46 (m, 2H), 2.33 (s, 3H), 2.23-2.19 (m, 3H), 1.73 (br s, 4H), 1.49 (s, 3H), 1.46-1.42 (m, 6H), 0.95-0.92 (m, 2H). Mixture of rotamers. |
| Example 49 | (R)-2-(7-azabicyclo[2.2.1]heptan-7-yl)-N-(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 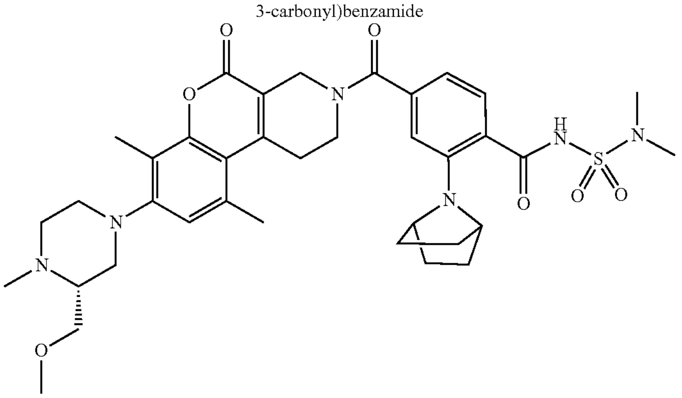 Synthesised from Intermediates 51 and 6 | HPLC: (System 1, Method D) Rt = 7.28 min, m/z 721.4 $(M + H)^+$ $(ES^+)$. $^1$H NMR (400 MHz, DMSO-$d_6$) δ: 11.61 (br s, 1H), 7.41 (d, J = 7.6 Hz, 1H), 7.07-7.03 (m, 1H), 6.98-6.92 (m, 1H), 6.85 (s, 1H), 4.47 (br s, 1H), 4.27 (br s, 1H), 4.13-4.09 (m, 2H), 3.82 (br s, 1H), 3.57-3.54 (m, 1H), 3.48 (br s, 1H), 3.35 (br s, 1H), 3.26 (s, 3H), 3.20 (br s, 2H), 3.15-3.12 (m, 1H), 3.04-3.02 (m, 1H), 2.87-2.79 (m, 8H), 2.68-2.60 (m, 4H), 2.45-2.43 (m, 2H), 2.32 (s, 3H), 2.23-2.19 (m, 3H), 1.73 (br s, 4H), 1.44 (br s, 4H). |
| Example 50 | (R)-2-cyclobutoxy-N-(N,N-dimethylsulfamoyl)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide 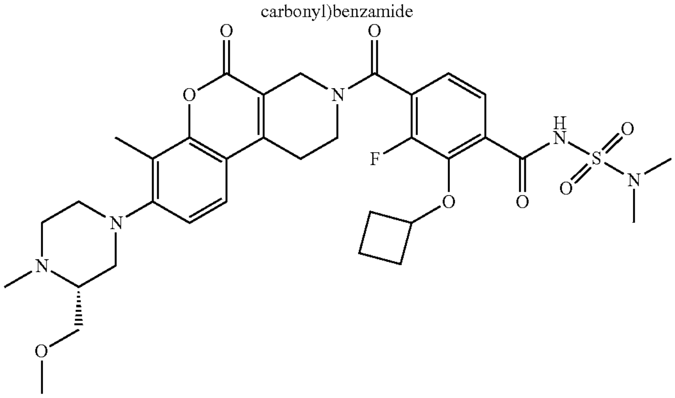 Synthesised from Intermediates 20 and 5 | HPLC: (System 1, Method D) Rt = 7.37 min, m/z 700.0 $(M + H)^+$ $(ES^+)$. $^1$H NMR (400 MHz, DMSO-$d_6$) δ: 11.31 (br s, 1H), 7.60-7.51 (m, 1H), 7.35-7.32 (m, 1H), 7.22-7.14 (m, 1H), 7.11-7.07 (m, 1H), 4.73-4.65 (m, 1H), 4.52 (br s, 1H), 4.17 (s, 1H), 3.97 (t, J = 6.0 Hz, 1H), 3.59-3.53 (m, 2H), 3.45-3.42 (m, 1H), 3.28 (br s, 3H), 3.20-3.17 (m, 1H), 3.10-3.07 (m, 1H), 2.99-2.88 (m, 4H), 2.30-2.24 (m, 6H), 2.72-2.59 (m, 3H), 2.41 (s, 3H), 2.30-2.16 (m, 5H), 2.13-2.08 (m, 2H), 1.70-1.66 (m, 1H), 1.50-1.43 (m, 1H). Mixture of rotamers. |

-continued

| Example No. | Name/Structure/Intermediates | LCMS/$^1$H NMR data |
| --- | --- | --- |
| Example 51 | (R)-2-cyclobutoxy-N-(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide<br>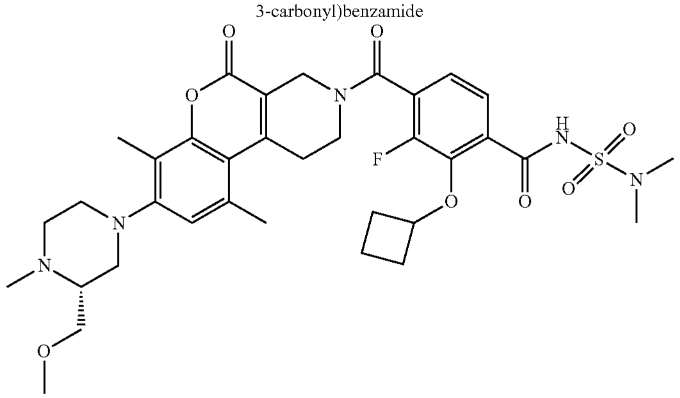<br>Synthesised from Intermediates 20 and 6 | HPLC: (System 1, Method D) Rt = 7.51 min, m/z 714.0 $(M + H)^+$ $(ES^+)$. $^1$H NMR (400 MHz, DMSO-$d_6$) δ: 11.33 (br s, 1H), 7.33 (br s, 1H), 7.22-7.17 (m, 1H), 6.86-6.85 (m, 1H), 4.71-4.68 (m, 1H), 4.50 (br s, 1H), 4.17 (s, 1H), 3.87 (br s, 1H), 3.56-3.34 (m, 5H), 3.24-3.02 (m, 5H), 2.94-2.91 (m, 1H), 2.85 (s, 7H), 2.77-2.54 (m, 6H), 2.41 (s, 3H), 2.24-2.11 (m, 7H), 1.68 (br s, 1H), 1.45-1.41 (m, 1H). Mixture of rotamers. |
| Example 52 | (R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-cyclobutoxy-N-(N,N-dimethylsulfamoyl)-3-fluorobenzamide<br>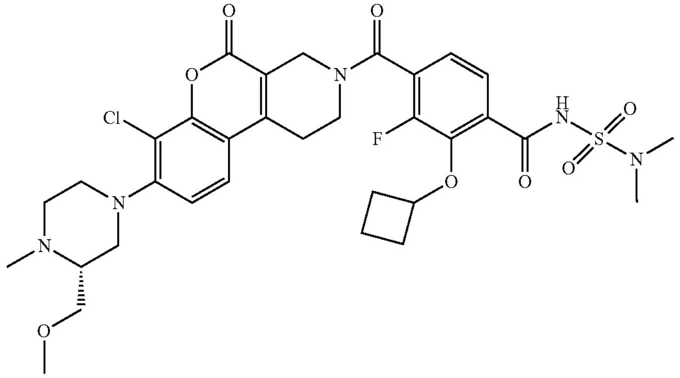<br>Synthesised from Intermediates 20 and 7 | HPLC: (System 1, Method D) Rt = 7.41 min, m/z 721.0 $(M + H)^+$ $(ES^+)$. $^1$H NMR (400 MHz, DMSO-$d_6$) δ: 11.44 (br s, 1H), 7.70-7.62 (m, 1H), 7.35-7.34 (m, 1H), 7.21-7.16 (m, 2H), 4.73-4.65 (m, 1H), 4.54 (br s, 1H), 4.19 (s, 1H), 3.97 (m, 1H), 3.59-3.56 (m, 2H), 3.47-3.31 (m, 6H), 2.99-2.93 (m, 4H), 2.86 (s, 6H), 2.77-2.72 (m, 1H), 2.61-2.55 (m, 2H), 2.38 (s, 3H), 2.24-2.11 (m, 4H), 1.71-1.69 (m, 1H), 1.48-1.43 (m, 1H). Mixture of rotamers. |
| Example 53 | (R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-cyclobutoxy-3-fluoro-N-(pyrrolidin-1-ylsulfonyl)benzamide<br>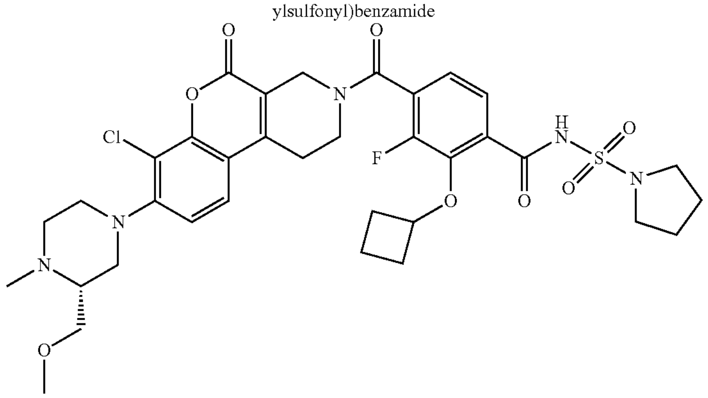<br>Synthesised from Intermediates 13 and 7 | HPLC: (System 1, Method D) Rt = 7.22 min, m/z 746.3 $(M + H)^+$ $(ES^+)$. $^1$H NMR (400 MHz, DMSO-$d_6$) δ: 11.59 (br s, 1H), 7.71-7.62 (m, 1H), 7.36-7.33 (m, 1H), 7.24-7.16 (m, 2H), 4.73-4.65 (m, 1H), 4.51 (br s, 1H), 4.18 (s, 1H), 3.97 (br s, 1H), 3.59-3.51 (m, 3H), 3.49-3.41 (m, 6H), 3.29 (br s, 1H), 3.27 (s, 3H), 3.01-2.89 (m, 4H), 2.74-2.68 (m, 1H), 2.50 (br s, 1H), 2.39 (s, 3H), 2.34-2.21 (m, 2H), 2.19-2.07 (m, 2H), 1.86 (br s, 4H), 1.71-1.66 (m, 1H), 1.50-1.44 (m, 1H). Mixture of rotamers. |

-continued

| Example No. | Name/Structure/Intermediates | LCMS/$^1$H NMR data |
| --- | --- | --- |
| Example 54 | (R)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide 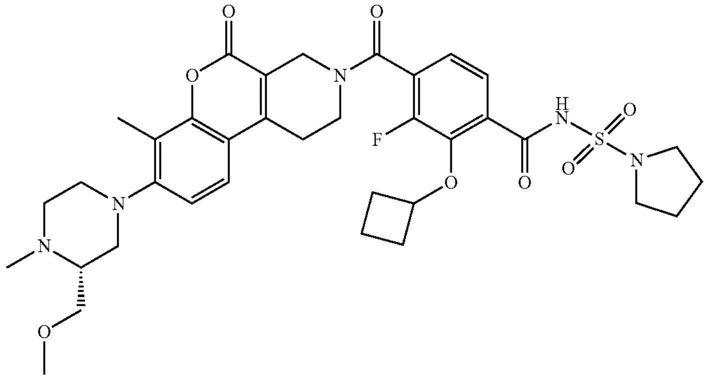 [SMILES: COC[C@H]1CN(c2ccc3c4c(c(=O)oc3c2C)CN(C(=O)c2ccc(C(=O)NS(=O)(=O)N3CCCC3)c(OC3CCC3)c2F)CC4)CCN1C] Synthesised from Intermediates 13 and 5 | HPLC: (System 1, Method D) Rt = 7.20 min, m/z 726.4 $(M + H)^+$ $(ES^+)$. $^1$H NMR (400 MHz, DMSO-$d_6$) δ: 11.53 (br s, 1H), 7.60-7.51 (m, 1H), 7.35-7.32 (m, 1H), 7.24-7.16 (m, 1H), 7.10-7.06 (m, 1H), 4.73-4.65 (m, 1H), 4.53 (br s, 1H), 4.17 (s, 1H), 3.97 (t, J = 6.0 Hz, 1H), 3.58-3.53 (m, 2H), 3.43-3.34 (m, 9H), 3.18-3.15 (m, 1H), 3.08-3.05 (m, 1H), 2.99 (br s, 1H), 2.91-2.83 (m, 3H), 2.68-2.63 (m, 1H), 2.51 (br s, 1H), 2.36 (s, 3H), 2.29-2.18 (m, 5H), 2.15-2.06 (m, 2H), 1.86-1.84 (m, 4H), 1.71-1.66 (m, 1H), 1.50-1.41 (m, 1H). Mixture of rotamers. |
| Example 55 | (R)-2-(cyclobutyl(methyl)amino)-N-(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 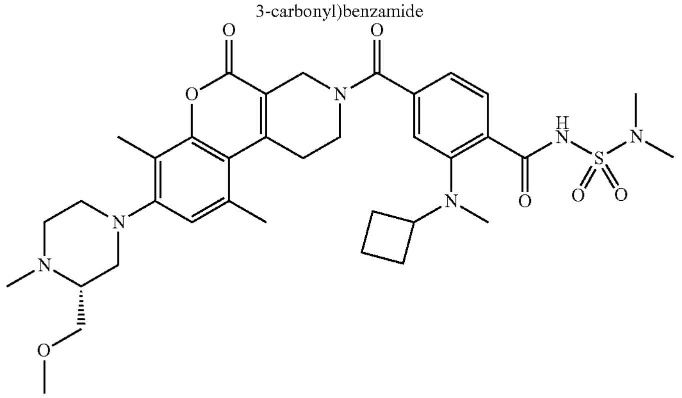 Synthesised from Intermediates 83 and 6 | HPLC: (System 1, Method D) Rt = 8.90 min, m/z 709.5 $(M + H)^+$ $(ES^+)$. $^1$H NMR (400 MHz, DMSO-$d_6$) δ: 14.72 (br s, 1H), 8.03-7.97 (m, 1H), 7.59-7.52 (m, 1H), 7.44-7.39 (m, 1H), 6.85 (s, 1H), 4.49 (br s, 1H), 4.26 (br s, 1H), 3.92-3.84 (m, 2H), 3.57-3.53 (m, 1H), 3.45 (br s, 1H), 3.31 (br s, 1H), 3.26 (s, 3H), 3.21 (br s, 2H), 3.14-3.12 (m, 1H), 3.04-3.02 (m, 1H), 2.91 (s, 6H), 2.84-2.79 (m, 2H), 2.67-2.65 (m, 6H), 2.62-2.59 (m, 1H), 2.40 (br s, 2H), 2.30 (s, 3H), 2.24-2.19 (m, 3H), 2.09-2.07 (m, 2H), 1.92-1.88 (m, 2H), 1.72-1.63 (m, 2H). Mixture of rotamers. |
| Example 56 | (R)-2-cyclobutoxy-3-fluoro-N-(N-isopropyl-N-methylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide 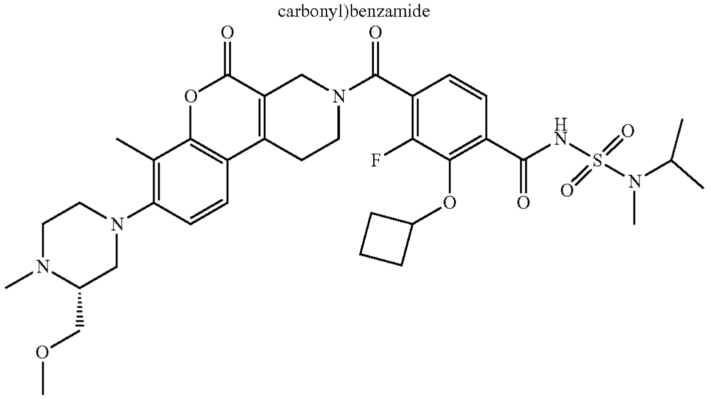 Synthesised from Intermediates 18 and 5 | HPLC: (System 1, Method D) Rt = 7.67 min, m/z 728.0 $(M + H)^+$ $(ES^+)$. $^1$H NMR (400 MHz, DMSO-$d_6$) δ: 11.53 (br s, 1H), 7.59-7.50 (m, 1H), 7.32-7.24 (m, 1H), 7.23-7.16 (m, 1H), 7.10-7.05 (m, 1H), 4.72-4.64 (m, 1H), 4.52 (br s, 1H), 4.17 (s, 1H), 4.12-4.08 (m, 1H), 3.98-3.96 (m, 1H), 3.58-3.53 (m, 2H), 3.38-3.34 (m, 4H), 3.17-3.14 (m, 1H), 3.07-2.99 (m, 2H), 2.89-2.85 (m, 3H), 2.82 (s, 3H), 2.67-2.61 (m, 1H), 2.50-2.46 (m, 2H), 2.33 (s, 3H), 2.29-2.19 (m, 5H), 2.16-2.07 (m, 2H), 1.71-1.66 (m, 1H), 1.50-1.43 (m, 1H), 1.15-1.13 (m, 6H). Mixture of rotamers. |

-continued

| Example No. | Name/Structure/Intermediates | LCMS/$^1$H NMR data |
|---|---|---|
| Example 57 | (R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-(cyclopentyloxy)-3-fluoro-N-((1-methylcyclopropyl)sulfonyl)benzamide 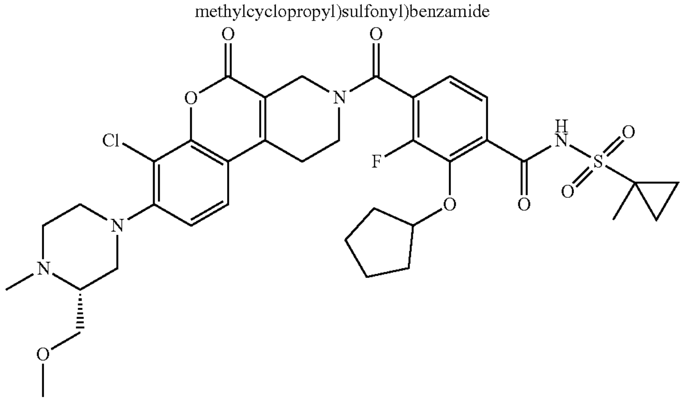 Synthesised from Intermediates 16 and 7 | HPLC: (System 1, Method D) Rt = 7.08 min, m/z 745.3 (M + H)$^+$ (ES$^+$). $^1$H NMR (400 MHz, DMSO-d$_6$) δ: 11.51 (br s, 1H), 7.71-7.62 (m, 1H), 7.33-7.31 (m, 1H), 7.21-7.14 (m, 2H), 4.88-4.82 (m, 1H), 4.54 (br s, 1H), 4.20 (s, 1H), 3.98 (br s, 1H), 3.60-3.55 (m, 2H), 3.47-3.39 (m, 3H), 3.28 (s, 3H), 3.01-2.94 (m, 4H), 2.79-2.73 (m, 1H), 2.67-2.58 (m, 2H), 2.40 (s, 3H), 1.83-1.72 (m, 6H), 1.55-1.54 (m, 2H), 1.48 (s, 3H), 1.41-1.40 (m, 2H), 0.89-0.88 (m, 2H). Mixture of rotamers. |
| Example 58 | (R)-2-(cyclopentyloxy)-3-fluoro-N-(N-isopropyl-N-methylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide 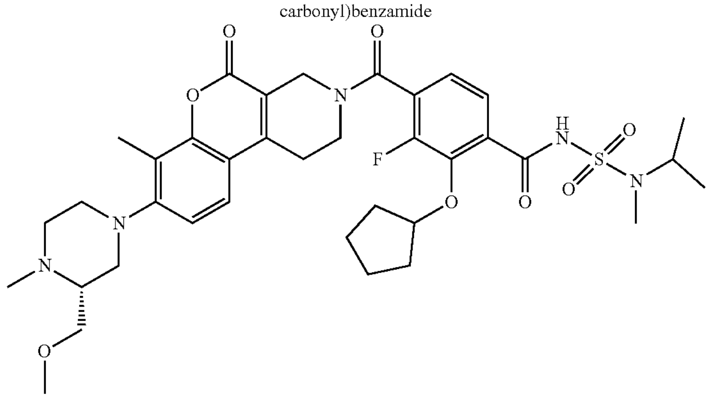 Synthesised from Intermediates 17 and 5 | HPLC: (System 1, Method D) Rt = 8.13 min, m/z 741.5 (M + H)$^+$ (ES$^+$). $^1$H NMR (400 MHz, DMSO-d$_6$) δ: 11.69 (br s, 1H), 7.59-7.50 (m, 1H), 7.28-7.27 (m, 1H), 7.21-7.13 (m, 1H), 7.09-7.05 (m, 1H), 4.87-4.81 (m, 1H), 4.52 (br s, 1H), 4.17 (s, 1H), 4.11-4.05 (m, 1H), 3.99-3.96 (m, 1H), 3.57-3.54 (m, 2H), 3.32 (br s, 1H), 3.26 (s, 3H), 3.16-3.13 (m, 1H), 3.05-2.99 (m, 2H), 2.90-2.81 (m, 3H), 2.77 (s, 3H), 2.65-2.59 (m, 1H), 2.44-2.39 (m, 2H), 2.30-2.25 (m, 6H), 1.82-1.72 (m, 6H), 1.57-1.55 (m, 2H), 1.12-1.10 (m, 6H). mixture of rotamers. |
| Example 59 | 2-(((1R,3r,5S)-bicyclo[3.1.0]hexan-3-yl)oxy)-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide 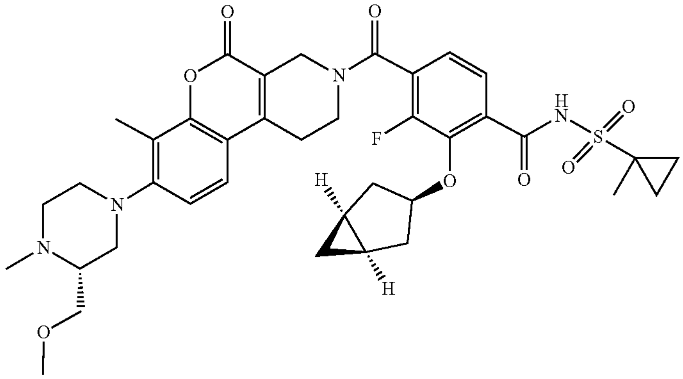 [SMILES: COC[C@H]1CN(c2ccc3c4c(c(=O)oc3c2C)CN(C(=O)c2ccc(C(=O)NS(=O)(=O)C3(C)CC3)c(O[C@@H]3C[C@@H]5C[C@@H]5C3)c2F)CC4)CCN1C] Synthesised from Intermediates 25 and 5 | HPLC: (System 1, Method D) Rt = 7.14 min, m/z 737.4 (M + H)$^+$ (ES$^+$). $^1$H NMR (400 MHz, DMSO-d$_6$) δ: 11.24 (br s, 1H), 7.60-7.51 (m, 1H), 7.29-7.27 (m, 1H), 7.17-7.07 (m, 2H), 4.83-4.74 (m, 1H), 4.51 (br s, 1H), 4.18 (s, 1H), 3.99-3.96 (m, 1H), 3.59-3.54 (m, 2H), 3.46-3.40 (m, 1H), 3.29 (s, 3H), 3.21-3.19 (m, 1H), 3.12-3.09 (m, 1H), 2.99-2.96 (m, 2H), 2.92-2.87 (m, 2H), 2.72-2.67 (m, 3H), 2.46 (s, 3H), 2.30-2.26 (m, 3H), 2.10-2.06 (m, 2H), 2.01-1.95 (m, 2H), 1.48 (s, 3H), 1.43-1.39 (m, 2H), 1.31-1.27 (m, 2H), 0.86-0.85 (m, 2H), 0.70-1.63 (m, 1H), 0.47-0.39 (m, 1H). Mixture of rotamers. |

-continued

| Example No. | Name/Structure/Intermediates | LCMS/$^1$H NMR data |
|---|---|---|
| Example 60 | 2-(((1R,3r,5S)-bicyclo[3.1.0]hexan-3-yl)oxy)-4-(7-chloro-8-((R)-3-(methoxymethyl)-4-methylpiperazin-1-yl)-5-oxo-1,3,4,5-tetrahydro-2H-chromeno[3,4-c]pyridine-3-carbonyl)-3-fluoro-N-((1-methylcyclopropyl)sulfonyl)benzamide 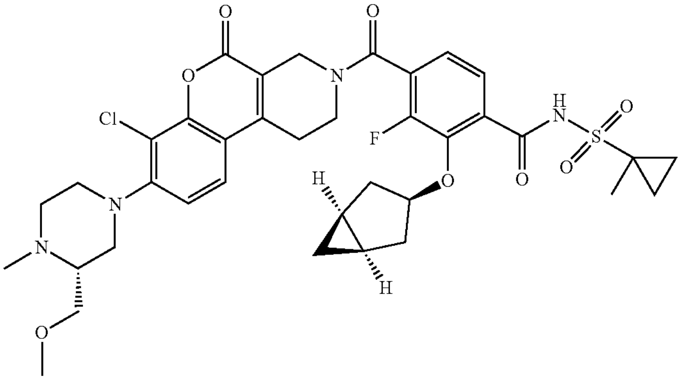 [SMILES: COC[C@H]1CN(c2ccc3c4c(c(=O)oc3c2Cl)CN(C(=O)c2ccc(C(=O)NS(=O)(=O)C3(C)CC3)c(O[C@@H]3C[C@@H]5C[C@@H]5C3)c2F)CC4)CCN1C] Synthesised from Intermediates 25 and 7 | HPLC: (System 1, Method D) Rt = 7.17 min, m/z 757.5 $(M + H)^+$ $(ES^+)$. $^1$H NMR (400 MHz, DMSO-$d_6$) δ: 11.50 (br s, 1H), 7.71-7.62- (m, 1H), 7.28-7.27 (m, 1H), 7.21-7.10 (m, 2H), 4.84-4.75 (m, 1H), 4.53 (br s, 1H), 4.19 (s, 1H), 3.97 (br s, 1H), 3.60-3.54 (m, 2H), 3.47-3.40 (m, 2H), 3.34 (br s, 1H), 3.28 (s, 3H), 3.00-2.93 (m, 4H), 2.77-2.72 (m, 1H), 2.68-2.51 (m, 2H), 2.39 (s, 3H), 2.10-2.05 (m, 2H), 2.01-1.94 (m, 2H), 1.48 (s, 3H), 1.45-1.38 (m, 2H), 1.31-1.29 (m, 2H), 0.85-0.82 (m, 2H), 0.71-0.65 (m, 1H), 0.45-0.39 (m, 1H). Mixture of rotamers. |
| Example 61 | 2-(((1R,3r,5S)-bicyclo[3.1.0]hexan-3-yl)oxy)-4-(7-chloro-8-((R)-3-(methoxymethyl)-4-methylpiperazin-1-yl)-5-oxo-1,3,4,5-tetrahydro-2H-chromeno[3,4-c]pyridine-3-carbonyl)-N-(N,N-dimethylsulfamoyl)-3-fluorobenzamide 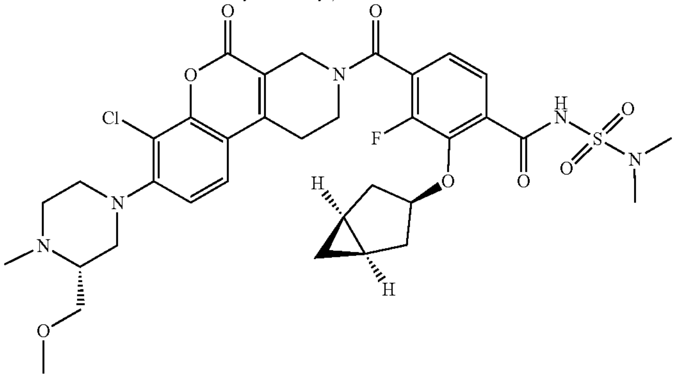 Synthesised from Intermediates 23 and 7 | HPLC: (System 1, Method D) Rt = 7.09 min, m/z 746.4 $(M + H)^+$ $(ES^+)$. $^1$H NMR (400 MHz, DMSO-$d_6$) δ: 11.54 (br s, 1H), 7.71-7.61 (m, 1H), 7.32-7.30 (m, 1H), 7.21-7.13 (m, 2H), 4.81-4.72 (m, 1H), 4.53 (br s, 1H), 4.19 (s, 1H), 3.97 (br s, 1H), 3.60-3.54 (m, 2H), 3.47-337 (m, 2H), 3.32 (br s, 1H), 3.28 (s, 3H), 3.00-2.93 (m, 4H), 2.85 (s, 6H), 2.77-2.71 (m, 1H), 2.60-2.51 (m, 2H), 2.38 (s, 3H), 2.13-2.08 (m, 2H), 2.01-1.95 (m, 2H), 1.32-1.30 (m, 2H), 0.69-0.63 (m, 1H), 0.47-0.43 (m, 1H). Mixture of rotamers. |
| Example 62 | 2-(((1R,3r,5S)-bicyclo[3.1.0]hexan-3-yl)oxy)-4-(7-chloro-8-((R)-3-(methoxymethyl)-4-methylpiperazin-1-yl)-5-oxo-1,3,4,5-tetrahydro-2H-chromeno[3,4-c]pyridine-3-carbonyl)-3-fluoro-N-(pyrrolidin-1-ylsulfonyl)benzamide 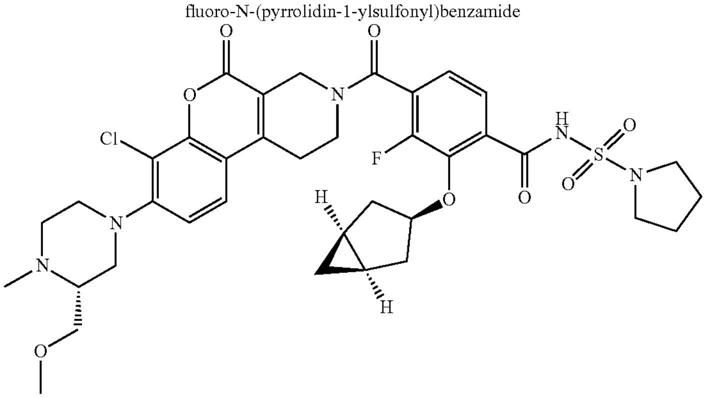 Synthesised from Intermediates 22 and 7 | HPLC: (System 1, Method D) Rt = 7.44 min, m/z 772.4 $(M + H)^+$ $(ES^+)$. $^1$H NMR (400 MHz, DMSO-$d_6$) δ: 11.62 (br s, 1H), 7.71-7.61 (m, 1H), 7.30-7.29 (m, 1H), 7.20-7.13 (m, 2H), 4.79-4.70 (m, 1H), 4.53 (br s, 1H), 4.19 (s, 1H), 3.98-3.96 (m, 1H), 3.59-3.54 (m, 2H), 3.45-3.41 (m, 5H), 3.36-3.34 (m, 1H), 3.29-3.27 (m, 4H), 3.00-2.88 (m, 4H), 2.73-2.68 (m, 1H), 2.50-2.45 (m, 2H), 2.34 (s, 3H), 2.15-2.08 (m, 2H), 2.02-1.95 (m, 2H), 1.87-1.85 (m, 4H), 1.32-1.29 (m, 2H), 0.65-0.59 (m, 1H), 0.47-0.41 (m, 1H). Mixture of rotamers. |

-continued

| Example No. | Name/Structure/Intermediates | LCMS/$^1$H NMR data |
|---|---|---|
| Example 63 | 2-(((1R,3r,5S)-bicyclo[3.1.0]hexan-3-yl)oxy)-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide 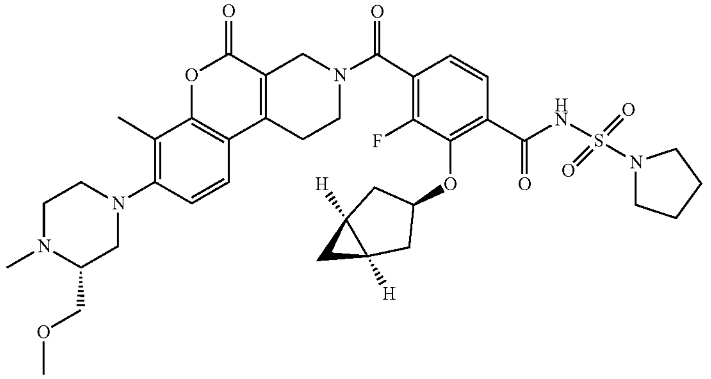 [SMILES: COC[C@H]1CN(c2ccc3c4c(c(=O)oc3c2C)CN(C(=O)c2ccc(C(=O)NS(=O)(=O)N3CCCC3)c(O[C@@H]3C[C@@H]5C[C@@H]5C3)c2F)CC4)CCN1C] Synthesised from Intermediates 22 and 5 | HPLC: (System 1, Method D) Rt = 7.42 min, m/z 752.4 $(M + H)^+$ $(ES^+)$. $^1$H NMR (400 MHz, DMSO-$d_6$) δ: 11.60 (br s, 1H), 7.59-7.50 (m, 1H), 7.30-7.28 (m, 1H), 7.20-7.16 (m, 2H), 4.79-4.70 (m, 1H), 4.52 (br s, 1H), 4.17 (s, 1H), 3.97 (t, J = 6.0 Hz, 1H), 3.58-3.53 (m, 2H), 3.42-3.39 (m, 5H), 3.27 (s, 3H), 3.18-3.15 (m, 1H), 3.08-3.00 (m, 2H), 2.89-2.83 (m, 3H), 2.68-2.66 (m, 1H), 2.54 (br s, 1H), 2.50 (br s, 1H), 2.36 (s, 3H), 2.30-2.26 (m, 3H), 2.14-2.08 (m, 2H), 2.01-1.95 (m, 2H), 1.86 (br s, 4H), 1.32-1.28 (m, 2H), 0.65-0.60 (m, 1H), 0.47-0.43 (m, 1H). Mixture of rotamers. |
| Example 64 | 2-(((1R,3r,5S)-bicyclo[3.1.0]hexan-3-yl)oxy)-3-fluoro-N-(N-isopropyl-N-methylsulfamoyl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide 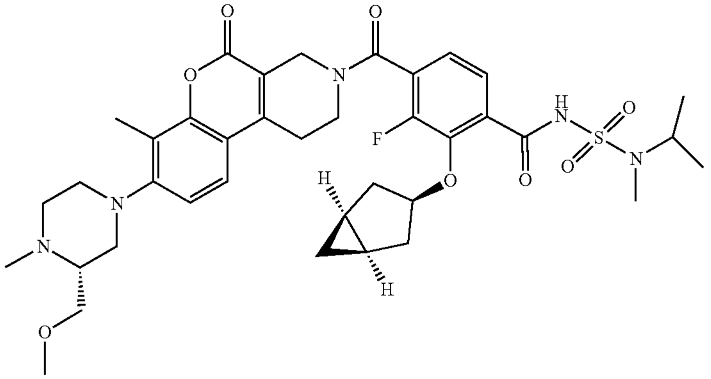 [SMILES: COC[C@H]1CN(c2ccc3c4c(c(=O)oc3c2C)CN(C(=O)c2ccc(C(=O)NS(=O)(=O)N(C)C(C)C)c(O[C@@H]3C[C@@H]5C[C@@H]5C3)c2F)CC4)CCN1C] Synthesised from Intermediates 24 and 5 | HPLC: (System 1, Method D) Rt = 7.93 min, m/z 754.4 $(M + H)^+$ $(ES^+)$. $^1$H NMR (400 MHz, DMSO-$d_6$) δ: 11.66 (br s, 1H), 7.60-7.50 (m, 1H), 7.27-7.25 (m, 1H), 7.21-7.13 (m, 1H), 7.10-7.06 (m, 1H), 4.76-4.70 (m, 1H), 4.51 (br s, 1H), 4.17 (s, 1H), 4.12-4.08 (m, 1H), 3.97 (t, J = 5.6 Hz, 1H), 3.58-3.53 (m, 2H), 3.38-3.37 (m, 1H), 3.27 (s, 3H), 3.17-3.14 (m, 1H), 3.07-2.99 (m, 2H), 2.90-2.82 (m, 3H), 2.80 (s, 3H), 2.67-2.62 (m, 1H), 2.50 (br s, 2H), 2.34 (s, 3H), 2.29-2.26 (m, 3H), 2.14-2.06 (m, 2H), 2.01-1.94 (m, 2H), 1.32-1.28 (m, 2H), 1.14-1.12 (m, 6H), 0.66-0.62 (m, 1H), 0.47-0.43 (m, 1H). Mixture of rotamers. |
| Example 65 | 2-(((1R,3r,5S)-bicyclo[3.1.0]hexan-3-yl)oxy)-4-(7-chloro-8-((R)-3-(methoxymethyl)-4-methylpiperazin-1-yl)-5-oxo-1,3,4,5-tetrahydro-2H-chromeno[3,4-c]pyridine-3-carbonyl)-3-fluoro-N-(N-isopropyl-N-methylsulfamoyl)benzamide 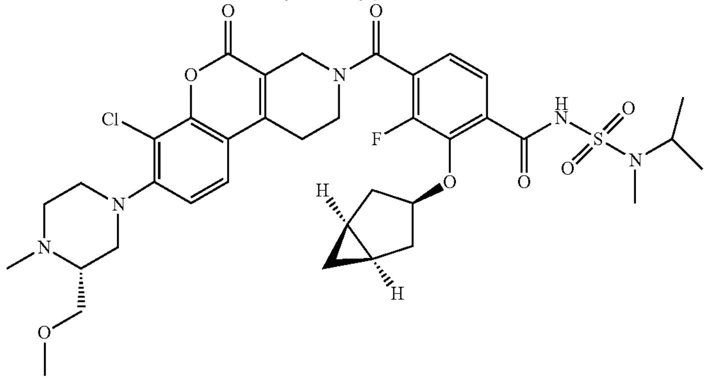 Synthesised from Intermediates 24 and 7 | HPLC: (System 1, Method D) Rt = 7.93 min, m/z 774.4 $(M + H)^+$ $(ES^+)$. $^1$H NMR (400 MHz, DMSO-$d_6$) δ: 11.73 (br s, 1H), 7.71-7.61 (m, 1H), 7.27-7.25 (m, 1H), 7.21-7.14 (m, 2H), 4.78-4.70 (m, 1H), 4.52 (br s, 1H), 4.18 (s, 1H), 4.12-4.08 (m, 1H), 3.97 (br s, 1H), 3.59-3.54 (m, 2H), 3.45-3.42 (m, 1H), 3.36 (br s, 1H), 3.32-3.28 (m, 1H), 3.27 (s, 3H), 3.00-2.86 (m, 4H), 2.80 (s, 3H), 2.72-2.67 (m, 1H), 2.50-2.41 (m, 2H), 2.32 (s, 3H), 2.14-2.07 (m, 2H), 2.01-1.95 (m, 2H), 1.32-1.28 (m, 2H), 1.14-1.12 (m, 6H), 0.66-0.62 (m, 1H), 0.47-0.43 (m, 1H). Mixture of rotamers. |

-continued

| Example No. | Name/Structure/Intermediates | LCMS/$^1$H NMR data |
|---|---|---|
| Example 66 | 2-(((1R,3s,5S)-bicyclo[3.1.0]hexan-3-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 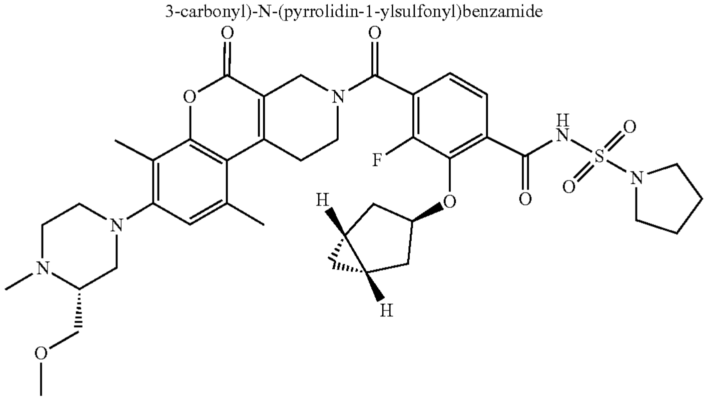 Synthesised from Intermediates 29 and 6 | HPLC: (System 1, Method D) Rt = 7.84 min, m/z 766.4 (M + H)$^+$ (ES$^+$). $^1$H NMR (400 MHz, DMSO-d$_6$) δ: 11.56 (br s, 1H), 7.34-7.31 (m, 1H), 7.26-7.16 (m, 1H), 6.86 (d, J = 6.8 Hz, 1H), 4.60-4.40 (m, 2H), 4.17 (s, 1H), 3.88-3.86 (m, 1H), 3.58-3.54 (m, 1H), 3.44-3.34 (m, 6H), 3.27 (s, 3H), 3.23 (br s, 1H), 3.16-3.14 (m, 2H), 3.07-3.04 (m, 1H), 2.91-2.81 (m, 2H), 2.69-2.62 (m, 4H), 2.51 (br s, 2H), 2.36 (s, 3H), 2.24-2.20 (m, 3H), 2.18-2.10 (m, 2H), 1.95-1.88 (m, 2H), 1.87-1.84 (m, 4H), 1.32-1.27 (m, 2H), 0.36-0.32 (m, 1H), 0.05-0.01 (m, 1H). |
| Example 67 | 2-(((1R,3s,5S)-bicyclo[3.1.0]hexan-3-yl)oxy)-N-(N,N-dimethylsulfamoyl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 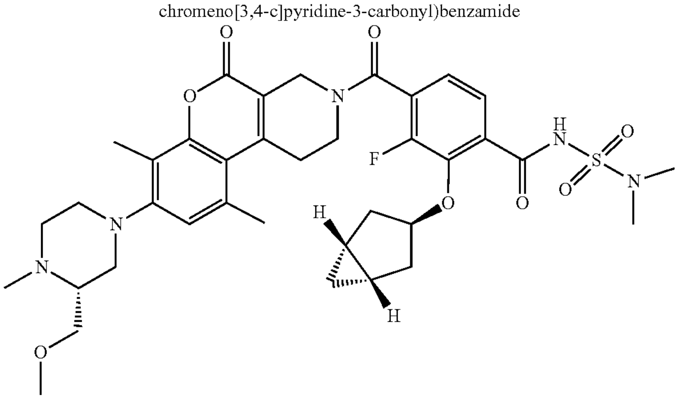 Synthesised from Intermediates 30 and 6 | HPLC: (System 1, Method D) Rt = 7.27 min, m/z 740.5 (M + H)$^+$ (ES$^+$). $^1$H NMR (400 MHz, DMSO-d$_6$) δ: 11.31 (br s, 1H), 7.33-7.31 (m, 1H), 7.24-7.15 (m, 1H), 6.87-6.86 (m, 1H), 4.52-4.40 (m, 2H), 4.17 (s, 1H), 3.88-3.86 (m, 1H), 3.58-3.55 (m, 1H), 3.45-3.40 (m, 2H), 3.28 (s, 3H), 3.23 (br s, 1H), 3.19-3.16 (m, 2H), 3.10-3.07 (m, 1H), 2.97-2.95 (m, 1H), 2.88-2.85 (m, 1H), 2.83-2.82 (m, 6H), 2.73-2.62 (m, 6H), 2.42 (s, 3H), 2.24-2.10 (m, 3H), 2.18-2.10 (m, 2H), 1.96-1.89 (m, 2H), 1.31-1.27 (m, 2H), 0.36-0.32 (m, 1H), 0.05-0.01 (m, 1H). Mixture of rotamers. |
| Example 68 | 2-(((1R,3s,5S)-bicyclo[3.1.0]hexan-3-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 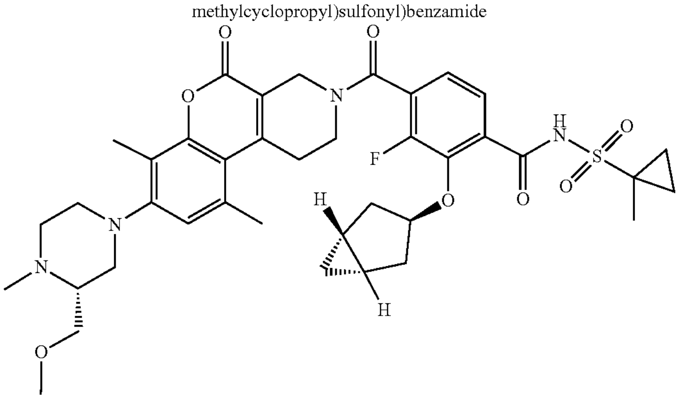 Synthesised from Intermediates 31 and 6 | HPLC: (System 1, Method D) Rt = 7.55 min, m/z 751.4 (M + H)$^+$ (ES$^+$). $^1$H NMR (400 MHz, DMSO-d$_6$) δ: 11.31 (br s, 1H), 7.30-7.28 (m, 1H), 7.21-7.13 (m, 1H), 6.87-6.86 (m, 1H), 4.52-4.41 (m, 2H), 4.18 (s, 1H), 3.88-3.86 (m, 1H), 3.59-3.56 (m, 1H), 3.45-3.44 (m, 2H), 3.29 (s, 3H), 3.23-3.08 (m, 4H), 3.00-2.97 (m, 1H), 2.89-2.84 (m, 1H), 2.73-2.63 (m, 6H), 2.44 (s, 3H), 2.24-2.21 (m, 3H), 2.18-2.10 (m, 2H), 1.96-1.88 (m, 2H), 1.48 (s, 3H), 1.38 (br s, 2H), 1.31-1.27 (m, 2H), 0.85-0.83 (m, 2H), 0.35-0.31 (m, 1H), 0.03-0.00 (m, 1H). Mixture of rotamers. |

-continued

| Example No. | Name/Structure/Intermediates | LCMS/$^1$H NMR data |
|---|---|---|
| Example 69 | (R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-(pyrrolidin-1-yl)benzamide 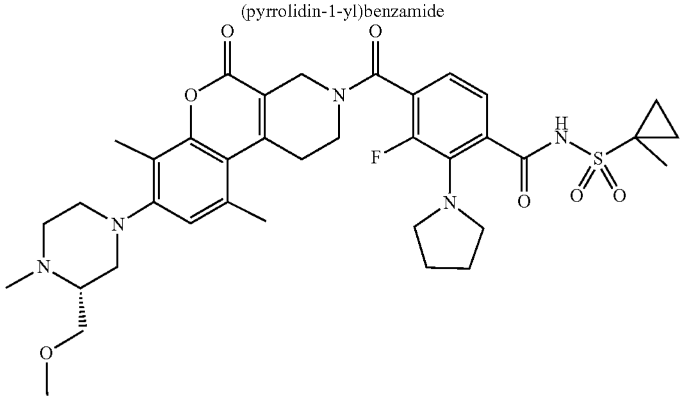 Synthesised from Intermediates 70 and 6 | HPLC: (System 1, Method D) Rt = 7.30 min, m/z 724.0 $(M + H)^+$ $(ES^+)$. $^1$H NMR (400 MHz, DMSO-$d_6$) δ: 12.99 (br s, 1H), 7.44-7.37 (m, 1H), 7.12-6.99 (m, 1H), 6.86-6.84 (m, 1H), 4.57 (br s, 1H), 4.40 (br s, 1H), 3.86 (t, J = 6.4, 1H), 3.57-3.54 (m, 1H), 3.48 (br s, 1H), 3.39 (br s, 3H), 3.34 (br s, 2H), 3.27 (s, 3H), 3.23 (br s, 1H), 3.19-3.16 (m, 2H), 3.07-3.04 (m, 1H), 2.91-2.81 (m, 2H), 2.69-2.62 (m, 4H), 2.51 (br s, 2H), 2.35 (s, 3H), 2.24-2.20 (m, 3H), 1.93-1.86 (m, 4H), 1.50 (s, 3H), 1.44 (br s, 2H), 0.91 (br s, 2H). Mixture of rotamers. |
| Example 70 | (R)-N-(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)benzamide 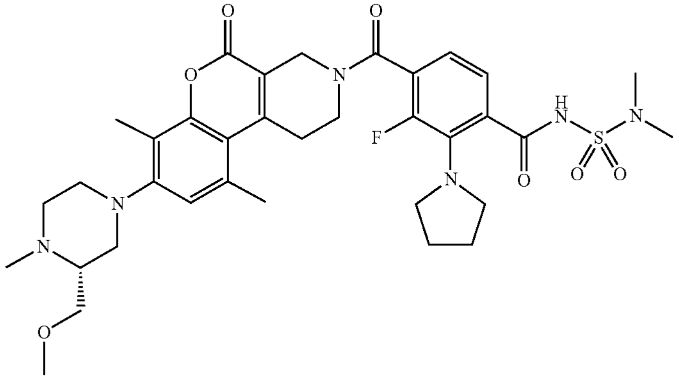 Synthesised from Intermediates 71 and 6 | HPLC: (System 1, Method D) Rt = 7.54 min, m/z 713.0 $(M + H)^+$ $(ES^+)$. $^1$H NMR (400 MHz, DMSO-$d_6$) δ: 12.84 (br s, 1H), 7.44-7.38 (m, 1H), 7.11-6.99 (m, 1H), 6.86-6.84 (m, 1H), 4.60-4.40 (m, 1H), 4.19 (br s, 1H), 3.88-3.86 (m, 1H), 3.57-3.54 (m, 1H), 3.47 (br s, 1H), 3.38 (br s, 2H), 3.32 (br s, 3H), 3.27 (s, 3H), 3.23 (br s, 1H), 3.16-3.13 (m, 2H), 3.06-3.04 (m, 1H), 2.87-2.80 (m, 8H), 2.69-2.62 (m, 4H), 2.49 (br s, 2H), 2.34 (s, 3H), 2.23-2.20 (m, 3H), 1.93-1.87 (m, 4H). Mixture of rotamers. |
| Example 71 | 2-(3-azabicyclo[3.1.0]hexan-3-yl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 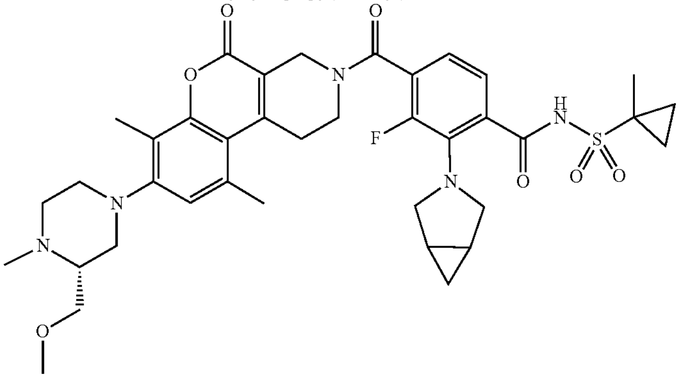 [SMILES: COC[C@H]1CN(c2cc(C)c3c4c(c(=O)oc3c2C)CN(C(=O)c2ccc(C(=O)NS(=O)(=O)C3(C)CC3)c(N3CC5CC5C3)c2F)CC4)CCN1C] Synthesised from Intermediates 73 and 6 | HPLC: (System 1, Method D) Rt = 7.39 min, m/z 735.5 $(M + H)^+$ $(ES^+)$. $^1$H NMR (400 MHz, DMSO-$d_6$) δ: 12.22 (br s, 1H), 7.38-7.33 (m, 1H), 7.19-7.10 (m, 1H), 6.87-6.85 (m, 1H), 4.62-4.38 (m, 1H), 4.18 (s, 1H), 3.86 (br s, 1H), 3.58-3.55 (m, 1H), 3.52 (br s, 1H), 3.45-3.38 (m, 3H), 3.31 (br s, 2H), 3.28 (s, 3H), 3.23 (br s, 1H), 3.17-3.05 (m, 3H), 2.93-2.91 (m, 1H), 2.87-2.82 (m, 1H), 2.73-2.69 (m, 2H), 2.68-2.54 (m, 4H), 2.38 (s, 3H), 2.24-2.20 (m, 3H), 1.57-1.54 (m, 2H), 1.50 (s, 3H), 1.44 (br s, 2H), 0.91-0.88 (m, 2H), 0.66-0.59 (m, 1H), 0.55-0.49 (m, 1H). Mixture of rotamers. |

-continued

| Example No. | Name/Structure/Intermediates | LCMS/$^1$H NMR data |
|---|---|---|
| Example 72 | 2-(3-azabicyclo[3.1.0]hexan-3-yl)-N-(N,N-dimethylsulfamoyl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide<br>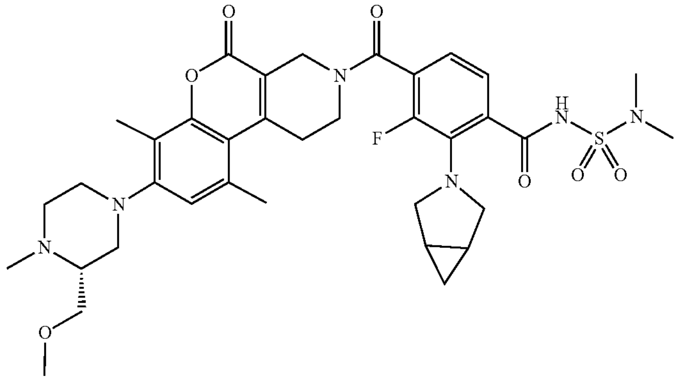<br>Synthesised from Intermediates 74 and 6 | HPLC: (System 1, Method D) Rt = 7.55 min, m/z 724.6 (M + H)$^+$ (ES$^+$).<br>$^1$H NMR (400 MHz, DMSO-$d_6$) δ: 12.21 (br s, 1H), 7.39-7.37 (m, 1H), 7.20-7.10 (m, 1H), 6.86-6.84 (m, 1H), 4.64-4.37 (m, 1H), 4.18 (s, 1H), 3.86 (br s, 1H), 3.58-3.54 (m, 1H), 3.45-3.42 (m, 2H), 3.39-3.38 (m, 2H), 3.29 (br s, 2H), 3.27-3.23 (m, 4H), 3.16-3.13 (m, 2H), 3.09-3.04 (m, 1H), 2.90-2.80 (m, 8H), 2.73-2.69 (m, 2H), 2.66-2.62 (m, 2H), 2.58 (br s, 1H), 2.43 (br s, 1H), 2.35 (s, 3H), 2.23-2.20 (m, 3H), 1.57-1.54 (m, 2H), 0.66-0.59 (m, 1H), 0.55-0.49 (m, 1H). Mixture of rotamers. |
| Example 73 | (R)-2-(7-azabicyclo[2.2.1]heptan-7-yl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide<br>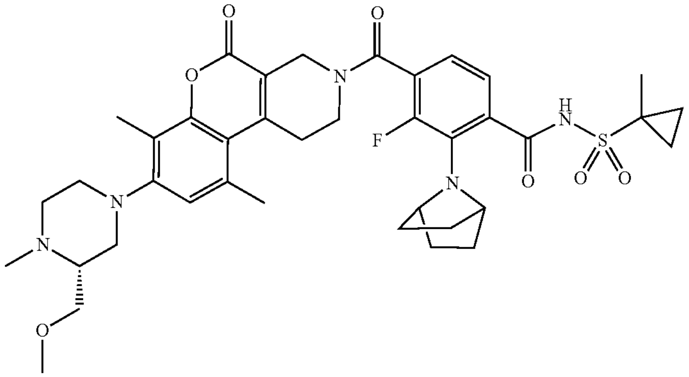 [SMILES: COC[C@H]1CN(c2cc(C)c3c4c(c(=O)oc3c2C)CN(C(=O)c2ccc(C(=O)NS(=O)(=O)C3(C)CC3)c(N3C5CCC3CC5)c2F)CC4)CCN1C]<br>Synthesised from Intermediates 76 and 6 | HPLC: (System 1, Method D) Rt = 7.12 min, m/z 749.5 (M + H)$^+$ (ES$^+$).<br>$^1$H NMR (400 MHz, DMSO-$d_6$) δ: 11.52 (br s, 1H), 7.15-7.14 (m, 1H), 6.87-6.77 (m, 2H), 4.62-4.37 (m, 1H), 4.26-4.16 (m, 3H), 3.85 (br s, 1H), 3.58-3.55 (m, 1H), 3.44-3.36 (m, 2H), 3.28 (s, 3H), 3.22-3.05 (m, 4H), 2.94-2.82 (m, 2H), 2.36-2.53 (m, 6H), 2.39 (s, 3H), 2.24-2.20 (m, 3H), 1.74-1.69 (m, 4H), 1.47 (s, 3H), 1.43-1.39 (m, 6H), 0.90 (br s, 2H). Mixture of rotamers. |
| Example 74 | (R)-2-(7-azabicyclo[2.2.1]heptan-7-yl)-N-(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide<br>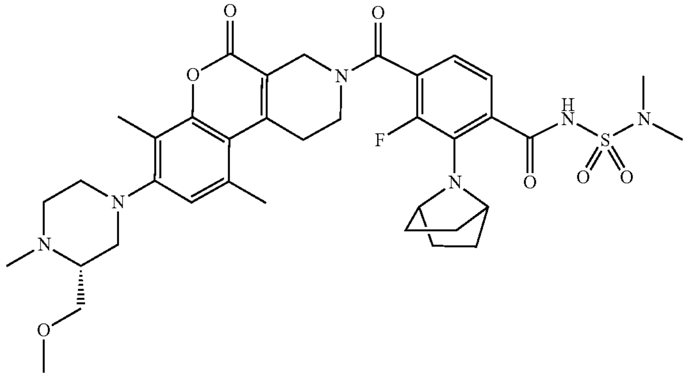<br>Synthesised from Intermediates 77 and 6 | HPLC: (System 1, Method D) Rt = 7.17 min, m/z 739.4 (M + H)$^+$ (ES$^+$).<br>$^1$H NMR (400 MHz, DMSO-$d_6$) δ: 11.54 (br s, 1H), 7.18-7.16 (m, 1H), 6.88-6.78 (m, 2H), 4.61-4.36 (m, 1H), 4.25-4.15 (m, 3H), 3.85 (br s, 1H), 3.58-3.54 (m, 1H), 3.44-3.37 (m, 2H), 3.27 (s, 3H), 3.22 (br s, 1H), 3.16-3.04 (m, 3H), 2.91-2.80 (m, 8H), 2.69-2.62 (m, 4H), 2.51 (br s, 1H), 2.49 (br s, 1H), 2.35 (s, 3H), 2.23-2.20 (m, 3H), 1.73-1.68 (m, 4H), 1.44-1.40 (m, 4H). Mixture of rotamers. |

-continued

| Example No. | Name/Structure/Intermediates | LCMS/$^1$H NMR data |
|---|---|---|
| Example 75 | (R)-2-(3,3-difluoropiperidin-1-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 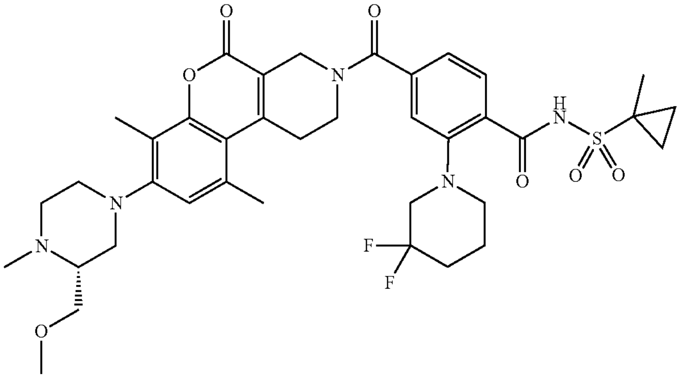 [SMILES: COC[C@H]1CN(c2cc(C)c3c4c(c(=O)oc3c2C)CN(C(=O)c2ccc(C(=O)NS(=O)(=O)C3(C)CC3)c(N3CCCC(F)(F)C3)c2)CC4)CCN1C] Synthesised from Intermediates 54 and 6 | HPLC: (System 1, Method D) Rt = 7.94 min, m/z 756.1 $(M + H)^+$ $(ES^+)$. $^1$H NMR (400 MHz, DMSO-$d_6$) δ: 12.70 (br s, 1H), 7.85-7.80 (m, 1H), 7.55-7.48 (m, 1H), 7.39-7.34 (m, 1H), 6.85 (s, 1H), 4.49 (br s, 1H), 4.30 (br s, 1H), 3.84 (br s, 1H), 3.57-3.54 (m, 1H), 3.50 (br s, 1H), 3.45-3.34 (m, 3H), 3.27 (s, 3H), 3.21 (br s, 2H), 3.16-3.13 (m, 1H), 3.06 (br s, 3H), 2.88-2.80 (m, 2H), 2.69-2.62 (m, 4H), 2.50-2.47 (m, 2H), 2.33 (s, 3H), 2.24-2.19 (m, 3H), 2.04 (br s, 2H), 1.88 (br s, 2H), 1.49-1.45 (m, 5H), 0.93 (br s, 2H). Mixture of rotamers. |
| Example 76 | (R)-2-(3,3-difluoropiperidin-1-yl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 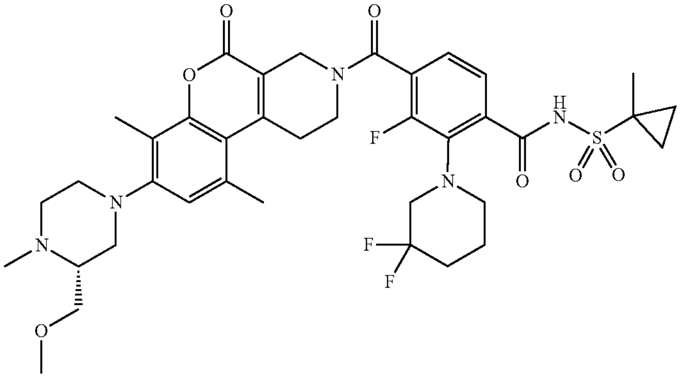 [SMILES: COC[C@H]1CN(c2cc(C)c3c4c(c(=O)oc3c2C)CN(C(=O)c2ccc(C(=O)NS(=O)(=O)C3(C)CC3)c(N3CCCC(F)(F)C3)c2F)CC4)CCN1C] Synthesised from Intermediates 79 and 6 | HPLC: (System 1, Method D) Rt = 7.34 min, m/z 773.6 $(M + H)^+$ $(ES^+)$. $^1$H NMR (400 MHz, DMSO-$d_6$) δ: 11.80 (br s, 1H), 7.48-7.42 (m, 1H), 7.32-7.23 (m, 1H), 6.87-6.85 (m, 1H), 4.65-4.50 (m,1H), 4.20 (br s, 1H), 3.87 (br s, 1H), 3.59-3.53 (m, 1H), 3.46-3.43 (m, 2H), 3.43-3.38 (m, 2H), 3.35-3.28 (m, 3H), 3.28-3.11 (m, 6H), 3.10-3.00 (m, 1H), 2.97-2.83 (m, 1H), 2.80-2.62 (m, 4H), 2.62 (br s, 2H), 2.50-2.25 (br s, 3H), 2.24-2.20 (m, 3H), 2.05-1.90 (m, 2H), 1.82-1.75 (m, 2H), 1.45 (s, 3H), 1.40 (br s, 2H), 0.84 (br s, 2H). Mixture of rotamers. |
| Example 77 | (R)-2-(3,3-difluoropiperidin-1-yl)-N-(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 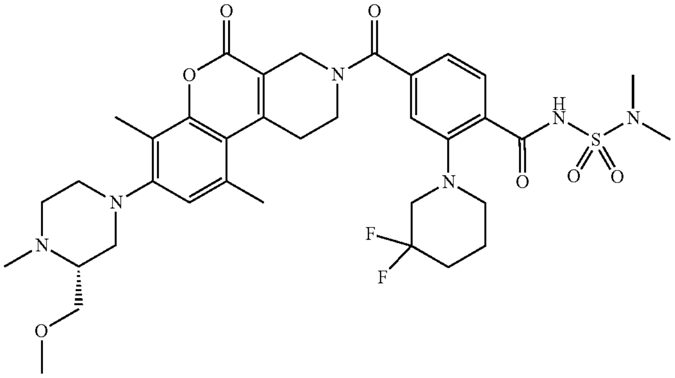 Synthesised from Intermediates 55 and 6 | HPLC: (System 1, Method D) Rt = 8.34 min, m/z 745.0 $(M + H)^+$ $(ES^+)$. $^1$H NMR (400 MHz, DMSO-$d_6$) δ: 12.65 (br s, 1H), 7.88-7.86 (m, 1H), 7.56-7.49 (m, 1H), 7.41-7.39 (m, 1H), 6.85 (s, 1H), 4.49 (br s, 1H), 4.29 (br s, 1H), 3.84 (br s, 1H), 3.57-3.54 (m, 1H), 3.50 (br s, 1H), 3.47-3.36 (m, 3H), 3.26 (s, 3H), 3.21 (br s, 2H), 3.15-3.12 (m, 1H), 3.05 (br s, 3H), 2.88 (s, 6H), 2.84-2.79 (m, 2H), 2.69-2.60 (m, 4H), 2.46-2.43 (m, 2H), 2.32 (s, 3H), 2.24-2.19 (m, 3H), 2.05 (br s, 2H), 1.88 (br s, 2H). Mixture of rotamers. |

-continued

| Example No. | Name/Structure/Intermediates | LCMS/$^1$H NMR data |
|---|---|---|
| Example 78 | (R)-2-(3,3-difluoropiperidin-1-yl)-N-(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 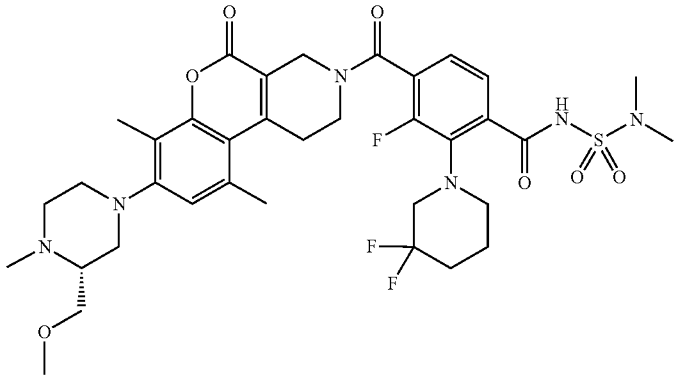 Synthesised from Intermediates 80 and 6 | HPLC: (System 1, Method D) Rt = 7.46 min, m/z 762.6 (M + H)$^+$ (ES$^+$). $^1$H NMR (400 MHz, DMSO-d$_6$) δ: 11.90 (br s, 1H), 7.53-7.47 (m, 1H), 7.38-7.27 (m, 1H), 6.87-6.85 (d, J = 7.6 Hz, 1H), 4.70-4.30 (m, 1H), 4.19 (br s, 1H), 3.88 (br s, 1H), 3.58-3.55 (m, 1H), 3.48-3.45 (m, 1H), 3.46-3.38 (m, 3H), 3.34 (br s, 3H), 3.24-3.31 (m, 1H), 3.18-3.01 (m, 5H), 2.96-2.93 (m,1H), 2.87 (br s, 1H), 2.85 (s, 6H), 2.70-2.67 (m, 3H), 2.62-2.54 (m, 3H), 2.40 (br s, 3H), 2.23-2.20 (m, 3H), 2.08-1.98 (m, 2H), 1.85-1.75 (m, 2H). Mixture of rotamers. |
| Example 79 | (R)-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 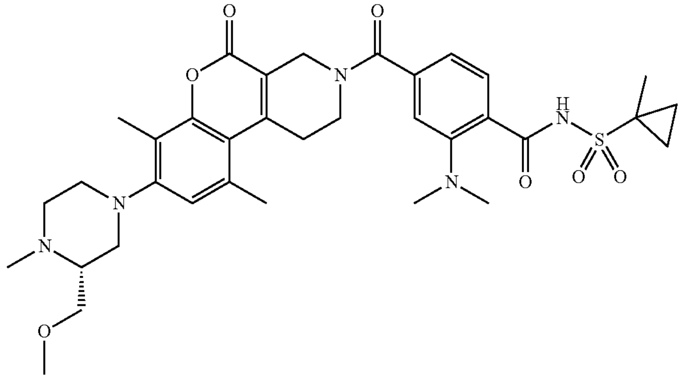 [SMILES: COC[C@H]1CN(c2cc(C)c3c4c(c(=O)oc3c2C)CN(C(=O)c2ccc(C(=O)NS(=O)(=O)C3(C)CC3)c(N(C)C)c2)CC4)CCN1C] Synthesised from Intermediates 82 and 6 | HPLC: (System 1, Method D) Rt = 6.73 min, m/z 680.4 (M + H)$^+$ (ES$^+$). $^1$H NMR (400 MHz, DMSO-d$_6$) δ: 12.95 (br s, 1H), 7.65-7.58 (m, 1H), 7.31-7.21 (m, 1H), 7.16-7.06 (m, 1H), 6.84 (s, 1H), 4.48 (br s, 1H), 4.30 (br s, 1H), 3.83 (s, 1H), 3.58-3.51 (m, 2H), 3.50-3.27 (m, 3H), 3.26-3.19 (m, 3H), 3.15-3.13 (m, 1H), 3.06-3.03 (m, 1H), 2.86-2.79 (m, 8H), 2.69-2.60 (m, 4H), 2.48-2.42 (m, 2H), 2.33 (s, 3H), 2.24-2.18 (m, 3H), 1.50 (s, 3H), 1.48-1.44 (m, 2H), 0.95-0.91 (m, 2H). Mixture of rotamers. |
| Example 80 | (R)-2-(7-azabicyclo[2.2.1]heptan-7-yl)-6-chloro-N-(N,N-dimethylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide 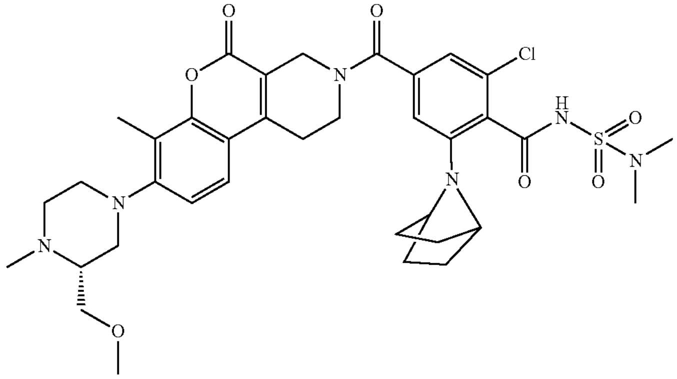 Synthesised from Intermediates 93 and 5 | HPLC: (System 1, Method D) Rt = 6.78 min, m/z 741.4 (M + H)$^+$ (ES$^+$). $^1$H NMR (400 MHz, DMSO-d$_6$) δ: 11.86 (br s, 1H), 7.57-7.53 (m, 1H), 7.08 (d, J = 8.8 Hz, 1H), 6.96 (s, 2H), 4.47 (br s, 1H), 4.29-4.28 (m, 3H), 3.90 (br s, 1H), 3.58-3.55 (m, 2H), 3.40.3.38 (m, 1H), 3.27 (s, 3H), 3.18-3.15 (m, 1H), 3.08-3.05 (m, 1H), 2.96 (br s, 2H), 2.87-2.83 (m, 8H), 2.69-2.63 (m, 1H), 2.54 (br s, 2H), 2.37 (s, 3H), 2.29-2.26 (m, 3H), 1.69 (br s, 4H), 1.42-1.40 (m, 4H). |

-continued

| Example No. | Name/Structure/Intermediates | LCMS/$^1$H NMR data |
|---|---|---|
| Example 81 | (R)-2-(3,3-difluoropyrrolidin-1-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 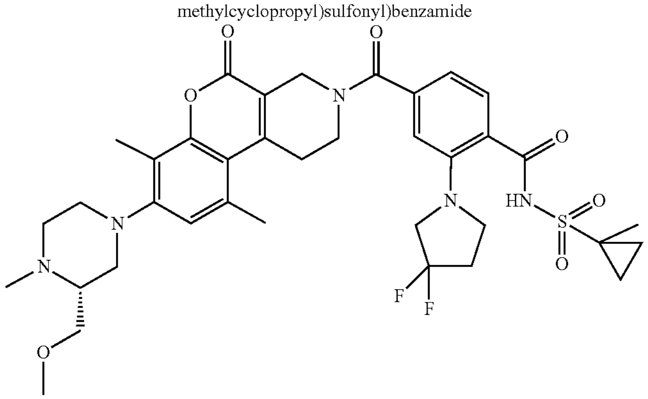 Synthesised from Intermediates 56 and 6 | HPLC: (System 1, Method D) Rt = 6.85 min, m/z 741.5 $(M + H)^+$ $(ES^+)$. $^1$H NMR (400 MHz, DMSO-$d_6$) δ: 11.70 (br s, 1H), 7.41 (d, J = 7.6 Hz, 1H), 6.90-6.86 (m, 3H), 4.47 (br s, 1H), 4.29 (br s, 1H), 3.82 (br s, 1H), 3.69-3.63 (m, 2H), 3.58-3.50 (m, 5H), 3.50-3.39 (m, 2H), 3.27 (s, 3H), 3.20-3.15 (m, 3H), 3.08-3.06 (m, 1H), 2.94-2.92 (m, 1H), 2.87-2.84 (m, 1H), 2.69-2.65 (m, 4H), 2.61-2.46 (m, 2H), 2.39 (s, 3H), 2.23-2.19 (m, 3H), 1.49 (s, 3H), 1.44 (br s, 2H), 0.87 (br s, 2H). |
| Example 82 | (R)-2-(3,3-difluoropyrrolidin-1-yl)-N-(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 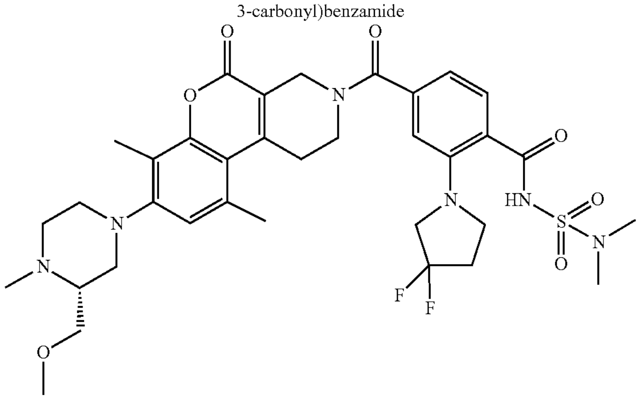 Synthesised from Intermediates 57 and 6 | HPLC: (System 1, Method D) Rt = 6.81 min, m/z 730.5 $(M + H)^+$ $(ES^+)$. $^1$H NMR (400 MHz, DMSO-$d_6$) δ: 11.70 (br s, 1H), 7.41 (d, J = 8.0 Hz, 1H), 6.91-6.85 (m, 3H), 4.47 (br s, 1H), 4.29 (br s, 1H), 3.82 (br s, 1H), 3.65-3.58 (m, 2H), 3.57-3.54 (m, 1H), 3.50 (br s, 3H), 3.40-3.34 (m, 1H), 3.38 (br s, 2H), 3.27 (s, 3H), 3.19-3.14 (m, 3H), 3.10-3.04 (m, 1H), 2.95-2.89 (m, 1H), 2.86 (s, 6H), 2.85-2.79 (m, 1H), 2.69-2.64 (m, 4H), 2.57-2.53 (m, 2H), 2.37 (s, 3H), 2.24-2.19 (m, 3H). |
| Example 83 | (R)-2-(cyclopropyl(methyl)amino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 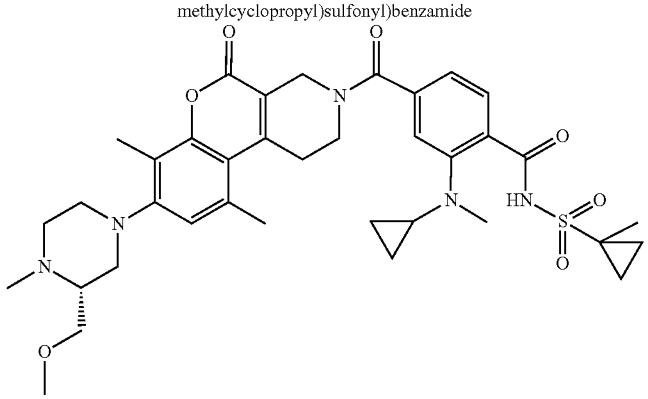 Synthesised from Intermediates 59 and 6 | HPLC: (System 1, Method D) Rt = 7.22 min, m/z 706.4 $(M + H)^+$ $(ES^+)$. $^1$H NMR (400 MHz, DMSO-$d_6$) δ: 12.40 (br s, 1H), 7.62-7.56 (m, 1H), 7.45-7.39 (m, 1H), 7.15-7.09 (m, 1H), 6.85 (s, 1H), 4.48 (br s, 1H), 4.34 (br s, 1H), 3.84 (br s, 1H), 3.57-3.54 (m, 2H), 3.37 (br s, 1H), 3.26 (s, 3H), 3.22 (br s, 2H), 3.15-3.12 (m, 1H), 3.05-3.02 (m, 1H), 2.90 (s, 3H), 2.84-2.79 (m, 2H), 2.69-2.60 (m, 5H), 2.44-2.40 (m, 2H), 2.32 (s, 3H), 2.24-2.20 (m, 3H), 1.49 (s, 3H), 1.47-1.44 (m, 2H), 0.94 (br s, 2H), 0.72 (br s, 2H), 0.52 (br s, 2H). Mixture of rotamers. |

-continued

| Example No. | Name/Structure/Intermediates | LCMS/$^1$H NMR data |
|---|---|---|
| Example 84 | (R)-2-(cyclopropyl(methyl)amino)-N-(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 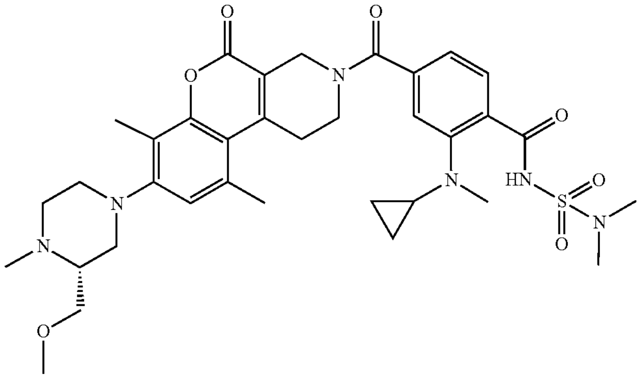 Synthesised from Intermediates 60 and 6 | HPLC: (System 1, Method D) Rt = 7.51 min, m/z 695.4 $(M + H)^+$ $(ES^+)$. $^1$H NMR (400 MHz, DMSO-$d_6$) δ: 12.30 (br s, 1H), 7.64-7.58 (m, 1H), 7.45-7.39 (m, 1H), 7.16-7.08 (m, 1H), 6.85 (s, 1H), 4.48 (br s, 1H), 4.33 (br s, 1H), 3.84 (br s, 1H), 3.57-3.52 (m, 2H), 3.34 (br s, 1H), 3.26 (s, 3H), 3.22 (br s, 2H), 3.15-3.12 (m, 1H), 3.05-3.03 (m, 1H), 2.88 (s, 9H), 2.85-2.79 (m, 2H), 2.69-2.61 (m, 5H), 2.45-2.39 (m, 2H), 2.32 (s, 3H), 2.24-2.19 (m, 3H), 0.72 (br s, 2H), 0.51 (br s, 2H). Mixture of rotamers. |
| Example 85 | (R)-2-((4,4-difluorocyclohexyl)oxy)-N-(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 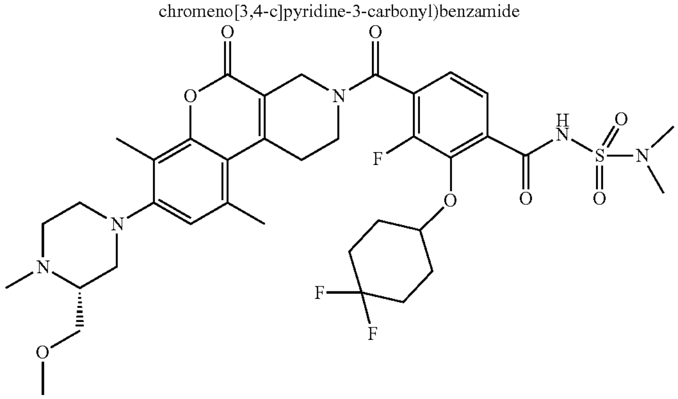 Synthesised from Intermediates 32 and 6 | UPLC: (System 3, Method K) Rt = 3.46 min, m/z 778.5 $(M + H)^+$ $(ES^+)$. $^1$H NMR (400 MHz, DMSO-$d_6$) δ: 7.33-7.31 (m, 1H), 7.22-7.14 (m, 1H), 6.86-6.84 (m, 1H), 4.47-4.43 (m, 2H), 4.18 (s, 1H), 3.87 (t, J = 5.5 Hz, 1H), 3.58-3.54 (m, 1H), 3.46-3.39 (m, 3H), 3.27 (s, 3H), 3.17-3.05 (m, 3H), 2.93-2.82 (m, 2H), 2.77-2.76 (m, 6H), 2.69-2.62 (m, 6H), 2.38-2.32 (m, 3H), 2.23-2.20 (m, 3H), 2.11-2.04 (m, 2H), 1.90-1.86 (m, 6H). One exchangeable proton not observed. Mixture of rotamers. |
| Example 86 | (R)-2-((4,4-difluorocyclohexyl)oxy)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 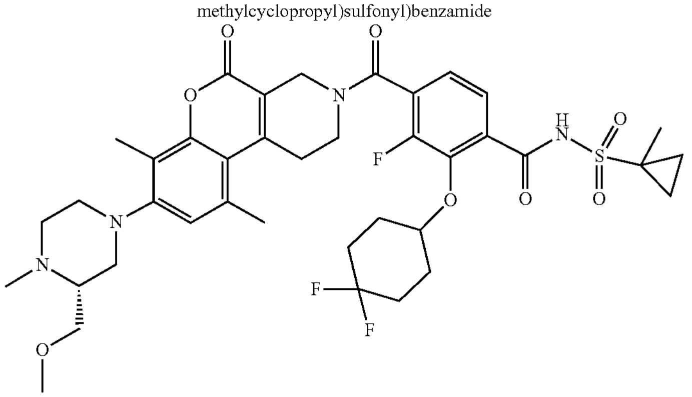 Synthesised from Intermediates 33 and 6 | UPLC: (System 3, Method K) Rt = 3.41 min, m/z 789.4 $(M + H)^+$ $(ES^+)$. $^1$H NMR (400 MHz, DMSO-$d_6$) δ: 7.31-7.29 (m, 1H), 7.21-7.14 (m, 1H), 6.87-6.85 (m, 1H), 4.49-4.49 (m, 2H), 4.19 (s, 1H), 3.87-3.86 (m, 1H), 3.62-3.55 (m, 1H), 3.47-3.43 (m, 2H), 3.28 (s, 3H), 3.18-3.06 (m, 3H), 2.88-2.83 (m, 1H), 2.69-2.62 (m, 6H), 2.41 (s, 3H), 2.24-2.17 (m, 3H), 2.17-2.04 (m, 2H), 1.91-1.86 (m, 8H), 1.45 (s, 3H), 1.32 (s, 2H), 0.85-0.76 (m, 2H). One exchangeable proton not observed. Mixture of rotamers. |

-continued

| Example No. | Name/Structure/Intermediates | LCMS/$^1$H NMR data |
|---|---|---|
| Example 87 | (R)-2-(3,3-dimethylpyrrolidin-1-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 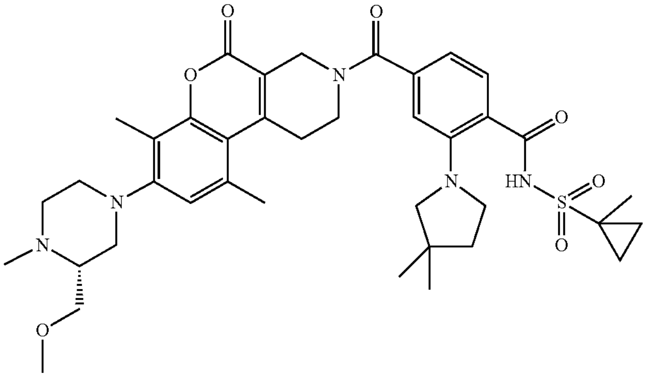 [SMILES: COC[C@H]1CN(c2cc(C)c3c4c(c(=O)oc3c2C)CN(C(=O)c2ccc(C(=O)NS(=O)(=O)C3(C)CC3)c(N3CCC(C)(C)C3)c2)CC4)CCN1C] Synthesised from Intermediates 61 and 6 | HPLC: (System 1, Method D) Rt = 7.23 min, m/z 734.0 $(M + H)^+$ $(ES^+)$. $^1$H NMR (400 MHz, DMSO-$d_6$) δ: 11.85 (br s, 1H), 7.36 (d, J = 8.0 Hz, 1H), 6.85 (s, 1H), 6.78-6.74 (m, 2H), 4.46 (br s, 1H), 4.30 (br s, 1H), 3.82 (br s, 1H), 3.57-3.54 (m, 2H), 3.34 (br s, 3H), 3.26 (s, 3H), 3.19-3.12 (m, 3H), 3.05-3.03 (m, 1H), 2.97-2.96 (m, 2H), 2.87-2.79 (m, 2H), 2.68-2.61 (m, 4H), 2.45 (br s, 2H), 2.32 (s, 3H), 2.23-2.19 (m, 3H), 1.73 (br s, 2H), 1.51-1.48 (m, 5H), 1.06 (s, 6H), 0.91 (br s, 2H). |
| Example 88 | (R)-2-(3,3-dimethylpyrrolidin-1-yl)-N-(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 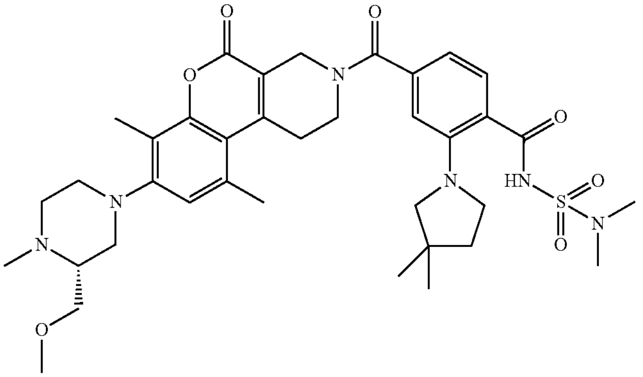 Synthesised from Intermediates 62 and 6 | HPLC: (System 1, Method D) Rt = 7.32 min, m/z 723.0 $(M + H)^+$ $(ES^+)$. $^1$H NMR (400 MHz, DMSO-$d_6$) δ: 11.81 (br s, 1H), 7.35 (d, J = 8.0 Hz, 1H), 6.85 (s, 1H), 6.77-6.73 (m, 2H), 4.46 (br s, 1H), 4.30 (br s, 1H), 3.82 (br s, 1H), 3.57-3.52 (m, 2H), 3.34 (br s, 3H), 3.26 (s, 3H), 3.20-3.12 (m, 3H), 3.05-2.96 (m, 3H), 2.88-2.79 (m, 8H), 2.68-2.60 (m, 4H), 2.42 (br s, 2H), 2.31 (s, 3H), 2.23-2.19 (m, 3H), 1.74-1.71 (m, 2H), 1.07 (s, 6H). |
| Example 89 | (R)-2-(azetidin-1-yl)-N-(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 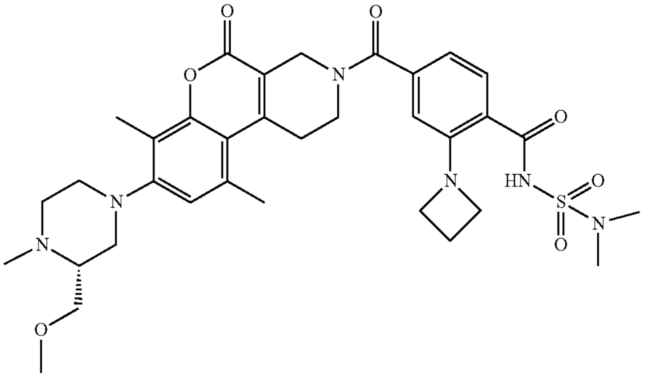 Synthesised from Intermediates 64 and 6 | HPLC: (System 1, Method D) Rt = 6.44 min, m/z 681.4 $(M + H)^+$ $(ES^+)$. $^1$H NMR (400 MHz, DMSO-$d_6$) δ: 11.70 (br s, 1H), 7.36-7.34 (m, 1H), 6.85 (s, 1H), 6.80-6.74 (m, 1H), 6.54-6.50 (m, 1H), 4.45 (br s, 1H), 4.28 (br s, 1H), 3.85-3.84 (m, 5H), 3.57-3.54 (m, 1H), 3.50 (br s, 1H), 3.37 (br s, 1H), 3.26 (s, 3H), 3.19-3.12 (m, 3H), 3.05-3.03 (m, 1H), 2.86-2.79 (m, 8H), 2.68-2.61 (m, 4H), 2.47-2.45 (m, 2H), 2.32-2.25 (m, 5H), 2.23-2.19 (m, 3H). Mixture of rotamers. |

-continued

| Example No. | Name/Structure/Intermediates | LCMS/$^1$H NMR data |
| --- | --- | --- |
| Example 90 | 2-((adamantan-2-yl)oxy)-N-(N,N-dimethylsulfamoyl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 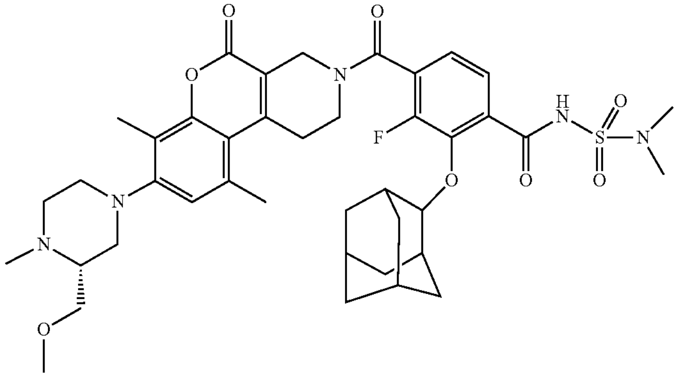 Synthesised from Intermediates 35 and 6 | UPLC: (System 3, Method K) Rt = 4.38 min, m/z 792.3 (M + H)$^+$ (ES$^+$). $^1$H NMR (400 MHz, DMSO-d$_6$) δ: 7.29-7.27 (m, 1H), 7.14-7.10 (m, 1H), 6.86-6.84 (m, 1H), 4.51-4.38 (m, 2H), 4.17 (s, 1H), 3.87 (t, J = 5.7 Hz, 1H), 3.57-3.54 (m, 1H), 3.46-3.42 (m, 1H), 3.27 (s, 3H), 3.15-3.13 (m, 2H), 3.06-3.03 (m, 1H), 2.86-2.77 (m, 7H), 2.69-2.62 (m, 6H), 2.34-2.32 (m, 3H), 2.22 (m, 4H), 2.16-2.05 (m, 4H), 1.78-1.78 (m, 5H), 1.68-1.62 (m, 5H), 1.48 (t, J = 11.0 Hz, 2H). One exchangeable proton not observed. Mixture of rotamers. |
| Example 91 | (R)-2-(azetidin-1-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 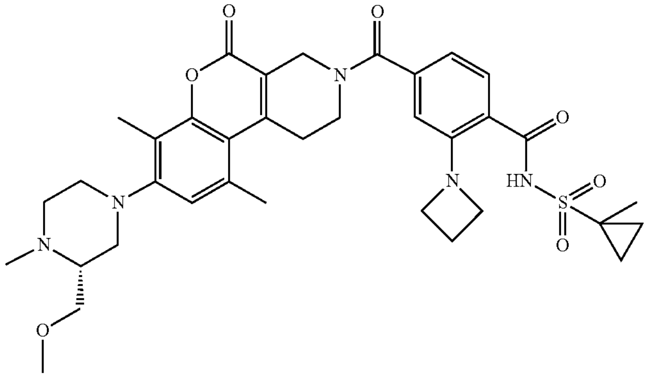 [SMILES: COC[C@H]1CN(c2cc(C)c3c4c(c(=O)oc3c2C)CN(C(=O)c2ccc(C(=O)NS(=O)(=O)C3(C)CC3)c(N3CCC3)c2)CC4)CCN1C] Synthesised from Intermediates 63 and 6 | HPLC: (System 1, Method D) Rt = 6.51 min, m/z 692.4 (M + H)$^+$ (ES$^+$). $^1$H NMR (400 MHz, DMSO-d$_6$) δ: 11.71 (br s, 1H), 7.37-7.35 (m, 1H), 6.85 (s, 1H), 6.82-6.75 (m, 1H), 6.55-6.51 (m, 1H), 4.46 (br s, 1H), 4.28 (br s, 1H), 3.84-3.83 (m, 5H), 3.58-3.54 (m, 1H), 3.50 (br s, 1H), 3.37-3.34 (m, 1H), 3.29 (br s, 1H), 3.27 (s, 3H), 3.19-3.14 (m, 3H), 3.07-3.04 (m, 1H), 2.91-2.81 (m, 2H), 2.69-2.65 (m, 4H), 2.51 (br s, 1H), 2.36 (s, 3H), 2.33-2.26 (m, 2H), 2.24-2.19 (m, 3H), 1.49 (s, 3H), 1.47-1.44 (m, 2H), 0.93 (br s, 2H). Mixture of rotamers. |
| Example 92 | (R)-2-(3,3-difluoropyrrolidin-1-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 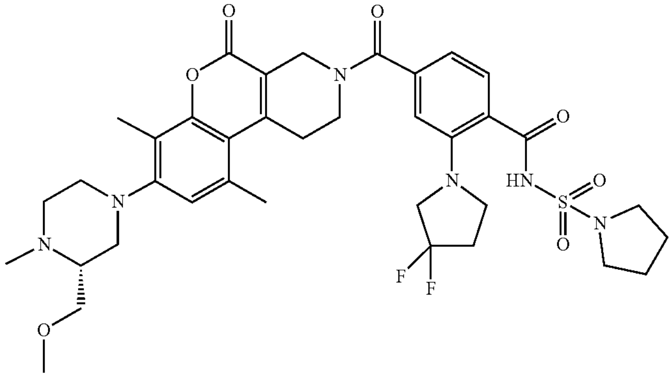 [SMILES: COC[C@H]1CN(c2cc(C)c3c4c(c(=O)oc3c2C)CN(C(=O)c2ccc(C(=O)NS(=O)(=O)N3CCCC3)c(N3CCC(F)(F)C3)c2)CC4)CCN1C] Synthesised from Intermediates 58 and 6 | HPLC: (System 1, Method D) Rt = 7.05 min, m/z 757.4 (M + H)$^+$ (ES$^+$). $^1$H NMR (400 MHz, DMSO-d$_6$) δ: 11.82 (br s, 1H), 7.41 (d, J = 8.0 Hz, 1H), 6.93-6.84 (m, 3H), 4.47 (br s, 1H), 4.28 (br s, 1H), 3.82 (br s, 1H), 3.66-3.60 (m, 2H), 3.55-3.54 (m, 1H), 3.44 (br s, 3H), 3.51-3.49 (m, 4H), 3.37-3.34 (m, 2H), 3.26 (s, 3H), 3.20 (br s, 2H), 3.16-3.12 (m, 1H), 3.06-3.02 (m, 1H), 2.88-2.79 (m, 2H), 2.69-2.61 (m, 4H), 2.55-2.53 (m, 1H), 2.48-2.40 (m, 2H), 2.33 (s, 3H), 2.24-2.17 (m, 3H), 1.87-1.83 (m, 4H). |

-continued

| Example No. | Name/Structure/Intermediates | LCMS/¹H NMR data |
|---|---|---|
| Example 93 | (R)-2-cyclobutoxy-N-(N,N-dimethylsulfamoyl)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 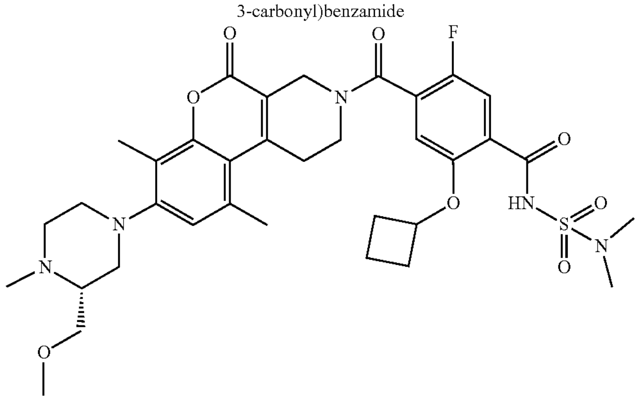 Synthesised from Intermediates 36 and 6 | UPLC (System 3, Method K) Rt = 3.87 min, m/z 714.5 $(M + H)^+$ $(ES^+)$. $^1H$ NMR (400 MHz, ACN-$d_3$) δ: 7.75-7.70 (m, 1H), 6.96-6.89 (m, 1H), 6.80-6.78 (m, 1H), 4.89-4.77 (m, 1H), 4.52 (br s, 1H), 4.16 (br s, 1H), 3.88 (br s, 1H), 3.55-3.44 (m, 2H), 3.35-3.31 (m, 1H), 3.26 (s, 3H), 3.22-3.00 (m, 4H), 2.93 (s, 6H), 2.86-2.80 (m, 2H), 2.66-2.36 (m, 8H), 2.29-2.21 (m, 8H), 1.79-1.89 (m, 1H), 1.75-1.62 (m, 1H). One exchangeable proton not visible. Mixture of rotamers. |
| Example 94 | 2-((adamantan-2-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 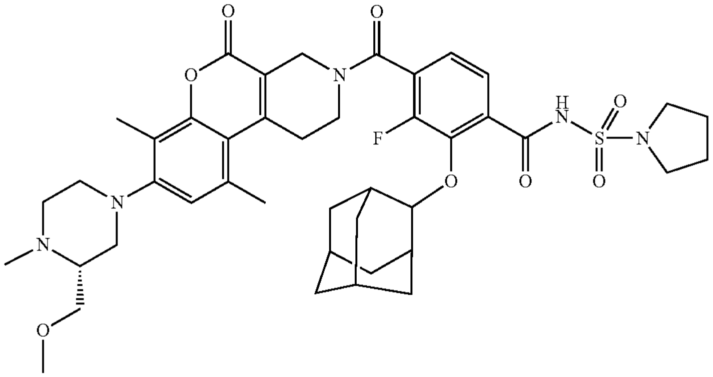 [SMILES: COC[C@H]1CN(c2cc(C)c3c4c(c(=O)oc3c2C)CN(C(=O)c2ccc(C(=O)NS(=O)(=O)N3CCCC3)c(OC3C5CC6CC(C5)CC3C6)c2F)CC4)CCN1C] Synthesised from Intermediates 34 and 6 | UPLC: (System 3, Method K) Rt = 4.61 min, m/z 820.5 $(M + H)^+$ $(ES^+)$. $^1H$ NMR (400 MHz, DMSO-$d_6$) δ: 7.27-7.25 (m, 1H), 7.12-7.12 (m, 1H), 6.85-6.84 (m, 1H), 4.50-4.39 (m, 2H), 4.17 (br s, 1H), 3.87-3.87 (m, 1H), 3.57-3.53 (m, 1H), 3.46-3.39 (m, 2H), 3.25 (s, 3H), 3.14-3.11 (m, 2H), 3.04-3.01 (m, 1H), 2.84-2.79 (m, 2H), 2.71-2.64 (m, 3H), 2.60 (s, 3H), 2.44-2.32 (m, 3H), 2.29 (s, 3H), 2.23-2.13 (m, 6H), 2.08-2.05 (m, 2H), 1.79-1.79 (m, 9H), 1.68-1.61 (m, 4H), 1.50-1.44 (m, 2H). One exchangeable proton not observed. Mixture of rotamers. |
| Example 95 | 2-(3-azabicyclo[3.1.0]hexan-3-yl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 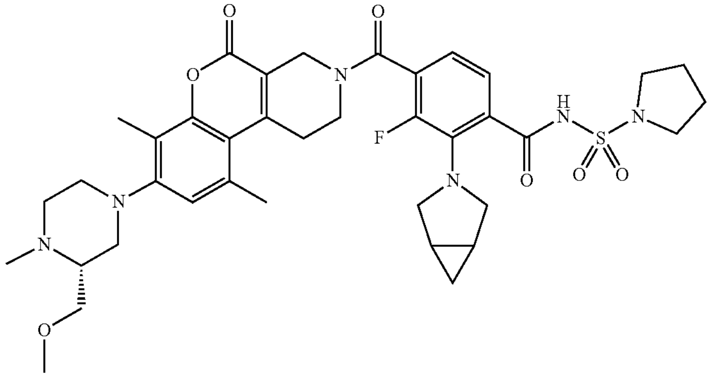 [SMILES: COC[C@H]1CN(c2cc(C)c3c4c(c(=O)oc3c2C)CN(C(=O)c2ccc(C(=O)NS(=O)(=O)N3CCCC3)c(N3CC5CC5C3)c2F)CC4)CCN1C] Synthesised from Intermediates 75 and 6 | HPLC: (System 1, Method D) Rt = 8.32 min, m/z 751.4 $(M + H)^+$ $(ES^+)$. $^1H$ NMR (400 MHz, DMSO-$d_6$) δ: 12.31 (br s, 1H), 7.41-7.36 (m, 1H), 7.20-7.11 (m, 1H), 6.86-6.84 (m, 1H), 4.60-4.38 (m, 1H), 4.18 (s, 1H), 3.86 (br s, 1H), 3.56-3.54 (m, 1H), 3.43-3.37 (m, 8H), 3.31-3.29 (m, 2H), 3.27 (s, 3H), 3.23 (br s, 1H), 3.15-3.12 (m, 2H), 3.05-3.03 (m, 1H), 2.87-2.79 (m, 2H), 2.69-2.61 (m, 4H), 2.50-2.44 (m, 2H), 2.32 (s, 3H), 2.23-2.20 (m, 3H), 1.87-1.84 (m, 4H), 1.58-1.54 (m, 2H), 0.65-0.61 (m, 1H), 0.55-0.50 (m, 1H). Mixture of rotamers. |

-continued

| Example No. | Name/Structure/Intermediates | LCMS/$^1$H NMR data |
|---|---|---|
| Example 96 | (R)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)-N-(pyrrolidin-1-ylsulfonyl)benzamide 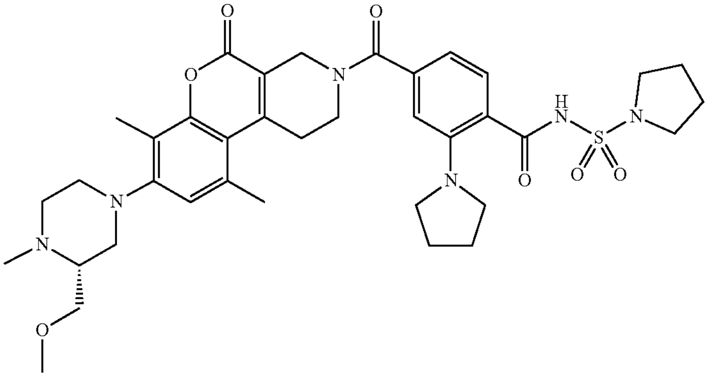 [SMILES: COC[C@H]1CN(c2cc(C)c3c4c(c(=O)oc3c2C)CN(C(=O)c2ccc(C(=O)NS(=O)(=O)N3CCCC3)c(N3CCCC3)c2)CC4)CCN1C] Synthesised from Intermediates 48 and 6 | HPLC: (System 1, Method D) Rt = 7.38 min, m/z 721.3 (M + H)$^+$ (ES$^+$). $^1$H NMR (400 MHz, DMSO-$d_6$) δ: 11.85 (br s, 1H), 7.35 (d, J = 7.6 Hz, 1H), 6.84 (s, 1H), 6.79-6.76 (m, 2H), 4.46 (br s, 1H), 4.29 (br s, 1H), 3.82 (br s, 1H), 3.57-3.52 (m, 2H), 3.44-3.41 (m, 4H), 3.31 (br s, 1H), 3.26 (s, 3H), 3.19 (br s, 6H), 3.14-3.11 (m, 1H), 3.04-3.01 (m, 1H), 2.84-2.78 (m, 2H), 2.68-2.59 (m, 4H), 2.42-2.40 (m, 2H), 2.30 (s, 3H), 2.23-2.19 (m, 3H), 1.91 (br s, 4H), 1.87-1.83 (m, 4H). |
| Example 97 | (R)-2-(7-azabicyclo[2.2.1]heptan-7-yl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 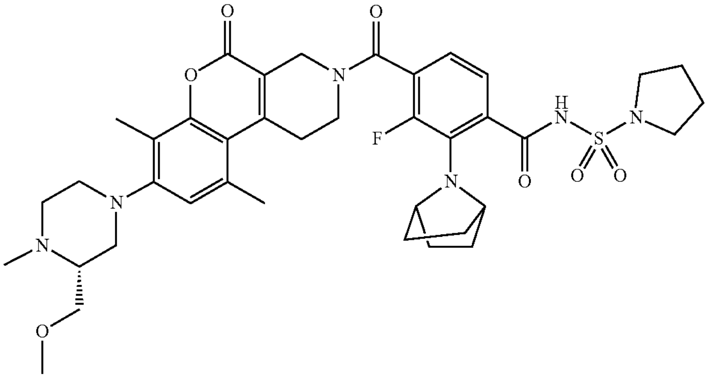 [SMILES: COC[C@H]1CN(c2cc(C)c3c4c(c(=O)oc3c2C)CN(C(=O)c2ccc(C(=O)NS(=O)(=O)N3CCCC3)c(N3C5CCC3CC5)c2F)CC4)CCN1C] Synthesised from Intermediates 78 and 6 | HPLC: (System 1, Method D) Rt = 7.73 min, m/z 765.4 (M + H)$^+$ (ES$^+$). $^1$H NMR (400 MHz, DMSO-$d_6$) δ: 11.65 (br s, 1H), 7.18-7.15 (m, 1H), 6.89-6.79 (m, 2H), 4.61-4.37 (m, 1H), 4.18-4.15 (m, 3H), 3.86 (br s, 1H), 3.57-3.54 (m, 1H), 3.44-3.34 (m, 6H), 3.26 (s, 3H), 3.22 (br s, 1H), 3.15-3.12 (m, 2H), 3.05-3.02 (m, 1H), 2.87-2.79 (m, 2H), 2.69-2.62 (m, 4H), 2.46-2.44 (m, 2H), 2.32 (s, 3H), 2.23-2.19 (m, 3H), 1.84-1.80 (m, 4H), 1.74-1.68 (m, 4H), 1.45-1.40 (m, 4H). Mixture of rotamers. |
| Example 98 | (R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)-N-(pyrrolidin-1-ylsulfonyl)benzamide 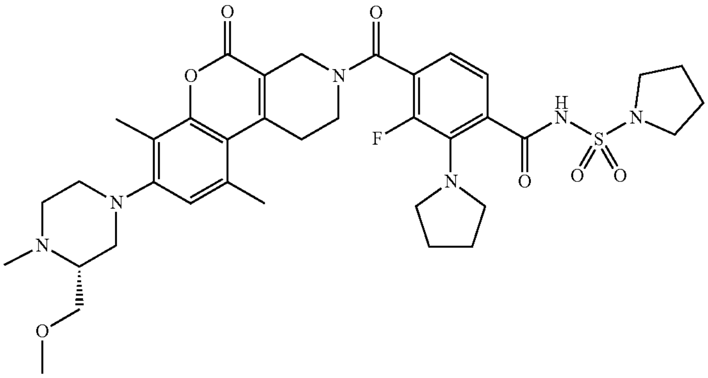 [SMILES: COC[C@H]1CN(c2cc(C)c3c4c(c(=O)oc3c2C)CN(C(=O)c2ccc(C(=O)NS(=O)(=O)N3CCCC3)c(N3CCCC3)c2F)CC4)CCN1C] Synthesised from Intermediates 72 and 6 | HPLC: (System 1, Method D) Rt = 8.51 min, m/z 739.4 (M + H)$^+$ (ES$^+$). $^1$H NMR (400 MHz, DMSO-$d_6$) δ: 12.88 (br s, 1H), 7.44.738 (m, 1H), 7.13-7.10 (m, 1H), 6.86-6.84 (m, 1H), 4.59-4.41 (m, 1H), 4.19 (s, 1H), 3.86 (br s, 1H), 3.57-3.53 (m, 1H), 3.47 (br s, 1H), 3.43-3.40 (m, 4H), 3.34 (br s, 1H), 3.33-3.30 (m, 4H), 3.26 (s, 3H), 3.23 (br s, 1H), 3.14-3.12 (m, 2H), 3.05-3.02 (m, 1H), 2.86-2.79 (m, 2H), 2.69-2.61 (m, 4H), 2.45-2.43 (m, 2H), 2.31 (s, 3H), 2.23-2.19 (m, 3H), 1.93-1.87 (m, 4H), 1.84-1.80 (m, 4H). Mixture of rotamers. |

-continued

| Example No. | Name/Structure/Intermediates | LCMS/$^1$H NMR data |
|---|---|---|
| Example 99 | (R)-2-((4,4-difluorocyclohexyl)oxy)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 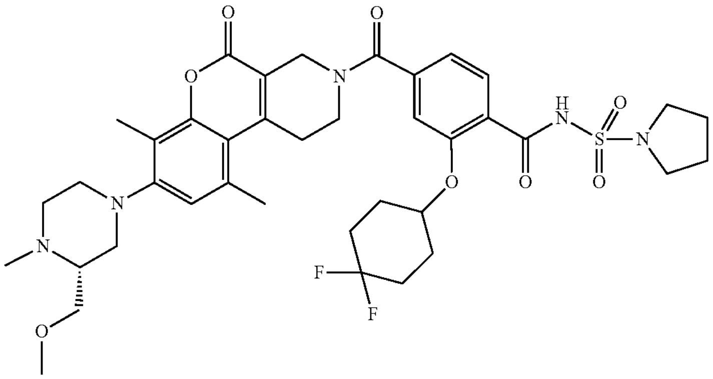 [SMILES: COC[C@H]1CN(c2cc(C)c3c4c(c(=O)oc3c2C)CN(C(=O)c2ccc(C(=O)NS(=O)(=O)N3CCCC3)c(OC3CCC(F)(F)CC3)c2)CC4)CCN1C] Synthesised from Intermediates 40 and 6 | UPLC: (System 3, Method K) Rt = 4.28 min, m/z 786.6 (M + H)$^+$ (ES$^+$). $^1$H NMR (400 MHz, DMSO-d$_6$) δ: 7.53-7.51 (m, 1H), 7.30-7.10 (m, 2H), 6.85 (s, 1H), 4.82 (br s, 1H), 4.48-4.29 (m, 2H), 3.84 (br s, 1H), 3.57-3.50 (m, 2H), 3.39-3.39 (m, 4H), 3.26 (s, 3H), 3.21 (br s, 2H), 3.14-3.01 (m, 2H), 2.88-2.58 (m, 6H), 2.41-2.39 (m, 2H), 2.30 (s, 3H), 2.23-2.15 (m, 4H), 1.91-1.90 (m, 8H), 1.85-1.82 (m, 4H). One exchangeable proton not observed. Mixture of rotamers. |
| Example 100 | 2-((adamantan-2-yl)oxy)-N-(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 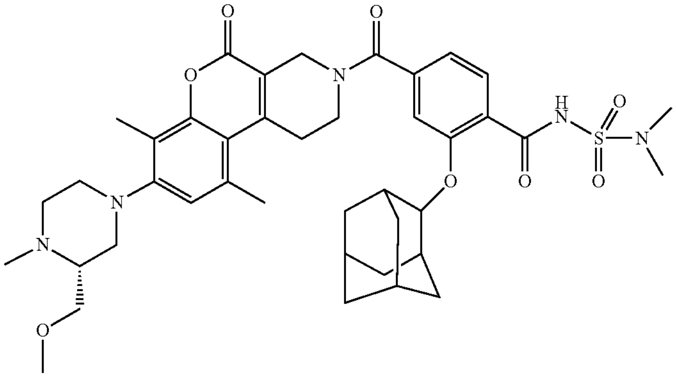 Synthesised from Intermediates 41 and 6 | UPLC: (System 3, Method K) Rt = 4.92 min, m/z 774.4 (M − H)$^-$ (ES$^-$). $^1$H NMR (400 MHz, DMSO-d$_6$) δ: 7.59-7.53 (m, 1H), 7.27-7.08 (m, 2H), 6.85 (s, 1H), 4.78-4.70 (m, 1H), 4.47-4.28 (m, 2H), 3.84 (br s, 1H), 3.57-3.49 (m, 2H), 3.26 (s, 3H), 3.21-3.21 (m, 2H), 3.14-3.11 (m, 1H), 3.04-3.01 (m, 1H), 2.86 (s, 6H), 2.68-2.59 (m, 6H), 2.42-2.39 (m, 1H), 2.30-2.28 (m, 3H), 2.23-2.19 (m, 3H), 2.12 (br s, 4H), 1.91-1.71 (m, 10H), 1.52-1.49 (m, 2H). One exchangeable proton not observed. Mixture of rotamers. |
| Example 101 | (R)-2-(cyclopentyloxy)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)-6-(trifluoromethyl)benzamide 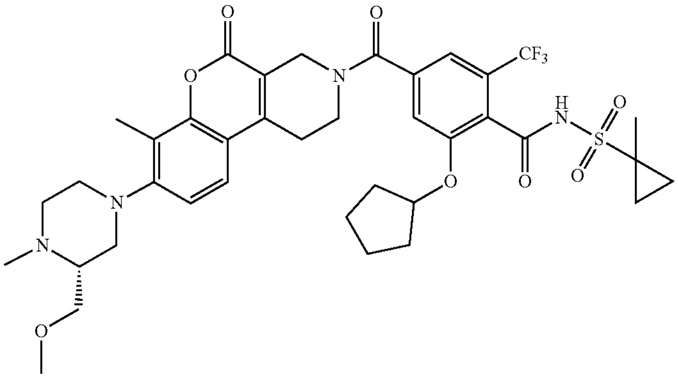 [SMILES: COC[C@H]1CN(c2ccc3c4c(c(=O)oc3c2C)CN(C(=O)c2cc(OC3CCCC3)c(C(=O)NS(=O)(=O)C3(C)CC3)c(C(F)(F)F)c2)CC4)CCN1C] Synthesised from Intermediates 43 and 5 | HPLC: (System 1, Method D) Rt = 7.08 min, m/z 775.3 (M + H)$^+$ (ES$^+$). $^1$H NMR (400 MHz, DMSO-d$_6$) δ: 11.82 (br s, 1H), 7.60-7.53 (m, 1H), 7.49 (s, 1H), 7.36 (s, 1H), 7.09-7.07 (m, 1H), 5.04 (br s, 1H), 4.51 (br s, 1H), 4.29 (br s, 1H), 3.94 (br s, 1H), 3.59-3.55 (m, 2H), 3.38 (br s, 2H), 3.27 (s, 3H), 3.18-3.15 (m, 1H), 3.08-3.06 (m, 1H), 2.98 (br s, 2H), 2.93-2.83 (m, 2H), 2.69-2.64 (m, 1H), 2.51 (br s, 1H), 2.37 (s, 3H), 2.30-2.26 (m, 3H), 1.87-1.86 (m, 2H), 1.77-1.74 (m, 4H), 1.56 (br s, 2H), 1.50 (s, 3H), 1.42 (br s, 2H), 0.89 (br s, 2H). Mixture of rotamers. |

-continued

| Example No. | Name/Structure/Intermediates | LCMS/$^{1}$H NMR data |
|---|---|---|
| Example 102 | N-(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-2-((R)-2-methylpyrrolidin-1-yl)benzamide 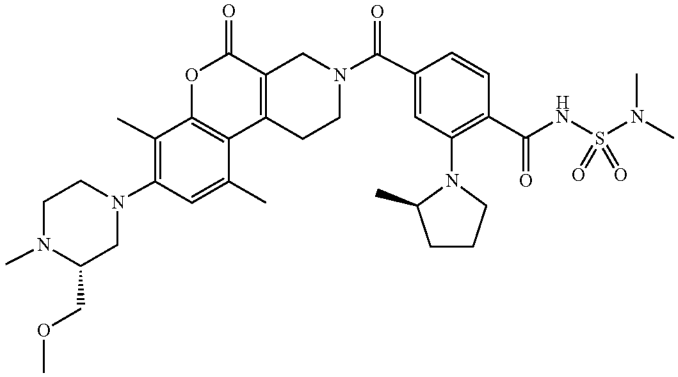 Synthesised from Intermediates 65 and 6 | HPLC: (System 1, Method D) Rt = 7.75 min, m/z 709.3 $(M + H)^+$ $(ES^+)$. $^{1}$H NMR (400 MHz, DMSO-$d_6$) δ: 12.56 (br s, 1H), 7.56-7.51 (m, 1H), 7.08-7.00 (m, 1H), 6.98-6.89 (m, 1H), 6.84 (s, 1H), 4.50-4.44 (m, 1H), 4.32-4.31 (m, 1H), 3.91-3.71 (m, 2H), 3.57-3.45 (m, 3H), 3.34 (br s, 1H), 3.26 (s, 3H), 3.20 (br s, 2H), 3.14-3.12 (m, 1H), 3.05-3.02 (m, 1H), 2.97 (br s, 1H), 2.88 (s, 6H), 2.84-2.79 (m, 2H), 2.68-2.59 (m, 4H), 2.44-2.42 (m, 2H), 2.31 (s, 3H), 2.23-2.19 (m, 4H), 1.92 (br s, 1H), 1.78 (br s, 1H), 1.60-1.56 (m, 1H), 1.10 (br s, 3H). Mixture of rotamers. |
| Example 103 | N-(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-2-((S)-2-methylpyrrolidin-1-yl)benzamide 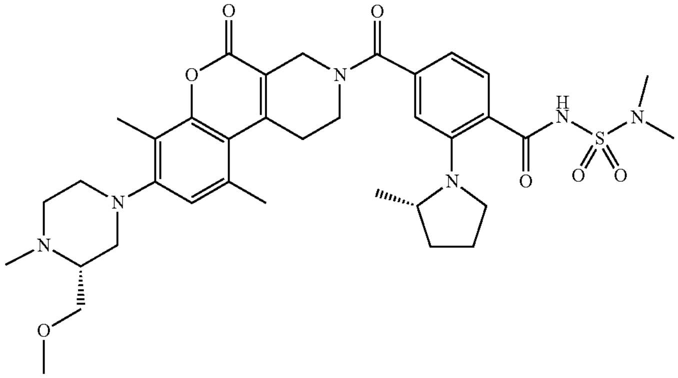 Synthesised from Intermediates 66 and 6 | HPLC: (System 1, Method D) Rt = 7.75 min, m/z 709.4 $(M + H)^+$ $(ES^+)$. $^{1}$H NMR (400 MHz, DMSO-$d_6$) δ: 12.58 (br s, 1H), 7.56-7.51 (m, 1H), 7.08-6.89 (m, 2H), 6.85 (s, 1H), 4.54-4.30 (m, 2H), 3.91-3.71 (m, 2H), 3.57-3.45 (m, 3H), 3.34 (br s, 1H), 3.26 (s, 3H), 3.20 (br s, 2H), 3.15-3.12 (m, 1H), 3.05-3.02 (m, 1H), 2.88 (s, 6H), 2.84-2.79 (m, 2H), 2.68-2.60 (m, 4H), 2.45-2.43 (m, 2H), 2.31 (s, 3H), 2.23-2.19 (m, 4H), 1.92 (br s, 1H), 1.80-1.77 (m, 1H), 1.60-1.57 (m, 1H), 1.10 (br s, 3H). Mixture of rotamers. |
| Example 104 | 2-(3-azabicyclo[3.1.0]hexan-3-yl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)-6-(trifluoromethyl)benzamide 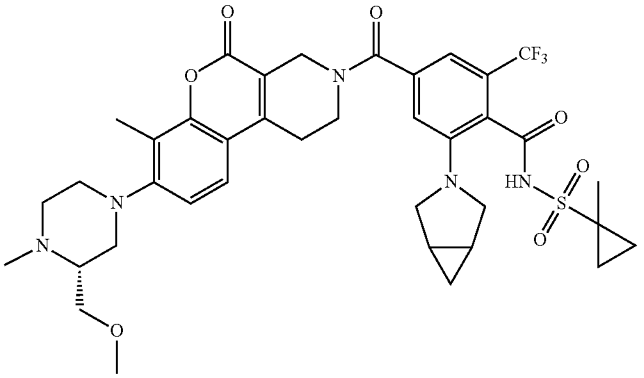 [SMILES: COC[C@H]1CN(c2ccc3c4c(c(=O)oc3c2C)CN(C(=O)c2cc(N3CC5CC5C3)c(C(=O)NS(=O)(=O)C3(C)CC3)c(C(F)(F)F)c2)CC4)CCN1C] Synthesised from Intermediates 97 and 5 | HPLC: (System 1, Method D) Rt = 7.07 min, m/z 772.3 $(M + H)^+$ $(ES^+)$. $^{1}$H NMR (400 MHz, DMSO-$d_6$) δ: 11.89 (br s, 1H), 7.56-7.54 (m, 1H), 7.12-7.07 (m, 3H), 4.48 (br s, 1H), 4.29 (br s, 1H), 3.92 (br s, 1H), 3.59-3.57 (m, 4H), 3.42 (br s, 1H), 3.32-3.28 (m, 6H), 3.20-3.17 (m, 1H), 3.10-3.08 (m, 1H), 2.96-2.85 (m, 4H), 2.70-2.68 (m, 2H), 2.42 (br s, 3H), 2.30-2.26 (m, 3H), 1.60 (br s, 2H), 1.46 (s, 3H), 1.42 (br s, 2H), 0.85 (br s, 2H), 0.61-0.56 (m, 1H), 0.41 (br s, 1H). |

-continued

| Example No. | Name/Structure/Intermediates | LCMS/$^1$H NMR data |
|---|---|---|
| Example 105 | 2-(3-azabicyclo[3.1.0]hexan-3-yl)-6-chloro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide 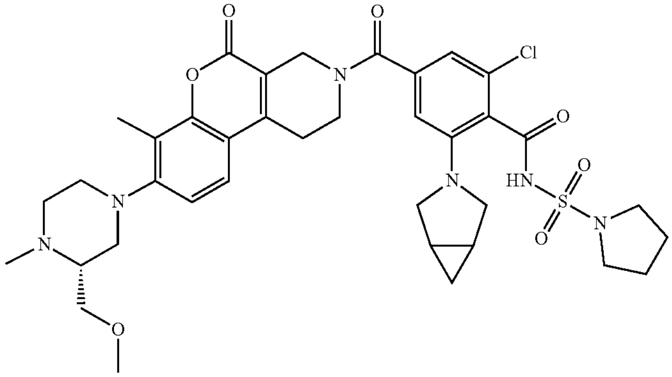 [SMILES: COC[C@H]1CN(c2ccc3c4c(c(=O)oc3c2C)CN(C(=O)c2cc(Cl)c(C(=O)NS(=O)(=O)N3CCCC3)c(N3CC5CC5C3)c2)CC4)CCN1C] Synthesised from Intermediates 94 and 5 | HPLC: (System 1, Method D) Rt = 7.12 min, m/z 753.0 $(M + H)^+$ $(ES^+)$. 1H NMR (400 MHz, DMSO-$d_6$) δ: 11.98 (br s, 1H), 7.56 (br s, 1H), 7.08 (d, J = 8.4 Hz, 1H), 6.85 (s, 1H), 6.67 (s, 1H), 4.46 (br s, 1H), 4.28 (br s, 1H), 3.89 (br s, 1H), 3.59-3.54 (m, 4H), 3.45 (br s, 4H), 3.38 (br s, 1H), 3.33 (br s, 2H), 3.27 (s, 3H), 3.17-3.14 (m, 1H), 3.07-3.04 (m, 1H), 2.95 (br s, 2H), 2.87-2.85 (m, 2H), 2.67-2.61 (m, 1H), 2.47 (br s, 2H), 2.33 (s, 3H), 2.29-2.26 (m, 3H), 1.88-1.84 (m, 4H), 1.65-1.64 (m, 2H), 0.66-0.65 (m, 1H), 0.24 (br s, 1H). |
| Example 106 | (R)-N-(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-methyl-6-(pyrrolidin-1-yl)benzamide 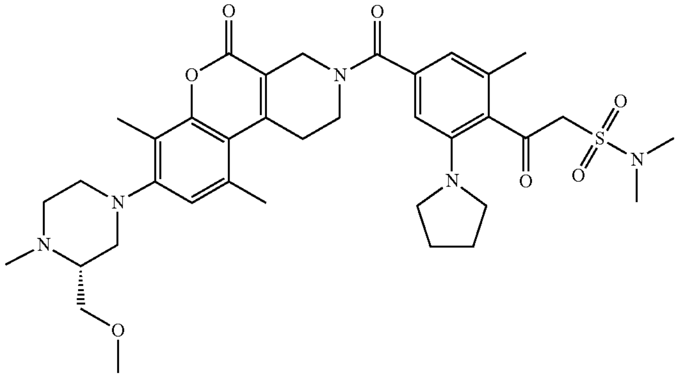 Synthesised from Intermediates 96 and 6 | HPLC: (System 1, Method D) Rt = 6.87 min, m/z 709.3 $(M + H)^+$ $(ES^+)$. $^1$H NMR (400 MHz, DMSO-$d_6$) δ: 11.78 (br s, 1H), 6.84 (s, 1H), 6.63-6.59 (m, 2H), 4.45-4.32 (m, 2H), 3.80 (br s, 1H), 3.57-3.54 (m, 2H), 3.37-3.34 (m, 5H), 3.26 (s, 3H), 3.19-3.12 (m, 3H), 3.06-3.02 (m, 1H), 2.89 (s, 6H), 2.84-2.79 (m, 2H), 2.67-2.60 (m, 4H), 2.46-2.44 (m, 2H), 2.32 (s, 3H), 2.28 (s, 3H), 2.22-2.20 (m, 3H), 1.89 (br s, 4H). |
| Example 107 | (R)-2-(cyclopentyloxy)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide 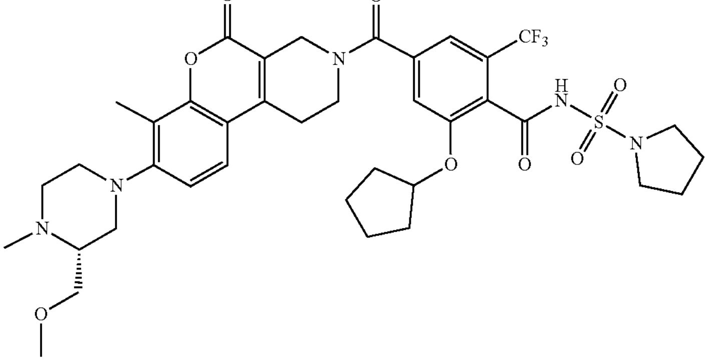 Synthesised from Intermediates 44 and 5 | HPLC: (System 1, Method D) Rt = 7.53 min, m/z 790.4 $(M + H)^+$ $(ES^+)$. $^1$H NMR (400 MHz, DMSO-$d_6$) δ: 11.86 (br s, 1H), 7.60-7.49 (m, 2H), 7.38-7.36 (m, 1H), 7.09-7.07 (m, 1H), 5.04 (br s, 1H), 4.51-4.28 (m, 2H), 3.94 (br s, 1H), 3.58-3.54 (m, 2H), 3.42-3.40 (m, 4H), 3.37 (br s, 1H), 3.26 (s, 3H), 3.16-3.13 (m, 1H), 3.06-2.98 (m, 3H), 2.87-2.82 (m, 2H), 2.65-2.60 (m, 1H), 2.46-2.44 (m, 2H), 2.3-2.25 (m, 6H), 1.87-1.84 (m, 6H), 1.75-1.72 (m, 4H), 1.57 (br s, 2H). Mixture of rotamers. |

-continued

| Example No. | Name/Structure/Intermediates | LCMS/$^1$H NMR data |
|---|---|---|
| Example 108 | 2-(bicyclo[3.1.0]hexan-3-yloxy)-N-(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide. Mixture of diastereomers cis/trans 83/17. 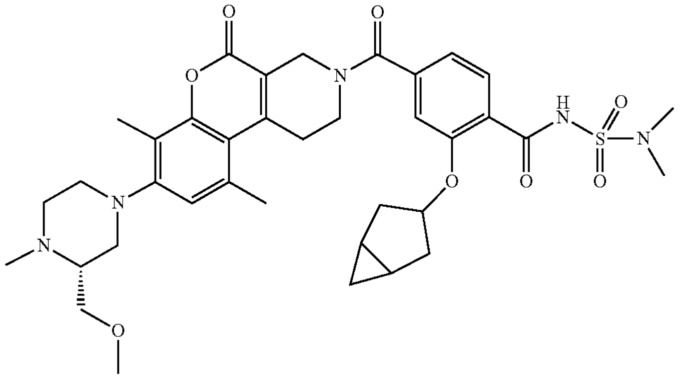 Synthesised from Intermediates 38 and 6 | HPLC: (System 1, Method D) Rt = 7.73 min, m/z 722.4 $(M + H)^+$ $(ES^+)$. $^1$H NMR (400 MHz, DMSO-$d_6$) δ: 11.35 (br s, 1H), 7.55-7.48 (m, 1H), 7.26-7.03 (m, 2H), 6.85 (s, 1H), 5.03-4.67 (m, 1H), 4.48-4.28 (m, 2H), 3.83 (br s, 1H), 3.57-3.54 (m, 1H), 3.50 (br s, 1H), 3.34 (br s, 1H), 3.26 (s, 3H), 3.21 (br s, 2H), 3.15-3.12 (m, 1H), 3.05-3.02 (m, 1H), 2.88-2.86 (m, 6H), 2.83-2.79 (m, 2H), 2.69-2.60 (m, 4H), 2.50-2.42 (m, 2H), 2.31 (s, 4H), 2.24-2.19 (m, 4H), 1.96-1.90 (m, 2H), 1.34 (br s, 2H), 0.56-0.17 (m, 2H). Mixture of diastereomers and rotamers. |
| Example 109 | 2-(bicyclo[3.1.0]hexan-3-yloxy)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide Mixture of diastereomers cis/trans 90/10. 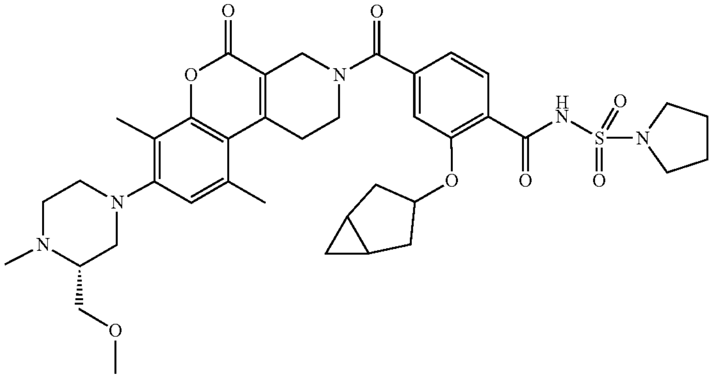 [SMILES: COC[C@H]1CN(c2cc(C)c3c4c(c(=O)oc3c2C)CN(C(=O)c2ccc(C(=O)NS(=O)(=O)N3CCCC3)c(OC3CC5CC5C3)c2)CC4)CCN1C] Synthesised from Intermediates 39 and 6 | HPLC: (System 1, Method D) Rt = 8.67 min, m/z 748.4 $(M + H)^+$ $(ES^+)$. $^1$H NMR (400 MHz, DMSO-$d_6$) δ: 11.41 (br s, 1H), 7.54-7.47 (m, 1H), 7.29-7.02 (m, 2H), 6.85 (s, 1H), 5.01-4.67 (m, 1H), 4.48-4.28 (m, 2H), 3.83 (br s, 1H), 3.57-3.54 (m, 1H), 3.53 (br s, 1H), 3.49-3.43 (m, 4H), 3.30 (br s, 1H), 3.26 (s, 3H), 3.21 (br s, 2H), 3.14-3.11 (m, 1H), 3.04-3.02 (m, 1H), 2.84-2.79 (m, 2H), 2.69-2.59 (m, 4H), 2.42-2.40 (m, 2H), 2.36-2.19 (m, 8H), 1.95-1.86 (m, 6H), 1.33 (br s, 2H), 0.51-0.17 (m, 2H). Mixture of diastereomers and rotamers. |
| Example 110 | (R)-2-(cyclopentyloxy)-N-(N,N-dimethylsulfamoyl)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 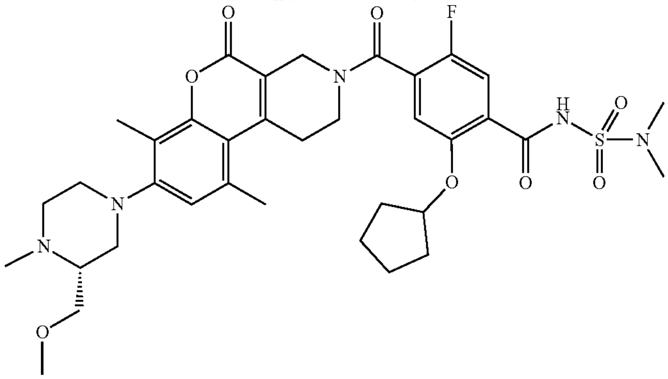 Synthesised from Intermediates 164 and 6 | UPLC: (System 3, Method K) Rt = 4.13 min, m/z 728.5 $(M + H)^+$ $(ES^+)$. $^1$H NMR (400 MHz, DMSO-$d_6$) δ: 7.47-7.44 (m, 1H), 7.26-7.15 (m, 1H), 6.86-6.84 (m, 1H), 4.98-4.92 (m, 1H), 4.52-4.52 (m, 1H), 4.19 (s, 1H), 3.87 (t, J = 5.3 Hz, 1H), 3.57-3.54 (m, 1H), 3.47-3.47 (m, 2H), 3.25 (s, 3H), 3.15-3.03 (m, 3H), 2.86-2.80 (m, 8H), 2.69-2.61 (m, 6H), 2.33 (s, 3H), 2.27-2.20 (m, 3H), 1.91-1.70 (m, 7H), 1.58-1.57 (m, 2H). One exchangeable proton not observed. Mixture of rotamers. |

-continued

| Example No. | Name/Structure/Intermediates | LCMS/$^1$H NMR data |
|---|---|---|
| Example 111 | (R)-2-(cyclopentyloxy)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 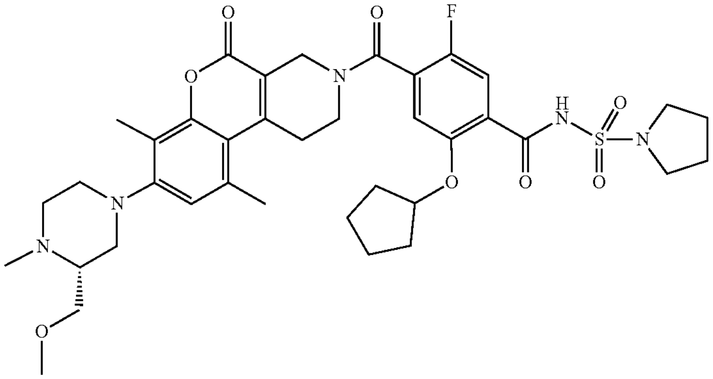 [SMILES: COC[C@H]1CN(c2cc(C)c3c4c(c(=O)oc3c2C)CN(C(=O)c2cc(OC3CCCC3)c(C(=O)NS(=O)(=O)N3CCCC3)cc2F)CC4)CCN1C] Synthesised from Intermediates 165 and 6 | UPLC: (System 3, Method K) Rt = 4.51 min, m/z 754.5 $(M + H)^+$ $(ES^+)$. $^1$H NMR (400 MHz, DMSO-$d_6$) δ: 7.44-7.44 (m, 1H), 7.24-7.13 (m, 1H), 6.86-6.84 (m, 1H), 4.97-4.91 (m, 1H), 4.52-4.52 (m, 1H), 4.19 (br s, 1H), 3.87 (t, J = 5.7 Hz, 1H), 3.57-3.53 (m, 1H), 3.49-3.46 (m, 1H), 3.40-3.39 (m, 4H), 3.26 (s, 3H), 3.14-3.01 (m, 3H), 2.84-2.79 (m, 2H), 2.69-2.59 (m, 6H), 2.42-2.40 (m, 2H), 2.29 (s, 3H), 2.24-2.21 (m, 3H), 1.91-1.67 (m, 10H), 1.58-1.57 (m, 2H). One exchangeable proton not observed. Mixture of rotamers. |
| Example 112 | 2-(3-azabicyclo[3.1.0]hexan-3-yl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide 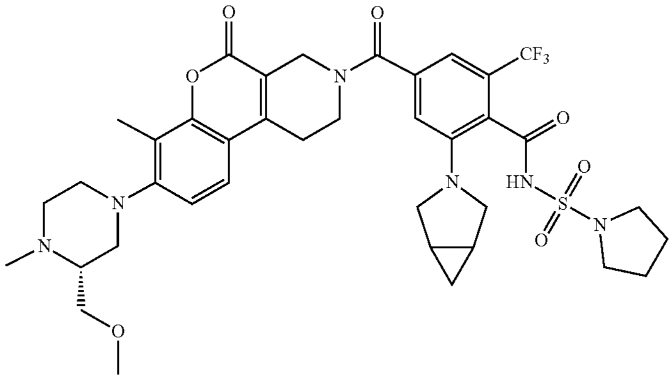 [SMILES: COC[C@H]1CN(c2ccc3c4c(c(=O)oc3c2C)CN(C(=O)c2cc(N3CC5CC5C3)c(C(=O)NS(=O)(=O)N3CCCC3)c(C(F)(F)F)c2)CC4)CCN1C] Synthesised from Intermediates 98 and 5 | HPLC: (System 1, Method D) Rt = 7.49 min, m/z 787.3 $(M + H)^+$ $(ES^+)$. $^1$H NMR (400 MHz, DMSO-$d_6$) δ: 11.84 (br s, 1H), 7.59-7.54 (m, 1H), 7.14-7.07 (m, 3H), 4.48 (br s, 1H), 4.28 (br s, 1H), 3.92 (br s, 1H), 3.58-3.55 (m, 4H), 3.39-3.33 (m, 6H), 3.30 (br s, 2H), 3.27 (s, 3H), 3.17-3.14 (m, 1H), 3.07-3.04 (m, 1H), 2.95 (br s, 2H), 2.88-2.83 (m, 2H), 2.67-2.62 (m, 1H), 2.50 (br s, 1H), 2.34 (s, 3H), 2.29-2.26 (m, 3H), 1.87-1.84 (m, 4H), 1.61 (br s, 2H), 0.62-0.60 (m, 1H), 0.40 (br s, 1H). |
| Example 113 | 2-(bicyclo[3.1.0]hexan-3-yloxy)-N-(N,N-dimethylsulfamoyl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide. Mixture of diastereomers cis/trans 76/24. 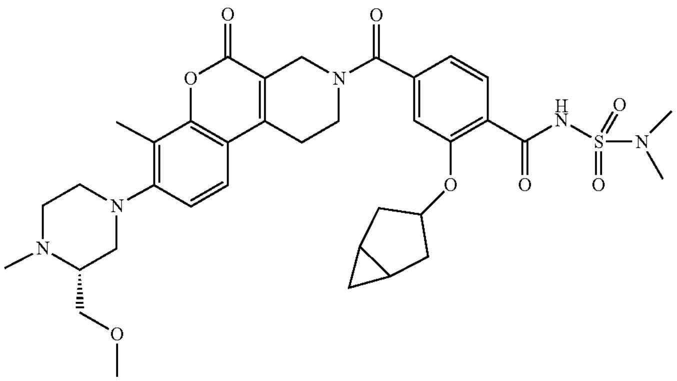 Synthesised from Intermediates 38 and 5 | HPLC: (System 1, Method D) Rt = 7.55 min, m/z 708.4 $(M + H)^+$ $(ES^+)$. $^1$H NMR (400 MHz, DMSO-$d_6$) δ: 11.32 (br s, 1H), 7.59-7.48 (m, 2H), 7.22-7.02 (m, 3H), 5.01-4.66 (m, 1H), 4.49-4.27 (m, 2H), 3.93 (br s, 1H), 3.58-3.54 (m, 2H), 3.37 (br s, 1H), 3.26 (s, 3H), 3.16-3.14 (m, 1H), 3.06-3.03 (m, 1H), 2.96 (br s, 2H), 2.90-2.88 (m, 6H), 2.85-2.82 (m, 2H), 2.66-2.60 (m, 1H), 2.47-2.42 (m, 2H), 2.32 (s, 3H), 2.29-2.25 (m, 5H), 1.95-1.89 (m, 2H), 1.34 (br s, 2H), 0.55-0.17 (m, 2H). Mixture of diastereomers and rotamers. |

-continued

| Example No. | Name/Structure/Intermediates | LCMS/$^1$H NMR data |
|---|---|---|
| Example 114 | 2-(bicyclo[3.1.0]hexan-3-yloxy)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide. Mixture of diastereomers cis/trans 85/15. 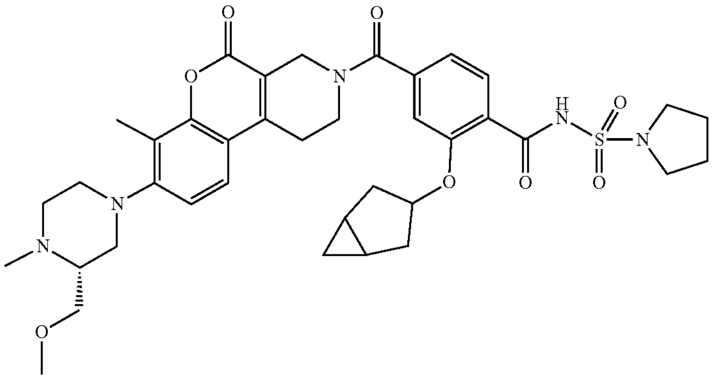 [SMILES: COC[C@H]1CN(c2ccc3c4c(c(=O)oc3c2C)CN(C(=O)c2ccc(C(=O)NS(=O)(=O)N3CCCC3)c(OC3CC5CC5C3)c2)CC4)CCN1C] Synthesised from Intermediates 39 and 5 | HPLC: (System 1, Method D) Rt = 8.45 min, m/z 734.4 $(M + H)^+$ $(ES^+)$. $^1$H NMR (400 MHz, DMSO-$d_6$) δ: 11.40 (br s, 1H), 7.57-7.47 (m, 2H), 7.23-7.00 (m, 3H), 5.00-4.69 (m, 1H), 4.49-4.27 (m, 2H), 3.93 (br s, 1H), 3.57-3.54 (m, 2H), 3.45-3.43 (m, 4H), 3.36 (br s, 1H), 3.26 (s, 3H), 3.16-3.13 (m, 1H), 3.05-3.03 (m, 1H), 2.96 (br s, 2H), 2.86-2.81 (m, 2H), 2.64-2.59 (m, 1H), 2.43-2.38 (m, 2H), 2.33-2.25 (m, 8H), 1.93-1.86 (m, 6H), 1.33 (br s, 2H), 0.50-0.16 (m, 2H). Mixture of diastereomers and rotamers. |
| Example 115 | 2-(2-azabicyclo[2.2.1]heptan-2-yl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 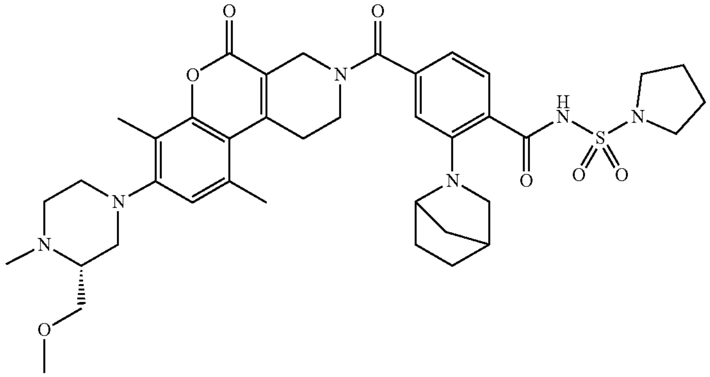 [SMILES: COC[C@H]1CN(c2cc(C)c3c4c(c(=O)oc3c2C)CN(C(=O)c2ccc(C(=O)NS(=O)(=O)N3CCCC3)c(N3CC5CCC3C5)c2)CC4)CCN1C] Synthesised from Intermediates 67 and 6 | HPLC: (System 1, Method D) Rt = 7.59 min, m/z 747.4 $(M + H)^+$ $(ES^+)$. $^1$H NMR (400 MHz, DMSO-$d_6$) δ: 11.77 (br s, 1H), 7.32-7.31 (m, 1H), 6.84 (s, 1H), 6.81-6.68 (m, 2H), 4.48-4.40 (m, 1H), 4.30-4.19 (m, 2H), 3.82 (br s, 1H), 3.57-3.53 (m, 3H), 3.46-3.44 (m, 2H), 3.39-3.37 (m, 2H), 3.31 (br s, 1H), 3.26 (s, 3H), 3.20 (br s, 2H), 3.14-3.11 (m, 1H), 3.04-3.01 (m, 1H), 2.84-2.78 (m, 2H), 2.68-2.59 (m, 4H), 2.54 (br s, 1H), 2.41-2.39 (m, 3H), 2.29 (s, 3H), 2.23-2.19 (m, 3H), 1.89-1.80 (m, 4H), 1.71-1.66 (m, 4H), 1.50-1.48 (m, 1H), 1.23 (br s, 1H). Mixture of rotamers. |
| Example 116 | 2-(2-azabicyclo[2.2.1]heptan-2-yl)-N-(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 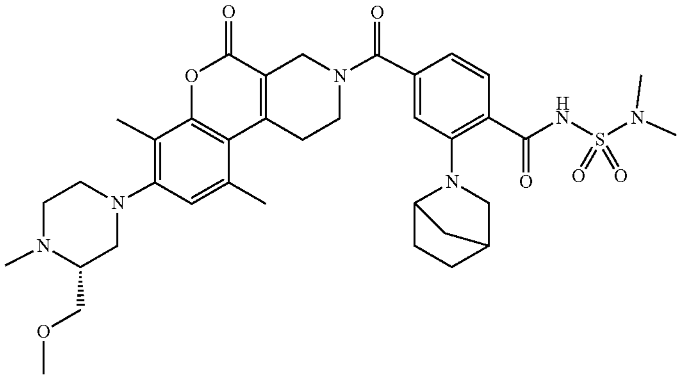 Synthesised from Intermediates 68 and 6 | HPLC: (System 1, Method D) Rt = 7.03 min, m/z 721.4 $(M + H)^+$ $(ES^+)$. $^1$H NMR (400 MHz, DMSO-$d_6$) δ: 11.74 (br s, 1H), 7.33-7.32 (d, J = 7.2 Hz, 1H), 6.85 (s, 1H), 6.81-6.68 (m, 2H), 4.52-4.45 (m, 1H), 4.30-4.19 (m, 2H), 3.82 (br s, 1H), 3.57-3.49 (m, 3H), 3.36 (br s, 1H), 3.26 (s, 3H), 3.21 (br s, 2H), 3.15-3.12 (m, 1H), 3.04-3.02 (m, 1H), 2.87 (s, 6H), 2.84-2.79 (m, 2H), 2.69-2.60 (m, 4H), 2.56 (br s, 1H), 2.45-2.40 (m, 3H), 2.31 (s, 3H), 2.23-2.19 (m, 3H), 1.71-1.64 (m, 4H), 1.50-1.48 (m, 1H), 1.23 (br s, 1H). Mixture of rotamers. |

-continued

| Example No. | Name/Structure/Intermediates | LCMS/$^1$H NMR data |
|---|---|---|
| Example 117 | (R)-2-(cyclopentyloxy)-N-(N,N-dimethylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-6-(trifluoromethyl)benzamide 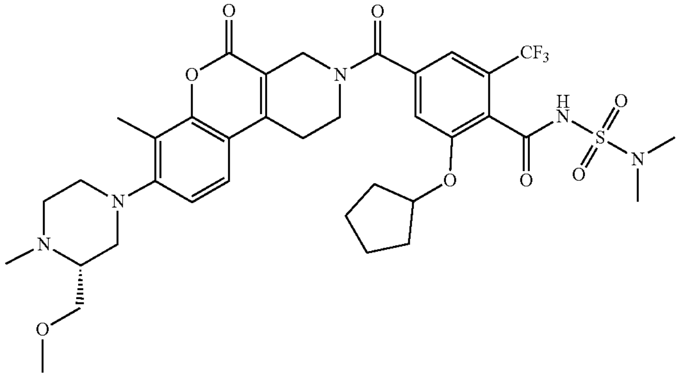 Synthesised from Intermediates 45 and 5 | HPLC: (System 1, Method D) Rt = 7.10 min, m/z 764.0 $(M + H)^+$ $(ES)^+$. $^1$H NMR (400 MHz, DMSO-$d_6$) δ: 11.81 (br s, 1H), 7.60-7.53 (m, 1H), 7.50 (br s, 1H), 7.37-7.36 (m, 1H), 7.09-7.07 (m, 1H), 5.04 (br s, 1H), 4.51 (br s, 1H), 4.28 (br s, 1H), 3.94 (br s, 1H), 3.58-3.55 (m, 2H), 3.38 (br s, 1H), 3.27 (s, 3H), 3.17-3.14 (m, 1H), 3.07-3.04 (m, 1H), 2.98 (br s, 2H), 2.85-2.80 (m, 8H), 2.65 (t, J = 10.6 Hz, 1H), 2.50 (br s, 2H), 2.34 (s, 3H), 2.30-2.25 (m, 3H), 1.88-1.87 (m, 2H), 1.77-1.74 (m, 4H), 1.57 (br s, 2H). |
| Example 118 | 2-(3-azabicyclo[3.1.0]hexan-3-yl)-N-(N,N-dimethylsulfamoyl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-6-(trifluoromethyl)benzamide 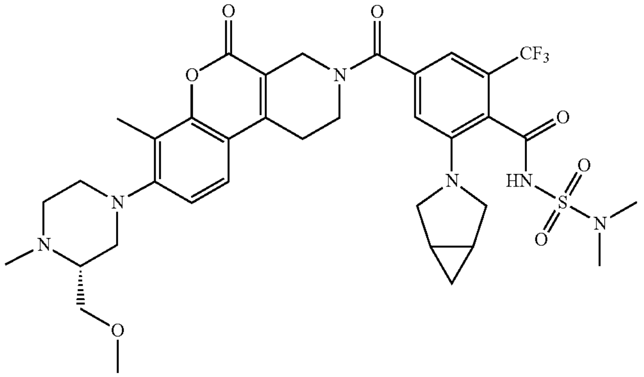 Synthesised from Intermediates 99 and 5 | HPLC: (System 1, Method D) Rt = 7.21 min, m/z 761.3 $(M + H)^+$ $(ES)^+$. $^1$H NMR (400 MHz, DMSO-$d_6$) δ: 11.76 (br s, 1H), 7.56-7.54 (m, 1H), 7.12-7.07 (m, 3H), 4.48 (br s, 1H), 4.29 (br s, 1H), 3.92 (br s, 1H), 3.60-3.55 (m, 4H), 3.40 (br s, 1H), 3.34-3.29 (m, 2H), 3.28 (s, 3H), 3.19-3.16 (m, 1H), 3.09-3.06 (m, 1H), 2.95-2.90 (m, 3H), 2.87-2.82 (m, 7H), 2.68-2.66 (m, 1H), 2.58-2.55 (m, 2H), 2.33 (s, 3H), 2.30-2.26 (m, 3H), 1.61-1.60 (m, 2H), 0.62-0.57 (m, 1H), 0.39-0.38 (m, 1H). Mixture of rotamers. |
| Example 119 | (R)-N-(N,N-dimethylsulfamoyl)-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-6-(pyrrolidin-1-yl)benzamide 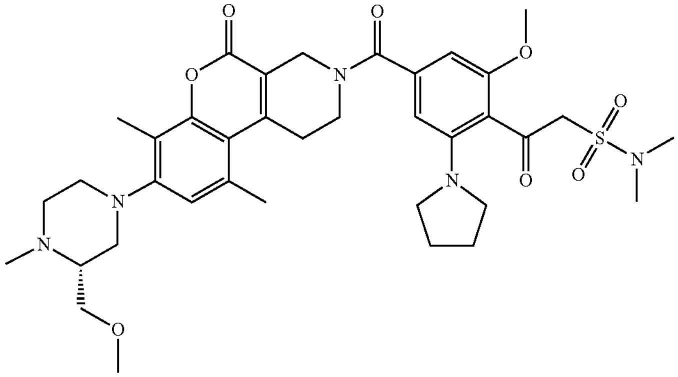 Synthesised from Intermediates 95 and 6 | HPLC: (System 1, Method D) Rt = 7.14 min, m/z 725.3 $(M + H)^+$ $(ES)^+$. $^1$H NMR (400 MHz, DMSO-$d_6$) δ: 11.75 (br s, 1H), 6.84 (s, 1H), 6.44-6.40 (m, 1H), 6.35-6.33 (m, 1H), 4.56-4.32 (m, 2H), 3.79-3.76 (m, 4H), 3.57-3.53 (m, 2H), 3.33-3.26 (m, 8H), 3.19 (br s, 2H), 3.14-3.11 (m, 1H), 3.03-3.01 (m, 1H), 2.89 (s, 6H), 2.83-2.78 (m, 2H), 2.68-2.58 (m, 4H), 2.41-2.38 (m, 2H), 2.29 (s, 3H), 2.23-2.20 (m, 3H), 1.88 (br s, 4H). Mixture of rotamers. |

-continued

| Example No. | Name/Structure/Intermediates | LCMS/$^1$H NMR data |
|---|---|---|
| Example 120 | (R)-N-(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(5-azaspiro[2.5]octan-5-yl)benzamide 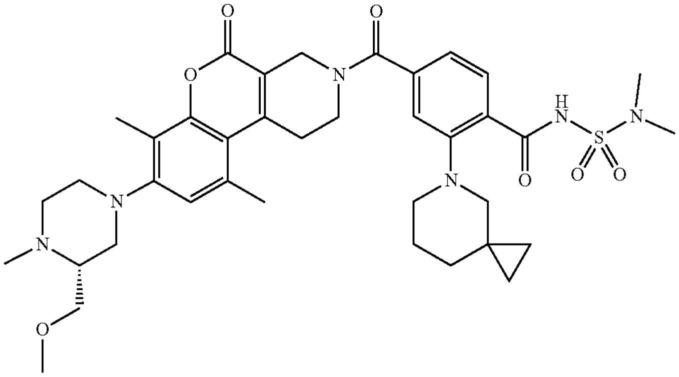 Synthesised from Intermediates 69 and 6 | HPLC: (System 1, Method D) Rt = 9.56 min, m/z 735.4 $(M + H)^+$ $(ES)^+$. $^1$H NMR (400 MHz, DMSO-$d_6$) δ: 14.82 (br s, 1H), 8.10-8.08 (m, 1H), 7.72-7.65 (m, 1H), 7.50-7.43 (m, 1H), 6.85 (s, 1H), 4.49-4.26 (m, 2H), 3.84 (br s, 1H), 3.57-3.53 (m, 1H), 3.48 (br s, 1H), 3.31 (br s, 1H), 3.26 (s, 3H), 3.20 (br s, 2H), 3.14-3.11 (m, 1H), 3.08-3.02 (m, 3H), 2.90 (br s, 7H), 2.86-2.78 (m, 3H), 2.68-2.58 (m, 4H), 2.39 (br s, 2H), 2.29 (s, 3H), 2.23-2.19 (m, 3H), 1.87 (br s, 2H), 1.44 (br s, 2H), 0.48 (br s, 2H), 0.40 (br s, 2H). Mixture of rotamers. |
| Example 121 | (R)-2-(7-azabicyclo[2.2.1]heptan-7-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 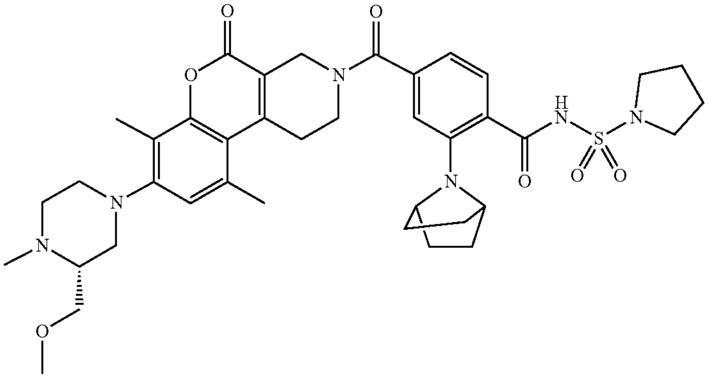 [SMILES: COC[C@H]1CN(c2cc(C)c3c4c(c(=O)oc3c2C)CN(C(=O)c2ccc(C(=O)NS(=O)(=O)N3CCCC3)c(N3C5CCC3CC5)c2)CC4)CCN1C] Synthesised from Intermediates 6 and 123 | HPLC: (System 1, Method D) Rt = 8.17 min, m/z 747.4 $(M + H)^+$ $(ES)^+$. $^1$H NMR (400 MHz, DMSO-$d_6$) δ: 11.66 (br s, 1H), 7.41 (d, J = 8.0 Hz, 1H), 7.07-7.03 (m, 1H), 6.98-6.94 (m, 1H), 6.84 (s, 1H), 4.47 (br s, 1H), 4.27 (br s, 1H), 4.11-4.07 (m, 2H), 3.84 (br s, 1H), 3.57-3.53 (m, 1H), 3.47 (br s, 1H), 3.44-3.41 (m, 4H), 3.31 (br s, 1H), 3.26 (s, 3H), 3.20 (br s, 2H), 3.14-3.11 (m, 1H), 3.04-3.01 (m, 1H), 2.84-2.79 (m, 2H), 2.68-2.59 (m, 4H), 2.42-2.40 (m, 2H), 2.30 (s, 3H), 2.23-2.19 (m, 3H), 1.86-1.83 (m, 4H), 1.73 (br s, 4H), 1.44 (br s, 4H). |
| Example 122 | 4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-2-((S)-2-methylpyrrolidin-1-yl)-N-(pyrrolidin-1-ylsulfonyl)benzamide 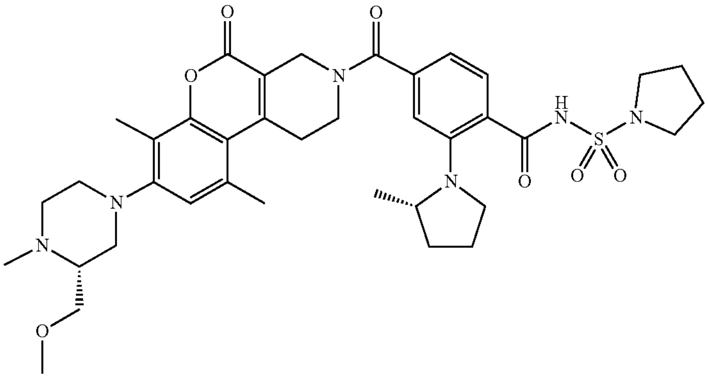 [SMILES: COC[C@H]1CN(c2cc(C)c3c4c(c(=O)oc3c2C)CN(C(=O)c2ccc(C(=O)NS(=O)(=O)N3CCCC3)c(N3CCC[C@@H]3C)c2)CC4)CCN1C] Synthesised from Intermediates 6 and 124 | HPLC: (System 1, Method D) Rt = 8.62 min, m/z 735.4 $(M + H)^+$ $(ES)^+$. $^1$H NMR (400 MHz, DMSO-$d_6$) δ: 12.59 (br s, 1H), 7.52 (br s, 1H), 7.07-6.89 (m, 2H), 6.84 (s, 1H), 4.50-4.30 (m, 2H), 3.90-3.70 (m, 2H), 3.57-3.50 (m, 2H), 3.46-3.39 (m, 5H), 3.33 (br s, 1H), 3.26 (s, 3H), 3.20 (br s, 2H), 3.14-3.11 (m, 1H), 3.04-2.95 (m, 2H), 2.83-2.78 (m, 2H), 2.68-2.59 (m, 4H), 2.41-2.39 (m, 2H), 2.29 (s, 3H), 2.23-2.13 (m, 4H), 1.91-1.74 (m, 6H), 1.60-1.55 (m, 1H), 1.09 (br s, 3H). |

-continued

| Example No. | Name/Structure/Intermediates | LCMS/$^1$H NMR data |
| --- | --- | --- |
| Example 123 | 4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-((R)-2-methylpyrrolidin-1-yl)benzamide 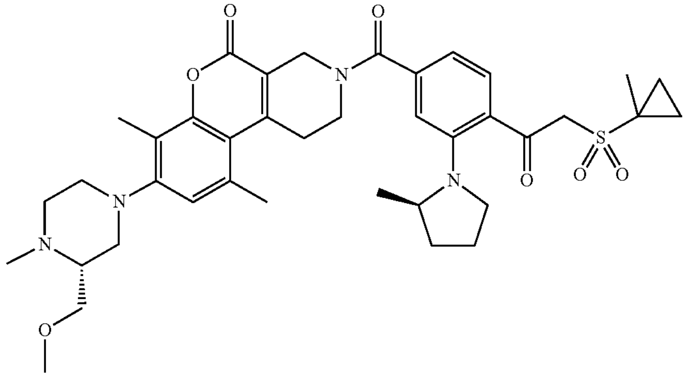 [SMILES: COC[C@H]1CN(c2cc(C)c3c4c(c(=O)oc3c2C)CN(C(=O)c2ccc(C(=O)CS(=O)(=O)C3(C)CC3)c(N3CCC[C@H]3C)c2)CC4)CCN1C] Synthesised from Intermediates 6 and 127 | HPLC: (System 1, Method D) Rt = 7.58 min, m/z 720.4 $(M + H)^+$ $(ES)^+$. $^1$H NMR (400 MHz, DMSO-$d_6$) δ: 12.78 (br s, 1H), 7.58-7.52 (m, 1H), 7.11-6.91 (m, 2H), 6.84 (s, 1H), 4.55-4.31 (m, 2H), 3.92-3.70 (m, 2H), 3.57-3.44 (m, 3H), 3.37 (br s, 1H), 3.26 (s, 3H), 3.20 (br s, 2H), 3.15-3.12 (m, 1H), 3.05-2.98 (m, 2H), 2.87-2.79 (m, 2H), 2.68-2.60 (m, 4H), 2.46-2.44 (m, 2H), 2.32 (s, 3H), 2.23-2.19 (m, 4H), 1.92-1.91 (m, 1H), 1.79 (br s, 1H), 1.61-1.56 (m, 1H), 1.54-1.47 (m, 4H), 1.45-1.39 (m, 1H), 1.11 (br s, 3H), 0.97-0.90 (m, 2H). Mixture of rotamers. |
| Example 124 | 4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-2-((R)-2-methylpyrrolidin-1-yl)-N-(pyrrolidin-1-ylsulfonyl)benzamide 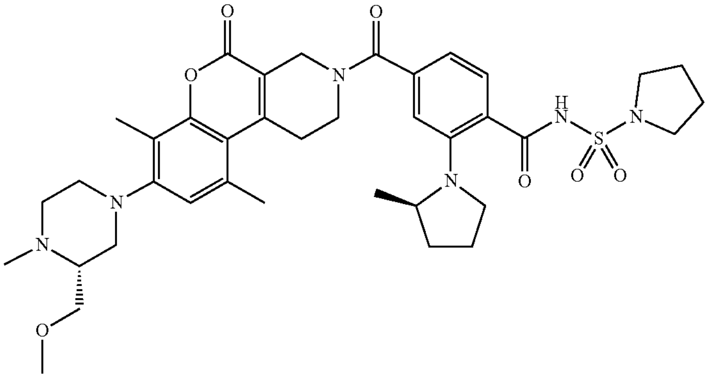 [SMILES: COC[C@H]1CN(c2cc(C)c3c4c(c(=O)oc3c2C)CN(C(=O)c2ccc(C(=O)NS(=O)(=O)N3CCCC3)c(N3CCC[C@H]3C)c2)CC4)CCN1C] Synthesised from Intermediates 6 and 126 | HPLC: (System 1, Method D) Rt = 8.61 min, m/z 735.4 $(M + H)^+$ $(ES)^+$. $^1$H NMR (400 MHz, DMSO-$d_6$) δ: 12.57 (br s, 1H), 7.55-7.50 (m, 1H), 7.07-6.89 (m, 2H), 6.84 (s, 1H), 4.50-4.30 (m, 2H), 3.92-3.69 (m, 2H), 3.57-3.53 (m, 2H), 3.47-3.41 (m, 5H), 3.31 (br s, 1H), 3.26 (s, 3H), 3.20 (br s, 2H), 3.14-3.11 (m, 1H), 3.04-2.95 (m, 2H), 2.84-2.78 (m, 2H), 2.68-2.58 (m, 4H), 2.42-2.40 (m, 2H), 2.29 (s, 3H), 2.23-2.19 (m, 4H), 1.91-1.78 (m, 6H), 1.60-1.55 (m, 1H), 1.09 (br s, 3H). Mixture of rotamers. |
| Example 125 | 4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-((S)-2-methylpyrrolidin-1-yl)benzamide 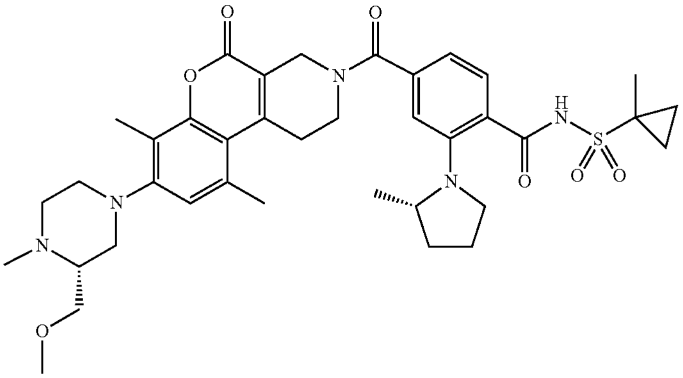 [SMILES: COC[C@H]1CN(c2cc(C)c3c4c(c(=O)oc3c2C)CN(C(=O)c2ccc(C(=O)NS(=O)(=O)C3(C)CC3)c(N3CCC[C@@H]3C)c2)CC4)CCN1C] Synthesised from Intermediates 6 and 125 | HPLC: (System 1, Method D) Rt = 7.54 min, m/z 720.4 $(M + H)^+$ $(ES^+)$. $^1$H NMR (400 MHz, DMSO-$d_6$) δ: 12.79 (br s, 1H), 7.58-7.53 (m, 1H), 7.11-6.92 (m, 2H), 6.85 (s, 1H), 4.50-4.31 (m, 2H), 3.90-3.70 (m, 2H), 3.57-3.44 (m, 3H), 3.37 (br s, 1H), 3.26 (s, 3H), 3.20 (br s, 2H), 3.15-3.12 (m, 1H), 3.05-2.98 (m, 2H), 2.87-2.79 (m, 2H), 2.68-2.60 (m, 4H), 2.46-2.43 (m, 2H), 2.32 (s, 3H), 2.23-2.19 (m, 4H), 1.92-1.91 (m, 1H), 1.79-1.75 (m, 1H), 1.61-1.56 (m, 1H), 1.52-1.46 (m, 4H), 1.43-1.39 (m, 1H), 1.10 (br s, 3H), 0.97-0.90 (m, 2H). Mixture of rotamers. |

-continued

| Example No. | Name/Structure/Intermediates | LCMS/$^1$H NMR data |
|---|---|---|
| Example 126 | 2-(3-azabicyclo[3.1.0]hexan-3-yl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 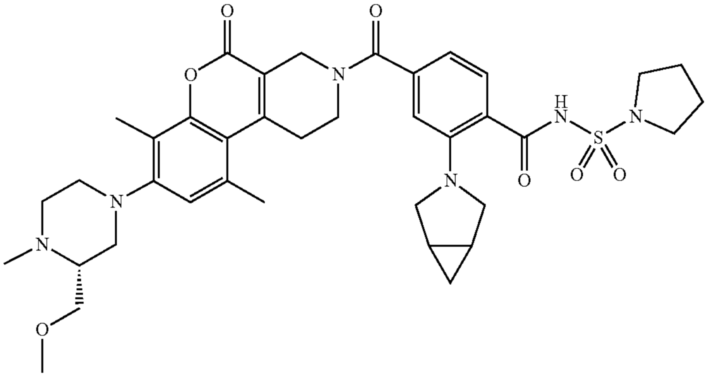 [SMILES: COC[C@H]1CN(c2cc(C)c3c4c(c(=O)oc3c2C)CN(C(=O)c2ccc(C(=O)NS(=O)(=O)N3CCCC3)c(N3CC5CC5C3)c2)CC4)CCN1C] Synthesised from Intermediates 6 and 128 | HPLC: (System 1, Method D) Rt = 7.62 min, m/z 733.4 $(M + H)^+$ $(ES^+)$. 1H NMR (400 MHz, DMSO-$d_6$) δ: 11.83 (br s, 1H), 7.29 (d, J = 8.0 Hz, 1H), 6.85-6.81 (m, 3H), 4.46-4.29 (m, 2H), 3.81 (br s, 1H), 3.57-3.53 (m, 1H), 3.49-3.43 (m, 7H), 3.34 (br s, 1H), 3.26-3.24 (m, 4H), 3.19-3.12 (m, 4H), 3.04-3.02 (m, 1H), 2.84-2.79 (m, 2H), 2.68-2.59 (m, 4H), 2.43-2.41 (m, 2H), 2.30 (s, 3H), 2.23-2.19 (m, 3H), 1.88-1.85 (m, 4H), 1.64 (br s, 2H), 0.64-0.63 (m, 1H), 0.31 (br s, 1H). |
| Example 127 | (R)-2-(cyclopentyloxy)-N-(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-6-(pyrrolidin-1-yl)benzamide 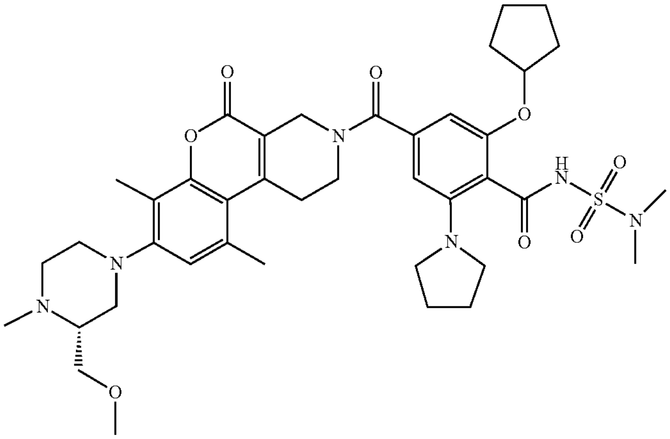 Synthesised from Intermediates 6 and 131 | HPLC: (System 1, Method D) Rt = 8.61 min, m/z 779.0 $(M + H)^+$ $(ES^+)$. $^1$H NMR (400 MHz, DMSO-$d_6$) δ: 11.67 (br s, 1H), 6.84 (s, 1H), 6.41-6.36 (m, 1H), 6.30-6.29 (m, 1H), 4.94-4.82 (m, 1H), 4.45 (br s, 1H), 4.33 (br s, 1H), 3.80 (br s, 1H), 3.57-3.53 (m, 2H), 3.33-3.32 (m, 1H), 3.30-3.23 (m, 7H), 3.20 (br s, 2H), 3.14-3.11 (m, 1H), 3.04-3.01 (m, 1H), 2.88 (s, 6H), 2.83-2.78 (m, 2H), 2.69-2.58 (m, 4H), 2.40-2.38 (m, 2H), 2.28 (s, 3H), 2.23-2.19 (m, 3H), 1.88 (br s, 6H), 1.75-1.72 (m, 4H), 1.54 (br s, 2H). Mixture of rotamers. |
| Example 128 | (R)-2-(cyclopentyloxy)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-6-(trifluoromethyl)benzamide 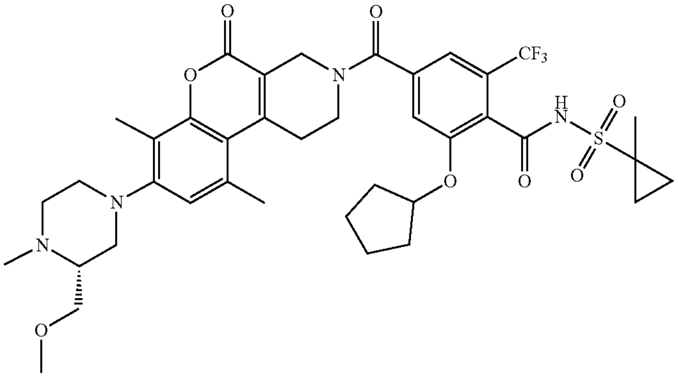 [SMILES: COC[C@H]1CN(c2cc(C)c3c4c(c(=O)oc3c2C)CN(C(=O)c2cc(OC3CCCC3)c(C(=O)NS(=O)(=O)C3(C)CC3)c(C(F)(F)F)c2)CC4)CCN1C] Synthesised from Intermediates 6 and 43 | HPLC: (System 1, Method D) Rt = 7.26 min, m/z 789.3 $(M + H)^+$ $(ES^+)$. $^1$H NMR (400 MHz, DMSO-$d_6$) δ: 11.84 (br s, 1H), 7.52-7.50 (m, 1H), 7.37-7.36 (m, 1H), 6.85 (s, 1H), 5.06-5.05 (m, 1H), 4.50 (br s, 1H), 4.30 (br s, 1H), 3.84 (br s, 1H), 3.58-3.51 (m, 2H), 3.33 (br s, 2H), 3.27 (s, 3H), 3.22 (br s, 2H), 3.17-3.14 (m, 1H), 3.07-3.04 (m, 1H), 2.90-2.81 (m, 2H), 2.69-2.63 (m, 4H), 2.51 (br s, 1H), 2.36 (s, 3H), 2.24-2.20 (m, 3H), 1.88 (br s, 2H), 1.78-1.74 (m, 4H), 1.57 (br s, 2H), 1.50 (s, 3H), 1.42 (br s, 2H), 0.89 (br s, 2H). |

-continued

| Example No. | Name/Structure/Intermediates | LCMS/$^1$H NMR data |
|---|---|---|
| Example 129 | (R)-2-(cyclopentyloxy)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide 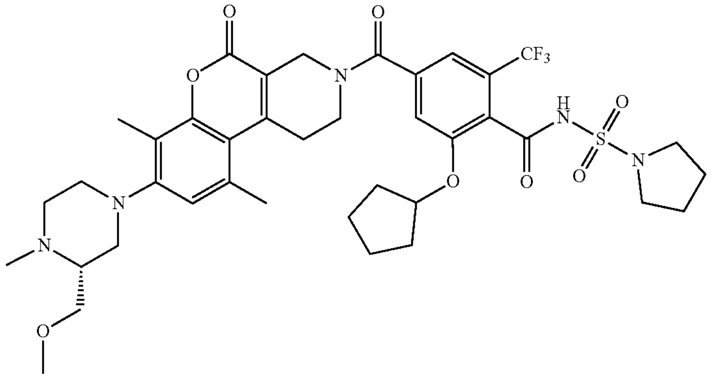 [SMILES: COC[C@H]1CN(c2cc(C)c3c4c(c(=O)oc3c2C)CN(C(=O)c2cc(OC3CCCC3)c(C(=O)NS(=O)(=O)N3CCCC3)c(C(F)(F)F)c2)CC4)CCN1C] Synthesised from Intermediates 6 and 44 | HPLC: (System 1, Method D) Rt = 7.73 min, m/z 804.3 (M + H)$^+$ (ES$^+$). $^1$H NMR (400 MHz, DMSO-d$_6$) δ: 11.86 (br s, 1H), 7.52-7.50 (m, 1H), 7.38-7.36 (m, 1H), 6.85 (s, 1H), 5.07-5.04 (m, 1H), 4.50 (br s, 1H), 4.29 (br s, 1H), 3.84 (br s, 1H), 3.57-3.54 (m, 1H), 3.50 (br s, 1H), 3.41 (br s, 4H), 3.36 (br s, 1H), 3.26 (s, 3H), 3.22 (br s, 2H), 3.15-3.12 (m, 1H), 3.05-3.02 (m, 1H), 2.84-2.79 (m, 2H), 2.69-2.60 (m, 4H), 2.44-2.40 (m, 2H), 2.31 (s, 3H), 2.24-2.20 (m, 3H), 1.87-1.84 (m, 6H), 1.75-1.72 (m, 4H), 1.58 (br s, 2H). Mixture of rotamers. |
| Example 130 | (R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-6-(trifluoromethyl)benzamide 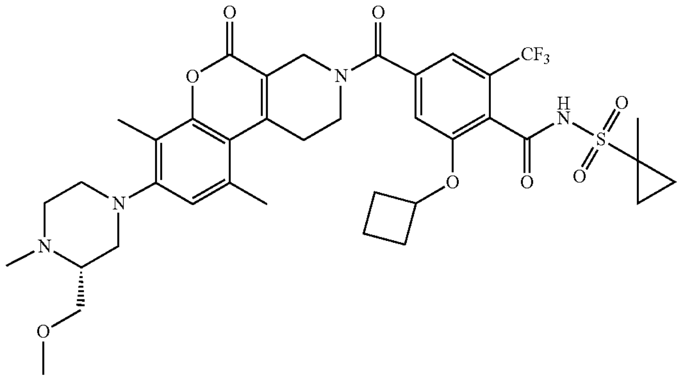 [SMILES: COC[C@H]1CN(c2cc(C)c3c4c(c(=O)oc3c2C)CN(C(=O)c2cc(OC3CCC3)c(C(=O)NS(=O)(=O)C3(C)CC3)c(C(F)(F)F)c2)CC4)CCN1C] Synthesised from Intermediates 6 and 129 | HPLC: (System 1, Method D) Rt = 7.10 min, m/z 775.0 (M + H)$^+$ (ES$^+$). $^1$H NMR (400 MHz, DMSO-d$_6$) δ: 11.80 (br s, 1H), 7.39 (br s, 1H), 7.32 (s, 1H), 6.86 (s, 1H), 4.90-4.89 (m, 1H), 4.50 (br s, 1H), 4.29 (br s, 1H), 3.84 (br s, 1H), 3.57-3.55 (m, 1H), 3.50 (br s, 1H), 3.40-3.38 (m, 1H), 3.28 (s, 3H), 3.21-3.15 (m, 3H), 3.08-3.05 (m, 1H), 2.93-2.91 (m, 1H), 2.87-2.82 (m, 1H), 2.69 (br s, 2H), 2.65-2.56 (m, 4H), 2.44-2.38 (m, 5H), 2.24-2.20 (m, 3H), 2.10-2.05 (m, 2H), 1.81-1.79 (m, 1H), 1.63-1.60 (m, 1H),1.53 (s, 3H), 1.43 (br s, 2H), 0.89 (br s, 2H). |
| Example 131 | (S)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 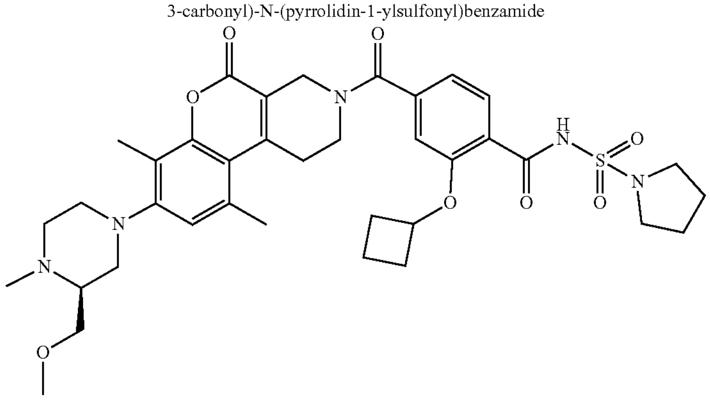 Synthesised from Intermediates 166 and 10 | UPLC (System 3, Method K) Rt = 4.19 min, m/z 722.5 (M + H)$^+$ (ES)$^+$. $^1$H NMR (400 MHz, DMSO-d$_6$) δ: 11.32 (br s, 1H), 7.51 (d, J = 7.8 Hz, 1H), 7.10-7.06 (m, 1H), 6.98-6.95 (m, 1H), 6.80 (s, 1H), 4.84-4.76 (m, 1H), 4.44 (br s, 1H), 4.23 (br s, 1H), 3.79 (br s, 1H), 3.51 (dd, J = 10.1, 4.1 Hz, 1H), 3.45-3.39 (m, 5H), 3.32-3.29 (m, 1H), 3.22 (s, 3H), 3.16 (br s, 2H), 3.10-3.04 (m, 1H), 3.00-2.97 (m, 1H), 2.80-2.75 (m, 2H), 2.64-2.55 (m, 4H), 2.38-2.36 (m, 4H), 2.25 (s, 3H), 2.19-2.15 (m, 3H), 2.07-2.03 (m, 2H), 1.87-1.76 (m, 5H), 1.63-1.58 (m, 1H). |

-continued

| Example No. | Name/Structure/Intermediates | LCMS/$^1$H NMR data |
|---|---|---|
| Example 132 | (R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide 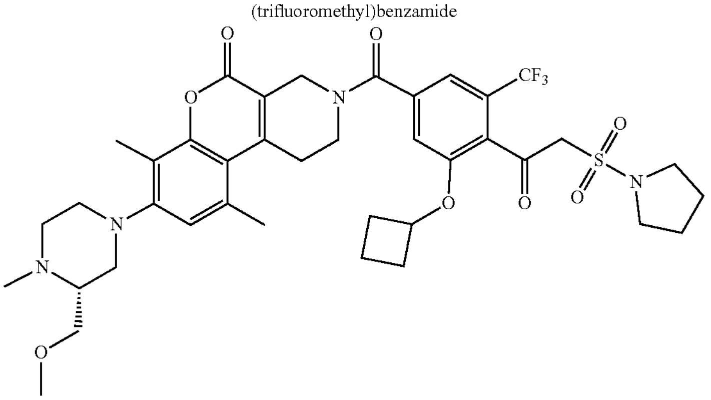 Synthesised from Intermediates 6 and 130 | HPLC: (System 1, Method D) Rt = 7.42 min, m/z 790.0 $(M + H)^+$ $(ES)^+$. $^1$H NMR (400 MHz, DMSO-$d_6$) δ: 11.86 (br s, 1H), 7.41-7.39 (m, 1H), 7.34-7.32 (m, 1H), 6.85 (s, 1H), 4.91-4.87 (m, 1H), 4.50 (br s, 1H), 4.27 (br s, 1H), 3.84 (br s, 1H), 3.58-3.54 (m, 1H), 3.48-3.43 (m, 5H), 3.37 (br s, 1H), 3.26 (s, 3H), 3.21 (br s, 2H), 3.15-3.12 (m, 1H), 3.05-3.03 (m, 1H), 2.87-2.79 (m, 2H), 2.69-2.63 (m, 4H), 2.45 (br s, 4H), 2.32 (s, 3H), 2.24-2.19 (m, 3H), 2.06-2.01 (m, 2H), 1.88-1.80 (m, 5H), 1.65-1.60 (m, 1H). Mixture of rotamers. |
| Example 133 | (R)-2-cyclobutoxy-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide 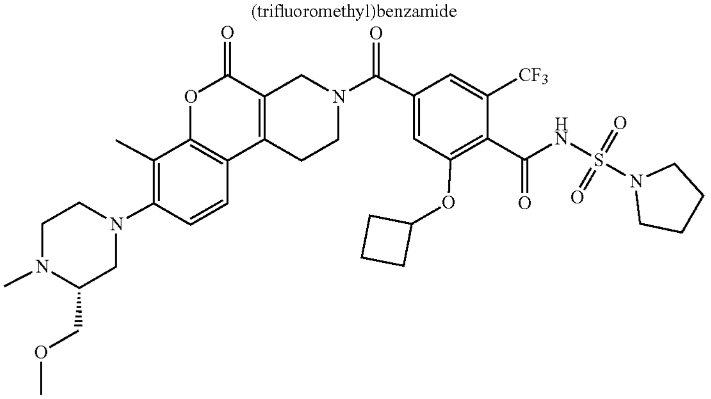 Synthesised from Intermediates 5 and 130 | HPLC: (System 1, Method D) Rt = 7.26 min, m/z 775.9 $(M + H)^+$ $(ES)^+$. $^1$H NMR (400 MHz, DMSO-$d_6$) δ: 11.86 (br s, 1H), 7.58-7.52 (m, 1H), 7.40-7.39 (m, 1H), 7.31 (s, 1H), 7.08 (d, J = 8.8 Hz, 1H), 4.88-4.87 (m, 1H), 4.50 (br s, 1H), 4.26 (br s, 1H), 3.94 (br s, 1H), 3.58-3.54 (m, 2H), 3.44-3.43 (m, 4H), 3.34 (br s, 1H), 3.27 (s, 3H), 3.17-3.14 (m, 1H), 3.06-3.04 (m, 1H), 2.99-2.96 (m, 2H), 2.85-2.82 (m, 2H), 2.66-2.61 (m, 1H), 2.48-2.45 (m, 4H), 2.33 (s, 3H), 2.30-2.25 (m, 3H), 2.05-2.01 (m, 2H), 1.86-1.79 (m, 5H), 1.64-1.61 (m, 1H). Mixture of rotamers. |
| Example 134 | (R)-N-(N,N-dimethylsulfamoyl)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 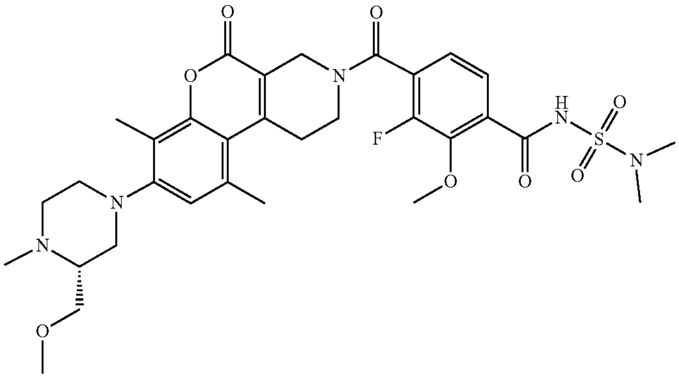 Synthesised from Intermediates 6 and 153 | UPLC: (System 3, Method K) Rt = 3.60 min, m/z 674.80 $(M + H)^+$ $(ES)^+$. $^1$H NMR (400 MHz, DMSO-$d_6$) δ: 7.34-7.32 (m, 1H), 7.23-7.15 (m, 1H), 6.87-6.85 (m, 1H), 4.51 (br s, 1H), 4.19 (br s, 1H), 3.94-3.87 (m, 4H), 3.58-3.56 (m, 1H), 3.49-3.40 (m, 2H), 3.28-3.06 (m, 8H), 2.97-2.94 (m, 1H), 2.88-2.86 (m, 1H), 2.82-2.81 (m, 6H), 2.69-2.62 (m, 6H), 2.41 (br s, 2H), 2.24-2.20 (m, 3H). One exchangeable proton not visible. Mixture of rotamers. |

-continued

| Example No. | Name/Structure/Intermediates | LCMS/$^1$H NMR data |
| --- | --- | --- |
| Example 135 | (R)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 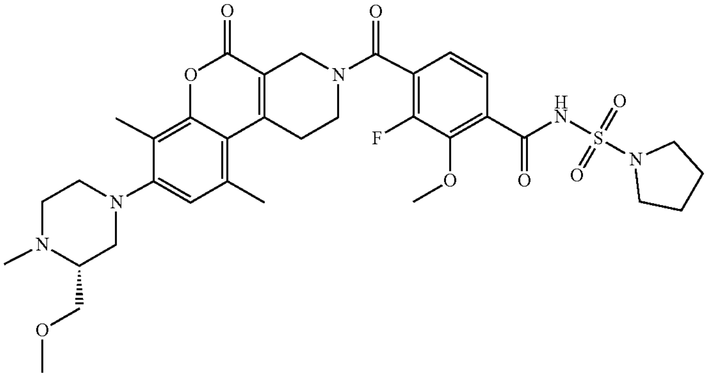 [SMILES: COC[C@H]1CN(c2cc(C)c3c4c(c(=O)oc3c2C)CN(C(=O)c2ccc(C(=O)NS(=O)(=O)N3CCCC3)c(OC)c2F)CC4)CCN1C] Synthesised from Intermediates 6 and 154 | UPLC: (System 3, Method K) Rt = 3.70 min, m/z 700.7 (M + H)$^+$ (ES)$^+$. $^1$H NMR (400 MHz, DMSO-$d_6$) δ: 7.33-7.31 (m, 1H), 7.25-7.17 (m, 1H), 6.86-6.84 (m, 1H), 4.51 (br s, 1H), 4.19 (br s, 1H), 3.94-3.86 (m, 4H), 3.58-3.54 (m, 1H), 3.48-3.34 (m, 10H), 3.23-3.04 (m, 4H), 2.92-2.81 (m, 2H), 2.69-2.62 (m, 5H), 2.36 (br s, 3H), 2.24-2.20 (m, 3H), 1.86-1.82 (m, 4H). One exchangeable proton not visible. Mixture of rotamers. |
| Example 136 | (R)-2-(dimethylamino)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 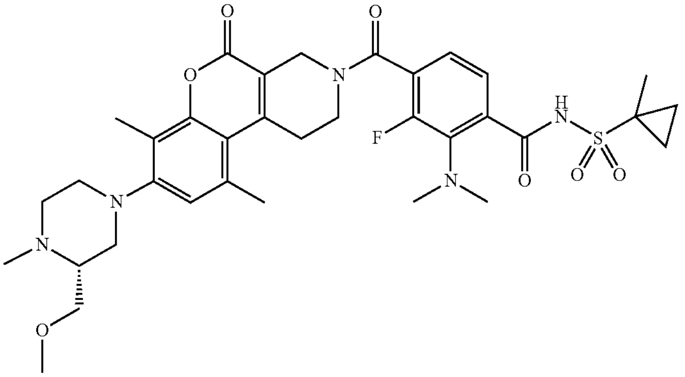 [SMILES: COC[C@H]1CN(c2cc(C)c3c4c(c(=O)oc3c2C)CN(C(=O)c2ccc(C(=O)NS(=O)(=O)C3(C)CC3)c(N(C)C)c2F)CC4)CCN1C] Synthesised from Intermediates 6 and 104 | HPLC: (System 1, Method D) Rt = 6.88 min, m/z 698.4 (M + H)$^+$ (ES)$^+$. $^1$H NMR (400 MHz, DMSO-$d_6$) δ: 12.81 (br s, 1H), 7.52-7.45 (m, 1H), 7.33-7.21 (m, 1H), 6.86-6.84 (m, 1H), 4.55-4.45 (m, 1H), 4.20 (s, 1H), 3.88 (br s, 1H), 3.58-3.54 (m, 1H), 3.48 (br s, 1H), 3.41-3.37 (m, 1H), 3.27 (s, 3H), 3.24 (br s, 1H), 3.17-3.14 (m, 2H), 3.08-3.05 (m, 1H), 2.93-2.90 (m, 1H), 2.86-2.85 (m, 4H), 2.81 (m, 3H), 2.70-2.62 (m, 4H), 2.55 (br s, 2H), 2.37 (s, 3H), 2.24-2.20 (m, 3H), 1.51 (m, 3H), 1.45-1.43 (m, 2H), 0.93-0.91 (m, 2H). Mixture of rotamers. |
| Example 137 | (R)-2-(dimethylamino)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide 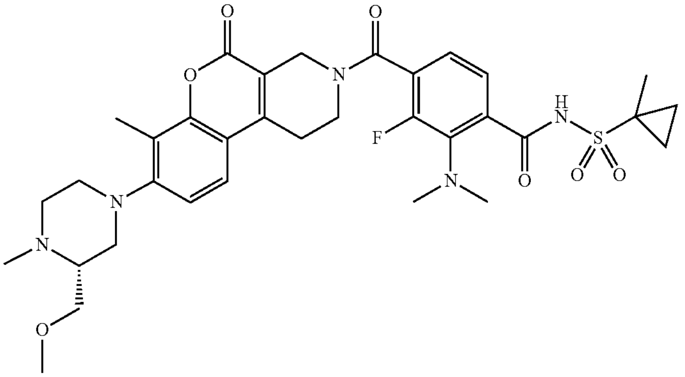 [SMILES: COC[C@H]1CN(c2ccc3c4c(c(=O)oc3c2C)CN(C(=O)c2ccc(C(=O)NS(=O)(=O)C3(C)CC3)c(N(C)C)c2F)CC4)CCN1C] Synthesised from Intermediates 5 and 104 | HPLC: (System 1, Method D) Rt = 6.88 min, m/z 684.4 (M + H)$^+$ (ES)$^+$. $^1$H NMR (400 MHz, DMSO-$d_6$) δ: 12.86 (br s, 1H), 7.60-7.45 (m, 2H), 7.31-7.21 (m, 1H), 7.011-7.06 (m, 1H), 4.54-4.52 (m, 1H), 4.19 (s, 1H), 3.98-3.97 (m, 1H), 3.58-3.55 (m, 2H), 3.41-3.37 (m, 1H), 3.27 (s, 3H), 3.18-3.16 (m, 1H), 3.09-3.00 (m, 2H), 2.91-2.90 (m, 2H), 2.85-2.80 (m, 7H), 2.70-2.65 (m, 1H), 2.55 (br s, 2H), 2.37 (s, 3H), 2.30-2.26 (m, 3H), 1.52-1.51 (m, 3H), 1.46-1.43 (m, 2H), 0.92 (br s, 2H). Mixture of rotamers. |

-continued

| Example No. | Name/Structure/Intermediates | LCMS/$^1$H NMR data |
|---|---|---|
| Example 138 | (R)-2-(dimethylamino)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 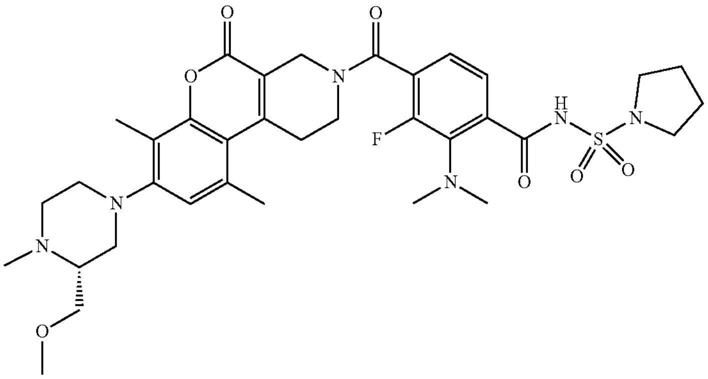 [SMILES: COC[C@H]1CN(c2cc(C)c3c4c(c(=O)oc3c2C)CN(C(=O)c2ccc(C(=O)NS(=O)(=O)N3CCCC3)c(N(C)C)c2F)CC4)CCN1C] Synthesised from Intermediates 6 and 105 | HPLC: (System 1, Method D) Rt = 7.79 min, m/z 713.3 $(M + H)^+$ $(ES)^+$. $^1$H NMR (400 MHz, DMSO-$d_6$) δ: 12.73 (br s, 1H), 7.53-7.46 (m, 1H), 7.36-7.24 (m, 1H), 6.86-6.84 (m, 1H), 4.61-4.42 (m, 1H), 4.19 (s, 1H), 3.87 (br s, 1H), 3.54-3.51 (m, 1H), 3.45-3.42 (m, 5H), 3.37 (br s, 1H), 3.26 (s, 3H), 3.24 (br s, 1H), 3.15-3.12 (m, 2H), 3.05-3.03 (m, 1H), 2.87-2.79 (m, 8H), 2.69-2.61 (m, 4H), 2.46-2.44 (m, 2H), 2.32 (s, 3H), 2.23-2.20 (m, 3H), 1.86-1.85 (m, 4H). Mixture of rotamers. |
| Example 139 | (R)-2-(dimethylamino)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide 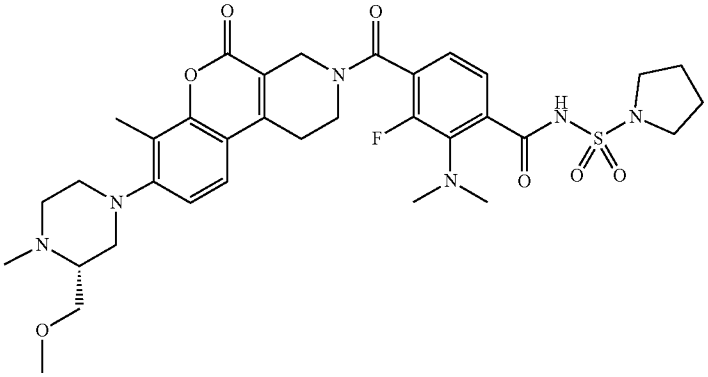 [SMILES: COC[C@H]1CN(c2ccc3c4c(c(=O)oc3c2C)CN(C(=O)c2ccc(C(=O)NS(=O)(=O)N3CCCC3)c(N(C)C)c2F)CC4)CCN1C] Synthesised from Intermediates 5 and 105 | HPLC: (System 1, Method D) Rt = 7.47 min, m/z 699.4 $(M + H)^+$ $(ES)^+$. $^1$H NMR (400 MHz, DMSO-$d_6$) δ: 12.75 (br s, 1H), 7.60-7.45 (m, 2H), 7.33-7.23 (m, 1H), 7.10-7.05 (m, 1H), 4.55-4.52 (m, 1H), 4.19 (s, 1H), 3.97 (br s, 1H), 3.58-3.54 (m, 2H), 3.45-3.42 (m, 4H), 3.37-3.33 (m, 1H), 3.26 (s, 3H), 3.16-3.14 (m, 1H), 3.06-3.00 (m, 2H), 2.90-2.85 (m, 3H), 2.83-2.78 (m, 6H), 2.66-2.61 (m, 1H), 2.47-2.44 (m, 2H), 2.32 (s, 3H), 2.29-2.26 (m, 3H), 1.86-1.84 (m, 4H). Mixture of rotamers. |
| Example 140 | (R)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-5-methyl-N-(pyrrolidin-1-ylsulfonyl) benzamide 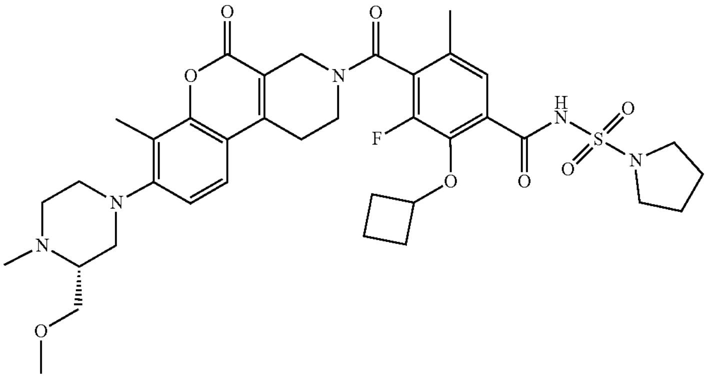 [SMILES: COC[C@H]1CN(c2ccc3c4c(c(=O)oc3c2C)CN(C(=O)c2c(C)cc(C(=O)NS(=O)(=O)N3CCCC3)c(OC3CCC3)c2F)CC4)CCN1C] Synthesised from Intermediates 5 and 132 | HPLC: (System 1, Method D) Rt = 7.43 min, m/z 740.3 $(M + H)^+$ $(ES)^+$. $^1$H NMR (400 MHz, DMSO-$d_6$) δ: 11.51 (br s, 1H), 7.60-7.49 (m, 1H), 7.25-7.22 (m, 1H), 7.11-7.06 (dd, J = 10.8, 8.4 Hz, 1H), 4.66-4.49 (m, 2H), 4.10-3.91 (m, 2H), 3.58-3.55 (m, 1H), 3.53-3.50 (m, 1H), 3.43-3.37 (m, 5H), 3.34 (br s, 1H), 3.27 (s, 3H), 3.17-3.15 (m, 1H), 3.09-3.01 (m, 2H), 2.91-2.83 (m, 3H), 2.68-2.63 (m, 1H), 2.57 (br s, 1H), 2.35 (s, 3H), 2.29-2.26 (m, 3H), 2.24-2.19 (m, 3H), 2.17-2.03 (m, 4H), 1.87-1.84 (m, 4H), 1.69-1.64 (m, 1H), 1.49-1.40 (m, 1H). Mixture of rotamers. |

-continued

| Ex-ample No. | Name/Structure/Intermediates | LCMS/$^1$H NMR data |
|---|---|---|
| Ex-ample 141 | (R)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)-N-(pyrrolidin-1-ylsulfonyl)benzamide 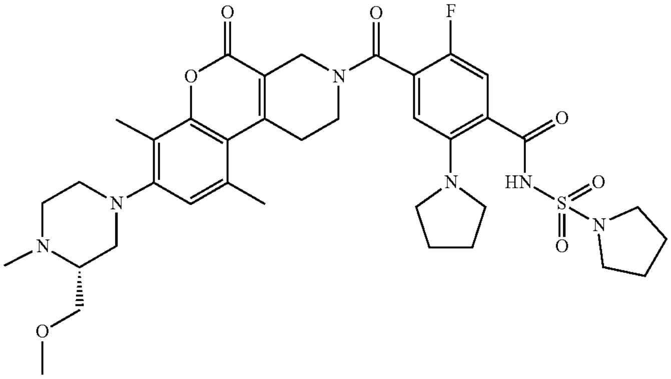 [SMILES: COC[C@H]1CN(c2cc(C)c3c4c(c(=O)oc3c2C)CN(C(=O)c2cc(N3CCCC3)c(C(=O)NS(=O)(=O)N3CCCC3)cc2F)CC4)CCN1C] Synthesised from Intermediates 6 and 137 | HPLC: (System 1, Method D) Rt = 8.01 min, m/z 739.4 (M + H)$^+$ (ES)$^+$. $^1$H NMR (400 MHz, DMSO-d$_6$) δ: 11.91 (br s, 1H), 7.27-7.24 (m, 1H), 6.86-6.84 (m, 1H), 6.80-6.71 (m, 1H), 4.49 (br s, 1H), 4.20 (s, 1H), 3.86 (br s, 1H), 3.57-3.54 (m, 1H), 3.47-3.46 (m, 1H), 3.43-3.40 (m, 4H), 3.37 (br s, 1H), 3.26 (s, 3H), 3.22 (br s, 1H), 3.17-3.13 (m, 6H), 3.05-3.02 (m, 1H), 2.87-2.79 (m, 2H), 2.69-2.61 (m, 4H), 2.46-2.44 (m, 2H), 2.32 (s, 3H), 2.23-2.19 (m, 3H), 1.90-1.83 (m, 8H). Mixture of rotamers. |
| Ex-ample 142 | (R)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-(pyrrolidin-1-yl)benzamide 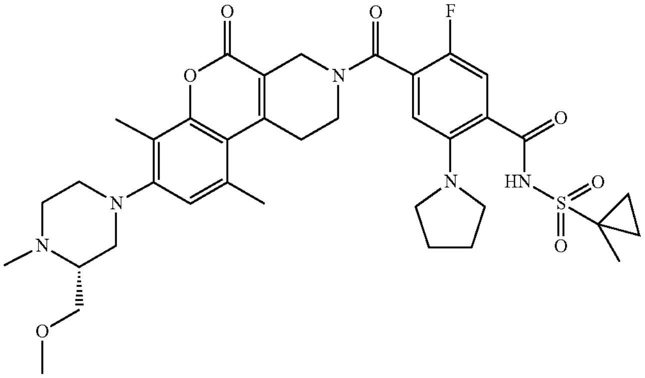 [SMILES: COC[C@H]1CN(c2cc(C)c3c4c(c(=O)oc3c2C)CN(C(=O)c2cc(N3CCCC3)c(C(=O)NS(=O)(=O)C3(C)CC3)cc2F)CC4)CCN1C] Synthesised from Intermediates 6 and 136 | HPLC: (System 1, Method D) Rt = 6.91 min, m/z 724.5 (M + H)$^+$ (ES$^+$). $^1$H NMR (400 MHz, DMSO-d$_6$) δ: 11.89 (br s, 1H), 7.26-7.23 (m, 1H), 6.86-6.85 (m, 1H), 6.80-71 (m, 1H), 4.50 (br s, 1H), 4.20 (s, 1H), 3.86 (br s, 1H), 3.58-3.54 (m, 1H), 3.48-3.47 (m, 1H), 3.45-3.41 (m, 1H), 3.28 (s, 3H), 3.23-3.15 (m, 7H), 3.08-3.05 (m, 1H), 2.93-2.81 (m, 2H), 2.69-2.62 (m, 4H), 2.59-2.53 (m, 2H), 2.38 (s, 3H), 2.24-2.20 (m, 3H), 1.90-1.89 (m, 4H), 1.49 (s, 3H), 1.43 (br s, 2H), 0.90-0.88 (m, 2H). Mixture of rotamers. |
| Ex-ample 143 | (R)-2-cyclobutoxy-4-(8-(3-(ethoxymethyl)-4-methylpiperazin-1-yl)-7-methyl-5-oxo-1,3,4,5-tetrahydro-2H-chromeno[3,4-c]pyridine-3-carbonyl)-3-fluoro-N-(pyrrolidin-1-ylsulfonyl)benzamide 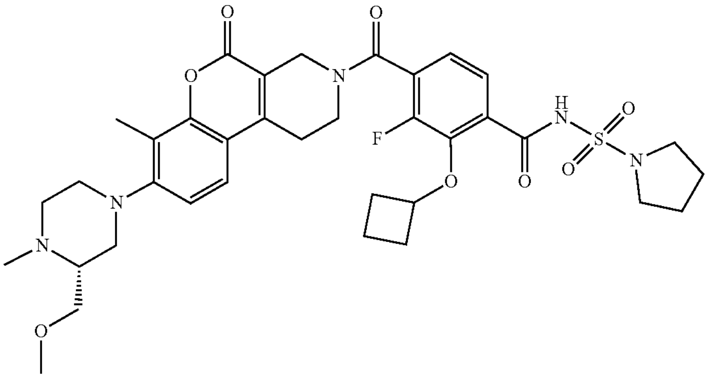 Synthesised from Intermediates 13 and 140 | HPLC: (System 1, Method D) Rt = 8.31 min, m/z 740.0 (M + H)$^+$ (ES$^+$). $^1$H NMR (400 MHz, DMSO-d$_6$) δ: 11.48 (br s, 1H), 7.60-7.51 (m, 1H), 7.35-7.32 (m, 1H), 7.23-7.16 (m, 1H), 7.10-7.06 (m, 1H), 4.73-4.65 (m, 1H), 4.53 (br s, 1H), 4.17 (br s, 1H), 3.99-3.96 (m, 1H), 3.63-3.59 (m, 1H), 3.56-3.53 (m, 1H), 3.50-3.38 (m, 7H), 3.19-3.16 (m, 1H), 3.08-3.05 (m, 1H), 2.99 (br s, 1H), 2.89-2.84 (m, 3H), 3.68-2.63 (m, 1H), 2.52 (br s, 2H), 2.36 (s, 3H), 2.30-2.18 (m, 5H), 2.13-2.07 (m, 2H), 1.88-1.84 (m, 4H), 1.71-1.68 (m, 1H), 1.50-1.41 (m, 1H), 1.13-1.09 (m, 3H). Mixture of rotamers. |

-continued

| Example No. | Name/Structure/Intermediates | LCMS/$^1$H NMR data |
|---|---|---|
| Example 144 | (R)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 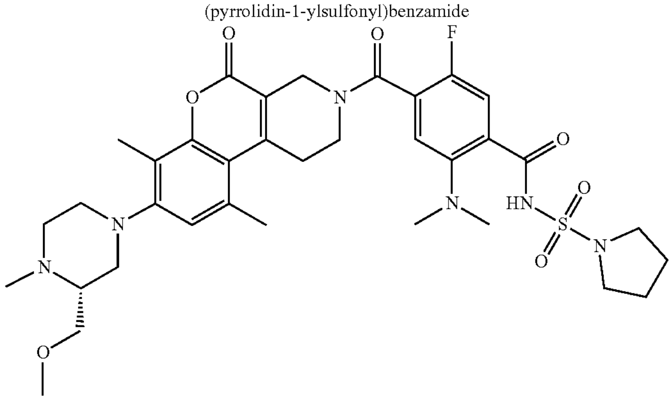 Synthesised from Intermediates 6 and 134 | HPLC: (System 1, Method D) Rt = 7.66 min, m/z 713.4 $(M + H)^+$ $(ES^+)$. $^1$H NMR (400 MHz, DMSO-$d_6$) δ: 13.00 (br s, 1H), 7.56-7.50 (m, 1H), 7.46-7.31 (m, 1H), 6.86-6.84 (m, 1H), 4.52 (br s, 1H), 4.20 (s, 1H), 3.87 (br s, 1H), 3.57-3.54 (m, 1H), 3.48-3.41 (m, 5H), 3.36 (br s, 1H), 3.26 (s, 3H), 3.23 (br s, 1H), 3.15-3.12 (m, 2H), 3.05-3.02 (m, 1H), 2.86-2.82 (m, 2H), 2.78-7.75 (m, 6H), 2.69-2.61 (m, 4H), 2.45-2.43 (m, 2H), 2.31 (s, 3H), 2.23-2.19 (m, 3H), 1.86-1.83 (m, 4H). Mixture of rotamers. |
| Example 145 | (R)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 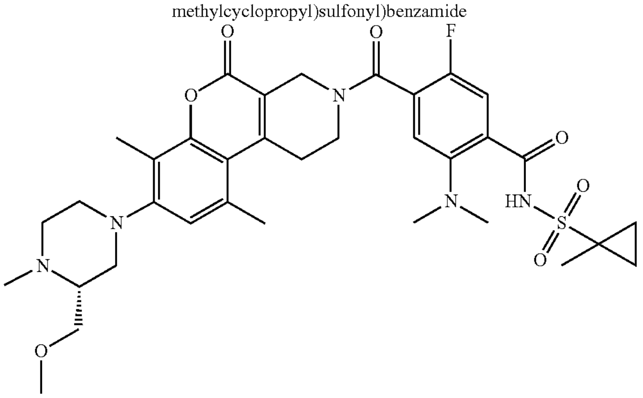 Synthesised from Intermediates 6 and 135 | HPLC: (System 1, Method D) Rt = 6.88 min, m/z 698.4 $(M + H)^+$ $(ES^+)$. $^1$H NMR (400 MHz, DMSO-$d_6$) δ: 13.33 (br s, 1H), 7.55-7.33 (m, 2H), 6.86-6.85 (m, 1H), 4.52 (br s, 1H), 4.20 (s, 1H), 3.88 (br s, 1H), 3.58-3.54 (m, 1H), 3.49-3.46 (m, 1H), 3.40-3.36 (m, 1H), 3.27 (s, 3H), 3.23 (br s, 1H), 3.16-3.14 (m, 2H), 3.07-3.04 (m, 1H), 2.91-2.83 (m, 2H), 2.80 (d, J = 13.2 Hz, 6H), 2.69-2.62 (m, 4H), 2.51 (br s, 1H), 2.49 (br s, 1H), 2.36 (s, 3H), 2.24-2.20 (m, 3H), 1.50 (s, 3H), 1.45-1.42 (m, 2H), 0.91-0.89 (m, 2H). Mixture of rotamers. |
| Example 146 | (R)-N-(N,N-dimethylsulfamoyl)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 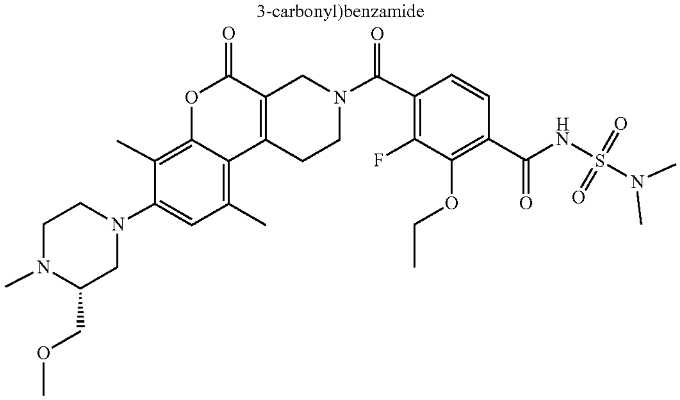 Synthesised from Intermediates 6 and 160 | UPLC: (System 3, Method K) Rt = 3.73 min, m/z 688.5 $(M + H)^+$ $(ES^+)$. $^1$H NMR (400 MHz, ACN-$d_3$) δ: 7.78-7.72 (m, 1H), 7.24-7.17 (m, 1H), 6.82-6.80 (m, 1H), 4.55 (s, 1H), 4.41-4.30 (m, 2H), 4.20 (s, 1H), 3.91 (t, J = 5.7 Hz, 1H), 3.58-3.55 (m, 1H), 3.50-3.47 (m, 1H), 3.39-3.33 (m, 1H), 3.29 (s, 3H), 3.23-3.03 (m, 4H), 2.95 (s, 6H), 2.89-2.82 (m, 2H), 2.68-2.61 (m, 4H), 2.48-2.42 (m, 2H), 2.33-2.23 (m, 6H), 1.48-1.41 (m, 3H). One exchangeable proton not visible. Mixture of rotamers. |

-continued

| Example No. | Name/Structure/Intermediates | LCMS/$^1$H NMR data |
|---|---|---|
| Example 147 | (R)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 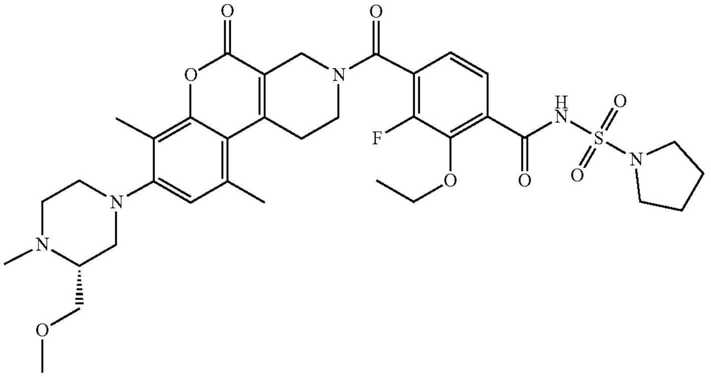 [SMILES: CCOc1c(C(=O)NS(=O)(=O)N2CCCC2)ccc(C(=O)N2CCc3c(c(=O)oc4c(C)c(N5CCN(C)[C@@H](COC)C5)cc(C)c34)C2)c1F] Synthesised from Intermediates 6 and 161 | UPLC: (System 3, Method K) Rt = 3.85 min, m/z 714.8 $(M + H)^+$ $(ES^+)$. $^1$H NMR (400 MHz, ACN-$d_3$) δ: 7.79-7.73 (m, 1H), 7.24-7.17 (m, 1H), 6.82-6.81 (m, 1H), 4.55 (br s, 1H), 4.41-4.32 (m, 2H), 4.20 (br s, 1H), 3.91 (t, J = 5.7 Hz, 1H), 3.58-3.54 (m, 1H), 3.53-3.47 (m, 5H), 3.38-3.34 (m, 1H), 3.29 (s, 3H), 3.24-3.03 (m, 4H), 2.88-2.83 (m, 2H), 2.68-2.61 (m, 4H), 2.47-2.41 (m, 2H), 2.32-2.24 (m, 6H), 1.92-1.88 (m, 4H), 1.48-1.42 (m, 3H). One exchangeable proton not visible. Mixture of rotamers. |
| Example 148 | (R)-N-(N,N-dimethylsulfamoyl)-3-fluoro-2-isopropoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 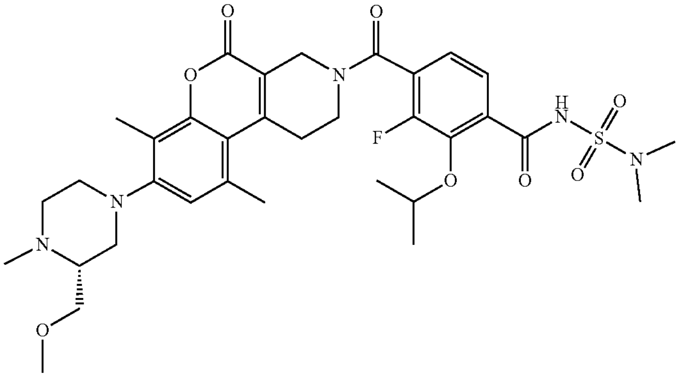 Synthesised from Intermediates 6 and 162 | UPLC: (System 3, Method K) Rt = 3.81 min, m/z 702.5 $(M + H)^+$ $(ES^+)$. $^1$H NMR (400 MHz, ACN-$d_3$) δ: 7.80-7.74 (m, 1H), 7.25-7.18 (m, 1H), 6.82-6.81 (m, 1H), 4.80-4.69 (m, 1H), 4.55 (br s, 1H), 4.20 (br s, 1H), 3.91 (t, J = 4.8 Hz, 1H), 3.58-3.55 (m, 1H), 3.49-3.47 (m, 1H), 3.38-3.33 (m, 1H), 3.29 (s, 3H), 3.22-3.03 (m, 4H), 2.95-2.95 (m, 6H), 2.89-2.83 (m, 2H), 2.68-2.61 (m, 4H), 2.47-2.42 (m, 2H), 2.33-2.24 (m, 6H), 1.41-1.36 (m, 6H). One exchangeable proton not visible. Mixture of rotamers. |
| Example 149 | (R)-3-fluoro-2-isopropoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 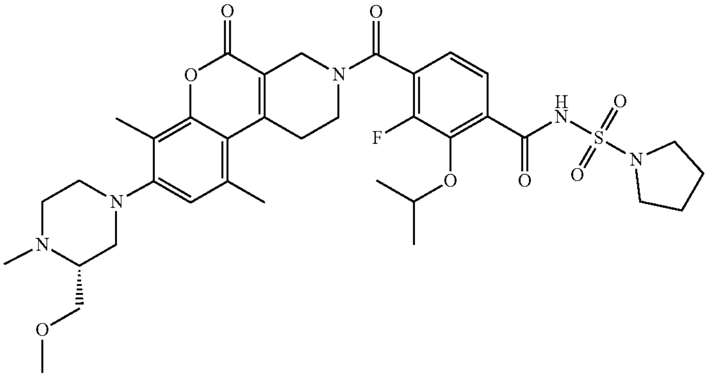 [SMILES: COC[C@H]1CN(c2cc(C)c3c4c(c(=O)oc3c2C)CN(C(=O)c2ccc(C(=O)NS(=O)(=O)N3CCCC3)c(OC(C)C)c2F)CC4)CCN1C] Synthesised from Intermediates 6 and 163 | UPLC: (System 3, Method K) Rt = 3.95 min, m/z 728.5 $(M + H)^+$ $(ES^+)$. $^1$H NMR (400 MHz, ACN-$d_3$) δ: 7.81-7.75 (m, 1H), 7.25-7.18 (m, 1H), 6.81-6.80 (m, 1H), 4.82-4.69 (m, 1H), 4.54 (br s, 1H), 4.19 (br s, 1H), 3.91 (br s, 1H), 3.58-3.47 (m, 6H), 3.38-3.34 (m, 1H), 3.29 (s, 3H), 3.23-3.02 (m, 4H), 2.88-2.82 (m, 2H), 2.67-2.60 (m, 4H), 2.47-2.41 (m, 2H), 2.32-2.23 (m, 6H), 1.92-1.88 (m, 4H), 1.41-1.37 (m, 6H). One exchangeable proton not visible. Mixture of rotamers. |

-continued

| Example No. | Name/Structure/Intermediates | LCMS/$^1$H NMR data |
|---|---|---|
| Example 150 | (R)-5-chloro-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 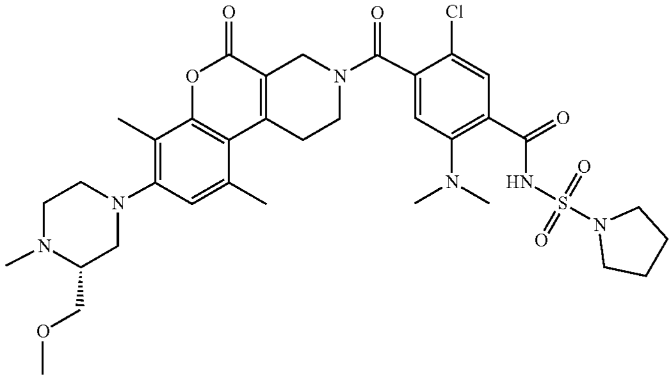 Synthesised from Intermediates 6 and 111 | HPLC: (System 1, Method D) Rt = 7.52 min, m/z 729.4 (M + H)$^+$ (ES)$^+$. $^1$H NMR (400 MHz, DMSO-$d_6$) δ: 12.10 (br s, 1H), 7.52-7.47 (m, 1H), 7.13-7.02 (m, 1H), 6.87-6.84 (m, 1H), 4.66-4.36 (m, 1H), 4.10 (br s, 1H), 3.99-3.74 (m, 1H), 3.57-3.54 (m, 1H), 3.43-3.36 (m, 6H), 3.27 (s, 3H), 3.23-3.12 (m, 3H), 3.05-3.03 (m, 1H), 2.88-2.85 (m, 2H), 2.82-2.80 (m, 6H), 2.70-2.60 (m, 4H), 2.50-2.49 (m, 2H), 2.33 (s, 3H), 2.24-2.20 (m, 3H), 1.85-1.83 (m, 4H). Mixture of rotamers. |
| Example 151 | (R)-5-chloro-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide 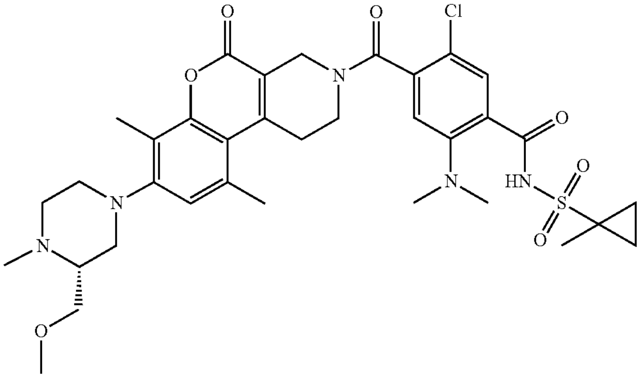 Synthesised from Intermediates 6 and 112 | HPLC: (System 1, Method D) Rt = 6.98 min, m/z 714.3 (M + H)$^+$ (ES)$^+$. $^1$H NMR (400 MHz, DMSO-$d_6$) δ: 12.09 (br s, 1H), 7.50-7.45 (m, 1H), 7.12-7.01 (m, 1H), 6.87-6.85 (m, 1H), 4.66-4.37 (m, 1H), 4.11 (br s, 1H), 4.01-3.73 (m, 1H), 3.58-3.55 (m, 1H), 3.45-3.38 (m, 2H), 3.28 (s, 3H), 3.21-3.05 (m, 4H), 2.99-2.87 (m, 2H), 2.84-2.82 (m, 6H), 2.70-2.55 (m, 6H), 2.39 (s, 3H), 2.24-2.20 (m, 3H), 1.49 (s, 3H), 1.43 (br s, 2H), 0.89 (br s, 2H). Mixture of rotamers. |
| Example 152 | (R)-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-5-(trifluoromethyl)benzamide 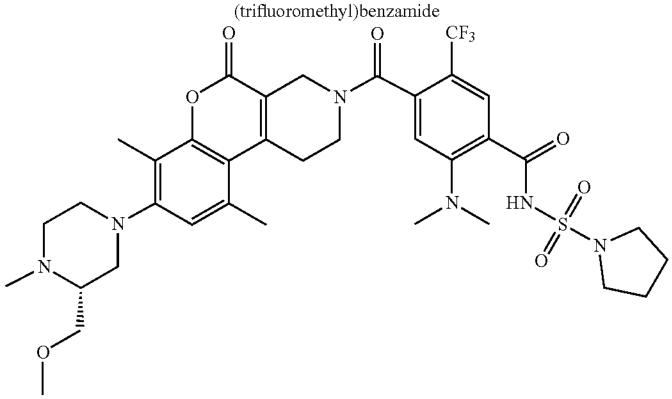 Synthesised from Intermediates 6 and 108 | HPLC: (System 1, Method D) Rt = 7.23 min, m/z 763.4 (M + H)$^+$ (ES)$^+$. $^1$H NMR (400 MHz, DMSO-$d_6$) δ: 11.75 (br s, 1H), 7.60-7.56 (m, 1H), 6.96-6.84 (m, 2H), 4.72-4.13 (m, 2H), 3.98-3.54 (m, 2H), 3.42-3.37 (m, 6H), 3.27 (s, 3H), 3.21-2.98 (m, 4H), 2.94-2.93 (m, 6H), 2.90-2.80 (m, 2H), 2.69-2.60 (m, 4H), 2.51 (br s, 1H), 2.49 (br s, 1H), 2.35 (s, 3H), 2.24-2.19 (m, 3H), 1.86-1.83 (m, 4H). Mixture of rotamers. |

-continued

| Example No. | Name/Structure/Intermediates | LCMS/$^1$H NMR data |
|---|---|---|
| Example 153 | (R)-2-(cyclopentyloxy)-N-(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-6-(trifluoromethyl)benzamide 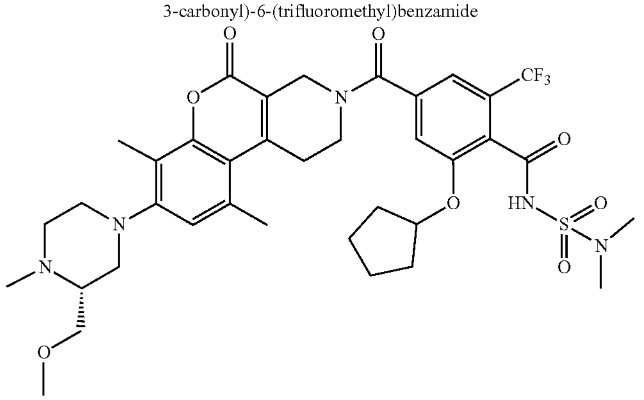 Synthesised from Intermediates 6 and 45 | HPLC: (System 1, Method D) Rt = 7.93 min, m/z 778.0 $(M + H)^+$ $(ES)^+$. $^1$H NMR (400 MHz, DMSO-$d_6$) δ: 11.79 (br s, 1H), 7.51 (d, J = 9.2 Hz, 1H), 7.37 (d, J = 6.8 Hz, 1H), 6.85 (s, 1H), 5.07-5.06 (m, 1H), 4.50 (br s, 1H), 4.30 (br s, 1H), 3.84 (br s, 1H), 3.57-3.54 (m, 1H), 3.50 (br s, 1H), 3.38-3.37 (m, 1H), 3.27 (s, 3H), 3.22 (br s, 2H), 3.16-3.13 (m, 1H), 3.06-3.03 (m, 1H), 2.86-2.81 (m, 8H), 2.69-2.63 (m, 4H), 2.49 (br s, 2H), 2.34 (s, 3H), 2.24-2.20 (m, 3H), 1.89-1.88 (m, 2H), 1.78-1.74 (m, 4H), 1.58 (br s, 2H). |
| Example 154 | (R)-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide 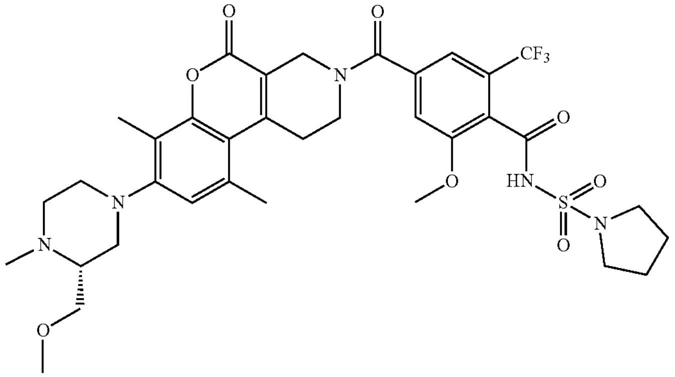 [SMILES: COC[C@H]1CN(c2cc(C)c3c4c(c(=O)oc3c2C)CN(C(=O)c2cc(OC)c(C(=O)NS(=O)(=O)N3CCCC3)c(C(F)(F)F)c2)CC4)CCN1C] Synthesised from Intermediates 6 and 100 | HPLC: (System 1, Method D) Rt = 6.86 min, m/z 750.3 $(M + H)^+$ $(ES)^+$. $^1$H NMR (400 MHz, DMSO-$d_6$) δ: 11.85 (br s, 1H), 7.55-7.53 (m, 1H), 7.44-7.42 (m, 1H), 6.85 (s, 1H), 4.51 (br s, 1H), 4.27 (br s, 1H), 3.91 (br s, 3H), 3.84 (br s, 1H), 3.57-3.54 (m, 1H), 3.50 (br s, 1H), 3.43-3.41 (m, 4H), 3.38-3.33 (m, 1H), 3.27 (s, 3H), 3.22 (br s, 2H), 3.16-3.13 (m, 1H), 3.06-3.03 (m, 1H), 2.88-2.80 (m, 2H), 2.69-2.63 (m, 4H), 2.49 (br s, 2H), 2.33 (s, 3H), 2.24-2.20 (m, 3H), 1.88-1.85 (m, 4H). Mixture of rotamers. |
| Example 155 | (R)-N-((6-azaspiro[2.5]octan-6-yl)sulfonyl)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 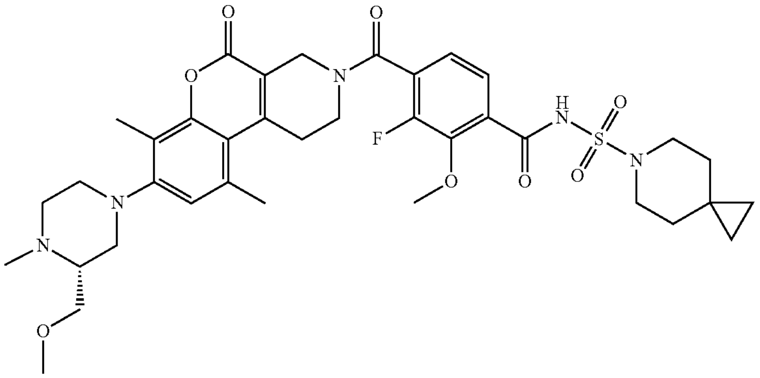 [SMILES: COC[C@H]1CN(c2cc(C)c3c4c(c(=O)oc3c2C)CN(C(=O)c2ccc(C(=O)NS(=O)(=O)N3CCC5(CC3)CC5)c(OC)c2F)CC4)CCN1C] Synthesised from Intermediates 6 and 155 | UPLC: (System 3, Method K) Rt = 4.07 min, m/z 738.8 $(M + H)^+$ $(ES^+)$. $^1$H NMR (400 MHz, ACN-$d_3$) δ: 7.71-7.65 (m, 1H), 7.24-7.17 (m, 1H), 6.83-6.81 (m, 1H), 4.55 (br s, 1H), 4.21 (br s, 1H), 4.11-4.06 (m, 3H), 3.91 (t, J = 5.7 Hz, 1H), 3.62-3.58 (m, 1H), 3.50 (t, J = 5.5 Hz, 1H), 3.46-3.38 (m, 5H), 3.30 (s, 3H), 3.24-3.05 (m, 5H), 2.96-2.88 (m, 2H), 2.74-2.68 (m, 2H), 2.61-2.51 (m, 3H), 2.40 (s, 3H), 2.28-2.24 (m, 3H), 1.49-1.46 (m, 4H), 0.36-0.35 (m, 4H). One exchangeable proton not visible. Mixture of rotamers. |

-continued

| Example No. | Name/Structure/Intermediates | LCMS/$^1$H NMR data |
|---|---|---|
| Example 156 | N-((3-azabicyclo[3.1.0]hexan-3-yl)sulfonyl)-3-fluoro-2-methoxy-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 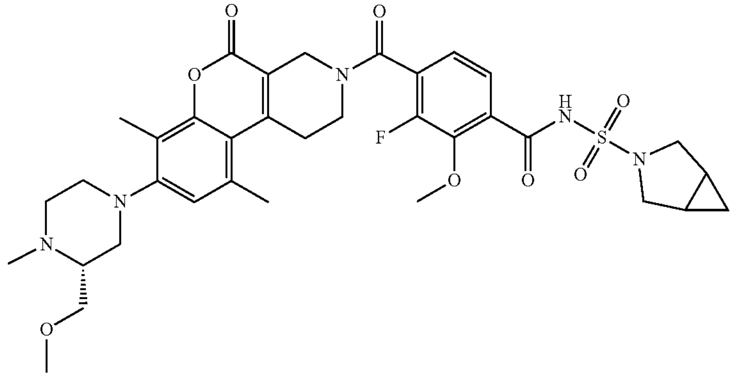 [SMILES: COC[C@H]1CN(c2cc(C)c3c4c(c(=O)oc3c2C)CN(C(=O)c2ccc(C(=O)NS(=O)(=O)N3CC5CC5C3)c(OC)c2F)CC4)CCN1C] Synthesised from Intermediates 6 and 156 | UPLC: (System 3, Method K) Rt = 3.79 min, m/z 711.0 $(M + H)^+$ $(ES^+)$. $^1$H NMR (400 MHz, ACN-$d_3$) δ: 7.65-7.60 (m, 1H), 7.20-7.14 (m, 1H), 6.82-6.81 (m, 1H), 4.55 (br s, 1H), 4.20 (br s, 1H), 4.08-4.04 (m, 3H), 3.97-3.93 (m, 1H), 3.58-3.48 (m, 6H), 3.39-3.35 (m, 1H), 3.29 (s, 3H), 3.24-3.03 (m, 4H), 2.89-2.83 (m, 2H), 2.69-2.61 (m, 4H), 2.48-2.42 (m, 3H), 2.33-2.24 (m, 6H), 1.57 (s, 2H), 0.69-0.64 (m, 1H), 0.38-0.33 (m, 1H). One exchangeable proton not visible. Mixture of rotamers. |
| Example 157 | (R)-N-((7-azabicyclo[2.2.1]heptan-7-yl)sulfonyl)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 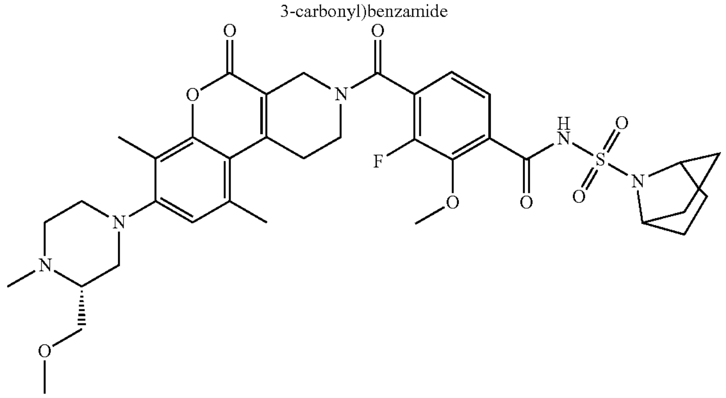 Synthesised from Intermediates 6 and 152 | UPLC: (System 3, Method K) Rt = 3.42 min, m/z 726.9 $(M + H)^+$ $(ES^+)$. $^1$H NMR (400 MHz, ACN-$d_3$) δ: 7.61-7.55 (m, 1H), 7.18-7.11 (m, 1H), 6.78-6.77 (m, 1H), 4.51 (br s, 1H), 4.27 (br s, 2H), 4.15 (br s, 1H), 4.04-4.01 (m, 3H), 3.87 (t, J = 5.3 Hz, 1H), 3.56-3.45 (m, 2H), 3.37-3.32 (m, 1H), 3.25 (s, 3H), 3.18-3.00 (m, 5H), 2.86-2.82 (m, 2H), 2.64-2.57 (m, 6H), 2.45-2.45 (m, 3H), 2.32 (s, 3H), 2.24-2.21 (m, 3H), 1.48-1.46 (br s, 4H). One exchangeable proton not visible. Mixture of rotamers. |
| Example 158 | N-((3-oxa-8-azabicyclo[3.2.1]octan-8-yl)sulfonyl)-3-fluoro-2-methoxy-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 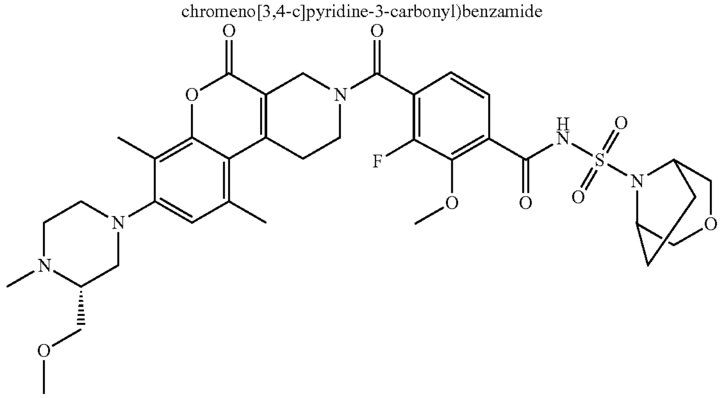 Synthesised from Intermediates 6 and 157 | UPLC: (System 3, Method K) Rt = 3.60 min, m/z 740.9 $(M - H)^-$ $(ES^-)$. $^1$H NMR (400 MHz, ACN-$d_3$) δ: 7.58-7.53 (m, 1H), 7.16-7.10 (m, 1H), 6.79-6.78 (m, 1H), 4.52 (br s, 1H), 4.19 (br s, 3H), 4.04-4.00 (m, 3H), 3.88 (t, J = 5.5 Hz, 1H), 3.68-3.65 (m, 2H), 3.58-3.53 (m, 3H), 3.47 (t, J = 5.5 Hz, 1H), 3.37-3.32 (m, 1H), 3.31-3.24 (m, 3H), 3.19-3.01 (m, 5H), 2.87-2.81 (m, 2H), 2.67-2.58 (m, 6H), 2.48-2.45 (m, 2H), 2.32 (s, 3H), 2.25-2.21 (m, 3H), 2.03-2.01 (m, 1H) One exchangeable proton not visible. Mixture of rotamers. |

-continued

| Example No. | Name/Structure/Intermediates | LCMS/$^1$H NMR data |
|---|---|---|
| Example 159 | (R)-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-5-(trifluoromethyl)benzamide 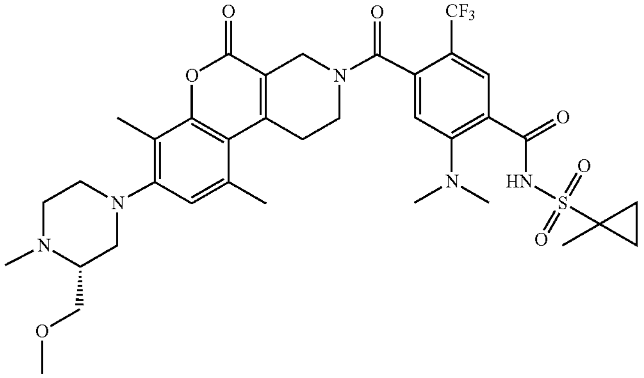 [SMILES: COC[C@H]1CN(c2cc(C)c3c4c(c(=O)oc3c2C)CN(C(=O)c2cc(N(C)C)c(C(=O)NS(=O)(=O)C3(C)CC3)cc2C(F)(F)F)CC4)CCN1C] Synthesised from Intermediates 6 and 109 | HPLC: (System 1, Method D) Rt = 6.95, m/z 748.5 $(M + H)^+$ $(ES)^+$. $^1$H NMR (400 MHz, DMSO-$d_6$) δ: 11.57 (br s, 1H), 7.61-7.57 (m, 1H), 6.92-6.85 (m, 2H), 4.72-4.15 (m, 2H), 3.98-3.56 (m, 2H), 3.43-3.40 (m, 2H), 3.28 (s, 3H), 3.23-3.17 (m, 2H), 3.10-3.07 (m, 2H), 3.03-2.94 (m, 7H), 2.86 (br s, 1H), 2.70-2.60 (m, 6H), 2.42 (s, 3H), 2.24-2.20 (m, 3H), 1.47 (s, 3H), 1.42 (br s, 2H), 0.87-0.85 (m, 2H). Mixture of rotamers. |
| Example 160 | (R)-2-ethoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide 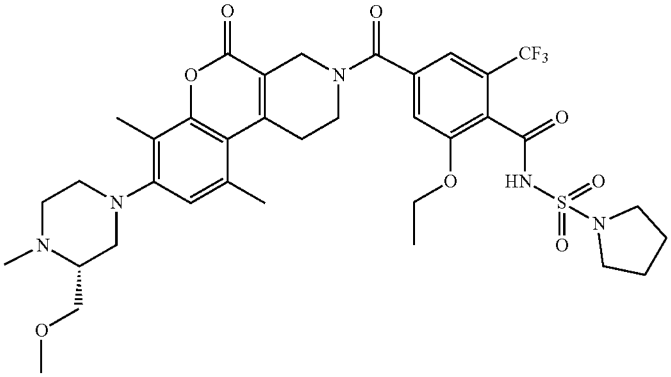 [SMILES: CCOc1cc(C(=O)N2CCc3c(c(=O)oc4c(C)c(N5CCN(C)[C@@H](COC)C5)cc(C)c34)C2)cc(C(F)(F)F)c1C(=O)NS(=O)(=O)N1CCCC1] Synthesised from Intermediates 6 and 101 | HPLC: (System 1, Method D) Rt = 7.06 min, m/z 764.4 $(M + H)^+$ $(ES)^+$. $^1$H NMR (400 MHz, DMSO-$d_6$) δ: 11.87 (br s, 1H), 7.52 (br s, 1H), 7.41-7.40 (m, 1H), 6.85 (s, 1H), 4.50 (br s, 1H), 4.27 (br s, 1H), 4.19 (br s, 2H), 3.84 (br s, 1H), 3.57-3.54 (m, 1H), 3.49-3.40 (m, 5H), 3.36-3.34 (m, 1H), 3.26 (s, 3H), 3.21 (br s, 2H), 3.15-3.12 (m, 1H), 3.05-3.02 (m, 1H), 2.85-2.80 (m, 2H), 2.69-2.61 (m, 4H), 2.49-2.43 (m, 2H), 2.32 (s, 3H), 2.24-2.20 (m, 3H), 1.88-1.84 (m, 4H), 1.32 (t, J = 6.8 Hz, 3H). Mixture of rotamers. |
| Example 161 | (R)-2-isopropoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide 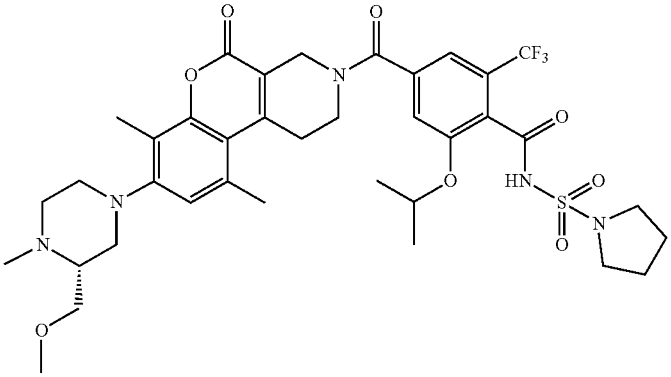 [SMILES: COC[C@H]1CN(c2cc(C)c3c4c(c(=O)oc3c2C)CN(C(=O)c2cc(OC(C)C)c(C(=O)NS(=O)(=O)N3CCCC3)c(C(F)(F)F)c2)CC4)CCN1C] Synthesised from Intermediates 6 and 102 | HPLC: (System 1, Method D) Rt = 7.31 min, m/z 778.3 $(M + H)^+$ $(ES)^+$. $^1$H NMR (400 MHz, DMSO-$d_6$) δ: 11.85 (br s, 1H), 7.56 (br s, 1H), 7.39-7.37 (m, 1H), 6.85 (s, 1H), 4.85-4.83 (m, 1H), 4.50 (br s, 1H), 4.29 (br s, 1H), 3.84 (br s, 1H), 3.57-3.54 (m, 1H), 3.49 (br s, 1H), 3.45-3.42 (m, 4H), 3.37 (br s, 1H), 3.26 (s, 3H), 3.21 (br s, 2H), 3.15-3.12 (m, 1H), 3.05-3.02 (m, 1H), 2.86-2.79 (m, 2H), 2.69-2.60 (m, 4H), 2.45-2.43 (m, 2H), 2.31 (s, 3H), 2.24-2.20 (m, 3H), 1.88-1.85 (m, 4H), 1.28 (d, J = 5.6 Hz, 6H). Mixture of rotamers. |

-continued

| Example No. | Name/Structure/Intermediates | LCMS/$^1$H NMR data |
|---|---|---|
| Example 162 | (S)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide 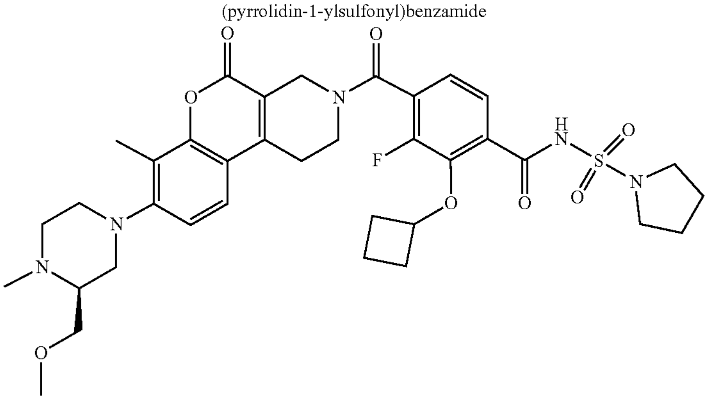 Synthesised from Intermediates 106 and 13 | HPLC: (System 1, Method D) Rt = 7.22 min, m/z 726.4 $(M + H)^+$ $(ES)^+$. $^1$H NMR (400 MHz, DMSO-$d_6$) δ: 11.48 (br s, 1H), 7.59-7.50 (m, 1H), 7.34-7.32 (m, 1H), 7.23-7.15 (m, 1H), 7.10-7.06 (m, 1H), 4.73-4.65 (m, 1H), 4.53 (br s, 1H), 4.17 (s, 1H), 3.97 (t, J = 5.6 Hz, 1H), 3.58-3.53 (m, 2H), 3.43-3.36 (m, 6H), 3.27 (s, 3H), 3.17-3.15 (m, 1H), 3.07-3.05 (m, 1H), 2.99 (br s, 1H), 2.91-2.83 (m, 3H), 2.68-2.63 (m, 1H), 2.52 (br s, 1H), 2.36 (s, 3H), 2.26-2.18 (m, 5H), 2.15-2.07 (m, 2H), 1.88-1.84 (m, 4H), 1.71-1.66 (m, 1H), 1.51-1.41 (m, 1H). Mixture of rotamers. |
| Example 163 | (R)-2-cyclobutoxy-5-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 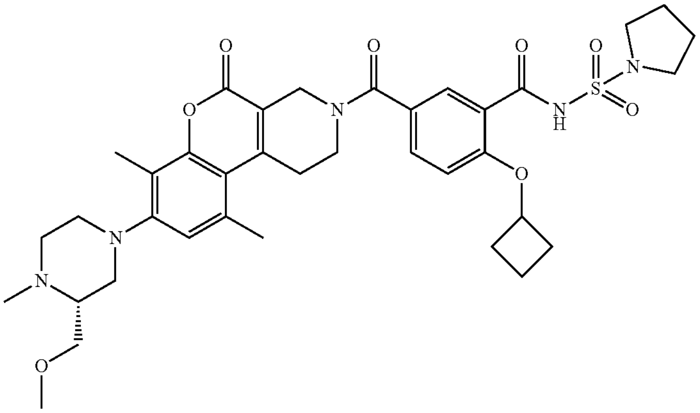 [SMILES: COC[C@H]1CN(c2cc(C)c3c4c(c(=O)oc3c2C)CN(C(=O)c2ccc(OC3CCC3)c(C(=O)NS(=O)(=O)N3CCCC3)c2)CC4)CCN1C] Synthesised from Intermediates 113 and 6 | HPLC: (System 1, Method D) Rt = 8.13 min, m/z 722.4 $(M + H)^+$ $(ES)^+$. $^1$H NMR (400 MHz, DMSO-$d_6$) δ: 11.36 (br s, 1H), 7.64-7.59 (m, 2H), 7.03 (d, J = 8.8 Hz, 1H), 6.84 (s, 1H), 4.87-4.83 (m, 1H), 4.40 (br s, 2H), 3.68 (br s, 2H), 3.57-3.53 (m, 1H), 3.45-3.42 (m, 4H), 3.35-3.31 (m, 1H), 3.26 (s, 3H), 3.21 (br s, 2H), 3.14-3.11 (m, 1H), 3.04-3.01 (m, 1H), 2.84-2.79 (m, 2H), 2.66 (s, 3H), 2.64-2.59 (m, 1H), 2.49-2.41 (m, 4H), 2.30 (s, 3H), 2.21 (s, 3H), 2.18-2.07 (m, 2H), 1.86-1.80 (m, 5H), 1.71-1.63 (m, 1H). |
| Example 164 | (R)-3-cyclobutoxy-5-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 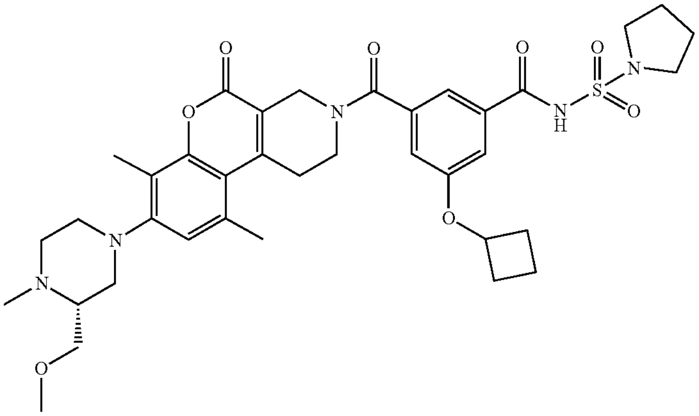 [SMILES: COC[C@H]1CN(c2cc(C)c3c4c(c(=O)oc3c2C)CN(C(=O)c2cc(OC3CCC3)cc(C(=O)NS(=O)(=O)N3CCCC3)c2)CC4)CCN1C] Synthesised from Intermediates 114 and 6 | HPLC: (System 1, Method D) Rt = 7.33 min, m/z 722.4 $(M + H)^+$ $(ES)^+$. $^1$H NMR (400 MHz, DMSO-$d_6$) δ: 11.34 (br s, 1H), 7.58 (br s, 1H), 7.46 (t, J = 2.0 Hz, 1H), 7.11 (br s, 1H), 6.86 (br s, 1H), 4.83-4.79 (m, 1H), 4.49 (br s, 1H), 4.28 (br s, 1H), 3.82 (br s, 1H), 3.58-3.50 (m, 2H), 3.44-3.43 (m, 1H), 3.33 (br s, 5H), 3.28 (s, 3H), 3.19 (br s, 3H), 3.10-3.07 (m, 1H), 2.98-2.95 (m, 1H), 2.89-2.83 (m, 1H), 2.71-2.65 (m, 5H), 2.49-2.39 (m, 5H), 2.23-2.20 (m, 3H), 2.09-2.04 (m, 2H), 1.79 (br s, 5H), 1.69-1.65 (m, 1H). |

-continued

| Example No. | Name/Structure/Intermediates | LCMS/$^1$H NMR data |
|---|---|---|
| Example 165 | (R)-2-cyclobutoxy-4-fluoro-5-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 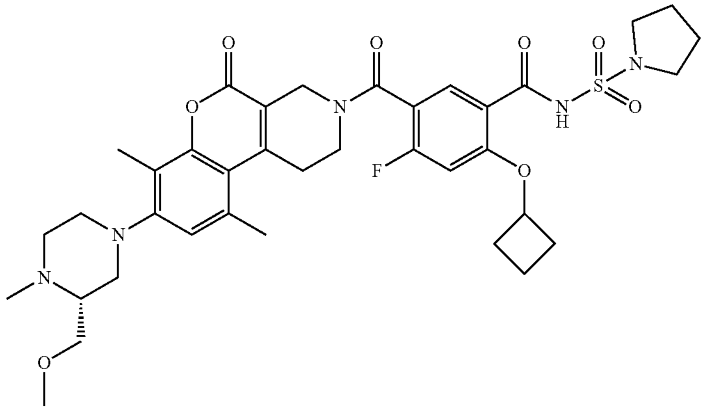 [SMILES: COC[C@H]1CN(c2cc(C)c3c4c(c(=O)oc3c2C)CN(C(=O)c2cc(C(=O)NS(=O)(=O)N3CCCC3)c(OC3CCC3)cc2F)CC4)CCN1C] Synthesised from Intermediates 116 and 6 | HPLC: (System 1, Method D) Rt = 8.06 min, m/z 740.4 $(M + H)^+$ $(ES)^+$. $^1$H NMR (400 MHz, DMSO-$d_6$) δ: 11.33 (br s, 1H), 7.62-7.55 (m, 1H), 6.98-6.95 (m, 1H), 6.85-6.84 (m, 1H), 4.87-4.84 (m, 1H), 4.48 (br s, 1H), 4.21 (br s, 1H), 3.81 (br s, 1H), 3.57-3.53 (m, 1H), 3.49 (br s, 1H), 3.43-3.41 (m, 4H), 3.34 (br s, 1H), 3.32 (br s, 1H), 3.26 (s, 3H), 3.24-3.21 (m, 1H), 3.14-3.12 (m, 2H), 3.04-3.02 (m, 1H), 2.86-2.79 (m, 2H), 2.68-2.59 (m, 4H), 2.50-2.42 (m, 3H), 2.30 (s, 3H), 2.23-2.19 (m, 3H), 2.16-2.06 (m, 2H), 1.84-1.82 (m, 5H), 1.69-1.62 (m, 1H). Mixture of rotamers. |
| Example 166 | (R)-3-cyclobutoxy-4-fluoro-5-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 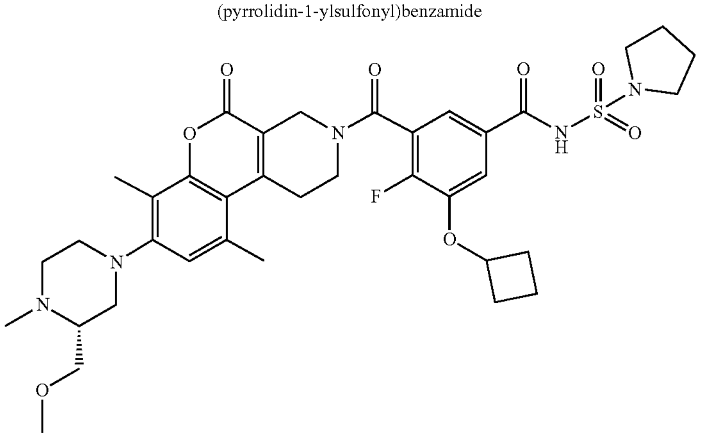 Synthesised from Intermediates 118 and 6 | HPLC: (System 1, Method D) Rt = 7.47 min, m/z 740.4 $(M + H)^+$ $(ES)^+$. $^1$H NMR (400 MHz, DMSO-$d_6$) δ: 11.16 (br s, 1H), 7.62-7.54 (m, 2H), 6.88-6.86 (m, 1H), 4.89-4.86 (m, 1H), 4.51 (br s, 1H), 4.17 (br s, 1H), 3.87 (br s, 1H), 3.60-3.56 (m, 1H), 3.34 (br s, 2H), 3.30 (br s, 7H), 3.23-3.20 (m, 2H), 3.13-3.04 (m, 3H), 2.92-2.77 (m, 4H), 2.70-2.67 (m, 3H), 2.51 (br s, 3H), 2.47 (br s, 2H), 2.25-2.20 (m, 3H), 2.16-2.12 (m, 2H), 1.85-1.75 (m, 5H), 1.73-1.62 (m, 1H). Mixture of rotamers. |

-continued

| Example No. | Name/Structure/Intermediates | LCMS/$^1$H NMR data |
|---|---|---|
| Example 167 | (R)-6-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)spiro[benzo[d][1,3]dioxole-2,1'-cyclobutane]-4-carboxamide 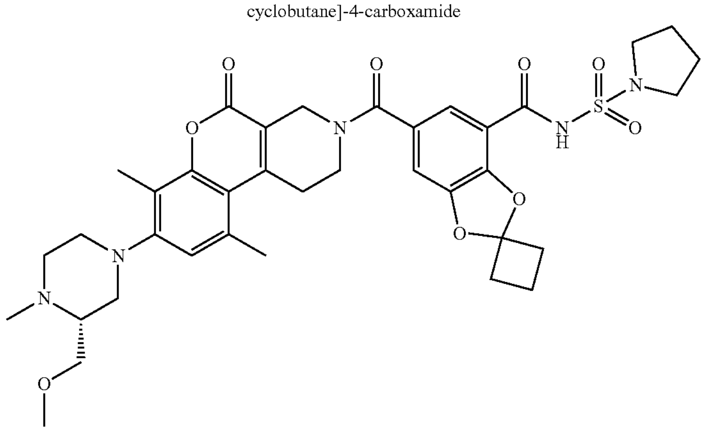 Synthesised from Intermediates 120 and 6 | HPLC: (System 1, Method D) Rt = 7.31 min, m/z 736.4 $(M + H)^+$ $(ES)^+$. $^1$H NMR (400 MHz, DMSO-$d_6$) δ: 10.99 (br s, 1H), 7.34 (s, 1H), 7.19 (s, 1H), 6.86 (s, 1H), 4.38 (br s, 2H), 3.70-3.56 (m, 3H), 3.46-3.42 (m, 1H), 3.36-3.34 (m, 4H), 3.29 (s, 3H), 3.20-3.17 (m, 3H), 3.11-3.08 (m, 1H), 3.00-2.97 (m, 1H), 2.89-2.84 (m, 1H), 2.74-2.61 (m, 10H), 2.44 (s, 3H), 2.22 (s, 3H), 1.87-1.79 (m, 6H). |
| Example 168 | (R)-4-fluoro-5-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)spiro[benzo[d][1,3]dioxole-2,1'-cyclobutane]-7-carboxamide 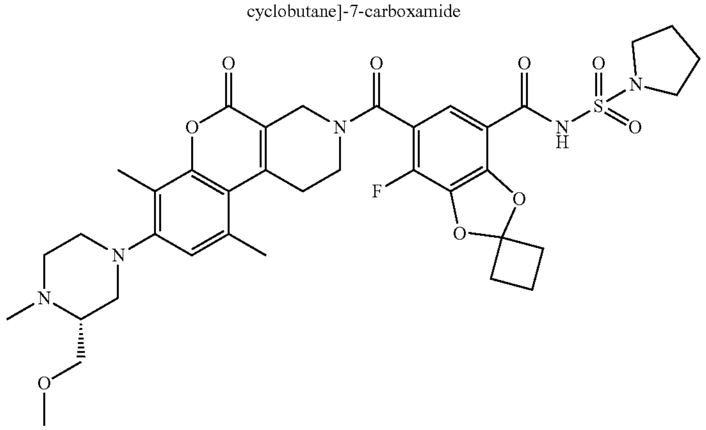 Synthesised from Intermediates 122 and 6 | HPLC: (System 1, Method D) Rt = 7.38 min, m/z 754.3 $(M + H)^+$ $(ES)^+$. $^1$H NMR (400 MHz, DMSO-$d_6$) δ: 10.86 (br s, 1H), 7.37-7.30 (m, 1H), 6.86 (s, 1H), 4.48 (br s, 1H), 4.23 (br s, 1H), 3.84 (br s, 1H), 3.59-3.45 (m, 3H), 3.29 (br s, 4H), 3.25 (s, 3H), 3.24-3.19 (m, 2H), 3.13-3.09 (m, 2H), 3.04-3.01 (m, 1H), 2.91-2.85 (m, 1H), 2.77-2.63 (m, 10H), 2.48 (br s, 3H), 2.24-2.20 (m, 3H), 1.86-1.78 (m, 6H). Mixture of rotamers. |

-continued

| Example No. | Name/Structure/Intermediates | LCMS/$^1$H NMR data |
|---|---|---|
| Example 169 | (R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-2-(trifluoromethoxy)benzamide 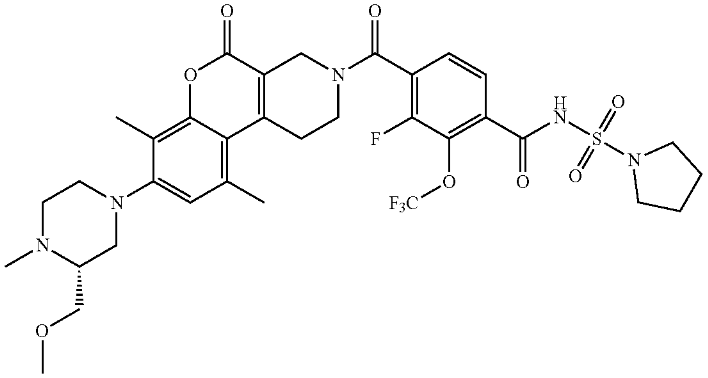 [SMILES: COC[C@H]1CN(c2cc(C)c3c4c(c(=O)oc3c2C)CN(C(=O)c2ccc(C(=O)NS(=O)(=O)N3CCCC3)c(OC(F)(F)F)c2F)CC4)CCN1C] Synthesised from Intermediates 138 and 6 | HPLC: (System 1, Method D) Rt = 7.21 min, m/z 754.3 $(M + H)^+$ $(ES)^+$. $^1$H NMR (400 MHz, DMSO-$d_6$) δ: 7.58-7.52 (m, 2H), 6.87-6.86 (m, 1H), 4.52 (br s, 1H), 4.18 (s, 1H), 3.90-3.87 (m, 1H), 3.60-3.57 (m, 1H), 3.47 (br s, 2H), 3.29 (s, 3H), 3.27 (br s, 5H), 3.21-3.15 (m, 2H), 3.12-3.08 (m, 2H), 3.06-2.97 (m, 1H), 2.91-2.74 (m, 3H), 2.70-2.60 (m, 4H), 2.47 (br s, 2H), 2.24-2.21 (m, 3H), 1.78 (br s, 4H). One exchangeable proton not visible. Mixture of rotamers. |
| Example 170 | (R)-2-cyclobutoxy-3-fluoro-4-(8-(4-isopropyl-3-(methoxymethyl)piperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide 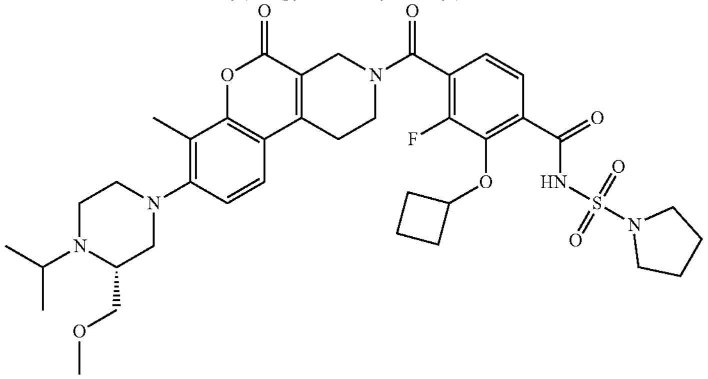 Synthesised from Intermediates 13 and 145 | HPLC: (System 1, Method D) Rt = 8.13 min, m/z 754.3 $(M + H)^+$ $(ES)^+$. $^1$H NMR (400 MHz, DMSO-$d_6$) δ: 11.50 (br s, 1H), 7.59-7.51 (m, 1H), 7.35-7.32 (m, 1H), 7.23-7.15 (m, 1H), 7.10-7.06 (m, 1H), 4.73-4.65 (m, 1H), 4.53 (br s, 1H), 4.17 (s, 1H), 3.97 (t, J = 5.6 Hz, 1H), 3.57-3.55 (m, 2H), 3.50-3.46 (m, 1H), 3.43-3.39 (m, 4H), 3.32-3.27 (m, 4H), 3.12-2.99 (m, 4H), 2.90-2.83 (m, 3H), 2.79-2.74 (m, 1H), 2.68-2.63 (m, 1H), 2.33-2.30 (m, 3H), 2.29-2.18 (m, 2H), 2.15-2.07 (m, 2H), 1.87-1.84 (m, 4H), 1.71-1.66 (m, 1H), 1.51-1.41 (m, 1H), 1.11-0.99 (m, 6H). Mixture of rotamers. |
| Example 171 | (R)-2-(difluoromethoxy)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 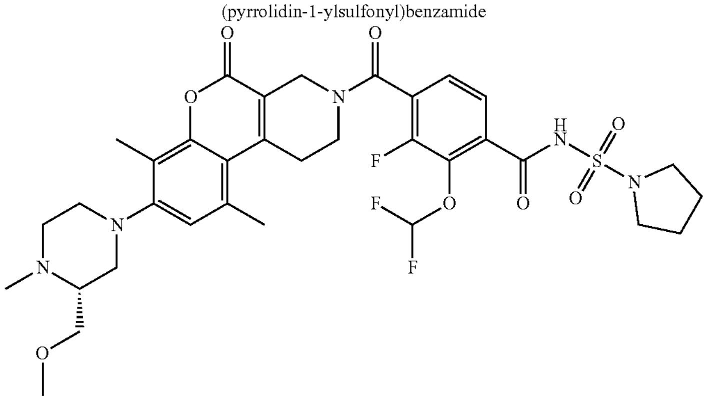 Synthesised from Intermediates 141 and 6 | HPLC: (System 1, Method D) Rt = 7.07 min, m/z 736.3 $(M + H)^+$ $(ES)^+$. $^1$H NMR (400 MHz, DMSO-$d_6$) δ: 11.05 (br s, 1H), 7.52-7.05 (m, 3H), 6.87-6.86 (m, 1H), 4.52 (br s, 1H), 4.19 (s, 1H), 3.88-3.87 (m, 1H), 3.59-3.57 (m, 1H), 3.49-3.46 (m, 2H), 3.33-3.32 (m, 6H), 3.30 (s, 3H), 3.24-3.10 (m, 5H), 3.05-3.02 (m, 1H), 2.91-2.86 (m, 1H), 2.78-2.62 (m, 6H), 2.23-2.21 (m, 3H), 1.82-1.79 (m, 4H). |

-continued

| Example No. | Name/Structure/Intermediates | LCMS/$^1$H NMR data |
|---|---|---|
| Example 172 | (R)-2-cyclobutoxy-4-(8-(4-ethyl-3-(methoxymethyl)piperazin-1-yl)-7-methyl-5-oxo-1,3,4,5-tetrahydro-2H-chromeno[3,4-c]pyridine-3-carbonyl)-3-fluoro-N-(pyrrolidin-1-ylsulfonyl)benzamide 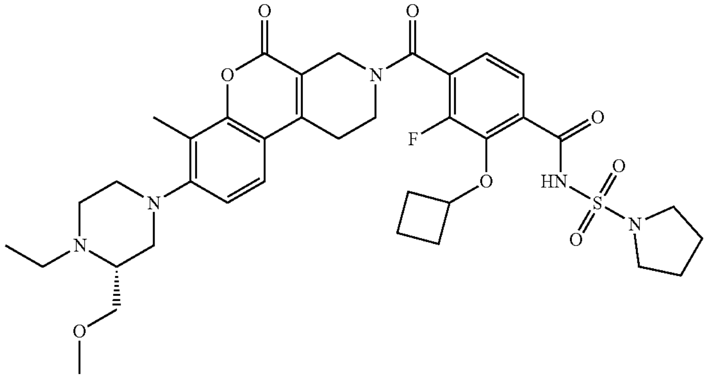 [SMILES: CCN1CCN(c2ccc3c4c(c(=O)oc3c2C)CN(C(=O)c2ccc(C(=O)NS(=O)(=O)N3CCCC3)c(OC3CCC3)c2F)CC4)C[C@@H]1COC] Synthesised from Intermediates 13 and 143 | HPLC: (System 1, Method D) Rt = 7.70 min, m/z 740.4 $(M + H)^+$ $(ES^+)$. $^1$H NMR (400 MHz, DMSO-$d_6$) δ: 11.49 (br s, 1H), 7.59-7.51 (m, 1H), 7.35-7.32 (m, 1H), 7.23-7.15 (m, 1H), 7.11-7.07 (m, 1H), 4.73-4.65 (m, 1H), 4.53 (br s, 1H), 4.17 (s, 1H), 3.99-3.96 (m, 1H), 3.60-3.53 (m, 2H), 3.50-3.46 (m, 1H), 3.42-3.39 (m, 4H), 3.27 (s, 3H), 3.11-2.99 (m, 3H), 2.96-2.74 (m, 6H), 2.58-2.53 (m, 2H), 2.33-2.18 (m, 5H), 2.15-2.07 (m, 2H), 1.86-1.84 (m, 4H), 1.71-1.66 (m, 1H), 1.50-1.41 (m, 1H), 1.04 (t, J = 7.2 Hz, 3H). Mixture of rotamers. |
| Example 173 | (R)-2-cyclobutoxy-4-(8-(4-cyclopropyl-3-(methoxymethyl)piperazin-1-yl)-7-methyl-5-oxo-1,3,4,5-tetrahydro-2H-chromeno[3,4-c]pyridine-3-carbonyl)-3-fluoro-N-(pyrrolidin-1-ylsulfonyl)benzamide 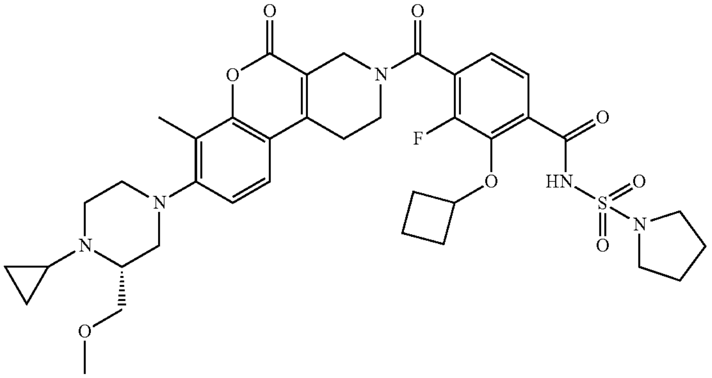 [SMILES: COC[C@H]1CN(c2ccc3c4c(c(=O)oc3c2C)CN(C(=O)c2ccc(C(=O)NS(=O)(=O)N3CCCC3)c(OC3CCC3)c2F)CC4)CCN1C1CC1] Synthesised from Intermediates 13 and 147 | HPLC: (System 1, Method D) Rt = 8.26 min, m/z 752.4 $(M + H)^+$ $(ES^+)$. $^1$H NMR (400 MHz, DMSO-$d_6$) δ: 11.72 (br s, 1H), 7.59-7.50 (m, 1H), 7.37-7.34 (m, 1H), 7.26-7.17 (m, 1H), 7.06 (t, J = 7.6 Hz, 1H), 4.72-4.64 (m, 1H), 4.53 (br s, 1H), 4.17 (s, 1H), 3.97 (t, J = 5.6 Hz, 1H), 3.81-3.78 (m, 1H), 3.54-3.49 (m, 2H), 3.44-3.43 (m, 4H), 3.27 (s, 3H), 3.13-3.10 (m, 1H), 3.02-3.00 (m, 3H), 2.90 (br s, 1H), 2.82-2.78 (m, 2H), 2.70-2.65 (m, 1H), 2.61-2.57 (m, 1H), 2.33-2.20 (m, 5H), 2.15-2.07 (m, 2H), 1.88-1.87 (m, 4H), 1.81 (br s, 1H), 1.71-1.67 (m, 1H), 1.51-1.44 (m, 1H), 0.58-0.57 (m, 1H), 0.46-0.41 (m, 2H), 0.31-0.29 (m, 1H). Mixture of rotamers. |
| Example 174 | (S)-2-cyclobutoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 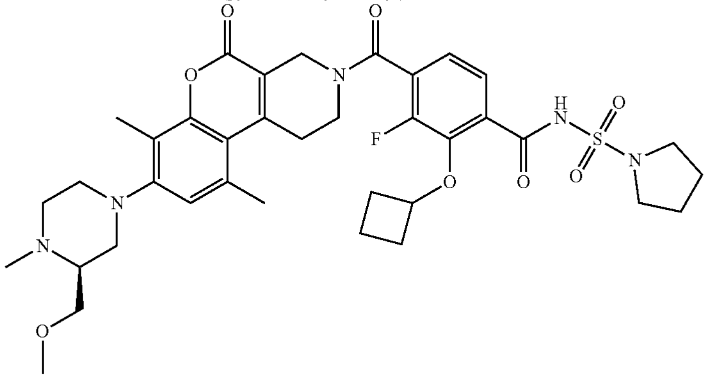 Synthesised from Intermediates 166 and 13 | HPLC: (System 1, Method D) Rt = 7.39 min, m/z 740.3 $(M + H)^+$ $(ES^+)$. $^1$H NMR (400 MHz, DMSO-$d_6$) δ: 11.48 (br s, 1H), 7.36-7.33 (m, 1H), 7.26-7.16 (m, 1H), 6.86-6.84 (m, 1H), 4.73-4.66 (m, 1H), 4.50 (br s, 1H), 4.17 (s, 1H), 3.88-3.86 (m, 1H), 3.58-3.54 (m, 1H), 3.45-3.37 (m, 7H), 3.27 (s, 3H), 3.23 (br s, 1H), 3.16-3.14 (m, 2H), 3.07-3.04 (m, 1H), 2.91-2.81 (m, 2H), 2.69-2.62 (m, 4H), 2.49 (br s, 1H), 2.35 (s, 3H), 2.29-2.20 (m, 5H), 2.16-2.07 (m, 2H), 1.87-1.84 (m, 4H), 1.71-1.66 (m, 1H), 1.50-1.40 (m, 1H). Mixture of rotamers. |

-continued

| Example No. | Name/Structure/Intermediates | LCMS/$^1$H NMR data |
|---|---|---|
| Example 175 | (R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 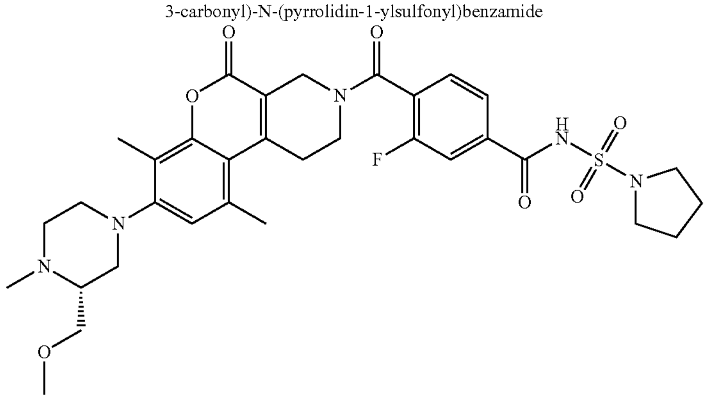 Synthesised from Intermediates 6 and 167 | UPLC: (System 3, Method K) Rt = 3.68 min, m/z 668.3 $(M - H)^-$ $(ES^-)$. $^1$H NMR (400 MHz, DMSO-$d_6$) δ 7.87-7.79 (m, 2H), 7.59-7.49 (m, 1H), 6.90-6.84 (m, 1H), 4.53 (s, 1H), 4.18 (s, 1H), 3.89 (s, 1H), 3.64-3.40 (m, 3H), 3.32 (s, 11H), 3.25-3.11 (m, 5H), 2.92-2.63 (m, 6H), 2.28-2.20 (m, 3H), 1.87-1.77 (m, 4H) One exchangeable proton not visible. Mixture of rotamers. |
| Example 181 | N-((3-azabicyclo[3.1.0]hexan-3-yl)sulfonyl)-2-(dimethylamino)-5-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide 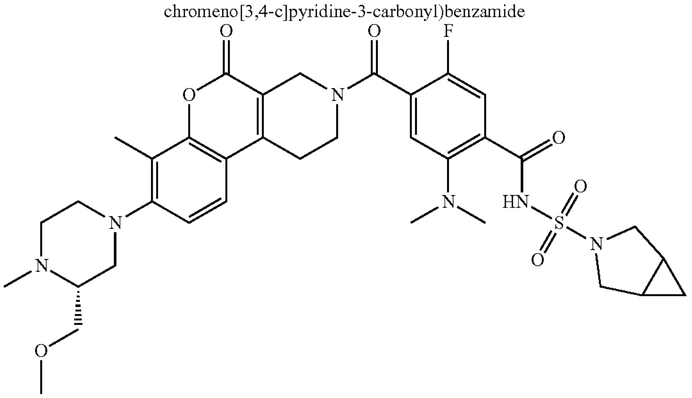 Synthesised from Intermediates 169 and 5 | HPLC: (System 1, Method H) Rt = 7.59 min, m/z 711.3 $(M + H)^+$ $(ES^+)$. $^1$H NMR (400 MHz, DMSO-$d_6$) δ: 13.03 (br s, 1H), 7.60-7.48 (m, 2H), 7.42-7.31 (m, 1H), 7.10-7.06 (m, 1H), 4.53 (br s, 1H), 4.20 (br s, 1H), 3.98 (br s, 1H), 3.58-3.54 (m, 4H), 3.48-3.45 (m, 2H), 3.38-3.34 (m, 2H), 3.27 (s, 3H), 3.17-3.14 (m, 1H), 3.07-3.04 (m, 1H), 3.00 (br s, 1H), 2.90-2.83 (m, 3H), 2.77-2.74 (m, 6H), 2.67-2.62 (m, 1H), 2.49-2.47 (m, 1H), 2.34 (s, 3H), 2.30-2.26 (m, 3H), 1.59 (br s, 2H), 0.68-0.63 (m, 1H), 0.29-0.28 (m, 1H). Mixture of rotamers. |
| Example 182 | (R)-2-cyclobutoxy-3-fluoro-4-(8-(3-(methoxymethyl)-4-methylpiperazin-1-yl)-5-oxo-1,3,4,5-tetrahydro-2H-chromeno[3,4-c]pyridine-3-carbonyl)-N-(pyrrolidin-1-ylsulfonyl)benzamide 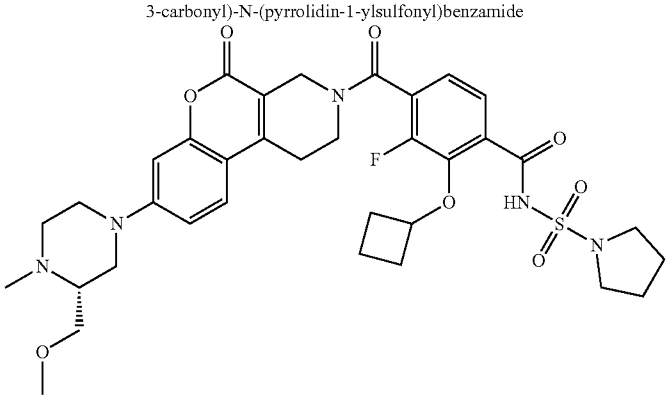 Synthesised from Intermediates 13 and 224 | HPLC: (System 1, Method H) Rt = 6.89 min, m/z 712.4 $(M + H)^+$ $(ES^+)$. $^1$H NMR (400 MHz, DMSO-$d_6$) δ: 11.56 (br s, 1H), 7.58-7.50 (m, 1H), 7.35-7.32 (m, 1H), 7.23-7.15 (m, 1H), 7.02-6.97 (m, 1H), 6.86-6.83 (m, 1H), 4.73-4.65 (m, 1H), 4.49 (br s, 1H), 4.13 (s, 1H), 3.97-3.94 (m, 1H), 3.82-3.74 (m, 2H), 3.56-3.51 (m, 2H), 3.43-3.37 (m, 5H), 3.29-3.28 (m, 3H), 2.99-2.94 (m, 2H), 2.87-2.84 (m, 2H), 2.80-2.74 (m, 1H), 2.36-2.31 (m, 5H), 2.27-2.18 (m, 2H), 2.15-2.07 (m, 2H), 1.86 (br s, 4H), 1.71-1.66 (m, 1H), 1.51-1.44 (m, 1H). Mixture of rotamers. |

-continued

| Example No. | Name/Structure/Intermediates | LCMS/$^1$H NMR data |
|---|---|---|
| Example 183 | (R)-2-(cyclopentyloxy)-3-fluoro-4-(8-(3-(methoxymethyl)-4-methylpiperazin-1-yl)-5-oxo-1,3,4,5-tetrahydro-2H-chromeno[3,4-c]pyridine-3-carbonyl)-N-(pyrrolidin-1-ylsulfonyl)benzamide 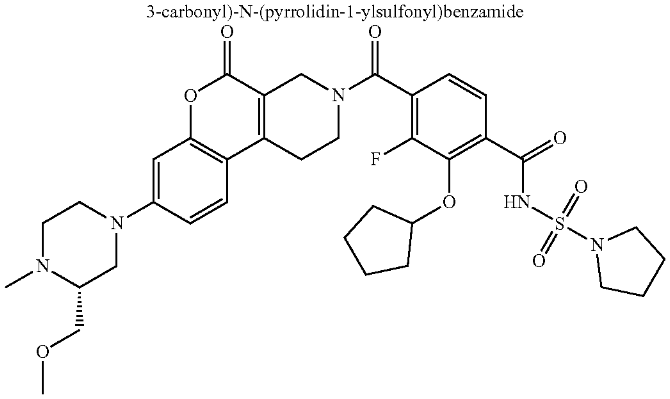 Synthesised from Intermediates 14 and 224 | HPLC: (System 1, Method H) Rt = 7.14 min, m/z 726.4 $(M + H)^+$ $(ES^+)$. $^1$H NMR (400 MHz, DMSO-$d_6$) δ: 11.57 (br s, 1H), 7.58-7.49 (m, 1H), 7.35-7.32 (m, 1H), 7.23-7.14 (m, 1H), 7.01-6.97 (m, 1H), 6.86-6.83 (m, 1H), 4.87-4.81 (m, 1H), 4.49 (br s, 1H), 4.14 (s, 1H), 3.97-3.94 (m, 1H), 3.82-3.74 (m, 2H), 3.56-3.52 (m, 2H), 3.41-3.37 (m, 5H), 3.29-3.28 (m, 3H), 2.99-2.94 (m, 2H), 2.87-2.84 (m, 2H), 2.80-2.74 (m, 1H), 2.36-2.31 (m, 5H), 1.87-1.83 (m, 4H), 1.79-1.73 (m, 6H), 1.57-1.54 (m, 2H). Mixture of rotamers. |
| Example 184 | (R)-3-chloro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 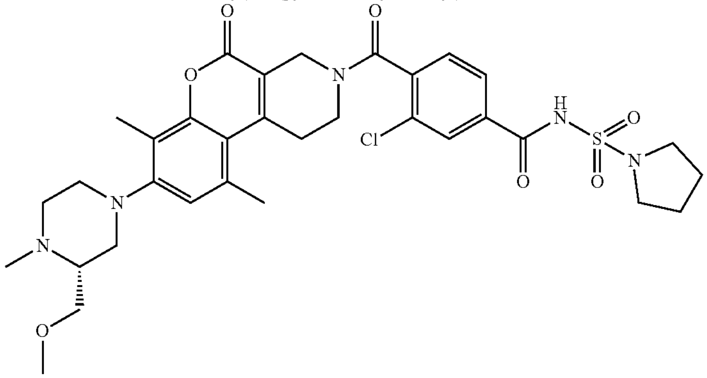 Synthesised from Intermediates 190 and 6 | UPLC: (System 3, Method K) Rt = 3.80 min, m/z 685.2 $(M - H)^-$ $(ES^-)$. $^1$H NMR (400 MHz, DMSO-$d_6$) δ: 8.06-8.02 (m, 1H), 7.97-7.92 (m, 1H), 7.55-7.47 (m, 1H), 6.94-6.85 (m, 1H), 4.66-4.38 (m, 1H), 4.06 (s, 1H), 3.96-3.82 (m, 1H), 3.68-3.47 (m, 2H), 3.38-3.31 (m, 9H), 3.22-3.04 (m, 6H), 2.92-2.75 (m, 4H), 2.69 (s, 2H), 2.61 (s, 2H), 2.25-2.20 (m, 3H), 1.82-1.75 (m, 4H). One exchangeable proton not visible. Mixture of rotamers. |
| Example 185 | (R)-N-((7-azabicyclo[2.2.1]heptan-7-yl)sulfonyl)-3-chloro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 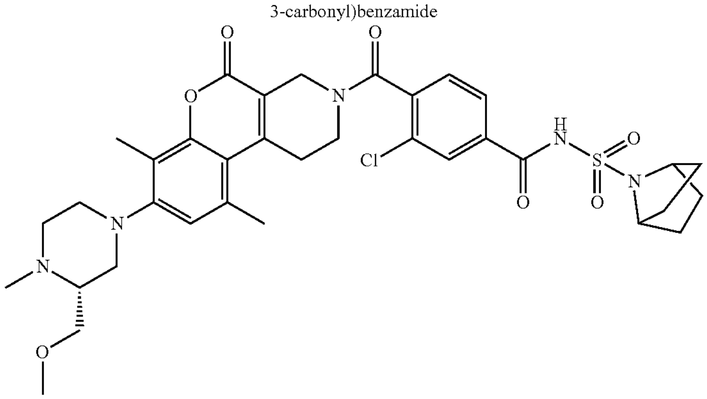 Synthesised from Intermediates 191 and 6 | UPLC: (System 3, Method K) Rt = 3.93 min, m/z 711.9 $(M - H)^-$ $(ES^-)$. $^1$H NMR (400 MHz, DMSO-$d_6$) δ: 7.97-7.94 (m, 1H), 7.90-7.86 (m, 1H), 7.51-7.42 (m, 1H), 6.88-6.86 (m, 1H), 4.66-4.38 (m, 1H), 4.11-4.06 (m, 3H), 3.92-3.82 (m, 1H), 3.60-3.46 (m, 2H), 3.42-3.35 (m, 2H), 3.24-3.13 (m, 6H), 2.91-2.84 (m, 5H), 2.70-2.65 (m, 2H), 2.65-2.54 (m, 4H), 2.25-2.21 (m, 3H), 1.91-1.84 (m, 4H), 1.39-1.23 (m, 4H). One exchangeable proton not visible. Mixture of rotamers. |

-continued

| Example No. | Name/Structure/Intermediates | LCMS/$^1$H NMR data |
|---|---|---|
| Example 186 | (R)-2-cyclobutoxy-3-fluoro-4-(8-(3-(methoxymethyl)-4-methylpiperazin-1-yl)-10-methyl-5-oxo-1,3,4,5-tetrahydro-2H-chromeno[3,4-c]pyridine-3-carbonyl)-N-(pyrrolidin-1-ylsulfonyl)benzamide<br>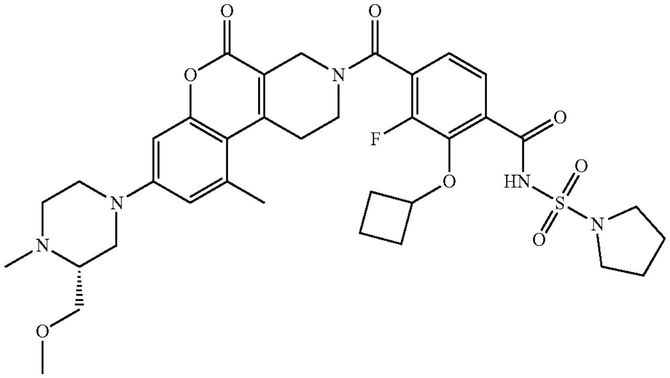 [SMILES: COC[C@H]1CN(c2cc(C)c3c4c(c(=O)oc3c2)CN(C(=O)c2ccc(C(=O)NS(=O)(=O)N3CCCC3)c(OC3CCC3)c2F)CC4)CCN1C]<br>Synthesised from Intermediates 13 and 226 | HPLC: (System 1, Method H) Rt = 7.05 min, m/z 726.3 (M + H)$^+$ (ES$^+$). $^1$H NMR (400 MHz, DMSO-$d_6$) δ: 11.51 (br s, 1H), 7.36-7.25 (m, 1H), 7.24-7.16 (m, 1H), 6.81-6.79 (m, 1H), 6.69-6.65 (m, 1H), 4.75-4.64 (m, 1H), 4.48 (br s, 1H), 4.13 (s, 1H), 3.88-3.85 (m, 1H), 3.81-3.73 (m, 2H), 3.56-3.51 (m, 1H), 3.43-3.36 (m, 6H), 3.29-3.27 (m, 3H), 3.20 (br s, 1H), 3.11-3.06 (m, 1H), 2.96-2.91 (m, 1H), 2.87-2.83 (m, 1H), 2.77-2.72 (m, 1H), 2.66-2.59 (m, 3H), 2.35-2.31 (m, 5H), 2.18-2.16 (m, 2H), 2.15-2.05 (m, 2H), 1.88-1.85 (m, 4H), 1.74-1.64 (m, 1H), 1.51-1.41 (m, 1H). Mixture of rotamers. |
| Example 187 | (R)-2-(cyclopentyloxy)-3-fluoro-4-(8-(3-(methoxymethyl)-4-methylpiperazin-1-yl)-10-methyl-5-oxo-1,3,4,5-tetrahydro-2H-chromeno[3,4-c]pyridine-3-carbonyl)-N-(pyrrolidin-1-ylsulfonyl)benzamide<br>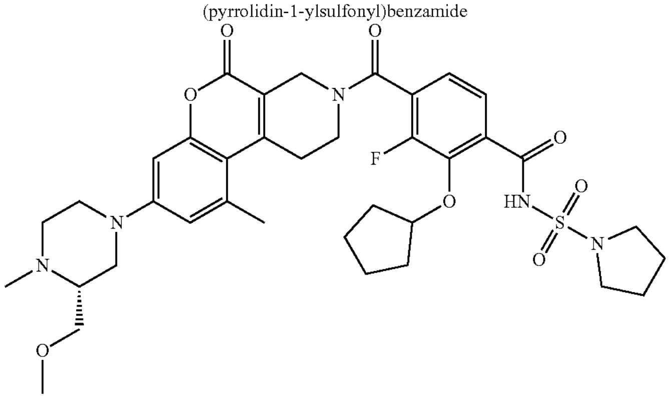<br>Synthesised from Intermediates 14 and 226 | HPLC: (System 1, Method H) Rt = 7.30 min, m/z 740.4 (M + H)$^+$ (ES$^+$). $^1$H NMR (400 MHz, DMSO-$d_6$) δ: 11.57 (br s, 1H), 7.35-7.33 (m, 1H), 7.24-7.15 (m, 1H), 6.81-6.79 (m, 1H), 6.69-6.66 (m, 1H), 4.87-4.82 (m, 1H), 4.46 (br s, 1H), 4.14 (S, 1H), 3.87-3.85 (m, 1H), 3.80-3.73 (m, 2H), 3.55-3.51 (m, 1H), 3.46-3.45 (m, 1H), 3.43-3.38 (m, 5H), 3.29-3.28 (m, 3H), 3.21 (br s, 1H), 3.11 (m, 1H), 2.96-2.91 (m, 1H), 2.86-2.83 (m, 1H), 2.77-2.71 (m, 1H), 2.66-2.59 (m, 3H), 2.33-2.30 (m, 5H), 1.85-1.74 (m, 10H), 1.59-1.55 (m, 2H). Mixture of rotamers. |
| Example 188 | (R)-N-((7-azabicyclo[2.2.1]heptan-7-yl)sulfonyl)-2-(dimethylamino)-5-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide<br>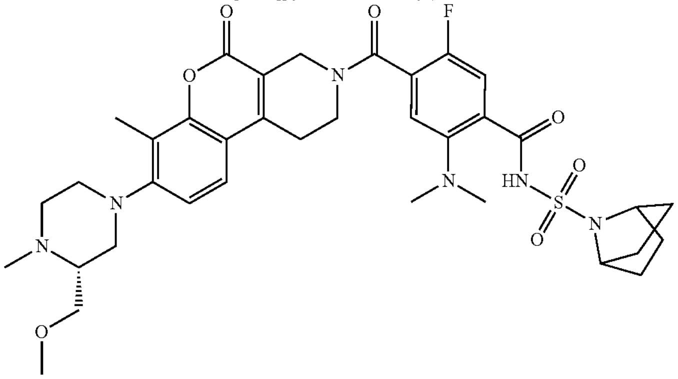<br>Synthesised from Intermediates 170 and 5 | HPLC: (System 1, Method H) Rt = 7.40 min, m/z 725.2 (M + H)$^+$ (ES$^+$). $^1$H NMR (400 MHz, DMSO-$d_6$) δ: 12.97 (br s, 1H), 7.60-7.50 (m, 1H), 7.46-7.41 (m, 1H), 7.37-7.25 (m, 1H), 7.10-7.06 (m, 1H), 4.53 (br s, 1H), 4.22-4.19 (m, 3H), 3.97 (br s, 1H), 3.58-3.55 (m, 2H), 3.39-3.36 (m, 2H), 3.27 (s, 3H), 3.17-3.14 (m, 1H), 3.07-3.04 (m, 1H), 2.99 (br s, 1H), 2.94-2.83 (m, 3H), 2.77-2.75 (m, 6H), 2.67-2.62 (m, 1H), 2.49-2.45 (m, 1H), 2.34 (s, 3H), 2.29-2.26 (m, 3H), 1.84-1.81 (m, 4H), 1.46-1.44 (m, 4H). Mixture of rotamers. |

-continued

| Example No. | Name/Structure/Intermediates | LCMS/$^1$H NMR data |
| --- | --- | --- |
| Example 189 | (R)-N-((6-azaspiro[2.5]octan-6-yl)sulfonyl)-2-(dimethylamino)-5-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide<br>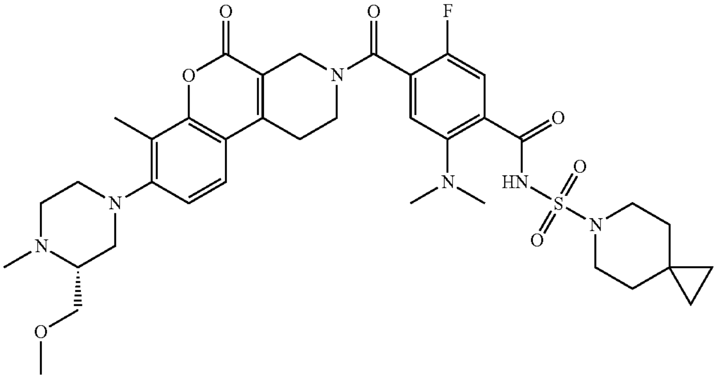<br>Synthesised from Intermediates 172 and 5 | HPLC: (System 1, Method H) Rt = 8.28 min, m/z 739.4 $(M + H)^+$ $(ES^+)$.<br>$^1$H NMR (400 MHz, DMSO-$d_6$) δ: 13.08 (br s, 1H), 7.60-7.49 (m, 2H), 7.44-7.33 (m, 1H), 7.10-7.06 (m, 1H), 4.53 (br s, 1H), 4.20 (br s, 1H), 3.98 (br s, 1H), 3.58-3.55 (m, 2H), 3.39-3.35 (m, 5H), 3.27 (s, 3H), 3.17-3.14 (m, 1H), 3.07-3.04 (m, 1H), 3.00 (br s, 1H), 2.90-2.83 (m, 3H), 2.79-2.76 (m, 6H), 2.68-2.62 (m, 1H), 2.51 (br s, 1H), 2.49 (br s, 1H), 2.34 (s, 3H), 2.30-2.26 (m, 3H), 1.42 (br s, 4H), 0.33 (s, 4H). Mixture of rotamers. |
| Example 190 | (R)-N-((6-azaspiro[2.5]octan-6-yl)sulfonyl)-5-chloro-2-(dimethylamino)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide<br>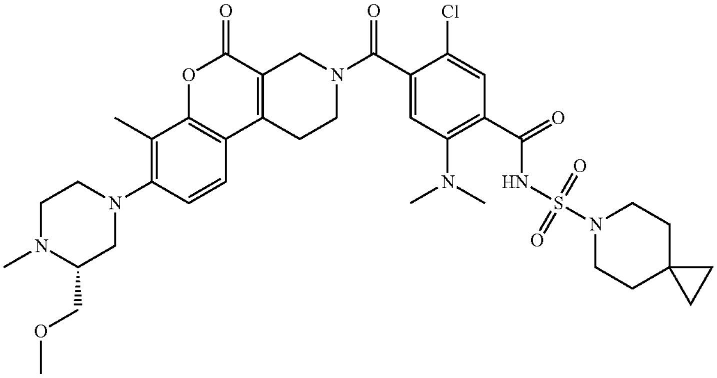 [SMILES: COC[C@H]1CN(c2ccc3c4c(c(=O)oc3c2C)CN(C(=O)c2cc(N(C)C)c(C(=O)NS(=O)(=O)N3CCC5(CC3)CC5)cc2Cl)CC4)CCN1C]<br>Synthesised from Intermediates 173 and 5 | HPLC: (System 1, Method H) Rt = 7.99 min, m/z 755.3 $(M + H)^+$ $(ES^+)$.<br>$^1$H NMR (400 MHz, DMSO-$d_6$) δ: 12.09 (br s, 1H), 7.60-7.45 (m, 2H), 7.10-7.02 (m, 2H), 4.63-4.43 (m, 1H), 4.16-3.78 (m, 2H), 3.58-3.55 (m, 1H), 3.51-3.49 (m, 1H), 3.44-3.36 (m, 5H), 3.27 (s, 3H), 3.17-3.15 (m, 1H), 3.09-2.98 (m, 2H), 2.91-2.86 (m, 3H), 2.82-2.81 (m, 6H), 2.68-2.63 (m, 1H), 2.51 (br s, 1H), 2.49 (br s, 1H), 2.35 (s, 3H), 2.33-2.26 (m, 3H), 1.41-1.40 (m, 4H), 0.33-032 (m, 4H). Mixture of rotamers. |
| Example 191 | (R)-N-((7-azabicyclo[2.2.1]heptan-7-yl)sulfonyl)-2-(dimethylamino)-5-fluoro-4-(8-(3-(methoxymethyl)-4-methylpiperazin-1-yl)-5-oxo-1,3,4,5-tetrahydro-2H-chromeno[3,4-c]pyridine-3-carbonyl)benzamide<br>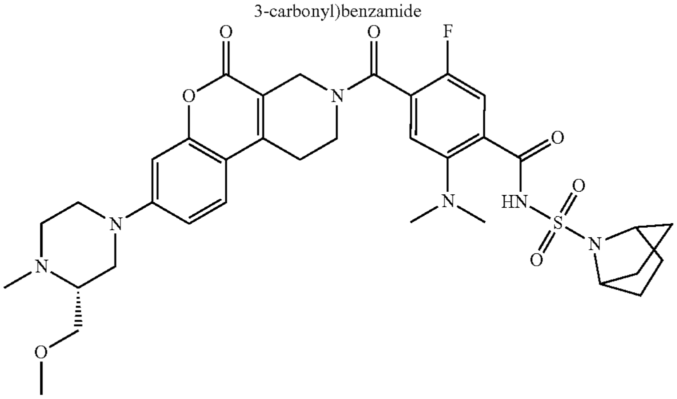<br>Synthesised from Intermediates 170 and 224 | HPLC: (System 1, Method H) Rt = 7.03 min, m/z 711.4 $(M + H)^+$ $(ES^+)$.<br>$^1$H NMR (400 MHz, DMSO-$d_6$) δ: 13.08 (br s, 1H), 7.59-7.50 (m, 1H), 7.47-7.41 (m, 1H), 7.39-7.37 (m, 1H), 7.01-6.97 (m, 1H), 6.86-6.83 (m, 1H), 4.49-4.47 (m, 1H), 4.22 (br s, 2H), 4.16 (br s, 1H), 3.95 (br s, 1H), 3.81-3.74 (m, 2H), 3.56-3.53 (m, 2H), 3.40-3.36 (m, 1H), 3.29 (s, 3H), 2.98-2.91 (m, 2H), 2.86-2.83 (m, 2H), 2.79-2.72 (m, 7H), 2.34-2.30 (m, 5H), 1.83-1.81 (m, 4H), 1.46-1.44 (m, 4H). Mixture of rotamers. |

-continued

| Example No. | Name/Structure/Intermediates | LCMS/$^1$H NMR data |
|---|---|---|
| Example 192 | (R)-2-cyclobutoxy-3-fluoro-4-(8-(3-(isopropoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide 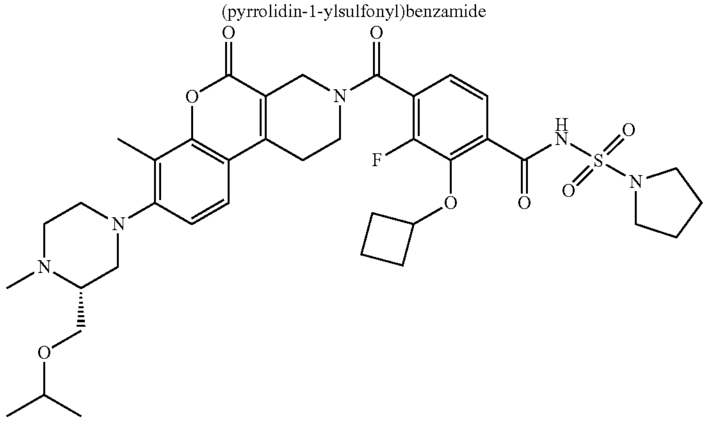 Synthesised from Intermediates 13 and 231 | HPLC: (System 1, Method H) Rt = 8.74 min, m/z 754.0 (M + H)$^+$ (ES$^+$). $^1$H NMR (400 MHz, DMSO-d$_6$) δ: 11.47 (br s, 1H), 7.60-7.51 (m, 1H), 7.35-7.32 (m, 1H), 7.23-7.15 (m, 1H), 7.10-7.05 (m, 1H), 4.73-4.65 (m, 1H), 4.53 (br s, 1H), 4.17 (br s, 1H), 4.00-3.96 (m, 1H), 3.63-3.60 (m, 1H), 3.57-3.51 (m, 2H), 3.43-3.35 (m, 5H), 3.21-3.18 (m, 1H), 3.07-3.04 (m, 1H), 2.99 (br s, 1H), 2.91-2.85 (m, 3H), 2.67-2.61 (m, 1H), 2.51 (br s, 1H), 2.49 (br s, 1H), 2.36 (s, 3H), 2.30-2.18 (m, 5H), 2.15-2.07 (m, 2H), 1.88-1.84 (m, 4H), 1.71-1.66 (m, 1H), 1.51-1.44 (m, 1H), 1.09-1.07 (m, 6H). Mixture of rotamers. |
| Example 193 | (R)-N-((7-azabicyclo[2.2.1]heptan-7-yl)sulfonyl)-5-chloro-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 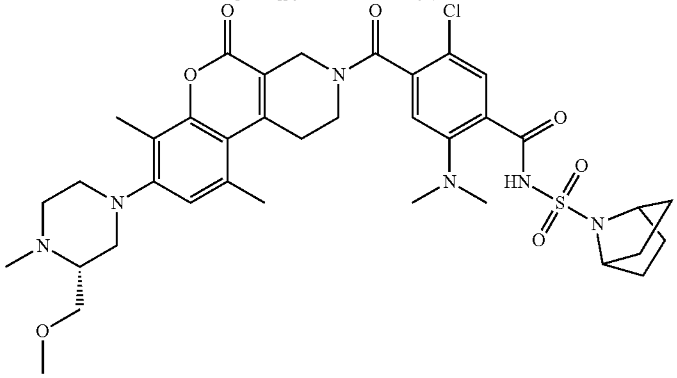 [SMILES: COC[C@H]1CN(c2cc(C)c3c4c(c(=O)oc3c2C)CN(C(=O)c2cc(N(C)C)c(C(=O)NS(=O)(=O)N3C5CCC3CC5)cc2Cl)CC4)CCN1C] Synthesised from Intermediates 174 and 6 | HPLC: (System 1, Method H) Rt = 7.39 min, m/z 755.3 (M + H)$^+$ (ES$^+$). $^1$H NMR (400 MHz, DMSO-d$_6$) δ: 12.04 (br s, 1H), 7.40-7.35 (m, 1H), 7.08-6.97 (m, 1H), 6.89-6.84 (m, 1H), 4.66-4.36 (m, 1H), 4.21 (br s, 2H), 4.10 (br s, 1H), 4.01-3.72 (m, 1H), 3.58-3.54 (m, 1H), 3.44-3.36 (m, 3H), 3.27 (s, 3H), 3.21-3.09 (m, 3H), 3.07-3.04 (m, 1H), 2.91-2.86 (m, 2H), 2.82-2.80 (m, 6H), 2.69-2.60 (m, 4H), 2.52-2.51 (m, 1H), 2.36 (s, 3H), 2.24-2.20 (m, 3H), 1.82-1.75 (m, 4H), 1.45-1.44 (m, 4H). Mixture of rotamers. |
| Example 194 | (R)-2-(azetidin-1-yl)-5-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide 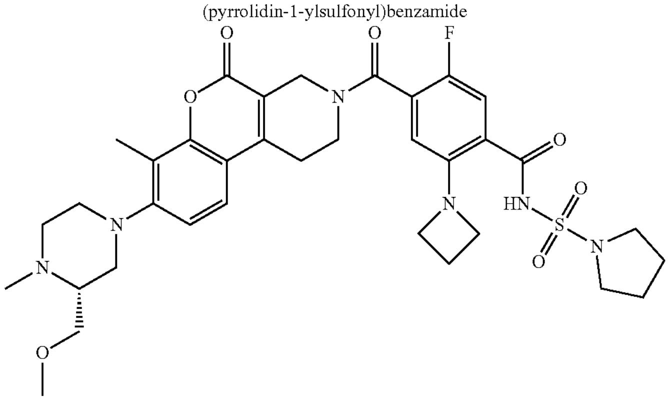 Synthesised from Intermediates 177 and 5 | HPLC: (System 1, Method H) Rt = 7.34 min, m/z 711.0 (M + H)$^+$ (ES$^+$). $^1$H NMR (400 MHz, DMSO-d$_6$) δ: 11.69 (br s, 1H), 7.59-7.50 (m, 1H), 7.25-7.22 (m, 1H), 7.10-7.06 (m, 1H), 6.51-6.44 (m, 1H), 4.52 (br s, 1H), 4.19 (s, 1H), 3.95 (br s, 1H), 3.82-3.77 (m, 4H), 3.58-3.54 (m, 2H), 3.41-3.36 (m, 5H), 3.27 (s, 3H), 3.17-3.14 (m, 1H), 3.07-3.04 (m, 1H), 2.98 (br s, 1H), 2.90-2.83 (m, 3H), 2.67-2.62 (m, 1H), 2.50-2.49 (m, 2H), 2.34 (s, 3H), 2.29-2.23 (m, 5H), 1.85-1.82 (m, 4H). Mixture of rotamers. |

-continued

| Example No. | Name/Structure/Intermediates | LCMS/$^1$H NMR data |
|---|---|---|
| Example 195 | (R)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 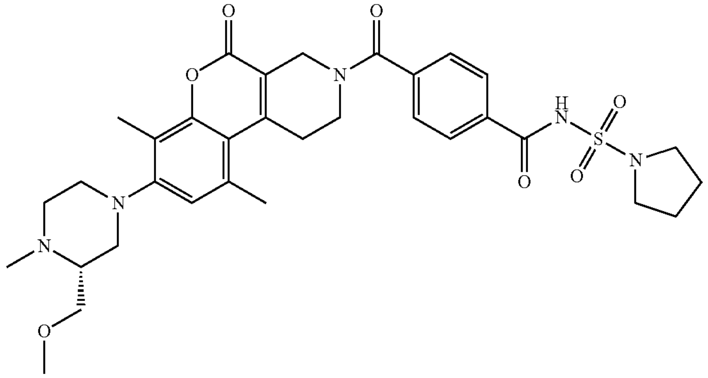 [SMILES: COC[C@H]1CN(c2cc(C)c3c4c(c(=O)oc3c2C)CN(C(=O)c2ccc(C(=O)NS(=O)(=O)N3CCCC3)cc2)CC4)CCN1C] Synthesised from Intermediates 192 and 6 | HPLC: (System 1, Method H) Rt = 6.58 min, m/z 652.0 (M + H)$^+$ (ES$^+$). $^1$H NMR (400 MHz, DMSO-d$_6$) δ: 11.43 (br s, 1H), 8.01-7.99 (m, 2H), 7.57 (br s, 2H), 6.86 (s, 1H), 4.48 (br s, 1H), 4.27 (br s, 1H), 3.84 (br s, 1H), 3.59-3.55 (m, 1H), 3.50 (br s, 1H), 3.43-3.36 (m, 5H), 3.28 (s, 3H), 3.21-3.16 (m, 3H), 3.09-3.06 (m, 1H), 2.96-2.93 (m, 1H), 2.88-2.83 (m, 1H), 2.72-2.58 (m, 6H), 2.41 (s, 3H), 2.24 (br s, 3H), 1.83-1.80 (m, 4H). |
| Example 196 | (R)-2-amino-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 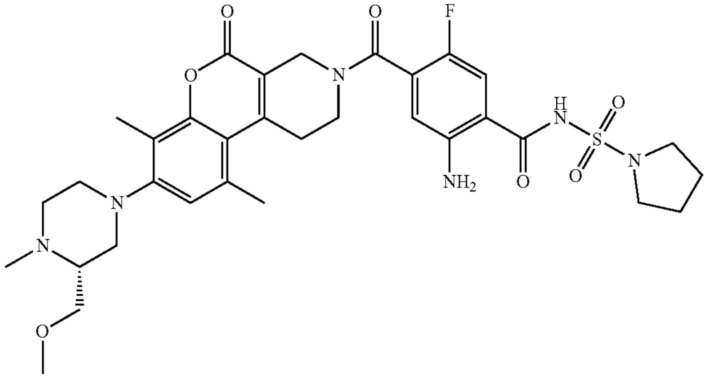 [SMILES: COC[C@H]1CN(c2cc(C)c3c4c(c(=O)oc3c2C)CN(C(=O)c2cc(N)c(C(=O)NS(=O)(=O)N3CCCC3)cc2F)CC4)CCN1C] Synthesised from Intermediates 175 and 6 | HPLC: (System 1, Method H) Rt = 7.40 min, m/z 685.0 (M + H)$^+$ (ES$^+$). $^1$H NMR (400 MHz, DMSO-d$_6$) δ: 7.96 (br s, 2H), 7.65-7.59 (m, 1H), 6.87-6.86 (m, 1H), 6.71-6.52 (m, 1H), 4.48 (br s, 1H), 4.20 (br s, 1H), 3.84 (br s, 1H), 3.60-3.57 (m, 1H), 3.49-3.48 (m, 2H), 3.32-3.31 (m, 7H), 3.22-3.20 (m, 2H), 3.13-3.11 (m, 2H), 3.07-3.04 (m, 1H), 2.92-2.75 (m, 4H), 2.69-2.63 (m, 3H), 2.51 (s, 3H), 2.24-2.21 (m, 3H), 1.81-1.78 (m, 4H). One exchangeable proton not visible. Mixture of rotamers. |
| Example 197 | (R)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(piperidin-1-ylsulfonyl)benzamide 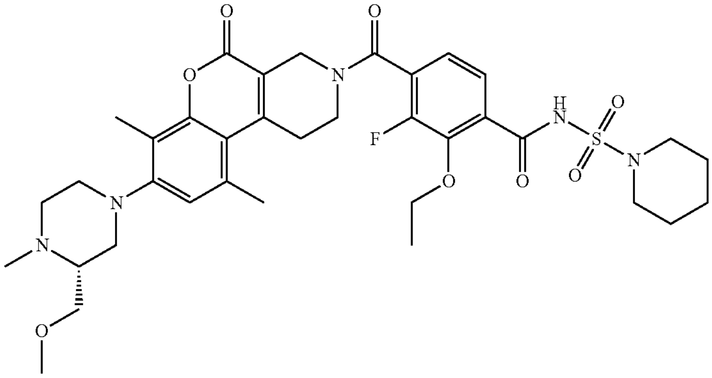 [SMILES: CCOc1c(C(=O)NS(=O)(=O)N2CCCCC2)ccc(C(=O)N2CCc3c(c(=O)oc4c(C)c(N5CCN(C)[C@@H](COC)C5)cc(C)c34)C2)c1F] Synthesised from Intermediates 202 and 6 | HPLC: (System 1, Method H) Rt = 7.24 min, m/z 728.3 (M + H)$^+$ (ES$^+$). $^1$H NMR (400 MHz, DMSO-d$_6$) δ: 11.39 (br s, 1H), 7.34-7.32 (m, 1H), 7.24-7.16 (m, 1H), 6.87-6.85 (m, 1H), 4.51 (br s, 1H), 4.22-4.13 (m, 3H), 3.89-3.86 (m, 1H), 3.58-3.55 (m, 1H), 3.48-3.45 (m, 1H), 3.42-3.38 (m, 1H), 3.28 (s, 3H), 3.23 (br s, 5H), 3.18-3.15 (m, 2H), 3.08-3.05 (m, 1H), 2.94-2.82 (m, 2H), 2.71-2.55 (m, 6H), 2.39 (s, 3H), 2.24-2.20 (m, 3H), 1.57-1.56 (m, 4H), 1.49-1.48 (m, 2H), 1.34-1.28 (m, 3H). Mixture of rotamers. |

-continued

| Example No. | Name/Structure/Intermediates | LCMS/$^1$H NMR data |
|---|---|---|
| Example 198 | (R)-2-ethoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(piperidin-1-ylsulfonyl)benzamide 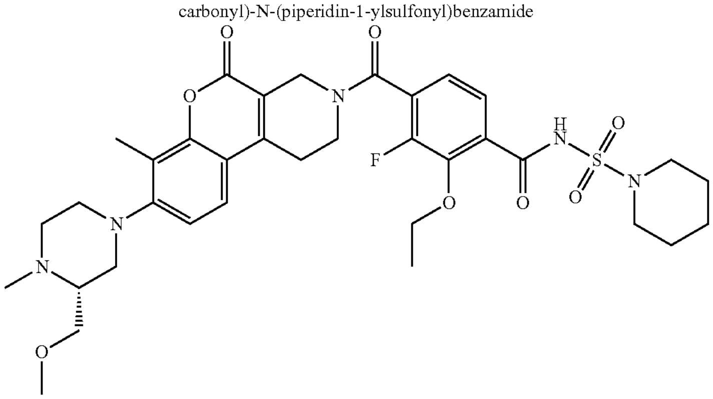 Synthesised from Intermediates 202 and 5 | HPLC: (System 1, Method H) Rt = 7.10 min, m/z 714.4 (M + H)$^+$ (ES$^+$). $^1$H NMR (400 MHz, DMSO-$d_6$) δ: 11.40 (br s, 1H), 7.55 (dd, J = 27.2, 8.8 Hz, 1H), 7.33 (dd, J = 8.0, 3.2 Hz, 1H), 7.22-7.15 (m, 1H), 7.08 (t, J = 8.8 Hz, 1H), 4.53 (br s, 1H), 4.22-4.13 (m, 3H), 3.99-3.96 (m, 1H), 3.59-3.55 (m, 2H), 3.42-3.38 (m, 1H), 3.28 (s, 3H), 3.24 (br s, 4H), 3.19-3.16 (m, 1H), 3.09-3.06 (m, 1H), 2.99-2.85 (m, 4H), 2.71-2.66 (m, 1H), 2.61-2.56 (m, 2H), 2.39 (s, 3H), 2.30-2.26 (m, 3H), 1.57-1.56 (m, 4H), 1.49-1.48 (m, 2H), 1.34-1.28 (m, 3H). Mixture of rotamers. |
| Example 199 | (R)-N-(N-cyclopentyl-N-methylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 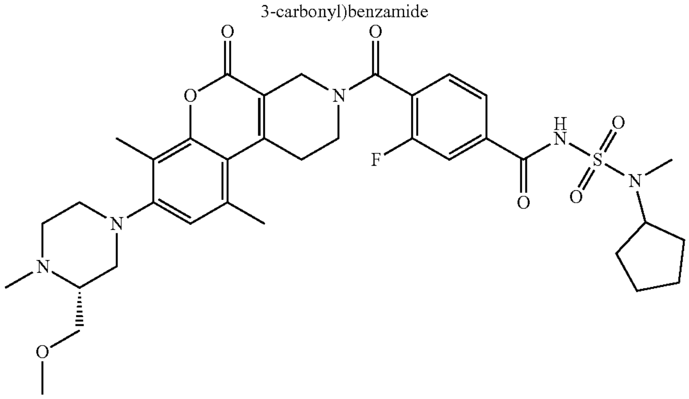 Synthesised from Intermediates 198 and 6 | UPLC: (System 3, Method K) Rt = 4.08 min, m/z 698.6 (M + H)$^+$ (ES$^+$). $^1$H NMR (400 MHz, DMSO-$d_6$) δ: 7.84-7.76 (m, 2H), 7.59-7.54 (m, 1H), 6.72-7.01 (1H), 4.52 (s, 1H), 4.20 (d, J = 8.2 Hz, 2H), 3.88 (s, 1H), 3.59-2.98 (m, 14H), 2.91-2.62 (m, 10H), 2.22 (d, J = 16.9 Hz, 3H), 1.71-1.40 (m, 8H). One exchangeable proton not visible. Mixture of rotamers. |
| Example 200 | (R)-2-(cyclobutyl(methyl)amino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 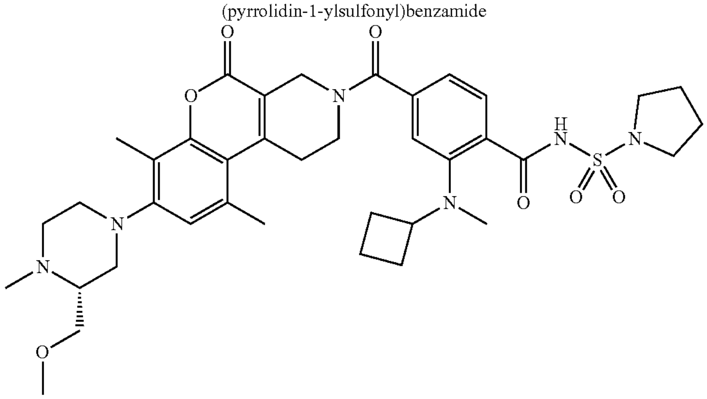 Synthesised from Intermediates 179 and 6 | HPLC: (System 1, Method H) Rt = 9.64 min, m/z 735.0 (M + H)$^+$ (ES$^+$). $^1$H NMR (400 MHz, DMSO-$d_6$) δ: 14.48 (br s, 1H), 8.02-7.97 (m, 1H), 7.57-7.50 (m, 1H), 7.43-7.36 (m, 1H), 6.85 (s, 1H), 4.49 (br s, 1H), 4.26 (br s, 1H), 3.91-3.84 (m, 2H), 3.57-3.53 (m, 1H), 3.47-3.44 (m, 5H), 3.35 (br s, 1H), 3.26 (s, 3H), 3.21 (br s, 2H), 3.14-3.11 (m, 1H), 3.04-3.01 (m, 1H), 2.84-2.79 (m, 2H), 2.68-2.58 (m, 7H), 2.41-2.39 (m, 2H), 2.29 (s, 3H), 2.24-2.19 (m, 3H), 2.11-2.05 (m, 2H), 1.90-1.84 (m, 6H), 1.72-1.63 (m, 2H). |

-continued

| Example No. | Name/Structure/Intermediates | LCMS/$^1$H NMR data |
| --- | --- | --- |
| Example 201 | (R)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(methylamino)-N-(pyrrolidin-1-ylsulfonyl)benzamide 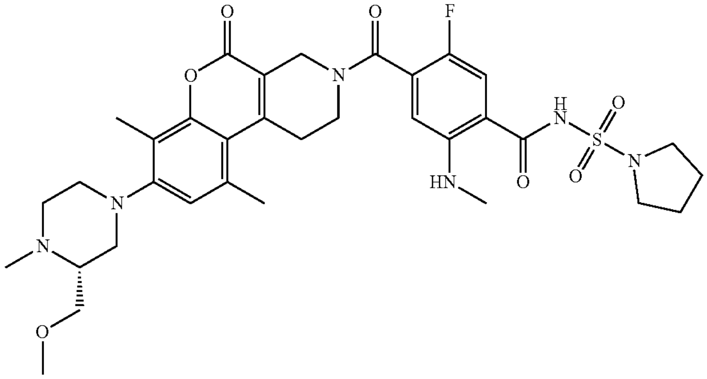 [SMILES: CNc1cc(C(=O)N2CCc3c(c(=O)oc4c(C)c(N5CCN(C)[C@@H](COC)C5)cc(C)c34)C2)c(F)cc1C(=O)NS(=O)(=O)N1CCCC1] Synthesised from Intermediates 176 and 6 | HPLC: (System 1, Method H) Rt = 7.02 min, m/z 699.3 $(M + H)^+$ $(ES^+)$. $^1$H NMR (400 MHz, DMSO-$d_6$) δ: 9.22 (br s, 1H), 7.72-7.66 (m, 1H), 6.88-6.86 (m, 1H), 6.58-6.51 (m, 1H), 4.50 (br s, 1H), 4.20 (br s, 1H), 3.86 (br s, 1H), 3.61-3.57 (m, 1H), 3.53-3.48 (m, 2H), 3.31 (s, 3H), 3.29-3.28 (m, 4H), 3.24-3.21 (m, 2H), 3.17-3.08 (m, 3H), 2.93-2.88 (m, 2H), 2.82-2.76 (m, 5H), 2.70-2.62 (m, 3H), 2.54 (s, 3H), 2.25-2.21 (m, 3H), 1.82-1.76 (m, 4H). One exchangeable proton not visible. Mixture of rotamers. |
| Example 202 | (R)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 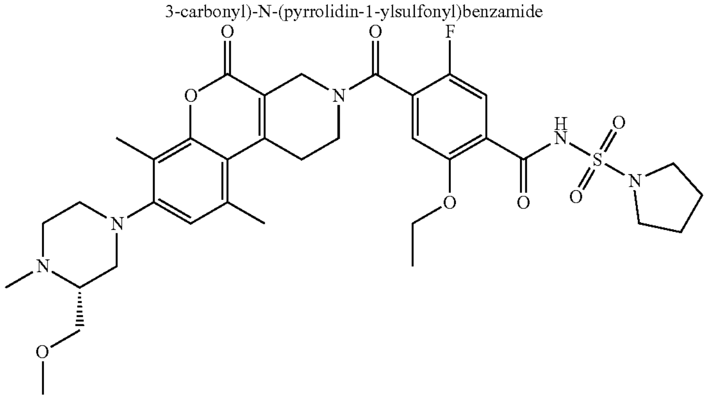 Synthesised from Intermediates 201 and 6 | HPLC: (System 1, Method H) Rt = 7.33 min, m/z 714.4 $(M + H)^+$ $(ES^+)$. $^1$H NMR (400 MHz, DMSO-$d_6$) δ: 11.41 (br s, 1H), 7.46-7.43 (m, 1H), 7.24-7.15 (m, 1H), 6.86-6.84 (m, 1H), 4.51 (br s, 1H), 4.19 (s, 1H), 4.14-4.06 (m, 2H), 3.87 (t, J = 5.2 Hz, 1H), 3.57-3.54 (m, 1H), 3.48-3.42 (m, 5H), 3.37-3.35 (m, 1H), 3.26 (s, 3H), 3.23 (br s, 1H), 3.17-3.12 (m, 2H), 3.05-3.02 (m, 1H), 2.87-2.80 (m, 2H), 2.69-2.61 (m, 4H), 2.46-2.43 (m, 2H), 2.32 (s, 3H), 2.24-2.20 (m, 3H), 1.86-1.83 (m, 4H), 1.35-1.30 (m, 3H). Mixture of rotamers. |
| Example 203 | N-((3-azabicyclo[3.1.0]hexan-3-yl)sulfonyl)-2-(azetidin-1-yl)-5-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide 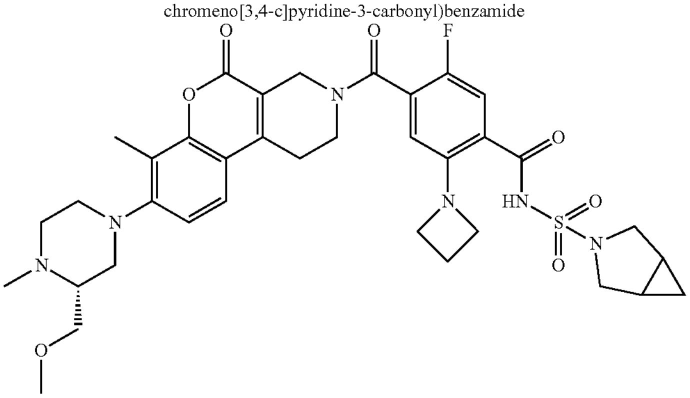 Synthesised from Intermediates 178 and 5 | HPLC: (System 1, Method H) Rt = 7.50 min, m/z 723.0 $(M + H)^+$ $(ES^+)$. $^1$H NMR (400 MHz, DMSO-$d_6$) δ: 11.60 (br s, 1H), 7.59-7.50 (m, 1H), 7.22-7.19 (m, 1H), 7.10-7.06 (m, 1H), 6.50-6.44 (m, 1H), 4.51 (br s, 1H), 4.19 (s, 1H), 3.95-3.94 (m, 1H), 3.82-3.76 (m, 4H), 3.58-3.51 (m, 4H), 3.45-3.43 (m, 2H), 3.41-3.37 (m, 1H), 3.27 (s, 3H), 3.18-3.16 (m, 1H), 3.08-3.06 (m, 1H), 2.98 (br s, 1H), 2.93-2.84 (m, 3H), 2.70-2.65 (m, 1H), 2.55 (br s, 2H), 2.38 (s, 3H), 2.30-2.23 (m, 5H), 1.58-1.57 (m, 2H), 0.66-0.63 (m, 1H), 0.27-0.25 (m, 1H). Mixture of rotamers. |

-continued

| Example No. | Name/Structure/Intermediates | LCMS/$^1$H NMR data |
|---|---|---|
| Example 204 | (R)-3-fluoro-N-((4-fluoropiperidin-1-yl)sulfonyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 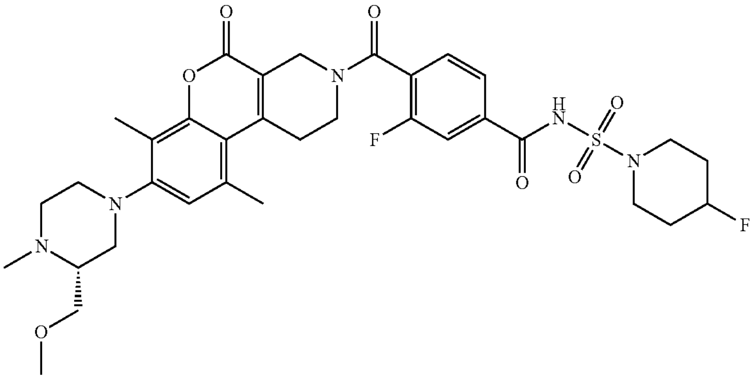 [SMILES: COC[C@H]1CN(c2cc(C)c3c4c(c(=O)oc3c2C)CN(C(=O)c2ccc(C(=O)NS(=O)(=O)N3CCC(F)CC3)cc2F)CC4)CCN1C] Synthesised from Intermediates 200 and 6 | UPLC: (System 3, Method K) Rt = 3.80 min, m/z 702.4 $(M + H)^+$ $(ES^+)$. $^1$H NMR (400 MHz, DMSO-$d_6$) δ: 7.86-7.74 (m, 2H), 7.53-7.44 (m, 1H), 6.90-6.86 (m, 1H), 4.88-4.80 (m, 1H), 4.55-4.49 (m, 1H), 4.20-4.15 (m, 1H), 3.91-3.88 (m, 1H), 3.67-3.43 (m, 3H), 3.31 (s, 7H), 3.26-3.14 (m, 8H), 2.98-2.63 (m, 7H), 2.28-2.20 (m, 3H), 1.94-1.75 (m, 4H). One exchangeable proton not visible. Mixture of rotamers. |
| Example 205 | (R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-propoxy-N-(pyrrolidin-1-ylsulfonyl)benzamide 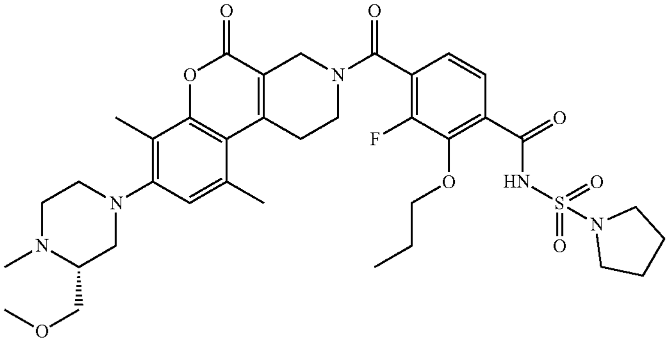 [SMILES: CCCOc1c(C(=O)NS(=O)(=O)N2CCCC2)ccc(C(=O)N2CCc3c(c(=O)oc4c(C)c(N5CCN(C)[C@@H](COC)C5)cc(C)c34)C2)c1F] Synthesised from Intermediates 203 and 6 | HPLC: (System 1, Method H) Rt = 7.28 min, m/z 728.0 $(M + H)^+$ $(ES^+)$. $^1$H NMR (400 MHz, DMSO-$d_6$) δ: 11.49 (br s, 1H), 7.35-7.33 (m, 1H), 7.25-7.16 (m, 1H), 6.86-6.84 (m, 1H), 4.51 (br s, 1H), 4.18 (s, 1H), 4.12-4.05 (m, 2H), 3.87 (t, J = 5.4 Hz, 1H), 3.58-3.54 (m, 1H), 3.47-3.45 (m, 1H), 3.42-3.36 (m, 5H), 3.27 (s, 3H), 3.23 (br s, 1H), 3.16-3.14 (m, 2H), 3.07-3.04 (m, 1H), 2.91-2.81 (m, 2H), 2.69-2.62 (m, 4H), 2.52-2.50 (m, 2H), 2.36 (s, 3H), 2.24-2.20 (m, 3H), 1.86-1.83 (m, 4H), 1.74-1.67 (m, 2H), 0.99-0.93 (m, 3H). Mixture of rotamers. |
| Example 206 | (R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-2-(2,2,2-trifluoroethoxy)benzamide 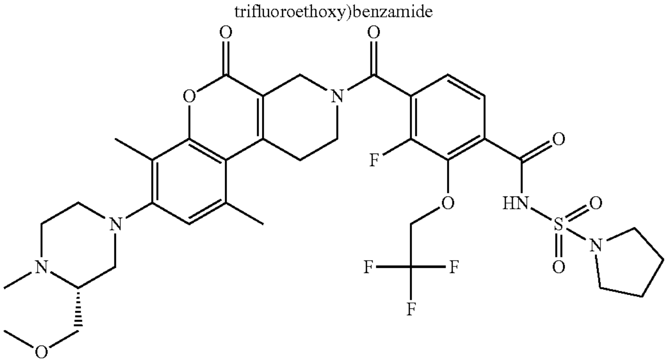 Synthesised from Intermediates 205 and 6 | HPLC: (System 1, Method H) Rt = 7.29 min, m/z 767.8 $(M + H)^+$ $(ES^+)$. $^1$H NMR (400 MHz, DMSO-$d_6$) δ: 11.20 (br s, 1H), 7.42-7.39 (m, 1H), 7.33-7.25 (m, 1H), 6.87-6.86 (m, 1H), 4.85-4.74 (m, 2H), 4.52 (br s, 1H), 4.19 (s, 1H), 3.87 (br s, 1H), 3.59-3.57 (m, 1H), 3.48-3.45 (m, 2H), 3.34-3.33 (m, 4H), 3.29 (s, 3H), 3.24-3.18 (m, 2H), 3.14-3.09 (m, 2H), 3.02-2.99 (m, 1H), 2.90-2.85 (m, 1H), 2.74-2.62 (m, 6H), 2.46 (s, 3H), 2.24-2.21 (m, 3H), 1.83-1.78 (m, 4H). Mixture of rotamers. |

-continued

| Example No. | Name/Structure/Intermediates | LCMS/$^1$H NMR data |
|---|---|---|
| Example 207 | N-((3-azabicyclo[3.1.0]hexan-3-yl)sulfonyl)-2-cyclopropoxy-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 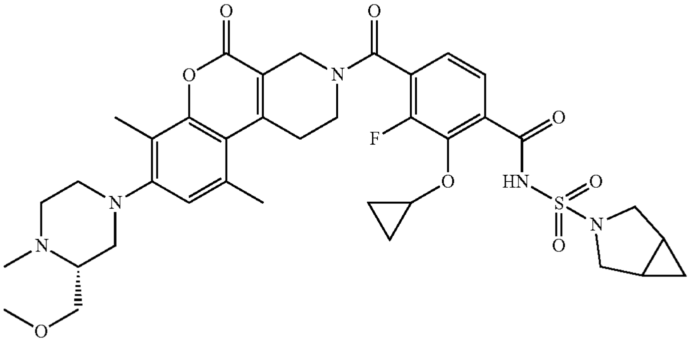 [SMILES: COC[C@H]1CN(c2cc(C)c3c4c(c(=O)oc3c2C)CN(C(=O)c2ccc(C(=O)NS(=O)(=O)N3CC5CC5C3)c(OC3CC3)c2F)CC4)CCN1C] Synthesised from Intermediates 204 and 6 | HPLC: (System 1, Method H) Rt = 7.12 min, m/z 737.9 (M + H)$^+$ (ES$^+$). $^1$H NMR (400 MHz, DMSO-$d_6$) δ: 11.38 (br s, 1H), 7.31-7.29 (m, 1H), 7.26-7.17 (m, 1H), 6.87-6.85 (m, 1H), 4.52 (br s, 1H), 4.30-4.24 (m, 1H), 4.19 (s, 1H), 3.89-3.87 (m, 1H), 3.59-3.55 (m, 1H), 3.50-3.40 (m, 6H), 3.28 (s, 3H), 3.24 (br s, 1H), 3.19-3.16 (m, 2H), 3.09-3.07 (m, 1H), 2.97-2.95 (m, 1H), 2.88-2.83 (m, 1H), 2.73-2.62 (m, 6H), 2.42 (s, 3H), 2.24-2.20 (m, 3H), 1.58-1.56 (m, 2H), 0.82-0.78 (m, 2H), 0.66-0.59 (m, 3H), 0.32-0.29 (m, 1H). Mixture of rotamers. |
| Example 208 | N-((3-azabicyclo[3.1.0]hexan-3-yl)sulfonyl)-4-(7-chloro-8-((R)-3-(methoxymethyl)-4-methylpiperazin-1-yl)-5-oxo-1,3,4,5-tetrahydro-2H-chromeno[3,4-c]pyridine-3-carbonyl)-2-ethoxy-3-fluorobenzamide 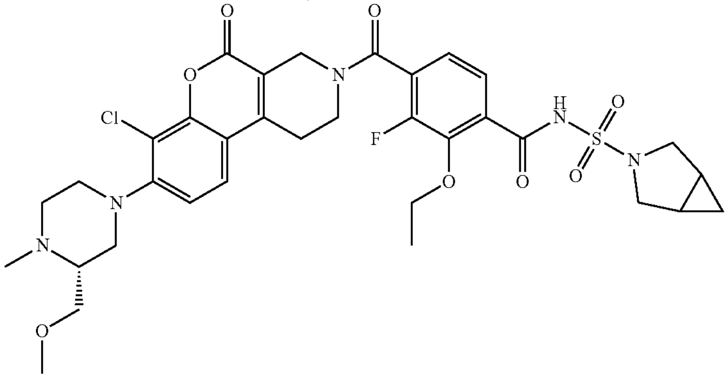 [SMILES: CCOc1c(C(=O)NS(=O)(=O)N2CC3CC3C2)ccc(C(=O)N2CCc3c(c(=O)oc4c(Cl)c(N5CCN(C)[C@@H](COC)C5)ccc34)C2)c1F] Synthesised from Intermediates 206 and 7 | HPLC: (System 1, Method H) Rt = 6.95 min, m/z 731.8 (M + H)$^+$ (ES$^+$). $^1$H NMR (400 MHz, DMSO-$d_6$) δ: 11.59 (br s, 1H), 7.71-7.62 (m, 1H), 7.34-7.31 (m, 1H), 7.23-7.16 (m, 2H), 4.54 (br s, 1H), 4.22-4.15 (m, 3H), 3.98 (t, J = 5.8 Hz, 1H), 3.60-3.51 (m, 4H), 3.47-3.37 (m, 5H), 3.28 (s, 3H), 3.01-2.92 (m, 4H), 2.77-2.72 (m, 1H), 2.59-2.51 (m, 2H), 2.37 (s, 3H), 1.60-1.58 (m, 2H), 1.34-1.28 (m, 3H), 0.67-0.65 (m, 1H), 0.31-0.29 (m, 1H). Mixture of rotamers. |
| Example 209 | (R)-N-((7-azabicyclo[2.2.1]heptan-7-yl)sulfonyl)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-ethoxy-3-fluorobenzamide 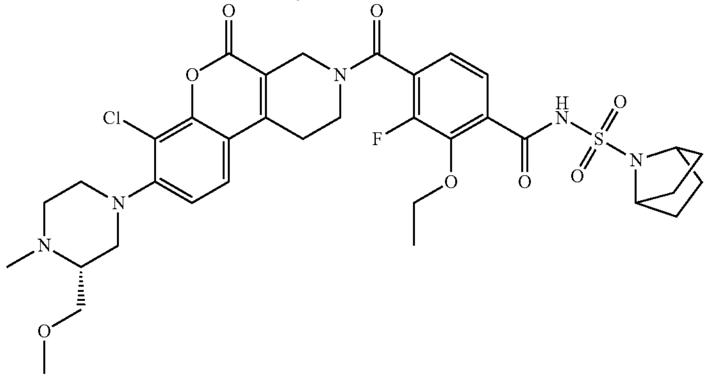 Synthesised from Intermediates 207 and 7 | HPLC: (System 1, Method H) Rt = 6.96 min, m/z 745.8 (M + H)$^+$ (ES$^+$). $^1$H NMR (400 MHz, DMSO-$d_6$) δ: 11.56 (br s, 1H), 7.71-7.62 (, 1H), 7.29-7.26 (m, 1H), 7.23-7.16 (m, 2H), 4.54 (br s, 1H), 4.20-4.11 (m, 5H), 3.97 (t, J = 5.6 Hz, 1H), 3.60-3.55 (m, 2H), 3.46-3.39 (m, 3H), 3.28 (s, 3H), 3.01-2.93 (m, 4H), 2.77-2.72 (m, 1H), 2.60-2.51 (m, 2H), 2.38 (s, 3H), 1.86-1.84 (m, 4H), 1.45-1.44 (m, 4H), 1.33-1.27 (m, 3H). Mixture of rotamers. |

-continued

| Example No. | Name/Structure/Intermediates | LCMS/$^1$H NMR data |
|---|---|---|
| Example 210 | N-(((3aR,6a S)-hexahydrocyclopenta[c]pyrrol-2(1H)-yl) sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 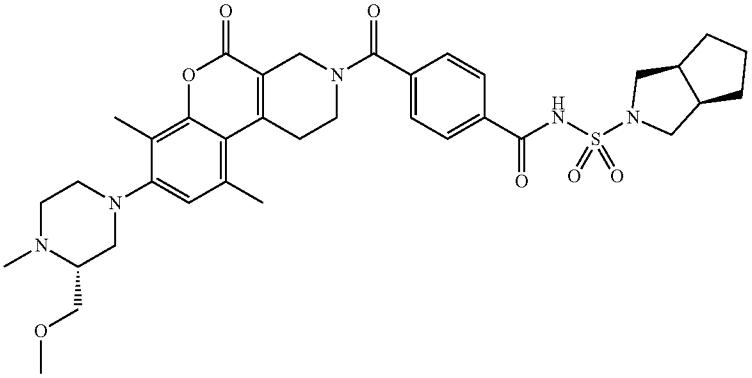 [SMILES: COC[C@H]1CN(c2cc(C)c3c4c(c(=O)oc3c2C)CN(C(=O)c2ccc(C(=O)NS(=O)(=O)N3C[C@H]5CCC[C@H]5C3)cc2)CC4)CCN1C] Synthesised from Intermediates 194 and 6 | UPLC: (System 3, Method K) Rt = 3.95 min, m/z 692.5 $(M + H)^+$ $(ES^+)$. $^1$H NMR (400 MHz, DMSO-$d_6$) δ: 11.55 (br s, 1H), 8.00-7.98 (m, 2H), 7.58 (s, 2H), 6.85 (s, 1H), 4.48 (br s, 1H), 4.27 (br s, 1H), 3.85 (br s, 1H), 3.56 (dd, J = 9.8, 3.9 Hz, 1H), 3.50-3.47 (m, 2H), 3.42-3.38 (m, 1H), 3.28-3.14 (m, 8H), 3.08-3.05 (m, 1H), 2.93-2.82 (m, 2H), 2.71-2.66 (m, 4H), 2.57-2.54 (m, 1H), 2.38 (s, 3H), 2.22-2.20 (m, 5H), 1.52-1.42 (m, 6H), 1.32-1.23 (m, 2H). |
| Example 211 | 4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((octahydro-2H-isoindol-2-yl)sulfonyl)benzamide 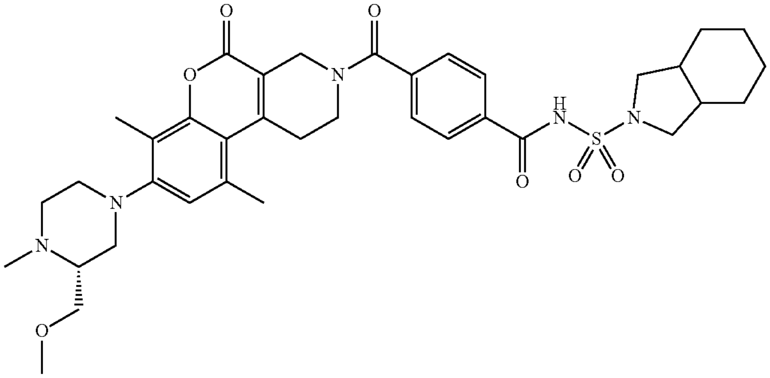 [SMILES: COC[C@H]1CN(c2cc(C)c3c4c(c(=O)oc3c2C)CN(C(=O)c2ccc(C(=O)NS(=O)(=O)N3CC5CCCCC5C3)cc2)CC4)CCN1C] Synthesised from Intermediates 196 and 6 | UPLC: (System 3, Method K) Rt = 4.04 min, m/z 706.5 $(M + H)^+$ $(ES^+)$. $^1$H NMR (400 MHz, DMSO-$d_6$) δ: 8.00-7.98 (m, 2H), 7.56 (s, 2H), 6.86 (s, 1H), 4.47-4.28 (m, 3H), 3.86-3.84 (m, 1H), 3.58 (dd, J = 10.3, 3.0 Hz, 1H), 3.49-3.47 (m, 4H), 3.34 (s, 7H), 3.21-3.16 (m, 3H), 3.12-2.98 (m, 5H), 2.91-2.58 (m, 8H), 2.35-2.20 (m, 3H), 1.74-1.59 (m, 3H), 1.54-1.31 (m, 3H). One exchangeable proton not observed. |
| Example 212 | (R)-2-cyclopropoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 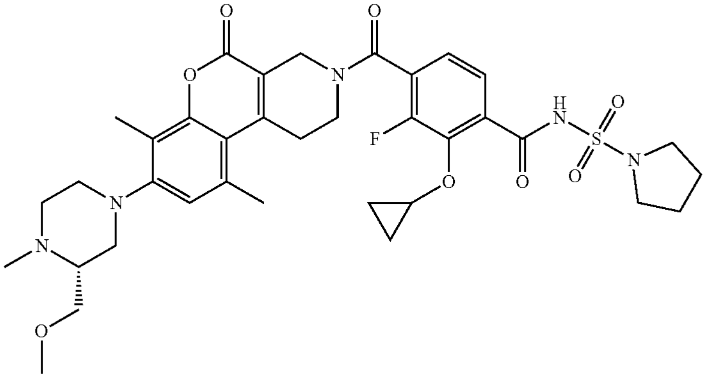 [SMILES: COC[C@H]1CN(c2cc(C)c3c4c(c(=O)oc3c2C)CN(C(=O)c2ccc(C(=O)NS(=O)(=O)N3CCCC3)c(OC3CC3)c2F)CC4)CCN1C] Synthesised from Intermediates 208 and 6 | HPLC: (System 1, Method H) Rt = 7.01 min, m/z 726.0 $(M + H)^+$ $(ES^+)$. $^1$H NMR (400 MHz, DMSO-$d_6$) δ: 11.53 (br s, 1H), 7.34-7.32 (m, 1H), 7.28-7.19 (m, 1H), 6.86-6.85 (m, 1H), 4.52 (br s, 1H), 4.28-4.23 (m, 1H), 4.23 (s, 1H), 3.89-3.87 (m, 1H), 3.58-3.54 (m, 1H), 3.46-3.45 (m, 1H), 3.40-3.37 (m, 5H), 3.27 (s, 3H), 3.24 (br s, 1H), 3.17-3.14 (m, 2H), 3.07-3.04 (m, 1H), 2.92-2.81 (m, 2H), 2.69-2.62 (m, 4H), 2.54-2.51 (m, 2H), 2.37 (s, 3H), 2.24-2.20 (m, 3H), 1.86-1.83 (m, 4H), 0.80-0.77 (m, 2H), 0.63-0.59 (m, 2H). Mixture of rotamers. |

-continued

| Example No. | Name/Structure/Intermediates | LCMS/$^1$H NMR data |
|---|---|---|
| Example 213 | (R)-N-((7-azabicyclo[2.2.1]heptan-7-yl)sulfonyl)-2-cyclopropoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 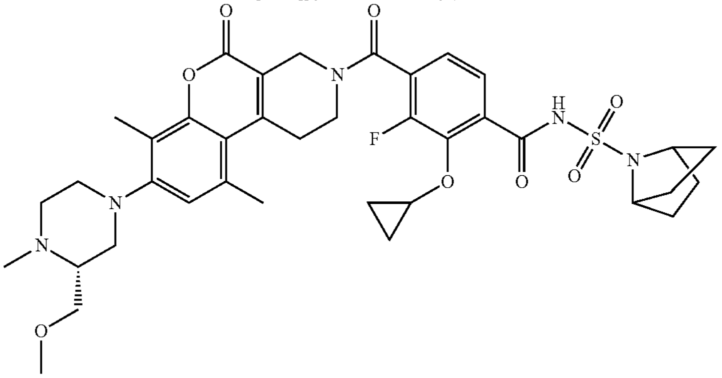 Synthesised from Intermediates 209 and 6 | HPLC: (System 1, Method H) Rt = 7.16 min, m/z 751.9 $(M + H)^+$ $(ES^+)$. $^1$H NMR (400 MHz, DMSO-$d_6$) δ: 11.44 (br s, 1H), 7.27-7.16 (m, 2H), 6.86-6.85 (m, 1H), 4.52 (br s, 1H), 4.28-4.21 (m, 1H), 4.18 (br s, 3H), 3.89-3.86 (m, 1H), 3.59-3.55 (m, 1H), 3.47-3.39 (m, 2H), 3.28 (s, 3H), 3.24 (br s, 1H), 3.18-3.16 (m, 2H), 3.09-3.06 (m, 1H), 2.96-2.93 (m, 1H), 2.88-2.83 (m, 1H), 2.72-2.58 (m, 6H), 2.41 (s, 3H), 2.24-2.20 (m, 3H), 1.85-1.83 (m, 4H), 1.43-1.41 (m, 4H), 0.81-0.77 (m, 2H), 0.61-0.57 (m, 2H). Mixture of rotamers. |
| Example 214 | N-((3-azabicyclo[3.1.0]hexan-3-yl)sulfonyl)-2-ethoxy-4-(7-ethyl-8-((R)-3-(methoxymethyl)-4-methylpiperazin-1-yl)-5-oxo-1,3,4,5-tetrahydro-2H-chromeno[3,4-c]pyridine-3-carbonyl)-3-fluorobenzamide 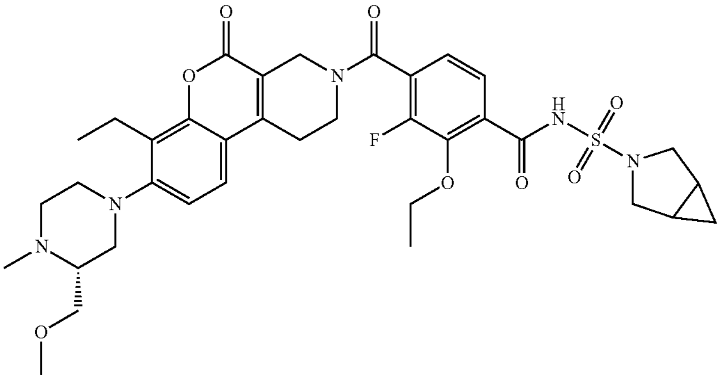 [SMILES: CCOc1c(C(=O)NS(=O)(=O)N2CC3CC3C2)ccc(C(=O)N2CCc3c(c(=O)oc4c(CC)c(N5CCN(C)[C@@H](COC)C5)ccc34)C2)c1F] Synthesised from Intermediates 206 and 229 | HPLC: (System 1, Method H) Rt = 7.2 min, m/z 726.0 $(M + H)^+$ $(ES^+)$. $^1$H NMR (400 MHz, DMSO-$d_6$) δ: 11.44 (br s, 1H), 7.61-7.52 (m, 1H), 7.34-7.31 (m, 1H), 7.23-7.13 (m, 2H), 4.54 (br s, 1H), 4.22-4.13 (m, 3H), 3.97 (t, J = 5.8 Hz, 1H), 3.60-3.55 (m, 2H), 3.53-3.50 (m, 2H), 3.46-3.44 (m, 2H), 3.41-3.37 (m, 1H), 3.28 (s, 3H), 3.13-3.10 (m, 1H), 2.99-2.89 (m, 5H), 2.86-2.78 (m, 2H), 2.73-2.68 (m, 1H), 2.63-2.51 (m, 2H), 2.39 (s, 3H), 1.59-1.57 (m, 2H), 1.34-1.28 (m, 3H), 1.24-1.16 (m, 3H), 0.67-0.62 (m, 1H), 0.32-0.29 (m, 1H). Mixture of rotamers. |
| Example 215 | (R)-N-((7-azabicyclo[2.2.1]heptan-7-yl)sulfonyl)-2-ethoxy-4-(7-ethyl-8-(3-(methoxymethyl)-4-methylpiperazin-1-yl)-5-oxo-1,3,4,5-tetrahydro-2H-chromeno[3,4-c]pyridine-3-carbonyl)-3-fluorobenzamide 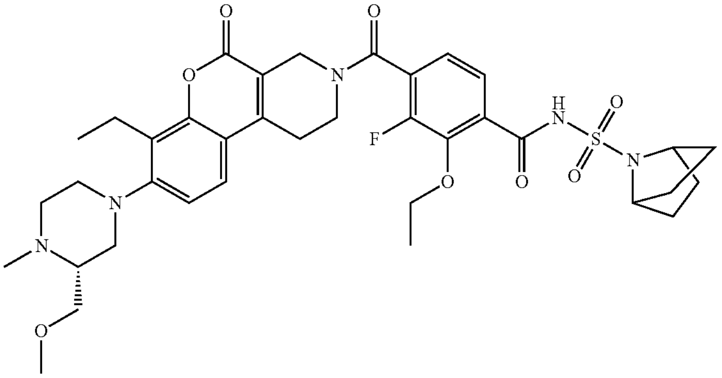 [SMILES: CCOc1c(C(=O)NS(=O)(=O)N2C3CCC2CC3)ccc(C(=O)N2CCc3c(c(=O)oc4c(CC)c(N5CCN(C)[C@@H](COC)C5)ccc34)C2)c1F] Synthesised from Intermediates 207 and 229 | HPLC: (System 1, Method H) Rt = 7.23 min, m/z 740.0 $(M + H)^+$ $(ES^+)$. $^1$H NMR (400 MHz, DMSO-$d_6$) δ: 11.48 (br s, 1H), 7.61-7.52 (m, 1H), 7.28-7.26 (m, 1H), 7.21-7.13 (m, 2H), 4.53 (br s, 1H), 4.20-4.11 (m, 5H), 3.97 (t, J = 5.8 Hz, 1H), 3.60-3.54 (m, 2H), 3.41-3.37 (m, 1H), 3.28 (s, 3H), 3.12-3.10 (m, 1H), 2.99-2.89 (m, 5H), 2.86-2.78 (m, 2H), 2.73-2.68 (m, 1H), 2.63-2.53 (m, 2H), 2.39 (s, 3H), 1.86-1.84 (m, 4H), 1.44-1.43 (m, 4H), 1.33-1.26 (m, 3H), 1.24-1.16 (m, 3H). Mixture of rotamers. |

-continued

| Example No. | Name/Structure/Intermediates | LCMS/$^1$H NMR data |
|---|---|---|
| Example 216 | (R)-N-(N,N-dicyclopropylsulfamoyl)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 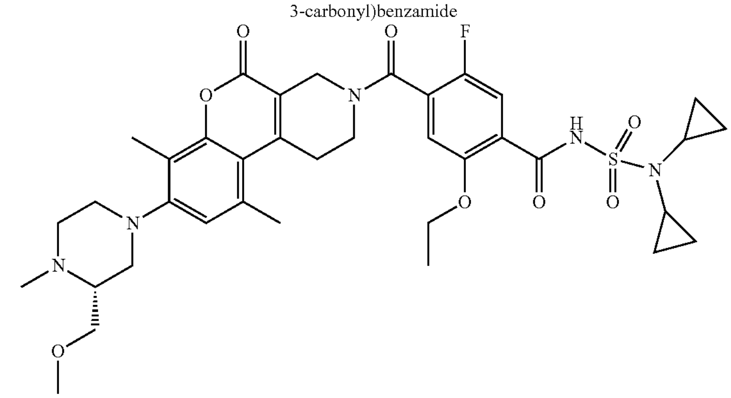 Synthesised from Intermediates 181 and 6 | UPLC: (System 3, Method K) Rt = 4.02 min, m/z 740.7 $(M + H)^+$ $(ES^+)$. $^1$H NMR (400 MHz, DMSO-$d_6$) δ: 7.45-7.43 (m, 1H), 7.24-7.15 (m, 1H), 6.86-6.84 (m, 1H), 4.51 (br s, 1H), 4.19 (s, 1H), 4.16-4.07 (m, 2H), 3.88-3.86 (m, 1H), 3.57-3.44 (m, 2H), 3.39-3.31 (m, 7H), 3.23-3.04 (m, 4H), 2.90-2.81 (m, 2H), 2.74-2.69 (m, 3H), 2.66-2.61 (m, 2H), 2.40-2.32 (m, 3H), 2.24-2.15 (m, 3H), 1.34-1.23 (m, 3H), 0.87-0.77 (m, 4H), 0.74-0.62 (m, 4H). One exchangeable proton not visible. Mixture of rotamers. |
| Example 217 | (R)-N-((3,3-dimethylpyrrolidin-1-yl)sulfonyl)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 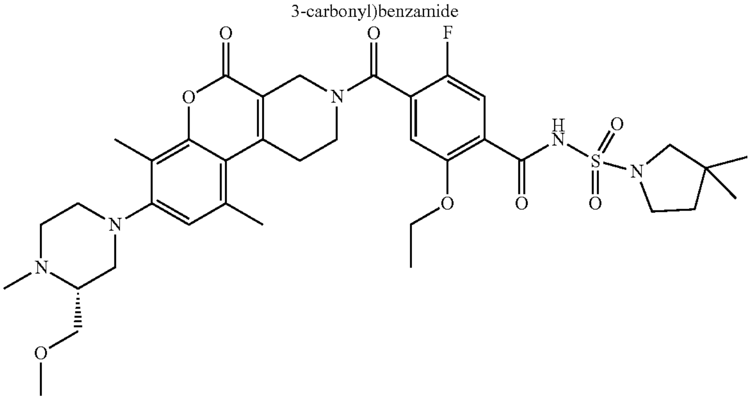 Synthesised from Intermediates 183 and 6 | UPLC: (System 3, Method K) Rt = 4.30 min, m/z 742.7 $(M + H)^+$ $(ES^+)$. $^1$H NMR (400 MHz, DMSO-$d_6$) δ: 11.38 (br s, 1H), 7.44-7.41 (m, 1H), 7.25-7.16 (m, 1H), 6.86-6.84 (m, 1H), 4.61 (br s, 1H), 4.19-4.07 (m, 3H), 3.88-3.86 (m, 1H), 3.59-3.53 (m, 3H), 3.48-3.44 (m, 1H), 3.36-3.31 (m, 6H), 3.23 (s, 1H), 3.16-3.12 (m, 3H), 3.05-3.02 (m, 1H), 2.86-2.79 (m, 2H), 2.69-2.61 (m, 3H), 2.46-2.38 (m, 2H), 2.31 (s, 3H), 2.23-2.19 (m, 3H), 1.69-1.65 (m, 2H), 1.36-1.27 (m, 3H), 1.06-1.05 (m, 6H). Mixture of rotamers. |
| Example 218 | (R)-N-((7-azabicyclo[2.2.1]heptan-7-yl)sulfonyl)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 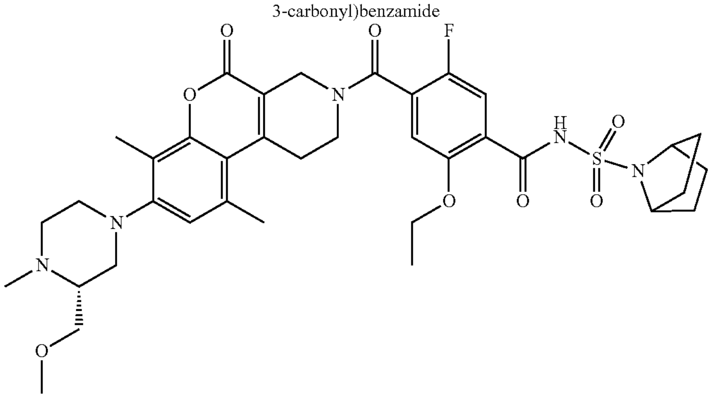 Synthesised from Intermediates 184 and 6 | UPLC: (System 3, Method K) Rt = 3.91 min, m/z 740.6 $(M + H)^+$ $(ES^+)$. $^1$H NMR (400 MHz, DMSO-$d_6$) δ: 11.4 (br s, 1H), 7.39-7.35 (m, 1H), 7.22-7.21 (m, 1H), 6.86-6.84 (m, 1H), 4.51 (br s, 1H), 4.21-4.04 (m, 5H), 3.87-3.85 (m, 1H), 3.57-3.54 (m, 1H), 3.47-3.44 (m, 1H), 3.41-3.34 (m, 2H), 3.26 (s, 3H), 3.22-3.03 (m, 5H), 2.89-2.76 (m, 2H), 2.69-2.61 (m, 4H), 2.41-2.32 (m, 3H), 2.23-2.19 (m, 3H), 1.91-1.79 (m, 4H), 1.50-1.38 (m, 4H), 1.38-1.28 (m, 3H). Mixture of rotamers. |

-continued

| Example No. | Name/Structure/Intermediates | LCMS/$^1$H NMR data |
|---|---|---|
| Example 219 | N-((3-azabicyclo[3.1.0]hexan-3-yl)sulfonyl)-2-ethoxy-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 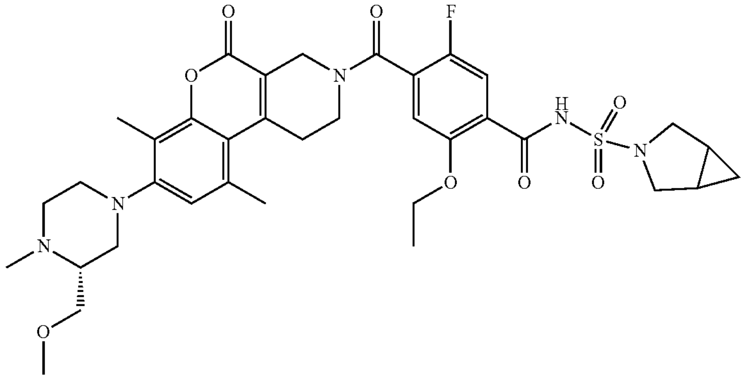 [SMILES: CCOc1cc(C(=O)N2CCc3c(c(=O)oc4c(C)c(N5CCN(C)[C@@H](COC)C5)cc(C)c34)C2)c(F)cc1C(=O)NS(=O)(=O)N1CC2CC2C1] Synthesised from Intermediates 185 and 6 | UPLC: (System 3, Method K) Rt = 3.92 min, m/z 726.7 $(M + H)^+$ $(ES^+)$. $^1$H NMR (400 MHz, DMSO-$d_6$) δ: 7.42-7.36 (m, 1H), 7.24-7.11 (m, 1H), 6.85-6.83 (m, 1H), 4.51 (br s, 1H), 4.19 (s, 1H), 4.14-4.05 (m, 2H), 3.87 (s, 1H), 3.57-3.42 (m, 5H), 3.35-3.32 (m, 6H), 3.14-3.01 (m, 3H), 2.84-2.79 (m, 2H), 2.68 (s, 1H), 2.65-2.59 (m, 3H), 2.43-2.39 (m, 2H), 2.33-2.30 (m, 3H), 2.23-2.19 (m, 3H), 1.57-1.50 (m, 2H), 1.36-1.31 (m, 3H), 0.64-0.59 (m, 1H), 0.33-0.29 (m, 1H). One exchangeable proton not visible. Mixture of rotamers. |
| Example 220 | (R)-N-((2-azaspiro[3.3]heptan-2-yl)sulfonyl)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 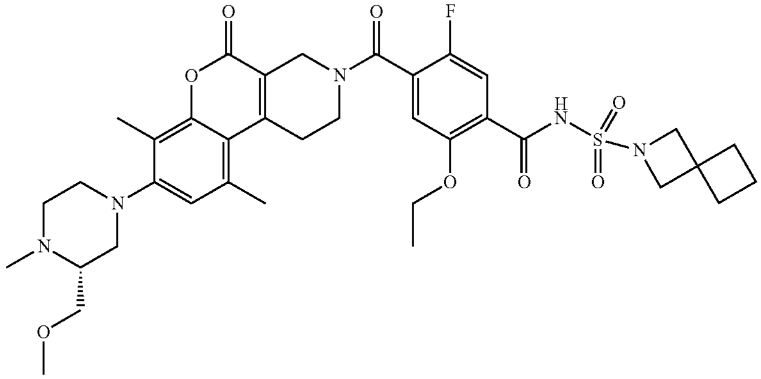 [SMILES: CCOc1cc(C(=O)N2CCc3c(c(=O)oc4c(C)c(N5CCN(C)[C@@H](COC)C5)cc(C)c34)C2)c(F)cc1C(=O)NS(=O)(=O)N1CC2(CCC2)C1] Synthesised from Intermediates 187 and 6 | UPLC: (System 3, Method K) Rt = 3.94 min, m/z 740.9 $(M + H)^+$ $(ES^+)$. $^1$H NMR (400 MHz, DMSO-$d_6$) δ: 11.24 (br s, 1H), 7.42-7.40 (m, 1H), 7.23-7.15 (m, 1H), 6.87-6.85 (m, 1H), 4.51 (br s, 1H), 4.19-4.07 (m, 3H), 4.00 (s, 4H), 3.88-3.81 (m, 1H), 3.58-3.38 (m, 3H), 3.28 (s, 3H), 3.23-3.05 (m, 4H), 2.93-2.82 (m, 2H), 2.69-2.65 (m, 3H), 2.62-2.54 (m, 3H), 2.38-2.33 (m, 3H), 2.27-2.20 (m, 3H), 2.12-2.09 (m, 4H), 1.79-1.72 (m, 2H), 1.36-1.31 (m, 3H). Mixture of rotamers. |
| Example 221 | N-((3-oxa-8-azabicyclo[3.2.1]octan-8-yl)sulfonyl)-2-ethoxy-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 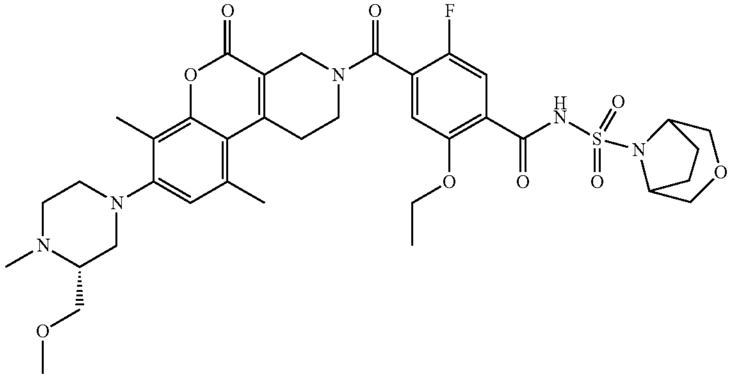 [SMILES: CCOc1cc(C(=O)N2CCc3c(c(=O)oc4c(C)c(N5CCN(C)[C@@H](COC)C5)cc(C)c34)C2)c(F)cc1C(=O)NS(=O)(=O)N1C2CCC1COC2] Synthesised from Intermediates 189 and 6 | UPLC: (System 3, Method K) Rt = 3.72 min, m/z 756.6 $(M + H)^+$ $(ES^+)$. $^1$H NMR (400 MHz, DMSO-$d_6$) δ: 11.41 (br s, 1H), 7.36-7.34 (m, 1H), 7.20-7.12 (m, 1H), 6.86-6.84 (m, 1H), 4.51 (br s, 1H), 4.19-4.04 (m, 5H), 3.87-3.85 (m, 1H), 3.61-3.54 (m, 5H), 3.48-3.45 (m, 1H), 3.39-3.35 (m, 2H), 3.27 (s, 3H), 3.23-3.04 (m, 5H), 2.90-2.81 (m, 2H), 2.69-2.61 (m, 4H), 2.34 (s, 3H), 2.24-2.20 (m, 3H), 2.03-1.95 (m, 2H), 1.85-1.80 (m, 2H), 1.34-1.23 (m, 3H). Mixture of rotamers. |

-continued

| Example No. | Name/Structure/Intermediates | LCMS/$^1$H NMR data |
|---|---|---|
| Example 222 | (R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-2-(3,3,3-trifluoropropoxy)benzamide 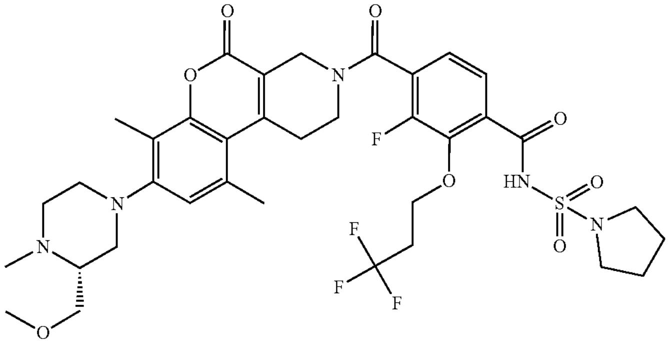 [SMILES: COC[C@H]1CN(c2cc(C)c3c4c(c(=O)oc3c2C)CN(C(=O)c2ccc(C(=O)NS(=O)(=O)N3CCCC3)c(OCCC(F)(F)F)c2F)CC4)CCN1C] Synthesised from Intermediates 210 and 6 | HPLC: (System 1, Method H) Rt = 7.34 min, m/z 781.9 $(M + H)^+$ $(ES^+)$. $^1$H NMR (400 MHz, DMSO-$d_6$) δ: 11.40 (br s, 1H), 7.37-7.35 (m, 1H), 7.29-7.21 (m, 1H), 6.87-6.85 (m, 1H), 4.52 (br s, 1H), 4.36-4.29 (m, 2H), 4.19 (br s, 1H), 3.88 (t, J = 5.4 Hz, 1H), 3.58-3.55 (m, 1H), 3.48-3.47 (m, 1H), 3.43-3.36 (m, 5H), 3.28 (s, 3H), 3.24 (br s, 1H), 3.18-3.15 (m, 2H), 3.09-3.06 (m, 1H), 2.96-2.93 (m, 1H), 2.88-2.85 (m, 1H), 2.84-2.73 (m, 2H), 2.71-2.51 (m, 6H), 2.40 (s, 3H), 2.24-2.20 (m, 3H), 1.85-1.82 (m, 4H). Mixture of rotamers. |
| Example 223 | (R)-3-ethoxy-2-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 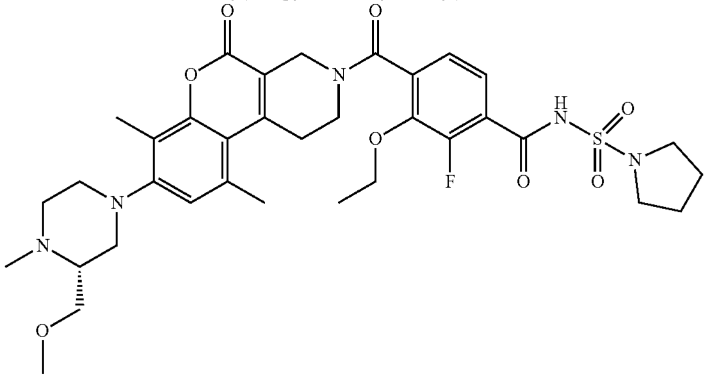 Synthesised from Intermediates 211 and 6 | UPLC: (System 3, Method K) Rt = 3.82 min, m/z 714.6 $(M + H)^+$ $(ES^+)$. $^1$H NMR (400 MHz, DMSO-$d_6$) δ: 7.35-7.33 (m, 1H), 7.25-7.16 (m, 1H), 6.86-6.84 (m, 1H), 4.51 (br s, 1H), 4.35-4.00 (m, 3H), 3.89-3.86 (m, 1H), 3.62-3.45 (m, 2H), 3.42-3.37 (m, 4H), 3.35-3.32 (m, 5H), 3.23-3.03 (m, 5H), 2.94-2.80 (m, 2H), 2.69-2.62 (m, 4H), 2.34 (s, 3H), 2.23-2.20 (m, 3H), 1.91-1.81 (m, 4H), 1.33-1.15 (m, 3H). One exchangeable proton not visible. Mixture of rotamers. |
| Example 224 | (R)-5-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 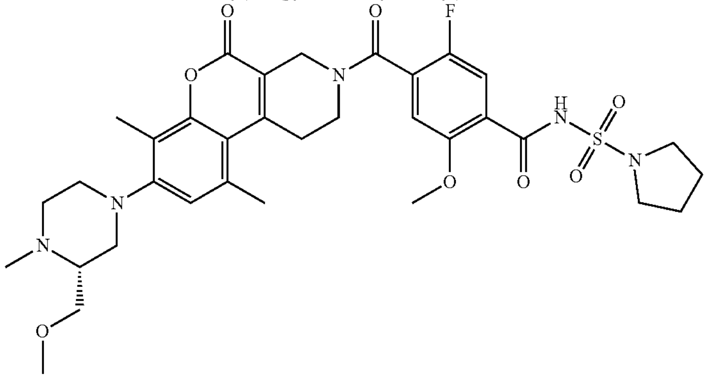 Synthesised from Intermediates 213 and 6 | HPLC: (System 1, Method H) Rt = 6.86 min, m/z 700.0 $(M + H)^+$ $(ES^+)$. $^1$H NMR (400 MHz, DMSO-$d_6$) δ: 11.40 (br s, 1H), 7.46-7.43 (m, 1H), 7.26-7.17 (m, 1H), 6.86-8.64 (m, 1H), 4.52 (br s, 1H), 4.19 (s, 1H), 3.88-3.82 (m, 4H), 3.57-3.54 (m, 1H), 3.48-3.46 (m, 1H), 3.43-3.40 (m, 4H), 3.37-3.35 (m, 1H), 3.27 (s, 3H), 3.23 (br s, 1H), 3.15-3.13 (m, 2H), 3.05-3.02 (m, 1H), 2.87-2.80 (m, 2H), 2.69-2.62 (m, 4H), 2.49-2.44 (m, 2H), 2.32 (s, 3H), 2.24-2.20 (m, 3H), 1.86-1.83 (m, 4H). Mixture of rotamers. |

-continued

| Example No. | Name/Structure/Intermediates | LCMS/$^1$H NMR data |
|---|---|---|
| Example 225 | (R)-5-fluoro-2-(methoxy-d3)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 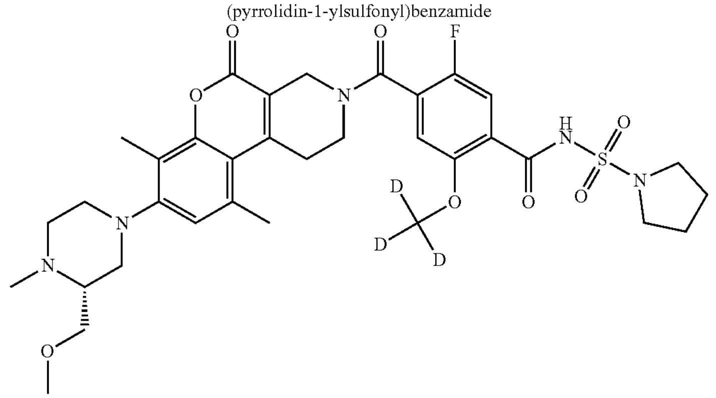 Synthesised from Intermediates 215 and 6 | HPLC: (System 1, Method H) Rt = 6.87 min, m/z 703.0 $(M + H)^+$ $(ES^+)$. $^1$H NMR (400 MHz, DMSO-$d_6$) δ: 11.42 (br s, 1H), 7.46-7.43 (m, 1H), 7.25-7.16 (m, 1H), 6.86-6.84 (m, 1H), 4.52 (br s, 1H), 4.19 (s, 1H), 3.88 (br s, 1H), 3.57-3.54 (m, 1H), 3.48-3.46 (m, 1H), 3.43-3.40 (m, 4H), 3.37-3.35 (m, 1H), 3.27 (s, 3H), 3.25-3.23 (m, 1H), 3.15-3.13 (m, 2H), 3.05-3.03 (m, 1H), 2.87-2.80 (m, 2H), 2.69-2.62 (m, 4H), 2.47-2.44 (m, 2H), 2.32 (s, 3H), 2.24-2.20 (m, 3H), 1.86-1.83 (m, 4H). Mixture of rotamers. |
| Example 226 | (R)-N-((7-azabicyclo[2.2.1]heptan-7-yl)sulfonyl)-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 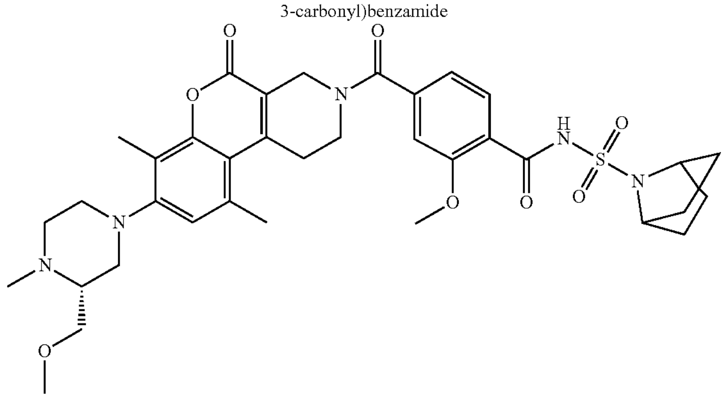 Synthesised from Intermediates 216 and 6 | HPLC: (System 1, Method H) Rt = 7.01 min, m/z 708.0 $(M + H)^+$ $(ES^+)$. $^1$H NMR (400 MHz, DMSO-$d_6$) δ: 11.45 (br s, 1H), 7.46 (d, J = 7.6 Hz, 1H), 7.21-7.17 (m, 1H), 7.13-7.11 (m, 1H), 6.85 (s, 1H), 4.48 (br s, 1H), 4.28 (br s, 1H), 4.21 (br s, 2H), 3.87-3.84 (m, 4H), 3.57-3.50 (m, 2H), 3.36-3.33 (m, 1H), 3.26 (s, 3H), 3.21 (br s, 2H), 3.14-3.12 (m, 1H), 3.04-3.02 (m, 1H), 2.86-2.79 (m, 2H), 2.68-2.60 (m, 4H), 2.44-2.39 (m, 2H), 2.31 (s, 3H), 2.23-2.20 (m, 3H), 1.86-1.85 (m, 4H), 1.46-1.44 (m, 4H). |
| Example 227 | (R)-N-((7-azabicyclo[2.2.1]heptan-7-yl)sulfonyl)-2-ethoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 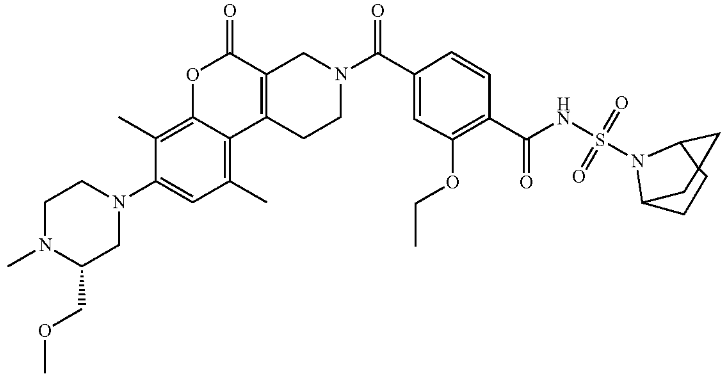 Synthesised from Intermediates 217 and 6 | HPLC: (System 1, Method H) Rt = 7.38 min, m/z 722.0 $(M + H)^+$ $(ES^+)$. $^1$H NMR (400 MHz, DMSO-$d_6$) δ: 11.44 (br s, 1H), 7.50 (d, J = 7.6 Hz, 1H), 7.20-7.17 (m, 1H), 7.13-7.11 (m, 1H), 6.84 (s, 1H), 4.48 (br s, 1H), 4.28-4.23 (m, 3H), 4.15 (br s, 2H), 3.83 (br s, 1H), 3.57-3.53 (m, 1H), 3.49 (br s, 1H), 3.36-3.33 (m, 1H), 3.26 (s, 3H), 3.20 (br s, 2H), 3.14-3.12 (m, 1H), 3.04-3.02 (m, 1H), 2.86-2.79 (m, 2H), 2.68-2.60 (m, 4H), 2.44-2.39 (m, 2H), 2.31 (s, 3H), 2.23-2.19 (m, 3H), 1.87-1.85 (m, 4H), 1.46-1.45 (m, 4H), 1.35 (br s, 3H). |

-continued

| Example No. | Name/Structure/Intermediates | LCMS/$^1$H NMR data |
| --- | --- | --- |
| Example 244 | (R)-2-ethoxy-4-(10-ethyl-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-N-(pyrrolidin-1-ylsulfonyl)benzamide 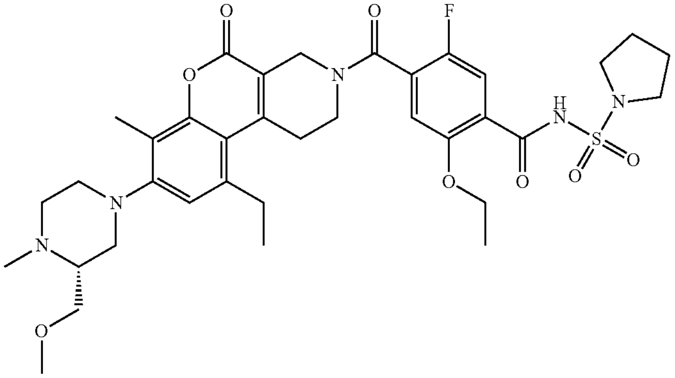 [SMILES: CCOc1cc(C(=O)N2CCc3c(c(=O)oc4c(C)c(N5CCN(C)[C@@H](COC)C5)cc(CC)c34)C2)c(F)cc1C(=O)NS(=O)(=O)N1CCCC1] Synthesised from Intermediates 201 and 255 | HPLC: (System 1, Method H) Rt = 7.64 min. m/z 728.0 (M + H)$^+$ (ES$^+$). $^1$H NMR (400 MHz, DMSO-d$_6$) δ: 11.42 (br s, 1H), 7.47-7.43 (m, 1H), 7.25-7.17 (m, 1H), 6.89-6.87 (m, 1H), 4.52 (br s, 1H), 4.20 (br s, 1H), 4.15-4.06 (m, 2H), 3.90-3.87 (m, 1H), 3.57-3.54 (m, 1H), 3.49-3.47 (m, 1H), 3.43-3.39 (m, 4H), 3.39-3.376. (m, 1H), 3.27 (s, 3H), 3.21 (br s, 1H), 3.16-3.14 (m, 2H), 3.06-3.00 (m, 2H), 2.97-2.92 (m, 1H), 2.87-2.82 (m, 2H), 2.66-2.61 (m, 1H), 2.46-2.41 (m, 2H), 2.32 (s, 3H), 2.24-2.20 (m, 3H), 1.85-1.83 (m, 4H), 1.35-1.30 (m, 3H), 1.25-1.16 (m, 3H) |
| Example 245 | (R)-2-(dimethylamino)-4-(10-ethyl-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-N-(pyrrolidin-1-ylsulfonyl)benzamide 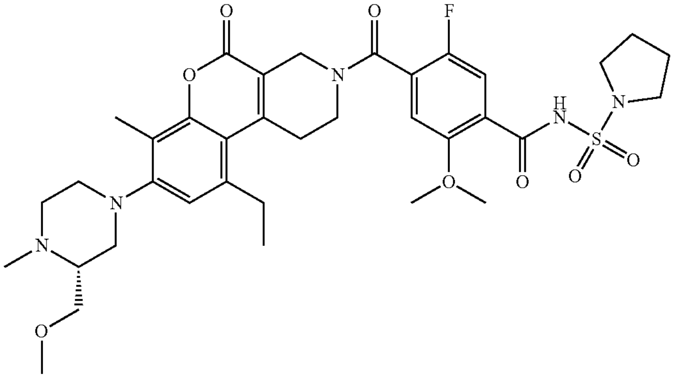 Synthesised from Intermediates 134 and 255 | HPLC: (System 1, Method H) Rt = 8.10 min. m/z 727.0 (M + H)$^+$ (ES$^+$). $^1$H NMR (400 MHz, DMSO-d$_6$) δ: 12.98 (br s, 1H), 7.56-7.50 (m, 1H), 7.46-7.33 (m, 1H), 6.89-6.87 (m, 1H), 4.53 (br s, 1H), 4.21 (br s, 1H), 3.89 (br, 1H), 3.57-3.54 (m, 1H), 3.49-3.47 (m, 1H), 3.44-3.41 (m, 4H), 3.37-3.35 (m, 1H), 3.27 (s, 3H), 3.21 (br, 1H), 3.16-3.14 (m, 2H), 3.06-3.00 (m, 2H), 2.97-2.92 (m, 1H), 2.86-2.81 (m, 2H), 2.78-2.75 (m, 6H), 2.66-2.61 (m, 1H), 2.46-2.43 (m, 2H), 2.32 (s, 3H), 2.24-2.20 (m, 3H), 1.85-1.83 (m, 4H), 1.25-1.16 (m, 3H). |
| Example 246 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-(methoxy-d$_3$)-N-(pyrrolidin-1-ylsulfonyl)benzamide 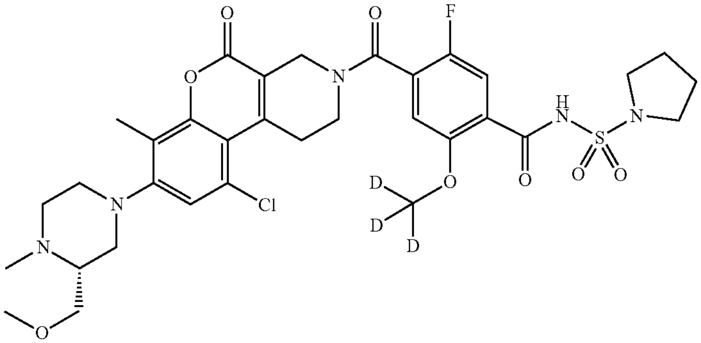 [SMILES: [2H]C([2H])([2H])Oc1cc(C(=O)N2CCc3c(c(=O)oc4c(C)c(N5CCN(C)[C@@H](COC)C5)cc(Cl)c34)C2)c(F)cc1C(=O)NS(=O)(=O)N1CCCC1] Synthesised from Intermediates 215 and 258 | HPLC: (System 1, Method H) Rt = 7.24 min. m/z 723.0 (M + H)$^+$ (ES$^+$). $^1$H NMR (400 MHz, DMSO-d$_6$) δ: 11.45 (br s, 1H), 7.47-7.44 (m, 1H), 7.25-7.19 (m, 1H), 7.07-7.05 (m, 1H), 4.53 (s, 1H), 4.21 (s, 1H), 3.88 (br s, 1H), 3.57-3.54 (m, 1H), 3.48 (br s, 1H), 3.43-3.40 (m, 4H), 3.37-3.33 (m, 3H), 3.27 (s, 3H), 3.17-3.15 (m, 1H), 3.09-3.06 (m, 1H), 2.88-2.83 (m, 2H), 2.68-2.65 (m, 1H), 2.45-2.42 (m, 2H), 2.31 (s, 3H), 2.25-2.21 (m, 3H), 1.86-1.83 (m, 4H). |

-continued

| Example No. | Name/Structure/Intermediates | LCMS/$^{1}$H NMR data |
|---|---|---|
| Example 247 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(pyrrolidin-1-ylsulfonyl)benzamide 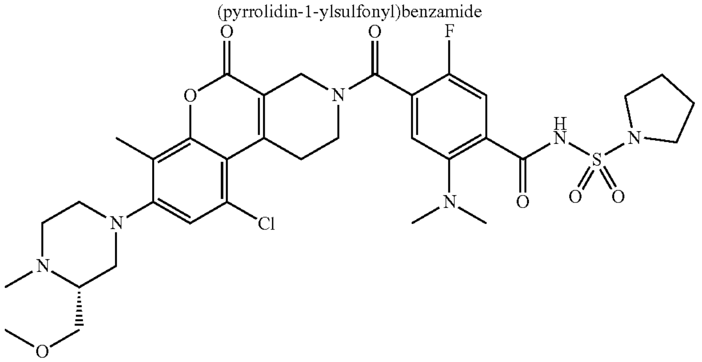 Synthesised from Intermediates 134 and 258 | HPLC: (System 1, Method H) Rt = 8.23 min. m/z 734.0 (M + H)$^{+}$ (ES$^{+}$). $^{1}$H NMR (400 MHz, DMSO-$d_6$) δ: 13.08 (br s, 1H), 7.55-7.50 (m, 1H), 7.42-7.34 (m, 1H), 7.06-7.04 (m, 1H), 4.53 (s, 1H), 4.21 (s, 1H), 3.87 (br s, 1H), 3.57-3.53 (m, 1H), 3.48 (br s, 1H), 3.43-3.40 (m, 4H), 3.33 (br s, 2H), 3.26 (br s, 4H), 3.17-3.14 (m, 1H), 3.08-3.05 (m, 1H), 2.87-2.82 (m, 2H), 2.77-2.75 (m, 6H), 2.67-2.61 (m, 1H), 2.43-2.38 (m, 2H), 2.30 (s, 3H), 2.25-2.21 (m, 3H), 1.84-1.83 (m, 4H). |
| Example 248 | (R)-N-((7-azabicyclo[2.2.1]heptan-7-yl)sulfonyl)-5-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 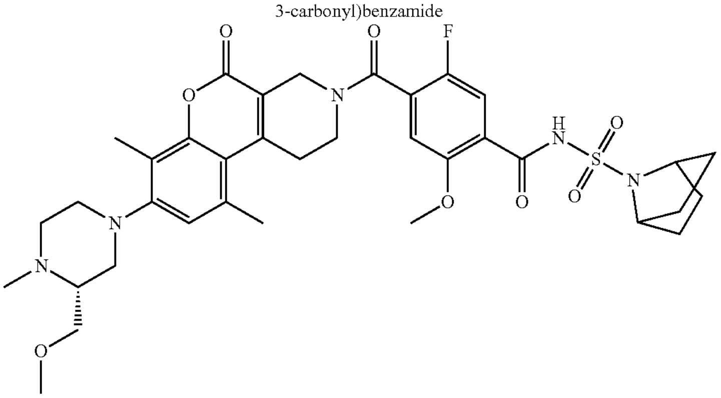 Synthesised from Intermediates 232 and 6 | HPLC: (System 1, Method H) Rt = 7.58 min, m/z 726.0 (M + H)$^{+}$ (ES$^{+}$). $^{1}$H NMR (400 MHz, DMSO-$d_6$) δ: 11.45 (br s, 1H), 7.36-7.34 (m, 1H), 7.22-7.14 (m, 1H), 6.86-6.84 (m, 1H), 4.52 (br s, 1H), 4.19 (s, 3H), 3.87-3.80 (m, 4H), 3.57-3.54 (m, 1H), 3.48-3.46 (m, 1H), 3.39-3.35 (m, 1H), 3.27 (s, 3H), 3.23 (br s, 1H), 3.16-3.13 (m, 2H), 3.06-3.04 (m, 1H), 2.90-2.81 (m, 2H), 2.69-2.62 (m, 4H), 2.49-2.45 (m, 2H), 2.34 (s, 3H), 2.24-2.20 (m, 3H), 1.86-1.84 (m, 4H), 1.45-1.43 (m, 4H). |
| Example 249 | N-((3-azabicyclo[3.1.0]hexan-3-yl)sulfonyl)-5-fluoro-2-methoxy-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 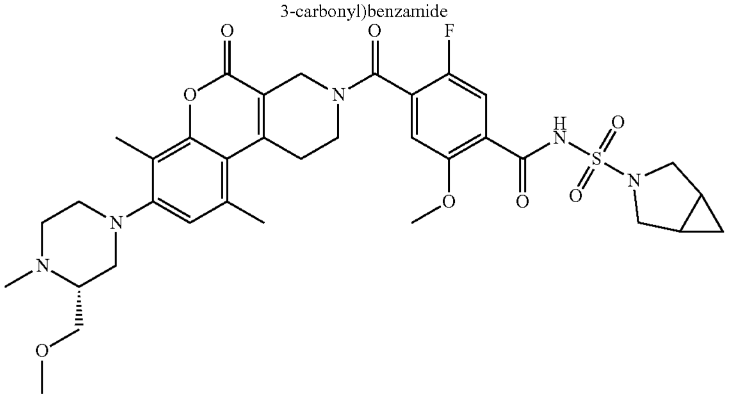 Synthesised from Intermediates 233 and 6 | HPLC: (System 1, Method H) Rt = 7.61 min, m/z 712.0 (M + H)$^{+}$ (ES$^{+}$). $^{1}$H NMR (400 MHz, DMSO-$d_6$) δ: 11.44 (br s, 1H), 7.43-7.41 (m, 1H), 7.24-7.16 (m, 1H), 6.86-6.84 (m, 1H), 4.52 (br s, 1H), 4.19 (s, 1H), 3.88-3.82 (m, 4H), 3.58-3.54 (m, 1H), 3.52-3.49 (m, 2H), 3.47-3.44 (m, 3H), 3.39-3.34 (m, 1H), 3.27 (s, 3H), 3.23 (br s, 1H), 3.16-3.13 (m, 2H), 3.06-3.04 (m, 1H), 2.89-2.81 (m, 2H), 2.69-2.62 (m, 4H), 2.49-2.45 (m, 2H), 2.34 (s, 3H), 2.24-2.20 (m, 3H), 1.59-1.57 (m, 2H), 0.68-0.62 (m, 1H), 0.31-0.27 (m, 1H). Mixture of rotamers. |

-continued

| Example No. | Name/Structure/Intermediates | LCMS/$^1$H NMR data |
|---|---|---|
| Example 250 | (R)-N-((7-azabicyclo[2.2.1]heptan-7-yl)sulfonyl)-5-fluoro-2-(methoxy-$d_3$)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 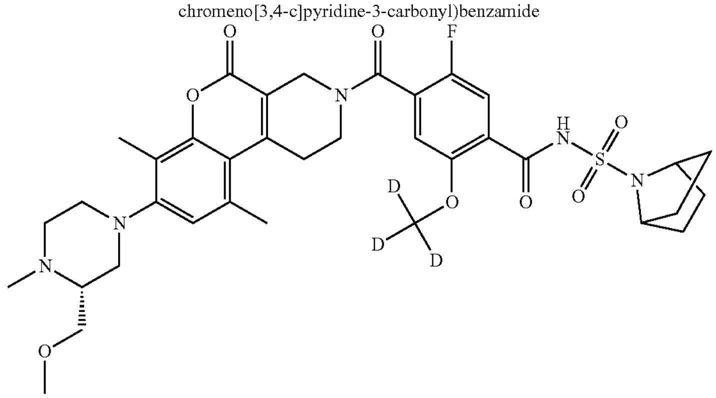 Synthesised from Intermediates 234 and 6 | HPLC: (System 1, Method H) Rt = 6.93 min, m/z 729.0 $(M + H)^+$ $(ES^+)$. $^1$H NMR (400 MHz, DMSO-$d_6$) δ: 11.37 (br s, 1H), 7.37-7.34 (m, 1H), 7.22-7.14 (m, 1H), 6.86-6.84 (m, 1H), 4.52 (br s, 1H), 4.20 (br s, 3H), 3.86 (br s, 1H), 3.58-3.54 (m, 1H), 3.48-3.46 (m, 1H), 3.39-3.35 (m, 1H), 3.27 (s, 3H), 3.23 (br s, 1H), 3.16-3.14 (m, 2H), 3.07-3.04 (m, 1H), 2.90-2.81 (m, 2H), 2.69-2.62 (m, 4H), 2.51-2.50 (m, 2H), 2.35 (s, 3H), 2.24-2.20 (m, 3H), 1.86-1.84 (m, 4H), 1.45-1.43 (m, 4H). Mixture of rotamers. |
| Example 251 | N-((3-azabicyclo[3.1.0]hexan-3-yl)sulfonyl)-5-fluoro-2-(methoxy-$d_3$)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 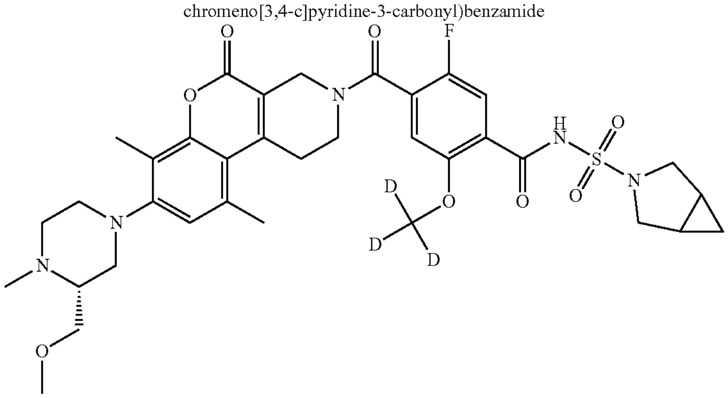 Synthesised from Intermediates 235 and 6 | HPLC: (System 1, Method H) Rt = 6.96 min, m/z 715 $(M + H)^+$ $(ES^+)$. $^1$H NMR (400 MHz, DMSO-$d_6$) δ: 11.37 (br s, 1H), 7.43-7.41 (m, 1H), 7.24-7.16 (m, 1H), 6.86-6.84 (m, 1H), 4.52 (br s, 1H), 4.19 (br s, 1H), 3.88 (br s, 1H), 3.58-3.54 (m, 1H), 3.53-3.50 (m, 2H), 3.47-3.45 (m, 3H), 3.39-3.35 (m, 1H), 3.27 (s, 3H), 3.23 (br s, 1H), 3.16-3.13 (m, 2H), 3.06-3.04 (m, 1H), 2.90-2.81 (m, 2H), 2.69-2.62 (m, 4H), 2.51-2.50 (m, 2H), 2.35 (s, 3H), 2.24-2.20 (m, 3H), 1.59-1.58 (m, 2H), 0.68-0.63 (m, 1H), 0.31-0.29 (m, 1H). Mixture of rotamers. |
| Example 252 | (R)-N-((7-azabicyclo[2.2.1]heptan-7-yl)sulfonyl)-3-fluoro-2-(methoxy-$d_3$)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 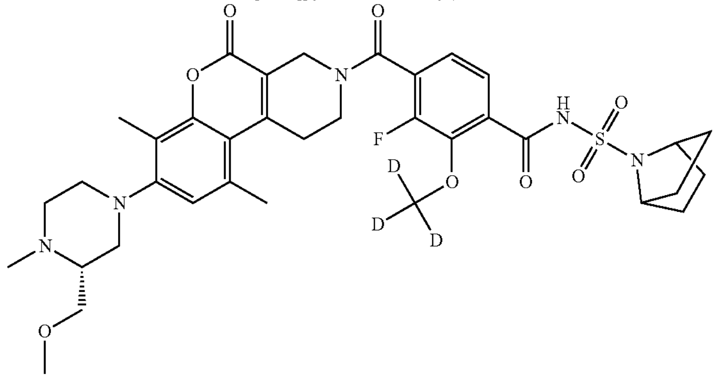 Synthesised from Intermediates 237 and 6 | HPLC: (System 1, Method H) Rt = 6.88 min, m/z 728.8 $(M + H)^+$ $(ES^+)$. $^1$H NMR (400 MHz, DMSO-$d_6$) δ: 11.44 (br s, 1H), 7.26-7.24 (m, 1H), 7.22-7.14 (m, 1H), 6.86-6.85 (m, 1H), 4.51 (br s, 1H), 4.18 (br s, 3H), 3.87-3.85 (m, 1H), 3.58-3.55 (m, 1H), 3.48-3.46 (m, 1H), 3.43-3.39 (m, 1H), 3.28 (s, 3H), 3.23 (br s, 1H), 3.18-3.15 (m, 2H), 3.09-3.06 (m, 1H), 2.95-2.92 (m, 1H), 2.87-2.82 (m, 1H), 2.72-2.56 (m, 6H), 2.40 (s, 3H), 2.24-2.20 (m, 3H), 1.86-1.84 (m, 4H), 1.42-1.41 (m, 4H). |

-continued

| Example No. | Name/Structure/Intermediates | LCMS/$^1$H NMR data |
| --- | --- | --- |
| Example 253 | (R)-N-((2-azaspiro[3.3]heptan-2-yl)sulfonyl)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 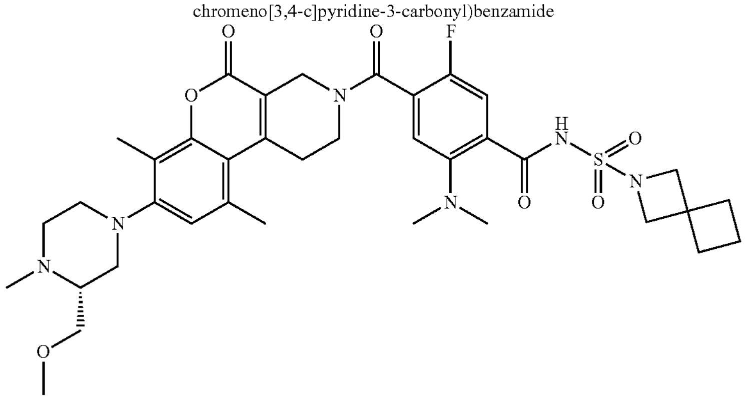 Synthesised from Intermediates 246 and 6 | UPLC: (System 3, Method K) Rt = 4.02 min, m/z 739.9 (M + H)$^+$ (ES$^+$). 1H NMR (400 MHz, ACN-$d_3$) δ: 7.93-7.88 (m, 1H), 7.60-7.53 (m, 1H), 6.83-6.81 (m, 1H), 4.56 (s, 1H), 4.22 (s, 1H), 4.08 (s, 4H), 3.92 (br s, 1H), 3.57 (dd, J = 9.8, 3.9 Hz, 1H), 3.49 (t, J = 5.5 Hz, 1H), 3.39-3.35 (m, 1H), 3.29 (s, 3H), 3.23-3.03 (m, 4H), 2.89-2.83 (m, 2H), 2.81-7.77 (m, 6H), 2.69-2.61 (m, 4H), 2.50-2.45 (m, 2H), 2.33 (s, 3H), 2.28-2.24 (m, 3H), 2.16-2.08 (m, 4H), 1.83-1.76 (m, 2H). One exchangeable proton not visible. Mixture of rotamers. |
| Example 254 | 2-(dimethylamino)-5-fluoro-N-(((S)-3-fluoropyrrolidin-1-yl) sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 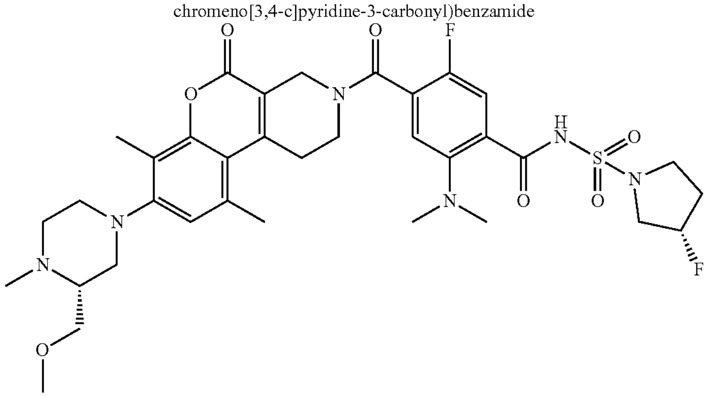 Synthesised from Intermediates 247 and 6 | UPLC: (System 3, Method K) Rt = 3.82 min, m/z 731.8 (M + H)$^+$ (ES$^+$). $^1$H NMR (400 MHz, ACN-$d_3$) δ: 7.90-7.85 (m, 1H), 7.60-7.53 (m, 1H), 6.82-6.80 (m, 1H), 5.36-5.22 (m, 1H), 4.55 (br s, 1H), 4.20 (br s, 1H), 3.91-3.56 (m, 5H), 3.49-3.36 (m, 2H), 3.29 (s, 3H), 3.22-3.03 (m, 4H), 2.89-2.84 (m, 2H), 2.80-2.76 (m, 6H), 2.68-2.60 (m, 4H), 2.48-2.45 (m, 2H), 2.35 (s, 3H), 2.27-2.00 (m, 6H). One exchangeable proton not visible. Mixture of rotamers. |
| Example 255 | (R)-N-((7-azabicyclo[2.2.1]heptan-7-yl)sulfonyl)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 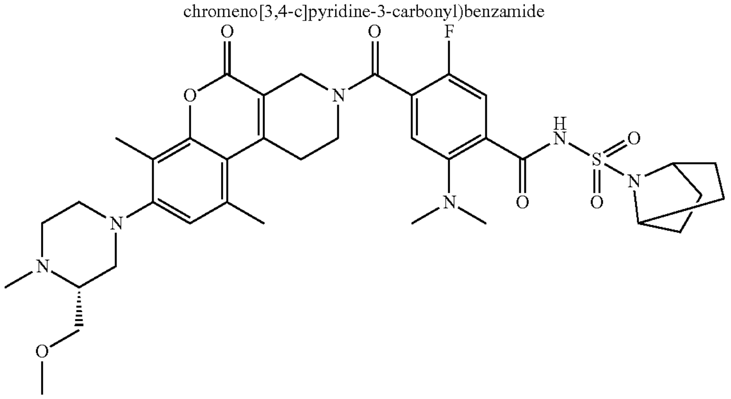 Synthesised from Intermediates 170 and 6 | UPLC: (System 3, Method K) Rt = 4.01 min, m/z 739.5 (M + H)$^+$ (ES$^+$). $^1$H NMR (400 MHz, ACN-$d_3$) δ: 7.89-7.84 (m, 1H), 7.57-5.50 (m, 1H), 6.83-6.81 (m, 1H), 4.55 (s, 1H), 4.31 (s, 2H), 4.21 (s, 1H), 3.97 (br s, 1H), 3.59-3.56 (m, 1H), 3.49-3.46 (m, 1H), 3.39-3.33 (m, 1H), 3.29 (s, 3H), 3.24-3.03 (m, 4H), 2.92-2.84 (m, 2H), 2.78-2.75 (m, 6H), 2.68-2.57 (m, 4H), 2.52-2.43 (m, 2H), 2.36 (s, 3H), 2.28-2.24 (m, 3H), 1.90-1.83 (m, 4H), 1.59-1.49 (m, 4H). One exchangeable proton not visible. Mixture of rotamers. |

-continued

| Example No. | Name/Structure/Intermediates | LCMS/$^1$H NMR data |
|---|---|---|
| Example 256 | N-((3-oxa-8-azabicyclo[3.2.1]octan-8-yl)sulfonyl)-2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 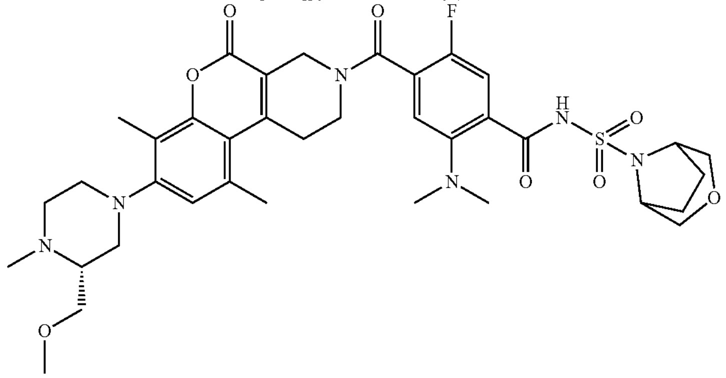 Synthesised from Intermediates 248 and 6 | UPLC: (System 3, Method K) Rt = 3.71 min, m/z 755.7 $(M + H)^+$ $(ES^+)$. $^1$H NMR (400 MHz, ACN-$d_3$) δ: 7.89-7.84 (m, 1H), 7.58-7.51 (m, 1H), 6.81-6.80 (m, 1H), 4.54 (br s, 1H), 4.20 (br s, 3H), 3.90-3.82 (br s, 1H), 3.70-3.67 (m, 2H), 3.61-3.56 (m, 4H), 3.49-3.46 (m, 1H), 3.40-3.33 (m, 1H), 3.29 (s, 3H), 3.23-3.03 (m, 5H), 2.93-2.84 (m, 3H), 2.78-2.72 (m, 6H), 2.72-2.59 (m, 5H), 2.52-2.45 (m, 2H), 2.37 (s, 3H), 2.27-2.22 (m, 3H). One exchangeable proton not visible. Mixture of rotamers. |
| Example 257 | (R)-N-(N-cyclopropyl-N-methylsulfamoyl)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 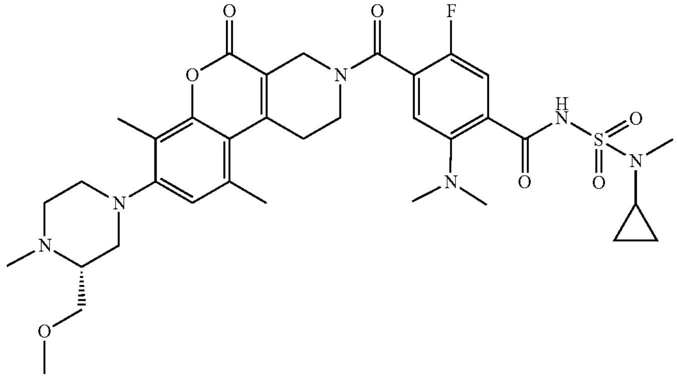 Synthesised from Intermediates 250 and 6 | UPLC: (System 3, Method K) Rt = 3.96 min, m/z 713.5 $(M + H)^+$ $(ES^+)$. $^1$H NMR (400 MHz, ACN-$d_3$) δ: 7.94-7.89 (m, 1H), 7.62-7.55 (m, 1H), 6.82-6.81 (m, 1H), 4.56 (br s, 1H), 4.21 (br s, 1H), 3.87 (br s, 1H), 3.59-3.35 (m, 3H), 3.30 (s, 3H), 3.24-3.06 (m, 4H), 3.03-3.02 (m, 3H), 2.89-2.84 (m, 2H), 2.81-2.78 (m, 6H), 2.68-2.56 (m, 5H), 2.49-2.40 (m, 2H), 2.33 (s, 3H), 2.28-2.24 (m, 3H), 0.89-0.71 (m, 4H). One exchangeable proton not visible. Mixture of rotamers. |
| Example 258 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-3-fluoro-N-(pyrrolidin-1-ylsulfonyl)benzamide 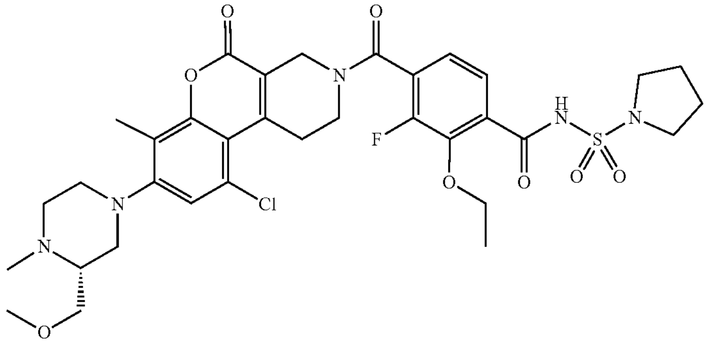 [SMILES: CCOc1c(C(=O)NS(=O)(=O)N2CCCC2)ccc(C(=O)N2CCc3c(c(=O)oc4c(C)c(N5CCN(C)[C@@H](COC)C5)cc(Cl)c34)C2)c1F] Synthesised from Intermediates 161 and 258 | HPLC: (System 1, Method H) Rt = 7.29 min, m/z 733.9 $(M + H)^+$ $(ES^+)$. $^1$H NMR (400 MHz, DMSO-$d_6$) δ: 11.55 (br s, 1H), 7.37-7.33 (m, 1H), 7.25-7.19 (m, 1H), 7.07-7.05 (m, 1H), 4.53 (br s, 1H), 4.22-4.14 (m, 3H), 3.87 (t, J = 5.6 Hz, 1H), 3.57-3.54 (m, 1H), 3.49-3.46 (m, 1H), 3.43-3.39 (m, 4H), 3.37-3.36 (m, 2H), 3.27 (s, 3H), 3.25 (br s, 1H), 3.18-3.16 (m, 1H), 3.09-3.07 (m, 1H), 2.89-2.84 (m, 2H), 2.70-2.64 (m, 1H), 2.49-2.44 (m, 2H), 2.34 (s, 3H), 2.25-2.21 (m, 3H), 1.87-1.84 (m, 4H), 1.33-1.28 (m, 3H). Mixture of rotamers. |

-continued

| Example No. | Name/Structure/Intermediates | LCMS/$^1$H NMR data |
|---|---|---|
| Example 259 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluoro-N-(pyrrolidin-1-ylsulfonyl)benzamide 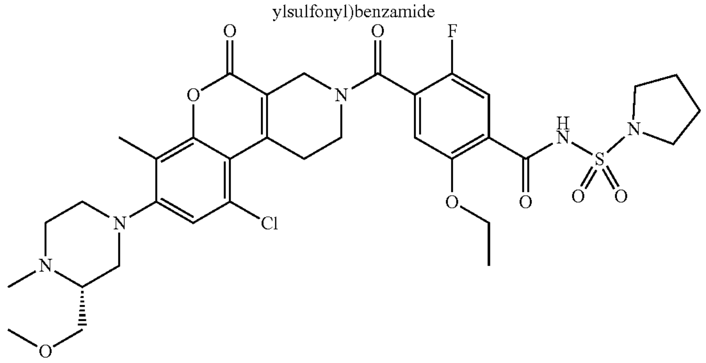 Synthesised from Intermediates 201 and 258 | HPLC: (System 1, Method H) Rt = 7.70 min. m/z 733.8 $(M + H)^+$ $(ES^+)$. $^1$H NMR (400 MHz, DMSO-$d_6$) δ: 11.44 (br s, 1H), 7.47-7.44 (m, 1H), 7.24-7.18 (m, 1H), 7.06-7.04 (m, 1H), 4.53 (s, 1H), 4.20 (s, 1H), 4.15-4.06 (m, 2H), 3.87 (br s, 1H), 3.57-3.53 (m, 1H), 3.47-3.43 (m, 5H), 3.36-3.33 (m, 2H), 3.27 (br s, 4H), 3.17-3.14 (m, 1H), 3.08-3.06 (m, 1H), 2.87-2.83 (m, 2H), 2.67-2.62 (m, 1H), 2.44-2.39 (m, 2H), 2.31 (s, 3H), 2.25-2.21 (m, 3H), 1.85-1.83 (m, 4H) , 1.35-1.30 (m, 3H). |
| Example 260 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-N-(N,N-dimethylsulfamoyl)-5-fluorobenzamide 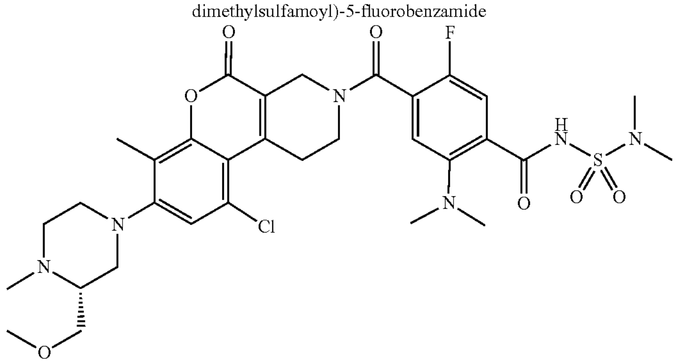 Synthesised from Intermediates 251 and 258 | HPLC: (System 1, Method H) Rt = 7.42 min. m/z 707.0 $(M + H)^+$ $(ES^+)$. $^1$H NMR (400 MHz, DMSO-$d_6$) δ: 13.14 (br s, 1H), 7.57-7.51 (m, 1H), 7.44-7.35 (m, 1H), 7.07-7.05 (m, 1H), 4.53 (s, 1H), 4.21 (s, 1H), 3.87 (br s, 1H), 3.57-3.54 (m, 1H), 3.48 (br s, 1H), 3.38-3.36 (m, 2H), 3.27 (br, 4H), 3.18-3.15 (m, 1H), 3.09-3.06 (m, 1H), 2.87-2.83 (m, 8H), 2.79-2.77 (m, 6H), 2.69-2.63 (m, 1H), 2.44-2.41 (m, 2H), 2.33 (s, 3H), 2.25-2.21 (m, 3H). |
| Example 261 | 2-ethoxy-5-fluoro-N-(((R)-3-fluoropyrrolidin-1-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 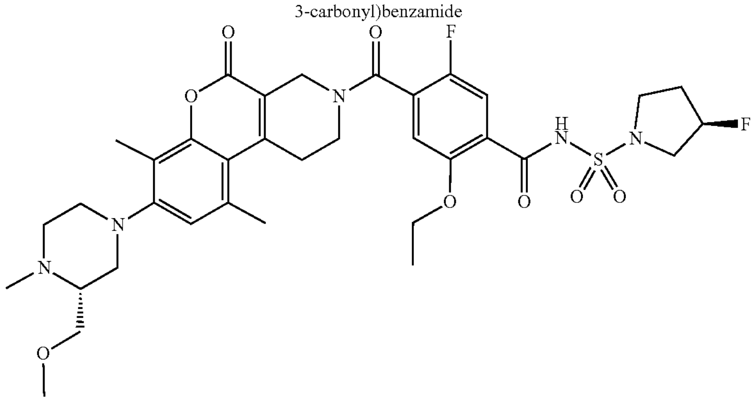 Synthesised from Intermediates 241 and 6 | UPLC: (System 3, Method K) Rt = 3.76 min, m/z 730.5 $(M + H)^+$ $(ES^+)$. $^1$H NMR (400 MHz, DMSO-$d_6$) δ: 11.19 (s, 1H), 7.41-7.39 (m, 1H), 7.22-7.14 (m, 1H), 6.86-6.84 (m, 1H), 5.36 (d, J = 53.1 Hz, 1H), 4.51 (s, 1H), 4.18 (s, 1H), 4.14-4.05 (m, 2H), 3.88-3.85 (m, 1H), 3.77-3.61 (m, 3H), 3.58-3.45 (m, 4H), 3.40-3.36 (m, 1H), 3.27 (s, 3H), 3.23-3.21 (m, 1H), 3.16-3.09 (m, 2H), 3.07-3.04 (m, 1H), 2.91-2.81 (m, 2H), 2.69-2.61 (m, 4H), 2.53 (s, 1H), 2.41-2.33 (m, 3H), 2.26-2.20 (m, 3H), 2.16-1.97 (m, 2H), 1.32 (q, J = 7.3 Hz, 3H). Mixture of rotamers. |

-continued

| Example No. | Name/Structure/Intermediates | LCMS/$^1$H NMR data |
| --- | --- | --- |
| Example 262 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-methoxy-N-(pyrrolidin-1-ylsulfonyl)benzamide 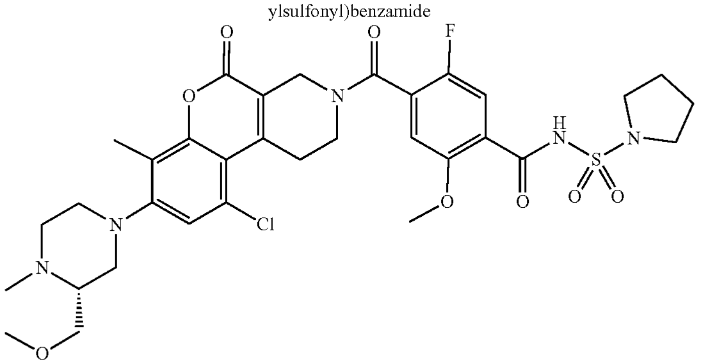 Synthesised from Intermediates 213 and 258 | HPLC: (System 1, Method H) Rt = 7.18 min. m/z 719.9 (M + H)$^+$ (ES$^+$). $^1$H NMR (400 MHz, DMSO-$d_6$) δ: 11.45 (br s, 1H), 7.47-7.44 (m, 1H), 7.26-7.20 (m, 1H), 7.06-7.04 (m, 1H), 4.53 (s, 1H), 4.21 (s, 1H), 3.85-3.82 (m, 4H), 3.57-3.53 (m, 1H), 3.48-3.47 (m, 1H), 3.43-3.40 (m, 4H), 3.37-3.33 (m, 2H), 3.27 (br s, 4H), 3.17-3.15 (m, 1H), 3.09-3.06 (m, 1H), 2.88-2.83 (m, 2H), 2.68-2.62 (m, 1H), 2.45-2.42 (m, 2H), 2.31 (s, 3H), 2.25-2.21 (m, 3H), 1.86-1.83 (m, 4H). |
| Example 263 | (R)-2-cyclopropoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 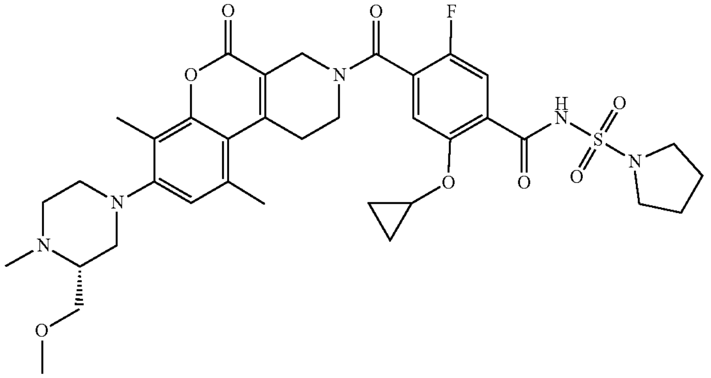 [SMILES: COC[C@H]1CN(c2cc(C)c3c4c(c(=O)oc3c2C)CN(C(=O)c2cc(OC3CC3)c(C(=O)NS(=O)(=O)N3CCCC3)cc2F)CC4)CCN1C] Synthesised from Intermediates 244 and 6 | HPLC: (System 1, Method H) Rt = 7.17 min. m/z 726.0 (M + H)$^+$ (ES$^+$). $^1$H NMR (400 MHz, DMSO-$d_6$) δ: 11.39 (br s, 1H), 7.48-7.38 (m, 2H), 6.86-6.84 (m, 1H), 4.53-4.52 (m, 1H), 4.22 (s, 1H), 4.00-3.92 (m, 1H), 3.89 (br s, 1H), 3.57-3.54 (m, 1H), 3.50-3.47 (m, 1H), 3.44-3.38 (m, 4H), 3.36-3.35 (m, 1H), 3.27-3.25 (m, 4H), 3.16-3.13 (m, 2H), 3.06-3.03 (m, 1H), 2.88-2.80 (m, 2H), 2.70-2.62 (m, 4H), 2.48-2.43 (m, 2H), 2.33 (s, 3H), 2.24-2.20 (m, 3H), 1.85-1.82 (m, 4H), 0.85-0.76 (m, 2H), 0.73-0.67 (m, 2H). |
| Example 264 | N-((3-azabicyclo[3.1.0]hexan-3-yl)sulfonyl)-2-cyclopropoxy-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 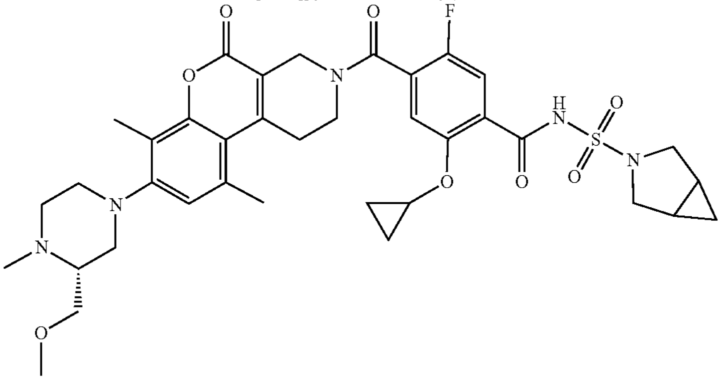 Synthesised from Intermediates 245 and 6 | HPLC: (System 1, Method H) Rt = 7.25 min. m/z 737.9 (M + H)$^+$ (ES$^+$). $^1$H NMR (400 MHz, DMSO-$d_6$) δ: 11.38 (br s, 1H), 7.47-7.38 (m, 2H), 6.86-6.85 (m, 1H), 4.53-4.52 (m, 1H), 4.22 (s, 1H), 4.00-3.92 (m, 1H), 3.89 (br s, 1H), 3.58-3.54 (m, 1H), 3.51-3.44 (m, 5H), 3.39-3.37 (m, 1H), 3.27 (s, 3H), 3.25 (br s, 1H), 3.16-3.14 (m, 2H), 3.07-3.04 (m, 1H), 2.90-2.81 (m, 2H), 2.70-2.62 (m, 4H), 2.51-2.50 (m, 2H), 2.35 (s, 3H), 2.24-2.20 (m, 3H), 1.59-1.57 (m, 2H), 0.85-0.72 (m, 4H), 0.67-0.62 (m, 1H), 0.30-0.26 (m, 1H). |

-continued

| Example No. | Name/Structure/Intermediates | LCMS/$^1$H NMR data |
|---|---|---|
| Example 265 | (R)-2-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 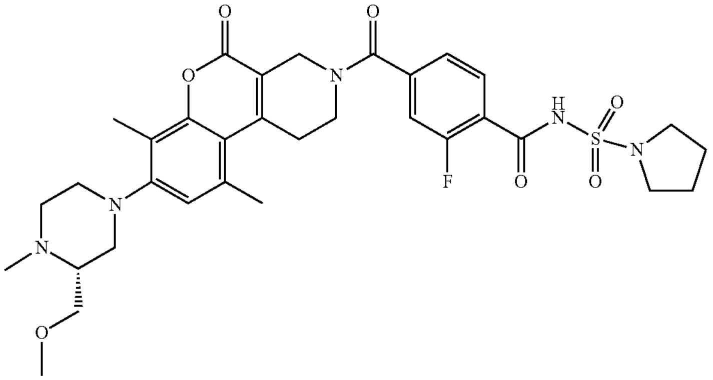 [SMILES: COC[C@H]1CN(c2cc(C)c3c4c(c(=O)oc3c2C)CN(C(=O)c2ccc(C(=O)NS(=O)(=O)N3CCCC3)c(F)c2)CC4)CCN1C] Synthesised from Intermediates 236 and 6 | HPLC: (System 1, Method H) Rt = 6.57 min, m/z 670.1 (M + H)$^+$ (ES$^+$). $^1$H NMR (400 MHz, DMSO-d$_6$) δ: 11.50 (br s, 1H), 7.71 (t, J = 7.4 Hz, 1H), 7.45 (d, J = 10.0 Hz, 1H), 7.39-7.38 (m, 1H), 6.86 (s, 1H), 4.47 (br s, 1H), 4.27 (br s, 1H), 3.83 (br 1H), 3.59-3.55 (m, 1H), 3.50 (br s, 1H), 3.45-3.41 (m, 1H), 3.38-3.36 (m, 4H), 3.28 (s, 3H), 3.22-3.16 (m, 3H), 3.10-3.07 (m, 1H), 2.98-2.95 (m, 1H), 2.89-2.83 (m, 1H), 2.74-2.61 (m, 6H), 2.42 (s, 3H), 2.24-2.20 (m, 3H), 1.83-1.81 (m, 4H). |
| Example 266 | (R)-2-fluoro-5-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 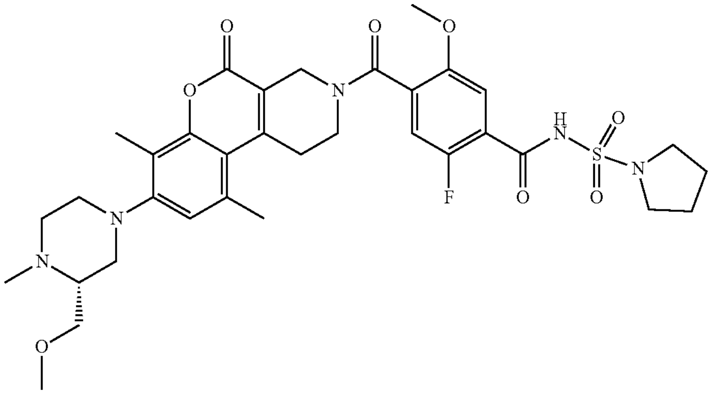 [SMILES: COC[C@H]1CN(c2cc(C)c3c4c(c(=O)oc3c2C)CN(C(=O)c2cc(F)c(C(=O)NS(=O)(=O)N3CCCC3)cc2OC)CC4)CCN1C] Synthesised from Intermediates 252 and 6 | HPLC: (System 1, Method H) Rt = 6.64 min. m/z 700.0 (M + H)$^+$ (ES$^+$). $^1$H NMR (400 MHz, DMSO-d$_6$) δ: 11.47 (br s, 1H), 7.30-7.22 (m, 2H), 6.87-6.85 (m, 1H), 4.56-4.39 (m, 1H), 4.08-4.07 (m, 1H), 3.94-3.76 (m, 4H), 3.59-3.55 (m, 1H), 3.44-3.41 (m, 2H), 3.37-3.34 (m, 4H), 3.28 (s, 3H), 3.19-3.16 (m, 2H), 3.12-3.07 (m, 2H), 2.97-2.94 (m, 1H), 2.88-2.83 (m, 1H), 2.73-2.62 (m, 6H), 2.42 (s, 3H), 2.24-2.20 (m, 3H), 1.86-1.80 (m, 4H). |
| Example 267 | N-(((1S,4S)-2-oxa-5-azabicyclo[2.2.1]heptan-5-yl)sulfonyl)-2-ethoxy-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 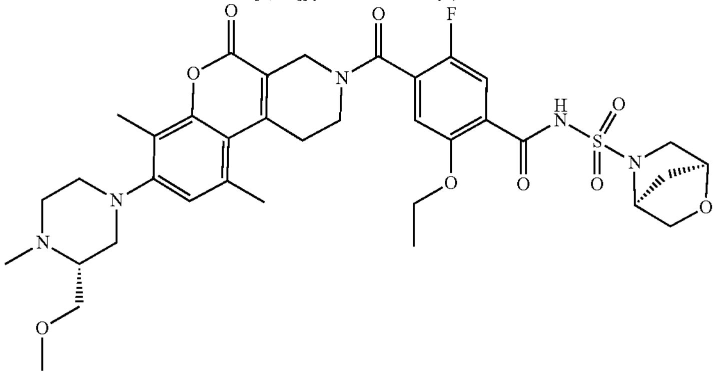 [SMILES: CCOc1cc(C(=O)N2CCc3c(c(=O)oc4c(C)c(N5CCN(C)[C@@H](COC)C5)cc(C)c34)C2)c(F)cc1C(=O)NS(=O)(=O)N1C[C@@H]2C[C@H]1CO2] Synthesised from Intermediates 243 and 6 | UPLC: (System 3, Method K) Rt = 3.59 min, m/z 742.4 (M + H)$^+$ (ES$^+$). $^1$H NMR (400 MHz, ACN-d$_3$) δ: 7.76-7.72 (m, 1H), 7.15-1.10 (m, 1H), 6.83-6.81 (m, 1H), 4.62-4.56 (m, 3H), 4.27-4.18 (m, 3H), 3.92-3.89 (m, 2H), 3.73-3.68 (m, 1H), 3.58-3.55 (m, 2H), 3.51-3.44 (m, 2H), 3.39-3.35 (m, 1H), 3.31-3.30 (m, 3H), 3.23-3.04 (m, 4H), 2.89-2.82 (m, 2H), 2.69-2.62 (m, 4H), 2.46-2.40 (m, 2H), 2.32-2.25 (m, 6H), 1.85 (s, 2H), 1.49-1.43 (m, 3H). One exchangeable proton no visible. Mixture of rotamers. |

-continued

| Example No. | Name/Structure/Intermediates | LCMS/$^1$H NMR data |
|---|---|---|
| Example 268 | 2-ethoxy-5-fluoro-N-(((S)-3-fluoropyrrolidin-1-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 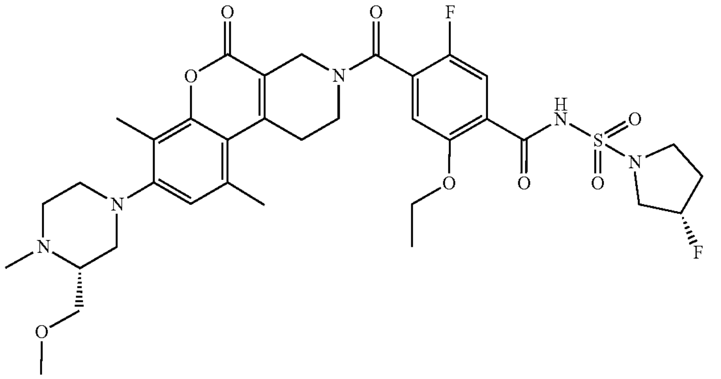 [SMILES: CCOc1cc(C(=O)N2CCc3c(c(=O)oc4c(C)c(N5CCN(C)[C@@H](COC)C5)cc(C)c34)C2)c(F)cc1C(=O)NS(=O)(=O)N1CC[C@H](F)C1] Synthesised from Intermediates 239 and 6 | UPLC: (System 3, Method K) Rt = 3.76 min, m/z 732.4 $(M + H)^+$ $(ES^+)$. $^1$H NMR (400 MHz, ACN-$d_3$) δ: 7.77-7.72 (m, 1H), 7.14-7.11 (m, 1H), 6.82-6.81 (m, 1H), 5.36-5.22 (m, 1H), 4.55 (s, 1H), 4.28-4.19 (m, 3H), 3.91-3.74 (m, 3H), 3.70-3.54 (m, 3H), 3.50-3.47 (m, 1H), 3.38-3.34 (m, 1H), 3.29-3.28 (m, 3H), 3.24-3.03 (m, 4H), 2.88-2.83 (m, 2H), 2.68-2.61 (m, 4H), 2.47-2.41 (m, 2H), 2.32-2.17 (m, 8H), 1.52-1.44 (m, 3H). One exchangeable proton no visible. Mixture of rotamers. |
| Example 269 | (R)-N-(N-cyclopropyl-N-methylsulfamoyl)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 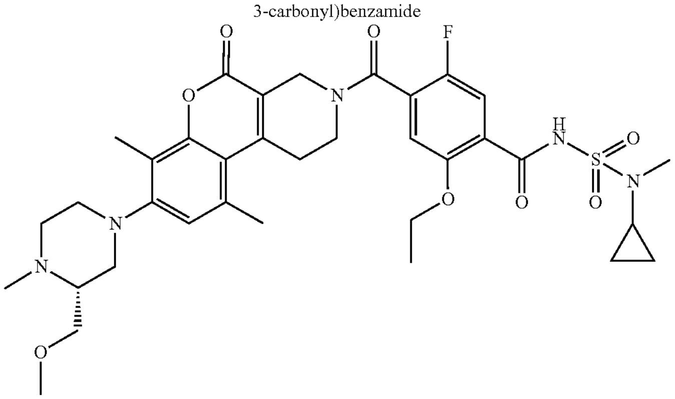 Synthesised from Intermediates 259 and 6 | UPLC: (System 3, Method K) Rt = 3.86 min, m/z 714.4 $(M + H)^+$ $(ES^+)$. $^1$H NMR (400 MHz, ACN-$d_3$) δ: 7.79-7.75 (m, 1H), 7.17-7.12 (m, 1H), 6.83-6.79 (m, 1H), 4.55 (s, 1H), 4.29-4.21 (m, 3H), 3.91 (br s, 1H), 3.58-3.48 (m, 2H), 3.38-3.34 (m, 1H), 3.29 (s, 3H), 3.23-3.12 (m, 3H), 3.06-2.98 (m, 4H), 2.88-2.82 (m, 2H), 2.68-2.61 (m, 5H), 2.48-2.41 (m, 2H), 2.31 (s, 3H), 2.28-2.24 (m, 3H), 1.50-1.44 (m, 3H), 0.83-0.75 (m, 4H). One exchangeable proton no visible. Mixture of rotamers. |
| Example 270 | (R)-2-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-5-methyl-N-(pyrrolidin-1-ylsulfonyl)benzamide 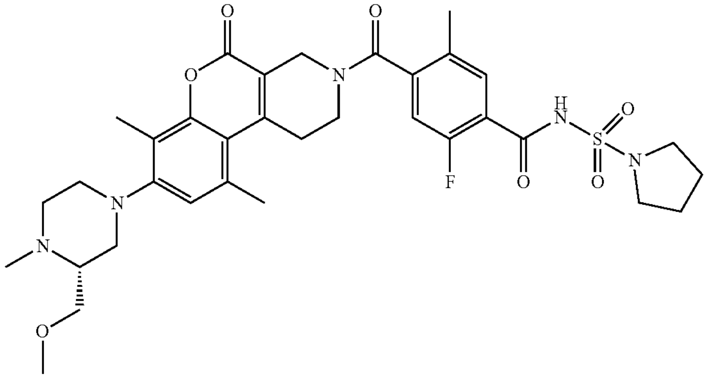 [SMILES: COC[C@H]1CN(c2cc(C)c3c4c(c(=O)oc3c2C)CN(C(=O)c2cc(F)c(C(=O)NS(=O)(=O)N3CCCC3)cc2C)CC4)CCN1C] Synthesised from Intermediates 260 and 6 | UPLC: (System 3, Method K) Rt = 3.69 min, m/z 684.5 $(M + H)^+$ $(ES^+)$. $^1$H NMR (400 MHz, ACN-$d_3$) δ: 7.69-7.64 (m, 1H), 7.16-7.10 (m, 1H), 6.84-6.82 (m, 1H), 4.68-4.36 (m, 1H), 4.08 (br s, 1H), 3.71 (s, 1H), 3.60-3.56 (m, 1H), 3.50-3.47 (m, 4H), 3.41-3.36 (m, 2H), 3.32 (s, 3H), 3.25-3.04 (m, 4H), 2.90-2.85 (m, 2H), 2.70-2.61 (m, 4H), 2.51-2.44 (m, 2H), 2.36-2.20 (m, 9H), 1.93-1.89 (m, 4H). One exchangeable proton no visible. Mixture of rotamers. |

-continued

| Example No. | Name/Structure/Intermediates | LCMS/$^1$H NMR data |
|---|---|---|
| Example 271 | (R)-N-((2-oxa-5-azaspiro[3.5]nonan-5-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide 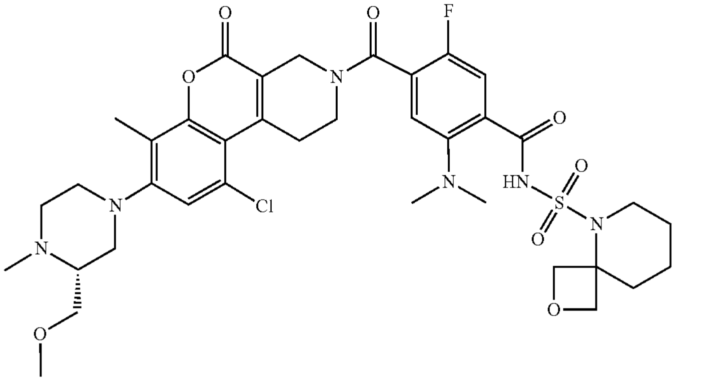 [SMILES: COC[C@H]1CN(c2cc(Cl)c3c4c(c(=O)oc3c2C)CN(C(=O)c2cc(N(C)C)c(C(=O)NS(=O)(=O)N3CCCCC35COC5)cc2F)CC4)CCN1C] Synthesised from Intermediates 258 and 262 | HPLC: (System 1, Method H) Rt = 7.42 min. m/z 789.0 $(M + H)^+$ $(ES^+)$. $^1$H NMR (400 MHz, DMSO-$d_6$) δ: 12.92 (br s, 1H), 7.48-7.41 (m, 1H), 7.35-7.25 (m, 1H), 7.07-7.05 (m, 1H), 4.90-4.85 (m, 2H), 3.53 (br s, 1H), 4.27-4.22 (m, 3H), 3.87 (br s, 1H), 3.57-3.54 (m, 1H), 3.49 (br s, 1H), 3.41 (br s, 1H), 3.31-3.27 (m, 7H), 3.19-3.16 (m, 1H), 3.10-3.07 (m, 1H), 2.89-2.84 (m, 2H), 2.81-2.78 (m, 6H), 2.72-2.64 (m, 1H), 2.41 (br s, 2H), 2.34 (s, 3H), 2.24-2.21 (m, 3H), 1.96-1.95 (m, 2H), 1.69 (br s, 2H), 1.49 (br s, 2H). |
| Example 272 | (R)-N-((2-oxa-6-azaspiro[3.5]nonan-6-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide 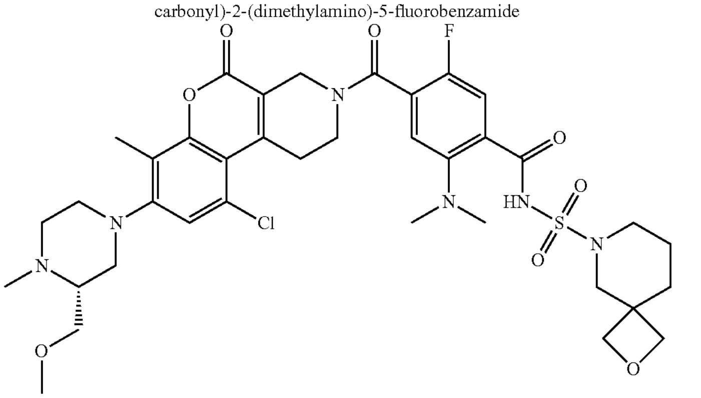 Synthesised from Intermediates 258 and 264 | HPLC: (System 1, Method H) Rt = 7.39 min. m/z 789.0 $(M + H)^+$ $(ES^+)$. $^1$H NMR (400 MHz, DMSO-$d_6$) δ: 13.24 (br s, 1H), 7.55-7.49 (m, 1H), 7.543-7.35 (m, 1H), 7.07-7.05 (m, 1H), 4.53 (br s, 1H), 4.30-4.21 (m, 5H), 3.87 (br s, 1H), 3.57-3.54 (m, 1H), 3.48-3.45 (m, 3H), 3.42-3.39 (m, 2H), 3.27 (br s, 4H), 3.23-3.17 (m, 3H), 3.10-3.08 (m, 1H), 2.89-2.84 (m, 2H), 2.80-2.77 (m, 6H), 2.71-2.65 (m, 1H), 2.51 (br s, 1H), 2.45 (br s, 1H), 2.35 (s, 3H), 2.25-2.21 (m, 3H), 1.75-1.73 (m, 2H), 1.51 (br s, 2H). |
| Example 273 | (R)-N-((2-oxa-6-azaspiro[3.4]octan-6-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide 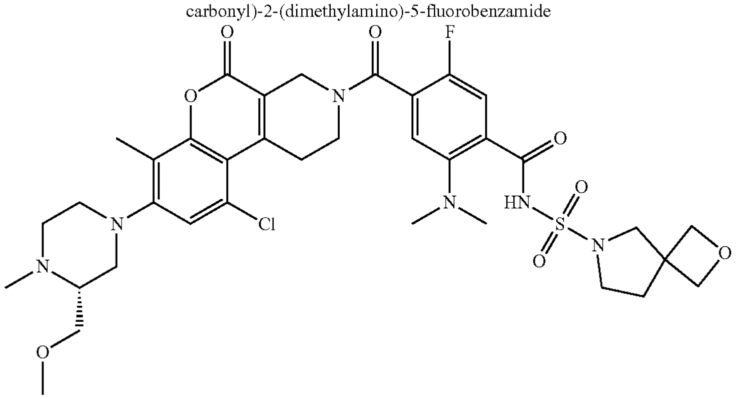 Synthesised from Intermediates 258 and 266 | HPLC: (System 1, Method H) Rt = 7.08 min. m/z 774.9 $(M + H)^+$ $(ES^+)$. $^1$H NMR (400 MHz, DMSO-$d_6$) δ: 13.05 (br s, 1H), 7.55-7.50 (m, 1H), 7.44-7.35 (m, 1H), 7.07-7.05 (m, 1H), 4.56-4.53 (m, 3H), 4.45-4.43 (m, 2H), 4.21 (br s, 1H), 3.87 (br s, 1H), 3.65 (s, 2H), 3.57-3.54 (m, 1H), 3.48-3.42 (m, 3H), 3.38-3.35 (m, 2H), 3.27 (br s, 4H), 3.18-3.15 (m, 1H), 3.09-3.07 (m, 1H), 2.89-2.84 (m, 2H), 2.77-2.75 (m, 6H), 2.69-2.64 (m, 1H), 2.49-2.45 (m, 2H), 2.33 (s, 3H), 2.25-2.21 (m, 3H), 2.19-2.15 (m, 2H). |

-continued

| Example No. | Name/Structure/Intermediates | LCMS/$^1$H NMR data |
|---|---|---|
| Example 274 | (R)-N-((5-azaspiro[2.4]heptan-5-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide 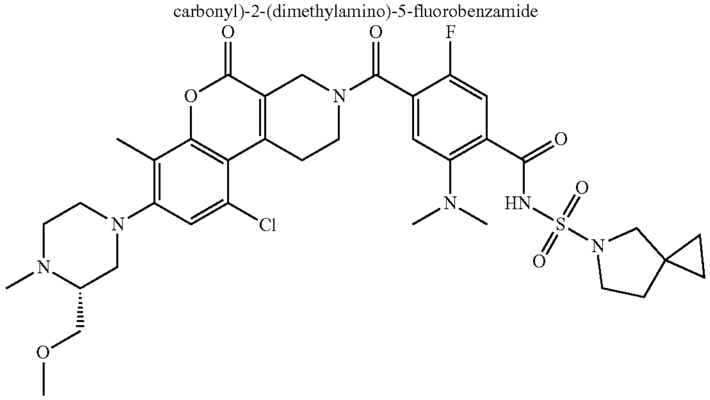 Synthesised from Intermediates 258 and 268 | HPLC: (System 1, Method H) Rt = 8.79 min. m/z 759.0 $(M + H)^+$ $(ES^+)$. $^1$H NMR (400 MHz, DMSO-$d_6$) δ: 13.01 (br s, 1H), 7.56-7.50 (m, 1H), 7.44-7.34 (m, 1H), 7.07-7.05 (m, 1H), 4.53 (br, 1H), 4.22 (br s, 1H), 3.87 (br s, 1H), 3.62-3.58 (m, 2H), 3.57-3.54 (m, 1H), 3.49 (br s, 1H), 3.37-3.34 (m, 4H), 3.27 (br s, 4H), 3.17-3.15 (m, 1H), 3.09-3.06 (m, 1H), 2.88-2.83 (m, 2H), 2.78-2.76 (m, 6H), 2.68-2.65 (m, 1H), 2.45-2.39 (m, 2H), 2.31 (s, 3H), 2.25-2.21 (m, 3H), 1.85-1.75 (m, 2H), 0.62-0.55 (m, 4H). |
| Example 275 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(piperidin-1-ylsulfonyl)benzamide 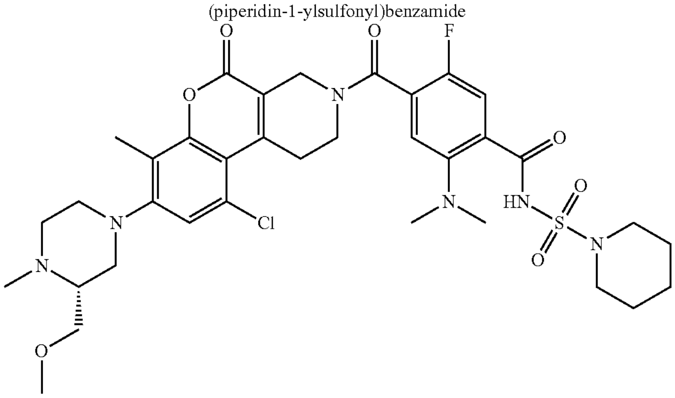 Synthesised from Intermediates 258 and 269 | HPLC: (System 1, Method H) Rt = 8.45 min. m/z 746.9 $(M + H)^+$ $(ES^+)$. $^1$H NMR (400 MHz, DMSO-$d_6$) δ: 13.09 (br s, 1H), 7.56-7.50 (m, 1H), 7.45-7.35 (m, 1H), 7.07-7.05 (m, 1H), 4.53 (br s, 1H), 4.21 (br s, 1H), 3.87 (br s, 1H), 3.57-3.54 (m, 1H), 3.48 (br s, 1H), 3.37-3.33 (m, 2H), 3.27-3.26 (m, 8H), 3.18-3.15 (m, 1H), 3.09-3.06 (m, 1H), 2.88-2.83 (m, 2H), 2.79-2.76 (m, 6H), 2.68-2.63 (m, 1H), 2.46-2.41 (m, 2H), 2.32 (s, 3H), 2.25-2.21 (m, 3H), 1.57 (br s, 4H), 1.50-1.49 (m, 2H). |
| Example 276 | (R)-N-(N,N-dicyclopropylsulfamoyl)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 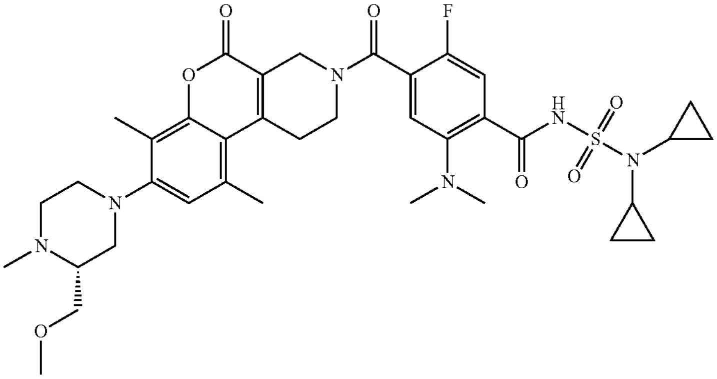 [SMILES: COC[C@H]1CN(c2cc(C)c3c4c(c(=O)oc3c2C)CN(C(=O)c2cc(N(C)C)c(C(=O)NS(=O)(=O)N(C3CC3)C3CC3)cc2F)CC4)CCN1C] Synthesised from Intermediates 6 and 270 | HPLC: (System 1, Method H) Rt = 8.00 min. m/z 739.0 $(M + H)^+$ $(ES^+)$. $^1$H NMR (400 MHz, DMSO-$d_6$) δ: 13.66 (br s, 1H), 7.62-7.41 (m, 2H), 6.86-6.85 (m, 1H), 4.52 (br s, 1H), 4.20 (br s, 1H), 3.87 (br s, 1H), 3.58-3.54 (m, 1H), 3.49-3.47 (m, 1H), 3.39-3.36 (m, 1H), 3.27 (s, 3H), 3.23 (br s, 1H), 3.16-3.13 (m, 2H), 3.06-3.04 (m, 1H), 2.90-2.83 (m, 2H), 2.81-2.78 (m, 6H), 2.75-2.62 (m, 6H), 2.51 (br s, 1H), 2.49 (br s, 1H), 2.34 (s, 3H), 2.24-2.20 (m, 3H), 0.81 (br s, 4H), 0.70-0.65 (m, 4H). |

-continued

| Example No. | Name/Structure/Intermediates | LCMS/$^1$H NMR data |
|---|---|---|
| Example 277 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-N-(N,N-dicyclopropylsulfamoyl)-2-(dimethylamino)-5-fluorobenzamide 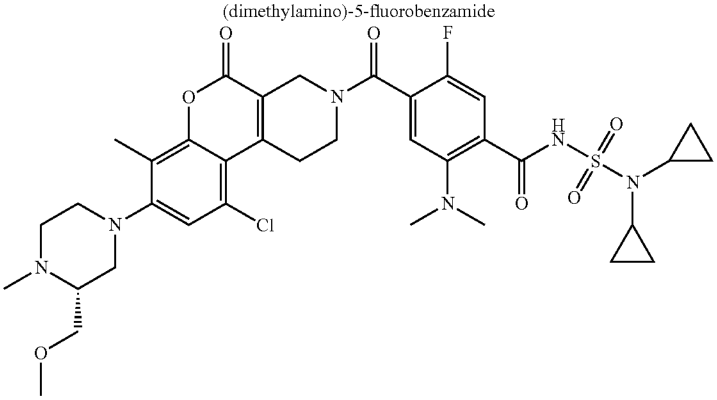 Synthesised from Intermediates 258 and 270 | HPLC: (System 1, Method H) Rt = 8.47 min. m/z 759.0 $(M + H)^+$ $(ES^+)$. $^1$H NMR (400 MHz, DMSO-$d_6$) δ: 13.74 (br s, 1H), 7.63-7.45 (m, 2H), 7.07-7.05 (m, 1H), 4.54 (br s, 1H), 4.22 (br s, 1H), 3.88 (br s, 1H), 3.57-3.54 (m, 1H), 3.49 (br, s 1H), 3.38-3.36 (m, 2H), 3.27 (br s, 4H), 3.18-3.15 (m, 1H), 3.09-3.07 (m, 1H), 2.89-2.84 (m, 2H), 2.81-2.78 (m, 6H), 2.74-2.70 (m, 2H), 2.67-2.64 (m, 1H), 2.49-2.46 (m, 2H), 2.33 (s, 3H), 2.25-2.21 (m, 3H), 0.81-0.80 (m, 4H), 0.69-0.67 (m, 4H). |
| Example 278 | 4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(((R)-2-(trifluoromethyl)pyrrolidin-1-yl)sulfonyl)benzamide 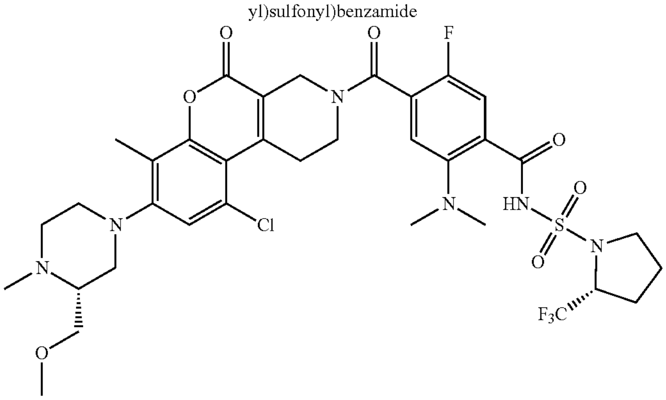 Synthesised from Intermediates 258 and 272 | HPLC: (System 1, Method H) Rt = 8.18 min. m/z 800.8 $(M + H)^+$ $(ES^+)$. $^1$H NMR (400 MHz, DMSO-$d_6$) δ: 13.04 (br s, 1H), 7.51-7.47 (m, 1H), 7.39-7.33 (m, 1H), 7.09-7.07 (m, 1H), 4.94-4.90 (m, 1H), 4.53 (br s, 1H), 4.22 (br s, 1H), 3.88 (br s 1H), 3.58-3.56 (m, 1H), 3.48-3.42 (m, 3H), 3.32 (br s, 1H), 3.29 (br s, 4H), 3.26-3.21 (m, 2H), 3.18-3.12 (m, 1H), 3.02-2.96 (m, 1H), 2.94-2.87 (m, 1H), 2.82-2.79 (m, 6H), 2.77-2.75 (m, 2H), 2.69-2.62 (m, 1H), 2.46 (s, 3H), 2.26-2.22 (m, 3H), 2.15-2.06 (m, 1H), 1.98-1.88 (m, 3H). |
| Example 279 | (R)-N-((2-azaspiro[3.3]heptan-2-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-methoxybenzamide 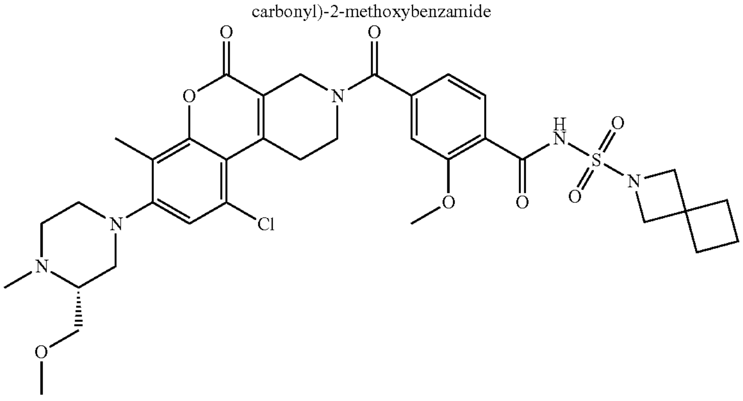 Synthesised from Intermediates 258 and 273 | HPLC: (System 1, Method H) Rt = 7.26 min. m/z 727.9 $(M + H)^+$ $(ES^+)$. $^1$H NMR (400 MHz, DMSO-$d_6$) δ: 11.36 (br s, 1H), 7.53-7.50 (m, 1H), 7.22 (s, 1H), 7.14-7.11 (m, 1H), 7.05 (s, 1H), 4.50 (br s, 1H), 4.32 (br s, 1H), 4.02 (s, 4H), 3.88-3.84 (m, 4H), 3.57-3.54 (m, 2H), 3.38-3.32 (m, 3H), 3.27 (s, 3H), 3.18-3.15 (m, 1H), 3.09-3.06 (m, 1H), 2.88-2.83 (m, 2H), 2.69-2.64 (m, 1H), 2.48-2.45 (m, 2H), 2.33 (s, 3H), 2.25-2.21 (m, 3H), 2.13-2.10 (m, 4H), 1.80-1.74 (m, 2H). |

-continued

| Example No. | Name/Structure/Intermediates | LCMS/$^1$H NMR data |
|---|---|---|
| Example 280 | N-((3-azabicyclo[3.1.0]hexan-3-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-methoxybenzamide 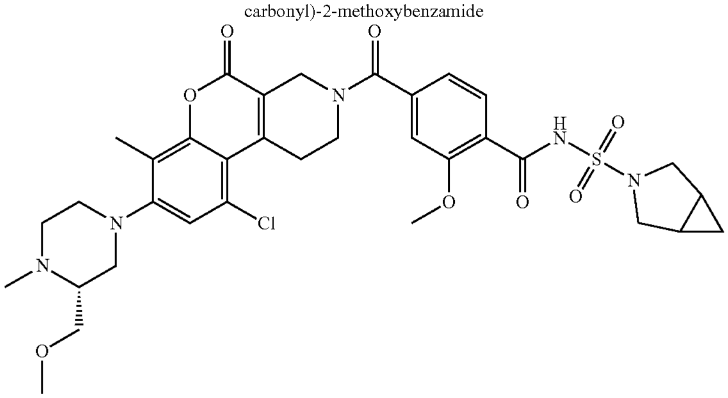 Synthesised from Intermediates 258 and 274 | HPLC: (System 1, Method H) Rt = 7.41 min. m/z 713.8 (M + H)$^+$ (ES$^+$). $^1$H NMR (400 MHz, DMSO-d$_6$) δ: 11.4 (br s, 1H), 7.52-7.51 (m, 1H), 7.22 (s, 1H), 7.12 (d, J = 7.6 Hz, 1H), 7.05 (s, 1H), 4.49 (br s, 1H), 4.30 (br s, 1H), 3.88 (br s, 4H), 3.57-3.47 (m, 6H), 3.35-3.32 (m, 3H), 3.26 (s, 3H), 3.16-3.14 (m, 1H), 3.07-3.05 (m, 1H), 2.87-2.82 (m, 2H), 2.67-2.61 (m, 1H), 2.42-2.40 (m, 2H), 2.30 (s, 3H), 2.25-2.21 (m, 3H), 1.59 (br s, 2H), 0.67-0.66 (m, 1H), 0.28-0.27 (m, 1H). |
| Example 281 | 2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(((S)-3-methoxypiperidin-1-yl)sulfonyl)benzamide 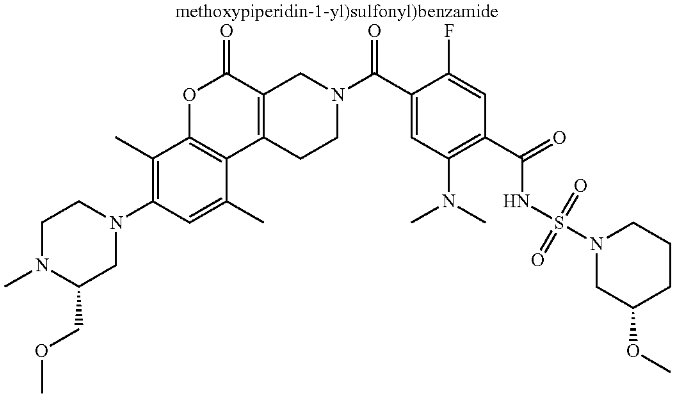 Synthesised from Intermediates 6 and 276 | HPLC: (System 1, Method H) Rt = 7.31 min. m/z 757.0 (M + H)$^+$ (ES$^+$). $^1$H NMR (400 MHz, DMSO-d$_6$) δ: 13.1 (br s, 1H), 7.52-7.46 (m, 1H), 7.40-7.28 (m, 1H), 6.86-6.84 (m, 1H), 4.52 (br s, 1H), 4.20 (s, 1H), 3.87 (br s, 1H), 3.57-3.53 (m, 2H), 3.47 (t, J = 5.2 Hz, 1H), 3.38-3.36 (m, 2H), 3.33 (br s, 1H), 3.27-3.26 (m, 6H), 3.23 (br s, 1H), 3.16-2.99 (m, 5H), 2.89-2.83 (m, 2H), 2.79-2.76 (m, 6H), 2.69-2.61 (m, 4H), 2.49-2.47 (m, 2H), 2.34 (s, 3H), 2.24-2.20 (m, 3H), 1.82-1.73 (m, 2H), 1.48-1.38 (m, 2H). |
| Example 282 | (R)-N-((2-oxa-6-azaspiro[3.3]heptan-6-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide 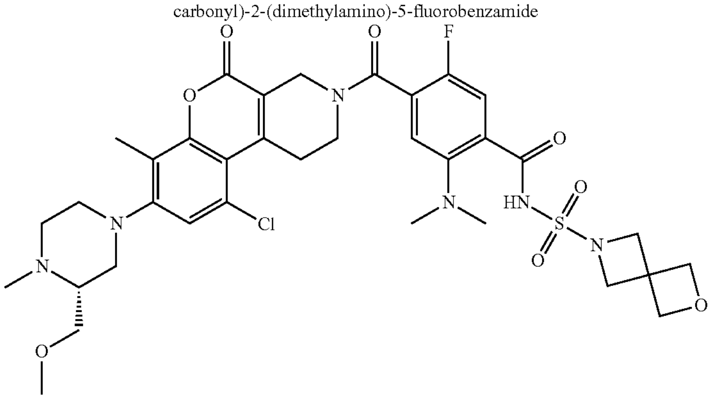 Synthesised from Intermediates 258 and 278 | HPLC: (System 1, Method H) Rt = 6.74 min. m/z 760.9 (M + H)$^+$ (ES$^+$). $^1$H NMR (400 MHz, DMSO-d$_6$) δ: 12.96 (br s, 1H), 7.53-7.49 (m, 1H), 7.40-7.34 (m, 1H), 7.08-7.06 (m, 1H), 4.64 (s, 4H), 4.53 (br s, 1H), 4.22 (br s, 1H), 4.17-4.16 (m, 4H), 3.88 (br s, 1H), 3.59-3.55 (m, 1H), 3.49-3.46 (m, 1H), 3.42-3.40 (m, 1H), 3.31 (br s, 1H), 3.28 (br s, 4H), 3.21-3.19 (m, 1H), 3.13-3.10 (m, 1H), 2.96-2.87 (m, 2H), 2.81-2.78 (m, 6H), 2.73-2.70 (m, 1H), 2.68-2.58 (m, 2H), 2.41 (s, 3H), 2.26-2.22 (m, 3H). |

-continued

| Example No. | Name/Structure/Intermediates | LCMS/$^1$H NMR data |
|---|---|---|
| Example 283 | 4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-methoxy-N-(((S)-2-(methoxymethyl)pyrrolidin-1-yl)sulfonyl)benzamide 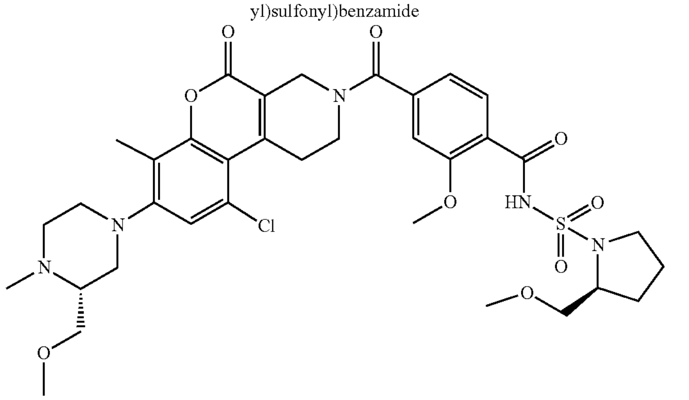 Synthesised from Intermediates 258 and 280 | HPLC: (System 1, Method H) Rt = 7.34 min. m/z 746.0 $(M + H)^+$ $(ES^+)$. $^1$H NMR (400 MHz, DMSO-$d_6$) δ: 11.49 (br s, 1H), 7.55-7.51 (m, 1H), 7.22 (s, 1H), 7.14-7.11 (m, 1H), 7.05 (s, 1H), 4.50 (br s, 1H), 4.30-4.24 (m, 2H), 3.88-3.86 (br s, 4H), 3.57-3.43 (m, 4H), 3.36 (br, 1H), 3.30 (br s, 3H), 3.28 (br s, 4H), 3.26 (s, 3H), 3.17-3.14 (m, 1H), 3.08-3.05 (m, 1H), 2.87-2.82 (m, 2H), 2.67-2.61 (m, 1H), 2.43-2.37 (m, 2H), 2.30 (s, 3H), 2.25-2.21 (m, 3H), 1.90-1.81 (m, 4H). |
| Example 284 | 4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(((S)-3-methoxypyrrolidin-1-yl)sulfonyl)benzamide 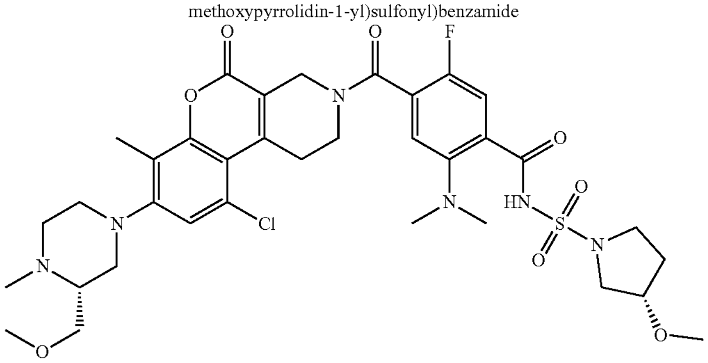 Synthesised from Intermediates 258 and 282 | HPLC: (System 1, Method H) Rt = 7.61 min. m/z 763.0 $(M + H)^+$ $(ES^+)$. $^1$H NMR (400 MHz, DMSO-$d_6$) δ: 13.02 (br s, 1H), 7.54-7.48 (m, 1H), 7.43-7.34 (m, 1H), 7.07-7.04 (m, 1H), 4.53 (br s, 1H), 4.21 (br s, 1H), 4.00 (br s, 1H), 3.87 (br s, 1H), 3.57-3.54 (m, 3H), 3.48-3.40 (m, 3H), 3.39-3.33 (m, 2H), 3.27 (br s, 4H), 3.21-3.20 (m, 3H), 3.18-3.15 (m, 1H), 3.09-3.06 (m, 1H), 2.88-2.83 (m, 2H), 2.78-2.75 (m, 6H), 2.68-2.63 (m, 1H), 2.46-2.43 (m, 2H), 2.32 (s, 3H), 2.25-2.21 (m, 3H), 1.97-1.95 (m, 2H). |
| Example 285 | 4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(((R)-3-methoxypyrrolidin-1-yl)sulfonyl)benzamide 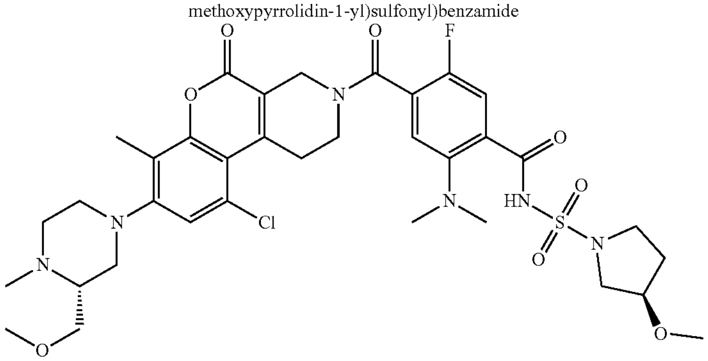 Synthesised from Intermediates 258 and 284 | HPLC: (System 1, Method H) Rt = 7.62 min. m/z 762.9 $(M + H)^+$ $(ES^+)$. $^1$H NMR (400 MHz, DMSO-$d_6$) δ: 13.08 (br s, 1H), 7.54-7.48 (m, 1H), 7.42-7.33 (m, wq1H), 7.07-7.05 (m, 1H), 4.53 (br s, 1H), 4.21 (br s, 1H), 3.99 (br s, 1H), 3.88 (br s, 1H), 3.56-3.51 (m, 3H), 3.48-3.40 (m, 3H), 3.38-3.33 (m, 2H), 3.27 (br s, 4H), 3.21-3.20 (m, 3H), 3.19-3.15 (m, 1H), 3.09-3.06 (m, 1H), 2.88-2.83 (m, 2H), 2.78-2.75 (m, 6H), 2.68-2.63 (m, 1H), 2.45-2.43 (m, 2H), 2.31 (s, 3H), 2.25-2.21 (m, 3H), 1.97-1.94 (m, 2H). |

-continued

| Example No. | Name/Structure/Intermediates | LCMS/$^1$H NMR data |
|---|---|---|
| Example 286 | 2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(((R)-3-methoxypiperidin-1-yl)sulfonyl)benzamide 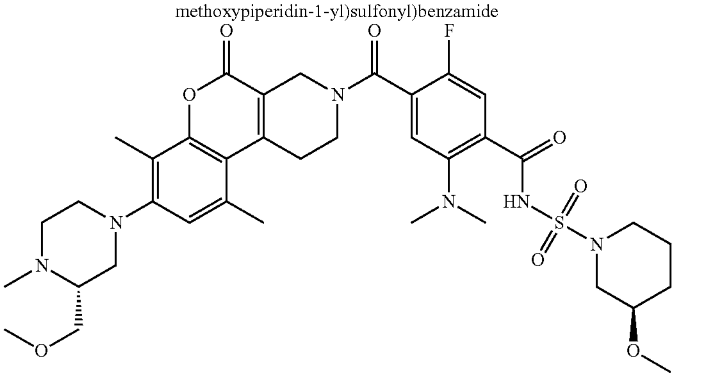 Synthesised from Intermediates 6 and 286 | HPLC: (System 1, Method H) Rt = 7.29 min. m/z 757.0 $(M + H)^+$ $(ES^+)$. $^1$H NMR (400 MHz, DMSO-$d_6$) δ: 13.10 (br s, 1H), 7.54-7.48 (m, 1H), 7.43-7.29 (m, 1H), 6.86-6.84 (m, 1H), 4.52 (br s, 1H), 4.20 (br s, 1H), 3.87 (br s, 1H), 3.58-3.53 (m, 2H), 3.48-3.46 (m, 1H), 3.38-3.33 (m, 3H), 3.27-3.26 (m, 6H), 3.23 (br s, 1H), 3.16-3.01 (m, 5H), 2.90-2.83 (m, 2H), 2.79-2.76 (m, 6H), 2.69-2.61 (m, 4H), 2.51 (br s, 1H), 2.49 (br s, 1H), 2.35 (s, 3H), 2.24-2.20 (m, 3H), 1.82-1.73 (m, 2H), 1.49-1.38 (m, 2H). |
| Example 287 | 2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(((R)-2-(trifluoromethyl)pyrrolidin-1-yl)sulfonyl)benzamide 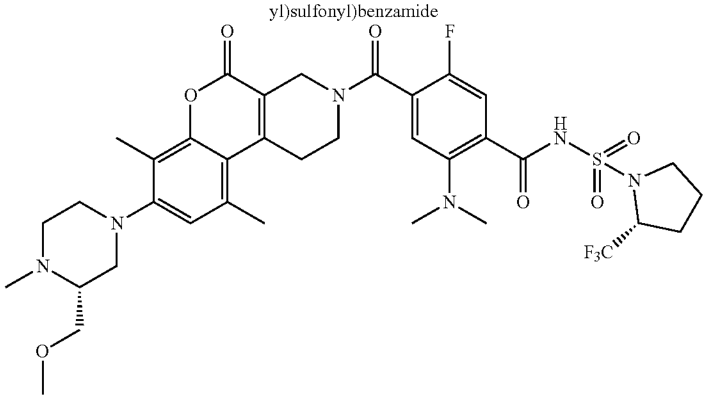 Synthesised from Intermediates 6 and 272 | HPLC: (System 1, Method H) Rt = 7.82 min. m/z 780.9 $(M + H)^+$ $(ES^+)$. $^1$H NMR (400 MHz, DMSO-$d_6$) δ: 7.48-7.46 (m, 1H), 7.36-7.27 (m, 1H), 6.88-6.86 (m, 1H), 4.94-4.90 (m, 1H), 4.52 (br s, 1H), 4.21 (br s, 1H), 3.87 (br s, 1H), 3.59-3.57 (m, 1H), 3.48-3.40 (m, 4H), 3.30 (br s, 4H), 3.23-3.18 (m, 2H), 3.13-3.10 (m, 2H), 3.05-3.03 (m, 1H), 2.91-2.86 (m, 1H), 2.82-2.74 (m, 8H), 2.70-2.62 (m, 4H), 3.50 (br s, 2H), 2.25-2.21 (m, 3H), 2.15-2.07 (m, 1H), 1.96-1.89 (m, 3H). |
| Example 288 | 4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-methoxy-N-(((R)-2-(methoxymethyl)pyrrolidin-1-yl)sulfonyl)benzamide 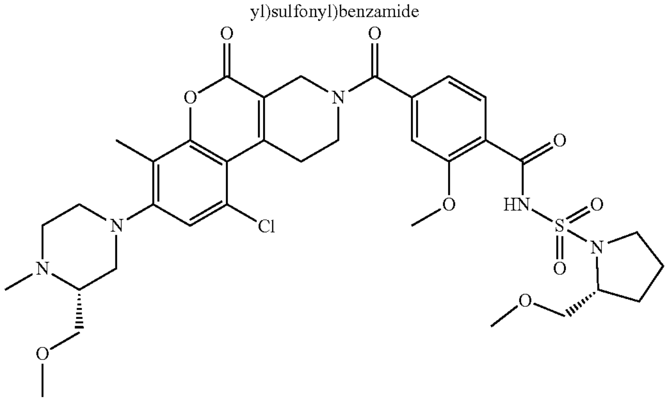 Synthesised from Intermediates 258 and 288 | HPLC: (System 1, Method H) Rt = 7.33 min. m/z 745.9 $(M + H)^+$ $(ES^+)$. $^1$H NMR (400 MHz, DMSO-$d_6$) δ: 11.51 (br s, 1H), 7.53 (d, J = 7.6 Hz, 1H), 7.22 (s, 1H), 7.12 (dd, J = 7.6, 1.2 Hz, 1H), 7.05 (s, 1H), 4.49 (br s, 1H), 4.30-4.24 (m, 2H), 3.87 (br s, 4H), 3.57-3.54 (m, 1H), 3.52-3.43 (m, 3H), 3.36 (br s, 2H), 3.30-3.28 (m, 6H), 3.26 (s, 3H), 3.16-3.14 (m, 1H), 3.08-3.05 (m, 1H), 2.87-2.82 (m, 2H), 2.67-2.61 (m, 1H), 2.43-2.37 (m, 2H), 2.30 (s, 3H), 2.24-2.21 (m, 3H), 1.90-1.81 (m, 4H) |

-continued

| Example No. | Name/Structure/Intermediates | LCMS/$^1$H NMR data |
|---|---|---|
| Example 289 | (R)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((4-methoxypiperidin-1-yl)sulfonyl)benzamide 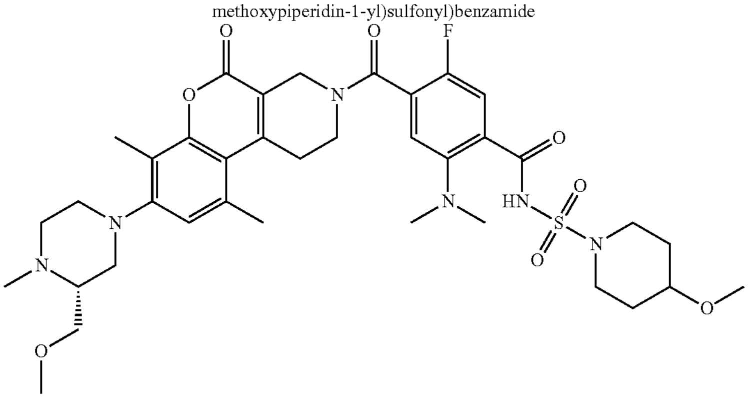 Synthesised from Intermediates 6 and 290 | HPLC: (System 1, Method H) Rt = 7.20 min. m/z 757.0 $(M + H)^+$ $(ES^+)$. $^1$H NMR (400 MHz, DMSO-$d_6$) δ: 13.11 (br s, 1H), 7.53-7.47 (m, 1H), 7.45-7.30 (m, 1H), 6.86-6.84 (m, 1H), 4.52 (br s, 1H), 4.20 (br s, 1H), 3.87 (br s, 1H), 3.58-3.54 (m, 1H), 3.47-3.44 (m, 3H), 3.39-3.36 (m, 2H), 3.27 (s, 3H), 3.24 (br s, 4H), 3.16-3.11 (m, 4H), 3.06-3.04 (m, 1H), 2.90-2.83 (m, 2H), 2.79-2.76 (m, 6H), 2.69-2.62 (m, 4H), 3.51 (br s, 1H), 3.49 (br s, 1H), 2.35 (s, 3H), 2.24-2.20 (m, 3H), 1.89-1.84 (m, 2H), 1.56-1.51 (m, 2H). |
| Example 290 | 4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(((R)-2-(methoxymethyl)pyrrolidin-1-yl)sulfonyl)benzamide 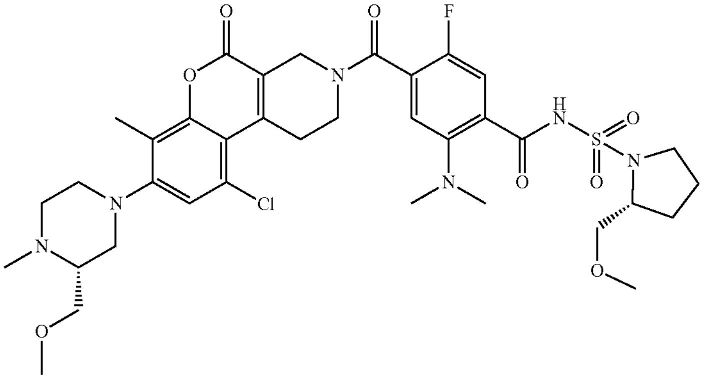 [SMILES: COC[C@H]1CN(c2cc(Cl)c3c4c(c(=O)oc3c2C)CN(C(=O)c2cc(N(C)C)c(C(=O)NS(=O)(=O)N3CCC[C@@H]3COC)cc2F)CC4)CCN1C] Synthesised from Intermediates 258 and 291 | HPLC: (System 1, Method H) Rt = 8.20 min. m/z 776.9 $(M + H)^+$ $(ES^+)$. $^1$H NMR (400 MHz, DMSO-$d_6$) δ: 13.12 (br s, 1H), 7.57-7.51 (m, 1H), 7.45-7.36 (m, 1H), 7.07-7.05 (m, 1H), 4.53 (br s, 1H), 4.27-4.21 (m, 2H), 3.87 (br s, 1H), 3.57-3.54 (m, 1H), 3.48-3.42 (m, 3H), 3.37-3.33 (m, 2H), 3.30-3.27 (m, 9H), 3.18-3.15 (m, 1H), 3.09-3.06 (m, 1H), 2.88-2.83 (m, 2H), 2.77-2.75 (m, 6H), 2.68-2.63 (m, 1H), 2.46-2.44 (m, 2H), 2.32 (s, 3H), 2.25-2.21 (m, 3H), 1.88-1.81 (m, 4H). |
| Example 291 | (R)-5-chloro-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-N-(N,N-dimethylsulfamoyl)benzamide 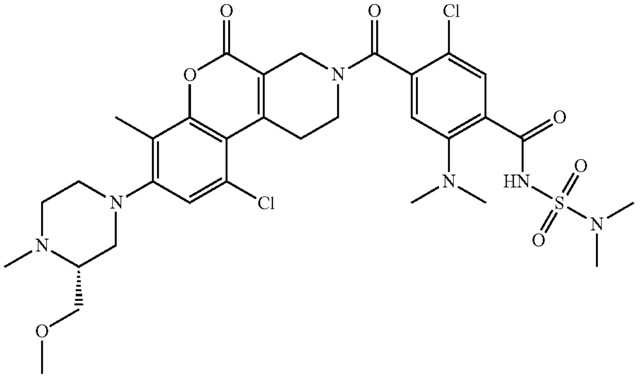 Synthesised from Intermediates 258 and 292 | HPLC: (System 1, Method H) Rt = 7.17 min. m/z 722.8 $(M + H)^+$ $(ES^+)$. $^1$H NMR (400 MHz, DMSO-$d_6$) δ: 12.10 (br s, 1H), 7.52-7.47 (m, 1H), 7.11-7.04 (m, 2H), 4.60-4.45 (m, 1H), 4.12 (br s, 1H), 3.98-3.77 (m, 1H), 3.57-3.54 (m, 1H), 3.44-3.36 (m, 2H), 3.27 (br s, 4H), 3.18-3.16 (m, 1H), 3.09-3.07 (m, 1H), 2.89-2.81 (m, 15H), 2.70-2.64 (m, 1H), 2.50-2.47 (m, 2H), 2.34 (s, 3H), 2.25-2.21 (m, 3H). |

-continued

| Example No. | Name/Structure/Intermediates | LCMS/$^1$H NMR data |
|---|---|---|
| Example 292 | 2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(((S)-2-(trifluoromethyl)pyrrolidin-1-yl)sulfonyl)benzamide 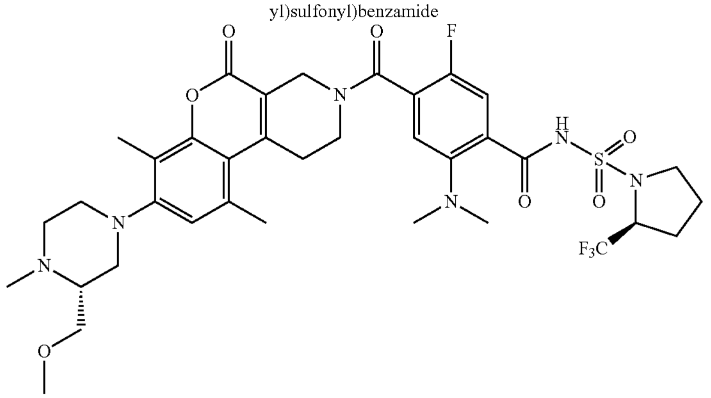 Synthesised from Intermediates 6 and 294 | HPLC: (System 1, Method H) Rt = 7.77 min. m/z 780.9 (M + H)$^+$ (ES$^+$). $^1$H NMR (400 MHz, DMSO-$d_6$) δ: 7.45-7.25 (m, 2H), 6.88-6.86 (m, 1H), 4.94-4.90 (m, 1H), 4.52 (br s, 1H), 4.21 (br, 1H), 3.87 (br s, 1H), 3.59-3.57 (m, 1H), 3.49-3.42 (m, 4H), 3.30 (br s, 4H), 3.23-3.20 (m, 2H), 3.13-3.10 (m, 2H), 3.08-3.03 (m, 1H), 2.91-2.86 (m, 1H), 2.82-2.74 (m, 8H), 2.70-2.62 (m, 4H), 3.50 (br s, 2H), 2.25-2.21 (m, 3H), 2.14-2.09 (m, 1H), 1.96-1.89 (m, 3H). |
| Example 293 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-((4-(trifluoromethyl)piperidin-1-yl)sulfonyl)benzamide 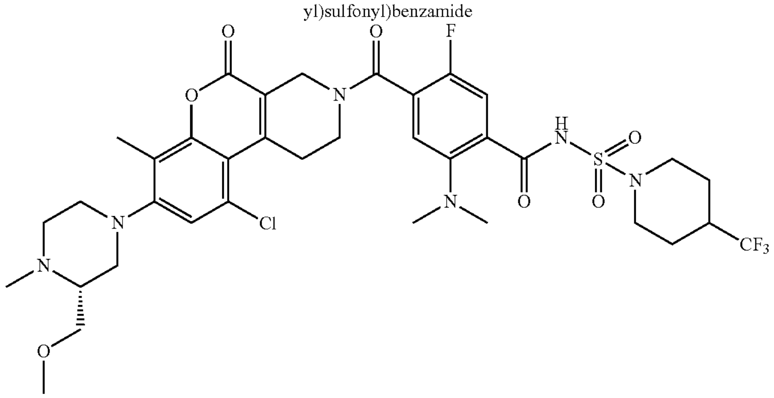 Synthesised from Intermediates 258 and 296 | HPLC: (System 1, Method H) Rt = 8.40 min. m/z 814.9 (M + H)$^+$ (ES$^+$). $^1$H NMR (400 MHz, DMSO-$d_6$) δ: 13.08 (br s, 1H), 7.52-7.46 (m, 1H), 7.42-7.34 (m, 1H), 7.08-7.06 (m, 1H), 4.53 (br s, 1H), 4.21 (br s, 1H), 3.88 (br s, 1H), 3.82-3.79 (m, 2H), 3.58-3.54 (m, 1H), 3.48-3.45 (m, 1H), 3.41-3.37 (m, 2H), 3.28 (br s, 5H), 3.20-3.17 (m, 1H), 3.11-3.08 (m, 1H), 2.91-2.85 (m, 4H), 2.81-2.78 (m, 6H), 2.72-2.67 (m, 1H), 2.60-2.51 (m, 2H), 2.37 (s, 3H), 2.25-2.21 (m, 3H), 1.92-1.89 (m, 2H), 1.52-1.42 (m, 2H). |

-continued

| Example No. | Name/Structure/Intermediates | LCMS/$^1$H NMR data |
|---|---|---|
| Example 294 | N-(((1R,4R)-2-oxa-5-azabicyclo[2.2.1]heptan-5-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide 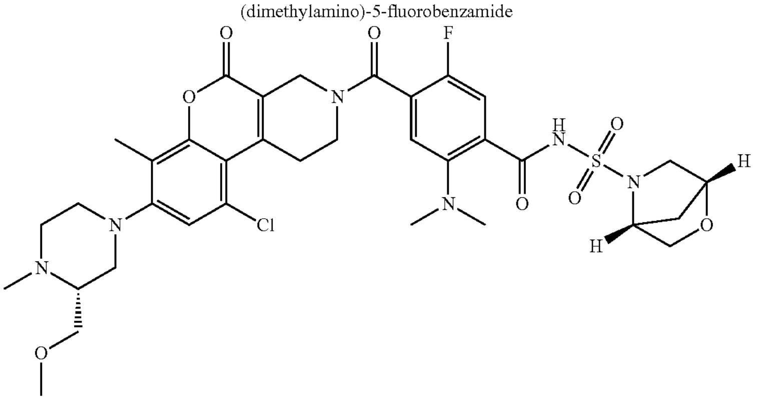 Synthesised from Intermediates 258 and 298 | HPLC: (System 1, Method H) Rt = 6.92 min. m/z 760.8 $(M + H)^+$ $(ES^+)$. $^1$H NMR (400 MHz, DMSO-$d_6$) δ: 13.05 (br s, 1H), 7.55-7.49 (m, 1H), 7.43-7.35 (m, 1H), 7.08-7.05 (m, 1H), 4.62 (br s, 1H), 4.53 (br s, 2H), 4.22 (br s, 1H), 3.87 (br s, 1H), 3.84-3.81 (m, 1H), 3.68-3.66 (m, 1H), 3.58-3.44 (m, 3H), 3.40-3.38 (m, 1H), 3.30-3.27 (m, 6H), 3.19-3.17 (m, 1H), 3.11-3.08 (m, 1H), 2.92-2.85 (m, 2H), 2.78-2.76 (m, 6H), 2.73-2.66 (m, 1H), 2.58-2.51 (m, 2H), 2.33 (s, 3H), 2.25-2.21 (m, 3H), 1.85-1.76 (m, 2H). |
| Example 295 | 4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(((S)-2-(trifluoromethyl)pyrrolidin-1-yl)sulfonyl)benzamide 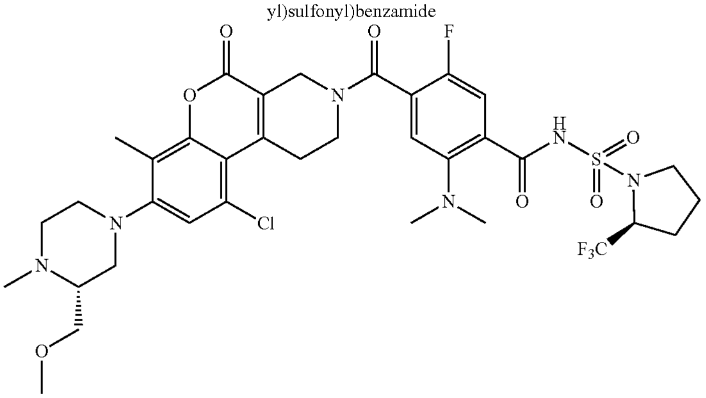 Synthesised from Intermediates 258 and 294 | HPLC: (System 1, Method H) Rt = 8.13 min. m/z 800.8 $(M + H)^+$ $(ES^+)$. $^1$H NMR (400 MHz, DMSO-$d_6$) δ: 12.94 (br s, 1H), 7.50-7.47 (m, 1H), 7.37-7.33 (m, 1H), 7.09-7.07 (m, 1H), 4.94-4.90 (m, 1H), 4.53 (br s, 1H), 4.22 (br s, 1H), 3.87 (br s, 1H), 3.59-3.56 (m, 1H), 3.48-3.41 (m, 4H), 3.29 (br s, 4H), 3.26-3.22 (m, 2H), 3.16-3.13 (m, 1H), 3.03-3.00 (m, 1H), 2.94-2.88 (m, 1H), 2.82-2.76 (m, 8H), 2.67-2.65 (m, 1H), 2.47 (s, 3H), 2.26-2.22 (m, 3H), 2.15-2.09 (m, 1H), 1.96-1.92 (m, 3H). |

-continued

| Example No. | Name/Structure/Intermediates | LCMS/$^1$H NMR data |
|---|---|---|
| Example 296 | (R)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((4-(trifluoromethyl)piperidin-1-yl)sulfonyl)benzamide 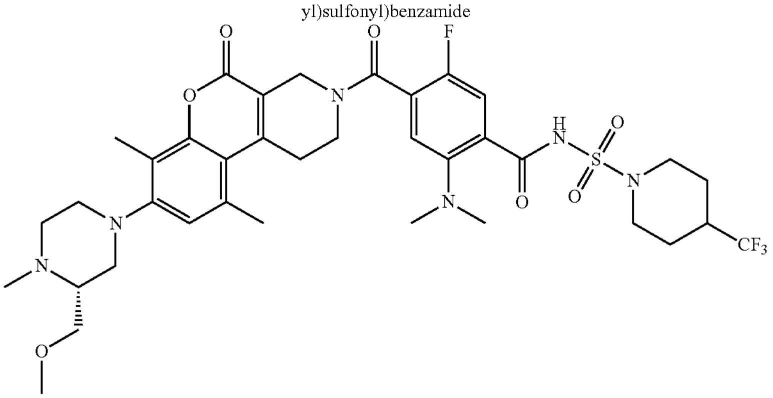 Synthesised from Intermediates 6 and 296 | HPLC: (System 1, Method H) Rt = 8.07 min. m/z 814.9 $(M + H)^+$ $(ES^+)$. $^1$H NMR (400 MHz, DMSO-$d_6$) δ: 13.02 (br s, 1H), 7.50-7.28 (m, 2H), 6.87-6.85 (m, 1H), 4.52 (br s, 1H), 4.20 (br s, 1H), 3.87 (br s, 1H), 3.81-3.78 (m, 2H), 3.58-3.55 (m, 1H), 3.49-3.46 (m, 1H), 3.41-3.37 (m, 2H), 3.28 (s, 3H), 3.23 (br s, 1H), 3.17-3.15 (m, 2H), 3.08-3.05 (m, 1H), 2.92-2.84 (m, 4H), 2.81-2.78 (m, 6H), 2.69-2.53 (m, 6H), 2.38 (s, 3H), 2.24-2.20 (m, 3H), 1.91-1.88 (m, 2H), 1.52-1.45 (m, 2H). |
| Example 297 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-N-(N,N-dicyclopropylsulfamoyl)-5-fluoro-2-methoxybenzamide 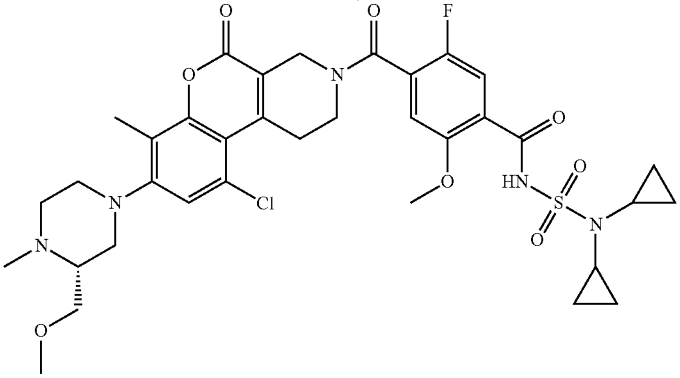 [SMILES: COC[C@H]1CN(c2cc(Cl)c3c4c(c(=O)oc3c2C)CN(C(=O)c2cc(OC)c(C(=O)NS(=O)(=O)N(C3CC3)C3CC3)cc2F)CC4)CCN1C] Synthesised from Intermediates 258 and 299 | HPLC: (System 1, Method H) Rt = 7.50 min. m/z 746.0 $(M + H)^+$ $(ES^+)$. $^1$H NMR (400 MHz, DMSO-$d_6$) δ: 11.57 (br s, 1H), 7.45-7.42 (m, 1H), 7.24-7.19 (m, 1H), 7.07-7.05 (m, 1H), 4.53 (br s, 1H), 4.22 (br s, 1H), 3.87-3.81 (m, 4H), 3.58-3.54 (m, 1H), 3.49 (br s, 1H), 3.40-3.36 (m, 2H), 3.27 (br s, 4H), 3.19-3.17 (m, 1H), 3.10-3.08 (m, 1H), 2.91-2.84 (m, 2H), 2.73-2.66 (m, 3H), 2.55 (br s, 1H), 2.47 (br s, 1H), 2.36 (s, 3H), 2.25-2.21 (m, 3H), 0.84-0.80 (m, 4H), 0.71-0.66 (m, 4H). |
| Example 298 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-N-(N-cyclopropyl-N-methylsulfamoyl)-2-ethoxy-5-fluorobenzamide 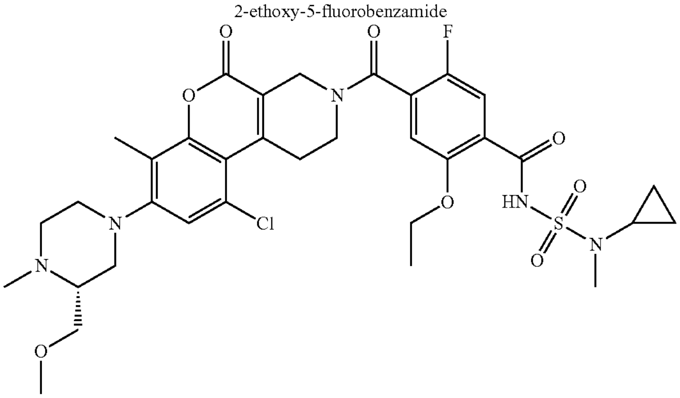 Synthesised from Intermediates 259 and 258 | HPLC: (System 1, Method H) Rt = 7.46 min. m/z 733.8 $(M + H)^+$ $(ES^+)$. $^1$H NMR (400 MHz, DMSO-$d_6$) δ: 11.48 (br s, 1H), 7.47-7.44 (m, 1H), 7.24-7.18 (m, 1H), 7.07-7.05 (m, 1H), 4.53 (br s, 1H), 4.21 (br s, 1H), 4.15-4.06 (m, 2H), 3.87 (br s, 1H), 3.57-3.54 (m, 1H), 3.48 (br s, 1H), 3.39-3.36 (m, 2H), 3.27 (br s, 4H), 3.19-3.16 (m, 1H), 3.10-3.07 (m, 1H), 2.92 (s, 3H), 2.89-2.84 (m, 2H), 2.70-2.65 (m, 1H), 2.62-2.58 (m, 1H), 2.51 (br s, 1H), 2.50-2.47 (m, 1H), 2.34 (s, 3H), 2.25-2.21 (m, 3H), 1.34-1.28 (m, 3H), 0.78-0.67 (m, 4H). |

-continued

| Example No. | Name/Structure/Intermediates | LCMS/$^1$H NMR data |
|---|---|---|
| Example 299 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluoro-N-((1-methylcyclopropyl)sulfonyl)benzamide 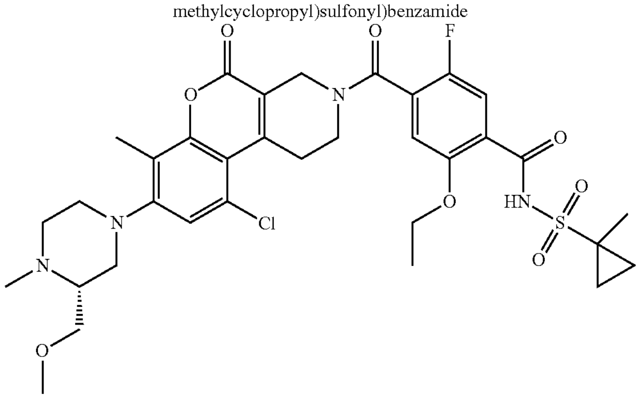 Synthesised from Intermediates 258 and 300 | HPLC: (System 1, Method H) Rt = 7.00 min. m/z 718.9 $(M + H)^+$ $(ES^+)$. $^1$H NMR (400 MHz, DMSO-$d_6$) δ: 11.37 (br s, 1H), 7.44-7.41 (m, 1H), 7.23-7.18 (m, 1H), 7.07-7.05 (m, 1H), 4.53 (br s, 1H), 4.21 (br s, 1H), 4.15-4.07 (m, 2H), 3.87 (br s, 1H), 3.58-3.54 (m, 1H), 3.48-3.47 (m, 1H), 3.40-3.36 (m, 2H), 3.27 (br s, 4H), 3.19-3.16 (m, 1H), 3.10-3.07 (m, 1H), 2.90-2.84 (m, 2H), 2.71-2.66 (m, 1H), 2.51 (br s, 1H), 2.49 (br s, 1H), 2.35 (s, 3H), 2.25-2.21 (m, 3H), 1.52 (s, 3H), 1.44-1.41 (m, 2H), 1.34-1.30 (m, 3H), 0.94-0.91 (m, 2H). |
| Example 300 | (R)-N-((2-azaspiro[3.3]heptan-2-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluorobenzamide 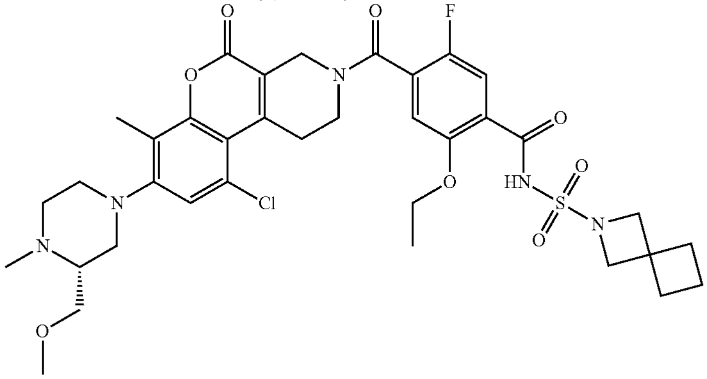 Synthesised from Intermediates 258 and 187 | HPLC: (System 1, Method H) Rt = 8.23 min. m/z 759.6 $(M + H)^+$ $(ES^+)$. $^1$H NMR (400 MHz, DMSO-$d_6$) δ: 11.32 (br s, 1H), 7.44-7.41 (m, 1H), 7.23-7.18 (m, 1H), 7.08-7.06 (m, 1H), 4.53 (br s, 1H), 4.21 (br s, 1H), 4.16-4.07 (m, 2H), 4.00 (s, 4H), 3.87 (br s, 1H), 3.58-3.54 (m, 1H), 3.48 (br s, 1H), 3.40-3.36 (m, 2H), 3.27 (br s, 4H), 3.20-3.17 (m, 1H), 3.11-3.08 (m, 1H), 2.92-2.85 (m, 2H), 2.72-2.66 (m, 1H), 2.53-2.51 (m, 2H), 2.36 (s, 3H), 2.24-2.21 (m, 3H), 2.12-2.09 (m, 4H), 1.79-1.74 (m, 2H), 1.36-1.31 (m, 3H). |
| Example 301 | N-((8-oxa-3-azabicyclo[3.2.1]octan-3-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluorobenzamide 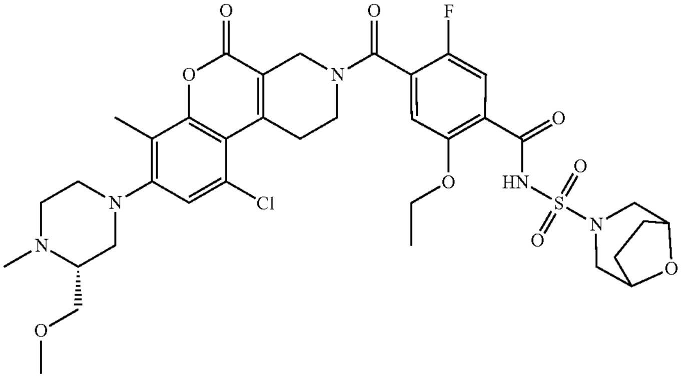 [SMILES: CCOc1cc(C(=O)N2CCc3c(c(=O)oc4c(C)c(N5CCN(C)[C@@H](COC)C5)cc(Cl)c34)C2)c(F)cc1C(=O)NS(=O)(=O)N1CC2CCC(C1)O2] Synthesised from Intermediates 258 and 302 | HPLC: (System 1, Method H) Rt = 6.99 min. m/z 775.8 $(M + H)^+$ $(ES^+)$. $^1$H NMR (400 MHz, DMSO-$d_6$) δ: 11.42 (br s, 1H), 7.43-7.41 (m, 1H), 7.22-7.17 (m, 1H), 7.07-7.05 (m, 1H), 4.53 (br s, 1H), 4.38 (br s, 2H), 4.21 (br s, 1H), 4.12-4.07 (m, 2H), 3.86 (br s, 1H), 3.58-3.54 (m, 1H), 3.48 (b sr, 1H), 3.40-3.36 (m, 2H), 3.29-3.26 (m, 6H), 3.19-3.13 (m, 3H), 3.11-3.08 (m, 1H), 2.91-2.84 (m, 2H), 2.71-2.66 (m, 1H), 2.51 (br s, 1H), 2.50 (br s, 1H), 2.36 (s, 3H), 2.25-2.21 (m, 3H), 1.80 (br s, 4H), 1.36-1.31 (m, 3H). |

-continued

| Example No. | Name/Structure/Intermediates | LCMS/$^1$H NMR data |
|---|---|---|
| Example 302 | 4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(((S)-3-fluoropyrrolidin-1-yl)sulfonyl)benzamide 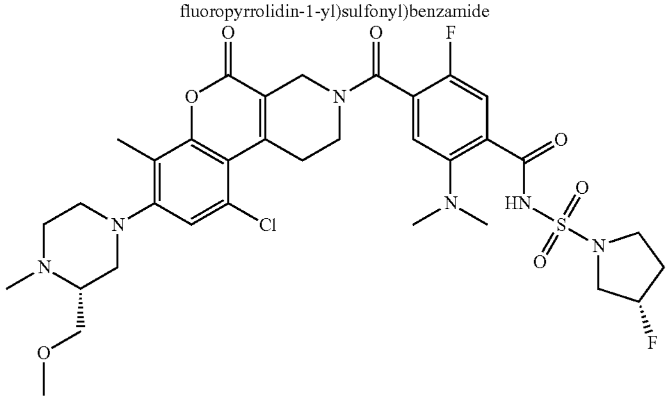 Synthesised from Intermediates 258 and 304 | HPLC: (System 1, Method H) Rt = 7.54 min. m/z 750.9 $(M + H)^+$ $(ES^+)$. 1H NMR (400 MHz, DMSO-$d_6$) δ: 13.10 (br s, 1H), 7.53-7.33 (m, 2H), 7.07-7.05 (m, 1H), 5.42-5.29 (m, 1H), 4.53 (br s, 1H), 4.21 (br s, 1H), 3.87 (br s, 1H), 3.75-3.66 (m, 2H), 3.63 (br s, 1H), 3.57-3.54 (m, 1H), 3.52-3.45 (m, 2H), 3.39-3.34 (m, 2H), 3.27 (br s, 4H), 3.18-3.16 (m, 1H), 3.09-3.07 (m, 1H), 2.89-2.84 (m, 2H), 2.78-2.76 (m, 6H), 2.70-2.64 (m, 1H), 2.50-2.49 (m, 2H), 2.34 (s, 3H), 2.25-2.21 (m, 3H), 2.16-2.00 (m, 2H). |
| Example 303 | 4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(((R)-3-fluoropyrrolidin-1-yl)sulfonyl)benzamide 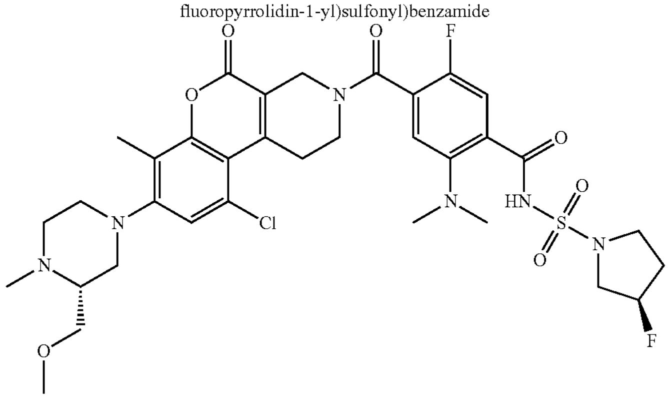 Synthesised from Intermediates 258 and 306 | HPLC: (System 1, Method H) Rt = 7.49 min. m/z 750.8 $(M + H)^+$ $(ES^+)$. $^1$H NMR (400 MHz, DMSO-$d_6$) δ: 13.10 (br, s 1H), 7.53-7.33 (m, 2H), 7.07-7.05 (m, 1H), 5.42-5.29 (m, 1H), 4.53 (br s, 1H), 4.21 (br s, 1H), 3.87 (br s, 1H), 3.75-3.66 (m, 2H), 3.63 (br, 1H), 3.57-3.54 (m, 1H), 3.51-3.49 (m, 2H), 3.39-3.36 (m, 1H), 3.33 (br, 1H), 3.27 (br s, 4H), 3.19-3.16 (m, 1H), 3.10-3.07 (m, 1H), 2.88-2.84 (m, 2H), 2.78-2.76 (m, 6H), 2.70-2.65 (m, 1H), 2.50 (br, 2H), 2.34 (s, 3H), 2.25-2.21 (m, 3H), 2.16-2.01 (m, 2H). |
| Example 304 | (R)-N-((7-azabicyclo[2.2.1]heptan-7-yl)sulfonyl)-2-(dimethylamino)-5-fluoro-4-(10-fluoro-8-(3-(methoxymethyl)-4-methylpiperazin-1-yl)-7-methyl-5-oxo-1,3,4,5-tetrahydro-2H-chromeno[3,4-c]pyridine-3-carbonyl)benzamide 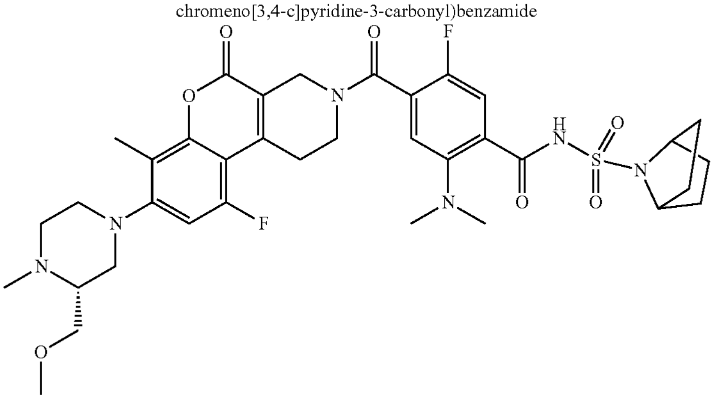 Synthesised from Intermediates 309 and 170 | HPLC: (System 1, Method H) Rt = 7.43 min. m/z 773.0 $(M + H)^+$ $(ES^+)$. $^1$H NMR (400 MHz, DMSO-$d_6$) δ: 13.07 (br s, 1H), 7.46-7.25 (m, 2H), 6.93-6.87 (m, 1H), 4.52 (br s, 1H), 4.22-4.20 (m, 3H), 3.92 (br s, 1H), 3.57-3.52 (m, 2H), 3.37-3.34 (m, 1H), 3.27 (s, 3H), 3.18-3.15 (m, 1H), 3.09-3.05 (m, 3H), 2.87-2.82 (m, 2H), 2.77-2.75 (m, 6H), 2.66-2.60 (m, 1H), 2.46-2.44 (m, 2H), 2.32 (s, 3H), 2.22-2.19 (m, 3H), 1.83-1.81 (m, 4H), 1.45-1.44 (m, 4H). |

-continued

| Example No. | Name/Structure/Intermediates | LCMS/$^1$H NMR data |
|---|---|---|
| Example 305 | (R)-N-((7-azabicyclo[2.2.1]heptan-7-yl)sulfonyl)-5-fluoro-4-(10-fluoro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-methoxybenzamide 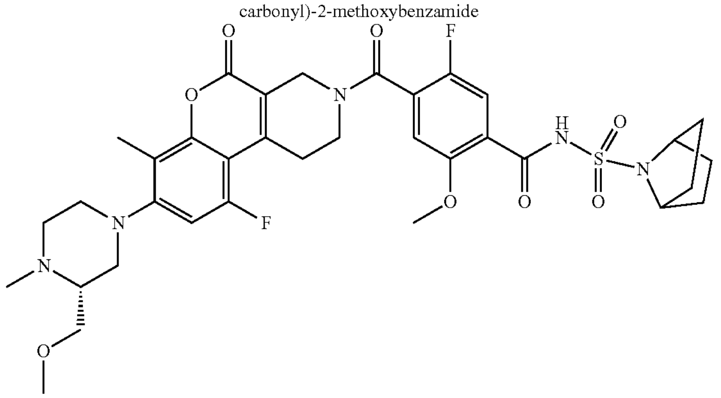 Synthesised from Intermediates 309 and 232 | HPLC: (System 1, Method H) Rt = 6.99 min. m/z 730.0 $(M + H)^+$ $(ES^+)$. $^1$H NMR (400 MHz, DMSO-$d_6$) δ: 11.48 (br s, 1H), 7.38-7.34 (m, 1H), 7.21-7.15 (m, 1H), 6.93-6.88 (m, 1H), 4.53 (br s, 1H), 4.20 (br s, 3H), 3.92 (br s, 1H), 3.82-3.79 (m, 3H), 3.57-3.52 (m, 2H), 3.38-3.36 (m, 1H), 3.27 (s, 3H), 3.19-3.16 (m, 1H), 3.09-3.06 (m, 3H), 2.90-2.83 (m, 2H), 2.67-2.62 (m, 1H), 2.47-2.44 (m, 2H), 2.34 (s, 3H), 2.22-2.19 (m, 3H), 1.86-1.84 (m, 4H), 1.45-1.44 (m, 4H). |
| Example 306 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-cyclopropoxy-N-(N,N-dimethylsulfamoyl)-5-fluorobenzamide 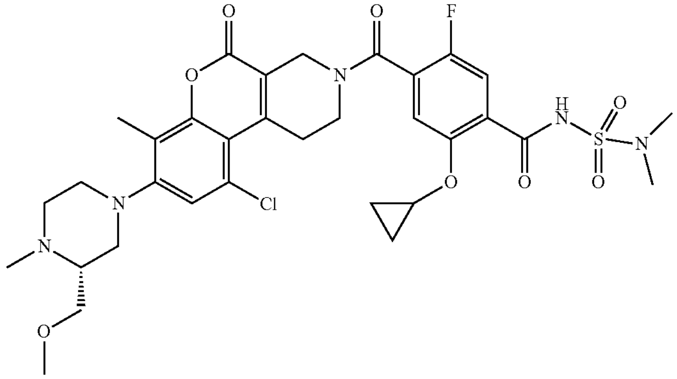 Synthesised from Intermediates 258 and 310 | HPLC: (System 1, Method H) Rt = 7.62 min. m/z 719.8 $(M + H)^+$ $(ES^+)$. $^1$H NMR (400 MHz, DMSO-$d_6$) δ: 11.35 (br s, 1H), 7.47-7.41 (m, 2H), 7.07-7.05 (m, 1H), 4.54 (br s, 1H), 4.24 (s, 1H), 3.99-3.89 (m, 2H), 3.58-3.54 (m, 1H), 3.52-3.47 (m, 1H), 3.39-3.37 (m, 2H), 3.27 (br s, 4H), 3.19-3.16 (m, 1H), 3.10-3.07 (m, 1H), 2.89-2.87 (m, 2H), 2.84 (s, 6H), 2.70-2.65 (m, 1H), 2.51-2.50 (m, 1H), 2.49-2.47 (m, 1H), 2.34 (s, 3H), 2.25-2.21 (m, 3H), 0.82-0.70 (m, 4H). |
| Example 307 | N-((3-oxa-8-azabicyclo[3.2.1]octan-8-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-cyclopropoxy-5-fluorobenzamide 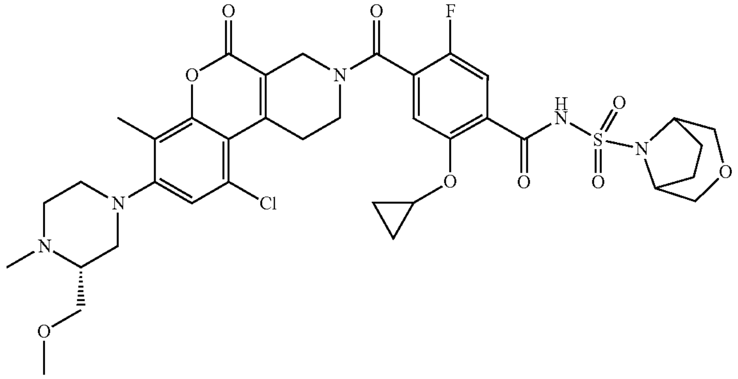 [SMILES: COC[C@H]1CN(c2cc(Cl)c3c4c(c(=O)oc3c2C)CN(C(=O)c2cc(OC3CC3)c(C(=O)NS(=O)(=O)N3C5CCC3COC5)cc2F)CC4)CCN1C] Synthesised from Intermediates 258 and 311 | HPLC: (System 1, Method H) Rt = 7.56 min. m/z 787.7 $(M + H)^+$ $(ES^+)$. $^1$H NMR (400 MHz, DMSO-$d_6$) δ: 11.43 (br s, 1H), 7.44-7.39 (m, 1H), 7.37-7.35 (m, 1H), 7.08-7.06 (m, 1H), 4.54 (br s, 1H), 4.24 (s, 1H), 4.08 (br s, 2H), 3.95-3.88 (m, 2H), 3.58-3.54 (m, 5H), 3.52-3.48 (m, 1H), 3.40-3.38 (m, 2H), 3.27 (br s, 4H), 3.20-3.17 (m, 1H), 3.11-3.08 (m, 1H), 2.92-2.85 (m, 2H), 2.72-2.66 (m, 1H), 2.51-2.50 (m, 2H), 2.36 (s, 3H), 2.25-2.22 (m, 3H), 2.01-1.99 (m, 2H), 1.85-1.82 (m, 2H), 0.82-0.76 (m, 2H), 0.72-0.68 (m, 2H). |

-continued

| Example No. | Name/Structure/Intermediates | LCMS/$^1$H NMR data |
|---|---|---|
| Example 308 | (R)-2-(dimethylamino)-5-fluoro-4-(10-fluoro-8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide 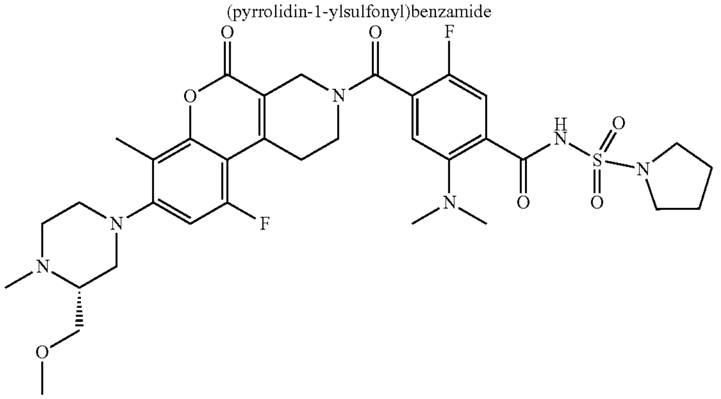 Synthesised from Intermediates 309 and 134 | HPLC: (System 1, Method H) Rt = 7.67 min. m/z 717.0 (M + H)$^+$ (ES$^+$). $^1$H NMR (400 MHz, DMSO-d$_6$) δ: 13.07 (br s, 1H), 7.56-7.50 (m, 1H), 7.44-7.33 (m, 1H), 6.93-6.87 (m, 1H), 4.53 (br s, 1H), 4.20 (s, 1H), 3.92 (br s, 1H), 3.57-3.52 (m, 2H), 3.43-3.41 (m, 4H), 3.38-3.36 (m, 1H), 3.26 (s, 3H), 3.18-3.15 (m, 1H), 3.10-3.05 (m, 3H), 2.87-2.82 (m, 2H), 2.7-2.74 (m, 6H), 2.65-2.59 (m, 1H), 2.44-2.38 (m, 2H), 2.31 (s, 3H), 2.22-2.18 (m, 3H), 1.85-1.83 (m, 4H). |
| Example 309 | (R)-5-fluoro-4-(10-fluoro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-methoxy-N-(pyrrolidin-1-ylsulfonyl)benzamide 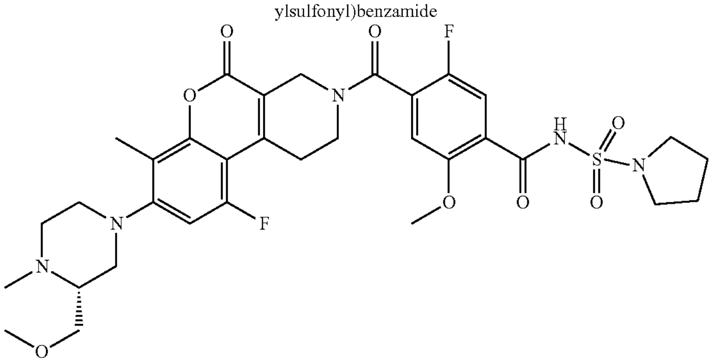 Synthesised from Intermediates 309 and 213 | HPLC: (System 1, Method H) Rt = 6.82 min. m/z 704.0 (M + H)$^+$ (ES$^+$). $^1$H NMR (400 MHz, DMSO-d$_6$) δ: 11.49 (br s, 1H), 7.46-7.43 (m, 1H), 7.23-7.17 (m, 1H), 6.93-6.87 (m, 1H), 4.53 (br s, 1H), 4.19 (s, 1H), 3.92 (br s, 1H), 3.84-3.81 (m, 3H), 3.57-3.52 (m, 2H), 3.41-3.40 (m, 4H), 3.36-3.33 (m, 1H), 3.26 (s, 3H), 3.18-3.15 (m, 1H), 3.10-3.05 (m, 3H), 2.87-2.82 (m, 2H), 2.65-2.60 (m, 1H), 2.44-2.39 (m, 2H), 2.31 (s, 3H), 2.22-2.19 (m, 3H), 1.86-1.83 (m, 4H). |
| Example 310 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-fluoro-5-methyl-N-(pyrrolidin-1-ylsulfonyl)benzamide 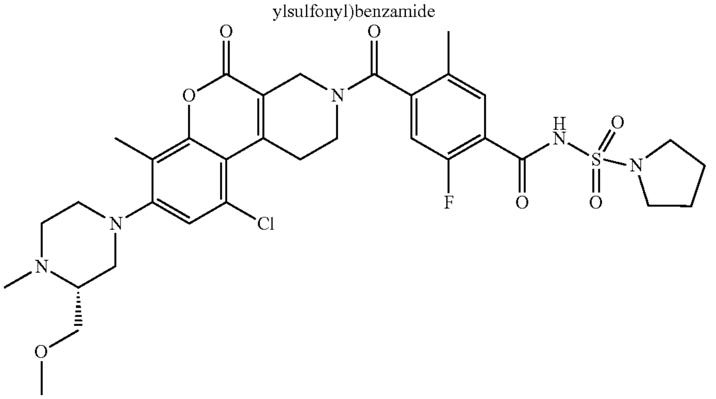 Synthesised from Intermediates 258 and 260 | HPLC: (System 1, Method H) Rt = 7.53 min. m/z 704.0 (M + H)$^+$ (ES$^+$). $^1$H NMR (400 MHz, DMSO-d$_6$) δ: 11.58 (br s, 1H), 7.57-7.54 (m, 1H), 7.35-7.28 (m, 1H), 7.08-7.05 (m, 1H), 4.65-4.42 (m, 1H), 4.11-3.72 (m, 2H), 3.58-3.54 (m, 1H), 3.45-3.36 (m, 7H), 3.28 (s, 3H), 3.20-3.14 (m, 2H), 3.11-3.08 (m, 1H), 2.93-2.85 (m, 2H), 2.73-2.67 (m, 1H), 2.56 (br s, 2H), 2.38 (s, 3H), 2.25-2.18 (m, 6H), 1.86-1.80 (m, 4H). |

-continued

| Example No. | Name/Structure/Intermediates | LCMS/$^1$H NMR data |
|---|---|---|
| Example 311 | 2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(((R)-2-(methoxymethyl)pyrrolidin-1-yl)sulfonyl)benzamide 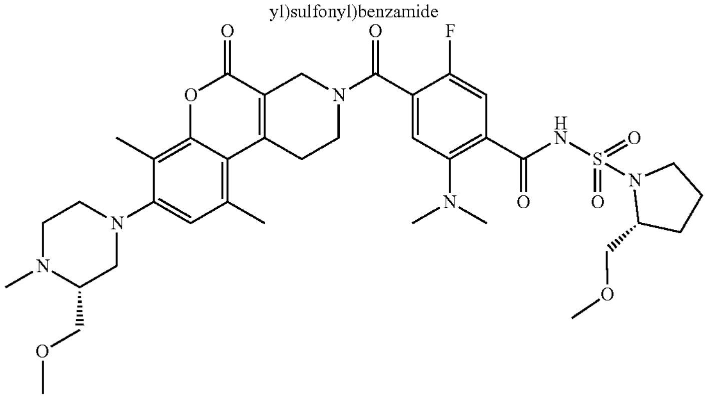 Synthesised from Intermediates 6 and 291 | UPLC: (System 3, Method K) Rt = 4.06 min, m/z 757.5 $(M + H)^+$ $(ES^+)$. $^1$H-NMR (400 MHz, CD3CN) δ 7.91-7.86 (m, 1H), 7.59-7.52 (m, 1H), 6.83-6.81 (m, 1H), 4.56 (s, 1H), 4.30 (br s, 1H), 4.21 (s, 1H), 3.92-3.83 (br s, 1H), 3.58-3.47 (m, 4H), 3.42-3.35 (m, 3H), 3.32-3.29 (m, 6H), 3.23-3.03 (m, 4H), 2.88-2.83 (m, 2H), 2.79-2.73 (m, 6H), 2.69-2.61 (m, 4H), 2.50-2.41 (m, 2H), 2.32-2.24 (m, 7H), 2.08 (br s, 3H) One exchangeable proton not visible. Mixture of rotamers. |
| Example 312 | 2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(((S)-2-(methoxymethyl)pyrrolidin-1-yl)sulfonyl)benzamide 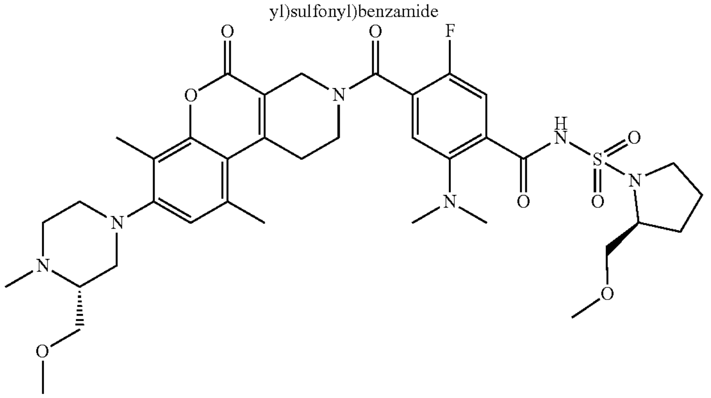 Synthesised from Intermediates 6 and 312 | UPLC: (System 3, Method K) Rt = 4.07 min, m/z 757.4 $(M + H)^+$ $(ES^+)$. $^1$H-NMR (400 MHz, CD3CN) δ 7.93-7.83 (m, 1H), 7.60-7.53 (m, 1H), 6.84-6.83 (m, 1H), 4.57 (s, 1H), 4.31 (br s, 1H), 4.22 (s, 1H), 3.92 (br s, 1H), 3.60-3.46 (m, 4H), 3.43-3.37 (m, 3H), 3.33-3.29 (m, 6H), 3.26-3.05 (m, 4H), 2.91-2.85 (m, 2H), 2.80-2.74 (m, 6H), 2.70-2.60 (m, 4H), 2.50-2.44 (m, 2H), 2.35-2.26 (m, 7H), 2.15 (br s, 3H). One exchangeable proton not visible. Mixture of rotamers. |
| Example 313 | N-(((1S,4S)-2-oxa-5-azabicyclo[2.2.1]heptan-5-yl)sulfonyl)-2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 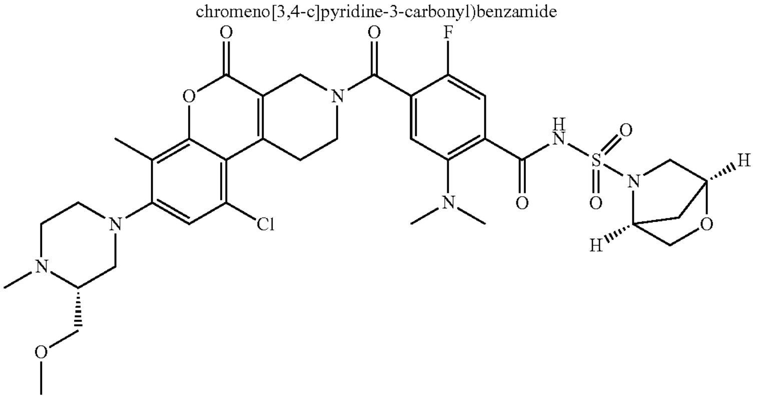 Synthesised from Intermediates 6 and 313 | UPLC: (System 3, Method K) Rt = 3.61 min, m/z 741.5 $(M + H)^+$ $(ES^+)$. $^1$H-NMR (400 MHz, CD3CN) δ 7.88-7.83 (m, 1H), 7.55-7.48 (m, 1H), 6.83-6.82 (m, 1H), 4.60-4.56 (m, 3H), 4.21 (s, 1H), 3.93-3.89 (m, 1H), 3.72-3.67 (m, 1H), 3.58-3.54 (m, 2H), 3.50-3.34 (m, 3H), 3.31-3.29 (m, 3H), 3.25-3.03 (m, 4H), 2.88-2.82 (m, 2H), 2.83-2.76 (m, 6H), 2.69-2.61 (m, 4H), 2.48-2.39 (m, 2H), 2.32-2.22 (m, 7H), 1.85-1.81 (m, 2H). One exchangeable proton not visible. Mixture of rotamers. |

-continued

| Example No. | Name/Structure/Intermediates | LCMS/$^1$H NMR data |
|---|---|---|
| Example 314 | 2-(dimethylamino)-5-fluoro-N-(((R)-3-fluoropyrrolidin-1-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 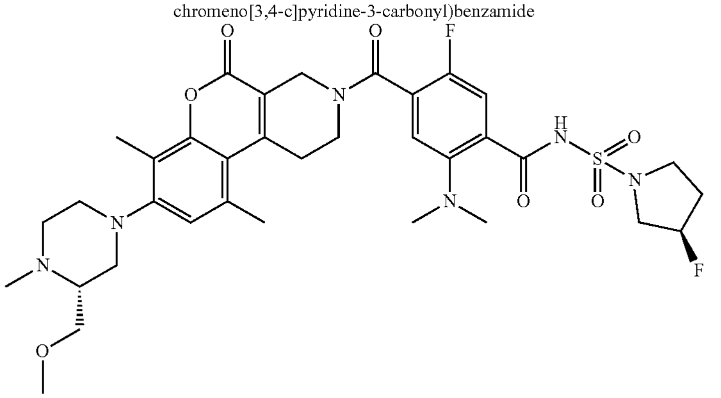 Synthesised from Intermediates 6 and 306 | UPLC: (System 3, Method K) Rt = 3.82 min, m/z 731.4 $(M + H)^+$ $(ES^+)$. $^1$H-NMR (400 MHz, CD3CN) δ 7.90-7.85 (m, 1H), 7.60-7.53 (m, 1H), 6.83-6.81 (m, 1H), 5.34-5.28 (m,1H), 4.56 (s, 1H), 4.20 (s, 1H), 3.91 (br s, 1H), 3.86-3.54 (m, 5H), 3.51-3.44 (m, 1H), 3.39-3.33 (m, 1H), 3.31-3.29 (m, 3H), 3.24-3.03 (m, 4H), 2.91-2.83 (m, 2H), 2.80-2.73 (m, 6H), 2.70-2.61 (m, 4H), 2.48-2.42 (m, 2H), 2.33-2.19 (m, 8H). One exchangeable proton not visible. Mixture of rotamers. |
| Example 315 | N-((3-azabicyclo[3.1.0]hexan-3-yl)sulfonyl)-2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 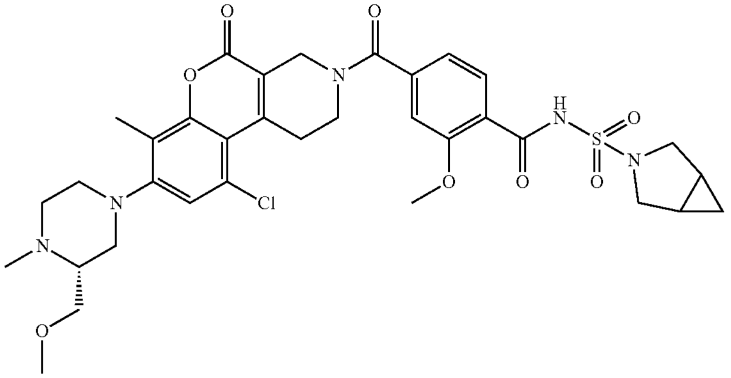 Synthesised from Intermediates 6 and 314 | UPLC: (System 3, Method K) Rt = 4.08 min, m/z 725.5 $(M + H)^+$ $(ES^+)$. $^1$H-NMR (400 MHz, CD3CN) δ 7.92-7.87 (m, 1H), 7.59-7.52 (m, 1H), 6.84-6.82 (m, 1H), 4.56 (s, 1H), 4.21 (s, 1H), 3.93 (br s, 1H), 3.63-3.55 (m, 5H), 3.52-3.47 (m, 1H), 3.39-3.35 (m, 1H), 3.30 (s, 3H), 3.24-3.04 (m, 4H), 2.88-2.83 (m, 2H), 2.79-2.73 (m, 6H), 2.69-2.58 (m, 4H), 2.48-2.45 (m, 2H), 2.33-2.25 (m, 6H), 1.58-1.57 (m, 2H), 0.71-0.65 (m, 1H), 0.34-0.31 (m, 1H). One exchangeable proton not visible. Mixture of rotamers. |
| Example 316 | (R)-N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide 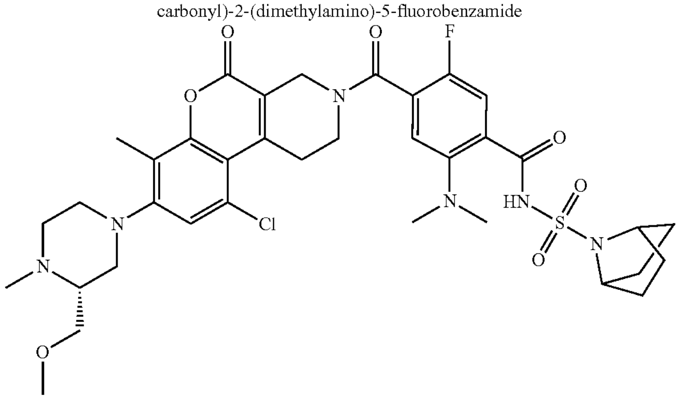 Synthesised from Intermediates 258 and 170 | HPLC: (System 1, Method H) Rt = 8.11 min. m/z 759.0 $(M + H)^+$ $(ES^+)$. $^1$H NMR (400 MHz, DMSO-$d_6$) δ: 13.09 (br, s, 1H), 7.47-7.40 (m, 1H), 7.39-7.28 (m, 1H), 7.07-7.05 (m, 1H), 4.53 (br s, 1H), 4.22 (br s, 3H), 3.87 (br s, 1H), 3.57-3.54 (m, 1H), 3.48 (br s, 1H), 3.37-3.33 (m, 2H), 3.27 (br s, 4H), 3.18-3.15 (m, 1H), 3.09-3.06 (m, 1H), 2.88-2.83 (m, 2H), 2.78-2.75 (m, 6H), 2.69-2.63 (m, 1H), 2.44-2.41 (m, 2H), 2.32 (s, 3H), 2.25-2.21 (m, 3H), 1.83-1.81 (m, 4H), 1.46-1.44 (m, 4H). |

-continued

| Example No. | Name/Structure/Intermediates | LCMS/$^1$H NMR data |
|---|---|---|
| Example 317 | (R)-N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluorobenzamide 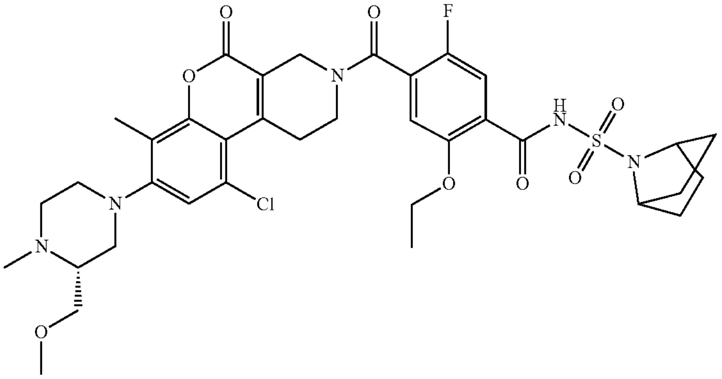 Synthesised from Intermediates 258 and 184 | HPLC: (System 1, Method H) Rt = 8.27 min. m/z 759.8 $(M + H)^+$ $(ES^+)$. $^1$H NMR (400 MHz, DMSO-$d_6$) δ: 11.46 (br s, 1H), 7.40-7.37 (m, 1H), 7.23-7.17 (m, 1H), 7.07-7.05 (m, 1H), 4.52 (br s, 1H), 4.22-4.20 (m, 3H), 4.13-4.05 (m, 2H), 3.87 (br s, 1H), 3.57-3.54 (m, 1H), 3.47 (br s, 1H), 3.38-3.35 (m, 1H), 3.33-3.27 (m, 5H), 3.18-3.15 (m, 1H), 3.09-3.07 (m, 1H), 2.88-2.83 (m, 2H), 2.69-2.64 (m, 1H), 2.45-2.43 (m, 2H), 2.33 (s, 3H), 2.25-2.21 (m, 3H), 1.87-1.85 (m, 4H), 1.46-1.44 (m, 4H), 1.35-1.29 (m, 3H). |
| Example 318 | (R)-N-((2-azaspiro[3.3]heptan-2-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide 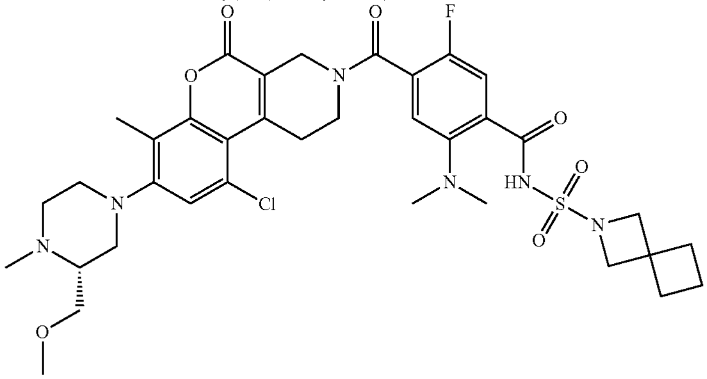 Synthesised from Intermediates 258 and 246 | HPLC: (System 1, Method H) Rt = 7.68 min. m/z 759.0 $(M + H)^+$ $(ES^+)$. $^1$H NMR (400 MHz, DMSO-$d_6$) δ: 13.01 (br s, 1H), 7.54-7.48 (m, 1H), 7.42-7.33 (m, 1H), 7.07-7.05 (m, 1H), 4.53 (br s, 1H), 4.22 (br s, 1H), 3.98 (s, 4H), 3.87 (br s, 1H), 3.58-3.54 (m, 1H), 3.49 (br s, 1H), 3.39-3.36 (m, 1H), 3.28 (br s, 5H), 3.20-3.17 (m, 1H), 3.11-3.08 (m, 1H), 2.92-2.85 (m, 2H), 2.81-2.78 (m, 6H), 2.72-2.66 (m, 1H), 2.54-2.51 (m, 2H), 2.37 (s, 3H), 2.25-2.21 (m, 3H), 2.12-2.08 (m, 4H), 1.79-1.72 (m, 2H). |
| Example 319 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-fluoro-5-methoxy-N-(pyrrolidin-1-ylsulfonyl)benzamide 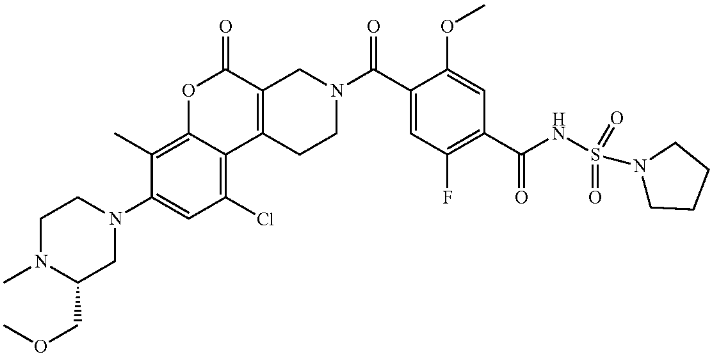 [SMILES: COC[C@H]1CN(c2cc(Cl)c3c4c(c(=O)oc3c2C)CN(C(=O)c2cc(F)c(C(=O)NS(=O)(=O)N3CCCC3)cc2OC)CC4)CCN1C] Synthesised from Intermediates 258 and 252 | HPLC: (System 1, Method H) Rt = 6.93 min. m/z 719.8 $(M + H)^+$ $(ES^+)$. $^1$H NMR (400 MHz, DMSO-$d_6$) δ: 11.53 (br s, 1H), 7.32-7.26 (m, 2H), 7.08-7.06 (m, 1H), 4.49 (br s, 1H), 4.09 (br s, 1H), 3.94-3.72 (m, 4H), 3.58-3.55 (m, 1H), 3.45-3.37 (m, 6H), 3.32-3.28 (m, 4H), 3.21-3.18 (m, 2H), 3.13-3.10 (m, 1H), 2.96-2.86 (m, 2H), 2.74-2.69 (m, 1H), 2.67-2.57 (m, 2H), 2.40 (s, 3H), 2.25-2.22 (m, 3H), 1.85-1.82 (m, 4H). |

-continued

| Example No. | Name/Structure/Intermediates | LCMS/$^1$H NMR data |
|---|---|---|
| Example 320 | (R)-N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxybenzamide 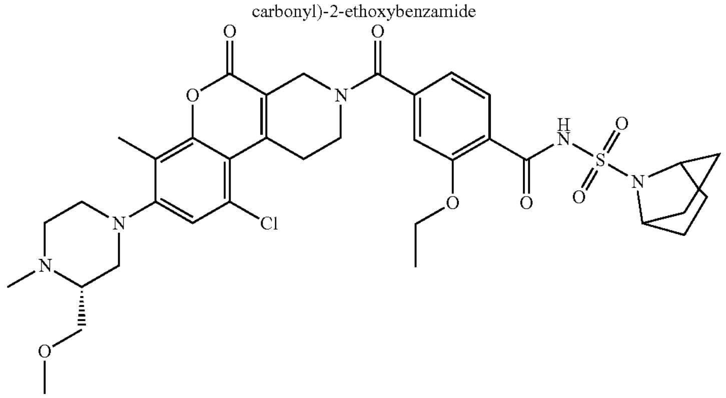 Synthesised from Intermediates 258 and 217 | HPLC: (System 1, Method H) Rt = 7.42 min. m/z 785.0 (M + H)$^+$ (ES$^+$). $^1$H NMR (400 MHz, DMSO-d$_6$) δ: 11.44 (br s, 1H), 7.49 (br s, 1H), 7.19 (s, 1H), 7.14-7.09 (m, 1H), 7.05 (s, 1H), 4.49 (br s, 1H), 4.29 (br s, 1H), 4.22 (br s, 2H), 4.14 (br s, 2H), 3.83 (br s, 1H), 3.57-3.50 (m, 2H), 3.31 (br s, 3H), 3.26 (s, 3H), 3.16-3.14 (m, 1H), 3.07-3.05 (m, 1H), 2.87-2.82 (m, 2H), 2.66-2.61 (m, 1H), 2.42-2.37 (m, 2H), 2.30 (s, 3H), 2.25-2.21 (m, 3H), 1.87-1.85 (m, 4H), 1.46-1.44 (m, 4H), 1.35 (br s, 3H). |
| Example 321 | (R)-N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-methoxybenzamide 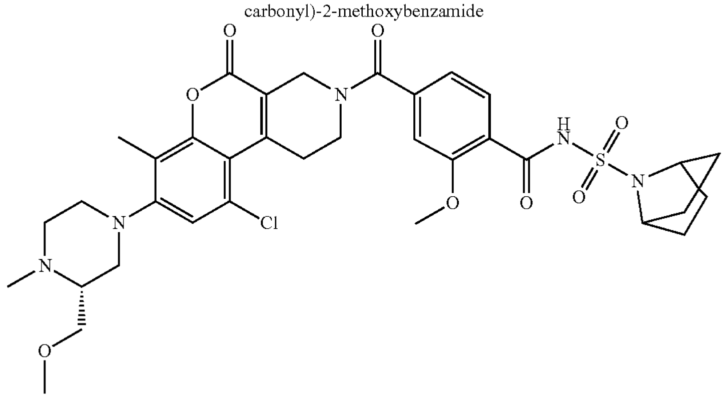 Synthesised from Intermediates 258 and 216 | HPLC: (System 1, Method H) Rt = 7.22 min. m/z 727.9 (M + H)$^+$ (ES$^+$). $^1$H NMR (400 MHz, DMSO-d$_6$) δ: 11.48 (br s, 1H), 7.48-7.45 (m, 1H), 7.21 (s, 1H), 7.14-7.10 (m, 1H), 7.05 (s, 1H), 4.49 (br s, 1H), 4.30 (br s, 1H), 4.22 (s, 2H), 3.86-3.84 (m, 4H), 3.57-3.51 (m, 2H), 3.34-3.33 (m, 1H), 3.32 (br s, 2H), 3.26 (s, 3H), 3.17-3.14 (m, 1H), 3.08-3.05 (m, 1H), 2.85 (br s, 2H), 2.67-2.62 (m, 1H), 2.43-2.41 (m, 2H), 2.30 (s, 3H), 2.25-2.21 (m, 3H), 1.86-1.84 (m, 4H), 1.46-1.45 (m, 4H) |
| Example 322 | N-((3-oxa-8-azabicyclo[3.2. 1]octan-8-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide 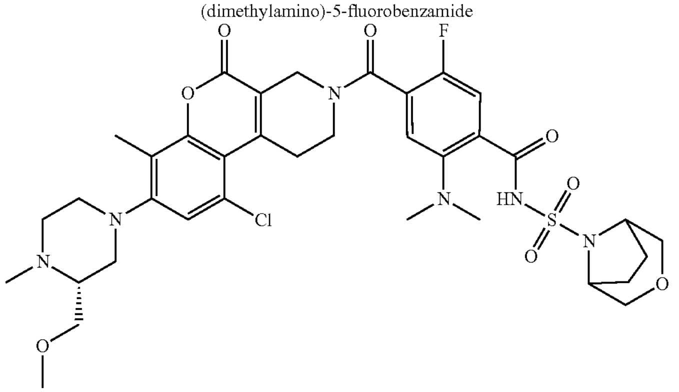 Synthesised from Intermediates 258 and 248 | HPLC: (System 1, Method H) Rt = 7.38 min. m/z 774.8 (M + H)$^+$ (ES$^+$). $^1$H NMR (400 MHz, DMSO-d$_6$) δ: 13.00 (br s, 1H), 7.48-7.41 (m, 1H), 7.39-7.31 (m, 1H), 7.07-7.05 (m, 1H), 4.53 (br s, 1H), 4.22 (br s, 1H), 4.13 (br s, 2H), 3.88 (br s, 1H), 3.59-3.54 (m, 5H), 3.49 (br s, 1H), 3.40-3.38 (m, 2H), 3.27 (br s, 4H), 3.19-3.17 (m, 1H), 3.11-3.08 (m, 1H), 2.92-2.84 (m, 2H), 2.79-2.76 (m, 6H), 2.71-2.66 (m, 1H), 2.54-2.51 (m, 2H), 2.36 (s, 3H), 2.25-2.21 (m, 3H), 1.95-1.89 (m, 2H), 1.85-1.82 (m, 2H). |

-continued

| Example No. | Name/Structure/Intermediates | LCMS/$^1$H NMR data |
|---|---|---|
| Example 323 | (R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-N-(N-cyclopropyl-N-methylsulfamoyl)-2-(dimethylamino)-5-fluorobenzamide 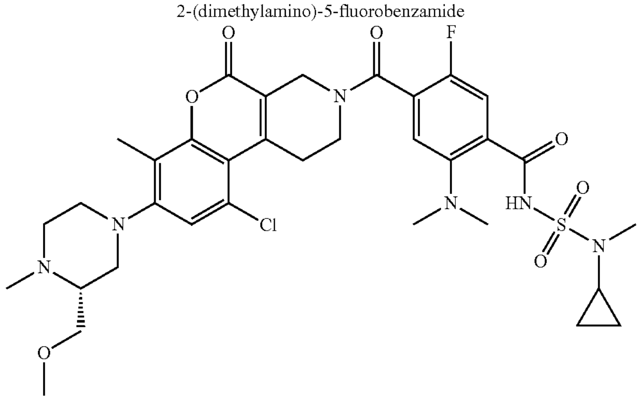 Synthesised from Intermediates 258 and 250 | HPLC: (System 1, Method H) Rt = 8.05 min. m/z 733.0 $(M + H)^+$ $(ES^+)$. $^1$H NMR (400 MHz, DMSO-$d_6$) δ: 13.45 (br s, 1H), 7.59-7.53 (m, 1H), 7.48-7.39 (m, 1H), 7.07-7.05 (m, 1H), 4.53 (br s, 1H), 4.22 (br s, 1H), 3.88-3.87 (m, 1H), 3.57-3.54 (m, 1H), 3.48 (br s, 1H), 3.38-3.34 (m, 2H), 3.27 (br s, 4H), 3.18-3.15 (m, 1H), 3.09-3.07 (m, 1H), 2.92 (s, 3H), 2.89-2.83 (m, 2H), 2.80-2.77 (m, 6H), 2.69-2.64 (m, 1H), 2.61-2.54 (m, 1H), 2.50-2.46 (m, 2H), 2.33 (s, 3H), 2.25-2.21 (m, 3H), 0.75-0.69 (m, 4H). |
| Example 324 | (R)-N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-methoxybenzamide 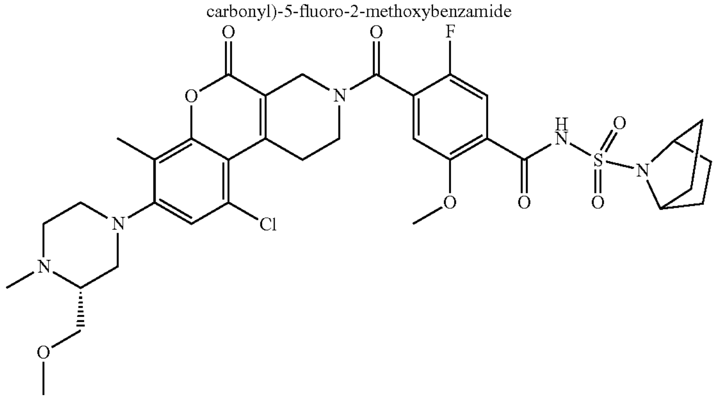 Synthesised from Intermediates 258 and 232 | HPLC: (System 1, Method H) Rt = 7.21 min. m/z 746.0 $(M + H)^+$ $(ES^+)$. $^1$H NMR (400 MHz, DMSO-$d_6$) δ: 11.49 (br s, 1H), 7.38-7.34 (m, 1H), 7.22-7.17 (m, 1H), 7.07-7.05 (m, 1H), 4.53 (br s, 1H), 4.20 (br s, 3H), 3.87-3.80 (m, 4H), 3.57-3.54 (m, 1H), 3.48 (br s, 1H), 3.38-3.34 (m, 2H), 3.27 (br s, 4H), 3.18-3.15 (m, 1H), 3.09-3.07 (m, 1H), 2.89-2.84 (m, 2H), 2.69-2.64 (m, 1H), 2.50-2.46 (m, 2H), 2.33 (s, 3H), 2.25-2.21 (m, 3H), 1.86-1.84 (m, 4H), 1.45-1.43 (m, 4H). |
| Example 325 | N-((3-azabicyclo[3.1.0]hexan-3-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-methoxybenzamide 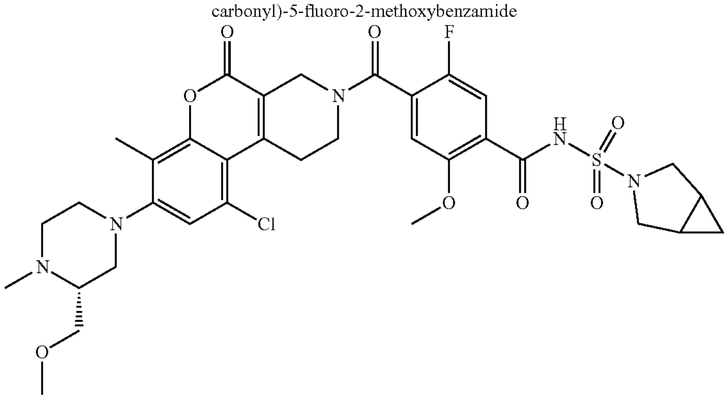 Synthesised from Intermediates 258 and 233 | HPLC: (System 1, Method H) Rt = 7.28 min. m/z 731.8 $(M + H)^+$ $(ES^+)$. 11.49 (br s, 1H), 7.45-7.42 (m, 1H), 7.25-7.19 (m, 1H), 7.07-7.05 (m, 1H), 4.53 (br s, 1H), 4.21 (br s, 1H), 3.85-3.82 (m, 4H), 3.57-3.45 (m, 6H), 3.38-3.34 (m, 2H), 3.27 (br s, 4H), 3.18-3.16 (m, 1H), 3.09-3.07 (m, 1H), 2.89-2.83 (m, 2H), 2.69-2.64 (m, 1H), 2.50-2.45 (m, 2H), 2.33 (s, 3H), 2.25-2.21 (m, 3H), 1.59-1.58 (m, 2H), 0.68-0.63 (m, 1H), 0.31-0.29 (m, 1H). |

-continued

| Example No. | Name/Structure/Intermediates | LCMS/$^1$H NMR data |
|---|---|---|
| Example 326 | (R)-N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-(methoxy-$d_3$)benzamide 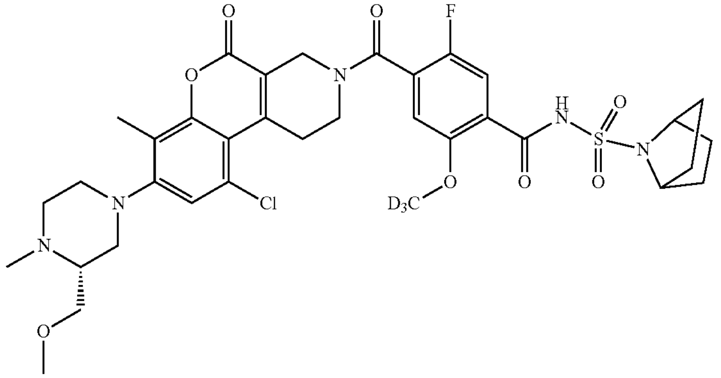 [SMILES: [2H]C([2H])([2H])Oc1cc(C(=O)N2CCc3c(c(=O)oc4c(C)c(N5CCN(C)[C@@H](COC)C5)cc(Cl)c34)C2)c(F)cc1C(=O)NS(=O)(=O)N1C2CCC1CC2] Synthesised from Intermediates 258 and 234 | HPLC: (System 1, Method H) Rt = 7.21 min. m/z 748.9 $(M + H)^+$ $(ES^+)$. $^1$H NMR (400 MHz, DMSO-$d_6$) δ: 11.48 (br s, 1H), 7.39-7.35 (m, 1H), 7.23-7.17 (m, 1H), 7.07-7.05 (m, 1H), 4.53 (br s, 1H), 4.20 (br s, 3H), 3.86 (br s, 1H), 3.57-3.54 (m, 1H), 3.48 (br s, 1H), 3.39-3.37 (m, 2H), 3.27 (br s, 4H), 3.19-3.16 (m, 1H), 3.10-3.07 (m, 1H), 2.89-2.84 (m, 2H), 2.70-2.64 (m, 1H), 2.50-2.47 (m, 2H), 2.34 (s, 3H), 2.25-2.21 (m, 3H), 1.86-1.84 (m, 4H), 1.45-1.44 (m, 4H). |
| Example 327 | N-((3-azabicyclo[3.1.0]hexan-3-yl) sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-(methoxy-$d_3$)benzamide 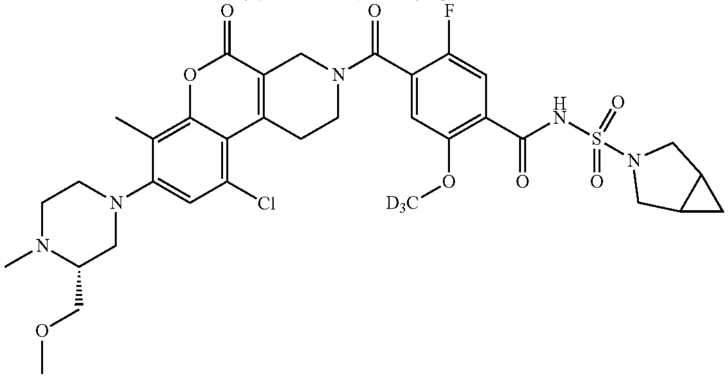 Synthesised from Intermediates 258 and 235 | HPLC: (System 1, Method H) Rt = 7.28 min. m/z 735.0 $(M + H)^+$ $(ES^+)$. $^1$H NMR (400 MHz, DMSO-$d_6$) δ: 11.49 (br s, 1H), 7.45-7.42 (m, 1H), 7.24-7.19 (m, 1H), 7.07-7.05 (m, 1H), 4.53 (br s, 1H), 4.21 (br s, 1H), 3.86 (br s, 1H), 3.57-3.45 (m, 6H), 3.38-3.34 (m, 2H), 3.27 (br s, 4H), 3.18-3.15 (m, 1H), 3.10-3.07 (m, 1H), 2.89-2.84 (m, 2H), 2.69-2.64 (m, 1H), 2.50-2.46 (m, 2H), 2.33 (s, 3H), 2.25-2.21 (m, 3H), 1.59 (br s, 2H), 0.68-0.63 (m, 1H), 0.29-0.28 (m, 1H). |
| Example 328 | (R)-5-chloro-2-(methoxy-$d_3$)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 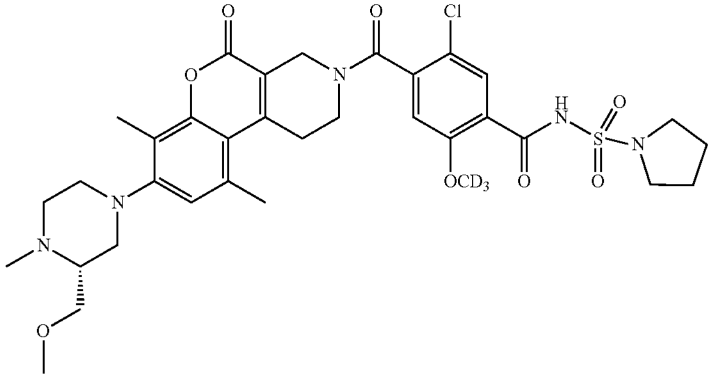 Synthesised from Intermediates 6 and 316 | HPLC: (System 1, Method H) Rt = 6.99 min. m/z 719.0 $(M + H)^+$ $(ES^+)$. $^1$H NMR (400 MHz, DMSO-$d_6$) δ: 11.47 (br s, 1H), 7.59-7.57 (m, 1H), 7.28-7.20 (m, 1H), 6.87-6.84 (m, 1H), 4.70-4.35 (m, 1H), 4.09-4.08 (m, 1H), 4.01-3.76 (m, 1H), 3.57-3.54 (m, 1H), 3.42-3.37 (m, 6H), 3.26 (s, 3H), 3.24-3.23 (m, 1H), 3.18-3.03 (m, 3H), 2.87-2.79 (m, 2H), 2.70-2.61 (m, 4H), 2.45-2.42 (m, 2H), 2.32 (s, 3H), 2.24-2.20 (m, 3H), 1.86-1.83 (m, 4H). |

-continued

| Example No. | Name/Structure/Intermediates | LCMS/$^1$H NMR data |
|---|---|---|
| Example 329 | (R)-5-chloro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 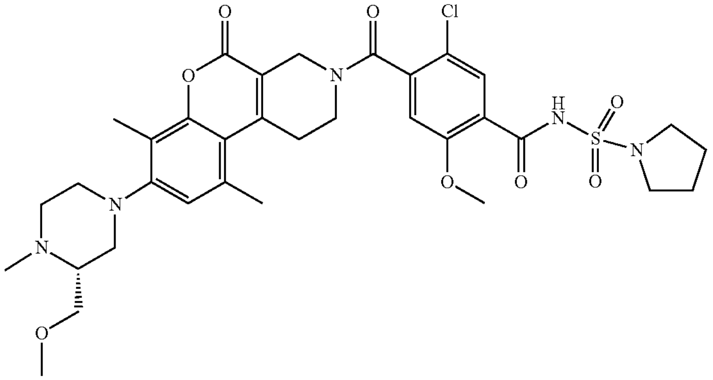 [SMILES: COC[C@H]1CN(c2cc(C)c3c4c(c(=O)oc3c2C)CN(C(=O)c2cc(OC)c(C(=O)NS(=O)(=O)N3CCCC3)cc2Cl)CC4)CCN1C] Synthesised from Intermediates 6 and 317 | HPLC: (System 1, Method H) Rt = 6.99 min. m/z 715.8 $(M + H)^+$ $(ES^+)$. $^1$H NMR (400 MHz, DMSO-$d_6$) δ: 11.47 (br s, 1H), 7.59-7.57 (m, 1H), 7.29-7.20 (m, 1H), 6.87-6.84 (m, 1H), 4.70-4.65 (m, 0.5H), 4.39-4.35 (m, 0.5H), 4.10-4.09 (m, 1H), 4.01-3.96 (m, 0.5H), 3.86-3.84 (m, 3H), 3.79-3.75 (m, 0.5H), 3.57-3.54 (m, 1H), 3.42-3.36 (m, 6H), 3.26-3.23 (m, 4H), 3.19-3.09 (m, 2H), 3.05-3.03 (m, 1H), 2.87-2.79 (m, 2H), 2.70-2.61 (m, 4H), 2.47-2.42 (m, 2H), 2.32 (s, 3H), 2.24-2.20 (m, 3H), 1.86-1.83 (m, 4H). |
| Example 330 | (R)-5-chloro-2-ethoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 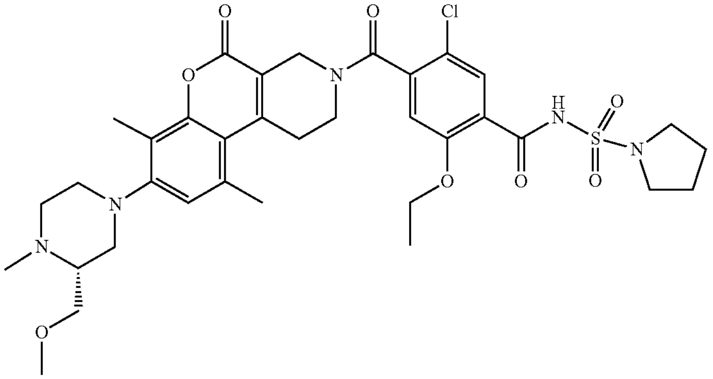 [SMILES: CCOc1cc(C(=O)N2CCc3c(c(=O)oc4c(C)c(N5CCN(C)[C@@H](COC)C5)cc(C)c34)C2)c(Cl)cc1C(=O)NS(=O)(=O)N1CCCC1] Synthesised from Intermediates 6 and 318 | HPLC: (System 1, Method H) Rt = 7.49 min. m/z 729.9 $(M + H)^+$ $(ES^+)$. 1H NMR (400 MHz, DMSO-$d_6$) δ: 11.49 (br s, 1H), 7.56-7.55 (m, 1H), 7.25-7.17 (m, 1H), 6.86-6.84 (m, 1H), 4.70-4.33 (m, 1H), 4.19-4.09 (m, 3H), 4.07-3.78 (m, 1H), 3.57-3.53 (m, 1H), 3.41-3.38 (m, 6H), 3.26 (s, 3H), 3.22 (br s, 1H), 3.17-3.11 (m, 2H), 3.04-3.02 (m, 1H), 2.85-2.78 (m, 2H), 2.70-2.60 (m, 4H), 2.43-2.38 (m, 2H), 2.30 (s, 3H), 2.23-2.20 (m, 3H), 1.85-1.82 (m, 4H), 1.35-1.29 (m, 3H). |
| Example 331 | (R)-N-((7-azabicyclo[2.2.1]heptan-7-yl)sulfonyl)-2-cyclopropoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 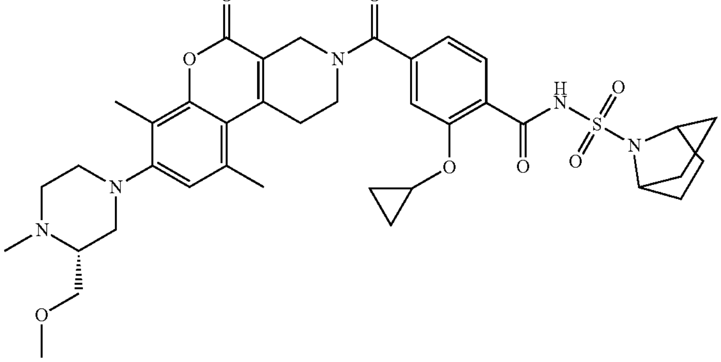 Synthesised from Intermediates 6 and 319 | HPLC: (System 1, Method H) Rt = 7.16 min. m/z 752.0 $(M + H)^+$ $(ES^+)$. $^1$H NMR (400 MHz, DMSO-$d_6$) δ: 11.43 (br s, 1H), 7.45-7.34 (m, 2H), 6.86-6.85 (m, 1H), 4.53 (br s, 1H), 4.21-4.18 (m, 3H), 3.97-3.88 (m, 2H), 3.58-3.54 (m, 1H), 3.50-3.47 (m, 1H), 3.39-3.37 (m, 1H), 3.27 (s, 3H), 3.24 (br s, 1H), 3.16-3.14 (m, 2H), 3.07-3.04 (m, 1H), 2.90-2.81 (m, 2H), 2.70-2.62 (m, 4H), 2.51-2.50 (m, 2H), 2.35 (s, 3H), 2.24-2.20 (m, 3H), 1.86-1.84 (m, 4H), 1.44-1.42 (m, 4H), 0.82-0.68 (m, 4H). |

Example 176: (R)—N-((7-azabicyclo[2.2.1]heptan-7-yl)sulfonyl)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide
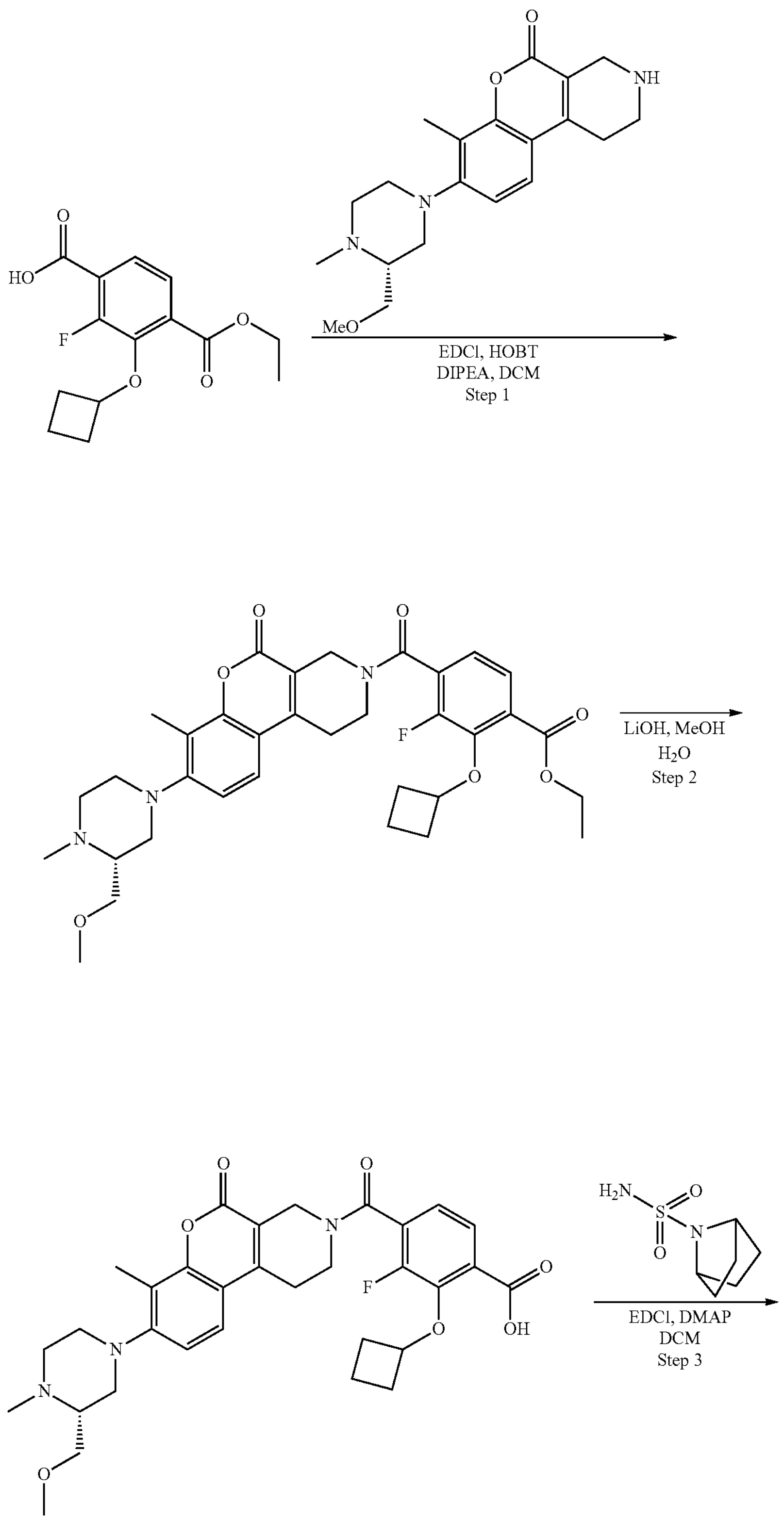

-continued

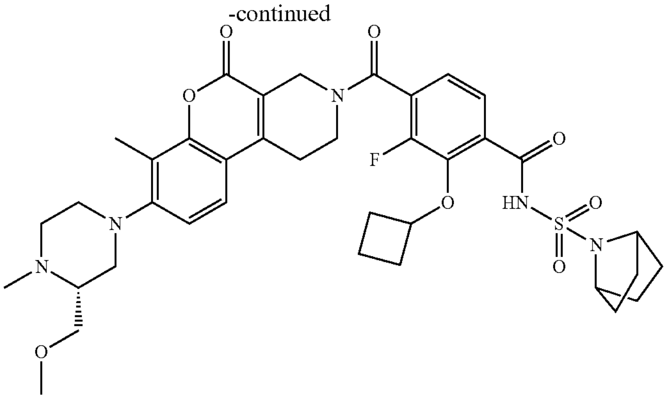

Step 1

A mixture of 3-cyclobutoxy-4-(ethoxycarbonyl)-2-fluorobenzoic acid (Intermediate 149, 420 mg, 1.49 mmol), (R)-8-(3-(methoxymethyl)-4-methylpiperazin-1-yl)-7-methyl-3,4-dihydro-1H-chromeno[3,4-c]pyridin-5(2H)-one (Intermediate 5, 553 mg, 1.49 mmol), EDCI (572 mg, 2.98 mmol), HOBt (402 mg, 2.98 mmol) and DIPEA (1.2 g, 8.94 mmol) in DCM (10 mL) was stirred at RT overnight. The reaction mixture was partitioned between water (10 mL) and DCM (3×10 mL). The combined organic layers were washed with brine, dried ($Na_2SO_4$), filtered and concentrated under reduced pressure. The crude product was purified by column chromatography on silica gel (1-5% MeOH/DCM) to afford (R)-ethyl 2-cyclobutoxy-3-fluoro-4-(8-(3-(methoxymethyl)-4-methylpiperazin-1-yl)-7-methyl-5-oxo-2,3,4,5-tetrahydro-1H-chromeno[3,4-c]pyridine-3-carbonyl)benzoate (600 mg, 0.97 mmol) as a brown solid. LCMS: (System 1, Method F) Rt=1.88 min, m/z 622.3 $(M+H)^+$ $(ES^+)$.

Step 2

A mixture of (R)-ethyl 2-cyclobutoxy-3-fluoro-4-(8-(3-(methoxymethyl)-4-methylpiperazin-1-yl)-7-methyl-5-oxo-2,3,4,5-tetrahydro-1H-chromeno[3,4-c]pyridine-3-carbonyl)benzoate (600 mg, 0.97 mmol) and $LiOH \cdot H_2O$ (158 mg, 3.86 mmol) in MeOH (8 mL) was stirred at RT overnight. The organic solvents were removed under reduced pressure, the pH of mixture was adjusted to ca. 3 with HCl aq. 1N and the aqueous layer extracted with EtOAc (7×10 mL). The combined organic layers were dried ($Na_2SO_4$), filtered and concentrated under reduced pressure to afford (R)-2-cyclobutoxy-3-fluoro-4-(8-(3-(methoxymethyl)-4-methylpiperazin-1-yl)-7-methyl-5-oxo-2,3,4,5-tetrahydro-1H-chromeno[3,4-c]pyridine-3-carbonyl)benzoic acid (520 mg, 0.88 mmol) as a brown solid. LCMS: (System 1, Method A) Rt=1.44 min, m/z 594.4 $(M+H)^+$ $(ES^+)$.

Step 3

A mixture of (R)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzoic acid (255 mg, 0.43 mmol), 7-azabicyclo[2.2.1]heptane-7-sulfonamide (Intermediate 148, 227 mg, 1.29 mmol), EDCI (165 mg, 0.86 mmol) and DMAP (105 mg, 0.86 mmol) in DCM (10 mL) was stirred at RT overnight. The reaction mixture was partitioned between water (10 mL) and DCM (3×10 mL). The combined organic layers were dried ($Na_2SO_4$), filtered and concentrated under reduced pressure. The crude product was purified by prep-HPLC (Column: Waters X-SELECT C18 OBD 10 μm 19×250 mm; Flow Rate: 20 mL/min; solvent system: ACN/(10 mmol/L $NH_4HCO_3$/water) gradient: ACN: 30-95%; collection wavelength: 214 nm). The fractions were concentrated under reduced pressure to remove ACN, and the residue was lyophilized to afford (R)—N-((7-azabicyclo[2.2.1]heptan-7-yl)sulfonyl)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide (91 mg, 0.12 mmol) as a white solid. HPLC: (System 1, Method D) Rt=7.26 min, m/z 752.4 $(M+H)^+$ $(ES^+)$. $^1H$ NMR (400 MHz, DMSO-$d_6$) δ: 11.43 (br s, 1H), 7.59-7.51 (m, 1H), 7.28-7.21 (m, 1H), 7.20-7.14 (m, 1H), 7.10-7.06 (m, 1H), 4.72-4.63 (m, 1H), 4.52 (br s, 1H), 4.20 (br s, 2H), 4.17 (br s, 1H), 3.97 (t, J=6.0 Hz, 1H), 3.59-3.53 (m, 2H), 3.43-3.41 (m, 1H), 3.28 (s, 3H), 3.19-3.17 (m, 1H), 3.10-3.07 (m, 1H), 2.99-2.85 (m, 4H), 2.72-2.57 (m, 3H), 2.40 (s, 3H), 2.30-2.17 (m, 5H), 2.15-2.06 (m, 2H), 1.87-1.85 (m, 4H), 1.70-1.65 (m, 1H), 1.49-1.41 (m, 5H). Mixture of rotamers.

Example 177: 2-cyclobutoxy-N-(((2R,5R)-2,5-dimethylpyrrolidin-1-yl)sulfonyl)-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide

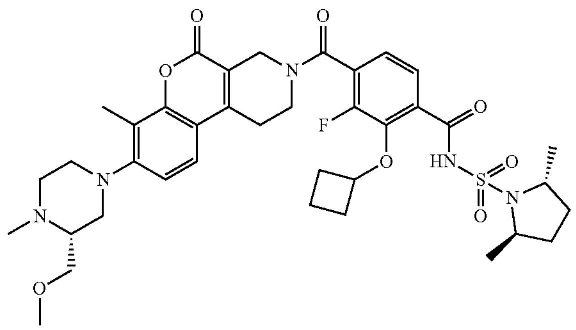 [SMILES: COC[C@H]1CN(c2ccc3c4c(c(=O)oc3c2C)CN(C(=O)c2ccc(C(=O)NS(=O)(=O)N3[C@H](C)CC[C@H]3C)c(OC3CCC3)c2F)CC4)CCN1C]

Prepared by analogous method to Example 176 starting from 3-cyclobutoxy-4-(ethoxycarbonyl)-2-fluorobenzoic acid (Intermediate 149, 420 mg, 1.49 mmol) and (R)-8-(3-

(methoxymethyl)-4-methylpiperazin-1-yl)-7-methyl-3,4-dihydro-1H-chromeno[3,4-c]pyridin-5(2H)-one (Intermediate 5, 553 mg, 1.49 mmol) except the Step 3 was carried out with (2R,5R)-2,5-dimethylpyrrolidine-1-sulfonamide in place of 7-azabicyclo[2.2.1]heptane-7-sulfonamide. Yield: 92 mg, 0.12 mmol. White solid. HPLC: (System 1, Method D) Rt=8.40 min, 754.3 $(M+H)^+$ $(ES^+)$. $^1H$ NMR (400 MHz, DMSO-$d_6$) δ: 11.76 (br s, 1H), 7.59-7.50 (m, 1H), 7.29-7.17 (m, 2H), 7.10-7.06 (m, 1H), 4.71-4.65 (m, 1H), 4.52 (br s, 1H), 4.27-4.24 (m, 2H), 4.17 (br s, 1H), 3.98-3.96 (m, 1H), 3.58-3.54 (m, 2H), 3.37 (br s, 1H), 3.26 (s, 3H), 3.16-3.14 (m, 1H), 3.06-2.99 (m, 2H), 2.90-2.82 (m, 3H), 2.65-2.60 (m, 1H), 2.46-2.43 (m, 2H), 2.31 (s, 3H), 2.29-2.25 (m, 4H), 2.22-2.07 (m, 5H), 1.71-1.66 (m, 1H), 1.55-1.54 (m, 2H), 1.51-1.43 (m, 1H), 1.23-1.21 (m, 6H). Mixture of rotamers.

Example 178: (R)-2-chloro-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide

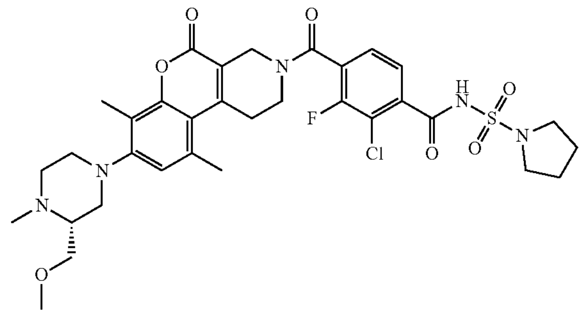 [SMILES: COC[C@H]1CN(c2cc(C)c3c4c(c(=O)oc3c2C)CN(C(=O)c2ccc(C(=O)NS(=O)(=O)N3CCCC3)c(Cl)c2F)CC4)CCN1C]

Prepared by analogous method to Example 176 starting from 3-chloro-4-(ethoxycarbonyl)-2-fluorobenzoic acid (Intermediate 150, 246 mg, 1.00 mmol) and (R)-8-(3-(methoxymethyl)-4-methylpiperazin-1-yl)-7,10-dimethyl-1,2,3,4-tetrahydro-5H-chromeno[3,4-c]pyridin-5-one (Intermediate 6, 352 mg, 0.95 mmol) except the Step 2 was performed as described below and Step 3 was carried out with pyrrolidine-1-sulfonamide in place of 7-azabicyclo[2.2.1]heptane-7-sulfonamide. Yield: 91 mg, 0.13 mmol. White solid. HPLC: (System 1, Method D) Rt=6.80 min, m/z 704.3 $(M+H)^+$ $(ES^+)$. $^1H$ NMR (400 MHz, DMSO-$d_6$) δ: 11.28 (br s, 1H), 7.53-7.44 (m, 2H), 6.87-6.86 (m, 1H), 4.52 (br s, 1H), 4.19 (s, 1H), 3.89-3.86 (m, 1H), 3.59-3.56 (m, 1H), 3.48-3.46 (m, 2H), 3.36 (br s, 2H), 3.35 (br s, 1H), 3.30 (s, 3H), 3.24-3.19 (m, 3H), 3.15-3.09 (m, 2H), 3.04-3.01 (m, 1H), 2.91-2.86 (m, 1H), 2.77-2.72 (m, 2H), 2.72-2.60 (m, 4H), 2.48 (s, 3H), 2.24-2.21 (m, 3H), 1.84-1.82 (m, 4H). Mixture of rotamers.

Modified Step 2

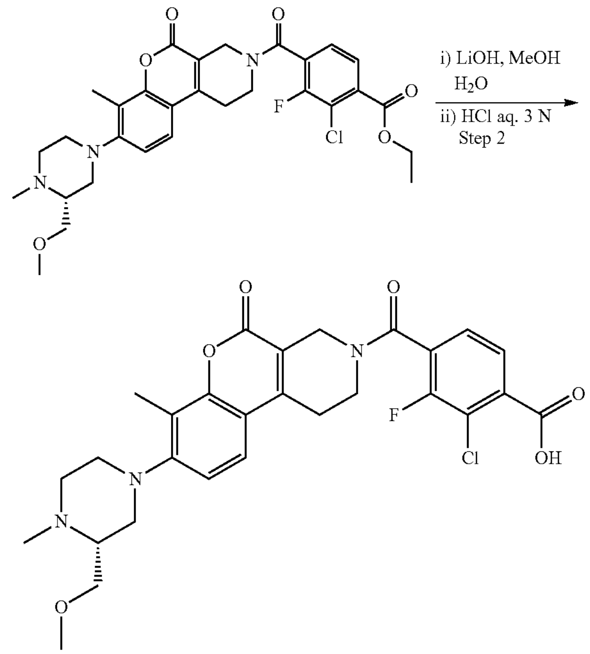

A mixture of (R)-ethyl 2-chloro-3-fluoro-4-(8-(3-(methoxymethyl)-4-methylpiperazin-1-yl)-7,10-dimethyl-5-oxo-2,3,4,5-tetrahydro-1H-chromeno[3,4-c]pyridine-3-carbonyl)benzoate (350 mg, 0.58 mmol) and LiOH·$H_2O$ (146 mg, 3.48 mmol) in MeOH (8 mL) and $H_2O$ (2 mL) was stirred at RT overnight. Organic solvents were removed under reduced pressure and the pH of the mixture was adjusted to ca. 5 by adding HCl aq. 1N. The resulting aqueous layer was extracted with DCM (3×15 mL), the combined organic layers were dried ($Na_2SO_4$), filtered and concentrated under reduced pressure to give (R)-1-(4-carboxy-3-chloro-2-fluorobenzoyl)-4-(2-hydroxy-4-(3-(methoxymethyl)-4-methylpiperazin-1-yl)-3,6-dimethylphenyl)-1,2,5,6-tetrahydropyridine-3-carboxylic acid (340 mg) as a yellow solid. LCMS: (System 1, Method A) Rt=1.23 min; m/z 590.2 $(M+H)^+$ $(ES^+)$.

(R)-1-(4-carboxy-3-chloro-2-fluorobenzoyl)-4-(2-hydroxy-4-(3-(methoxymethyl)-4-methylpiperazin-1-yl)-3,6-dimethylphenyl)-1,2,5,6-tetrahydropyridine-3-carboxylic acid (340 mg, 0.58 mmol) was dissolved in HCl aq. 3N (10 mL) and the solution stirred at RT overnight. The mixture was partitioned between water (10 mL) and DCM (3×20 mL). The combined organic layers were dried ($Na_2SO_4$), filtered and concentrated under reduced pressure to afford (R)-2-chloro-3-fluoro-4-(8-(3-(methoxymethyl)-4-methylpiperazin-1-yl)-7,10-dimethyl-5-oxo-2,3,4,5-tetrahydro-1H-chromeno[3,4-c]pyridine-3-carbonyl)benzoic acid (280 mg, 0.49 mmol) as a yellow solid which was used in the next step without further purification. LCMS: (System 1, Method A) Rt=1.56 min, m/z 572.3 $(M+H)^+$ $(ES^+)$.

Example 179: (R)-2-cyclobutoxy-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide
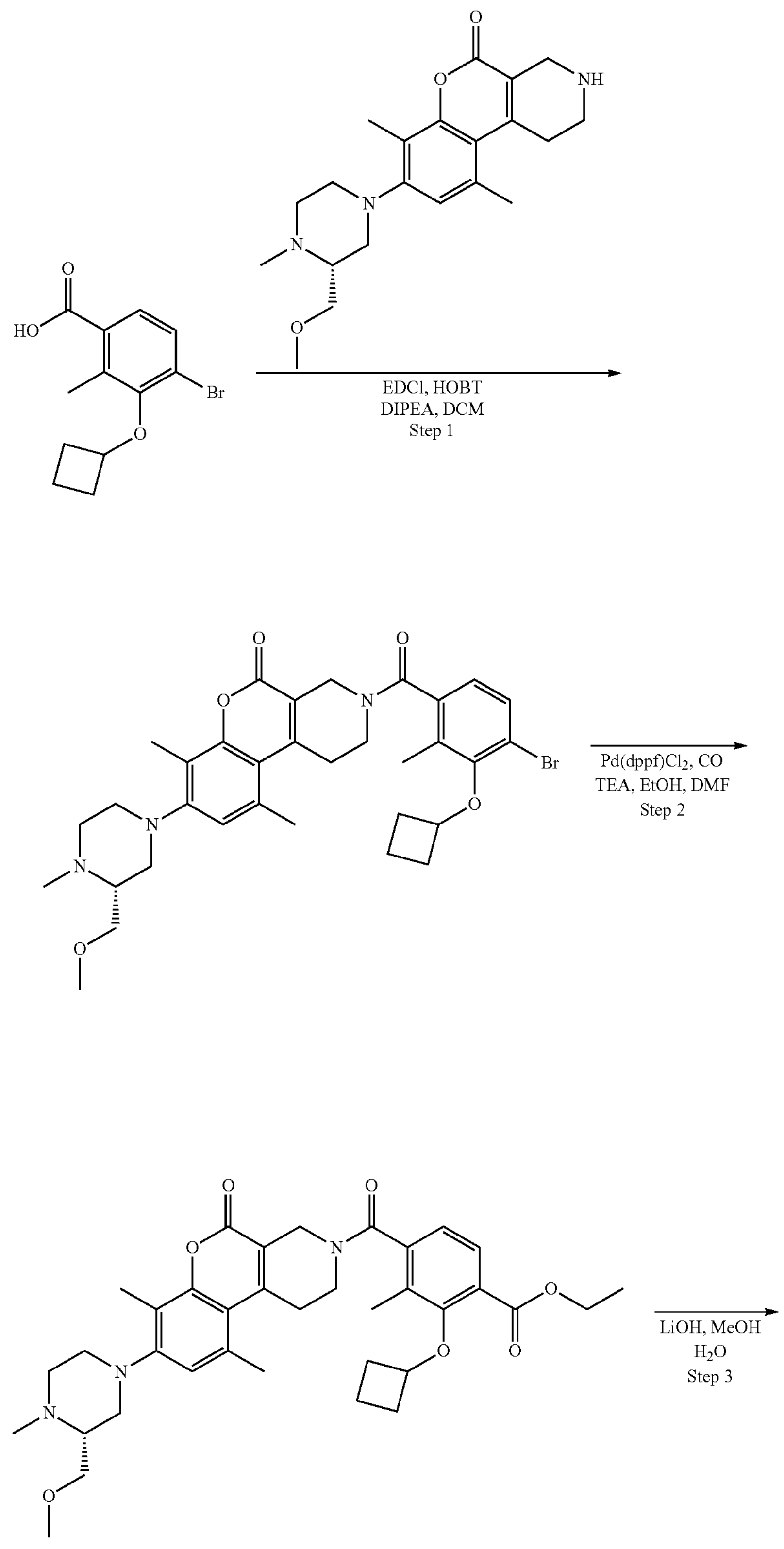

-continued

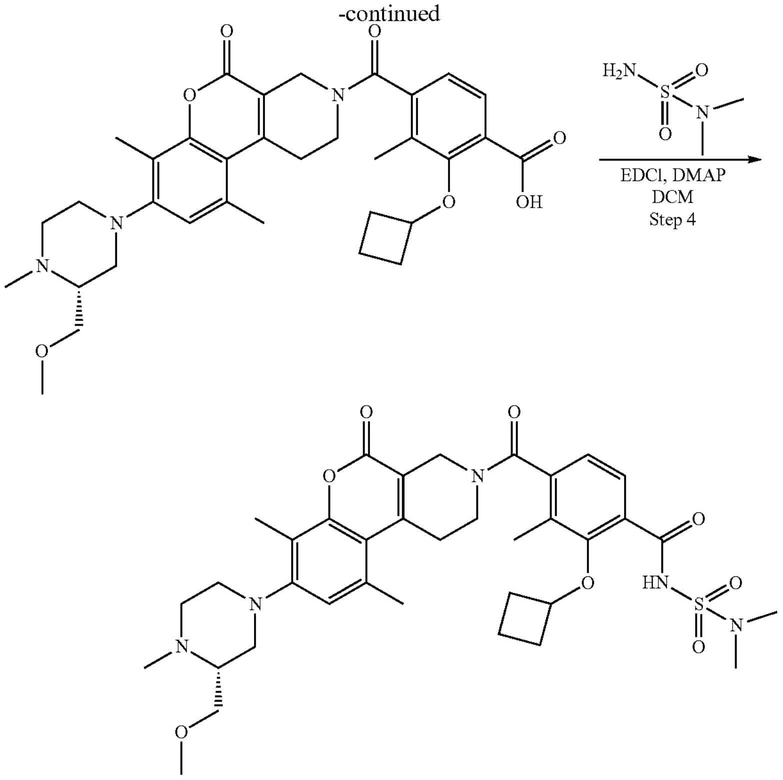

Step 1

A mixture of 4-bromo-3-(cyclobutoxy)-2-methyl-benzoic acid (Intermediate 151, 241 mg, 0.84 mmol), 8-[(3R)-3-(methoxymethyl)-4-methyl-piperazin-1-yl]-7,10-dimethyl-1,2,3,4-tetrahydrochromeno[3,4-c]pyridin-5-one (Intermediate 6, 285 mg, 0.77 mmol), 1-(3-dimethylaminopropyl)-3-ethyl-carbodiimide hydrochloride (EDCI) (221 mg, 1.15 mmol), 1-hydroxybenzotriazole monohydrate (176 mg, 1.15 mmol), TEA (0.32 mL, 2.30 mmol) in DCM (5.1 mL) was stirred at RT overnight. The reaction was partitioned between water (20 mL) and DCM (3x20 mL). The combined organic layers were washed with brine, dried ($Na_2SO_4$), filtered and concentrated under reduced pressure. The crude product was purified by column chromatography on silica gel (20-100% EtOAc/iso-hexane and then 1-10% MeOH/DCM) to afford (R)-3-(4-bromo-3-cyclobutoxy-2-methyl-benzoyl)-8-(3-(methoxymethyl)-4-methylpiperazin-1-yl)-7,10-dimethyl-1,2,3,4-tetrahydro-5H-chromeno[3,4-c]pyridin-5-one (308 mg, 0.48 mmol) as a white solid. LCMS (System 3, method I) Rt=2.09 min, m/z 636.2 $(M-H)^-$ $(ES^-)$.

Step 2

A mixture of (R)-3-(4-bromo-3-cyclobutoxy-2-methyl-benzoyl)-8-(3-(methoxymethyl)-4-methylpiperazin-1-yl)-7,10-dimethyl-1,2,3,4-tetrahydro-5H-chromeno[3,4-c]pyridin-5-one (302 mg, 0.473 mmol), [1,1'-bis(diphenylphosphino)ferrocene]dichloropalladium(II) (17 mg, 0.02 mmol) and triethylamine (0.33 mL, 2.37 mmol) in DMF (1.2 mL) and EtOH (1.2 mL) was stirred at 100° C. overnight under CO atmosphere. The reaction was cooled to RT, diluted with EtOAc (20 mL), filtered through celite, and the filtrate was concentrated under reduced pressure. The crude product was purified by column chromatography on silica gel (20-100% EtOAc/iso-hexane and then 1-10% MeOH/DCM) to afford ethyl (R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-3-methylbenzoate (300 mg, 0.48 mmol) as a brown solid. LCMS (System 3, method I) Rt=2.00 min, m/z 632.4 $(M+H)^+$ $(ES^+)$.

Step 3

A mixture of (R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-3-methylbenzoate (300 mg, 0.48 mmol) and LiOH aq. 1N (2.4 mL) in MeOH (2.4 mL) and THE (2.4 mL) was stirred at 40° C. overnight. Organic solvents were evaporated under reduced pressure and the pH of the aqueous phase was adjusted to ca. 4 with HCl aq. 1N. The resulting solution was extracted with EtOAc (4x30 mL). The combined organic layers were dried ($Na_2SO_4$) and concentrated under reduced pressure. The crude product was purified by column chromatography on C18-modified silica (5-100% ACN/0.1% formic acid in water) to afford (R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-3-methylbenzoic acid (144 mg, 0.24 mmol) as an off-white solid. LCMS (System 3, method I) Rt=1.39 min, m/z 604.3 $(M+H)^+$ $(ES^+)$.

Step 4

A mixture of (R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-3-methylbenzoic acid (48 mg, 0.08 mmol), N,N-dimethylsulfamide (20 mg, 0.16 mmol), EDCI (23 mg, 0.12 mmol) and DMAP (19 mg, 0.16 mmol) in DCM (1.2 mL) was stirred at RT overnight. The reaction mixture was partitioned between water (15 mL) and DCM (3×20 mL). The combined organic layers were washed with brine, dried ($Na_2SO_4$), filtered and concentrated under reduced pressure. The crude product was purified by prep-HPLC (Column: Waters X-SELECT C18 OBD 10 μm 19×250 mm; Flow Rate: 20 mL/min; solvent system: ACN/(10 mmol/L $NH_4HCO_3$/water) gradient: ACN: 30-95%; collection wavelength: 214 nm). The fractions were concentrated under reduced pressure to remove ACN, and the residue was lyophilized to afford (R)-2-cyclobutoxy-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide (28 mg, 0.04 mmol) as a white solid. UPLC: (System 3, Method K) Rt=3.75 min, 710.3 $(M+H)^+$ $(ES^+)$. $^1H$ NMR (400 MHz, DMSO-$d_6$) δ: 11.44 (br s, 1H), 7.38-7.36 (m, 1H), 7.05-7.03 (m, 1H), 6.84 (s, 1H), 4.50 (br s, 2H), 4.08 (br s, 1H), 3.86 (br s, 1H), 3.59-3.55 (m, 1H), 3.38-3.34 (m, 2H), 3.28 (s, 3H), 3.24-3.22 (m, 1H), 3.15-3.12 (m, 2H), 3.05-3.01 (s, 2H), 2.90-2.83 (m, 8H), 2.70-2.57 (m, 5H), 2.46-2.41 (m, 1H), 2.32 (s, 3H), 2.25-2.12 (m, 8H), 1.70-1.68 (m, 1H), 1.46-1.42 (m, 1H). Mixture of rotamers.

Example 180: (R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-3-methyl-N-((1-methylcyclopropyl)sulfonyl)benzamide

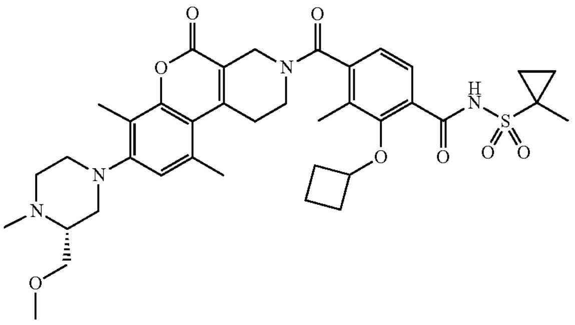

Prepared by analogous method to Example 179 except the Step 4 was carried out with 1-methylcyclopropane-1-sulfonamide in place of N,N-dimethylsulfamide. Yield: 33 mg, 0.05 mmol. White solid. UPLC: (System 3, Method K) Rt=3.76 min, 721.3 $(M+H)^+$ $(ES^+)$. $^1H$ NMR (400 MHz, DMSO-$d_6$) δ: 11.36 (br s, 1H), 7.32-7.30 (m, 1H), 6.92-7.11 (m, 1H), 6.80 (s, 1H), 4.47 (br s, 2H), 4.04 (br s, 1H), 3.82 (br s, 1H), 3.55-3.52 (m, 1H), 3.35-3.31 (m, 2H), 3.25 (s, 3H), 3.21-3.18 (m, 1H), 3.11-3.08 (m, 2H), 2.99-2.97 (m, 2H), 2.85-2.80 (m, 2H), 2.65-2.58 (m, 4H), 2.41 (s, 1H), 2.30 (s, 3H), 2.22-2.09 (m, 9H), 1.66 (s, 1H), 1.51 (s, 3H), 1.46-1.43 (m, 3H), 0.88 (s, 2H). Mixture of rotamers.

The following examples were prepared by analogous methods to Examples 176 or 178:

| Example No. | Name/Structure/Method | LCMS/$^1H$ NMR data |
|---|---|---|
| Example 228 | (R)-N-((7-azabicyclo[2.2.1]heptan-7-yl)sulfonyl)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 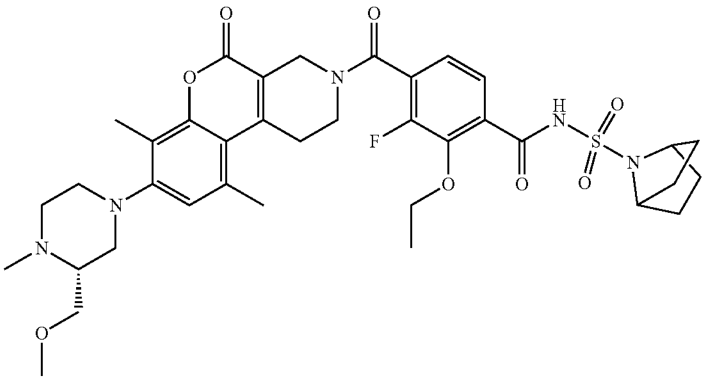 Method of Example 176 | UPLC: (System 3, Method K) Rt = 3.88 min, 740.7 $(M + H)^+$ (ES+). $^1H$ NMR (400 MHz, DMSO-$d_6$) δ: 7.29-7.16 (m, 2H), 6.87-6.85 (m, 1H), 4.51 (s, 1H), 4.20-4.10 (m, 5H), 3.92-3.75 (m, 1H), 3.60-3.51 (m, 1H), 3.47-3.40 (m, 2H), 3.28 (s, 4H), 3.23-3.05 (m, 5H), 2.91-2.82 (m, 2H), 2.71-2.62 (m, 5H), 2.39 (s, 2H), 2.25-2.15 (m, 3H), 1.92-1.80 (m, 4H), 1.47-1.40 (m, 4H), 1.32-1.26 (m, 3H). One exchangeable proton not visible. Mixture of rotamers. |

-continued

| Example No. | Name/Structure/Method | LCMS/$^1$H NMR data |
|---|---|---|
| Example 229 | N-((3-azabicyclo[3.1.0]hexan-3-yl)sulfonyl)-2-ethoxy-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 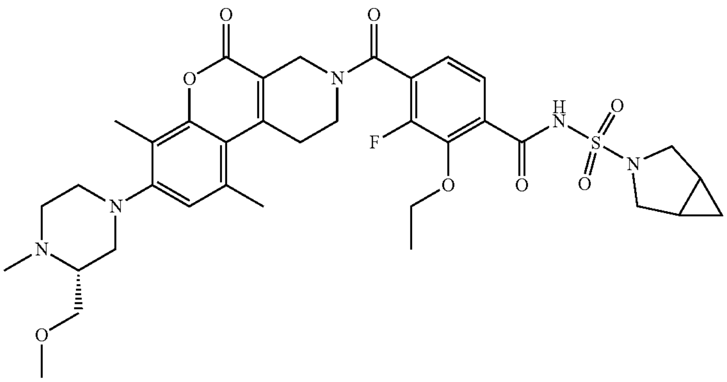 Method of Example 176 | UPLC: (System 3, Method K) Rt = 3.85 min, 726.7 $(M + H)^+$ (ES+). $^1$H NMR (400 MHz, DMSO-$d_6$) δ: 11.48 (br s, 1H), 7.35-7.30 (m, 1H), 7.24-7.15 (m, 1H), 6.90-6.85 (m, 1H), 4.51 (s, 1H), 4.22-4.10 (m, 3H), 3.90-3.82 (m, 1H), 3.58-3.31 (m, 10H), 3.23-3.05 (m, 4H), 2.93-2.82 (m, 2H), 2.69-2.54 (m, 6H), 2.41-2.34 (m, 3H), 2.27-2.18 (m, 3H), 1.60-1.53 (m, 2H), 1.34-1.23 (m, 3H), 0.72-0.59 (m, 1H), 0.35-0.25 (m, 1H). Mixture of rotamers. |
| Example 230 | N-((2-azabicyclo[2.2.1]heptan-2-yl)sulfonyl)-2-ethoxy-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide 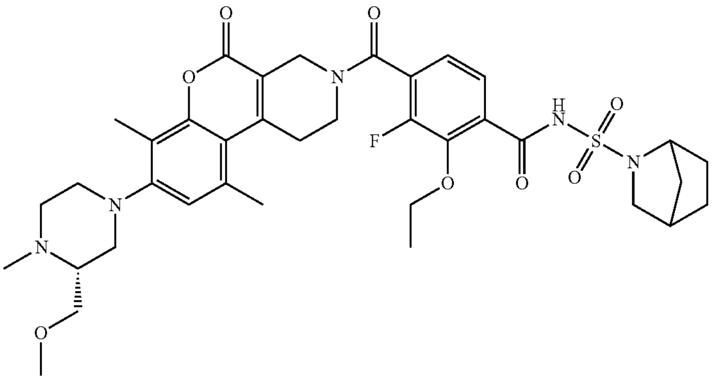 Method of Example 176 | HPLC: (System 1, Method H) Rt = 7.29 min, 726.2 $(M + H)^+$ (ES+). $^1$H NMR (400 MHz, DMSO-$d_6$) δ: 11.54 (br s, 1H), 7.59-7.50 (m, 1H), 7.33-7.30 (m, 1H), 7.24-7.17 (m, 1H), 7.10-7.06 (m, 1H), 4.53 (br s, 1H), 4.24-4.13 (m, 4H), 3.98 (t, J = 5.6 Hz, 1H), 3.58-3.55 (m, 2H), 3.45-3.43 (m, 1H), 3.39-3.35 (m, 1H), 3.27 (s, 3H), 3.17-3.15 (m, 1H), 3.09-3.04 (m, 2H), 3.00 (br s, 1H), 2.90-2.83 (m, 3H), 2.68-2.63 (m, 1H), 2.59 (br s, 1H), 2.50-2.46 (m, 2H), 2.35 (s, 3H), 2.29-2.26 (m, 3H), 1.71-1.61 (m, 4H), 1.44-1.38 (m, 2H), 1.34-1.27 (m, 3H). Mixture of rotamers. |

-continued

| Example No. | Name/Structure/Method | LCMS/$^1$H NMR data |
|---|---|---|
| Example 231 | (R)-N-(N,N-dicyclopropylsulfamoyl)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 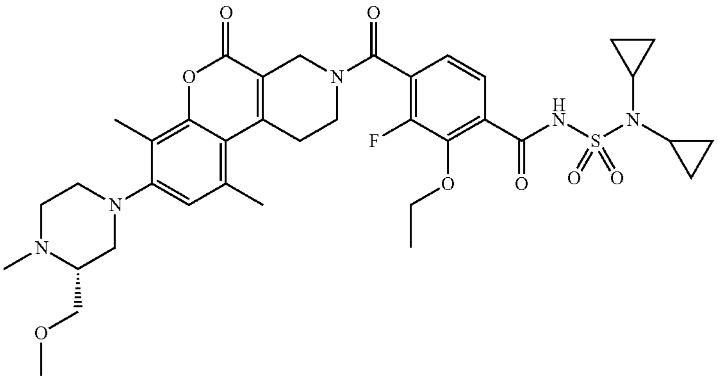 Method of Example 176 | UPLC: (System 3, Method K) Rt = 3.98 min, 740.5 (M + H)$^+$ (ES+). $^1$H NMR (400 MHz, DMSO-$d_6$) δ: 11.11-11.88 (br s, 1H), 7.32-7.29 (m, 1H), 7.20-7.11 (m, 1H), 6.83-6.81 (m, 1H), 4.56-4.48 (m, 1H), 4.18-4.05 (m, 3H), 3.83 (t, J = 5.7 Hz, 1H), 3.53 (dd, J = 10.3, 3.4 Hz, 1H), 3.43-3.36 (m, 2H), 3.24-3.18 (m, 4H), 3.14-3.11 (m, 2H), 3.05-3.03 (m, 1H), 2.93-2.90 (m, 1H), 2.84-2.79 (m, 1H), 2.69-2.50 (m, 8H), 2.37 (br s, 3H), 2.20-2.16 (m, 3H), 1.28-1.22 (m, 3H), 0.81-0.70 (m, 4H), 0.66-0.60 (m, 4H). Mixture of rotamers. |
| Example 232 | 2-ethoxy-3-fluoro-N-(((3aR,6aS)-hexahydrocyclopenta[c]pyrrol-2(1H)-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 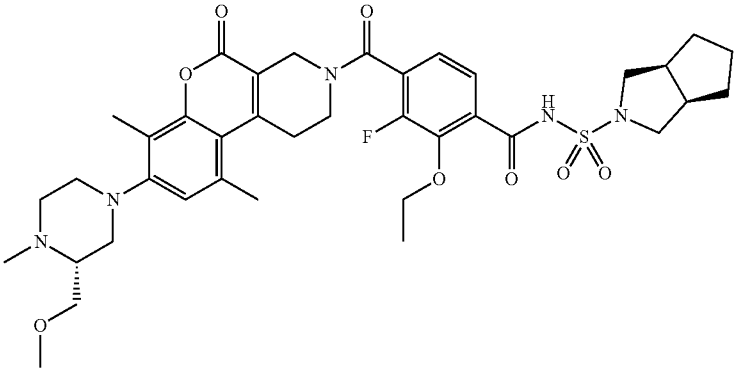 Method of Example 176 | UPLC: (System 3, Method K) Rt = 4.13 min, 754.7 (M + H)$^+$ (ES+). $^1$H NMR (400 MHz, DMSO-$d_6$) δ: 7.28-7.26 (m, 1H), 7.19-7.10 (m, 1H), 6.82-6.80 (m, 1H), 4.48 (br s, 1H), 4.17-4.08 (m, 3H), 3.84-3.82 (m, 1H), 3.54-3.41 (m, 4H), 3.38-3.32 (m, 1H), 3.23 (s, 3H), 3.19-3.18 (m, 2H), 3.12-3.05 (m, 2H), 3.05-2.97 (m, 3H), 2.87-2.77 (m, 2H), 2.65-2.58 (m, 6H), 2.50 (s, 1H), 2.32-2.28 (m, 3H), 2.25-2.16 (m, 3H), 1.72-1.57 (m, 3H), 1.52-1.35 (m, 3H), 1.29-1.22 (m, 3H). Mixture of rotamers. One exchangeable proton not visible |

-continued

| Example No. | Name/Structure/Method | LCMS/$^1$H NMR data |
|---|---|---|
| Example 233 | (R)-N-((2-azaspiro[3.3]heptan-2-yl)sulfonyl)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 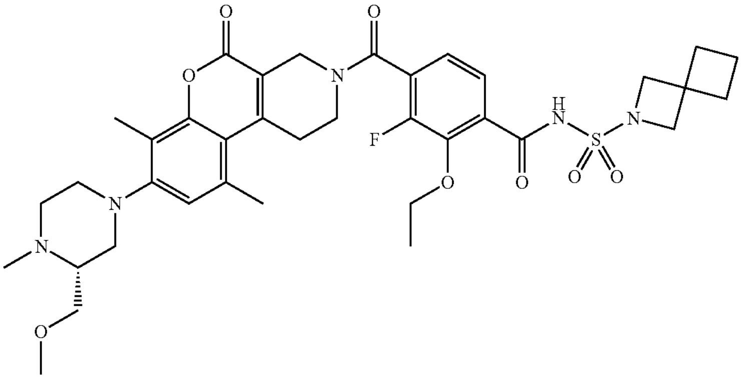 Method of Example 176 | HPLC: (System 3, Method K) Rt = 3.97 min, 740.8 (M + H)$^+$ (ES+). $^1$H NMR (400 MHz, DMSO-d$_6$) δ: 7.33-7.31 (m, 1H), 7.21-7.13 (m, 1H), 6.87-6.85 (m, 1H), 4.51 (br s, 1H), 4.22-4.13 (m, 3H), 3.91-3.86 (m, 5H), 3.58-3.56 (m, 1H), 3.47-3.40 (m, 2H), 3.29 (s, 3H), 3.25-3.22 (m, 1H), 3.19-3.07 (m, 3H), 2.99-2.97 (m, 1H), 2.87 (t, J = 10.3 Hz, 1H), 2.73-2.62 (m, 6H), 2.44 (br s, 2H), 2.24-2.21 (m, 3H), 2.09 (t, J = 7.8 Hz, 4H), 1.80-1.72 (m, 2H), 1.33-1.23 (m, 4H). Mixture of rotamers. One exchangeable proton not visible |
| Example 234 | N-((8-azabicyclo[3.2.1]octan-8-yl)sulfonyl)-2-ethoxy-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 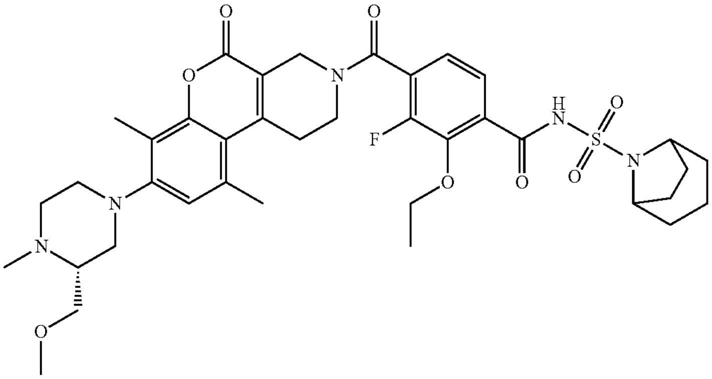 Method of Example 176 | HPLC: (System 1, Method H) Rt = 7.54 min, 754.0 (M + H)$^+$ (ES+). $^1$H NMR (400 MHz, DMSO-d$_6$) δ: 11.52 (br s, 1H), 7.30-7.17 (m, 2H), 6.86-6.84 (m, 1H), 4.51 (br s, 1H), 4.20-4.13 (m, 5H), 3.87 (t, J = 5.6 Hz, 1H), 3.58-3.54 (m, 1H), 3.46-3.45 (m, 1H), 3.39-3.35 (m, 1H), 3.27 (s, 3H), 3.23 (br s, 1H), 3.16-3.13 (m, 2H), 3.06-3.04 (m, 1H), 2.90-2.81 (m, 2H), 2.69-2.62 (m, 4H), 2.51-2.49 (m, 2H), 2.35 (s, 3H), 2.24-2.20 (m, 3H), 2.04-2.01 (m, 2H), 1.74-1.64 (m, 5H), 1.53-1.51 (m, 3H), 1.34-1.28 (m, 3H). Mixture of rotamers. |

-continued

| Example No. | Name/Structure/Method | LCMS/$^1$H NMR data |
|---|---|---|
| Example 235 | N-((3-azabicyclo[3.2.1]octan-3-yl)sulfonyl)-2-ethoxy-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 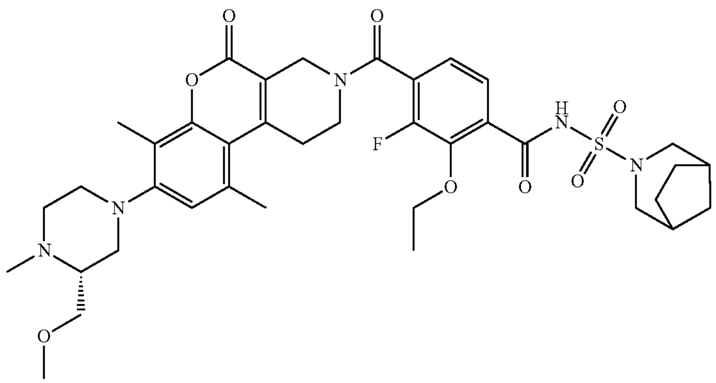 Method of Example 176. | HPLC: (System 1, Method H) Rt = 7.72 min, 754.0 (M + H)$^+$ (ES+). $^1$H NMR (400 MHz, DMSO-d$_6$) δ: 11.49 (br s, 1H), 7.34-7.32 (m, 1H), 7.26-7.17 (m, 1H), 6.86-6.85 (m, 1H), 4.50 (br s, 1H), 4.22-4.13 (m, 3H), 3.87 (t, J = 5.4 Hz, 1H), 3.58-3.54 (m, 1H), 3.48-3.45 (m, 1H), 3.40-3.38 (m, 3H), 3.27 (s, 3H), 3.24 (br s, 1H), 3.16-3.14 (m, 2H), 3.07-3.00 (m, 3H), 2.92-2.81 (m, 2H), 2.69-2.62 (m, 4H), 2.54-2.51 (m, 2H), 2.36 (s, 3H), 2.27 (br s, 2H), 2.24-2.20 (m, 3H), 1.62-1.48 (m, 5H), 1.44-1.41 (m, 1H), 1.34-1.28 (m, 3H). Mixture of rotamers. |
| Example 236 | N-((8-azabicyclo[3.2.1]octan-8-yl)sulfonyl)-2-ethoxy-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide 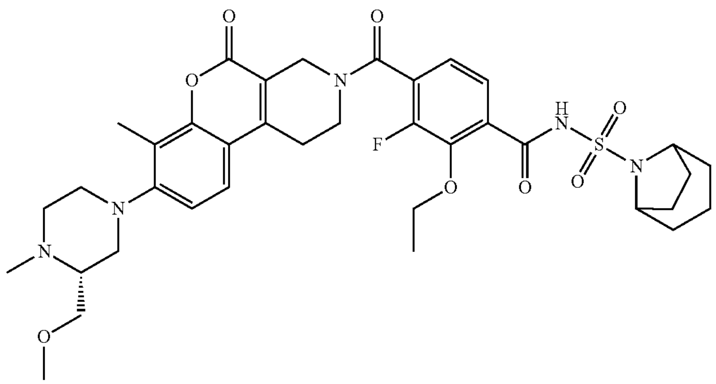 Method of Example 176. | HPLC: (System 1, Method H) Rt = 7.39 min, m/z 740.0 (M + H)$^+$ (ES+). $^1$H NMR (400 MHz, DMSO-d6) δ: 11.52 (br s, 1H), 7.59-7.50 (m, 1H), 7.30-7.26 (m, 1H), 7.24-7.16 (m, 1H), 7.10-7.06 (m, 1H), 4.53 (br s, 1H), 4.20-4.12 (m, 5H), 3.99-3.96 (m, 1H), 3.58-3.55 (m, 2H), 3.40-3.37 (m, 1H), 3.27 (s, 3H), 3.17-3.15 (m, 1H), 3.08-3.05 (m, 1H), 2.99 (br s, 1H), 2.91-2.83 (m, 3H), 2.68-2.63 (m, 1H), 2.53-2.49 (m, 2H), 2.36 (s, 3H), 2.29-2.26 (m, 3H), 2.04-2.01 (m, 2H), 1.74-1.64 (m, 5H), 1.53-1.51 (m, 3H), 1.33-1.27 (m, 3H). Mixture of rotamers. |

-continued

| Example No. | Name/Structure/Method | LCMS/$^1$H NMR data |
|---|---|---|
| Example 237 | N-((3-azabicyclo[3.2.1]octan-3-yl)sulfonyl)-2-ethoxy-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl) 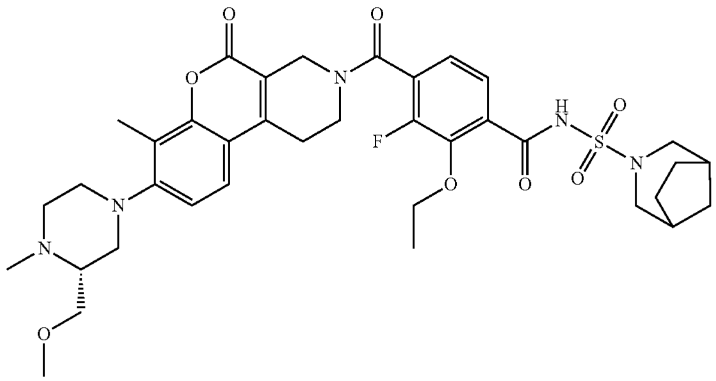 Method of Example 176 | HPLC: (System 1, Method H) Rt = 7.56 min, m/z 740.0 (M + H)$^+$ (ES+). $^1$H NMR (400 MHz, DMSO-d$_6$) δ: 11.44 (br s, 1H), 7.59-7.50 (m, 1H), 7.34-7.31 (m, 1H), 7.24-7.16 (m, 1H), 7.10-7.06 (m, 1H), 4.53 (br s, 1H), 4.22-4.13 (m, 3H), 3.99-3.96 (m, 1H), 3.59-3.56 (m, 2H), 3.40-3.38 (m, 3H), 3.28 (s, 3H), 3.18-3.16 (m, 1H), 3.09-3.00 (m, 4H), 2.94-2.84 (m, 3H), 2.70-2.65 (m, 1H), 2.57-2.51 (m, 2H), 2.38 (s, 3H), 2.33-2.26 (m, 5H), 1.63-1.41 (m, 6H), 1.34-1.28 (m, 3H). Mixture of rotamers. |
| Example 238 | (R)-N-(N-cyclopentyl-N-methylsulfamoyl)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 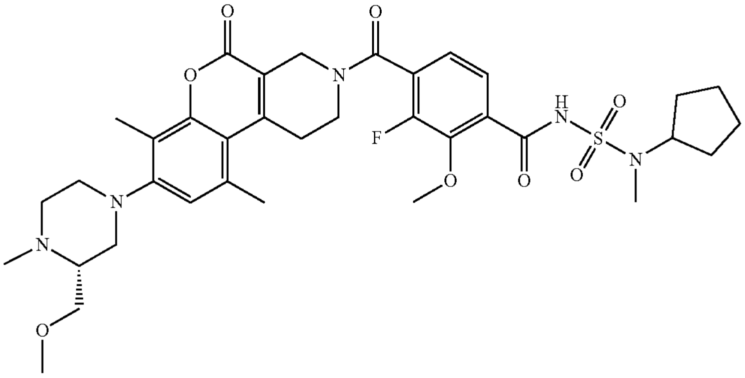 Method of Example 178 | UPLC: (System 3, Method K) Rt = 3.97 min, 728.6 (M + H)$^+$ (ES+). $^1$H NMR (400 MHz, DMSO-d$_6$) δ: 7.31-7.17 (m, 2H), 6.89-6.82 (m, 1H), 4.51 (s, 1H), 4.25-4.15 (m, 2H), 3.94-3.86 (m, 4H), 3.57-3.33 (m, 7H), 3.23-3.03 (m, 5H), 2.90-2.82 (m, 5H), 2.66-2.60 (m, 4H), 2.35 (s, 3H), 2.25-2.16 (m, 3H), 1.78-1.48 (m, 8H). One exchangeable proton not visible. Mixture of rotamers |

-continued

| Example No. | Name/Structure/Method | LCMS/$^1$H NMR data |
|---|---|---|
| Example 239 | (R)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(piperidin-1-ylsulfonyl)benzamide 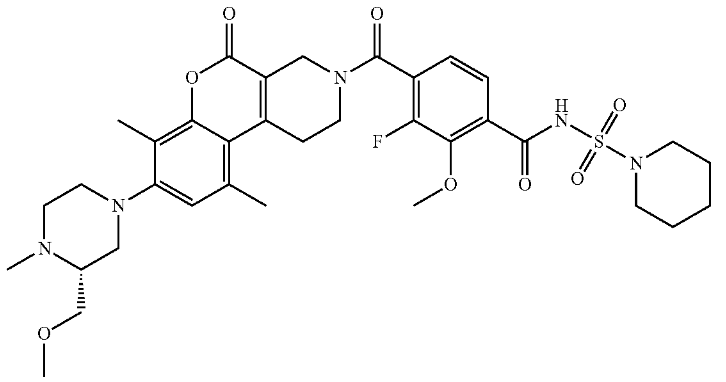 Method of Example 178 | HPLC: (System 1, Method H) Rt = 7.00 min, 714.4 (M + H)$^+$ (ES+). $^1$H NMR (400 MHz, DMSO-d$_6$) δ: 11.36 (br s, 1H), 7.33-7.31 (m, 1H), 7.24-7.15 (m, 1H), 6.87-6.85 (m, 1H), 4.51 (br s, 1H), 4.19 (s, 1H), 3.94-3.91 (m, 3H), 3.88 (t, J = 5.8 Hz, 1H), 3.58-3.55 (m, 1H), 3.49-3.46 (m, 1H), 3.43-3.39 (m, 1H), 3.28 (s, 3H), 3.23 (br s, 5H), 3.18-3.15 (m, 2H), 3.09-3.06 (m, 1H), 2.95-2.93 (m, 1H), 2.88-2.83 (m, 1H), 2.72-2.57 (m, 6H), 2.40 (s, 3H), 2.24-2.20 (m, 3H), 1.57-1.56 (m, 4H), 1.49-1.48 (m, 2H). Mixture of rotamers. |
| Example 240 | (R)-3-fluoro-N-((4-fluoropiperidin-1-yl)sulfonyl)-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 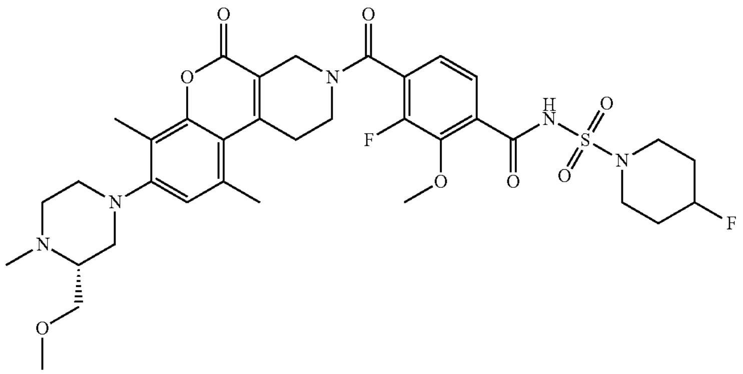 Method of Example 178 | UPLC: (System 3, Method K) Rt = 3.77 min, 732.4 (M + H)$^+$ (ES+). $^1$H NMR (400 MHz, ACN-d$_3$) δ: 7.22-7.13 (m, 1H), 6.83-6.76 (s, 1H), 4.88-4.75 (m, 1H), 4.54 (s, 1H), 4.19 (s, 1H), 4.10-4.02 (m, 3H), 3.90 (s, 1H), 3.59-3.35 (m, 8H), 3.22-3.04 (m, 5H), 2.95-2.83 (m, 2H), 2.72-2.52 (m, 6H), 2.37-2.23 (m, 6H), 2.05-1.83 (m, 5H). One exchangeable proton no visible. Mixture of rotamers. |

-continued

| Example No. | Name/Structure/Method | LCMS/$^1$H NMR data |
|---|---|---|
| Example 241 | (R)-N-((7-azabicyclo[2.2.1]heptan-7-yl)sulfonyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-methylbenzamide 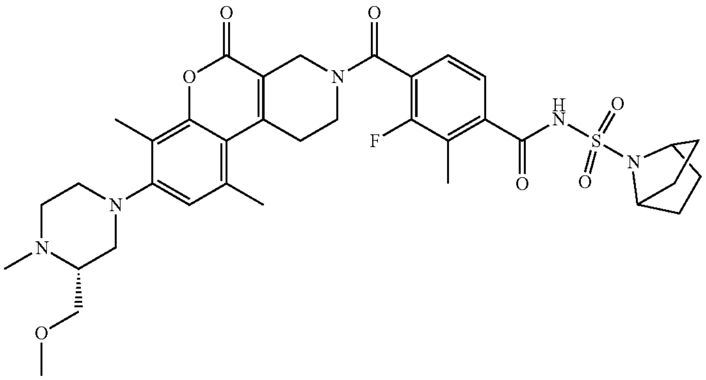 Method of Example 178 | HPLC: (System 1, Method H) Rt = 6.88 min, 710.0 $(M + H)^+$ (ES+). $^1$H NMR (400 MHz, DMSO-$d_6$) δ: 11.43 (br s, 1H), 7.37-7.30 (m, 2H), 6.87-6.85 (m, 1H), 4.51 (br s, 1H), 4.19-4.17 (m, 3H), 3.88-3.86 (m, 1H), 3.59-3.56 (m, 1H), 3.45 (br s, 2H), 3.29 (s, 3H), 3.23-3.17 (m, 2H), 3.13-3.07 (m, 2H), 2.99-2.96 (m, 1H), 2.89-2.84 (m, 1H), 2.75-2.62 (m, 6H), 2.44 (s, 3H), 2.31-2.28 (m, 3H), 2.24-2.20 (m, 3H), 1.85-1.83 (m, 4H), 1.43-1.41 (m, 4H). Mixture of rotamers. |
| Example 242 | (R)-N-((7-azabicyclo[2.2.1]heptan-7-yl)sulfonyl)-2-ethyl-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide 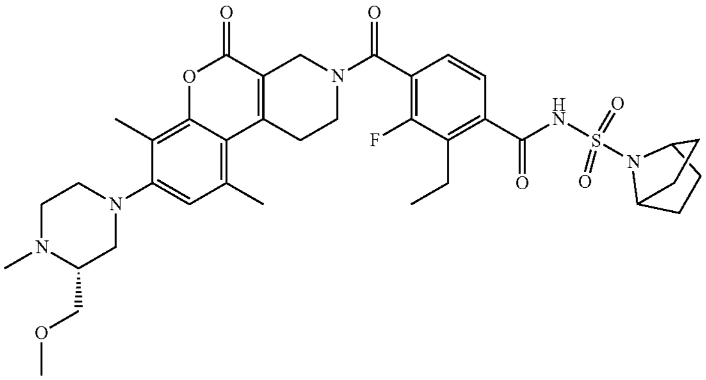 Method of Example 178 | HPLC: (System 1, Method H) Rt = 7.11 min, 724.0 $(M + H)^+$ (ES+). $^1$H NMR (400 MHz, DMSO-$d_6$) δ: 11.35 (br s, 1H), 7.37-7.26 (m, 2H), 6.87-6.85 (m, 1H), 4.52 (br s, 1H), 4.19-4.17 (m, 3H), 3.88 (br s, 1H), 3.59-3.56 (m, 1H), 3.45-3.43 (m, 2H), 3.29 (s, 3H), 3.23 (br s, 1H), 3.19-3.17 (m, 1H), 3.13-3.08 (m, 2H), 3.00-2.97 (m, 1H), 2.87-2.84 (m, 1H), 2.79-2.62 (m, 8H), 2.44 (s, 3H), 2.24-2.20 (m, 3H), 1.85-1.83 (m, 4H), 1.44-1.42 (m, 4H), 1.18-1.11 (m, 3H). Mixture of rotamers. |

-continued

| Example No. | Name/Structure/Method | LCMS/$^1$H NMR data |
|---|---|---|
| Example 243 | (R)-5-(dimethylamino)-2-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide 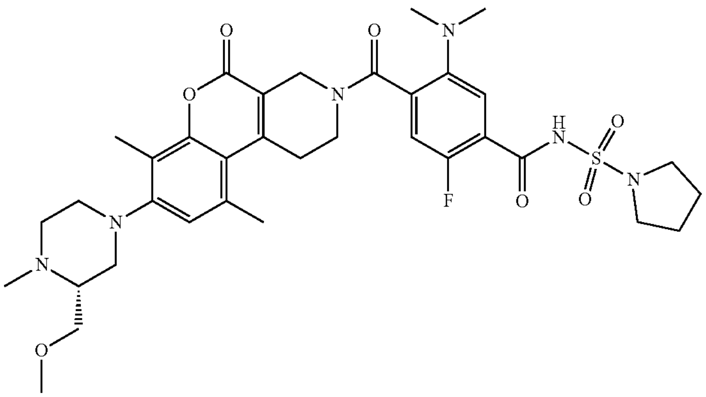 Method of Example 178 | UPLC: (System 3, Method K) Rt = 3.77 min, 713.6 (M + H)$^+$ (ES+). $^1$H NMR (400 MHz, DMSO-d$_6$) δ: 11.57 (br s, 1H), 7.21-7.10 (m, 2H), 6.88-6.84 (m, 1H), 4.56-4.39 (m, 1H), 4.20-3.99 (m, 2H), 3.68-3.54 (m, 2H), 3.46-3.34 (m, 5H), 3.27 (s, 3H), 3.18-3.00 (m, 4H), 2.90-2.81 (m, 2H), 2.74-2.69 (m, 5H), 2.67-2.61 (m, 3H), 2.58-2.53 (m, 4H), 2.35-2.32 (m, 3H), 2.22 (d, J = 12.4 Hz, 3H), 1.84-1.78 (m, 4H). One exchangeable proton not visible. Mixture of rotamers. |

Reference Example 1 (RE1) Corresponds to Example 5 in US2019/0284198A1 (Daiichi Sankyo Company Limited)

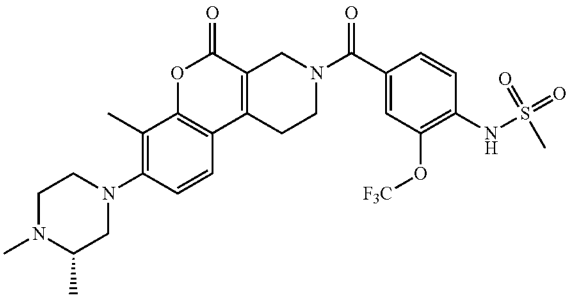 [SMILES: Cc1c(N2CCN(C)[C@@H](C)C2)ccc2c3c(c(=O)oc12)CN(C(=O)c1ccc(NS(C)(=O)=O)c(OC(F)(F)F)c1)CC3]

Biological Example 1-MTHFD1 and MTHFD2 Inhibition Assay

Experimental Protocol

30 μL of each compound to be tested resuspended in DMSO (Fisher, 2212435) at a concentration of 1-100 mM was added to 2×96 well plates (Corning U-bottom, 734-1547) and serially diluted 1 in 3 in DMSO (11×), and then further diluted 1 in 40 in distilled water. 2 μL of the serial dilutions were then quadrated in duplicate to 4×384 well plates (Grenier Bio-One Ltd, 788096). Two columns of DMSO wells without compound were also prepared (low and high signal controls). 2× assay plates were used for the MTHFD1 and MTHFD2 assays respectively. 7 μL of assay buffer containing 200 mM Hepes (Fisher, 2212435), pH 8, 10 mM $MgCl_2$ (Sigma, M1028), 10 mM $NaPO_4$ (Sigma, 71507), 0.010% Tween20 (VWR, 663684B), and distilled water and either 30 mM NADP (MTHFD1 assay) (Alfa Aesar, S08H026) or 600 μM NAD+ (MTHFD2 assay) (Thermo Scientific, T12H054). MTHFD1 and MTHFD2 recombinant human enzymes (Gustafsson R. 2017) were added to the assay buffer at final concentrations of 200 nM and 40 nM respectively prior to addition to the compound containing wells. Assay buffer without an enzyme were added to the low signal control wells. The assay plates were then sealed and incubated on a plate shaker for 30 minutes at room temperature at 600 rpm, before additions of Folitixorin (Toronto Research Chemicals Inc, F680350) to final concentrations of 360 μM and 800 μM for MTHFD1 and MTHFD2 respectively; the plates were re-sealed and incubated again as described above for 20 minutes. The enzyme reaction was stopped with the addition of 1 μL of a MTHFD1 D/C-d/MTHFD2 dual inhibitor (any MTHFD1 D/C-d/MTHFD2 dual inhibitor with an $IC_{50}$ of <30 nM against both MTHFD1 D/C-d/MTHFD2 may be used) to a final concentration of 10 μM. NAD(P)H-GLO™ Detection system (G9061) was used to measure reduced forms of NADH and NADPH, read using Pherastar Luminescence nodule.

The results were expressed as a percentage of luminescent signal that is directly proportional to the NADPH produced by the enzyme reaction, where 0% is an enzyme free reaction and 100% is an uninhibited enzyme. Test compounds and standard (Reference Compound 1) were tested in each experiment at several concentrations to obtain a competition curve from which its $IC_{50}$ was calculated.

Compounds of formula (I) were tested in this assay and the $IC_{50}$ results of those compounds tested are shown in Table 1 below. Reference Example 1 was also tested in this assay. MTHFD1 and MTHFD2 $IC_{50}$ values and MTHFD1/MTHFD2 $IC_{50}$ ratio thresholds (i.e. measure of the selectivity of MTHFD2 inhibition over MTHFD1) are defined below.

$IC_{50}$ Threshold:

| Band | $IC_{50}$ (μM) |
|---|---|
| A | >5 |
| B | 1 to 5 |
| C | 0.1 to <1 |
| D | 0.01 to <0.1 |
| E | 0.001 to <0.01 |

$IC_{50}$ Ratio Threshold:

| Band | MTHFD1/MTHFD2 $IC_{50}$ Ratio |
|---|---|
| F | <3 |
| G | 3 to 9.0 |
| H | >9.0 to 30 |
| J | >30 |

TABLE 1

MTHFD1 and MTHFD2 $IC_{50}$ Values

| | Compound | | |
|---|---|---|---|
| | MTHFD1 $IC_{50}$ | MTHFD2 $IC_{50}$ | MTHFD1/MTHFD2 $IC_{50}$ ratio |
| Reference Example 1 | $C^1$ | $D^1$ | G $H^{*,1}$ |
| Example 1 | C | C | F |
| Example 2 | C | D | G |
| Example 3 | D | D | F |
| Example 4 | E | E | F |
| Example 5 | E | D | F |
| Example 6 | E | D | F |
| Example 7 | D | D | F |
| Example 8 | D | D | F |
| Example 9 | D | D | F |
| Example 10 | D | D | F |
| Example 11 | E | E | F |
| Example 12 | E | E | F |
| Example 13 | E | E | F |
| Example 14 | D | D | F |
| Example 15 | D | D | F |
| Example 16 | E | E | F |
| Example 17 | E | D | F |
| Example 18 | D | E | G |
| Example 19 | C | C | F |
| Example 20 | E | E | G |
| Example 21 | C | C | F |
| Example 22 | E | E | F |
| Example 23 | E | E | F |
| Example 24 | E | E | F |
| Example 25 | E | E | F |
| Example 26 | E | E | F |
| Example 27 | E | E | F |
| Example 28 | E | E | F |
| Example 29 | D | D | F |
| Example 30 | D | D | F |
| Example 31 | D | E | G |
| Example 32 | C | D | J |
| Example 33 | C | D | H |
| Example 34 | C | E | J |
| Example 35 | E | E | F |
| Example 36 | E | E | F |
| Example 37 | E | E | F |
| Example 38 | D | E | G |
| Example 39 | D | E | G |
| Example 40 | D | E | H |
| Example 41 | E | E | G |
| Example 42 | E | E | G |
| Example 43 | E | E | F |
| Example 44 | E | E | F |

TABLE 1-continued

MTHFD1 and MTHFD2 $IC_{50}$ Values

| | Compound | | |
|---|---|---|---|
| | MTHFD1 $IC_{50}$ | MTHFD2 $IC_{50}$ | MTHFD1/MTHFD2 $IC_{50}$ ratio |
| Reference Example 1 | $C^1$ | $D^1$ | G $H^{*,1}$ |
| Example 45 | D | E | H |
| Example 46 | D | E | H |
| Example 47 | E | E | G |
| Example 48 | E | E | F |
| Example 49 | E | E | F |
| Example 50 | E | E | F |
| Example 51 | E | E | F |
| Example 52 | E | E | F |
| Example 53 | E | D | F |
| Example 54 | D | D | F |
| Example 55 | D | E | G |
| Example 56 | E | E | F |
| Example 57 | E | E | F |
| Example 58 | E | E | F |
| Example 59 | E | E | F |
| Example 60 | E | E | F |
| Example 61 | E | E | F |
| Example 62 | E | D | F |
| Example 63 | E | E | F |
| Example 64 | E | E | F |
| Example 65 | E | D | F |
| Example 66 | E | E | F |
| Example 67 | E | E | F |
| Example 68 | E | E | F |
| Example 69 | D | D | G |
| Example 70 | D | E | G |
| Example 71 | D | E | F |
| Example 72 | E | E | F |
| Example 73 | E | E | F |
| Example 74 | E | E | F |
| Example 75 | E | E | G |
| Example 76 | D | E | G |
| Example 77 | E | E | F |
| Example 78 | E | E | F |
| Example 79 | D | E | H |
| Example 80 | D | D | G |
| Example 81 | D | E | H |
| Example 82 | D | E | G |
| Example 83 | D | E | G H* |
| Example 84 | D | E | G |
| Example 85 | E | E | F |
| Example 86 | D | D | F |
| Example 87 | D | E | G |
| Example 88 | E | E | F |
| Example 89 | E | E | F |
| Example 90 | D | D | F |
| Example 91 | E | E | G |
| Example 92 | D | E | H |
| Example 93 | D | D | G |
| Example 94 | D | D | F |
| Example 95 | C | C | F |
| Example 96 | E | E | G |
| Example 97 | D | D | F |
| Example 98 | D | E | F |
| Example 99 | D | D | F |
| Example 100 | D | D | F |
| Example 101 | B | C | H |
| Example 102 | D | D | F |
| Example 103 | E | E | G |
| Example 104 | A | C | H |
| Example 105 | C | C | G |
| Example 106 | C | D | H |
| Example 107 | B | C | G |
| Example 108 | D | D | F |
| Example 109 | D | D | F |
| Example 110 | D | D | F |
| Example 111 | D | D | F |
| Example 112 | A | C | G |

TABLE 1-continued

| MTHFD1 and MTHFD2 $IC_{50}$ Values | | | |
|---|---|---|---|
| | Compound | | |
| | MTHFD1 $IC_{50}$ | MTHFD2 $IC_{50}$ Reference Example 1 | MTHFD1/MTHFD2 $IC_{50}$ ratio |
| | $C^1$ | $D^1$ | G $H^{*,1}$ |
| Example 113 | D | C | F |
| Example 114 | D | C | F |
| Example 115 | D | D | F |
| Example 116 | E | D | F |
| Example 117 | B | C | H |
| Example 118 | B | C | H |
| Example 119 | C | D | G |
| Example 120 | C | D | F |
| Example 121 | E | D | F |
| Example 122 | D | D | F |
| Example 123 | C | D | F |
| Example 124 | C | C | F |
| Example 125 | E | D | F |
| Example 126 | D | D | F |
| Example 127 | C | D | H |
| Example 128 | B | D | H |
| Example 129 | B | D | J |
| Example 130 | B | D | J |
| Example 131 | C | D | G |
| Example 132 | C | D | H |
| Example 133 | C | C | G |
| Example 134 | D | D | G |
| Example 135 | D | E | G |
| Example 136 | C | D | H |
| Example 137 | C | D | G |
| Example 138 | C | D | H |
| Example 139 | C | C | G |
| Example 140 | C | C | F |
| Example 141 | D | D | F |
| Example 142 | D | D | G |
| Example 143 | C | D | G |
| Example 144 | C | E | J |
| Example 145 | C | E | J |
| Example 146 | D | E | F |
| Example 147 | D | E | G |
| Example 148 | D | E | G |
| Example 149 | D | E | F |
| Example 150 | B | D | J |
| Example 151 | B | D | J |
| Example 152 | A | C | H |
| Example 153 | B | D | H |
| Example 154 | B | C | H |
| Example 155 | C | D | H |
| Example 156 | C | D | H |
| Example 157 | C | D | H |
| Example 158 | C | D | H |
| Example 159 | A | C | H |
| Example 160 | B | C | H |
| Example 161 | B | D | J |
| Example 162 | C | C | F |
| Example 163 | A | C | H |
| Example 164 | A | C | H |
| Example 165 | A | C | H |
| Example 166 | A | C | G |
| Example 167 | A | C | H |
| Example 168 | A | B | F |
| Example 169 | C | D | H |
| Example 170 | C | D | G |
| Example 171 | C | D | G |
| Example 172 | D | D | F |
| Example 173 | B | B | F |
| Example 174 | C | D | G |
| Example 175 | B | D | J |
| Example 176 | D | D | F |
| Example 177 | C | C | F |
| Example 178 | C | D | J |
| Example 179 | C | D | G |
| Example 180 | C | D | G |
| Example 181 | C | D | H |

TABLE 1-continued

| MTHFD1 and MTHFD2 $IC_{50}$ Values | | | |
|---|---|---|---|
| | Compound | | |
| | MTHFD1 $IC_{50}$ | MTHFD2 $IC_{50}$ Reference Example 1 | MTHFD1/MTHFD2 $IC_{50}$ ratio |
| | $C^1$ | $D^1$ | G $H^{*,1}$ |
| Example 182 | B | C | G |
| Example 183 | A | C | H |
| Example 184 | B | C | J |
| Example 185 | A | C | H |
| Example 186 | C | C | F |
| Example 187 | A | C | H |
| Example 188 | B | D | H |
| Example 189 | B | C | H |
| Example 190 | A | C | H |
| Example 191 | A | C | G |
| Example 192 | C | C | F |
| Example 193 | B | D | J |
| Example 194 | C | D | G |
| Example 195 | B | D | J |
| Example 196 | B | D | J |
| Example 197 | D | D | G |
| Example 198 | C | C | F |
| Example 199 | B | C | H |
| Example 200 | C | D | H |
| Example 201 | B | D | J |
| Example 202 | C | D | H |
| Example 203 | C | D | G |
| Example 204 | B | D | J |
| Example 205 | D | D | G |
| Example 206 | D | D | F |
| Example 207 | D | D | F |
| Example 208 | D | D | F |
| Example 209 | D | D | F |
| Example 210 | B | D | J |
| Example 211 | B | D | H |
| Example 212 | D | E | F |
| Example 213 | D | E | G |
| Example 214 | D | D | F |
| Example 215 | D | C | F |
| Example 216 | C | D | G |
| Example 217 | C | D | G |
| Example 218 | C | D | H |
| Example 219 | D | D | G |
| Example 220 | C | D | H |
| Example 221 | C | D | H |
| Example 222 | D | E | F |
| Example 223 | E | E | F |
| Example 224 | C | E | J |
| Example 225 | C | E | J |
| Example 226 | C | D | J |
| Example 227 | C | E | H |
| Example 228 | C | D | G |
| Example 229 | D | D | G |
| Example 230 | C | D | F |
| Example 231 | D | D | F |
| Example 232 | D | D | F |
| Example 233 | D | D | F |
| Example 234 | D | D | F |
| Example 235 | C | D | G |
| Example 236 | D | D | F |
| Example 237 | D | D | F |
| Example 238 | C | D | H |
| Example 239 | C | D | H |
| Example 240 | C | D | H |
| Example 241 | C | D | H |
| Example 242 | C | D | H |
| Example 243 | B | D | J |
| Example 244 | C | D | J |
| Example 245 | B | E | J |
| Example 246 | C | E | J |
| Example 247 | C | E | J |
| Example 248 | C | E | J |
| Example 249 | C | E | J |
| Example 250 | B | E | J |

TABLE 1-continued

MTHFD1 and MTHFD2 $IC_{50}$ Values

| | Compound | | |
|---|---|---|---|
| | MTHFD1 $IC_{50}$ | MTHFD2 $IC_{50}$ | MTHFD1/MTHFD2 $IC_{50}$ ratio |
| | Reference Example 1 | | |
| | C[1] | D[1] | G H*, [1] |
| Example 251 | C | E | J |
| Example 252 | C | E | J |
| Example 253 | C | E | J |
| Example 254 | C | E | J |
| Example 255 | B | E | J |
| Example 256 | B | E | J |
| Example 257 | C | E | J |
| Example 258 | D | E | H |
| Example 259 | C | E | J |
| Example 260 | C | E | J |
| Example 261 | C | E | J |
| Example 262 | B | E | J |
| Example 263 | D | E | J |
| Example 264 | D | E | J |
| Example 265 | C | E | J |
| Example 266 | C | E | J |
| Example 267 | C | E | J |
| Example 268 | C | E | J |
| Example 269 | D | E | J |
| Example 270 | B | E | J |
| Example 271 | B | D | H |
| Example 272 | C | D | H |
| Example 273 | C | D | H |
| Example 274 | C | D | H |
| Example 275 | C | D | G |
| Example 276 | C | D | H |
| Example 277 | C | D | H |
| Example 278 | C | D | H |
| Example 279 | C | D | H |
| Example 280 | C | D | H |
| Example 281 | C | D | H |
| Example 282 | C | D | H |
| Example 283 | B | D | H |
| Example 284 | C | D | H |
| Example 285 | C | D | H |
| Example 286 | C | D | J |
| Example 287 | C | D | H |
| Example 288 | B | D | J |
| Example 289 | C | D | J |
| Example 290 | C | D | J |
| Example 291 | B | D | J |
| Example 292 | C | D | J |
| Example 293 | C | D | J |
| Example 294 | C | D | J |
| Example 295 | B | D | J |
| Example 296 | C | D | H |
| Example 297 | C | D | H |
| Example 298 | C | D | G |
| Example 299 | C | D | H |
| Example 300 | C | D | H |
| Example 301 | C | D | J |
| Example 302 | C | D | J |
| Example 303 | C | E | J |
| Example 304 | B | D | J |
| Example 305 | B | D | J |
| Example 306 | C | D | J |
| Example 307 | B | D | J |
| Example 308 | C | E | J |
| Example 309 | B | D | J |
| Example 310 | B | D | J |
| Example 311 | B | E | J |
| Example 312 | C | E | J |
| Example 313 | C | E | J |
| Example 314 | C | E | H |
| Example 315 | C | E | J |
| Example 316 | B | D | J |
| Example 317 | C | D | J |
| Example 318 | C | E | J |
| Example 319 | B | D | J |
| Example 320 | C | E | J |
| Example 321 | B | D | J |
| Example 322 | B | E | J |
| Example 323 | C | E | J |
| Example 324 | C | D | J |
| Example 325 | C | E | J |
| Example 326 | B | E | J |
| Example 327 | C | E | J |
| Example 328 | B | D | J |
| Example 329 | B | E | J |
| Example 330 | C | D | J |
| Example 331 | C | E | J |

*mean value after increased number of repeats

[1]Specific values (average of multiple repeats) are: MTHFD1 $IC_{50}$ = 0.41 μM, MTHFD2 $IC_{50}$ = 0.045 μM, MTHFD1/MTHFD2 $IC_{50}$ ratio = 9.1.

All compounds of formula (I) which were tested in this assay showed inhibitory activity against at least MTHFD2, and certain compounds of formula (I) showed inhibitory activity against MTHFD1 and MTHFD2 as shown by the values in Table 1.

Certain compounds of formula (I) that were tested in this assay were more potent than the Reference Example 1 in the MTHFD1 assay. Certain compounds of formula (I) that were tested in this assay were more potent than the Reference Example 1 in the MTHFD2 assay. Certain compounds of formula (I) that were tested in this assay were more potent than the Reference Example 1 in the MTHFD1 and the MTHFD2 assay.

Certain compounds of formula (I) that were tested in this assay had comparable selectivity for MTHFD2 compared with Reference Example 1 as shown by the MTHFD1/MTHFD2 ratio values.

Certain compounds of formula (I) that were tested in this assay were more selective for MTHFD2 than the Reference Example 1 as shown by the MTHFD1/MTHFD2 ratio values. Preferred compounds were e.g. at least 10 fold, e.g. at least 20 fold e.g. at least 30 fold, e.g. at least 50 fold, e.g. at least 100 fold selective for MTHFD2, as shown by the MTHFD1/MTHFD2 ratio values. Other preferred compounds were at least 200 fold, e.g. at least 300 fold, e.g. at least 600 fold selective for MTHFD2, as shown by the MTHFD1/MTHFD2 ratio values.

Biological Example 2—α4β2 Neuronal Nicotinic Receptor Assay (Agonist Radioligand)

Experimental Protocol

The assay was purchased from Eurofins CEREP (catalogue reference 3029). Cell membrane homogenates (30 μg protein) were incubated for 120 min at 4° C. with 0.6 nM [3H]cytisine in the absence or presence of the test compound in a buffer containing 50 mM Tris-HCl (pH 7.4), 120 mM NaCl, 5 mM KCl, 2.5 mM $CaCl_2$ and 1 mM $MgCl_2$. Nonspecific binding was determined in the presence of 10 μM nicotine bitartrate. Following incubation, the samples were filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard).

The filters were dried then counted for radioactivity in a scintillation counter (Topcount, Packard) using a scintillation cocktail (Microscint 0, Packard). The results were expressed as a percent inhibition of the control radioligand specific binding. The standard reference compound was nicotine bitartrate. Test compounds and standard reference compound were tested in each experiment at several concentrations to obtain a competition curve from which its $IC_{50}$ was calculated.

A number of example compounds of formula (I) were tested to evaluate their affinity for the human α4β2 neuronal nicotinic receptor expressed in transfected SH-SY5Y cells, determined in a radioligand binding assay.

The results are shown in Table 2 below. Reference Example 1 was also tested in this assay.

$IC_{50}$ Thresholds:

| Band | α4β2 Nicotinic receptor $IC_{50}$ (μM) |
|---|---|
| K | <2 |
| L | 2 to 20 |
| M | >20 to 100 |
| N | >100 |

TABLE 2

| α4β2 nicotinic receptor $IC_{50}$ Values | |
|---|---|
| | Compound<br>α4β2 Nicotinic receptor $IC_{50}$ [μM]<br>Reference Example 1<br>K |
| Example 1 | L |
| Example 2 | M |
| Example 3 | M |
| Example 4 | M |
| Example 12 | N |
| Example 18 | N |
| Example 20 | L |
| Example 24 | M |
| Example 25 | M |
| Example 45 | M |
| Example 54 | N |
| Example 69 | N |
| Example 144 | M |
| Example 145 | N |
| Example 147 | M |
| Example 150 | M |
| Example 156 | M |
| Example 174 | M |
| Example 175 | M |

The results shown in Table 2 show that Reference Example 1 has activity against the α4β2 nicotinic receptor with an $IC_{50}$ of <2 μM whereas all the tested compounds of formula (I) displayed an α4β2 nicotinic receptor $IC_{50}$ of >2 μM and typically >20 μM. Therefore, compounds of formula (I) are considerably less active against the α4β2 nicotinic receptor than Reference Example 1.

These data indicate that compounds of formula (I) are not expected to exhibit off-target effects associated with α4β2 nicotinic receptor in vivo, unlike Reference Example 1 which displays α4β2 nicotinic receptor $IC_{50}$ of <3 μM. Therefore, such compounds of formula (I) appear to be superior to Reference Example 1 as drug candidates for development due to the lack of off-target effects observed.

Biological Example 3—Human $CD4^+$ T-cell proliferation assay Stimulation by antigens promotes T cell metabolic reprogramming to meet increased biosynthetic and bioenergetic demands of the cell during inflammation. MTHFD2 is critical for activated CD4 T cells to maintain de novo purine synthesis and promote proliferation. MTHFD2 inhibition leads to depletion of purine pools and accumulation of purine biosynthetic intermediates as the cycle has been blocked and as a result proliferation is inhibited.

Activity in the human CD4+ T cell proliferation assay by a MTHFD2 inhibitor is an indication that the inhibitor can be used to treat inflammation and autoimmune diseases in vivo. Furthermore, it shows that the inhibitor is able to inhibit MTHFD2 in the mitochondria by permeating the cellular and mitochondrial membranes.

Experimental Protocol

Cryopreserved human CD4+ T cells from three donors, isolated from human blood cones using CD4+ isolation kit (StemCell, 17952), were thawed and centrifuged at 300×g for 10 minutes at room temperature. Supernatants were decanted and pellets resuspended in 10 mL cRPMI (10% dFBS (Gibco, 26400044)+1% PenStrep (Merk, P4333)+1% L-glutamine (Fisher, 11500626)+25 nM folic acid (Sigma, F8758)+folate free RPMI (ThermoFisher, 27016021). Cells were counted using the Auto2000 Cellometer (Nexcelom) and AOPI viability stain (Nexcelom, NEXCCS2-0106). Cells were centrifuged at 500×g for 4 minutes at room temperature before pellets were resuspended in 1 mL of 1×dPBS (Invitrogen, 14190250). A 20 μL sample was taken as an unstained control and topped up with cRPMI. 1 vial of CFSE (Invitrogen, C34554) was reconstituted with 18 μL DMSO (Merk, D2650) and the stock was diluted 1 in 2500 in 1×dPBS to achieve final CFSE concentration of 1 μM. Cells were incubated at room temperature for 8 minutes in a rotator in the dark. 13 mL cRPMI was added to each tube and cells were centrifuged at 500×g for 4 minutes at room temperature before pellets were resuspended in 10 mL cRPMI. Cells were counted using the Auto2000 Cellometer and AO/PI viability stain and concentration adjusted to $0.6\times10^6$ cells/mL in cRPMI. 150 μL of cells were added to tissue culture treated 96 well U bottom plates (Corning, 734-0027) for 100 k cells/well and 50 μL of 4×CD3/28 stimulatory beads (Gibco, 10548353), at 1:1 bead to cell ratio, which had been washed in 1×dPBS before use. Control wells were included for flow cytometry and edge wells were filled with 200 μL 1×dPBS. Cells were incubated at 37° C., 5% $CO_2$ for 2 days before compound treatment. Compounds were added in an 8-point dose response using the Tecan D300e, concentration range 10 μM-316 μM and Example 4 (10 μM) was added to every plate as a positive control. Cells were incubated at 37° C., 5% $CO_2$ for a further 2 days prior to flow staining and supernatant harvest.

On the final day plates were centrifuged at 500×g for 4 minutes at room temperature. 125 μL of supernatants were transferred to a V bottom 96 well polystyrene plate and stored at −80° C. Plates were gently vortexed to disrupt the cell pellets before 125 μL 1×PBS was added to each well. Plates were centrifuged at 500×g for 4 minutes at room temperature and supernatants removed from the plates by aspirating. Plates were gently vortexed and 30 μL of live/dead stain (Invitrogen, L34975) in 1×dPBS was added and incubated for 15 minutes in the dark at 4° C. 170 μL of flow cytometry buffer (1×dPBS+2% FBS (Gibco, 11550356)+2 mM EDTA (Invitrogen, 15575020)) was added to each well and plates were centrifuged at 500×g for 4 minutes before supernatants were aspirated. Plates were gently vortexed and 100 μL of BD Cytofix fixation solution (BD Biosciences, 554655) was added to all wells and incubated for 10 minutes in the dark at 4° C. 100 μL of flow cytometry buffer was added and plates were centrifuged at 500×g for 4 minutes before supernatants were aspirated from the plates. Wells were resuspended in 200 μL flow cytometry buffer and plates stored at 4° C. before being run on the flow cytometer.

Data was analysed using FlowJo and the compensation matrix applied to all samples. The gates were set using unstained and unstimulated samples. The data was normalised to the DMSO vehicle control, where 0% is full inhibition of proliferation. Test compounds were tested in each experiment at several concentrations to obtain a competition curve from which its $IC_{50}$ was calculated.

Compounds of formula (I) were tested in this assay and the $IC_{50}$ results of those compounds tested are shown in Table 3 below. Reference Example 1 was also tested in this assay.

Proliferation $IC_{50}$ values are defined below.

$IC_{50}$ Threshold:

| Band | $IC_{50}$ (μM) |
|---|---|
| A | >5 |
| B | 1 to 5 |
| C | 0.1 to <1 |
| D | 0.03 to <0.1 |
| E | 0.01 to <0.03 |
| F | 0.001 to <0.01 |

TABLE 3

Human CD4+ T cell proliferation $IC_{50}$ Values

| Compound | Proliferation $IC_{50}$ |
|---|---|
| Reference Example 1 | D[1] |
| Example 1 | F |
| Example 3 | F |
| Example 4 | F |
| Example 15 | F |
| Example 22 | E |
| Example 50 | F |
| Example 54 | E |
| Example 69 | F |
| Example 98 | E |
| Example 128 | B |
| Example 129 | C |
| Example 130 | B |
| Example 135 | E |
| Example 136 | D |
| Example 144 | F |
| Example 145 | E |
| Example 147 | F |
| Example 149 | F |
| Example 150 | E |
| Example 151 | C |
| Example 155 | E |
| Example 156 | D |
| Example 157 | D |
| Example 169 | C |
| Example 171 | C |
| Example 174 | E |
| Example 175 | B |
| Example 178 | C |
| Example 181 | E |
| Example 193 | D |
| Example 195 | B |
| Example 196 | A |
| Example 199 | C |
| Example 201 | C |
| Example 202 | E |

TABLE 3-continued

Human CD4+ T cell proliferation $IC_{50}$ Values

| Compound | Proliferation $IC_{50}$ |
|---|---|
| Reference Example 1 | D[1] |
| Example 210 | A |
| Example 211 | B |
| Example 216 | E |
| Example 217 | E |
| Example 218 | D |
| Example 219 | E |
| Example 221 | D |
| Example 223 | F |
| Example 224 | D |
| Example 225 | D |
| Example 226 | D |
| Example 228 | F |
| Example 241 | C |
| Example 244 | C |
| Example 245 | D |
| Example 246 | C |
| Example 247 | E |
| Example 248 | D |
| Example 249 | D |
| Example 250 | D |
| Example 251 | D |
| Example 253 | E |
| Example 254 | E |
| Example 255 | E |
| Example 256 | E |
| Example 257 | F |
| Example 259 | D |
| Example 260 | E |
| Example 262 | D |
| Example 263 | E |
| Example 264 | E |
| Example 265 | C |
| Example 266 | B |
| Example 267 | C |
| Example 268 | F |
| Example 270 | B |
| Example 276 | F |
| Example 281 | F |
| Example 291 | D |
| Example 292 | F |
| Example 294 | E |
| Example 302 | E |
| Example 303 | E |
| Example 304 | E |
| Example 308 | F |
| Example 310 | D |
| Example 311 | F |
| Example 312 | E |
| Example 313 | D |
| Example 314 | F |
| Example 315 | F |
| Example 316 | D |
| Example 318 | E |
| Example 319 | C |
| Example 320 | E |
| Example 321 | D |
| Example 322 | D |
| Example 324 | C |
| Example 325 | C |
| Example 326 | C |
| Example 327 | C |
| Example 328 | C |
| Example 329 | C |
| Example 330 | C |
| Example 331 | D |

[1]Specific value (average of multiple repeats) is: Proliferation $IC_{50}$ = 0.035 μM Most compounds of formula (I) which were tested in this assay showed inhibitory activity as shown by the values in Table 3. Certain compounds of formula (I) that were tested in this assay were more potent than the Reference Example 1.

REFERENCES

The following publication cited in this specification are herein incorporated by reference in their entirety.

Adewale Fadaka, Basiru Ajiboye, Oluwafemi Ojo, Olusola Adewale, Israel Olayide, Rosemary Emuowhochere. Biology of glucose metabolization in cancer cells. *Journal of Oncological Sciences* 2017; 3(2):45-51

Aune, T. M., Crooke, P. S., Patrick, A. E., Tossberg, J. T., Olsen, N. J., and Spurlock, C. F. Expression of long non-coding RNAs in autoimmunity and linkage to enhancer function and autoimmune disease risk genetic variants. *Journal of Autoimmunity* 2017; 81, 99-109.

Barbara Frigerio, Claudia Bizzoni, Gerrit Jansen, Christopher P Leamon, Godefridus J Peters, Philip S Low, Larry H Matherly, Mariangela Figini. Folate receptors and transporters: biological role and diagnostic/therapeutic targets in cancer and other diseases. *J Exp Clin Cancer Res.* 2019 Mar. 12; 38(1):125.

Chan E S, Cronstein B N. Methotrexate—how does it really work?*Nat Rev Rheumatol.* 2010 March; 6(3):175-8.

Christensen K E, Patel H, Kuzmanov U, Mejia N R, MacKenzie R E. Disruption of the mthfd1 gene reveals a monofunctional 10-formyltetrahydrofolate synthetase in mammalian mitochondria. *J Biol Chem.* 2005 Mar. 4; 280(9):7597-602.

Christine R Cuthbertson, Zahra Arabzada, Armand Bankhead 3rd, Armita Kyani, Nouri Neamati. A Review of Small-Molecule Inhibitors of One-Carbon Enzymes: SHMT2 and MTHFD2 in the Spotlight. *ACS Pharmacol Transl Sci.* 2021 Mar. 1; 4(2):624-646.

Derek Lee, Iris Ming-Jing Xu, David Kung-Chun Chiu, Robin Kit-Ho Lai, Aki Pui-Wah Tse, Lynna Lan Li, Cheuk-Ting Law, Felice Ho-Ching Tsang, Larry Lai Wei, Cerise Yuen-Ki Chan, Chun-Ming Wong, Irene Oi-Lin Ng, Carmen Chak-Lui Wong. Folate cycle enzyme MTHFD1 L confers metabolic advantages in hepatocellular carcinoma. J Clin Invest. 2017 May 1; 127(5):1856-1872.

Ducker, G. S., and Rabinowitz, J. D. One-Carbon Metabolism in Health and Disease. *Cell Metabolism.* 2017; 25, 27-42.

Field M S, Kamynina E, Watkins D, Rosenblatt D S, Stover P J. Human mutations in methylenetetrahydrofolate dehydrogenase 1 impair nuclear de novo thymidylate biosynthesis. *Proc Natl Acad Sci USA.* 2015 Jan. 13; 112(2): 400-5.

Freidman, N., Chen, I., Wu, Q., Briot, C., Hoist, J., Font, J., Vandenberg, R., and Ryan, R. Amino acid transporters and exchangers from the SLC1A family: structure, mechanism and roles in physiology and cancer. Neurochem. *Res.* 2020; 45, 1268-1286

J L Grem. 5-Fluorouracil: forty-plus and still ticking. A review of its preclinical and clinical development *Invest New Drugs.* 2000 November; 18(4):299-313.

Robert Gustafsson, Ann-Sofie Jemth, Nina M S Gustafsson, Katarina Färnegårdh, Olga Loseva, Elisee Wiita, Nadilly Bonagas, Leif Dahllund, Sabin Llona-Minguez, Maria Häggblad, Martin Henriksson, Yasmin Andersson, Evert Homan, Thomas Helleday, Pål Stenmark. Crystal Structure of the Emerging Cancer Target MTHFD2 in Complex with a Substrate-Based Inhibitor. *Cancer Res.* 2017 Feb. 15; 77(4):937-948.

Kawai, J., Toki, T., Ota, M., Inoue, H., Takata, Y., Asahi, T., Suzuki, M., Shimada, T., Ono, K., Suzuki, K., et al. Discovery of a Potent, Selective, and Orally Available MTHFD2 Inhibitor (DS18561882) with in Vivo Antitumor Activity. J. Med. Chem. 2019; 62, 10204-10220.

Henry Kurniawan, Takumi Kobayashi, Dirk Brenner. The emerging role of one-carbon metabolism in T cells. *Curr Opin Biotechnol.* 2021 April; 68:193-201

Li A M., and Ye, J. The PHGDH enigma: Do cancer cells only need serine or also a redox modulator?*Cancer Lett.* 2020; 476, 97-105.

Marie-Lisa Eich, Maria Del Carmen Rodriguez Pena, Darshan Shimoga Chandrashekar, Alcides Chaux, Sumit Agarwal, Jennifer B Gordetsky, James E Ferguson, Guru P Sonpavde, George J Netto, Sooryanarayana Varambally. Expression and Role of Methylenetetrahydrofolate Dehydrogenase 1 Like (MTHFD1 L) in Bladder Cancer. Transl Oncol. 2019 November; 12(11):1416-1424.

Roland Nilsson, Mohit Jain, Nikhil Madhusudhan Nina Gustafsson Sheppard, Laura Strittmatter, Caroline Kampf, Jenny Huang, Anna Asplund, Vamsi K Mootha. Metabolic enzyme expression highlights a key role for MTHFD2 and the mitochondrial folate pathway in cancer. *Nat Commun.* 2014; 5:3128.

Ayaka Sugiura, Gabriela Andrejeva, Kelsey Voss, Darren R Heintzman, Xincheng Xu, Matthew Z Madden, Xiang Ye, Katherine L Beier, Nowrin U Chowdhury, Melissa M Wolf, Arissa C Young, Dalton L Greenwood, Allison E Sewell, Shailesh K Shahi, Samantha N Freedman, Alanna M Cameron, Patrik Foerch, Tim Bourne, Juan C Garcia-Canaveras, John Karijolich, Dawn C Newcomb, Ashutosh K Mangalam, Joshua D Rabinowitz, Jeffrey C Rathmell. MTHFD2 is a metabolic checkpoint controlling effector and regulatory T cell fate and function. *Immunity.* 2022 Jan. 11; 55(1):65-81.

Toriello H V. Folic acid and neural tube defects. *Genet Med.* 2005; 7:283-4.

Yang, M., and Vousden, K. H. Serine and one-carbon metabolism in cancer. *Nat Rev Cancer.* 2016; 16, 650-662.

Yuan Li, Zhang Chen, Jikai Cui, Jizhang Yu, Yuqing Niu, Shuan Ran, Song Wang, Weicong Ye, Heng Xu, Xi Zhang, Jie Wu, Jiahong Xia. MTHFD2 ablation in T cells protects against heart transplant rejection by perturbing IRF4/PD-1 pathway through the metabolic-epigenetic nexus. *J Heart Lung Transplant.* 2023 Jul. 24; S1053-2498(23).

Yulia Shulpekova, Vladimir Nechaev, Svetlana Kardasheva, Alla Sedova, Anastasia Kurbatova, Elena Bueverova, Arthur Kopylov, Kristina Malsagova, Jabulani Clement Dlamini, Vladimir Ivashkin. The Concept of Folic Acid in Health and Disease. *Molecules.* 2021 Jun. 18; 26(12): 3731.

Zhao R, Matherly L H, Goldman I D. Membrane transporters and folate homeostasis: intestinal absorption and transport into systemic compartments and tissues. *Expert Rev Mol Med.* 2009; 11:e4.

Kerschbaumer A., Sepriano A., Smolen J. S., van der Heijde D., Dougados M., van Vollenhoven R., McInnes I. B., Bijlsma J. W. J., Burmester G. R., de Wit M., et al. Efficacy of pharmacological treatment in rheumatoid arthritis: A systematic literature research informing the 2019 update of the EULAR recommendations for management of rheumatoid arthritis. *Ann. Rheum. Dis.* 2020: 1-15.

Smolen J. S., Aletaha D., Bijlsma J. W., Breedveld F. C., Boumpas D., Burmester G., Combe B., Cutolo M., de Wit M., Dougados M., et al. Treating rheumatoid arthritis to target: Recommendations of an international task force. Ann. Rheum. Dis. 2010; 69:631-637.
Diaz-Manera J., Garcia R. R., Ilia I. Treatment strategies for myasthenia gravis: An update. *Expert Opin. Pharmacother.* 2012; 13:1873-1883.
Gotterer L., Li Y. Maintenance immunosuppression in myasthenia gravis. *J. Neurol. Sci.* 2016; 369:294-302.
Chantam W. Rheumatic manifestations of systemic disease: Sarcoidosis. *Curr. Opin. Rheumatol.* 2010; 22:85-90.
Baughman R. P., Lower E. E. A clinical approach to the use of methotrexate for sarcoidosis. *Thorax.* 1999; 54:742-746.
Mahr A. D., Jover J. A., Spiera R. F., Hernandez-Garcia C., Fernández-Gutiérrez B., LaValley M. P., Merkel P. A. Adjunctive Methotrexate for Treatment of Giant Cell Arteritis. An Individual Patient Data Meta-Analysis. *Arthritis Rheum.* 2007; 56:2789-2797.
Ferrara G., Mastrangelo G., Barone P., La Torre F., Martino S., Pappagallo G., Ravelli A., Taddio A., Zulian F., Cimaz R. Methotrexate in juvenile idiopathic arthritis: Advice and recommendations from the MARAJIA expert consensus meeting. *Pediatr. Rheumatol.* 2018; 16:46.
Przemyslaw Kozminski, Pawel Krzysztof Halik, Raphael Chesori, Ewa Gniazdowska. Overview of Dual-Acting Drug Methotrexate in Different Neurological Diseases, Autoimmune Pathologies and Cancers. *Int J Mol Sci.* 2020 May 14; 21(10):3483
Canellos G. P., Skarin A. T., Rosenthal D. S., Moloney W. C., Frei E. Methotrexate as a single agent and in combination chemotherapy for the treatment of non-Hodgkin's lymphoma of unfavorable histology. *Cancer Treat. Rep.* 1981; 65:125-129.
Khan R. B., Shi W., Thaler H. T., DeAngelis L. M., Abrey L. E. Is Intrathecal Methotrexate Necessary in the Treatment of Primary CNS Lymphoma?*J. Neurooncol.* 2002; 58:175-178. doi: 10.1023/A:1016077907952.
Batchelor T. T., Kolak G., Ciordia R., Foster C. S., Henson J. W. High-Dose Methotrexate for Intraocular Lymphoma. *Clin. Cancer Res.* 2003; 9:711-715.
Fahey J. B. High-Dose Methotrexate and Primary Central Nervous System Lymphoma. J. *Neurosci. Nurs.* 2007; 39:83-88.
Zhu J.-J., Gerstner E. R., Engler D. A., Mrugala M. M., Nugent W., Nierenberg K., Hochberg F. H., Betensky R. A., Batchelor T. T. High-dose methotrexate for elderly patients with primary CNS lymphoma. Neuro-Oncology. 2009; 11:211-215.
Gong F., Meng Q., Liu C., Zhao Y. Efficacy and association analysis of high-dose methotrexate in the treatment of children with acute lymphoblastic leukemia. *Oncol. Lett.* 2019; 17:4423-4428.
De Wilde V., Dierickx D., Schroyens W., Van Den Neste E., Bonnet C., Andre M., Janssens A., Van Hende V., Van Hoof A. BHS guidelines for primary central nervous system lymphoma. *Belg. J. Hematol.* 2016; 7:69-78.
Bergner N., Monsef I., Illerhaus G., Engert A., Skoetz N. Role of chemotherapy additional to high-dose methotrexate for primary central nervous system lymphoma (PCNSL) *Cochrane Database Syst. Rev.* 2012; 11
Rizzoli V., Mangoni L., Caramatti C., Degliantoni G., Costi D. High-dose methotrexate-leucovorin rescue therapy: Selected application in non-Hodgkin's lymphoma. *Tumori.* 1985; 71:155-158.
Krailo M., Ertel I., Makley J., Fryjer C. J., Baum E., Weetman R., Yunis E., Barnes L., Bleyer W. A., Hammond G. D. A randomized study comparing high-dose methotrexate with moderate-dose methotrexate as components of adjuvant chemotherapy in childhood nonmetastatic osteosarcoma: A report from the Childrens Cancer Study Group. *Med. Pediatr. Oncol.* 1987; 15:69-77
Meyers P. A., Schwartz C. L., Krailo M., Kleinerman E. S., Betcher D., Bernstein M. L., Conrad E., Ferguson W., Gebhardt M., Goorin A. M., et al. Osteosarcoma: A randomized, prospective trial of the addition of ifosfamide and/or muramyl tripeptide to cisplatin, doxorubicin, and high-dose methotrexate. *J. Clin. Oncol.* 2005; 23:2004-2011.
Abrio R., de Andrade J., Tiezzi D., Marana H., dos Reis F. C., Clagnan W. Treatment for Low-Risk Gestational Trophoblastic Disease: Comparison of Single-Agent Methotrexate, Dactinomycin and Combination Regimens. Gynecol. Oncol. 2008; 108:149-153.
Mantadakis E., Cole P. D., Kamen B. A. High-Dose Methotrexate in Acute Lymphoblastic Leukemia: Where Is the Evidence for Its Continued Use?*Pharmacotherapy.* 2005; 25:748-755.
Whittaker S., Hoppe R., Prince H. M. How I treat mycosis fungoides and Sèzary syndrome. *Blood.* 2016; 127:3142-3153.
Maiti R. Metronomic chemotherapy. *J. Pharmacol.* Pharmacother. 2014; 5:186-192.
Bertino J. B., Mosher M. B., DeConti R. C. Chemotherapy of cancer of the head and neck. *Cancer.* 1973; 31:1141-1149.
Pai P. S., Vaidya A. D., Prabhash K., Banavali S. D. Oral metronomic scheduling of anticancer therapy-based treatment compared to existing standard of care in locally advanced oral squamous cell cancers: A matched-pair analysis. *Indian J. Cancer.* 2013; 50:135-141.
Mateen A., Adil A. R., Maken R. N., Khan S. A., Arif M. Metronomic chemotherapy in recurrent head and neck cancer. *J. Clin. Oncol.* 2015; 33(Suppl. abstr)
Vincent R. G., Wilson H. E., Lane W. W., Chen T. Y., Raza S., Gutierrez A. C., Caracandas J. E. Progress in the Chemotherapy of Small Cell. Carcinoma of the Lung. *Cancer.* 1981; 47:229-235.
Hande K. R., Oldham R. K., Fer M. F., Richardson R. L., Greco F. A. Randomized study of high-dose versus low-dose methotrexate in the treatment of extensive small cell lung cancer. *Am. J. Med.* 1982; 73:413-419.
Ismaili N., Amzerin M., Flechon A. Chemotherapy in advanced bladder cancer: Current status and future. *J. Hematol. Oncol.* 2011; 4:35.
Kansara R. R., Shenkier T., Connors J. M., Gerrie A. S., Klasa R., Savage K. J., Sehn L. H., Villa D. Rituximab with High Dose Methotrexate in the Management of Primary Central Nervous System Diffuse Large B-Cell Lymphoma. Blood. 2014; 124:3090.
Fukuda T., Tanabe M., Kobayashi K., Fukada I., Takahashi S., Iwase T., Ito Y. Combination chemotherapy with mitomycin C and methotrexate is active against metastatic HER2-negative breast cancer even after treatment with anthracycline, taxane, capecitabine, and vinorelbine. *Springerplus.* 2015; 4:376.
Jaffe N., Gorlick R. High-Dose Methotrexate in Osteosarcoma: Let the Questions Surcease—Time for Final Acceptance. *J. Clin. Oncol.* 2008; 26:4365-4366.
Bacci G., Ferrari S., Bertoni F., Ruggieri R, Picci P., Longhi A., Casadei R., Fabbri N., Forni C., Versari M., et al. Long-term outcome for patients with nonmetastatic osteosarcoma of the extremity treated at the istituto ortopedico rizzoli according to the istituto ortopedico rizzoli/osteosarcoma-2 protocol: An updated report. *J. Clin. Oncol.* 2000; 18:4016-4027.

Zhiyuan Zhu., Gilberto Ka Kit Leung. More Than a Metabolic Enzyme: MTHFD2 as a Novel Target for Anticancer Therapy?*Front. Oncol.,* 28 Apr. 2020 *Sec. Cancer Metabolism Volume* 10-2020

Franziska Karl, Michael Hudecek, Friederike Berberich-Siebelt, Andreas Mackensen, Dimitrios Mougiakakos. T-Cell Metabolism in Graft Versus Host Disease. Front. *Immunol.* 2021 29; 12 Oct. 2021

Sun L, Su Y, Jiao A, Wang X, Zhang B. T cells in health and disease. *Signal Transduct Target Ther.* 2023 Jun. 19; 8(1):235.

Alyxzandria M Gaydosik, Tracy Tabib, Robyn Domsic, Dinesh Khanna, Robert Lafyatis, Patrizia Fuschiotti. Single-cell transcriptome analysis identifies skin-specific T-cell responses in systemic sclerosis. *Ann Rheum Dis.* 2021 November; 80(11):1453-1460.

Sabat R, Wolk K, Loyal L, Docke W D, Ghoreschi K. T cell pathology in skin inflammation. *Semin Immunopathol.* 2019 May; 41(3):359-377

Katrin Witte, Sylke Schneider-Burrus, Gabriela Salinas, Rotraut Mössner, Kamran Ghoreschi, Kerstin Wolk, Robert Sabat. Blood T Helper Memory Cells: A Tool for Studying Skin Inflammation in HS?*Int J Mol Sci.* 2023 May 16; 24(10):8854.

Raphael I, Joern R R, Forsthuber T G. Memory CD4+ T Cells in Immunity and Autoimmune Diseases. *Cells.* 2020 Feb. 25; 9(3):531.

Yanjie Gao, Bingfeng Zheng, Shuaiqi Xu, Zhibo Zhao, Wanyue Liu, Tingyu Wang, Manman Yuan, Xueqing Sun, Yang Tan, Qiang Xu, Xingxin Wu. Mitochondrial folate metabolism-mediated α-linolenic acid exhaustion masks liver fibrosis resolution. *J Biol Chem.* 2023 July; 299(7): 104909.

R. B. Hamanaka, A. Y. Meliton, R. Cetin-Atalay, P. S. Woods, K. A. Sun, O. Shamaa, G. M. Mutlu. One Carbon Metabolism Is Required for Glycine Biosynthesis and Collagen Production in Lung Fibroblasts. *American Journal of Respiratory and Critical Care Medicine* 2022; 205:A1932

Hiroshi Furukawa, Shomi Oka, Takashi Higuchi, Kota Shimada, Atsushi Hashimoto, Toshihiro Matsui, Shigeto Tohma. Biomarkers for interstitial lung disease and acute-onset diffuse interstitial lung disease in rheumatoid arthritis. *Ther Adv Musculoskelet Dis.* 2021(13).

Sugiura A, Andrejeva G, Voss K, Heintzman D R, Xu X, Madden M Z, Ye X, Beier K L, Chowdhury N U, Wolf M M, Young A C, Greenwood D L, Sewell A E, Shahi S K, Freedman S N, Cameron A M, Foerch P, Bourne T, Garcia-Canaveras J C, Karijolich J, Newcomb D C, Mangalam A K, Rabinowitz J D, Rathmell J C. MTHFD2 is a metabolic checkpoint controlling effector and regulatory T cell fate and function. *Immunity.* 2022 Jan. 11; 55(1):65-81.

Gopalakrishnan M., Monteggia L. M., Anderson D. J., Moliari E. J., Piottoni-Kaplan M., Donnelly-Roberts D., Arneric S. P., Sullivan, J. P. Stable expression, pharmacologic properties and regulation of the human neuronal nicotinic acetylcholine alpha 4 beta 2 receptor, *J. Pharmacol. Exp. Ther.,* 1996, 276: 289.

MISCELLANEOUS

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application, of which this description and claims form part, may be used as a basis for priority in respect of any subsequent application. The claims of such subsequent application may be directed to any feature or combination of features described herein. They may take the form of product, composition, process, or use claims and may include, by way of example and without limitation, the following claims.

The invention claimed is:

1. A compound of formula (I):

(I)

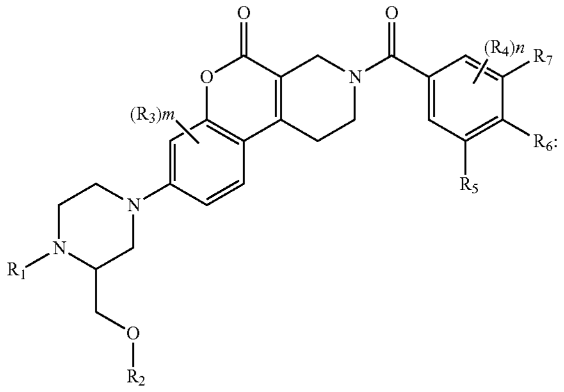

wherein:

$R_1$ is $C_{1-4}$ alkyl or $C_{3-5}$ cycloalkyl;

$R_2$ is $C_{1-4}$ alkyl; or $R_1$ and $R_2$ join to form a 5-7 membered heterocycloalkyl;

$R_3$ is selected from the group consisting of $C_{1-3}$ alkyl and halo;

$R_4$ is selected from the group consisting of $C_{1-3}$ alkyl, halo, $C_{1-3}$ haloalkyl, $C_{1-3}$ alkoxy, $C_{1-3}$ haloalkoxy, $NR_{4a}R_{4b}$ and 4-7 membered heterocycloalkyl;

wherein:

$R_{4a}$ is selected from the group consisting of H and $C_{1-3}$ alkyl;

$R_{4b}$ is selected from the group consisting of H and $C_{1-3}$ alkyl;

m is 0, 1 or 2;

n is 0, 1 or 2;

and $R_5$, $R_6$ and $R_7$ are defined as follows:

(a) $R_6$ is

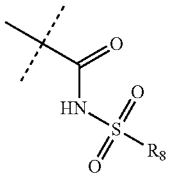

and $R_7$ is absent;

$R_5$ is selected from the group consisting of H, halo, $C_{1-3}$ alkyl, $C_{1-3}$ haloalkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{5b}$ is selected from the group consisting of H and $C_{1-3}$ alkyl; and $R_{5c}$ is selected from the group consisting of $C_{1-3}$ alkyl and $C_{3-6}$ cycloalkyl; and $R_8$ is selected from the group consisting of $C_{3-6}$ cycloalkyl, $NR_{8b}R_{8c}$ and 4-10 membered heterocycloalkyl, wherein the $C_{3-6}$ cycloalkyl and 4-10 membered heterocycloalkyl are optionally substituted by one or more $R_{8a}$, wherein:

$R_{8a}$ is selected from the group consisting of $C_{1-3}$ alkyl, $C_{1-3}$ alkyl substituted by OH, $C_{1-2}$ alkyl substituted by $OC_{1-2}$ alkyl, $C_{1-3}$ alkoxy, halo and $C_{1-3}$ haloalkyl;

$R_{8b}$ is selected from the group consisting of H, $C_{1-3}$ alkyl and $C_{3-6}$ cycloalkyl;

$R_{8c}$ is selected from the group consisting of H, $C_{1-3}$ alkyl and $C_{3-6}$ cycloalkyl;

or:

(b) $R_7$ is

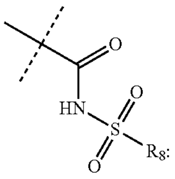

and (i) $R_6$ is H and $R_5$ is selected from the group consisting of H, halo, $C_{1-3}$ alkyl, $C_{1-3}$ haloalkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring, $R_{5b}$ is selected from the group consisting of H and $C_{1-3}$ alkyl; and $R_{5c}$ is selected from the group consisting of $C_{1-3}$ alkyl and $C_{3-6}$ cycloalkyl;

or (ii) $R_5$ is H and $R_6$ is selected from the group consisting of H, halo, $C_{1-3}$ alkyl, $C_{1-3}$ haloalkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{6b}R_{6c}$ and 4-7 membered heterocycloalkyl, wherein the $OC_{3-10}$ cycloalkyl and 4-7 membered heterocycloalkyl are optionally substituted by one or more $R_{6a}$;

wherein:

$R_{6a}$ is selected from the group consisting of halo and $C_{1-3}$ alkyl, or two $R_{6a}$ groups which are attached to the same carbon atom join to form a $C_{3-6}$ cycloalkyl or 4-7 membered heterocycloalkyl ring, $R_{6b}$ is selected from the group consisting of H and $C_{1-3}$ alkyl; and $R_{6c}$ is selected from the group consisting of $C_{1-3}$ alkyl and $C_{3-6}$ cycloalkyl;

or (iii) $R_5$ and $R_6$ join to form a 4-8 membered heterocyclic ring;

and $R_8$ is selected from the group consisting of $C_{3-6}$ cycloalkyl, $NR_{8b}R_{8c}$ and 4-10 membered heterocycloalkyl, wherein the $C_{3-6}$ cycloalkyl and 4-10 membered heterocycloalkyl are optionally substituted by one or more $R_{8a}$ wherein:

$R_{8a}$ is selected from the group consisting of $C_{1-3}$ alkyl, $C_{1-3}$ alkyl substituted by OH, $C_{1-2}$ alkyl substituted by $OC_{1-2}$ alkyl, $C_{1-3}$ alkoxy, halo and $C_{1-3}$ haloalkyl;

$R_{8b}$ is selected from the group consisting of H, $C_{1-3}$ alkyl and $C_{3-6}$ cycloalkyl; and $R_{8c}$ is selected from the group consisting of H, $C_{1-3}$ alkyl and $C_{3-6}$ cycloalkyl;

or a pharmaceutically acceptable salt and/or solvate thereof.

2. A compound of formula (I) according to claim 1:

(I)

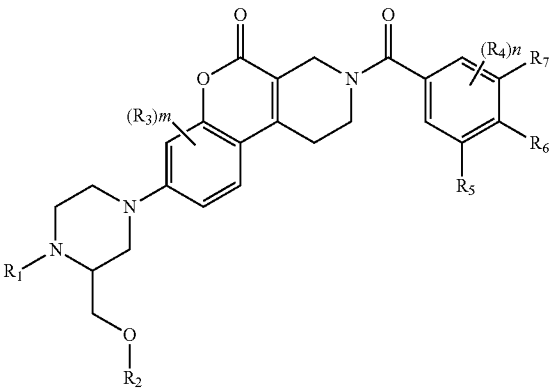

wherein:

$R_1$ is $C_{1-4}$ alkyl or $C_{3-5}$ cycloalkyl;

$R_2$ is $C_{1-4}$ alkyl; or $R_1$ and $R_2$ join to form a 5-7 membered heterocycloalkyl;

$R_3$ is selected from the group consisting of $C_{1-3}$ alkyl and halo;

$R_4$ is selected from the group consisting of $C_{1-3}$ alkyl, halo, $C_{1-3}$ haloalkyl, $C_{1-3}$ alkoxy, $C_{1-3}$ haloalkoxy, $NR_{4a}R_{4b}$ and 4-7 membered heterocycloalkyl;

wherein:

$R_{4a}$ is selected from the group consisting of H and $C_{1-3}$ alkyl;

$R_{4b}$ is selected from the group consisting of H and $C_{1-3}$ alkyl;

m is 0, 1 or 2;

n is 0, 1 or 2;

and $R_5$, $R_6$ and $R_7$ are defined as follows:

(a) $R_6$ is

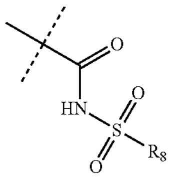

and $R_7$ is absent;

$R_5$ is selected from the group consisting of H, halo, $C_{1-3}$ alkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{5b}$ is selected from the group consisting of H and $C_{1-3}$ alkyl; and $R_{5c}$ is selected from the group consisting of $C_{1-3}$ alkyl and $C_{3-6}$ cycloalkyl; and $R_8$ is selected from the group consisting of $C_{3-6}$ cycloalkyl, $NR_{8b}R_{8c}$ and 4-8 membered heterocycloalkyl, wherein the $C_{3-6}$ cycloalkyl and 4-8 membered heterocycloalkyl are optionally substituted by one or more $R_{8a}$, wherein:

$R_{8a}$ is selected from the group consisting of $C_{1-3}$ alkyl, halo and $C_{1-3}$ haloalkyl;

$R_{8b}$ is selected from the group consisting of H, $C_{1-3}$ alkyl and $C_{3-6}$ cycloalkyl;

$R_{8c}$ is selected from the group consisting of H, $C_{1-3}$ alkyl and $C_{3-6}$ cycloalkyl;

or:

(b) $R_7$ is

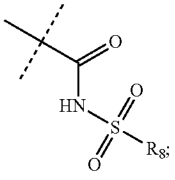

and (i) $R_6$ is H and $R_5$ is selected from the group consisting of H, halo, $C_{1-3}$ alkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring, $R_{5b}$ is selected from the group consisting of H and $C_{1-3}$ alkyl; and $R_{5c}$ is selected from the group consisting of $C_{1-3}$ alkyl and $C_{3-6}$ cycloalkyl;

or (ii) $R_5$ is H and $R_6$ is selected from the group consisting of H, halo, $C_{1-3}$ alkyl, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{6b}R_{6c}$ and 4-7 membered heterocycloalkyl, wherein the $OC_{3-10}$ cycloalkyl and 4-7 membered heterocycloalkyl are optionally substituted by one or more $R_{6a}$;

wherein:

$R_{6a}$ is selected from the group consisting of halo and $C_{1-3}$ alkyl, or two $R_{6a}$ groups which are attached to the same carbon atom join to form a $C_{3-6}$ cycloalkyl or 4-7 membered heterocycloalkyl ring, $R_{6b}$ is selected from the group consisting of H and $C_{1-3}$ alkyl; and $R_{6c}$ is selected from the group consisting of $C_{1-3}$ alkyl and $C_{3-6}$ cycloalkyl;

or (iii) $R_5$ and $R_6$ join to form a 4-8 membered heterocyclic ring;

and $R_8$ is selected from the group consisting of $C_{3-6}$ cycloalkyl, $NR_{8b}R_{8c}$ and 4-8 membered heterocycloalkyl, wherein the $C_{3-6}$ cycloalkyl and 4-8 membered heterocycloalkyl are optionally substituted by one or more $R_{8a}$ wherein:

$R_{8a}$ is selected from the group consisting of $C_{1-3}$ alkyl, halo and $C_{1-3}$ haloalkyl;

$R_{8b}$ is selected from the group consisting of H, $C_{1-3}$ alkyl and $C_{3-6}$ cycloalkyl; and $R_{8c}$ is selected from the group consisting of H, $C_{1-3}$ alkyl and $C_{3-6}$ cycloalkyl;

or a pharmaceutically acceptable salt and/or solvate thereof.

3. A compound of formula (I) according to claim 1:

(I)

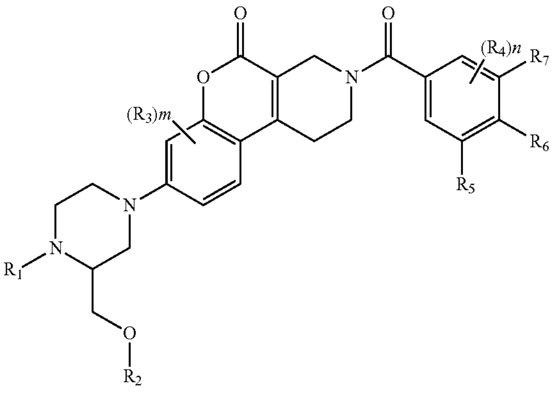

wherein:

$R_1$ is $C_{1-4}$ alkyl or $C_{3-5}$ cycloalkyl;

$R_2$ is $C_{1-4}$ alkyl; or $R_1$ and $R_2$ join to form a 5-7 membered heterocycloalkyl;

$R_3$ is selected from the group consisting of $C_{1-3}$ alkyl and halo;

$R_4$ is selected from the group consisting of $C_{1-3}$ alkyl, halo, $C_{1-3}$ haloalkyl, $C_{1-3}$ alkoxy, $C_{1-3}$ haloalkoxy and 4-7 membered heterocycloalkyl;

$R_6$ is

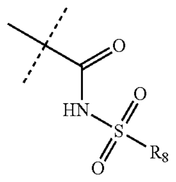

and $R_7$ is absent; or $R_7$ is

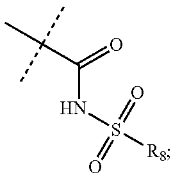

wherein:

when $R_6$ is

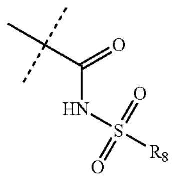

and $R_7$ is absent:

$R_5$ is selected from the group consisting of H, halo, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring;

$R_{5b}$ is selected from the group consisting of H and $C_{1-3}$ alkyl; and $R_{5c}$ is selected from the group consisting of $C_{1-3}$ alkyl and $C_{3-6}$ cycloalkyl; and $R_8$ is selected from the group consisting of $C_{3-6}$ cycloalkyl, $N(C_{1-3}\ alkyl)_2$ and 4-8 membered heterocycloalkyl, wherein the $C_{3-6}$ cycloalkyl and 4-8 membered heterocycloalkyl are optionally substituted by one or more $R_{8a}$, wherein $R_{8a}$ is selected from the group consisting of $C_{1-3}$ alkyl, halo and $C_{1-3}$ haloalkyl;

or:

when $R_7$ is

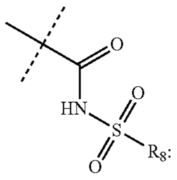

$R_6$ is H and $R_5$ is selected from the group consisting of H, halo, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{5b}R_{5c}$ and 4-7 membered heterocycloalkyl, wherein the $OC_{3-10}$ cycloalkyl and 4-7 membered heterocycloalkyl are optionally substituted by one or more $R_{5a}$;

wherein:

$R_{5a}$ is selected from the group consisting of halo and $C_{1-3}$ alkyl, or two $R_{5a}$ groups which are attached to the same carbon atom join to form a $C_{3-6}$ cycloalkyl or 4-7 membered heterocycloalkyl ring, $R_{5b}$ is selected from the group consisting of H and $C_{1-3}$ alkyl; and $R_{5c}$ is selected from the group consisting of $C_{1-3}$ alkyl and $C_{3-6}$ cycloalkyl;

or $R_5$ is H and $R_6$ is selected from the group consisting of H, halo, $C_{1-3}$ alkoxy, $C_{1-3}$ haloalkoxy, $SC_{1-3}$ alkyl, $SC_{1-3}$ haloalkyl, $OC_{3-10}$ cycloalkyl, $NR_{6b}R_{6c}$ and 4-7 membered heterocycloalkyl, wherein the $OC_{3-10}$ cycloalkyl and 4-7 membered heterocycloalkyl are optionally substituted by one or more $R_{6a}$;

wherein:

$R_{6a}$ is selected from the group consisting of halo and $C_{1-3}$ alkyl, or two $R_{6a}$ groups which are attached to the same carbon atom join to form a $C_{3-6}$ cycloalkyl or 4-7 membered heterocycloalkyl ring, $R_{6b}$ is selected from the group consisting of H and $C_{1-3}$ alkyl; and $R_{6c}$ is selected from the group consisting of $C_{1-3}$ alkyl and $C_{3-6}$ cycloalkyl;

or $R_5$ and $R_6$ join to form a 4-7 membered heterocyclic ring; and $R_8$ is selected from the group consisting of $C_{3-6}$ cycloalkyl, $N(C_{1-3}\ alkyl)_2$ and 4-8 membered heterocycloalkyl, wherein the $C_{3-6}$ cycloalkyl and 4-8 membered heterocycloalkyl are optionally substituted by one or more $R_{8a}$ wherein $R_{8a}$ is selected from the group consisting of $C_{1-3}$ alkyl, halo and $C_{1-3}$ haloalkyl;

m is 0, 1 or 2; and n is 0, 1 or 2;

or a pharmaceutically acceptable salt and/or solvate thereof.

4. The compound or a pharmaceutically acceptable salt and/or solvate thereof according to claim 1 wherein $R_1$ is methyl and $R_2$ is methyl.

5. The compound or a pharmaceutically acceptable salt and/or solvate thereof according to claim 1 wherein m is 2 and $R_3$ is methyl or wherein m is 1 and $R_3$ is chloro.

6. The compound or a pharmaceutically acceptable salt and/or solvate thereof according to claim 1 wherein n is 1 and $R_4$ is selected from the group consisting of chloro and fluoro.

7. The compound or a pharmaceutically acceptable salt and/or solvate thereof according to claim 1 wherein:

$R_6$ is

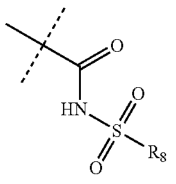

and $R_7$ is absent.

8. The compound or a pharmaceutically acceptable salt and/or solvate thereof according to claim 7 wherein $R_5$ is $C_{1-3}$ alkoxy e.g. methoxy or ethoxy, or $OC_{3-10}$ cycloalkyl e.g. cyclobutyloxy or cyclopentyloxy.

9. The compound or a pharmaceutically acceptable salt and/or solvate thereof according to claim 7 which is a compound of formula (IC):

(IC)

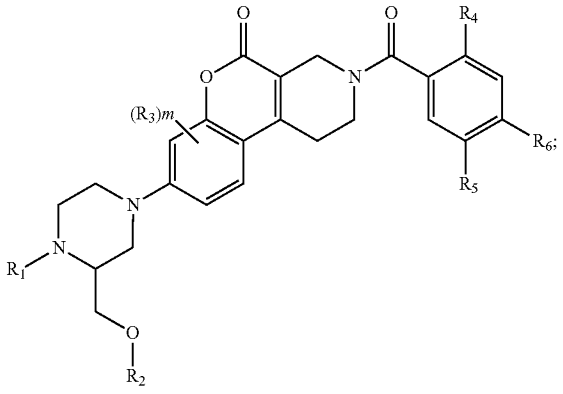

wherein $R_1$, $R_2$, $R_3$, m and $R_4$ are as defined in claim 1, $R_6$ as defined in claim 7 and $R_5$ is methoxy, ethoxy, cyclopropyloxy or $NR_{5b}R_{5c}$ and wherein $R_{5b}$ and $R_{5c}$ are as defined in claim 1.

10. The compound or a pharmaceutically acceptable salt and/or solvate thereof according to claim 1 wherein $R_5$ is $NR_{5b}R_{5c}$ wherein $R_{5b}$ and $R_{5c}$ are each methyl.

11. The compound or a pharmaceutically acceptable salt and/or solvate thereof according to claim 1 wherein $R_8$ is $C_{3-6}$ cycloalkyl e.g. cyclopropyl and $R_8$ is substituted by one $R_{8a}$ group e.g. methyl, or wherein $R_8$ is 4-8 membered heterocycloalkyl e.g. e.g. pyrrolidinyl, 7-azanorbornanyl, 3-azabicyclo[3.1.0]hexyl, 6-azaspiro[2.5]octyl or 3-oxa-6-azabicyclo[3.2.1]octyl.

12. The compound or a pharmaceutically acceptable salt and/or solvate thereof according to claim 11 wherein $R_8$ is pyrrolidinyl e.g. pyrrolidin-1-yl.

13. The compound or a pharmaceutically acceptable salt and/or solvate thereof according to claim 1 which is selected from the list consisting of:

(R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl) benzamide;

(R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl) benzamide;

(R)-2-cyclobutoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl) benzamide;

(R)-2-(cyclopentyloxy)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl) benzamide;

(R)-2-(cyclopentyloxy)-N—(N,N-dimethylsulfamoyl)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-(cyclopentyloxy)-3-fluoro-N-(pyrrolidin-1-ylsulfonyl)benzamide;

(R)-2-cyclobutoxy-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

(R)-2-(cyclopentyloxy)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

(R)-2-(cyclopentyloxy)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-cyclobutoxy-N-((1-methylcyclopropyl)sulfonyl)benzamide;

2-(((1R,3r,5S)-bicyclo[3.1.0]hexan-3-yl)oxy)-N—(N,N-dimethylsulfamoyl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(cyclopentyloxy)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

2-(((1R,3r,5S)-bicyclo[3.1.0]hexan-3-yl)oxy)-N—(N,N-dimethylsulfamoyl)-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-cyclobutoxy-N-(pyrrolidin-1-ylsulfonyl)benzamide;

(R)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)-2-(pyrrolidin-1-yl)benzamide;

(R)-2-(7-azabicyclo[2.2.1]heptan-7-yl)-N—(N,N-dimethylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-2-(7-azabicyclo[2.2.1]heptan-7-yl)-4-(8-(3-(methoxymethyl)-4-methylpiperazin-1-yl)-7-methyl-5- oxo-1,3,4,5-tetrahydro-2H-chromeno[3,4-c]pyridine-3-carbonyl)-N-((1-methylcyclopropyl)sulfonyl)benzamide;

(R)—N—(N,N-dimethylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-2-(pyrrolidin-1-yl)benzamide;

(R)-2-cyclobutoxy-4-(8-(hexahydropyrazino [2,1-c][1,4]oxazin-8(1H)-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)—N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)benzamide;

(R)-2-cyclobutoxy-4-(8-(hexahydropyrazino [2,1-c][1,4]oxazin-8(1H)-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-(7-azabicyclo[2.2.1]heptan-7-yl)-6-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

(R)-2-(7-azabicyclo[2.2.1]heptan-7-yl)-N—(N,N-dimethylsulfamoyl)-6-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-2-(cyclopentyloxy)-3-fluoro-N—(N-isopropyl-N-methylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-cyclobutoxy-3-fluoro-N—(N-isopropyl-N-methylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-(3-azabicyclo[3.1.0]hexan-3-yl)-6-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

2-(3-azabicyclo[3.1.0]hexan-3-yl)-N—(N,N-dimethylsulfamoyl)-6-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

2-(3-azabicyclo[3.1.0]hexan-3-yl)-N—(N,N-dimethylsulfamoyl)-6-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-(cyclopentyloxy)-3-fluoro-N—(N-isopropyl-N-methylsulfamoyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-cyclobutoxy-3-fluoro-N—(N-isopropyl-N-methylsulfamoyl)benzamide;

(R)—N—(N-isopropyl-N-methylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-2-(pyrrolidin-1-yl)benzamide;

2-(3-azabicyclo[3.1.0]hexan-3-yl)-6-chloro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

2-(3-azabicyclo[3.1.0]hexan-3-yl)-6-chloro-N—(N,N-dimethylsulfamoyl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

2-(3-azabicyclo[3.1.0]hexan-3-yl)-6-chloro-N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-(((1R,3r,5S)-bicyclo[3.1.0]hexan-3-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

2-(((1R,3r,5S)-bicyclo[3.1.0]hexan-3-yl)oxy)-3-fluoro-N—(N-isopropyl-N-methylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-(((1R,3r,5S)-bicyclo[3.1.0]hexan-3-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(cyclobutyl(methyl)amino)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(cyclobutyl(methyl)amino)-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(7-azabicyclo[2.2.1]heptan-7-yl)-6-chloro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

(R)-2-cyclobutoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

(R)-2-(cyclopentyloxy)-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-(cyclopentyloxy)-N—(N,N-dimethylsulfamoyl)-3-fluorobenzamide;

(R)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-(pyrrolidin-1-yl)benzamide;

2-(3-azabicyclo[3.1.0]hexan-3-yl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

2-(3-azabicyclo[3.1.0]hexan-3-yl)-N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(7-azabicyclo[2.2.1]heptan-7-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(7-azabicyclo[2.2.1]heptan-7-yl)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-cyclobutoxy-N—(N,N-dimethylsulfamoyl)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-2-cyclobutoxy-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-cyclobutoxy-N—(N,N-dimethylsulfamoyl)-3-fluorobenzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-cyclobutoxy-3-fluoro-N-(pyrrolidin-1-ylsulfonyl)benzamide;

(R)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)-2-(cyclobutyl(methyl)amino)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-cyclobutoxy-3-fluoro-N—(N-isopropyl-N-methylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-(cyclopentyloxy)-3-fluoro-N-((1-methylcyclopropyl)sulfonyl)benzamide;

(R)-2-(cyclopentyloxy)-3-fluoro-N—(N-isopropyl-N-methylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

2-(((1R,3r,5S)-bicyclo[3.1.0]hexan-3-yl)oxy)-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;

2-(((1R,3r,5S)-bicyclo[3.1.0]hexan-3-yl)oxy)-4-(7-chloro-8-((R)-3-(methoxymethyl)-4-methylpiperazin-1-yl)-5-oxo-1,3,4,5-tetrahydro-2H-chromeno[3,4-c]pyridine-3-carbonyl)-3-fluoro-N-((1-methylcyclopropyl)sulfonyl)benzamide;

2-(((1R,3r,5S)-bicyclo[3.1.0]hexan-3-yl)oxy)-4-(7-chloro-8-((R)-3-(methoxymethyl)-4-methylpiperazin-1-yl)-5-oxo-1,3,4,5-tetrahydro-2H-chromeno[3,4-c]pyridine-3-carbonyl)-N—(N,N-dimethylsulfamoyl)-3-fluorobenzamide;

2-(((1R,3r,5S)-bicyclo[3.1.0]hexan-3-yl)oxy)-4-(7-chloro-8-((R)-3-(methoxymethyl)-4-methylpiperazin-1-yl)-5-oxo-1,3,4,5-tetrahydro-2H-chromeno[3,4-c]pyridine-3-carbonyl)-3-fluoro-N-(pyrrolidin-1-ylsulfonyl)benzamide;

2-(((1R,3r,5S)-bicyclo[3.1.0]hexan-3-yl)oxy)-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

2-(((1R,3r,5S)-bicyclo[3.1.0]hexan-3-yl)oxy)-3-fluoro-N—(N-isopropyl-N-methylsulfamoyl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

2-(((1R,3r,5S)-bicyclo[3.1.0]hexan-3-yl)oxy)-4-(7-chloro-8-((R)-3-(methoxymethyl)-4-methylpiperazin-1-yl)-5-oxo-1,3,4,5-tetrahydro-2H-chromeno[3,4-c]pyridine-3-carbonyl)-3-fluoro-N—(N-isopropyl-N-methylsulfamoyl)benzamide;

2-(((1R,3s,5S)-bicyclo[3.1.0]hexan-3-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

2-(((1R,3s,5S)-bicyclo[3.1.0]hexan-3-yl)oxy)-N—(N,N-dimethylsulfamoyl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-(((1R,3,5S)-bicyclo[3.1.0]hexan-3-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-(pyrrolidin-1-yl)benzamide;

(R)—N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)benzamide;

2-(3-azabicyclo[3.1.0]hexan-3-yl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

2-(3-azabicyclo[3.1.0]hexan-3-yl)-N—(N,N-dimethylsulfamoyl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(7-azabicyclo[2.2.1]heptan-7-yl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(7-azabicyclo[2.2.1]heptan-7-yl)-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(3,3-difluoropiperidin-1-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(3,3-difluoropiperidin-1-yl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(3,3-difluoropiperidin-1-yl)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(3,3-difluoropiperidin-1-yl)-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(7-azabicyclo[2.2.1]heptan-7-yl)-6-chloro-N—(N,N-dimethylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-2-(3,3-difluoropyrrolidin-1-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(3,3-difluoropyrrolidin-1-yl)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(cyclopropyl(methyl)amino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(cyclopropyl(methyl)amino)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-((4,4-difluorocyclohexyl)oxy)-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-((4,4-difluorocyclohexyl)oxy)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(3,3-dimethylpyrrolidin-1-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(3,3-dimethylpyrrolidin-1-yl)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(azetidin-1-yl)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-((adamantan-2-yl)oxy)-N—(N,N-dimethylsulfamoyl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(azetidin-1-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;

(R)-2-(3,3-difluoropyrrolidin-1-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-N—(N,N-dimethylsulfamoyl)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-((adamantan-2-yl)oxy)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

2-(3-azabicyclo[3.1.0]hexan-3-yl)-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)-N-(pyrrolidin-1-ylsulfonyl)benzamide;

(R)-2-(7-azabicyclo[2.2.1]heptan-7-yl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)-N-(pyrrolidin-1-ylsulfonyl)benzamide;

(R)-2-((4,4-difluorocyclohexyl)oxy)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

2-((adamantan-2-yl)oxy)-N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(cyclopentyloxy)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)-6-(trifluoromethyl)benzamide;

N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-2-((R)-2-methylpyrrolidin-1-yl)benzamide;

N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-2-((S)-2-methylpyrrolidin-1-yl)benzamide;

2-(3-azabicyclo[3.1.0]hexan-3-yl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)-6-(trifluoromethyl)benzamide;

2-(3-azabicyclo[3.1.0]hexan-3-yl)-6-chloro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)—N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-methyl-6-(pyrrolidin-1-yl)benzamide;

(R)-2-(cyclopentyloxy)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;

2-(bicyclo[3.1.0]hexan-3-yloxy)-N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-(bicyclo[3.1.0]hexan-3-yloxy)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(24yrrolidine-1-ylsulfonyl)benzamide;

(R)-2-(cyclopentyloxy)-N—(N,N-dimethylsulfamoyl)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(cyclopentyloxy)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

2-(3-azabicyclo[3.1.0]hexan-3-yl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;

2-(bicyclo[3.1.0]hexan-3-yloxy)-N—(N,N-dimethylsulfamoyl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

2-(bicyclo[3.1.0]hexan-3-yloxy)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

2-(2-azabicyclo[2.2.1]heptan-2-yl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

2-(2-azabicyclo[2.2.1]heptan-2-yl)-N—(N,N-dimethylsulfamoyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(cyclopentyloxy)-N—(N,N-dimethylsulfamoyl)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-6-(trifluoromethyl)benzamide;

2-(3-azabicyclo[3.1.0]hexan-3-yl)-N—(N,N-dimethylsulfamoyl)-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)-6-(trifluoromethyl)benzamide;

(R)—N—(N,N-dimethylsulfamoyl)-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-6-(pyrrolidin-1-yl)benzamide;

(R)—N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(5-azaspiro[2.5]octan-5-yl)benzamide;

(R)-2-(7-azabicyclo[2.2.1]heptan-7-yl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-2-((S)-2-methylpyrrolidin-1-yl)-N-(pyrrolidin-1-ylsulfonyl)benzamide;

4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-((R)-2-methylpyrrolidin-1-yl)benzamide;

4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-2-((R)-2-methylpyrrolidin-1-yl)-N-(pyrrolidin-1-ylsulfonyl)benzamide;

4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-((S)-2-methylpyrrolidin-1-yl)benzamide;

2-(3-azabicyclo[3.1.0]hexan-3-yl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-(cyclopentyloxy)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-6-(pyrrolidin-1-yl)benzamide;

(R)-2-(cyclopentyloxy)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-6-(trifluoromethyl)benzamide;

(R)-2-(cyclopentyloxy)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;

(R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-6-(trifluoromethyl)benzamide;

(S)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;

(R)-2-cyclobutoxy-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;

(R)—N—(N,N-dimethylsulfamoyl)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-(dimethylamino)-3-fluoro-4-(8-(3-(methoxymethyl)-4-methylpiperazin-1-yl)-7,10-dimethyl-5-oxo-1, 3,4,5-tetrahydro-2H-chromeno[3,4-c]pyridine-3-carbonyl)-N-((1-methylcyclopropyl)sulfonyl)benzamide;
(R)-2-(dimethylamino)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-((1-methylcyclopropyl)sulfonyl)benzamide;
(R)-2-(dimethylamino)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;
(R)-2-(dimethylamino)-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;
(R)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-5-methyl-N-(pyrrolidin-1-ylsulfonyl)benzamide;
(R)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(pyrrolidin-1-yl)-N-(pyrrolidin-1-ylsulfonyl)benzamide;
(R)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-2-(pyrrolidin-1-yl)benzamide;
(R)-2-cyclobutoxy-4-(8-(3-(ethoxymethyl)-4-methylpiperazin-1-yl)-7-methyl-5-oxo-1,3,4,5-tetrahydro-2H-chromeno[3,4-c]pyridine-3-carbonyl)-3-fluoro-N-(pyrrolidin-1-ylsulfonyl)benzamide;
(R)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;
(R)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;
(R)—N—(N,N-dimethylsulfamoyl)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide; (R)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;
(R)—N—(N,N-dimethylsulfamoyl)-3-fluoro-2-isopropoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;
(R)-3-fluoro-2-isopropoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;
(R)-5-chloro-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;
(R)-5-chloro-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)benzamide;
(R)-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-5-(trifluoromethyl)benzamide;
(R)-2-(cyclopentyloxy)-N—(N,N-dimethylsulfamoyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-6-(trifluoromethyl)benzamide;
(R)-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;
(R)—N-((6-azaspiro[2.5]octan-6-yl)sulfonyl)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;
N-((3-azabicyclo[3.1.0]hexan-3-yl)sulfonyl)-3-fluoro-2-methoxy-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;
(R)—N-((7-azabicyclo[2.2.1]heptan-7-yl)sulfonyl)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;
N-((3-oxa-8-azabicyclo[3.2.1]octan-8-yl)sulfonyl)-3-fluoro-2-methoxy-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;
(R)-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-5-(trifluoromethyl)benzamide;
(R)-2-ethoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;
(R)-2-isopropoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-6-(trifluoromethyl)benzamide;
(R)-2-cyclobutoxy-5-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;
(R)-3-cyclobutoxy-5-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;
(R)-6-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)spiro[benzo[d][1,3]dioxole-2,1'-cyclobutane]-4-carboxamide;
(R)—N-((7-azabicyclo[2.2.1]heptan-7-yl)sulfonyl)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;
(R)-2-cyclobutoxy-4-fluoro-5-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;
(R)-3-cyclobutoxy-4-fluoro-5-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;
2-cyclobutoxy-N-(((2R,5R)-2,5-dimethylpyrrolidin-1-yl)sulfonyl)-3-fluoro-4-(8-((R)-3-(methoxymethyl)-4- methylpiperazin-1-yl)-7-methyl-5-oxo-1,3,4,5-tetrahydro-2H-chromeno[3,4-c]pyridine-3-carbonyl) benzamide;

(R)-2-cyclobutoxy-N—(N,N-dimethylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-cyclobutoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-3-methyl-N-((1-methylcyclopropyl)sulfonyl)benzamide;

(R)-4-fluoro-5-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)spiro[benzo[d][1,3]dioxole-2,1'-cyclobutane]-7-carboxamide;

(R)-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((1-methylcyclopropyl)sulfonyl)-5-(trifluoromethyl) benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-2-(trifluoromethoxy)benzamide;

(R)-2-chloro-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-3-fluoro-4-(8-(4-isopropyl-3-(methoxymethyl) piperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)-2-(difluoromethoxy)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-cyclobutoxy-4-(8-(4-ethyl-3-(methoxymethyl) piperazin-1-yl)-7-methyl-5-oxo-1,3,4,5-tetrahydro-2H-chromeno[3,4-c]pyridine-3-carbonyl)-3-fluoro-N-(pyrrolidin-1-ylsulfonyl)benzamide;

(R)-2-cyclobutoxy-4-(8-(4-cyclopropyl-3-(methoxymethyl) piperazin-1-yl)-7-methyl-5-oxo-1,3,4,5-tetrahydro-2H-chromeno[3,4-c]pyridine-3-carbonyl)-3-fluoro-N-(pyrrolidin-1-ylsulfonyl)benzamide;

(S)-2-cyclobutoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(S)-2-cyclobutoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

N-((3-azabicyclo[3.1.0]hexan-3-yl)sulfonyl)-2-(dimethylamino)-5-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl) benzamide;

(R)-2-cyclobutoxy-3-fluoro-4-(8-(3-(methoxymethyl)-4-methylpiperazin-1-yl)-5-oxo-1,3,4,5-tetrahydro-2H-chromeno[3,4-c]pyridine-3-carbonyl)-N-(pyrrolidin-1-ylsulfonyl)benzamide;

(R)-2-(cyclopentyloxy)-3-fluoro-4-(8-(3-(methoxymethyl)-4-methylpiperazin-1-yl)-5-oxo-1,3,4,5-tetrahydro-2H-chromeno[3,4-c]pyridine-3-carbonyl)-N-(pyrrolidin-1-ylsulfonyl)benzamide;

(R)-3-chloro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)—N-((7-azabicyclo[2.2.1]heptan-7-yl)sulfonyl)-3-chloro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-cyclobutoxy-3-fluoro-4-(8-(3-(methoxymethyl)-4-methylpiperazin-1-yl)-10-methyl-5-oxo-1,3,4,5-tetrahydro-2H-chromeno[3,4-c]pyridine-3-carbonyl)-N-(pyrrolidin-1-ylsulfonyl)benzamide;

(R)-2-(cyclopentyloxy)-3-fluoro-4-(8-(3-(methoxymethyl)-4-methylpiperazin-1-yl)-10-methyl-5-oxo-1,3,4,5-tetrahydro-2H-chromeno[3,4-c]pyridine-3-carbonyl)-N-(pyrrolidin-1-ylsulfonyl)benzamide;

(R)—N-((7-azabicyclo[2.2.1]heptan-7-yl)sulfonyl)-2-(dimethylamino)-5-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl) benzamide;

(R)—N-((6-azaspiro[2.5]octan-6-yl)sulfonyl)-2-(dimethylamino)-5-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)—N-((6-azaspiro[2.5]octan-6-yl)sulfonyl)-5-chloro-2-(dimethylamino)-4-(8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-2-(dimethylamino)-5-fluoro-4-(8-(3-(methoxymethyl)-4-methylpiperazin-1-yl)-5-oxo-1,3,4,5-tetrahydro-2H-chromeno[3,4-c]pyridine-3-carbonyl)benzamide;

(R)-2-cyclobutoxy-3-fluoro-4-(8-(3-(isopropoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)—N-((7-azabicyclo[2.2.1]heptan-7-yl)sulfonyl)-5-chloro-2-(dimethylamino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl) benzamide;

(R)-2-(azetidin-1-yl)-5-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-amino-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(piperidin-1-ylsulfonyl)benzamide;

(R)-2-ethoxy-3-fluoro-4-(8-(3-(methoxymethyl)-4-methylpiperazin-1-yl)-7-methyl-5-oxo-1,3,4,5-tetrahydro-2H-chromeno[3,4-c]pyridine-3-carbonyl)-N-(piperidin-1-ylsulfonyl)benzamide;

(R)—N—(N-cyclopentyl-N-methylsulfamoyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-(cyclobutyl(methyl)amino)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-(methylamino)-N-(pyrrolidin-1-ylsulfonyl)benzamide;

(R)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

N-((3-azabicyclo[3.1.0]hexan-3-yl)sulfonyl)-2-(azetidin-1-yl)-5-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)-3-fluoro-N-((4-fluoropiperidin-1-yl)sulfonyl)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-propoxy-N-(pyrrolidin-1-ylsulfonyl)benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-2-(2,2,2-trifluoroethoxy)benzamide;

N-((3-azabicyclo[3.1.0]hexan-3-yl)sulfonyl)-2-cyclopropoxy-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.1.0]hexan-3-yl)sulfonyl)-4-(7-chloro-8-((R)-3-(methoxymethyl)-4-methylpiperazin-1-yl)-5-oxo-1,3,4,5-tetrahydro-2H-chromeno[3,4-c]pyridine-3-carbonyl)-2-ethoxy-3-fluorobenzamide;

(R)—N-((7-azabicyclo[2.2.1]heptan-7-yl)sulfonyl)-4-(7-chloro-8-(3-(methoxymethyl)-4-methylpiperazin-1-yl)-5-oxo-1,3,4,5-tetrahydro-2H-chromeno[3,4-c]pyridine-3-carbonyl)-2-ethoxy-3-fluorobenzamide;

N-(((3aR,6aS)-hexahydrocyclopenta[c]pyrrol-2(1H)-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((octahydro-2H-isoindol-2-yl)sulfonyl)benzamide;

(R)-2-cyclopropoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)—N-((7-azabicyclo[2.2.1]heptan-7-yl)sulfonyl)-2-cyclopropoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.1.0]hexan-3-yl)sulfonyl)-2-ethoxy-4-(7-ethyl-8-((R)-3-(methoxymethyl)-4-methylpiperazin-1-yl)-5-oxo-1,3,4,5-tetrahydro-2H-chromeno[3,4-c]pyridine-3-carbonyl)-3-fluorobenzamide;

(R)—N-((7-azabicyclo[2.2.1]heptan-7-yl)sulfonyl)-2-ethoxy-4-(7-ethyl-8-(3-(methoxymethyl)-4-methylpiperazin-1-yl)-5-oxo-1,3,4,5-tetrahydro-2H-chromeno[3,4-c]pyridine-3-carbonyl)-3-fluorobenzamide;

(R)—N—(N,N-dicyclopropylsulfamoyl)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((3,3-dimethylpyrrolidin-1-yl)sulfonyl)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.1.0]hexan-3-yl)sulfonyl)-2-ethoxy-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((2-azaspiro[3.3]heptan-2-yl)sulfonyl)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-oxa-8-azabicyclo[3.2.1]octan-8-yl)sulfonyl)-2-ethoxy-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)-2-(3,3,3-trifluoropropoxy)benzamide;

(R)-3-ethoxy-2-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-fluoro-2-(methoxy-d3)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)—N-((7-azabicyclo[2.2.1]heptan-7-yl)sulfonyl)-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-2-ethoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.1.0]hexan-3-yl)sulfonyl)-2-ethoxy-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((2-azabicyclo[2.2.1]heptan-2-yl)sulfonyl)-2-ethoxy-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)—N—(N,N-dicyclopropylsulfamoyl)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-ethoxy-3-fluoro-N-(((3aR,6aS)-hexahydrocyclopenta[c]pyrrol-2(1H)-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((2-azaspiro[3.3]heptan-2-yl)sulfonyl)-2-ethoxy-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((8-azabicyclo[3.2.1]octan-8-yl)sulfonyl)-2-ethoxy-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.2.1]octan-3-yl)sulfonyl)-2-ethoxy-3-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((8-azabicyclo[3.2.1]octan-8-yl)sulfonyl)-2-ethoxy-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

N-((3-azabicyclo[3.2.1]octan-3-yl)sulfonyl)-2-ethoxy-3-fluoro-4-(8-((R)-3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)—N—(N-cyclopentyl-N-methylsulfamoyl)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-3-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(piperidin-1-ylsulfonyl)benzamide;

(R)-3-fluoro-N-((4-fluoropiperidin-1-yl)sulfonyl)-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-2-methylbenzamide;

(R)-5-(dimethylamino)-2-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)—N-((7-azabicyclo[2.2.1]heptan-7-yl)sulfonyl)-2-ethyl-3-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-ethoxy-4-(10-ethyl-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-N-(pyrrolidin-1-ylsulfonyl)benzamide;

(R)-2-(dimethylamino)-4-(10-ethyl-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-N-(pyrrolidin-1-ylsulfonyl)benzamide;

(R)-4-(10-chloro-8-(3-(methoxymethyl)-4-methylpiperazin-1-yl)-7-methyl-5-oxo-1,3,4,5-tetrahydro-2H- chromeno[3,4-c]pyridine-3-carbonyl)-5-fluoro-2-(methoxy-d3)-N-(pyrrolidin-1-ylsulfonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(pyrrolidin-1-ylsulfonyl)benzamide;

(R)—N-((7-azabicyclo[2.2.1]heptan-7-yl)sulfonyl)-5-fluoro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.1.0]hexan-3-yl)sulfonyl)-5-fluoro-2-methoxy-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-5-fluoro-2-(methoxy-d3)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.1.0]hexan-3-yl)sulfonyl)-5-fluoro-2-(methoxy-d3)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-3-fluoro-2-(methoxy-d3)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((2-azaspiro[3.3]heptan-2-yl)sulfonyl)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-(dimethylamino)-5-fluoro-N-(((S)-3-fluoropyrrolidin-1-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-oxa-8-azabicyclo[3.2.1]octan-8-yl)sulfonyl)-2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N—(N-cyclopropyl-N-methylsulfamoyl)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-3-fluoro-N-(pyrrolidin-1-ylsulfonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluoro-N-(pyrrolidin-1-ylsulfonyl)benzamide;

(R)-4-(10-chloro-8-(3-(methoxymethyl)-4-methylpiperazin-1-yl)-7-methyl-5-oxo-1,3,4,5-tetrahydro-2H- chromeno[3,4-c]pyridine-3-carbonyl)-2-(dimethylamino)-N—(N,N-dimethylsulfamoyl)-5-fluorobenzamide;

2-ethoxy-5-fluoro-N—(((R)-3-fluoropyrrolidin-1-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-methoxy-N-(pyrrolidin-1-ylsulfonyl)benzamide;

(R)-2-cyclopropoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

N-((3-azabicyclo[3.1.0]hexan-3-yl)sulfonyl)-2-cyclopropoxy-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-2-fluoro-5-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

N-(((1S,4S)-2-oxa-5-azabicyclo[2.2.1]heptan-5-yl)sulfonyl)-2-ethoxy-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-ethoxy-5-fluoro-N-(((S)-3-fluoropyrrolidin-1-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N—(N-cyclopropyl-N-methylsulfamoyl)-2-ethoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-2-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-5-methyl-N-(pyrrolidin-1-ylsulfonyl)benzamide;

(R)—N-((2-oxa-5-azaspiro[3.5]nonan-5-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

(R)—N-((2-oxa-6-azaspiro[3.5]nonan-6-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

R)—N-((2-oxa-6-azaspiro[3.4]octan-6-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

(R)—N-((5-azaspiro[2.4]heptan-5-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(piperidin-1-ylsulfonyl)benzamide;

(R)—N—(N,N-dicyclopropylsulfamoyl)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-N—(N, N-dicyclopropylsulfamoyl)-2-(dimethylamino)-5-fluorobenzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N—(((R)-2-(trifluoromethyl)pyrrolidin-1-yl)sulfonyl)benzamide;

(R)—N-((2-azaspiro[3.3]heptan-2-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-methoxybenzamide;

N-((3-azabicyclo[3.1.0]hexan-3-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-methoxybenzamide;

2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(((S)-3-methoxypiperidin-1-yl)sulfonyl)benzamide;

(R)—N-((2-oxa-6-azaspiro[3.3]heptan-6-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-methoxy-N-(((S)-2-(methoxymethyl) pyrrolidin-1-yl)sulfonyl)benzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(((S)-3-methoxypyrrolidin-1-yl)sulfonyl)benzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N—(((R)-3-methoxypyrrolidin-1-yl)sulfonyl)benzamide;

2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N—(((R)-3-methoxypiperidin-1-yl)sulfonyl)benzamide;

2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N—(((R)-2-(trifluoromethyl) pyrrolidin-1-yl)sulfonyl)benzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-methoxy-N—(((R)-2-(methoxymethyl) pyrrolidin-1-yl)sulfonyl)benzamide;

(R)-2-(dimethylamino)-5-fluoro-4-(8-(3-(methoxymethyl)-4-methylpiperazin-1-yl)-7,10-dimethyl-5-oxo-1, 3,4,5-tetrahydro-2H-chromeno[3,4-c]pyridine-3-carbonyl)-N-((4-methoxypiperidin-1-yl)sulfonyl)benzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N—(((R)-2-(methoxymethyl)pyrrolidin-1-yl)sulfonyl)benzamide;

(R)-5-chloro-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-N—(N,N-dimethylsulfamoyl)benzamide;

2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(((S)-2-(trifluoromethyl) pyrrolidin-1-yl)sulfonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-((4-(trifluoromethyl) piperidin-1-yl)sulfonyl)benzamide;

N-(((1R,4R)-2-oxa-5-azabicyclo[2.2.1]heptan-5-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(((S)-2-(trifluoromethyl)pyrrolidin-1-yl)sulfonyl)benzamide;

(R)-2-(dimethylamino)-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-((4-(trifluoromethyl) piperidin-1-yl)sulfonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-N—(N, N-dicyclopropylsulfamoyl)-5-fluoro-2-methoxybenzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-N—(N-cyclopropyl-N-methylsulfamoyl)-2-ethoxy-5-fluorobenzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluoro-N-((1-methylcyclopropyl)sulfonyl)benzamide;

(R)—N-((2-azaspiro[3.3]heptan-2-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluorobenzamide;

N-((8-oxa-3-azabicyclo[3.2.1]octan-3-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluorobenzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N-(((S)-3-fluoropyrrolidin-1-yl)sulfonyl)benzamide;

4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluoro-N—(((R)-3-fluoropyrrolidin-1-yl)sulfonyl)benzamide;

(R)—N-((7-azabicyclo[2.2.1]heptan-7-yl)sulfonyl)-2-(dimethylamino)-5-fluoro-4-(10-fluoro-8-(3-(methoxymethyl)-4-methylpiperazin-1-yl)-7-methyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-5-fluoro-4-(10-fluoro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-methoxybenzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-cyclopropoxy-N—(N,N-dimethylsulfamoyl)-5-fluorobenzamide;

N-((3-oxa-8-azabicyclo[3.2.1]octan-8-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-cyclopropoxy-5-fluorobenzamide;

(R)-2-(dimethylamino)-5-fluoro-4-(10-fluoro-8-(3-(methoxymethyl)-4-methylpiperazin-1-yl)-7-methyl-5-oxo-1,3,4,5-tetrahydro-2H-chromeno[3,4-c]pyridine-3-carbonyl)-N-(pyrrolidin-1-ylsulfonyl)benzamide;

(R)-5-fluoro-4-(10-fluoro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-methoxy-N-(pyrrolidin-1-ylsulfonyl)benzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-fluoro-5-methyl-N-(pyrrolidin-1-ylsulfonyl)benzamide;

2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N—(((R)-2-(methoxymethyl) pyrrolidin-1-yl)sulfonyl)benzamide;

2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(((S)-2-(methoxymethyl) pyrrolidin-1-yl)sulfonyl)benzamide;

N-(((1S,4S)-2-oxa-5-azabicyclo[2.2.1]heptan-5-yl)sulfonyl)-2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

2-(dimethylamino)-5-fluoro-N—(((R)-3-fluoropyrrolidin-1-yl)sulfonyl)-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

N-((3-azabicyclo[3.1.0]hexan-3-yl)sulfonyl)-2-(dimethylamino)-5-fluoro-4-(8-((R)-3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

(R)—N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

(R)—N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxy-5-fluorobenzamide;

(R)—N-((2-azaspiro[3.3]heptan-2-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-fluoro-5-methoxy-N-(pyrrolidin-1-ylsulfonyl)benzamide;

(R)—N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-ethoxybenzamide;

(R)—N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-2-methoxybenzamide;

N-((3-oxa-8-azabicyclo[3.2.1]octan-8-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-2-(dimethylamino)-5-fluorobenzamide;

(R)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-N—(N-cyclopropyl-N-methylsulfamoyl)-2-(dimethylamino)-5-fluorobenzamide;

(R)—N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-methoxybenzamide;

N-((3-azabicyclo[3.1.0]hexan-3-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-methoxybenzamide;

(R)—N-((7-azabicyclo[2.2.1]heptan-7-yl)sulfonyl)-4-(10-chloro-8-(3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-(methoxy-d3)benzamide;

N-((3-azabicyclo[3.1.0]hexan-3-yl)sulfonyl)-4-(10-chloro-8-((R)-3-(methoxymethyl)-4-methylpiperazin-1-yl)-7-methyl-5-oxo-1,3,4,5-tetrahydro-2H-chromeno[3,4-c]pyridine-3-carbonyl)-5-fluoro-2-(methoxy-d3)benzamide;

(R)-5-chloro-2-(methoxy-d3)-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-chloro-2-methoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide;

(R)-5-chloro-2-ethoxy-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)-N-(pyrrolidin-1-ylsulfonyl)benzamide; and (R)—N-((7-azabicyclo[2.2.1]heptan-7-yl)sulfonyl)-2-cyclopropoxy-5-fluoro-4-(8-(3-(methoxymethyl)-4-methylpiperazin-1-yl)-7,10-dimethyl-5-oxo-1,3,4,5-tetrahydro-2H-chromeno[3,4-c]pyridine-3-carbonyl)benzamide;

or a pharmaceutically acceptable salt and/or solvate of any one thereof.

14. A pharmaceutical composition comprising a compound or pharmaceutically acceptable salt and/or solvate thereof according to claim 1 and one or more pharmaceutically acceptable diluents or carriers.

15. A method of treating a disease selected from inflammatory, autoimmune and fibrotic diseases, and cancer, which comprises administering a compound or salt and/or solvate thereof according to claim 1.

16. The compound or a pharmaceutically acceptable salt and/or solvate thereof according to claim 9 wherein $R_1$ is methyl and $R_2$ is methyl.

17. The compound or a pharmaceutically acceptable salt and/or solvate thereof according to claim 9 wherein m is 2 and $R_3$ is methyl or wherein m is 1 and $R_3$ is chloro.

18. The compound or a pharmaceutically acceptable salt and/or solvate thereof according to claim 9 wherein $R_4$ is selected from the group consisting of chloro and fluoro.

* * * * *